United States Patent
Zhou et al.

(10) Patent No.: US 12,054,497 B2
(45) Date of Patent: Aug. 6, 2024

(54) SUBSTITUTED HETEROCYCLIC FUSED CYCLIC COMPOUND, PREPARATION METHOD THEREFOR AND PHARMACEUTICAL USE THEREOF

(71) Applicants: GENFLEET THERAPEUTICS (SHANGHAI) INC., Shanghai (CN); ZHEJIANG GENFLEET THERAPEUTICS CO., LTD., Shaoxing (CN)

(72) Inventors: Fusheng Zhou, Shanghai (CN); Tao Jiang, Shanghai (CN); Chonglan Lin, Shanghai (CN); Lijian Cai, Shanghai (CN); Wan He, Shanghai (CN); Jiong Lan, Shanghai (CN)

(73) Assignees: Genfleet Therapeutics (Shanghai)Inc., Shanghai (CN); Zhejiang Genfleet Therapeutics Co., Ltd., Shaoxing (CN)

( * ) Notice: Subject to any disclaimer, the term of this patent is extended or adjusted under 35 U.S.C. 154(b) by 0 days.

(21) Appl. No.: 17/773,607

(22) PCT Filed: Oct. 28, 2020

(86) PCT No.: PCT/CN2020/124226
§ 371 (c)(1),
(2) Date: Apr. 30, 2022

(87) PCT Pub. No.: WO2021/083167
PCT Pub. Date: May 6, 2021

(65) Prior Publication Data
US 2023/0084095 A1 Mar. 16, 2023

(30) Foreign Application Priority Data

Oct. 30, 2019 (CN) .................. 201911045542.X
Apr. 9, 2020 (CN) .................. 202010272563.1
Oct. 22, 2020 (CN) .................. 202011140832.5

(51) Int. Cl.
| | |
|---|---|
| *C07D 471/22* | (2006.01) |
| *A61K 31/4985* | (2006.01) |
| *A61K 31/5383* | (2006.01) |
| *A61K 31/55* | (2006.01) |
| *A61P 35/00* | (2006.01) |
| *C07D 471/14* | (2006.01) |
| *C07D 471/16* | (2006.01) |
| *C07D 498/22* | (2006.01) |

(52) U.S. Cl.
CPC ......... *C07D 498/22* (2013.01); *C07D 471/16* (2013.01); *C07D 471/22* (2013.01)

(58) Field of Classification Search
CPC ............. C07D 471/22; C07D 471/14; C07D 498/22; A61P 35/00; A61K 31/55; A61K 31/5383; A61K 31/4985
See application file for complete search history.

(56) References Cited

U.S. PATENT DOCUMENTS

2019/0144444 A1 5/2019 Blake et al.
2019/0177338 A1 6/2019 Kettle et al.

FOREIGN PATENT DOCUMENTS

| | | |
|---|---|---|
| AU | 2020350745 A1 | 4/2022 |
| CA | 3098574 A1 | 11/2019 |
| CA | 3155066 A1 | 3/2021 |
| CN | 106488910 A | 3/2017 |
| CN | 112300194 A | 2/2021 |
| CN | 112300196 A | 2/2021 |
| CN | 113396147 A | 9/2021 |
| CN | 114728968 A | 7/2022 |
| EP | 4043464 A1 | 8/2022 |

(Continued)

*Primary Examiner* — Brenda L Coleman
(74) *Attorney, Agent, or Firm* — Morrison & Foerster LLP

(57) ABSTRACT

A substituted heterocyclic fused cyclic compound as represented by formula (I) or formula (IA) and having a selective inhibitory effect on KRAS gene mutation, or a pharmaceutically-acceptable salt, a stereoisomer, a solvate or a prodrug thereof, a pharmaceutical composition containing the compound, and an application thereof in preparation of cancer drugs are provided.

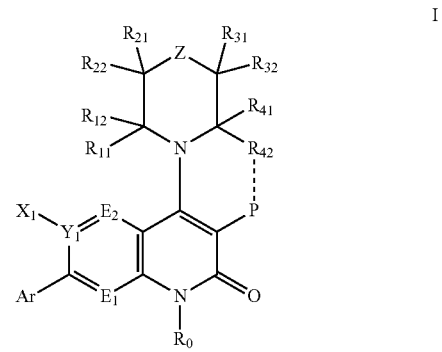

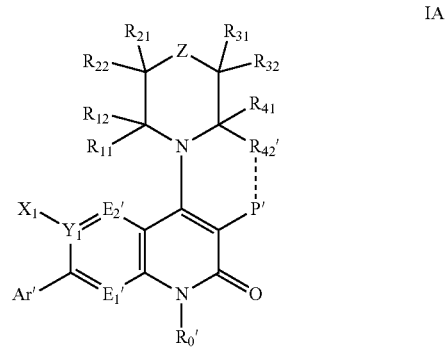

20 Claims, 1 Drawing Sheet

(56) References Cited

FOREIGN PATENT DOCUMENTS

| RU | 2673079 C2 | 11/2018 |
|---|---|---|
| TW | 1659021 B | 5/2019 |
| TW | 201922739 A | 6/2019 |
| TW | 201938555 A | 10/2019 |
| WO | 2018217651 A1 | 11/2018 |
| WO | 2019051291 | 3/2019 |
| WO | 2019213516 A1 | 11/2019 |
| WO | 2020239123 A1 | 12/2020 |
| WO | 2021052499 A1 | 3/2021 |

SUBSTITUTED HETEROCYCLIC FUSED CYCLIC COMPOUND, PREPARATION METHOD THEREFOR AND PHARMACEUTICAL USE THEREOF

CROSS REFERENCE TO THE RELATED APPLICATIONS

This application is the national phase entry of International Application No. PCT/CN2020/124226, filed on Oct. 28, 2020, which is based upon and claims priority to Chinese Patent Application No. 201911045542.X, filed on Oct. 30, 2019, Chinese Patent Application No. 202010272563.1, filed on Apr. 9, 2020, and Chinese Patent Application No. 202011140832.5, filed on Oct. 22, 2020, the entire contents of which are incorporated herein by reference.

TECHNICAL FIELD

The present invention relates to the technical field of medicine, and in particular, to a substituted heterocyclic fused cyclic compound, use thereof as a selective inhibitor for KRAS gene mutations, and a pharmaceutical composition prepared therefrom.

BACKGROUND

Lung cancer is the cancer with the highest global incidence. The incidence of lung cancer in China ranks first among all cancers. Lung cancer is also the cancer with the highest incidence and mortality in China. According to the data released by the American Cancer Society in 2016, about 1.8 million people in the world suffered from lung cancer, of which approximate 80% of lung cancer cases were non-small cell lung cancer (NSCLC).

RAS refers to a group of closely related monomeric globular proteins (with a molecular weight of 21 kDa) having 188-189 amino acids and binding to guanosine diphosphate (GDP) or guanosine triphosphate (GTP). Members in an RAS subfamily include HRAS, KRAS, and NRAS. RAS serves as a molecular switch. When containing the bound GDP, RAS is in the dormant or closed position and "inactive". When cells are exposed to some growth promoting somatotrophic irritants, RAS is induced such that the GDP binding thereto is transformed into GTP. When binding to GTP, RAS is "switched on" and able to interact with and activate other downstream target proteins. The RAS proteins are extremely low in their inherent capability of hydrolyzing GTP into GDP (allowing themselves to be switched off). Accordingly, an extrinsic protein, namely GTPase activating protein (GAP), is needed to switch off an RAS protein. The interaction between GAP and RAS greatly accelerates the transformation of GTP into GDP. Any mutation in RAS will affect the interaction between RAS and GAP and the ability to transform GTP into GDP. Such a mutation will result in prolonged protein activation time, leading to prolonged cell signal transduction and hence continuous cell growth and division. Since the signal transduction causes cell growth and division, excessively activated RAS signal transduction may eventually lead to cancer. It has been confirmed that mutations in the RAS genes were involved in about 32% of lung cancer cases. Any one of three major subtypes of the RAS (HRAS, NRAS, or KRAS) genes may result in tumorigenesis in a human body. It has been reported that mutations occurred most frequently in the KRAS gene among the RAS genes and the KRAS mutations were detected in 25-30% of tumors. In comparison, the ratios of carcinogenic mutations occurring in the family members NRAS and HRAS were much lower (which were 8% and 3%, respectively). The most common KRAS mutations were found on residues G12 and G13 and residue Q61 in the P-loop. G12C (glycine 12 to cysteine) mutation is a frequent one in the KRAS gene. This mutation has been found in about 43% of lung cancer cases and almost 100% of MYH-associated polyposis (familial colon cancer syndrome) cases among about 13% of cancers. Therefore, it is desirable to develop inhibitors for selectively inhibiting KRAS mutations. To reduce the inhibitory activity for wild-type KRAS while improving the inhibitory activity for KRAS mutations, it is of great significance to develop novel selective inhibitors for RAS mutants that have higher activity, better selectivity, and lower toxicity.

SUMMARY

The present invention provides a substituted heterocyclic fused cyclic compound having a novel structure, which is used as a selective inhibitor for KRAS mutations and has the advantages of high activity, good selectivity, low toxic and side effects, etc.

In one aspect, the present invention provides a compound of Formula (I), or a pharmaceutically acceptable salt, a stereoisomer, a solvate or a prodrug thereof:

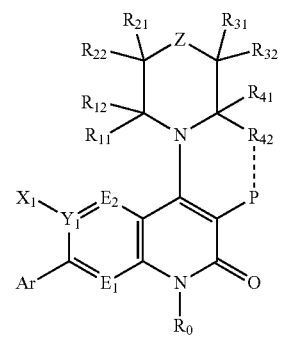

where,

Z is N—C(O)—CR$_3$=CR$_1$R$_2$ or N—C(O)—C≡CR$_4$;

R$_1$ and R$_2$ are each independently hydrogen, halogen, cyano, NR$^a$R$^b$, —C$_{1-3}$ alkyl, halogenated C$_{1-3}$ alkyl, —C$_{1-3}$ alkyl-hydroxyl, —C$_{1-3}$ alkyl-cyano, —C$_{1-3}$ alkyl-C$_{1-3}$ alkoxy, —C$_{1-3}$ alkyl-NR$^a$R$^b$, —C$_{1-3}$ alkyl-3- to 6-membered heterocycloalkyl, or —C$_{1-3}$ alkyl-5- or 6-membered monocyclic heteroaryl, where the 3- to 6-membered heterocycloalkyl or the 5- or 6-membered monocyclic heteroaryl has 1, 2, or 3 heteroatoms selected from N, O, and S as ring atoms;

R$_3$ is hydrogen, halogen, —C$_{1-3}$ alkyl, or —C$_{1-3}$ alkoxy;

R$_4$ is hydrogen, halogenated C$_{1-3}$ alkyl, —C$_{1-3}$ alkyl-hydroxyl, —C$_{1-3}$ alkyl-cyano, or —C$_{1-3}$ alkyl-C$_{1-3}$ alkoxy;

R$_{11}$ and R$_{12}$ are either identical or different and are each independently hydrogen, halogen, —C$_{1-3}$ alkyl, -halogenated C$_{1-3}$ alkyl, —C$_{1-3}$ alkyl-hydroxyl, —C$_{1-3}$ alkyl-cyano, —C$_{1-3}$ alkyl-C$_{1-6}$ alkoxy, —C$_{1-3}$ alkyl-halogenated C$_{1-6}$ alkyl, or —C$_{1-3}$ alkyl-halogenated C$_{1-6}$ alkoxy;

R$_{21}$ and R$_{22}$ are either identical or different and are each independently hydrogen, halogen, —C$_{1-3}$ alkyl, -halogenated C$_{1-3}$ alkyl, —C$_{1-3}$ alkyl-hydroxyl, —C$_{1-3}$ alkyl-cyano, —C$_{1-3}$ alkyl-C$_{1-6}$ alkoxy, —C$_{1-3}$ alkyl-halogenated C$_{1-6}$ alkyl, or —C$_{1-3}$ alkyl-halogenated C$_{1-6}$ alkoxy;

R$_{31}$ and R$_{32}$ are either identical or different and are each independently hydrogen, halogen, —C$_{1-3}$ alkyl, -halogenated C$_{1-3}$ alkyl, —C$_{1-3}$ alkyl-hydroxyl, —C$_{1-3}$ alkyl-cyano, —C$_{1-3}$ alkyl-C$_{1-6}$ alkoxy, —C$_{1-3}$ alkyl-halogenated C$_{1-6}$ alkyl, or —C$_{1-3}$ alkyl-halogenated C$_{1-6}$ alkoxy;

R$_{41}$ is hydrogen, halogen, —C$_{1-3}$ alkyl, -halogenated C$_{1-3}$ alkyl, —C$_{1-3}$ alkyl-hydroxyl, —C$_{1-3}$ alkyl-cyano, —C$_{1-3}$ alkyl-C$_{1-6}$ alkoxy, —C$_{1-3}$ alkyl-halogenated C$_{1-6}$ alkyl, or —C$_{1-3}$ alkyl-halogenated C$_{1-6}$ alkoxy;

when the dashed line in

is a single bond, P is O, NH or NR$^m$; R$^m$ is —C$_{1-6}$ alkyl, -halogenated C$_{1-6}$ alkyl, —C$_{1-6}$ alkyl-hydroxyl, —C$_{1-6}$ alkyl-cyano, —C$_{1-6}$ alkyl-C$_{1-6}$ alkoxy, —C$_{1-6}$ alkyl-halogenated C$_{1-6}$ alkoxy, —C$_{1-6}$ alkyl-C$_{3-6}$ cycloalkyl, or —C$_{1-6}$ alkyl-3- to 6-membered heterocycloalkyl; R$_{42}$ is —(C=O)—, —C$_{1-3}$ alkyl-, —C$_{1-3}$ alkyl (hydroxy)-, —C$_{1-3}$ alkyl (cyano)-, —C$_{1-3}$ alkyl (C$_{1-6}$ alkyl)-, —C$_{1-3}$ alkyl (halogenated C$_{1-6}$ alkyl)-, —C$_{1-3}$ alkyl (C$_{1-6}$ alkyl-hydroxy)-, —C$_{1-3}$ alkyl (C$_{1-6}$ alkyl-cyano)-, —C$_{1-3}$ alkyl (C$_{1-6}$ alkoxy)-, or —C$_{1-3}$ alkyl (halogenated C$_{1-6}$ alkoxy)-;

or when the dashed line in

is absent, P is hydrogen, halogen; R$_{42}$ is hydrogen, halogen, —C$_{1-3}$ alkyl, -halogenated C$_{1-3}$ alkyl, —C$_{1-3}$ alkyl-hydroxyl, —C$_{1-3}$ alkyl-cyano, —C$_{1-3}$ alkyl-C$_{1-6}$ alkoxy, —C$_{1-3}$ alkyl-halogenated C$_{1-6}$ alkyl, or —C$_{1-3}$ alkyl-halogenated C$_{1-6}$ alkoxy;

when Y$_1$ is C, X$_1$ is hydrogen, halogen, cyano, hydroxyl, amino, nitro, -substituted or unsubstituted C$_{1-6}$ alkyl, -substituted or unsubstituted C$_{3-6}$ cycloalkyl, -substituted or unsubstituted 3- to 6-membered heterocycloalkyl, —O— substituted or unsubstituted C$_{1-6}$ alkyl, —O-substituted or unsubstituted C$_{3-6}$ cycloalkyl, —O-substituted or unsubstituted 3- to 6-membered heterocycloalkyl, —NH-substituted or unsubstituted C$_{1-6}$ alkyl, —N(substituted or unsubstituted C$_{1-6}$ alkyl)$_2$, —NH-substituted or unsubstituted C$_{3-6}$ cycloalkyl, —NH-substituted or unsubstituted 3- to 6-membered heterocycloalkyl, —NH(C=O)-substituted or unsubstituted C$_{1-6}$ alkyl, —NH(C=O)—C$_{3-6}$ cycloalkyl, —NH(SO$_2$)-substituted or unsubstituted C$_{1-6}$ alkyl, —NH(SO$_2$)-substituted or unsubstituted C$_{3-6}$ cycloalkyl, —SO$_2$-substituted or unsubstituted C$_{1-6}$ alkyl, —SO$_2$-substituted or unsubstituted C$_{3-6}$ cycloalkyl, —(C=O)—NR$^j$R$^k$—, —(C=O)—O-substituted or unsubstituted C$_{1-6}$ alkyl, or —(C=O)—O-substituted or unsubstituted C$_{3-6}$ cycloalkyl, where R$^j$ and R$^k$ are each independently hydrogen or C$_{1-3}$ alkyl; or R$^j$ and R$^k$ form together with a nitrogen atom adjacent thereto substituted or unsubstituted 3- to 6-membered N-containing heterocycloalkyl; the 3- to 6-membered heterocycloalkyl has 1, 2 or 3 heteroatoms selected from N, O, and S as ring atoms; the 3- to 6-membered N-containing heterocycloalkyl has 3 to 6 ring atoms, and one of the ring atoms is nitrogen atom, while 0, 1 or 2 ring atoms among the rest of the ring atoms are optionally heteroatoms selected from N, O, and S; the "substituted" means 1, 2, 3, or 4 hydrogen atoms in a group being each independently substituted by a group-S substituent;

or when Y$_1$ is N, X$_1$ is absent;

the group-S substituent is selected from hydroxyl, halogen, nitro, oxo, —C$_{1-6}$ alkyl, -halogenated C$_{1-6}$ alkyl, hydroxyl-substituted C$_{1-6}$ alkyl, benzyl, —(CH$_2$)$_u$-cyano, —(CH$_2$)$_u$—C$_{1-6}$ alkoxy, —(CH$_2$)$_u$-halogenated C$_{1-6}$ alkoxy, —(CH$_2$)$_u$-halogenated C$_{1-6}$ alkyl, —(CH$_2$)$_u$-3- to 6-membered heterocycloalkyl, —(CH$_2$)$_u$-5- or 6-membered monocyclic heteroaryl, —(CH$_2$)$_u$—C$_{3-8}$ cycloalkyl, —(CH$_2$)$_u$—O—(CH$_2$)$^u$—C$_{3-8}$ cycloalkyl, —(CH$_2$)$_u$—O—(CH$_2$)$_v$—C$_{1-6}$ alkoxy, —(CH$_2$)$_u$—O—(CH$_2$)$_v$OH, —(CH$_2$)$_u$—SO$_2$C$_{1-6}$ alkyl, —(CH$_2$)$_u$—NR$_{a0}$R$_{b0}$, —(CH$_2$)$_u$—C(O)NR$_{a0}$R$_{b0}$, —(CH$_2$)$_u$—C(O)C$_{1-6}$ alkyl, —C(O)OC$_{1-6}$ alkyl, NR$_{a0}$C(O)—(CH$_2$)$_u$—NR$_{a0}$R$_{b0}$, NR$_{a0}$C(O)—(CH$_2$)$_u$OH, and NR$_{a0}$C(O)-halogenated C$_{1-6}$ alkyl, where the 3- to 6-membered heterocycloalkyl or the 5- or 6-membered monocyclic heteroaryl each independently has 1, 2 or 3 heteroatoms selected from N, O, and S as ring atoms; the 3- to 6-membered heterocycloalkyl and the 5- or 6-membered monocyclic heteroaryl are each optionally substituted by 1, 2, or 3 substituents selected from halogen, cyano, —C$_{1-3}$ alkyl, —C$_{1-3}$ alkoxy, and C$_{3-6}$ cycloalkyl; u and v are each independently 0, 1, 2, 3, or 4; R$_{a0}$ and R$_{b0}$ are each independently hydrogen or C$_{1-3}$ alkyl;

E$_1$ is N or CR$_5$, where R$_5$ is hydrogen, halogen, cyano, —C$_{1-6}$ alkyl, —C$_{1-6}$ alkoxy, -halogenated C$_{1-6}$ alkyl, -halogenated C$_{1-6}$ alkoxy, —C$_{3-6}$ cycloalkyl, —NR$^h$R$^i$, —C$_{1-4}$ alkyl-hydroxyl, —C$_{1-4}$ alkyl-cyano, —C$_{1-4}$ alkyl-C$_{1-6}$ alkoxy, —C$_{1-4}$ alkyl-halogenated C$_{1-6}$ alkyl, or —C$_{1-4}$alkyl-halogenated C$_{1-6}$ alkoxy;

E$_2$ is N or CR$_6$, where R$_6$ is hydrogen, halogen, cyano, —C$_{1-6}$ alkyl, —C$_{1-6}$ alkoxy, -halogenated C$_{1-6}$ alkyl, -halogenated C$_{1-6}$ alkoxy, —C$_{3-6}$ cycloalkyl, —NR$^h$R$^i$, —C$_{1-4}$ alkyl-hydroxyl, —C$_{1-4}$ alkyl-cyano, —C$_{1-4}$ alkyl-C$_{1-6}$ alkoxy, —C$_{1-4}$ alkyl-halogenated C$_{1-6}$ alkyl, or —C$_{1-4}$ alkyl-halogenated C$_{1-6}$ alkoxy, provided that Y$_1$, E$_1$ and E$_2$ are not simultaneously N;

Ar is C$_{6-10}$ aryl, 5- or 6-membered monocyclic heteroaryl or 8- to 10-membered bicyclic heteroaryl, where the 5- or 6-membered monocyclic heteroaryl has 1, 2 or 3 heteroatoms selected from N, O, and S as ring atoms; the 8- to 10-membered bicyclic heteroaryl has 1, 2, 3, 4, or 5 heteroatoms selected from N, O, and S as ring atoms; and the C$_{6-10}$ aryl, the 5- or 6-membered monocyclic heteroaryl or the 8- to 10-membered bicyclic heteroaryl is unsubstituted or substituted by 1, 2, 3, or 4 groups each independently selected from R$_{s1}$;

or,

Ar has a structure of Formula (B):

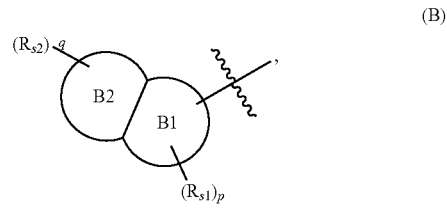

where the ring B1 is a benzene ring or a 5- or 6-membered monocyclic heteroaryl ring; the ring B2 is a fused 5- or 6-membered monocyclic heterocycloalkyl ring or a fused 5- or 6-membered monocyclic cycloalkyl ring, where the 5- or 6-membered monocyclic heteroaryl ring or the fused 5- or 6-membered monocyclic heterocycloalkyl ring has 1, 2, or 3 heteroatoms selected from N, O, and S as ring atoms;

$(R_{s1})_p$ represents that hydrogens on the ring B1 is substituted by p $R_{s1}$ groups, p being 0, 1, 2, or 3 and each $R_{s1}$ being either identical or different;

$(R_{s2})_q$ represents that hydrogens on the ring B2 is substituted by q $R_{s2}$ groups, q being 0, 1, 2, or 3 and each $R_{s2}$ being either identical or different;

$R_{s1}$ and $R_{s2}$ are each independently halogen, cyano, nitro, hydroxyl, —$C_{1-6}$ alkyl, —$C_{1-6}$ alkoxy, -halogenated $C_{1-6}$ alkyl, -halogenated $C_{1-6}$ alkoxy, —$C_{3-6}$ cycloalkyl, —$NR^cR^d$, —$C(O)NR^eR^f$, —$SO_2C_{1-3}$ alkyl, —$SO_2$halogenated $C_{1-3}$ alkyl, —$SO_2NR^eR^f$, —$C_{1-4}$ alkyl-hydroxyl, —$C_{1-4}$ alkyl-cyano, —$C_{1-4}$ alkyl-$C_{1-6}$ alkoxy, —$C_{1-4}$ alkyl-halogenated $C_{1-6}$ alkyl, —$C_{1-4}$ alkyl-halogenated $C_{1-6}$ alkoxy, —$C_{1-4}$ alkyl-3- to 6-membered heterocycloalkyl, —$C_{1-4}$ alkyl-$NR^eR^f$, —$C_{1-4}$ alkyl-$C(O)NR^eR^f$, —$C_{1-4}$ alkyl-$SO_2C_{1-3}$ alkyl, or $C_{2-4}$ alkynyl, where the 3- to 6-membered heterocycloalkyl has 1, 2, or 3 heteroatoms selected from N, O, and S as ring atoms;

$R_0$ is —$C_{1-6}$ alkyl, —$C_{3-6}$ cycloalkyl, 3- to 6-membered heterocycloalkyl, $C_{6-10}$ aryl, 5- or 6-membered monocyclic heteroaryl, 8- to 10-membered bicyclic heteroaryl, 7- to 11-membered spirocycloalkyl, —$C_{1-3}$ alkyl-$C_{6-10}$ aryl, —$C_{1-3}$ alkyl-5- or 6-membered monocyclic heteroaryl, —$NR^g$—$C_{6-10}$ aryl, —O—$C_{6-10}$ aryl, —$C_{1-3}$ alkyl-3- to 6-membered heterocycloalkyl, or —$C_{1-3}$ alkyl-$C_{3-6}$ cycloalkyl, where the 3- to 6-membered heterocycloalkyl, the 5- or 6-membered monocyclic heteroaryl or the 8- to 10-membered bicyclic heteroaryl has 1, 2 or 3 heteroatoms selected from N, O, and S as ring atoms; the $C_{1-6}$ alkyl, the $C_{3-6}$ cycloalkyl, the 3- to 6-membered heterocycloalkyl, the $C_{6-10}$ aryl, the 5- or 6-membered monocyclic heteroaryl, the 8- to 10-membered bicyclic heteroaryl and the 7- to 11-membered spirocycloalkyl are unsubstituted or each substituted by 1, 2, 3, or 4 groups each independently selected from $R_{s3}$; and the —$C_{1-3}$ alkyl- is unsubstituted or substituted by 1, 2, 3, or 4 groups each independently selected from $C_{1-3}$ alkyl;

or, $R_0$ has a structure of Formula (A-1) or Formula (A-2):

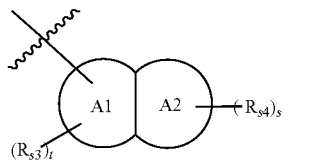

(A-1)

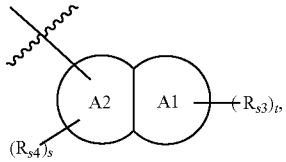

(A-2)

where the ring A1 is a benzene ring or a 5- or 6-membered monocyclic heteroaryl ring; the ring A2 is a fused 5- or 6-membered monocyclic heterocycloalkyl ring or a fused 5- or 6-membered monocyclic cycloalkyl ring, where the 5- or 6-membered monocyclic heteroaryl ring or the fused 5- or 6-membered monocyclic heterocycloalkyl ring has 1, 2, or 3 heteroatoms selected from N, O, and S as ring atoms;

$(R_{s3})_t$ represents that hydrogen on the ring A1 is substituted by t $R_{s3}$ groups, t being 0, 1, 2, or 3 and each $R_{s3}$ being either identical or different;

$(R_{s4})_s$ represents that hydrogen on the ring A2 is substituted by s $R_{s4}$ groups, s being 0, 1, 2, or 3 and each $R_{s4}$ being either identical or different;

$R_{s3}$ and $R_{s4}$ are each independently halogen, cyano, hydroxyl, —$C_{1-6}$ alkyl, —$C_{1-6}$ alkoxy, -halogenated $C_{1-6}$ alkyl, -halogenated $C_{1-6}$ alkoxy, —$C_{3-6}$ cycloalkyl, 3- to 6-membered heterocycloalkyl, —$NR^hR^i$, —$C(O)NR^eR^f$, —$SO_2C_{1-3}$ alkyl, —$SO_2$halogenated $C_{1-3}$ alkyl, —$SO_2NR^eR^f$, —$C_{1-3}$ alkyl-hydroxyl, —$C_{1-3}$ alkyl-$C_{2-4}$ alkynyl, —$C_{1-3}$ alkyl-cyano, —$C_{1-3}$ alkyl-$C_{1-6}$ alkoxy, —$C_{1-3}$ alkyl-halogenated $C_{1-6}$ alkyl, —$C_{1-3}$ alkyl-halogenated $C_{1-6}$ alkoxy, —$C_{1-3}$ alkyl-3-to 6-membered heterocycloalkyl, —$C_{1-3}$ alkyl-$C_{3-6}$ cycloalkyl, —$C_{1-3}$ alkyl-$NR^eR^f$, —$C_{1-3}$ alkyl-$C(O)NR^eR^f$, —$C_{1-3}$ alkyl-$SO_2C_{1-3}$ alkyl, or $C_{2-4}$ alkynyl, where the 3- to 6-membered heterocycloalkyl has 1, 2 or 3 heteroatoms selected from N, O, and S as ring atoms; and the $C_{1-6}$ alkyl, the —$C_{1-6}$ alkoxy, the —$C_{1-3}$ alkyl-, the —$C_{3-6}$ cycloalkyl and the 3- to 6-membered heterocycloalkyl are each optionally substituted by 1, 2, or 3 substituents each independently selected from halogen, methyl, ethyl, propyl (n-propyl), isopropyl, trifluoromethyl, amino, $N(CH_3)_2$, hydroxyl and carboxyl;

$R^a$, $R^b$, $R^e$, $R^f$, and $R^g$ are each independently hydrogen or $C_{1-3}$ alkyl; and $R^c$, $R^d$, $R^h$, and $R^i$ are each independently hydrogen, —$C_{1-3}$ alkyl, —$C(O)C_{1-3}$ alkyl, or —$CO_2C_{1-3}$ alkyl.

In an embodiment of the present invention, the compound of Formula (I) is the compound of Formula (I-1) or a compound of Formula (I-2):

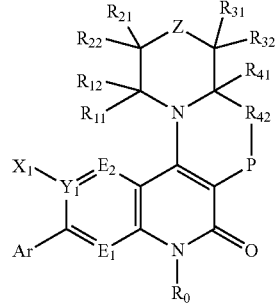

I-1

-continued

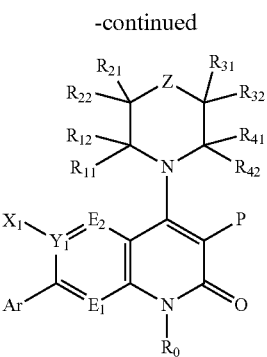
I-2

In Formula I-1, P is O, NH, or NR$^m$; R$^m$ is —C$_{1-6}$ alkyl, -halogenated C$_{1-6}$ alkyl, —C$_{1-6}$ alkyl-hydroxyl, —C$_{1-6}$ alkyl-cyano, —C$_{1-6}$ alkyl-C$_{1-6}$ alkoxy, —C$_{1-6}$ alkyl-halogenated C$_{1-6}$ alkoxy, —C$_{1-6}$ alkyl-C$_{3-6}$ cycloalkyl, or —C$_{1-6}$ alkyl-3- to 6-membered heterocycloalkyl; R$_{42}$ is —(C=O)—, —C$_{1-3}$ alkyl-, —C$_{1-3}$ alkyl (hydroxy)-, —C$_{1-3}$ alkyl (cyano)-, —C$_{1-3}$ alkyl (C$_{1-6}$ alkyl)-, —C$_{1-3}$ alkyl (halogenated C$_{1-6}$ alkyl)-, —C$_{1-3}$ alkyl (C$_{1-6}$ alkyl-hydroxy)-, —C$_{1-3}$ alkyl (C$_{1-6}$ alkyl-cyano)-, —C$_{1-3}$ alkyl(C$_{1-6}$alkoxy)-, or —C$_{1-3}$ alkyl (halogenated C$_{1-6}$ alkoxy)-; and R$_{11}$, R$_{12}$, R$_{21}$, R$_{22}$, R$_{31}$, R$_{32}$, R$_{41}$, Z, R$_0$, Ar, E$_1$, E$_2$, X$_1$, and Y$_1$ are as defined above.

In Formula I-2, P is hydrogen, halogen; R$_{42}$ is hydrogen, halogen, —C$_{1-3}$ alkyl, -halogenated C$_{1-3}$ alkyl, —C$_{1-3}$ alkyl-hydroxyl, —C$_{1-3}$ alkyl-cyano, —C$_{1-3}$ alkyl-C$_{1-6}$ alkoxy, —C$_{1-3}$ alkyl-halogenated C$_{1-6}$ alkyl, or —C$_{1-3}$ alkyl-halogenated C$_{1-6}$ alkoxy; and R$_{11}$, R$_{12}$, R$_{21}$, R$_{22}$, R$_{31}$, R$_{32}$, R$_{41}$, Z, R$_0$, Ar, E$_1$, E$_2$, X$_1$, and Y$_1$ are as defined above.

In another aspect, the present invention provides a compound of Formula (IA), or a tautomer, a cis-trans isomer, a mesomer, a raceme, an enantiomer, a diastereoisomer, an atropisomer or a mixture thereof, or a pharmaceutically acceptable salt, a solvate or a prodrug thereof:

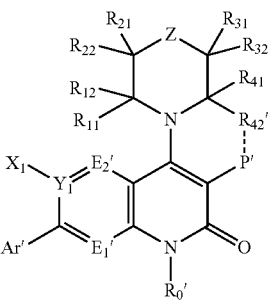
IA where:
Z is N—C(O)—CR$_3$=CR$_1$R$_2$ or N—C(O)—C≡CR$_4$;
R$_1$ and R$_2$ are each independently hydrogen, halogen, cyano, NR$^a$R$^b$, —C$_{1-3}$ alkyl, halogenated C$_{1-3}$ alkyl, —C$_{1-3}$ alkyl-hydroxyl, —C$_{1-3}$ alkyl-cyano, —C$_{1-3}$ alkyl-C$_{1-3}$ alkoxy, —C$_{1-3}$ alkyl-NR$^a$R$^b$, —C$_{1-3}$ alkyl-3- to 6-membered heterocycloalkyl, or —C$_{1-3}$ alkyl-5- or 6-membered monocyclic heteroaryl, where the 3- to 6-membered heterocycloalkyl or the 5- or 6-membered monocyclic heteroaryl has 1, 2, or 3 heteroatoms selected from N, O, and S as ring atoms;
R$_3$ is hydrogen, halogen, —C$_{1-3}$ alkyl, or —C$_{1-3}$ alkoxy;

R$_4$ is hydrogen, halogenated C$_{1-3}$ alkyl, —C$_{1-3}$ alkyl-hydroxyl, —C$_{1-3}$ alkyl-cyano, or —C$_{1-3}$ alkyl-C$_{1-3}$ alkoxy;
R$_{11}$ and R$_{12}$ are either identical or different and are each independently hydrogen, halogen, —C$_{1-3}$ alkyl, -halogenated C$_{1-3}$ alkyl, —C$_{1-3}$ alkyl-hydroxyl, —C$_{1-3}$ alkyl-cyano, —C$_{1-3}$ alkyl-C$_{1-6}$ alkoxy, —C$_{1-3}$ alkyl-halogenated C$_{1-6}$ alkyl, or —C$_{1-3}$ alkyl-halogenated C$_{1-6}$ alkoxy;
R$_{21}$ and R$_{22}$ are either identical or different and are each independently hydrogen, halogen, —C$_{1-3}$ alkyl, -halogenated C$_{1-3}$ alkyl, —C$_{1-3}$ alkyl-hydroxyl, —C$_{1-3}$ alkyl-cyano, —C$_{1-3}$ alkyl-C$_{1-6}$ alkoxy, —C$_{1-3}$ alkyl-halogenated C$_{1-6}$ alkyl, or —C$_{1-3}$ alkyl-halogenated C$_{1-6}$ alkoxy;
R$_{31}$ and R$_{32}$ are either identical or different and are each independently hydrogen, halogen, —C$_{1-3}$ alkyl, -halogenated C$_{1-3}$ alkyl, —C$_{1-3}$ alkyl-hydroxyl, —C$_{1-3}$ alkyl-cyano, —C$_{1-3}$ alkyl-C$_{1-6}$ alkoxy, —C$_{1-3}$ alkyl-halogenated C$_{1-6}$ alkyl, or —C$_{1-3}$ alkyl-halogenated C$_{1-6}$ alkoxy;
R$_{41}$ is hydrogen, halogen, —C$_{1-3}$ alkyl, -halogenated C$_{1-3}$ alkyl, —C$_{1-3}$ alkyl-hydroxyl, —C$_{1-3}$ alkyl-cyano, —C$_{1-3}$ alkyl-C$_{1-6}$ alkoxy, —C$_{1-3}$ alkyl-halogenated C$_{1-6}$ alkyl, or —C$_{1-3}$ alkyl-halogenated C$_{1-6}$ alkoxy;
when the dashed line in

is a single bond, P' is O, NH, or NR$^{m'}$; R$^{m'}$ is —C$_{1-6}$ deuteroalkyl, —C$_{1-6}$ alkyl, -halogenated C$_{1-6}$ alkyl, —C$_{1-6}$ alkyl-hydroxyl, —C$_{1-6}$ alkyl-cyano, —C$_{1-6}$ alkyl-C$_{1-6}$ alkoxy, —C$_{1-6}$ alkyl-halogenated C$_{1-6}$ alkoxy, —C$_{1-6}$ alkyl-C$_{3-6}$ cycloalkyl, or —C$_{1-6}$ alkyl-3- to 6-membered heterocycloalkyl; R$_{42'}$ is —C$_{1-3}$ alkyl-(C=O)—, —(C=O)—, —C$_{1-3}$ alkyl-, —C$_{1-3}$ alkyl (hydroxy)-, —C$_{1-3}$ alkyl (cyano)-, —C$_{1-3}$ alkyl (C$_{1-6}$ alkyl)-, —C$_{1-3}$ alkyl (halogenated C$_{1-6}$ alkyl)-, —C$_{1-3}$ alkyl (C$_{1-6}$ alkyl-hydroxy)-, —C$_{1-3}$ alkyl (C$_{1-6}$ alkyl-cyano)-, —C$_{1-3}$ alkyl (C$_{1-6}$ alkoxy)-, or —C$_{1-3}$ alkyl (halogenated C$_{1-6}$ alkoxy)-;
or when the dashed line in

is absent, P' is hydrogen or halogen; R$_{42'}$ is hydrogen, halogen, —C$_{1-3}$ alkyl, -halogenated C$_{1-3}$ alkyl, —C$_{1-3}$ alkyl-hydroxyl, —C$_{1-3}$ alkyl-cyano, —C$_{1-3}$ alkyl-C$_{1-6}$ alkoxy, —C$_{1-3}$ alkyl-halogenated C$_{1-6}$ alkyl, or —C$_{1-3}$ alkyl-halogenated C$_{1-6}$ alkoxy;
when Y$_1$ is C, X$_1$ is hydrogen, halogen, cyano, hydroxyl, amino, nitro, -substituted or unsubstituted C$_{1-6}$ alkyl, -substituted or unsubstituted C$_{3-6}$ cycloalkyl, -substituted or unsubstituted 3- to 6-membered heterocycloalkyl, —O— substituted or unsubstituted C$_{1-6}$ alkyl, —O-substituted or unsubstituted C$_{3-6}$ cycloalkyl, —O-substituted or unsubstituted 3- to 6-membered heterocycloalkyl, —NH-substituted or unsubstituted C$_{1-6}$ alkyl, —N(substituted or unsubstituted C$_{1-6}$ alkyl)$_2$, —NH-substituted or unsubstituted C$_{3-6}$ cycloalkyl, —NH-substituted or unsubstituted 3- to 6-membered heterocycloalkyl, —NH(C=O)-substituted or unsubstituted $C_{1-6}$ alkyl, —NH(C=O)—$C_{3-6}$ cycloalkyl, —NH($SO_2$)-substituted or unsubstituted $C_{1-6}$ alkyl, —NH($SO_2$)-substituted or unsubstituted $C_{3-6}$ cycloalkyl, —$SO_2$-substituted or unsubstituted $C_{1-6}$ alkyl, —$SO_2$-substituted or unsubstituted $C_{3-6}$ cycloalkyl, —(C=O)—$NR^jR^k$, —(C=O)—O-substituted or unsubstituted $C_{1-6}$ alkyl, or —(C=O)—O-substituted or unsubstituted $C_{3-6}$ cycloalkyl, where $R^j$ and $R^k$ are each independently hydrogen or $C_{1-3}$ alkyl; or $R^j$ and $R^k$ form together with a nitrogen atom adjacent thereto substituted or unsubstituted 3- to 6-membered N-containing heterocycloalkyl; the 3- to 6-membered heterocycloalkyl has 1, 2, or 3 heteroatoms selected from N, O, and S as ring atoms; the 3- to 6-membered N-containing heterocycloalkyl has 3 to 6 ring atoms, and one of the ring atoms is nitrogen atom, while 0, 1, or 2 ring atoms among the rest of the ring atoms are optionally heteroatoms selected from N, O, and S; the "substituted" means 1, 2, 3, or 4 hydrogen atoms in a group being each independently substituted by a group-S substituent;

or when $Y_1$ is N, $X_1$ is absent;

the group-S substituent is selected from hydroxyl, halogen, nitro, oxo, —$C_{1-6}$ alkyl, -halogenated $C_{1-6}$ alkyl, hydroxyl-substituted $C_{1-6}$ alkyl, benzyl, —$(CH_2)_u$-cyano, —$(CH_2)_u$—$C_{1-6}$ alkoxy, —$(CH_2)_u$-halogenated $C_{1-6}$ alkoxy, —$(CH_2)_u$-halogenated $C_{1-6}$ alkyl, —$(CH_2)_u$-3- to 6-membered heterocycloalkyl, —$(CH_2)_u$-5- or 6-membered monocyclic heteroaryl, —$(CH_2)_u$—$C_{3-8}$ cycloalkyl, —$(CH_2)_u$—O—$(CH_2)_v$—$C_{3-8}$ cycloalkyl, —$(CH_2)_u$—O—$(CH_2)_v$—$C_{1-6}$ alkoxy, —$(CH_2)_u$—O—$(CH_2)_v$OH, —$(CH_2)_u$—$SO_2C_{1-6}$ alkyl, —$(CH_2)_u$—$NR_{a0}R_{b0}$, —$(CH_2)_u$—$C(O)NR_{a0}R_{b0}$, —$(CH_2)_u$—$C(O)C_{1-6}$ alkyl, —$C(O)OC_{1-6}$ alkyl, $NR_{a0}C(O)$—$(CH_2)_u$—$NR_{a0}R_{b0}$, $NR_{a0}C(O)$—$(CH_2)_u$OH, and $NR_{a0}C(O)$-halogenated $C_{1-6}$ alkyl, where the 3- to 6-membered heterocycloalkyl or the 5- or 6-membered monocyclic heteroaryl each independently has 1, 2 or 3 heteroatoms selected from N, O, and S as ring atoms; the 3- to 6-membered heterocycloalkyl and the 5- or 6-membered monocyclic heteroaryl are each optionally substituted by 1, 2, or 3 substituents selected from halogen, cyano, —$C_{1-3}$ alkyl, —$C_{1-3}$ alkoxy, and $C_{3-6}$ cycloalkyl; u and v are each independently 0, 1, 2, 3, or 4; $R_{a0}$ and $R_{b0}$ are each independently hydrogen or $C_{1-3}$ alkyl;

$E_{1'}$ is N or $CR_{5'}$, where $R_{5'}$ is hydrogen, halogen, cyano, —$C_{1-6}$ alkyl, —$C_{1-6}$ alkoxy, -halogenated $C_{1-6}$ alkyl, -halogenated $C_{1-6}$ alkoxy, —$C_{3-6}$ cycloalkyl, —O—$C_{3-6}$ cycloalkyl, —$NR^hR^i$, —$C_{1-4}$ alkyl-hydroxyl, —$C_{1-4}$ alkyl-cyano, —$C_{1-4}$ alkyl-$C_{1-6}$ alkoxy, —$C_{1-4}$ alkyl-halogenated $C_{1-6}$ alkyl, or —$C_{1-4}$ alkyl-halogenated $C_{1-6}$ alkoxy;

$E_{2'}$ is N or $CR_{6'}$, where $R_{6'}$ is hydrogen, halogen, cyano, —$C_{1-6}$ alkyl, —$C_{1-6}$ alkoxy, -halogenated $C_{1-6}$ alkyl, -halogenated $C_{1-6}$ alkoxy, —$C_{3-6}$ cycloalkyl, —O—$C_{3-6}$ cycloalkyl, —$NR^hR^i$, —$C_{1-4}$ alkyl-hydroxyl, —$C_{1-4}$ alkyl-cyano, —$C_{1-4}$ alkyl-$C_{1-6}$ alkoxy, —$C_{1-4}$ alkyl-halogenated $C_{1-6}$ alkyl, or —$C_{1-4}$ alkyl-halogenated $C_{1-6}$ alkoxy, provided that $Y_1$, $E_{1'}$ and $E_{2'}$ are not simultaneously N;

Ar' is $C_{6-10}$ aryl, 5- or 6-membered monocyclic heteroaryl, 8- to 10-membered bicyclic heteroaryl, or pyridonyl, where the 5- or 6-membered monocyclic heteroaryl has 1, 2, or 3 heteroatoms selected from N, O, and S as ring atoms; the 8- to 10-membered bicyclic heteroaryl has 1, 2, 3, 4, or 5 heteroatoms selected from N, O, and S as ring atoms; and the $C_{6-10}$ aryl, the 5- or 6-membered monocyclic heteroaryl, the 8- to 10-membered bicyclic heteroaryl, and the pyridonyl are unsubstituted or each substituted by 1, 2, 3, or 4 groups each independently selected from $R_{s1}$;

or Ar' has a structure of Formula (B):

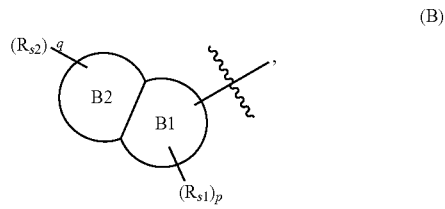

(B)

where the ring B1 is a benzene ring or a 5- or 6-membered monocyclic heteroaryl ring; the ring B2 is a fused 5- or 6-membered monocyclic heterocycloalkyl ring or a fused 5- or 6-membered monocyclic cycloalkyl ring, where the 5- or 6-membered monocyclic heteroaryl ring or the fused 5- or 6-membered monocyclic heterocycloalkyl ring has 1, 2, or 3 heteroatoms selected from N, O, and S as ring atoms;

$(R_{s1})_p$ represents that hydrogens on the ring B1 is substituted by p $R_{s1}$ groups, p being 0, 1, 2, or 3 and each $R_{s1}$ being either identical or different;

$(R_{s2})_q$ represents that hydrogens on the ring B2 is substituted by q $R_{s2}$ groups, q being 0, 1, 2, or 3 and each $R_{s2}$ being either identical or different;

$R_{s1}$ and $R_{s2}$ are each independently halogen, cyano, nitro, hydroxyl, —$C_{1-6}$ alkyl, —$C_{1-6}$ alkoxy, -halogenated $C_{1-6}$ alkyl, -halogenated $C_{1-6}$ alkoxy, —$C_{3-6}$ cycloalkyl, —$NR^cR^d$, —$C(O)NR^eR^f$, —$SO_2C_{1-3}$ alkyl, —$SO_2$halogenated $C_{1-3}$ alkyl, —$SO_2NR^eR^f$, —$C_{1-4}$ alkyl-hydroxyl, —$C_{1-4}$ alkyl-cyano, —$C_{1-4}$ alkyl-$C_{1-6}$ alkoxy, —$C_{1-4}$ alkyl-halogenated $C_{1-6}$ alkyl, —$C_{1-4}$ alkyl-halogenated $C_{1-6}$ alkoxy, —$C_{1-4}$ alkyl-3- to 6-membered heterocycloalkyl, —$C_{1-4}$ alkyl-$NR^eR^f$, —$C_{1-4}$ alkyl-C(O)$NR^eR^f$, —$C_{1-4}$ alkyl-$SO_2C_{1-3}$ alkyl, or $C_{2-4}$ alkynyl, where the 3- to 6-membered heterocycloalkyl has 1, 2, or 3 heteroatoms selected from N, O, and S as ring atoms;

$R_{0'}$ is —$C_{1-6}$ alkyl, —$C_{3-6}$ cycloalkyl, 3- to 6-membered heterocycloalkyl, $C_{6-10}$ aryl, 5- or 6-membered monocyclic heteroaryl, 8- to 10-membered bicyclic heteroaryl, 7- to 11-membered spirocycloalkyl, —$C_{1-3}$ alkyl-$C_{6-10}$ aryl, —$C_{1-3}$ alkyl-5- or 6-membered monocyclic heteroaryl, —$NR^g$—$C_{6-10}$ aryl, —O—$C_{6-10}$ aryl, —$C_{1-3}$ alkyl-3- to 6-membered heterocycloalkyl, —$C_{1-3}$ alkyl-$C_{3-6}$ cycloalkyl, or pyridonyl, where the 3- to 6-membered heterocycloalkyl, the 5- or 6-membered monocyclic heteroaryl or the 8- to 10-membered bicyclic heteroaryl has 1, 2 or 3 heteroatoms selected from N, O, and S as ring atoms; the $C_{1-6}$ alkyl, the $C_{3-6}$ cycloalkyl, the 3- to 6-membered heterocycloalkyl, the $C_{6-10}$ aryl, the 5- or 6-membered monocyclic heteroaryl, the 8- to 10-membered bicyclic heteroaryl, the 7- to 11-membered spirocycloalkyl, and the pyridonyl are unsubstituted or each substituted by 1, 2, 3, or 4 groups each independently selected from $R_{s3}$; and the —$C_{1-3}$ alkyl- is unsubstituted or substituted by 1, 2, 3, or 4 groups each independently selected from $C_{1-3}$ alkyl;

or $R_{0'}$ has a structure of Formula (A-1) or Formula (A-2):

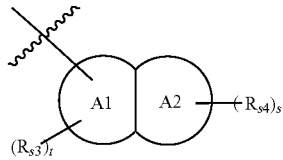

(A-1)

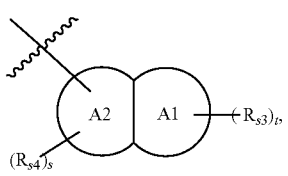

(A-2)

where the ring A1 is a benzene ring or a 5- or 6-membered monocyclic heteroaryl ring; the ring A2 is a fused 5- or 6-membered monocyclic heterocycloalkyl ring or a fused 5- or 6-membered monocyclic cycloalkyl ring, where the 5- or 6-membered monocyclic heteroaryl ring or the fused 5- or 6-membered monocyclic heterocycloalkyl ring has 1, 2 or 3 heteroatoms selected from N, O, and S as ring atoms;

$(R_{s3})_t$ represents that hydrogen on the ring A1 is substituted by t $R_{s3}$ groups, t being 0, 1, 2 or 3 and each $R_{s3}$ being either identical or different;

$(R_{s4})_s$ represents that hydrogen on the ring A2 is substituted by s $R_{s4}$ groups, s being 0, 1, 2 or 3 and each $R_{s4}$ being either identical or different;

$R_{s3}$ and $R_{s4}$ are each independently halogen, cyano, hydroxyl, —$C_{1-6}$ alkyl, —$C_{1-6}$ alkoxy, -halogenated $C_{1-6}$ alkyl, -halogenated $C_{1-6}$ alkoxy, —$C_{3-6}$ cycloalkyl, 3- to 6-membered heterocycloalkyl, —$NR^hR^i$, —$C(O)NR^eR^f$, —$SO_2C_{1-3}$ alkyl, —$SO_2$halogenated $C_{1-3}$ alkyl, —$SO_2NR^eR^f$, —$C_{1-3}$ alkyl-hydroxyl, —$C_{1-3}$ alkyl-$C_{2-4}$ alkynyl, —$C_{1-3}$ alkyl-cyano, —$C_{1-3}$ alkyl-$C_{1-6}$ alkoxy, —$C_{1-3}$ alkyl-halogenated $C_{1-6}$ alkyl, —$C_{1-3}$ alkyl-halogenated $C_{1-6}$ alkoxy, —$C_{1-3}$ alkyl-3-to 6-membered heterocycloalkyl, —$C_{1-3}$ alkyl-$C_{3-6}$ cycloalkyl, —$C_{1-3}$ alkyl-$NR^eR^f$, —$C_{1-3}$ alkyl-$C(O)NR^eR^f$, —$C_{1-3}$ alkyl-$SO_2C_{1-3}$ alkyl, or $C_{2-4}$ alkynyl, where the 3- to 6-membered heterocycloalkyl has 1, 2 or 3 heteroatoms selected from N, O, and S as ring atoms; and the $C_{1-6}$ alkyl, the —$C_{1-6}$ alkoxy, the —$C_{1-3}$ alkyl-, the —$C_{3-6}$ cycloalkyl and the 3- to 6-membered heterocycloalkyl are each optionally substituted by 1, 2, or 3 substituents each independently selected from halogen, methyl, ethyl, propyl (n-propyl), isopropyl, trifluoromethyl, amino, $N(CH_3)_2$, hydroxyl and carboxyl;

$R^a$, $R^b$, $R^e$, $R^f$, and $R^g$ are each independently hydrogen or $C_{1-3}$ alkyl; and $R^c$, $R^d$, $R^h$, and $R^i$ are each independently hydrogen, —$C_{1-3}$ alkyl, —$C(O)C_{1-3}$ alkyl, or —$CO_2C_{1-3}$ alkyl.

In an embodiment of the present invention, the compound of Formula (IA) is a compound of Formula (IB) or a compound of Formula (IC):

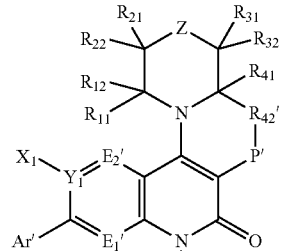

IB

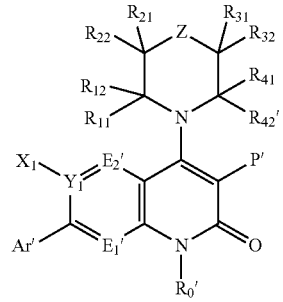

IC

In Formula IB, P' is O, NH, or $NR^{m'}$; $R^{m'}$ is —$C_{1-6}$ deuteroalkyl, —$C_{1-6}$ alkyl, -halogenated $C_{1-6}$ alkyl, —$C_{1-6}$ alkyl-hydroxyl, —$C_{1-6}$ alkyl-cyano, —$C_{1-6}$ alkyl-$C_{1-6}$ alkoxy, —$C_{1-6}$alkyl-halogenated $C_{1-6}$ alkoxy, —$C_{1-6}$ alkyl-$C_{3-6}$ cycloalkyl, or —$C_{1-6}$ alkyl-3- to 6-membered heterocycloalkyl; $R_{42'}$ is —$C_{1-3}$ alkyl-(C=O)—, —(C=O)—, —$C_{1-3}$ alkyl-, —$C_{1-3}$ alkyl (hydroxy)-, —$C_{1-3}$ alkyl (cyano)-, —$C_{1-3}$ alkyl ($C_{1-6}$ alkyl)-, —$C_{1-3}$ alkyl (halogenated $C_{1-6}$ alkyl)-, —$C_{1-3}$ alkyl ($C_{1-6}$ alkyl-hydroxy)-, —$C_{1-3}$ alkyl ($C_{1-6}$ alkyl-cyano)-, —$C_{1-3}$ alkyl ($C_{1-6}$ alkoxy)-, or —$C_{1-3}$ alkyl(halogenated $C_{1-6}$ alkoxy)-; and $R_{11}$, $R_{12}$, $R_{21}$, $R_{22}$, $R_{31}$, $R_{32}$, $R_{41}$, Z, $R_{0'}$, Ar', $E_{1'}$, $E_{2'}$, $X_1$, and $Y_1$ are defined as above.

In Formula IC, P' is hydrogen or halogen; $R_{42'}$ is hydrogen, halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$ alkoxy, —$C_{1-3}$ alkyl-halogenated $C_{1-6}$ alkyl, or —$C_{1-3}$ alkyl-halogenated $C_{1-6}$ alkoxy; $R_{11}$, $R_{12}$, $R_{21}$, $R_{22}$, $R_{31}$, $R_{32}$, $R_{41}$, Z, $R_{0'}$, Ar', $E_{1'}$, $E_{2'}$, $X_1$, and $Y_1$ are defined as above.

In an embodiment of the present invention, in Formula IB, P' is O, NH, or $NR^{m'}$; $R^{m'}$ is —$C_{1-6}$ deuteroalkyl or —$C_{1-6}$ alkyl; and $R_{42'}$ is —$C_{1-3}$ alkyl-(C=O)—, —(C=O)—, or —$C_{1-3}$ alkyl-.

In an embodiment of the present invention, in Formula IB, P' is O, NH, or $NR^{m'}$; $R^{m'}$ is —$C_{1-3}$ deuteroalkyl or —$C_{1-3}$ alkyl; $R_{42'}$ is —$C_{1-3}$ alkyl-(C=O)—, —(C=O)—, or —$C_{1-3}$ alkyl-.

In an embodiment of the present invention, in Formula IB, P' is O, NH, or $NR^{m'}$; $R^{m'}$ is deuteromethyl, deuteroethyl, deutero-n-propyl, deuteroisopropyl, methyl, ethyl, n-propyl, or isopropyl; and $R_{42'}$ is —$CH_2$—(C=O)—, —$CH_2CH_2$—(C=O)—, —(C=O)—, —$CH_2$—, —$CH_2CH_2$—, or —$CH_2CH_2CH_2$—.

In an embodiment of the present invention, in Formula IB, P' is NH or $NR^{m'}$; $R^{m'}$ is —$C_{1-6}$ deuteroalkyl or —$C_{1-6}$ alkyl; and $R_{42'}$ is —$C_{1-3}$ alkyl-(C=O)— or —(C=O)—.

In an embodiment of the present invention, in Formula IB, P' is NH or $NR^{m'}$; $R^{m'}$ is —$C_{1-3}$ deuteroalkyl or —$C_{1-3}$ alkyl; and $R_{42'}$ is —$C_{1-3}$ alkyl-(C=O)— or —(C=O)—.

In an embodiment of the present invention, in Formula IB, P' is NH or $NR^{m'}$; $R^{m'}$ is deuteromethyl or methyl; and $R_{42'}$ is —$CH_2$—(C=O)—, —$CH_2CH_2$—(C=O)—, or —(C=O)—.

In an embodiment of the present invention, in Formula IB, P' is O; and $R_{42'}$ is —$C_{1-3}$ alkyl-.

In an embodiment of the present invention, in Formula IB, P' is O; and $R_{42'}$ is —$CH_2$—.

In an embodiment of the present invention, the compound of Formula (IB) is a compound of Formula (IB-1) or a compound of Formula (IB-2):

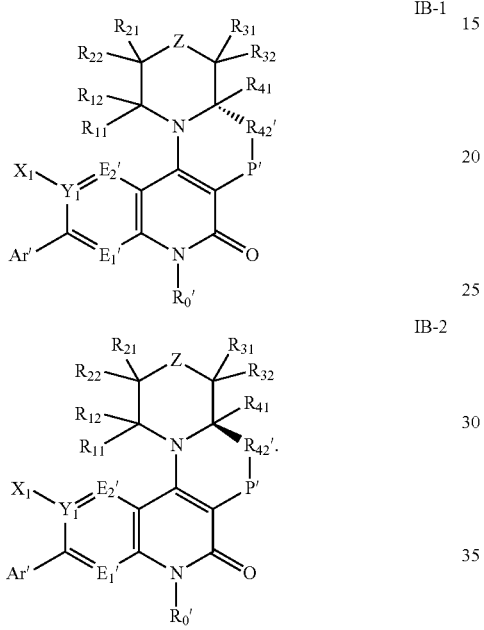

IB-1

IB-2

In Formula (IB-1) and Formula (IB-2), $R_{21}$, $R_{22}$, $R_{11}$, $R_{12}$, $R_{31}$, $R_{32}$, $R_{41}$, $R_{42'}$, Z, P', $R_{0'}$, Ar', $E_{1'}$, $E_{2'}$, $X_1$, and $Y_1$ are as defined above.

In an embodiment of the present invention, in Formula IB-1, P' is O, NH, or $NR^{m'}$; $R^{m'}$ is —$C_{1-6}$ deuteroalkyl or —$C_{1-6}$ alkyl; and $R_{42'}$ is —$C_{1-3}$ alkyl-(C=O)—, —(C=O)—, or —$C_{1-3}$ alkyl-.

In an embodiment of the present invention, in Formula IB-1, P' is NH or $NR^{m'}$; $R^{m'}$ is —$C_{1-6}$ deuteroalkyl or —$C_{1-6}$ alkyl; and $R_{42'}$ is —$C_{1-3}$ alkyl-(C=O)— or —(C=O)—.

In an embodiment of the present invention, in Formula IB-1, P' is NH or $NR^{m'}$; $R^{m'}$ is —$C_{1-3}$ deuteroalkyl or —$C_{1-3}$ alkyl; and $R_{42'}$ is —$C_{1-3}$ alkyl-(C=O)— or —(C=O)—.

In an embodiment of the present invention, in Formula IB-1, P' is NH or $NR^{m'}$; $R^{m'}$ is deuteromethyl or methyl; and $R_{42'}$ is —$CH_2$—(C=O)—, —$CH_2CH_2$—(C=O)—, or —(C=O)—.

In an embodiment of the present invention, in Formula IB-1, P' is O; and $R_{42'}$ is —$C_{1-3}$ alkyl-.

In an embodiment of the present invention, in Formula IB-1, P' is O; and $R_{42'}$ is —$CH_2$—.

In another aspect, the present invention provides a compound of Formula (IB-1a) or Formula (IB-2a), or a tautomer, a cis-trans isomer, a mesomer, a raceme, an enantiomer, a diastereoisomer, an atropisomer or a mixture thereof, or a pharmaceutically acceptable salt, a solvate or a prodrug thereof:

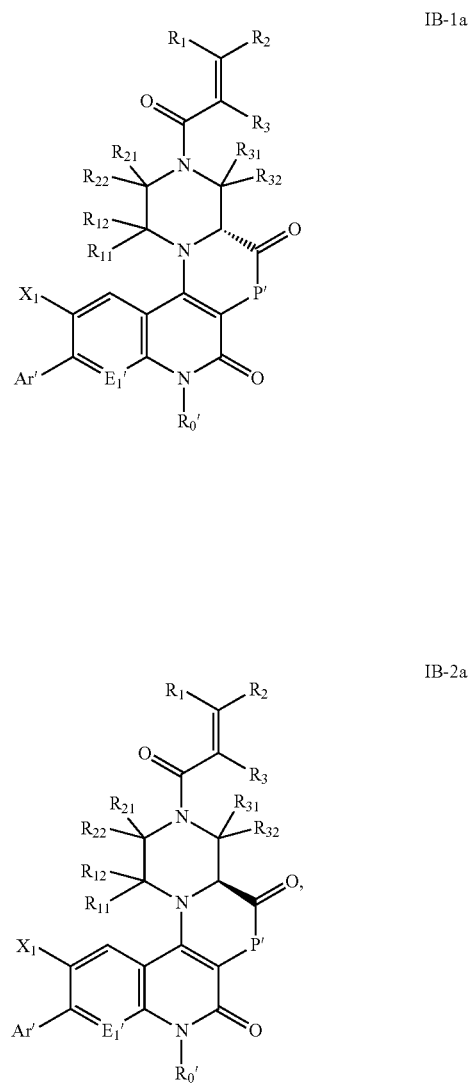

IB-1a

IB-2a where $R_1$, $R_2$, $R_3$, $R_{21}$, $R_{22}$, $R_{12}$, $R_{11}$, $R_{31}$, $R_{32}$, P', $R_{0'}$, Ar', $E_{1'}$, and $X_1$ are as defined above.

In an embodiment of the present invention, in Formula IB-1a, P' is NH or $NR^{m'}$; and $R^{m'}$ is —$C_{1-6}$ deuteroalkyl or —$C_{1-6}$ alkyl.

In an embodiment of the present invention, in Formula IB-1a, P' is NH or $NR^{m'}$; and $R^{m'}$ is —$C_{1-3}$ deuteroalkyl or —$C_{1-3}$ alkyl.

In an embodiment of the present invention, in Formula IB-1a, P' is NH or $NR^{m'}$; and $R^{m'}$ is deuteromethyl or methyl.

In an embodiment of the present invention, the compound of Formula (IB-1a) is a compound of Formula (IB-1aa), a compound of Formula (IB-1ab), a compound of Formula (IB-1ac), or a compound of Formula (IB-1ad):

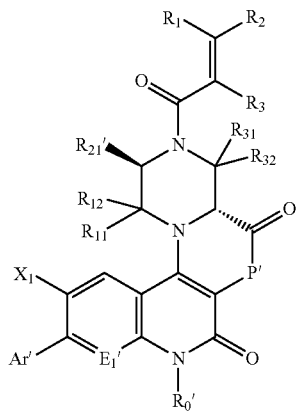

IB-1aa

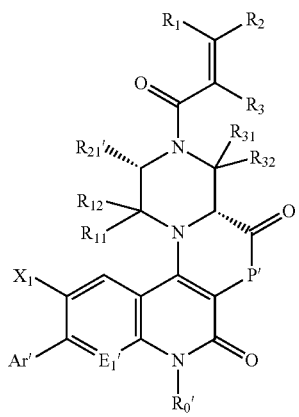

IB-1ab

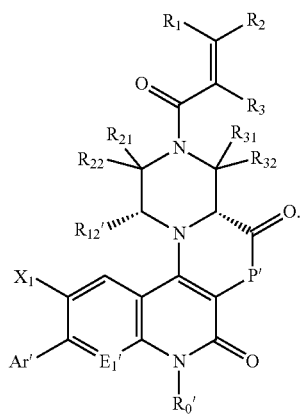

IB-1ad

In Formula (IB-1aa) and Formula (IB-1ab), $R_{21'}$ is independently halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$ alkoxy, —$C_3$ alkyl-halogenated $C_{1-6}$ alkyl, or —$C_{1-3}$ alkyl-halogenated $C_{1-6}$ alkoxy; and $R_1$, $R_2$, $R_3$, $R_{12}$, $R_{11}$, $R_{31}$, $R_{32}$, P', $R_{0'}$, Ar', $E_{1'}$, and $X_1$ are as defined above.

In Formula (IB3-1ac) and Formula (IB3-1ad), $R_{12'}$ is independently halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$ alkoxy, —$C_{1-3}$ alkyl-halogenated $C_{1-6}$ alkyl, or —$C_{1-3}$ alkyl-halogenated $C_{1-6}$ alkoxy; and $R_1$, $R_2$, $R_3$, $R_{21}$, $R_{22}$, $R_{31}$, $R_{32}$, P', $R_{0'}$, Ar', $E_{1'}$, and $X_1$ are as defined above.

In another aspect, the present invention provides a compound of Formula (IB-1c) or Formula (IB-2c), or a tautomer, a cis-trans isomer, a mesomer, a raceme, an enantiomer, a diastereoisomer, an atropisomer or a mixture thereof, or a pharmaceutically acceptable salt, a solvate or a prodrug thereof:

IB-1ac

IB-1c

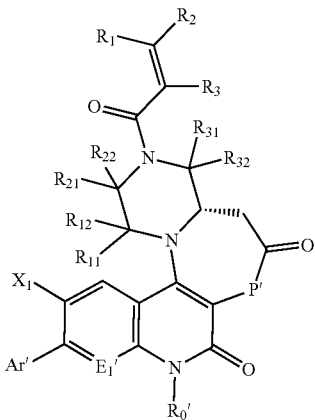

-continued

IB-2c

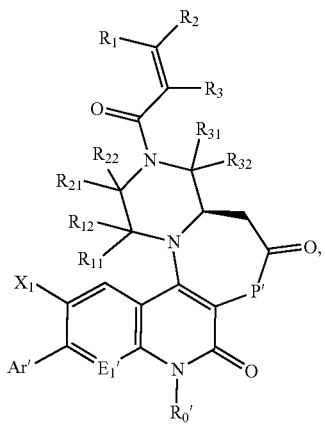

where $R_1$, $R_2$, $R_3$, $R_{21}$, $R_{22}$, $R_{12}$, $R_{11}$, $R_{31}$, $R_{32}$, P', $R_{0'}$, Ar', $E_{1'}$, and $X_1$ are as defined above.

In an embodiment of the present invention, in Formula IB-1c, P' is NH or $NR^{m'}$; and $R^{m'}$ is —$C_{1-6}$ deuteroalkyl or —$C_{1-6}$ alkyl.

In an embodiment of the present invention, in Formula IB-1c, P' is NH or $NR^{m'}$; and $R^{m'}$ is —$C_{1-3}$ deuteroalkyl or —$C_{1-3}$ alkyl.

In an embodiment of the present invention, in Formula IB-1c, P' is NH or $NR^{m'}$; and $R^{m'}$ is deuteromethyl or methyl.

In an embodiment of the present invention, the compound of Formula (IB-1c) is a compound of Formula (IB-1ca), a compound of Formula (IB-1cb), a compound of Formula (IB-1cc), or a compound of Formula (IB-1cd):

IB-1ca

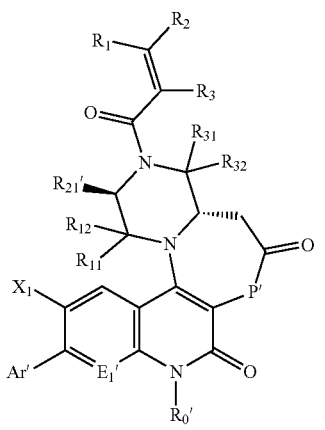

IB-1cb

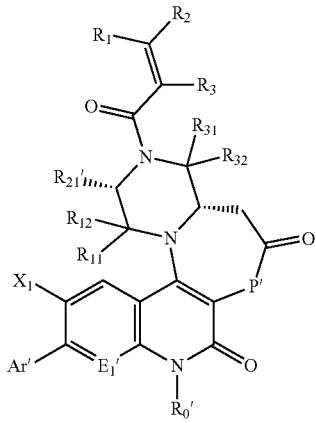

IB-1cc

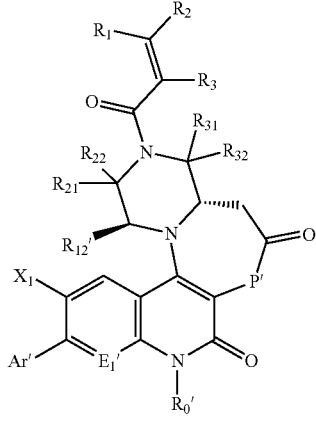

IB-1cd

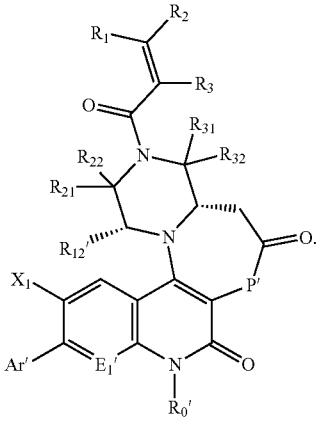

In Formula (IB-1ca) and Formula (IB-1cb), $R_{21'}$ is independently halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$alkoxy, —$C_{1-3}$ alkyl-halogenated $C_{1-6}$ alkyl, or —$C_{1-3}$ alkyl-halogenated $C_{1-6}$ alkoxy; and $R_1$, $R_2$, $R_3$, $R_{12}$, $R_{11}$, $R_{31}$, $R_{32}$, P', $R_{0'}$, Ar', $E_{1'}$, and $X_1$ are as defined above.

In Formula (IB-1cc) and Formula (IB-1cd), $R_{12'}$ is independently halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$ alkoxy, —$C_{1-3}$ alkyl-halogenated $C_{1-6}$ alkyl, or —$C_{1-3}$ alkyl-halogenated $C_{1-6}$ alkoxy; and $R_1$, $R_2$, $R_3$, $R_{21}$, $R_{22}$, $R_{31}$, $R_{32}$, P', $R_{0'}$, Ar', $E_{1'}$, and $X_1$ are as defined above.

In an embodiment of the present invention, in Formula IB-1a, Formula IB-1c, Formula IB-2a, and Formula IB-2c, P' is independently NH or NR$^{m'}$; and R$^{m'}$ is —C$_{1-6}$ deuteroalkyl or —C$_{1-6}$ alkyl.

In an embodiment of the present invention, in Formula IB-1a, Formula IB-1c, Formula IB-2a, and Formula IB-2c, P' is independently NH or NR$^{m'}$; and R$^{m'}$ is —C$_{1-3}$ deuteroalkyl or —C$_{1-3}$ alkyl.

In an embodiment of the present invention, in Formula IB-1a, Formula IB-1c, Formula IB-2a, and Formula IB-2c, P' is independently NH or NR$^{m'}$; and R$^{m'}$ is deuteromethyl, deuteroethyl, deutero-n-propyl, deuteroisopropyl, methyl, ethyl, n-propyl, or isopropyl.

In another aspect, the present invention provides a compound of Formula (IB-1b) or Formula (IB-2b), or a tautomer, a cis-trans isomer, a mesomer, a raceme, an enantiomer, a diastereoisomer, an atropisomer or a mixture thereof, or a pharmaceutically acceptable salt, a solvate or a prodrug thereof:

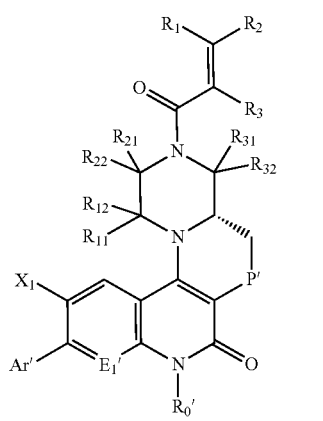

IB-1b

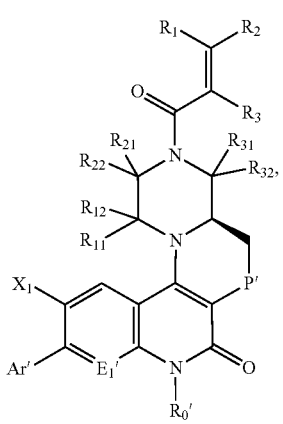

IB-2b where R$_1$, R$_2$, R$_3$, R$_{21}$, R$_{22}$, R$_{12}$, R$_{11}$, R$_{31}$, R$_{32}$, P', R$_{0'}$, Ar', E$_{1'}$, and X$_1$ are as defined above.

In an embodiment of the present invention, the compound of Formula (IB-1b) is a compound of Formula (IB-1ba), a compound of Formula (IB-1bb), a compound of Formula (IB-1bc), or a compound of Formula (IB-1bd):

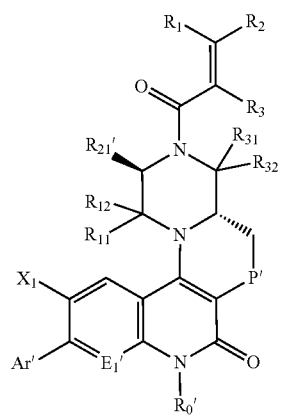

IB-1ba

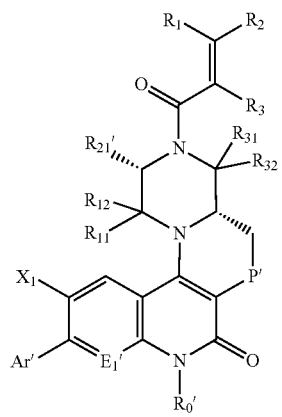

IB-1bb

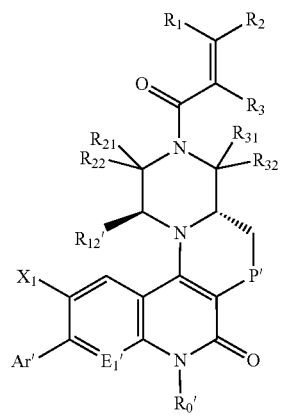

IB-1bc

-continued

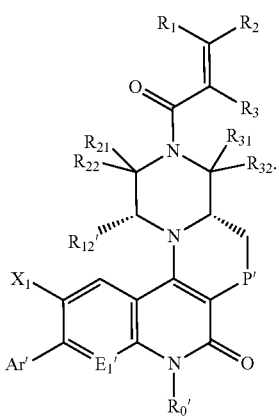

IB-1bd

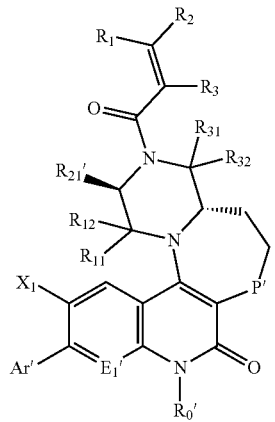

IB-2d where $R_1$, $R_2$, $R_3$, $R_{21}$, $R_{22}$, $R_{12}$, $R_{11}$, $R_{31}$, $R_{32}$, P', $R_{0'}$, Ar', $E_{1'}$, and $X_1$ are as defined above.

In an embodiment of the present invention, the compound of Formula (IB-1d) is a compound of Formula (IB-1da), a compound of Formula (IB-1db), a compound of Formula (IB-1 dc) or a compound of Formula (IB-1 dd):

In Formula (IB-1ba) and Formula (IB-1bb), $R_{21'}$ is independently halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$ alkoxy, —$C_{1-3}$ alkyl-halogenated $C_{1-6}$ alkyl or —$C_{1-3}$ alkyl-halogenated $C_{1-6}$ alkoxy; and $R_1$, $R_2$, $R_3$, $R_{12}$, $R_{11}$, $R_{31}$, $R_{32}$, P', $R_{0'}$, Ar', $E_{1'}$, and $X_1$ are as defined above.

In Formula (IB-1bc) and Formula (IB-1bd), $R_{12'}$ is independently halogen, —$C_{1-3}$ alkyl, -halogenated $C_{1-3}$ alkyl, —$C_{1-3}$alkyl-hydroxyl, —$C_{1-3}$ alkyl-cyano, —$C_{1-3}$ alkyl-$C_{1-6}$alkoxy, —$C_{1-3}$ alkyl-halogenated $C_{1-6}$ alkyl, or —$C_{1-3}$ alkyl-halogenated $C_{1-6}$ alkoxy; and $R_1$, $R_2$, $R_3$, $R_{21}$, $R_{22}$, $R_{31}$, $R_{32}$, P', $R_{0'}$, Ar', $E_{1'}$, and $X_1$ are as defined above.

In another aspect, the present invention provides a compound of Formula (IB-1d) or Formula (IB-2d), or a tautomer, a cis-trans isomer, a mesomer, a raceme, an enantiomer, a diastereoisomer, an atropisomer or a mixture thereof, or a pharmaceutically acceptable salt, a solvate or a prodrug thereof:

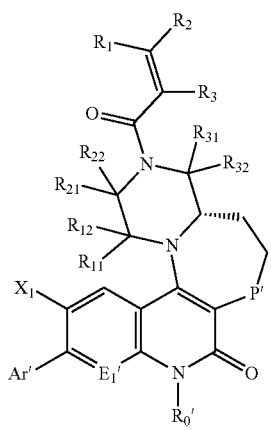

IB-1d

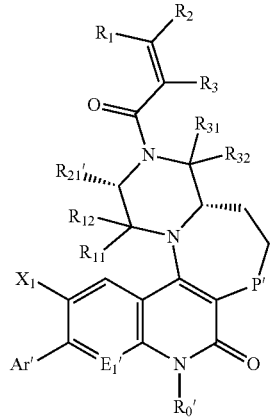

IB-1da

IB-1db

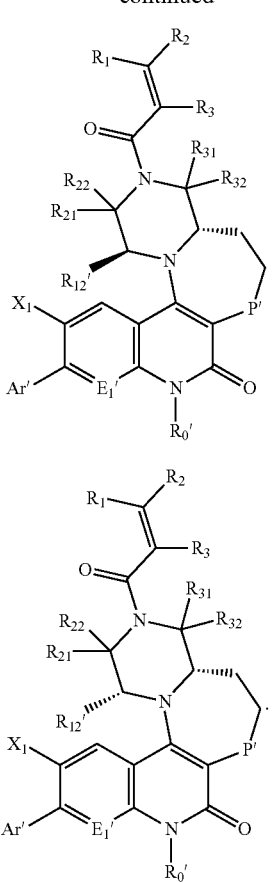

In Formula (IB-1da) and Formula (IB-1db), $R_{21'}$ is independently halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$ alkoxy, —$C_{1-3}$ alkyl-halogenated $C_{1-6}$ alkyl, or —$C_{1-3}$ alkyl-halogenated $C_{1-6}$ alkoxy; and $R_1$, $R_2$, $R_3$, $R_{12}$, $R_{11}$, $R_{31}$, $R_{32}$, P', $R_{0'}$, Ar', $E_{1'}$, and $X_1$ are as defined above.

In Formula (IB-1dc) and Formula (IB-1dd), $R_{12'}$ is independently halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$ alkoxy, —$C_{1-3}$ alkyl-halogenated $C_{1-6}$ alkyl, or —$C_{1-3}$ alkyl-halogenated $C_{1-6}$ alkoxy; and $R_1$, $R_2$, $R_3$, $R_{21}$, $R_{22}$, $R_{31}$, $R_{32}$, P', $R_{0'}$, Ar', $E_{1'}$, and $X_1$ are as defined above.

In an embodiment of the present invention, in Formula IB-1b, Formula IB-1d, Formula IB-2b, and Formula IB-2d, P' is independently O.

In an embodiment of the present invention, $R_{21'}$ and $R_{12'}$ are each independently —$C_{1-3}$ alkyl, —$C_{1-3}$ alkyl-hydroxyl, —$C_{1-3}$ alkyl-cyano, or —$C_{1-3}$ alkyl-$C_{1-6}$ alkoxy.

In an embodiment of the present invention, $R_{21'}$ and $R_{12'}$ are each independently —$C_{1-3}$ alkyl, —$CH_2$-hydroxyl, —$CH_2$-cyano, or —$CH_2$—$C_{1-3}$ alkoxy.

In an embodiment of the present invention, $R_{21'}$ and $R_{12'}$ are each independently methyl, ethyl, n-propyl, or isopropyl.

In an embodiment of the present invention, $X_1$ is hydrogen, halogen, -substituted or unsubstituted $C_{1-6}$ alkyl, -substituted or unsubstituted $C_{3-6}$ cycloalkyl, or —O-substituted or unsubstituted $C_{1-6}$ alkyl; and the "substituted" means 1, 2, 3 or 4 hydrogen atoms in a group being substituted by substituents each independently selected from the group S.

In an embodiment of the present invention, $X_1$ is hydrogen, halogen, unsubstituted $C_{1-3}$ alkyl, unsubstituted $C_{3-6}$ cycloalkyl, or —O-unsubstituted $C_{1-3}$ alkyl.

In an embodiment of the present invention, X, is hydrogen, fluorine, chlorine, methyl, ethyl, n-propyl, isopropyl, cyclopropyl, cyclobutyl, cyclopentyl, cyclohexyl, methoxy, ethoxy, n-propoxy, or isopropoxy.

In an embodiment of the present invention, $X_1$ is fluorine, chlorine, or cyclopropyl.

In an embodiment of the present invention, $Y_1$ is C; $E_{1'}$ is N or $CR_{5'}$; $E_{2'}$ is $CR_{6'}$; and $R_{5'}$ and $R_{6'}$ are each as defined above.

In an embodiment of the present invention, $Y_1$ is C; $E_{1'}$ is $CR_{5'}$; $E_{2'}$ is N; and $R_{5'}$ is as defined above.

In an embodiment of the present invention, $Y_1$ is C; $E_{1'}$ is N or $CR_{5'}$; $E_{2'}$ is CH; and $R_{5'}$ is as defined above.

In an embodiment of the present invention, $Y_1$ is C; $E_{1'}$ is N or $CR_{5'}$; and $E_{2'}$ is CH.

In an embodiment of the present invention, Ar' is phenyl, 5- or 6-membered monocyclic heteroaryl, or pyridonyl; and the phenyl, the 5- or 6-membered monocyclic heteroaryl, and the pyridonyl are unsubstituted or each substituted by 1, 2, 3, or 4 groups each independently selected from halogen, cyano, hydroxyl, —$C_{1-6}$ alkyl, —$C_{1-6}$ alkoxy, —$NR^cR^d$, —$C_{1-4}$ alkyl-$NR^eR^f$, where $R^e$ and $R^f$ are each independently hydrogen or $C_{1-3}$ alkyl; and $R^c$ and $R^d$ are each independently hydrogen, —$C_{1-3}$alkyl, —C(O)$C_{1-3}$ alkyl, or —$CO_2C_{1-3}$ alkyl.

In an embodiment of the present invention, Ar' is phenyl or pyridonyl; and the phenyl and the pyridonyl are unsubstituted or each substituted by 1, 2, 3, or 4 groups each independently selected from fluorine, chlorine, bromine, cyano, hydroxyl, —$C_{1-3}$ alkyl, —$C_{1-3}$ alkoxy, —$NH_2$, —$NHCH_3$, —$N(CH_3)_2$, —$CH_2$—$NH_2$, —$CH_2$—$NHCH_3$, and —$CH_2$—$N(CH_3)_2$.

In an embodiment of the present invention, Ar' is phenyl; the phenyl is substituted by one group selected from $R_{s1}$; $R_{s1}$ is halogen, cyano, —$C_{1-6}$ alkyl, —$C_{1-6}$ alkoxy, -halogenated $C_{1-6}$ alkyl, -halogenated $C_{1-6}$ alkoxy, or —$C_{3-6}$ cycloalkyl.

In an embodiment of the present invention, Ar' has a structured selected from:

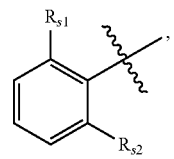

where $R_{s1}$ and $R_{s2}$ are as defined above.

In an embodiment of the present invention, Ar' has a structured selected from:

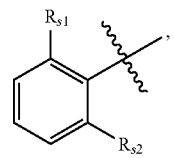

where $R_{s1}$ is hydroxyl; $R_{s2}$ is halogen, cyano, —$C_{1-6}$ alkyl, —$C_{1-6}$ alkoxy, -halogenated $C_{1-6}$ alkyl, -halogenated $C_{1-6}$ alkoxy, or —$C_{3-6}$ cycloalkyl.

In an embodiment of the present invention, the $R_{s1}$ is above the plane of the benzene ring.

In an embodiment of the present invention, Ar' has a structured selected from:

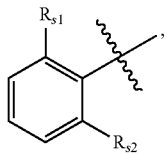

where $R_{s1}$ is —$C_{1-6}$ alkoxy; $R_{s2}$ is halogen, cyano, —$C_{1-6}$ alkyl, —$C_{1-6}$ alkoxy, -halogenated $C_{1-6}$ alkyl, -halogenated $C_{1-6}$ alkoxy, or —$C_{3-6}$ cycloalkyl. In an embodiment of the present invention, the $R_{s1}$ is above the plane of the benzene ring.

In an embodiment of the present invention, $R_{0'}$ is phenyl, 5- or 6-membered monocyclic heteroaryl, or pyridonyl, where the 5- or 6-membered monocyclic heteroaryl has 1, 2, or 3 heteroatoms selected from N, O, and S as ring atoms; and the phenyl, the 5- or 6-membered monocyclic heteroaryl, and the pyridonyl are unsubstituted or each substituted by 1, 2, 3, or 4 groups each independently selected from $R_{s3}$.

In an embodiment of the present invention, $R_{0'}$ is phenyl, thiazolyl, isothiazolyl, imidazolyl, oxazolyl, isoxazolyl, pyrazolyl, pyridyl, pyrimidyl, pyrazinyl or pyridonyl which is unsubstituted or each substituted by 1, 2, 3, or 4 groups each independently selected from $R_{s3}$.

In an embodiment of the present invention, $R_{0'}$ has a structure selected from:

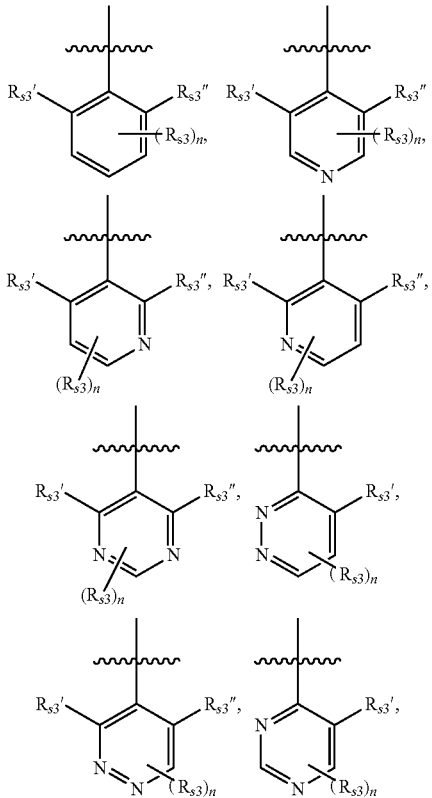

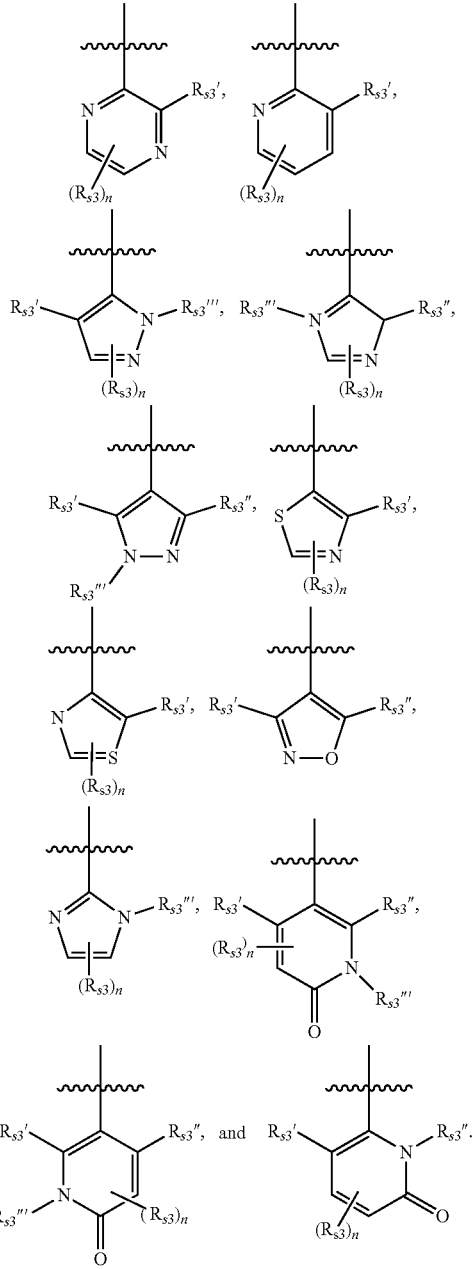

In each structure shown above, $R_{s3'}$ is either identical or different and is independently selected from hydrogen, halogen, cyano, hydroxyl, —$C_{1-6}$ alkyl, —$C_{1-6}$ alkoxy, -halogenated $C_{1-6}$ alkyl, -halogenated $C_{1-6}$ alkoxy, —$C_{3-6}$ cycloalkyl, —$NR^hR^i$, —$C(O)NR^eR^f$, —$C_{1-3}$ alkyl-hydroxyl, and —$C_{1-3}$ alkyl-$NR^eR^f$; and the —$C_{3-6}$cycloalkyl is optionally substituted by 1, 2, or 3 substituents each independently selected from halogen, methyl, ethyl, propyl (n-propyl), isopropyl, trifluoromethyl, amino, $N(CH_3)_2$, hydroxyl, and carboxyl, where $R^e$ and $R^f$ are each independently hydrogen or $C_{1-3}$ alkyl; and $R^h$ and $R^i$ are each independently hydrogen, —$C_{1-3}$ alkyl, —$C(O)C_{1-3}$ alkyl, or —$CO_2C_{1-3}$ alkyl.

In each structure shown above, $R_{s3''}$ is either identical or different and is independently selected from hydrogen, halogen, cyano, hydroxyl, —$C_{1-6}$ alkyl, —$C_{1-6}$ alkoxy, -halogenated $C_{1-6}$ alkyl, -halogenated $C_{1-6}$ alkoxy, —$C_{3-6}$ cycloalkyl, —NR$^h$R$^i$, —C(O)NR$^e$R$^f$, —C$_{1-3}$ alkyl-hydroxyl, and —C$_{1-3}$ alkyl-NR$^e$R$^f$; and the —C$_{3-6}$ cycloalkyl is optionally substituted by 1, 2, or 3 substituents each independently selected from halogen, methyl, ethyl, propyl (n-propyl), isopropyl, trifluoromethyl, amino, N(CH$_3$)$_2$, hydroxyl, and carboxyl, where R$^e$ and R$^f$ are each independently hydrogen or C$_{1-3}$ alkyl; R$^h$ and R$^i$ are each independently hydrogen, —C$_{1-3}$ alkyl, —C(O)C$_{1-3}$ alkyl, or —CO$_2$C$_{1-3}$ alkyl.

In each structure shown above, R$_{s3'''}$ is either identical or different and is independently selected from hydrogen, —C$_{1-6}$ alkyl, -halogenated C$_{1-6}$ alkyl, —C$_{3-6}$ cycloalkyl, —C$_{1-3}$ alkyl-C(O)NR$^e$R$^f$, —C(O)NR$^e$R$^f$, —C$_{1-4}$ alkyl-hydroxyl, and —C$_{1-4}$ alkyl-NR$^e$R$^f$; and the —C$_{3-6}$ cycloalkyl is optionally substituted by 1, 2, or 3 substituents each independently selected from halogen, methyl, ethyl, propyl (n-propyl), isopropyl, trifluoromethyl, amino, N(CH$_3$)$_2$, hydroxyl, and carboxyl, where R$^e$ and R$^f$ are each independently hydrogen or C$_{1-3}$ alkyl.

In each structure shown above, R$_{s3}$ is either identical or different and is independently selected from halogen, cyano, hydroxyl, —C$_{1-6}$ alkyl, —C$_{1-6}$ alkoxy, -halogenated C$_{1-6}$ alkyl, -halogenated C$_{1-6}$ alkoxy, —C$_{3-6}$ cycloalkyl, 3- to 6-membered heterocycloalkyl, —NR$^h$R$^i$, —C(O)NR$^e$R$^f$, —SO$_2$C$_{1-3}$ alkyl, —SO$_2$halogenated C$_{1-3}$ alkyl, —SO$_2$NR$^e$R$^f$, —C$_{1-3}$ alkyl-hydroxyl, —C$_{1-3}$ alkyl-C$_{2-4}$ alkynyl, —C$_{1-3}$ alkyl-cyano, —C$_{1-3}$ alkyl-C$_{1-6}$ alkoxy, —C$_{1-3}$ alkyl-halogenated C$_{1-6}$ alkyl, —C$_{1-3}$ alkyl-halogenated C$_{1-6}$ alkoxy, —C$_{1-3}$ alkyl-3- to 6-membered heterocycloalkyl, —C$_{1-3}$ alkyl-C$_{3-6}$ cycloalkyl, —C$_{1-3}$ alkyl-NR$^e$R$^f$, —C$_{1-3}$ alkyl-C(O)NR$^e$R$^f$, —C$_{1-3}$ alkyl-SO$_2$C$_{1-3}$ alkyl, or C$_{2-4}$ alkynyl, where the 3- to 6-membered heterocycloalkyl has 1, 2 or 3 heteroatoms selected from N, O, and S as ring atoms; and the C$_{1-6}$ alkyl, the —C$_{1-6}$ alkoxy, the —C$_{1-3}$ alkyl-, the —C$_{3-6}$ cycloalkyl, and the 3- to 6-membered heterocycloalkyl are each optionally substituted by 1, 2, or 3 substituents each independently selected from halogen, methyl, ethyl, propyl (n-propyl), isopropyl, trifluoromethyl, amino, N(CH$_3$)$_2$, hydroxyl, and carboxyl, where R$^h$ and R$^i$ are each independently hydrogen, —C$_{1-3}$alkyl, —C(O)C$_{1-3}$ alkyl, or —CO$_2$C$_{1-3}$ alkyl; and R$^e$ and R$^f$ are each independently hydrogen or C$_{1-3}$ alkyl. In each structure shown above, n is either identical or different and is independently 0, 1, 2, or 3.

In an embodiment of the present invention, R$_{0'}$ is

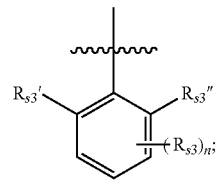

R$_{s3}$' is hydrogen, halogen, cyano, hydroxyl, —C$_{1-6}$ alkyl, —C$_{1-6}$ alkoxy, -halogenated C$_{1-6}$ alkyl, -halogenated C$_{1-6}$ alkoxy, —C$_{3-6}$ cycloalkyl, —NR$^h$R$^i$, —C(O)NR$^e$R$^f$, —C$_{1-3}$ alkyl-hydroxyl, and —C$_{1-3}$ alkyl-NR$^e$R$^f$; and the —C$_{3-6}$ cycloalkyl is optionally substituted by 1, 2, or 3 substituents each independently selected from halogen, methyl, ethyl, propyl (n-propyl), isopropyl, trifluoromethyl, amino, N(CH$_3$)$_2$, hydroxyl, and carboxyl, where R$^e$ and R$^f$ are each independently hydrogen or C$_{1-3}$ alkyl; R$^h$ and R$^i$ are each independently hydrogen, —C$_{1-3}$ alkyl, —C(O)C$_{1-3}$ alkyl, or —CO$_2$C$_{1-3}$ alkyl; R$_{s3''}$ is isopropyl; and n is 0. In an embodiment of the present invention, the R$_{s3''}$ is below the plane of the benzene ring.

In an embodiment of the present invention, R$_{0'}$ has a structure selected from:

R$^{s3'}$ is hydrogen, halogen, cyano, hydroxyl, —C$_{1-6}$ alkyl, —C$_{1-6}$ alkoxy, -halogenated C$_{1-6}$ alkyl, -halogenated C$_{1-6}$ alkoxy, —C$_{3-6}$ cycloalkyl, —NR$^h$R$^i$, —C(O)NR$^e$R$^f$, —C$_{1-3}$ alkyl-hydroxyl, and —C$_{1-3}$ alkyl-NR$^e$R$^f$; and the —C$_{3-6}$ cycloalkyl is optionally substituted by 1, 2, or 3 substituents each independently selected from halogen, methyl, ethyl, propyl (n-propyl), isopropyl, trifluoromethyl, amino, N(CH$_3$)$_2$, hydroxyl, and carboxyl, where R$^e$ and R$^f$ are each independently hydrogen or C$_{1-3}$alkyl; R$^h$ and R$^i$ are each independently hydrogen, —C$_{1-3}$ alkyl, —C(O)C$_{1-3}$ alkyl, or —CO$_2$C$_{1-3}$ alkyl; R$_{s3''}$ is isopropyl; R$_{s3}$ is —C$_{1-6}$ alkyl; and n is 0 or 1. In an embodiment, the R$_{s3''}$ is below the plane of the pyridine ring.

In an embodiment of the present invention, R$_{0'}$ has a structure selected from:

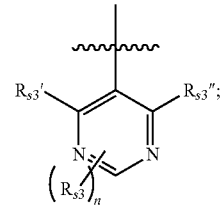

R$_{s3}$' is hydrogen, halogen, cyano, hydroxyl, —C$_{1-6}$ alkyl, —C$_{1-6}$ alkoxy, -halogenated C$_{1-6}$ alkyl, -halogenated C$_{1-6}$ alkoxy, —C$_{3-6}$ cycloalkyl, —NR$^h$R$^i$, —C(O)NR$^e$R$^f$, —C$_{1-3}$ alkyl-hydroxyl, and —C$_{1-3}$ alkyl-NR$^e$R$^f$; and the —C$_{3-6}$ cycloalkyl is optionally substituted by 1, 2, or 3 substituents each independently selected from halogen, methyl, ethyl, propyl (n-propyl), isopropyl, trifluoromethyl, amino, N(CH$_3$)$_2$, hydroxyl, and carboxyl, where R$^e$ and R$^f$ are each independently hydrogen or C$_{1-3}$ alkyl; R$^h$ and R$^i$ are each independently hydrogen, —C$_{1-3}$ alkyl, —C(O)C$_{1-3}$ alkyl, or —CO$_2$C$_{1-3}$ alkyl; R$_{s3''}$ is isopropyl; and n is 0. In an embodiment, the R$_{s3''}$ is below the plane of the pyrimidine ring.

In an embodiment of the present invention, R$_{0'}$ has a structure selected from:

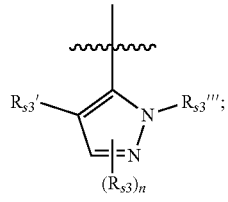

$R_{s3'}$ is hydrogen, halogen, cyano, hydroxyl, —$C_{1-6}$ alkyl, —$C_{1-6}$ alkoxy, -halogenated $C_{1-6}$ alkyl, -halogenated $C_{1-6}$ alkoxy, —$C_{3-6}$ cycloalkyl, —$NR^hR^i$, —$C(O)NR^eR^f$, —$C_{1-3}$ alkyl-hydroxyl, and —$C_{1-3}$ alkyl-$NR^eR^f$; and the —$C_{3-6}$ cycloalkyl is optionally substituted by 1, 2, or 3 substituents each independently selected from halogen, methyl, ethyl, propyl (n-propyl), isopropyl, trifluoromethyl, amino, $N(CH_3)_2$, hydroxyl, and carboxyl, where $R^e$ and $R^f$ are each independently hydrogen or $C_{1-3}$ alkyl; $R^h$ and $R^i$ are each independently hydrogen, —$C_{1-3}$ alkyl, —$C(O)C_{1-3}$ alkyl, or —$CO_2C_{1-3}$ alkyl; $R_{s3'''}$ is isopropyl; and n is 0. In an embodiment, the $R_{s3'''}$ is below the plane of the pyrazole ring.

In an embodiment of the present invention, $R_{0'}$ has a structure selected from:

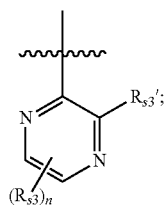

$R_{s3'}$ is isopropyl; and n is 0. In an embodiment, the $R_{s3'}$ is below the plane of the pyrazine ring.

In an embodiment of the present invention, $R_{0'}$ has a structure selected from:

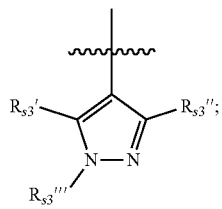

$R_{s3'}$ is hydrogen, halogen, cyano, hydroxyl, —$C_{1-6}$ alkyl, —$C_{1-6}$ alkoxy, -halogenated $C_{1-6}$ alkyl, -halogenated $C_{1-6}$ alkoxy, —$C_{3-6}$ cycloalkyl, —$NR^hR^i$, —$C(O)NR^eR^f$, —$C_{1-3}$ alkyl-hydroxyl, and —$C_{1-3}$ alkyl-$NR^eR^f$; and the —$C_{3-6}$ cycloalkyl is optionally substituted by 1, 2, or 3 substituents each independently selected from halogen, methyl, ethyl, propyl (n-propyl), isopropyl, trifluoromethyl, amino, $N(CH_3)_2$, hydroxyl, and carboxyl, where $R^e$ and $R^f$ are each independently hydrogen or $C_{1-3}$ alkyl; $R^h$ and $R^i$ are each independently hydrogen, —$C_{1-3}$ alkyl, —$C(O)C_{1-3}$ alkyl, or —$CO_2C_{1-3}$ alkyl; $R_{s3''}$ is isopropyl; and $R_{s3'''}$ is —$C_{1-6}$ alkyl. In an embodiment, the $R_{s3''}$ is below the plane of the pyrazole ring.

In an embodiment of the present invention, $R^{O'}$ has a structure selected from:

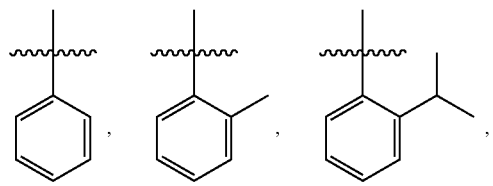

-continued

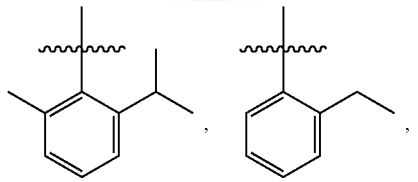

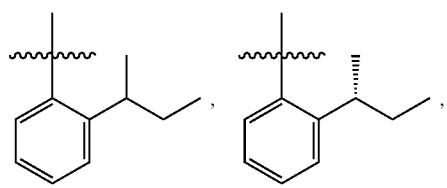

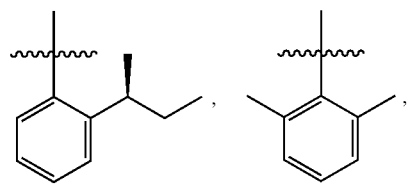

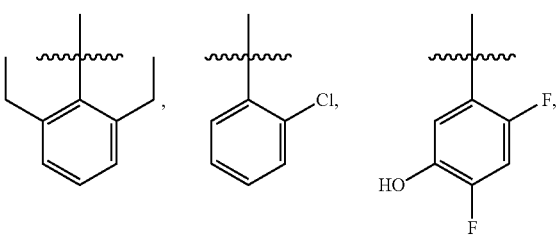

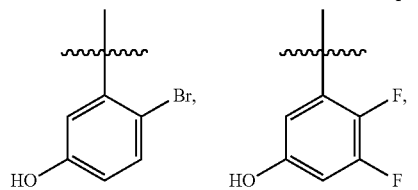

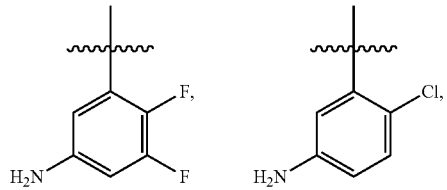

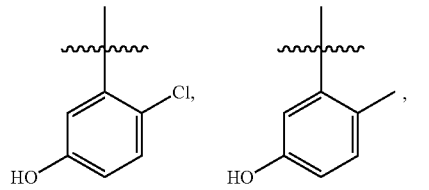

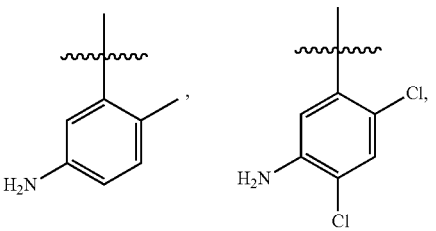

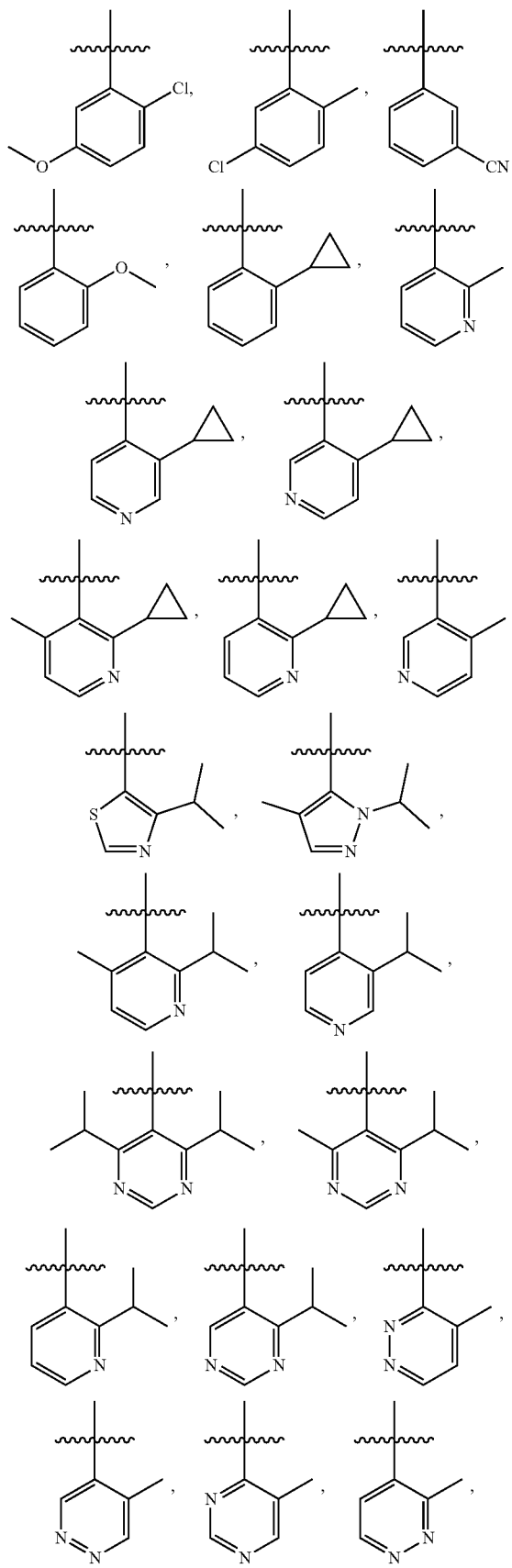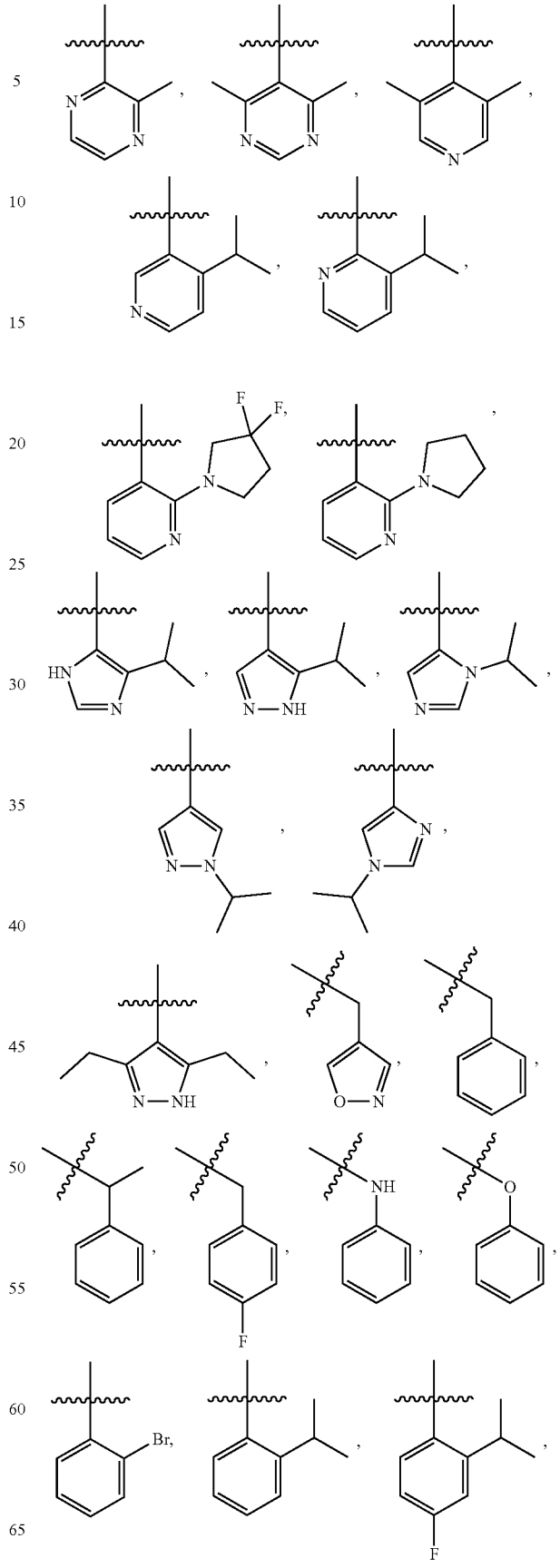

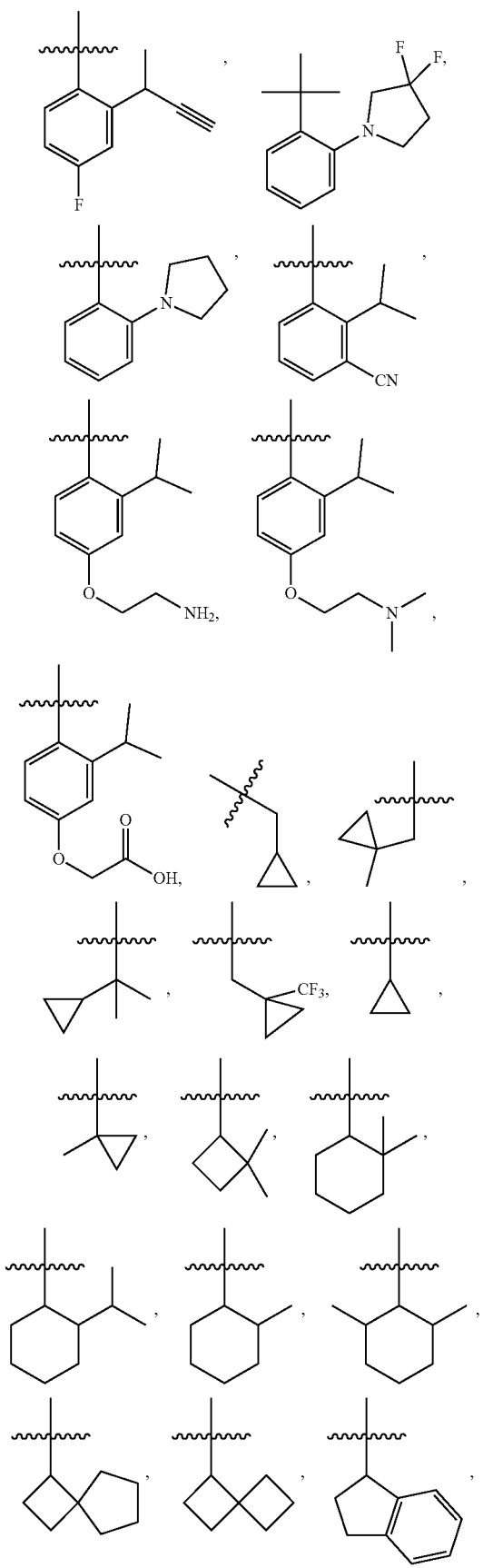
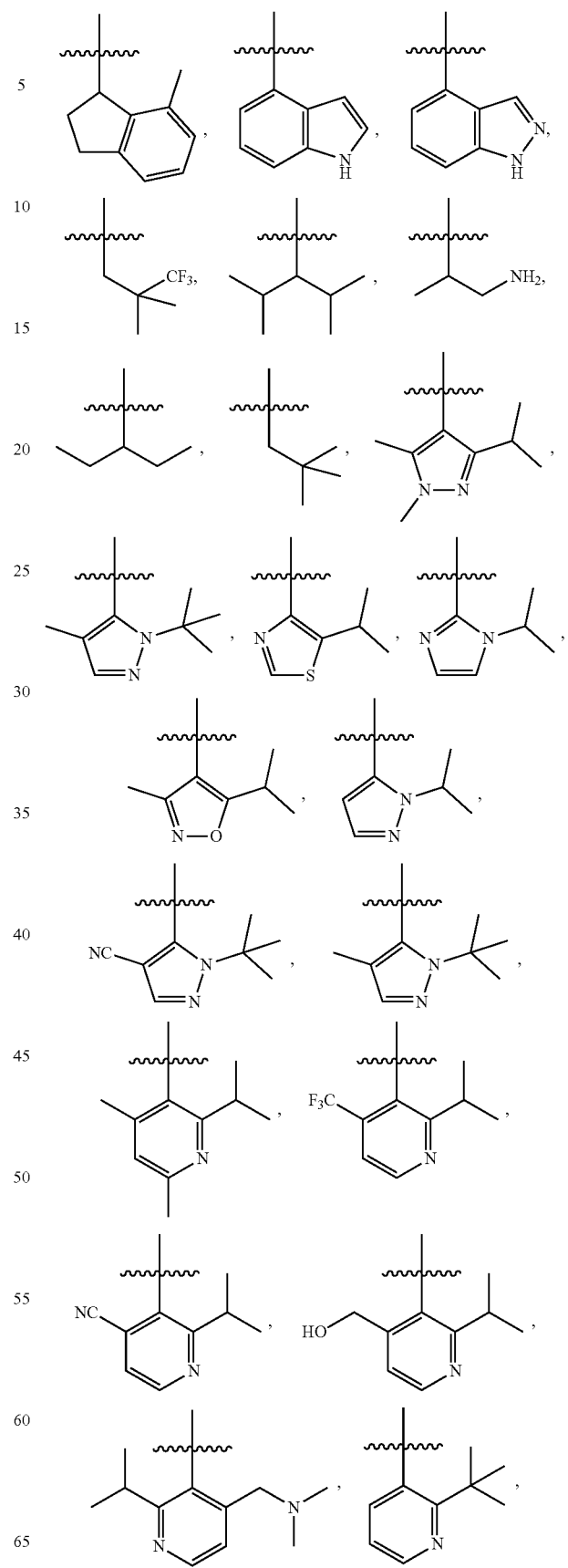

-continued

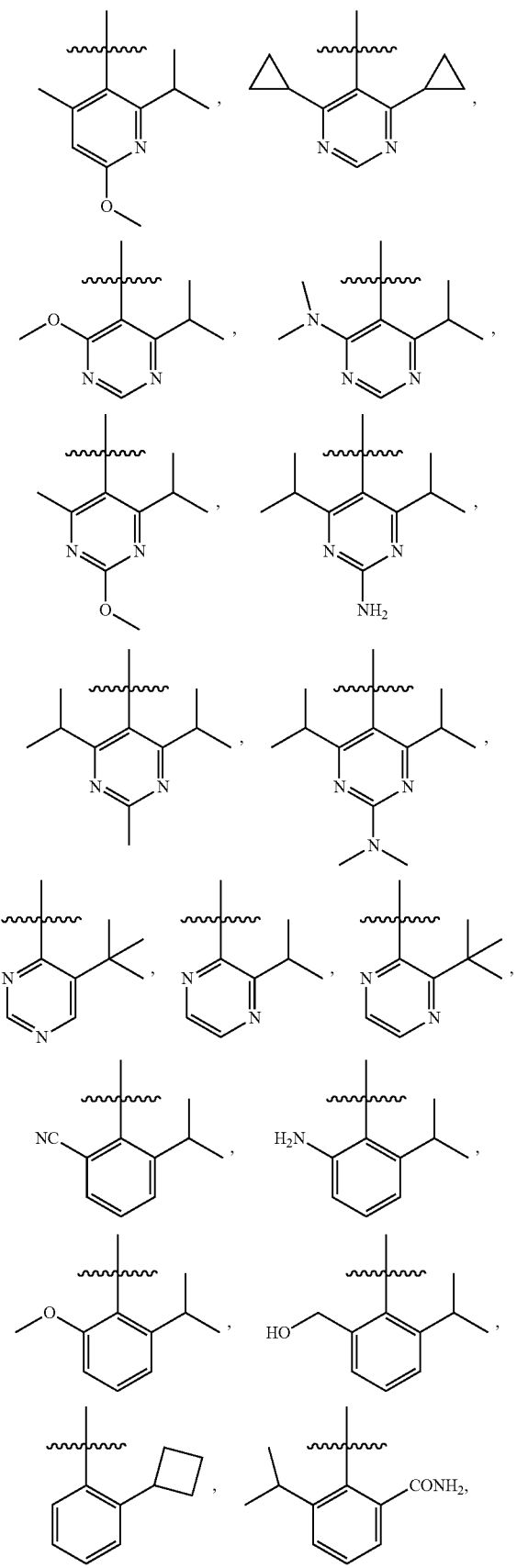

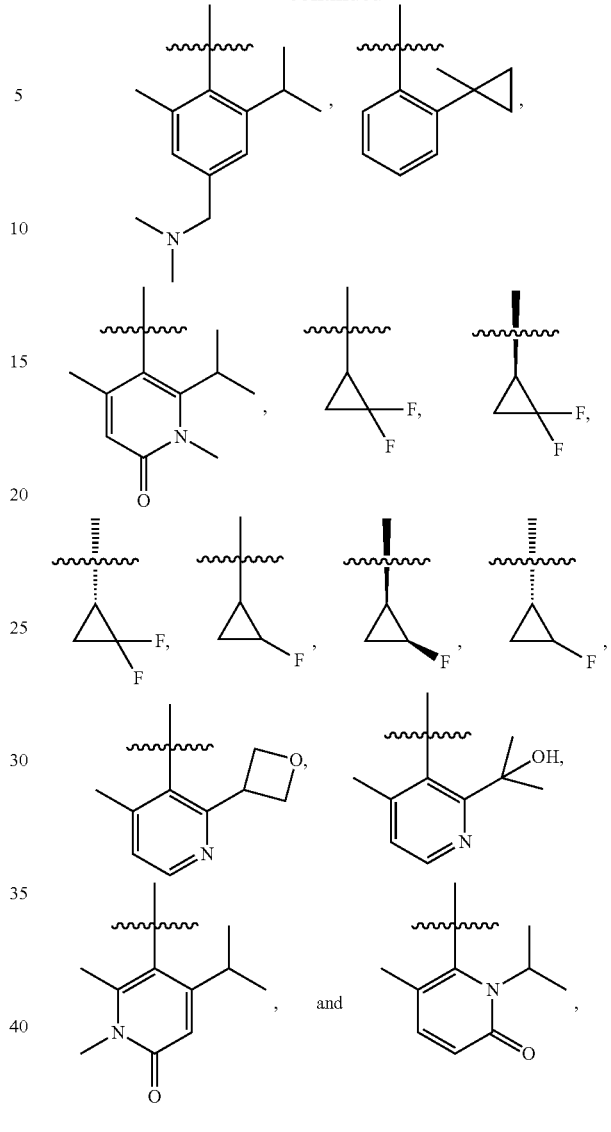

In another aspect, the present invention provides a compound of Formula (II), or a pharmaceutically acceptable salt, a stereoisomer, a solvate or a prodrug thereof:

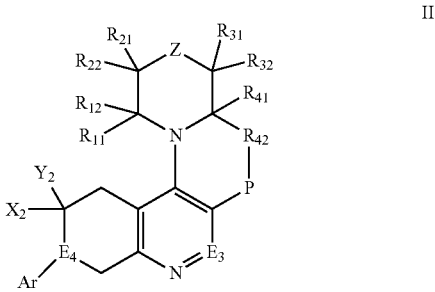

II where:
Z is N—C(O)—CR$_3$=CR$_1$R$_2$ or N—C(O)—C≡CR$_4$;
R$_1$ and R$_2$ are each independently hydrogen, halogen, cyano, NR$^a$R$^b$, —C$_{1-3}$ alkyl, halogenated C$_{1-3}$ alkyl, —C$_{1-3}$ alkyl-hydroxyl, —C$_{1-3}$ alkyl-cyano, —C$_{1-3}$ alkyl-C$_{1-3}$ alkoxy, —C$_{1-3}$ alkyl-NR$^a$R$^b$, —C$_{1-3}$ alkyl-3- to 6-membered heterocycloalkyl, or —$C_{1-3}$ alkyl-5- or 6-membered monocyclic heteroaryl, where the 3- to 6-membered heterocycloalkyl or the 5- or 6-membered monocyclic heteroaryl has 1, 2 or 3 heteroatoms selected from N, O, and S as ring atoms;

$R_3$ is hydrogen, halogen, —$C_{1-3}$ alkyl, or —$C_{1-3}$ alkoxy;

$R_4$ is hydrogen, halogenated $C_{1-3}$ alkyl, —$C_{1-3}$ alkyl-hydroxyl, —$C_{1-3}$ alkyl-cyano, or —$C_{1-3}$ alkyl-$C_{1-3}$ alkoxy;

$R_{11}$ and $R_{12}$ are either identical or different and are each independently hydrogen, halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$ alkoxy, —$C_{1-3}$ alkyl-halogenated $C_{1-6}$ alkyl, or —$C_{1-3}$ alkyl-halogenated $C_{1-6}$ alkoxy;

$R_{21}$ and $R_{22}$ are either identical or different and are each independently hydrogen, halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$ alkoxy, —$C_{1-3}$ alkyl-halogenated $C_{1-6}$ alkyl, or —$C_{1-3}$ alkyl-halogenated $C_{1-6}$ alkoxy;

$R_{31}$ and $R_{32}$ are either identical or different and are each independently hydrogen, halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$ alkoxy, —$C_{1-3}$ alkyl-halogenated $C_{1-6}$ alkyl, or —$C_{1-3}$ alkyl-halogenated $C_{1-6}$ alkoxy;

$R_{41}$ is hydrogen, halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$ alkoxy, —$C_{1-3}$ alkyl-halogenated $C_{1-6}$ alkyl, or —$C_{1-3}$ alkyl-halogenated $C_{1-6}$ alkoxy;

P is O, NH or NR$'''$; R$'''$ is —$C_{1-6}$ alkyl, -halogenated $C_{1-6}$ alkyl, —$C_{1-6}$ alkyl-hydroxyl, —$C_{1-6}$ alkyl-cyano, —$C_{1-6}$ alkyl-$C_{1-6}$ alkoxy, —$C_{1-6}$ alkyl-halogenated $C_{1-6}$ alkoxy, —$C_{1-6}$ alkyl-$C_{3-6}$ cycloalkyl, or —$C_{1-6}$ alkyl-3- to 6-membered heterocycloalkyl;

$R_{42}$ is —(C=O)—, —$C_{1-3}$ alkyl, —$C_{1-3}$ alkyl (hydroxy)-, —$C_{1-3}$ alkyl (cyano)-, —$C_{1-3}$ alkyl ($C_{1-6}$ alkyl), —$C_{1-3}$ alkyl (halogenated $C_{1-6}$ alkyl)-, —$C_{1-3}$ alkyl ($C_{1-6}$ alkyl-hydroxy)-, —$C_{1-3}$ alkyl ($C_{1-6}$ alkyl-cyano)-, —$C_{1-3}$ alkyl ($C_{1-6}$ alkoxy)-, or —$C_{1-3}$ alkyl (halogenated $C_{1-6}$ alkoxy)-;

$X_2$ and $Y_2$ are either identical or different and are each independently hydrogen, halogen, —$C_{1-3}$ alkyl, -halogenated $C_{1-3}$ alkyl, —$C_{1-3}$ alkyl-hydroxyl, —$C_{1-3}$ alkyl-cyano, —$C_{1-3}$ alkyl-$C_{1-6}$ alkoxy, —$C_{1-3}$ alkyl-halogenated $C_{1-6}$ alkyl, or —$C_{1-3}$ alkyl-halogenated $C_{1-6}$ alkoxy;

or $X_2$ and $Y_2$ form together with a carbon atom adjacent thereto substituted or unsubstituted $C_{3-6}$ cycloalkyl or substituted or unsubstituted 3- to 6-membered heterocycloalkyl; the 3- to 6-membered heterocycloalkyl has 1, 2, or 3 heteroatoms selected from N, O, and S as ring atoms; the "substituted" means 1, 2, 3, or 4 hydrogen atoms in a group being each independently substituted by a group-S substituent;

$E_3$ is N or C-L-$R_5$, where:

L is a bond, —$CR_{L1}R_{L2}$—, —O—$(CR_{L1}R_{L2})_u$—, or —NH—$(CR_{L3}R_{L4})_{t2}$—, where $R_{L1}$, $R_{L2}$, $R^{L3}$, and $R^{L4}$ are either identical or different and are each independently hydrogen, halogen, hydroxyl, hydroxymethyl, hydroxyethyl, —$C_{1-3}$ alkyl or oxo;

t1 and t2 are each independently 0, 1, 2, 3, or 4; when between $R_{L1}$ and $R_{L2}$ or between $R_{L3}$ and $R_{L4}$, when one is oxo, the other one is absent;

$R_5$ is hydrogen, halogen, hydroxyl, -substituted or unsubstituted $C_{1-6}$ alkyl, -substituted or unsubstituted $C_{3-6}$ cycloalkyl, -substituted or unsubstituted 3- to 6-membered heterocycloalkyl, —O-substituted or unsubstituted $C_{1-6}$ alkyl, —O-substituted or unsubstituted $C_{3-6}$ cycloalkyl, —O-substituted or unsubstituted 3- to 6-membered heterocycloalkyl, —$SO_2$-substituted or unsubstituted $C_{1-6}$ alkyl, —$SO_2$-substituted or unsubstituted $C_{3-6}$ cycloalkyl, —$SO_2$-substituted or unsubstituted 3- to 6-membered heterocycloalkyl, -substituted or unsubstituted 5- or 6-membered monocyclic heteroaryl, or $NR_{51}R_{52}$, where $R_{51}$ and $R_{52}$ are each independently hydrogen, substituted or unsubstituted $C_{1-6}$ alkyl, —$SO_2C_{1-6}$ alkyl, —$SO_2C_{3-6}$ cycloalkyl, —$C(O)C_{1-6}$ alkyl, or —$C(O)$halogenated $C_{1-6}$ alkyl; or $R_{51}$ and $R_{52}$ form together with a nitrogen atom adjacent thereto substituted or unsubstituted 3- to 6-membered N-containing heterocycloalkyl; where the 3- to 6-membered heterocycloalkyl and the 5- or 6-membered monocyclic heteroaryl each independently have 1, 2, or 3 heteroatoms selected from N, O, and S as ring atoms; the 3- to 6-membered N-containing heterocycloalkyl has 3 to 6 ring atoms, and one of the ring atoms is nitrogen atom, while 0, 1 or 2 ring atoms among the rest of the ring atoms are optionally heteroatoms selected from N, O, and S; the "substituted" means 1, 2, 3, or 4 hydrogen atoms in a group being each independently substituted by a group-S substituent;

the group-S substituent is selected from hydroxyl, halogen, nitro, oxo, —$C_{1-6}$ alkyl, -halogenated $C_{1-6}$ alkyl, hydroxyl-substituted $C_{1-6}$ alkyl, benzyl, —$(CH_2)_u$-cyano, —$(CH_2)_u$—$C_{1-6}$ alkoxy, —$(CH_2)_u$-halogenated $C_{1-6}$ alkoxy, —$(CH_2)_u$-halogenated $C_{1-6}$ alkyl, —$(CH_2)_u$-3- to 6-membered heterocycloalkyl, —$(CH_2)_u$-5- or 6-membered monocyclic heteroaryl, —$(CH_2)_u$—$C_{3-8}$ cycloalkyl, —$(CH_2)_u$—O—$(CH_2)_v$—$C_{3-8}$ cycloalkyl, —$(CH_2)_u$—O—$(CH_2)_v$—$C_{1-6}$ alkoxy, —$(CH_2)_u$—O—$(CH_2)_v$OH, —$(CH_2)_u$—$SO_2C_{1-6}$ alkyl, —$(CH_2)_u$—$NR_{a0}R_{b0}$, —$(CH_2)_u$—$C(O)NR_{a0}R_{b0}$, —$(CH_2)_u$—$C(O)C_{1-6}$ alkyl, —$C(O)OC_{1-6}$ alkyl, $NR_{a0}C(O)$—$(CH_2)_u$—$NR_{a0}R_{b0}$, $NR_{a0}C(O)$—$(CH_2)_u$OH, and $NR_{a0}C(O)$-halogenated $C_{1-6}$ alkyl, where the 3- to 6-membered heterocycloalkyl or the 5- or 6-membered monocyclic heteroaryl each independently has 1, 2 or 3 heteroatoms selected from N, O, and S as ring atoms; the 3- to 6-membered heterocycloalkyl and the 5- or 6-membered monocyclic heteroaryl are each optionally substituted by 1, 2, or 3 substituents selected from halogen, cyano, —$C_{1-3}$ alkyl, —$C_{1-3}$ alkoxy, and $C_{3-6}$ cycloalkyl; u and v are each independently 0, 1, 2, 3, or 4; $R_{a0}$ and $R_{b0}$ are each independently hydrogen or $C_{1-3}$ alkyl;

$E_4$ is N or CH;

Ar is $C_{6-10}$ aryl, 5- or 6-membered monocyclic heteroaryl or 8- to 10-membered bicyclic heteroaryl, where the 5- or 6-membered monocyclic heteroaryl has 1, 2, or 3 heteroatoms selected from N, O, and S as ring atoms; the 8- to 10-membered bicyclic heteroaryl has 1, 2, 3, 4, or 5 heteroatoms selected from N, O, and S as ring atoms; and the $C_{6-10}$ aryl, the 5- or 6-membered monocyclic heteroaryl or the 8- to 10-membered bicyclic heteroaryl is unsubstituted or substituted by 1, 2, 3, or 4 groups each independently selected from $R_{s1}$;

or,
Ar has a structure of Formula (B):

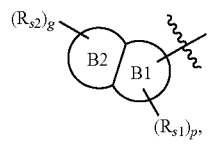

(B)

where the ring B1 is a benzene ring or a 5- or 6-membered monocyclic heteroaryl ring; the ring B2 is a fused 5- or 6-membered monocyclic heterocycloalkyl ring or a fused 5- or 6-membered monocyclic cycloalkyl ring, where the 5- or 6-membered monocyclic heteroaryl ring or the fused 5- or 6-membered monocyclic heterocycloalkyl ring has 1, 2, or 3 heteroatoms selected from N, O, and S as ring atoms;

$(R_{s1})_p$ represents that hydrogens on the ring B1 is substituted by p $R_{s1}$ groups, p being 0, 1, 2, or 3 and each $R_s$, being either identical or different;

$(R_{s2})_q$ represents that hydrogens on the ring B2 is substituted by q $R_{s2}$ groups, q being 0, 1, 2, or 3 and each $R_{s2}$ being either identical or different;

$R_{s1}$ and $R_{s2}$ are each independently halogen, cyano, nitro, hydroxyl, —$C_{1-6}$ alkyl, —$C_{1-6}$ alkoxy, -halogenated $C_{1-6}$ alkyl, -halogenated $C_{1-6}$ alkoxy, —$C_{3-6}$ cycloalkyl, —$NR^cR^d$, —$C(O)NR^eR^f$, —$SO_2C_{1-3}$ alkyl, —$SO_2$halogenated $C_{1-3}$ alkyl, —$SO_2NR^eR^f$, —$C_{1-4}$ alkyl-hydroxyl, —$C_{1-4}$ alkyl-cyano, —$C_{1-4}$ alkyl-$C_{1-6}$ alkoxy, —$C_{1-4}$ alkyl-halogenated $C_{1-6}$ alkyl, —$C_{1-4}$ alkyl-halogenated $C_{1-6}$ alkoxy, —$C_{1-4}$ alkyl-3- to 6-membered heterocycloalkyl, —$C_{1-4}$ alkyl-$NR^eR^f$, —$C_{1-4}$ alkyl-$C(O)NR^eR^f$, —$C_{1-4}$ alkyl-$SO_2C_{1-3}$ alkyl, or $C_{2-4}$ alkynyl, where the 3- to 6-membered heterocycloalkyl has 1, 2, or 3 heteroatoms selected from N, O, and S as ring atoms;

$R^a$, $R^b$, $R^c$, and $R^f$ are each independently hydrogen or $C_{1-3}$ alkyl;

$R^e$ and $R^d$ are each independently hydrogen, —$C_{1-3}$ alkyl, —$C(O)C_{1-3}$ alkyl, or —$CO_2C_{1-3}$ alkyl.

In an embodiment of the present invention, $R_{s1}$ and $R_{s2}$ are each independently halogen, cyano, nitro, hydroxyl, —$C_{1-3}$ alkyl, —$C_{1-3}$ alkoxy, halogenated $C_{1-3}$ alkyl, $C_{1-3}$ haloalkoxy, —$C_{3-6}$ cycloalkyl, —$NR^cR^d$, —$C(O)NR^eR^f$, —$SO_2C_{1-3}$ alkyl, —$SO_2$halogenated $C_{1-3}$ alkyl, —$SO_2NR^eR^f$, —$C_{1-2}$ alkyl-hydroxyl, —$C_{1-2}$ alkyl-cyano, —$C_{1-2}$ alkyl-$C_{1-3}$ alkoxy, —$C_{1-2}$ alkyl-halogenated $C_{1-3}$ alkyl, —$C_{1-2}$ alkyl-$C_{1-3}$ haloalkoxy, —$C_{1-2}$ alkyl-3- to 6-membered heterocycloalkyl, —$C_{1-2}$ alkyl-$NR^eR^f$, —$C_{1-2}$ alkyl-$C(O)NR^eR^f$, —$C_{1-2}$ alkyl-$SO_2C_{1-3}$ alkyl, or $C_{2-4}$ alkynyl, where $R^c$ and $R^d$ are each independently hydrogen, —$C_{1-3}$ alkyl, —$C(O)C_{1-3}$ alkyl, or —$CO_2C_{1-3}$ alkyl; and $R^e$ and $R^f$ are each independently hydrogen or $C_{1-3}$ alkyl.

In an embodiment of the present invention, $R_{s1}$ and $R_{s2}$ are each independently halogen, cyano, nitro, hydroxyl, —$C_{1-3}$ alkyl, —$C_{1-3}$ alkoxy, halogenated $C_{1-3}$ alkyl, $C_{1-3}$haloalkoxy, —$C_{3-6}$ cycloalkyl, —$NR^cR^d$, —$C(O)NR^eR^f$, —$SO_2C_{1-3}$ alkyl, —$SO_2$halogenated $C_{1-3}$ alkyl, —$SO_2NR^eR^f$, —$CH_2$-hydroxyl, —$CH_2$-cyano, —$CH_2$—$C_{1-3}$ alkoxy, —$CH_2$-halogenated $C_{1-3}$ alkyl, —$CH_2$—$C_{1-3}$ haloalkoxy, —$CH_2$-3- to 6-membered heterocycloalkyl, —$CH_2$—$NR^eR^f$, —$CH_2$—$C(O)NR^eR^f$, —$CH_2$—$SO_2C_{1-3}$ alkyl, or $C_{2-4}$ alkynyl, where $R^e$ is hydrogen, —$C_{1-3}$ alkyl, —$C(O)CH_3$, or —$CO_2CH_3$; and $R^e$, $R^f$, and $R^d$ are each independently hydrogen or $C_{1-3}$ alkyl.

In an embodiment of the present invention, $R_{s1}$ and $R_{s2}$ are each independently halogen, cyano, nitro, hydroxyl, —$C_{1-3}$ alkyl, —$C_{1-3}$ alkoxy, halogenated $C_{1-3}$ alkyl, $C_{1-3}$ haloalkoxy, —$C_{3-6}$ cycloalkyl, —$NR^cR^d$, —$C(O)NR^eR^f$, —$CH_2$-hydroxyl, —$CH_2$-cyano, where $R^e$ is hydrogen, —$C(O)CH_3$, or —$CO_2CH_3$; and $R^e$, $R^f$, and $R^d$ are each independently hydrogen or $C_{1-3}$ alkyl.

In an embodiment of the present invention, in $R_{s1}$ and $R_{s2}$, the $C_{3-6}$ cycloalkyl is selected from cyclopropyl, cyclobutyl, cyclopentyl, cyclopentenyl, cyclohexyl, cyclohexenyl, cyclohexadienyl, cyclobutanone, cyclobutan-1,2-dione, cyclopentanone, cyclopentan-1,3-dione, cyclohexanone, and cyclohexan-1, 3-dione.

In an embodiment of the present invention, in $R_{s1}$ and $R_{s2}$, the 3- to 6-membered heterocycloalkyl is selected from aziridine, ethylene oxide, azetidine, oxetane, oxazolidine, 1,3-dioxolane, imidazolidine, tetrahydrofuran, tetrahydrothiophene, tetrahydropyrrole, piperidine, piperazine, morpholine, thiomorpholine, thiomorpholin-1,1-dioxide, tetrahydropyrane, 1,3-oxazinane, hexahydropyrimidine, and 1,4-dioxane.

In an embodiment of the present invention, $R_{s1}$, $R_{s2}$ are each independently halogen, cyano, nitro, hydroxyl, methyl, ethyl, n-propyl, isopropyl, methoxy, ethoxy, propoxy (n-propoxy), isopropoxy, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, trifluoromethoxy, trifluoroethoxy, monofluoromethoxy, monofluoroethoxy, difluoromethoxy, difluoroethoxy, cyclopropyl, cyclobutyl, cyclopentyl, cyclohexyl, —$NR^cR^d$, —$C(O)NR^eR^f$, —$CH_2$-hydroxyl, and —$CH_2$-cyano, where $R^c$ is hydrogen, —$C(O)CH_3$, or —$CO_2CH_3$; and $R^e$, $R^f$, and $R^d$ are each independently hydrogen, methyl, or ethyl.

In an embodiment of the present invention, $R_{s3}$ and $R_{s4}$ are each independently halogen, cyano, hydroxyl, —$C_{1-6}$ alkyl, —$C_{1-3}$ alkoxy, halogenated $C_{1-3}$ alkyl, $C_{1-3}$ haloalkoxy, —$C_{3-6}$ cycloalkyl, 3- to 6-membered heterocycloalkyl, amino, $NHCH_3$, $N(CH_3)_2$, —$C(O)NR^eR^f$, —$SO_2C_{1-3}$ alkyl, —$SO_2$halogenated $C_{1-3}$ alkyl, —$SO_2NR^eR^f$, —$C_{1-2}$ alkyl-hydroxyl, —$C_{1-2}$ alkyl-acetenyl, —$C_{1-2}$ alkyl-cyano, —$C_{1-2}$ alkyl-$C_{1-3}$ alkoxy, —$C_{1-2}$ alkyl-halogenated $C_{1-3}$ alkyl, —$C_{1-2}$ alkyl-$C_{1-3}$ haloalkoxy, —$C_{1-2}$ alkyl-3- to 6-membered heterocycloalkyl, —$C_{1-2}$ alkyl-$C_{3-6}$ cycloalkyl, —$C_{1-2}$ alkyl-$NR^eR^f$, —$C_{1-2}$ alkyl-$C(O)NR^eR^f$, —$C_{1-2}$ alkyl-$SO_2C_{1-3}$ alkyl, or acetenyl, where the $C_{1-6}$ alkyl, the —$C_{1-3}$ alkoxy, the —$C_{1-2}$ alkyl-, the —$C_{3-6}$ cycloalkyl, and the 3- to 6-membered heterocycloalkyl are each optionally substituted by 1, 2, or 3 substituents each independently selected from halogen, methyl, ethyl, propyl (n-propyl), isopropyl, trifluoromethyl, amino, $N(CH_3)_2$, hydroxyl, and carboxyl; and $R^e$ and $R^f$ are each independently hydrogen or $C_{1-3}$ alkyl.

In an embodiment of the present invention, $R_{s3}$ and $R_{s4}$ are each independently halogen, cyano, hydroxyl, $C_{1-4}$ alkyl, —$C_{1-3}$ alkoxy, halogenated $C_{1-3}$ alkyl, $C_{1-3}$ haloalkoxy, —$C_{3-6}$ cycloalkyl, 3- to 6-membered heterocycloalkyl, amino, $NHCH_3$, $N(CH_3)_2$, —$C(O)NR^eR^f$, —$SO_2C_{1-3}$ alkyl, —$SO_2$halogenated $C_{1-3}$ alkyl, —$SO_2NR^eR^f$, —$CH_2$-hydroxyl, —$CH_2$-ethynyl, —$CH_2$-cyano, —$CH_2$—$C_{1-3}$ alkoxy, —$CH_2$-halogenated $C_{1-3}$ alkyl, —$CH_2$—$C_{1-3}$ haloalkoxy, —$CH_2$-3- to 6-membered heterocycloalkyl, —$CH_2$—$C_{3-6}$ cycloalkyl, —$CH_2$—$NR^eR^f$, —$CH_2$—$C(O)NR^eR^f$, —$CH_2$—$SO_2C_{1-3}$ alkyl, or ethynyl, where the $C_{1-4}$ alkyl, the —C$_{1-3}$ alkoxy, the —CH$_2$—, the —C$_{3-6}$ cycloalkyl, and the 3- to 6-membered heterocycloalkyl are each optionally substituted by 1, 2, or 3 substituents each independently selected from halogen, methyl, ethyl, propyl (n-propyl), isopropyl, trifluoromethyl, amino, N(CH$_3$)$_2$, hydroxyl, and carboxyl; and R$^e$ and R$^f$ are each independently hydrogen or C$_{1-3}$ alkyl.

In an embodiment of the present invention, R$_{s3}$ and R$_{s4}$ are each independently halogen, cyano, hydroxyl, C$_{1-4}$ alkyl, —C$_{1-3}$ alkoxy, halogenated C$_{1-3}$ alkyl, —C$_{3-6}$ cycloalkyl, 3- to 6-membered heterocycloalkyl, amino, NHCH$_3$, N(CH$_3$)$_2$, —CH$_2$-hydroxyl, or —CH$_2$-ethynyl, where the C$_1$ alkyl, the —C$_{1-3}$ alkoxy, the —CH$_2$—, the —C$_{3-6}$ cycloalkyl, and the 3- to 6-membered heterocycloalkyl are each optionally substituted by 1, 2, or 3 substituents each independently selected from halogen, methyl, ethyl, propyl (n-propyl), isopropyl, trifluoromethyl, amino, N(CH$_3$)$_2$, hydroxyl, and carboxyl.

In an embodiment of the present invention, in R$_{s3}$ and R$_{s4}$, the C$_{3-6}$ cycloalkyl is selected from cyclopropyl, cyclobutyl, cyclopentyl, and cyclohexyl.

In an embodiment of the present invention, in R$_{s3}$ and R$_{s4}$, the 3- to 6-membered heterocycloalkyl is selected from aziridine, ethylene oxide, azetidine, oxetane, tetrahydrofuran, tetrahydrothiophene, tetrahydropyrrole, piperidine, piperazine, morpholine, thiomorpholine, thiomorpholin-1,1-dioxide, and tetrahydropyrane.

In an embodiment of the present invention, R$_{s3}$ and R$_{s4}$ are each independently halogen, cyano, hydroxyl, methyl, ethyl, n-propyl, isopropyl, sec-butyl, methoxy, ethoxy, propoxy (n-propoxy), isopropoxy, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, cyclopropyl, cyclobutyl, cyclopentyl, cyclohexyl, aziridine, ethylene oxide, azetidine, oxetane, tetrahydrofuran, tetrahydrothiophene, tetrahydropyrrole, piperidine, piperazine, morpholine, thiomorpholine, thiomorpholin-1,1-dioxide, tetrahydropyrane, amino, NHCH$_3$, N(CH$_3$)$_2$, —CH$_2$-hydroxyl, and —CH$_2$-ethynyl, where each of the methyl, the ethyl, the n-propyl, the methoxy, the ethoxy, the propoxy (n-propoxy), the —CH$_2$—, the azetidine, the oxetane, the tetrahydrofuran, the tetrahydrothiophene, the tetrahydropyrrole, the piperidine, the piperazine, the morpholine, the thiomorpholine, the thiomorpholin-1,1-dioxide, and the tetrahydropyrane is optionally substituted by 1, 2, or 3 substituents each independently selected from halogen, methyl, ethyl, propyl (n-propyl), isopropyl, trifluoromethyl, amino, N(CH$_3$)$_2$, hydroxyl, and carboxyl.

In an embodiment of the present invention, the group-S substituent is selected from hydroxyl, halogen, nitro, oxo, —C$_{1-3}$ alkyl, hydroxy-substituted C$_{1-3}$ alkyl, benzyl, —(CH$_2$)$_u$-cyano, —(CH$_2$)$_u$—C$_{1-3}$ alkoxy, —(CH$_2$)$_u$—C$_{1-3}$ haloalkoxy, —(CH$_2$)$_u$-halogenated C$_{1-3}$ alkyl, —(CH$_2$)$_u$-3- to 6-membered heterocycloalkyl, —(CH$_2$)$_u$-5- or 6-membered monocyclic heteroaryl, —(CH$_2$)$_u$—C$_{3-6}$ cycloalkyl, —(CH$_2$)$_u$—O—(CH$_2$)$_v$—C$_{3-6}$ cycloalkyl, —(CH$_2$)$_u$—O—(CH$_2$)$_v$—C$_{1-3}$ alkoxy, —(CH$_2$)$_u$—O—(CH$_2$)$_v$OH, —(CH$_2$)$_u$—SO$_2$C$_{1-3}$ alkyl, —(CH$_2$)$_u$—NR$_{a0}$R$_{b0}$, —(CH$_2$)$_u$—C(O)NR$_{a0}$R$_{b0}$, —(CH$_2$)$_u$—C(O)C$_{1-3}$ alkyl, —C(O)OC$_{1-3}$ alkyl, NR$_{a0}$C(O)—(CH$_2$)$_u$—NR$_{a0}$R$_{b0}$, NR$_{a0}$C(O)—(CH$_2$)$_u$OH, and NR$_{a0}$C(O)-halogenated C$_{1-3}$ alkyl, where the 3- to 6-membered heterocycloalkyl and the 5- or 6-membered monocyclic heteroaryl each independently have 1, 2, or 3 heteroatoms selected from N, O, and S as ring atoms; the 3- to 6-membered heterocycloalkyl and the 5- or 6-membered monocyclic heteroaryl are each optionally substituted by 1, 2, or 3 substituents selected from halogen, cyano, —C$_{1-3}$ alkyl, —C$_{1-3}$ alkoxy, and C$_{3-6}$ cycloalkyl; u and v are each independently 0, 1, 2, 3, or 4; and R$_{a0}$ and R$_{b0}$ are each independently hydrogen or C$_{1-3}$ alkyl.

In an embodiment of the present invention, the group-S substituent is halogen.

In an embodiment of the present invention, the group-S substituent is selected from C$_{1-3}$ alkyl, —(CH$_2$)$_u$-3- to 6-membered heterocycloalkyl, —(CH$_2$)$_u$—SO$_2$C$_{1-3}$ alkyl, and —(CH$_2$)$_u$—NR$_{a0}$R$_{b0}$, where the 3- to 6-membered heterocycloalkyl has 1, 2, or 3 heteroatoms selected from N, O, and S as ring atoms; the 3- to 6-membered heterocycloalkyl is optionally substituted by 1, 2, or 3 substituents selected from halogen, cyano, —C$_{1-3}$ alkyl, —C$_{1-3}$ alkoxy, and C$_{3-6}$ cycloalkyl; u is 0, 1, 2, 3, or 4; and R$_{a0}$ and R$_{b0}$ are each independently hydrogen or C$_{1-3}$ alkyl.

In an embodiment of the present invention, in the above-mentioned groups (e.g., Ar, R$_0$), the C$_{6-10}$ aryl is independently phenyl or naphthyl.

In an embodiment of the present invention, in the above-mentioned groups (e.g., Ar), when the C$_{6-10}$ aryl is phenyl, it has a structure selected from:

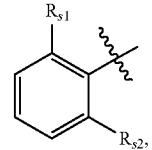

where R$_{s1}$ and R$_{s2}$ are as defined above.

In an embodiment of the present invention, in the above-mentioned groups (e.g., Ar, R$_0$), the 5- or 6-membered monocyclic heteroaryl is independently selected from thiophene, N-alkylcyclopyrrole, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine, and pyrazine.

In an embodiment of the present invention, in the above-mentioned groups (e.g., Ar, R$_0$), the 5- or 6-membered monocyclic heteroaryl each independently has a structure selected from:

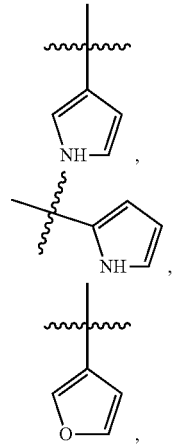

-continued
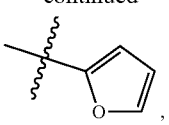,
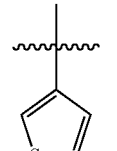,
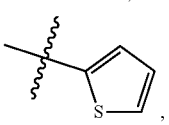,
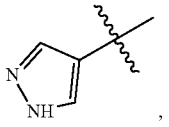,
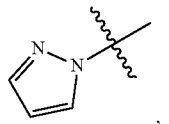,
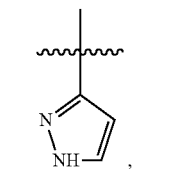,
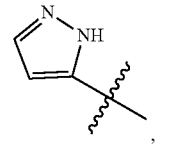,
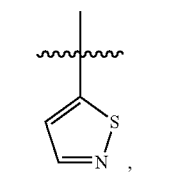,
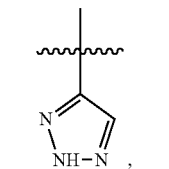,
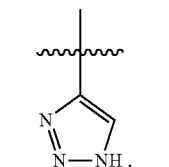,
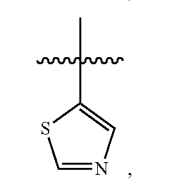,
-continued
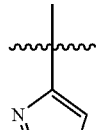,
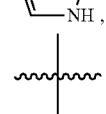,
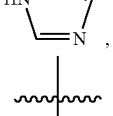,
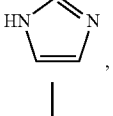,
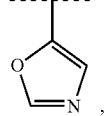,
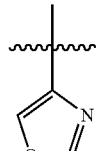,
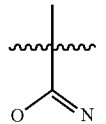,
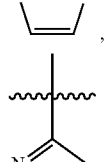,
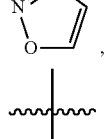,
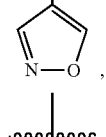,
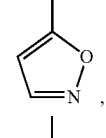,
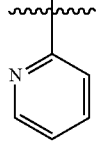, -continued

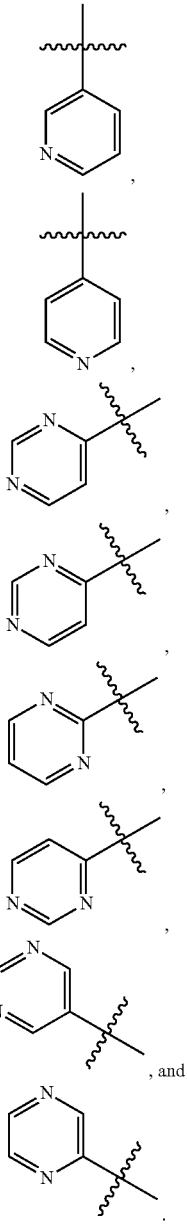

, and

In an embodiment of the present invention, in the above-mentioned groups (e.g., Ar, R₀), the 8- to 10-membered bicyclic heteroaryl is independently 9- to 10-membered bicyclic heteroaryl formed by a benzene ring fused with a 5- or 6-membered monocyclic heteroaryl ring, or 8- to 10-membered bicyclic heteroaryl formed by a 5- or 6-membered monocyclic heteroaryl ring fused with a 5- or 6-membered monocyclic heteroaryl ring.

In an embodiment of the present invention, the 5- or 6-membered monocyclic heteroaryl ring forming the 9- to 10-membered bicyclic heteroaryl or the 8- to 10-membered bicyclic heteroaryl is selected from a thiophene ring, an N-alkylcyclopyrrole ring, a furan ring, a thiazole ring, an isothiazole ring, an imidazole ring, an oxazole ring, a pyrrole ring, a pyrazole ring, a triazole ring, a 1,2,3-triazole ring, a 1,2,4-triazole ring, a 1,2,5-triazole ring, a 1,3,4-triazole ring, a tetrazole ring, an isoxazole ring, an oxadiazole ring, a 1,2,3-oxadiazole ring, a 1,2,4-oxadiazole ring, a 1,2,5-oxa- diazole ring, a 1,3,4-oxadiazole ring, a thiadiazole ring, a pyridine ring, a pyridazine ring, a pyrimidine ring, or a pyrazine ring.

In an embodiment of the present invention, the 5- or 6-membered monocyclic heteroaryl ring forming the 9- to 10-membered bicyclic heteroaryl or the 8- to 10-membered bicyclic heteroaryl has a structure selected from:

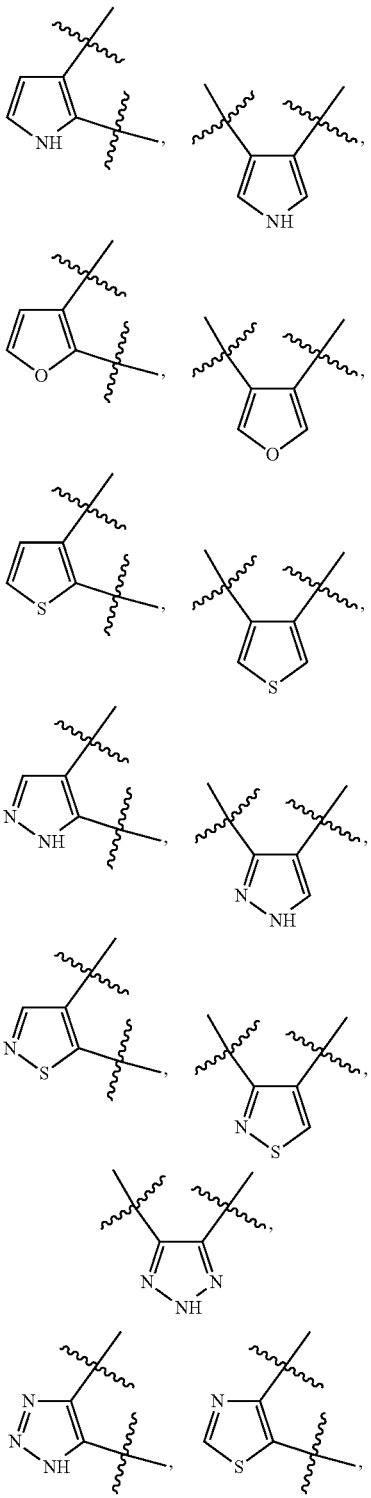

-continued

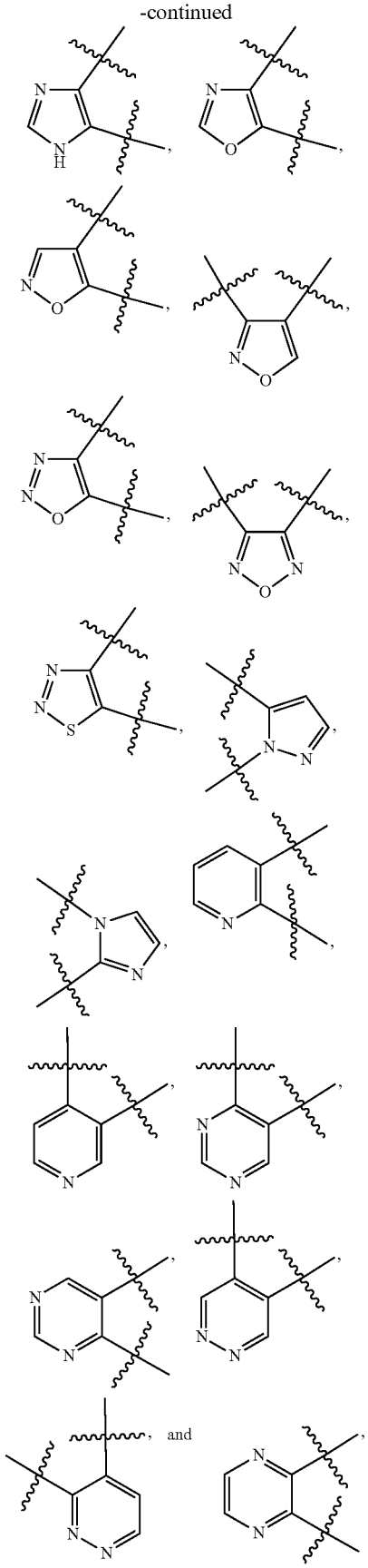

where two linked ring atoms represented by "⁓" are a pair of adjoining atoms shared when fused with other ring.

In an embodiment of the present invention, in the ring B1 and the ring A1, the 5- or 6-membered monocyclic heteroaryl ring is independently selected from a thiophene ring, an N-alkylcyclopyrrole ring, a furan ring, a thiazole ring, an isothiazole ring, an imidazole ring, an oxazole ring, a pyrrole ring, a pyrazole ring, a triazole ring, a 1,2,3-triazole ring, a 1,2,4-triazole ring, a 1,2,5-triazole ring, a 1,3,4-triazole ring, a tetrazole ring, an isoxazole ring, an oxadiazole ring, a 1,2,3-oxadiazole ring, a 1,2,4-oxadiazole ring, a 1,2,5-oxadiazole ring, a 1,3,4-oxadiazole ring, a thiadiazole ring, a pyridine ring, a pyridazine ring, a pyrimidine ring, or a pyrazine ring.

In an embodiment of the present invention, in the ring B1 and the ring A1, the 5- or 6-membered monocyclic heteroaryl ring independently has a structure selected from:

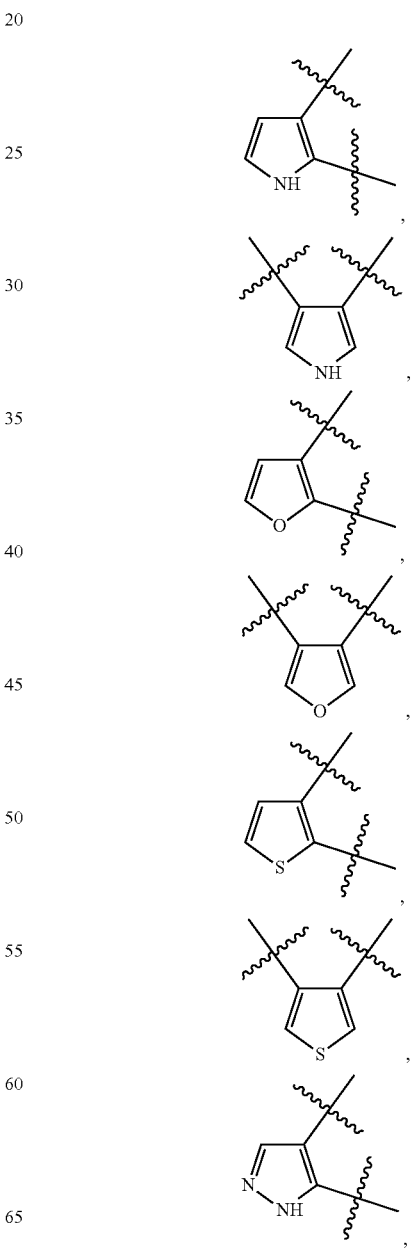

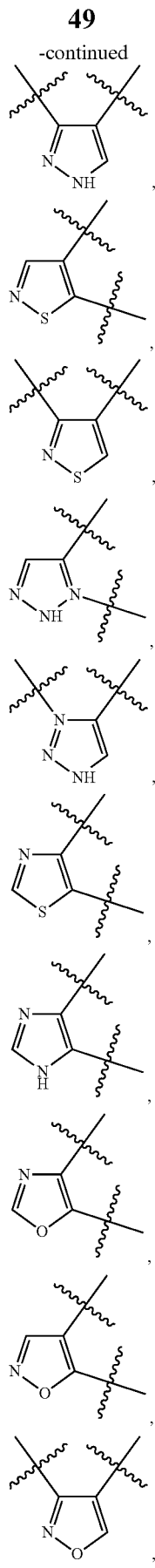
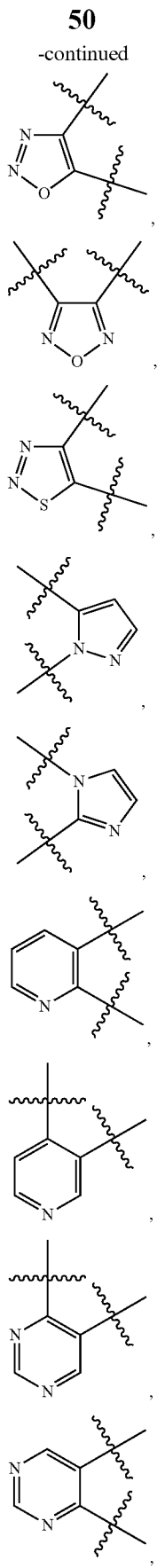

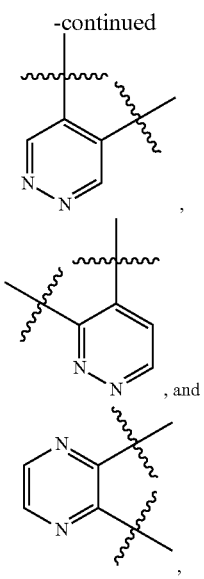

where two linked ring atoms represented by "~~" are a pair of adjoining atoms shared when fused with other ring.

In an embodiment of the present invention, in the ring B2 and the ring A2, the fused 5- or 6-membered monocyclic cycloalkyl ring is independently selected from a cyclopentyl ring, a cyclopentenyl ring, a cyclohexyl ring, a cyclohexenyl ring, a cyclohexadienyl ring, cyclopentanone, cyclopentan-1,3-dione, cyclohexanone, and cyclohexan-1,3-dione.

In an embodiment of the present invention, in the ring B2 and the ring A2, the fused 5- or 6-membered monocyclic heterocycloalkyl ring is independently selected from oxazolidine, pyrrolidin-2-one, pyrrolidin-2,5-dione, 1,3-dioxolane, dihydrofuro-2(3H)-one, dihydrofuro-2,5-dione, piperidin-2-one, piperidin-2,6-dione, tetrahydro-2H-pyran-2-one, imidazolidine, tetrahydrofuran, tetrahydrothiophene, tetrahydropyrrole, 1,3-dioxolan-2-one, oxazolidin-2-one, imidazolidin-2-one, piperidine, piperazine, piperazin-2-one, morpholine, morpholin-3-one, morpholin-2-one, thiomorpholin-3-one1,1-dioxide, thiomorpholine, thiomorpholin-1,1-dioxide, tetrahydropyrane, 1,2-dihydroazacyclobutadiene, 1,2-dihydrooxacyclobutadiene, 2,5-dihydro-1H-pyrrole, 2,5-dihydrofuran, 2,3-dihydrofuran, 2,3-dihydro-1H-pyrrole, 3,4-dihydro-2H-pyrane, 1,2,3,4-tetrahydropyridine, 3,6-dihydro-2H-pyrane, 1,2,3,6-tetrahydropyridine, 1,3-oxazinane, hexahydropyrimidine, 1,4-dioxane, tetrahydropyrimidin-2(1H)-one, 1,4-dioxan-2-one, 5,6-dihydro-2H-pyran-2-one, 5,6-dihydropyrimidin-4(3H)-one, 3,4-dihydropyridin-2(1H)-one, 5,6-dihydropyridin-2(1H)-one, 5,6-dihydropyrimidin-4(1H)-one, pyrimidin-4(3H)-one, pyrimidin-4(1H)-one, 4,5-dihydro-1H-imidazole, 2,3-dihydro-1H-imidazole, 2,3-dihydrooxazole, 1,3-dioxole, 2,3-dihydrothiophene, 2,5-dihydrothiophene, 3,4-dihydro-2H-1,4-oxazine, 3,4-dihydro-2H-1,4-thiazin1,1-dioxide, 1,2,3,4-tetrahydropyrazine, 1,3-dihydro-2H-pyrrol-2-one, 1,5-dihydro-2H-pyrrol-2-one, 1H-pyrrol-2,5-dione, furo-2(3H)-one, furo-2(5H)-one, 1,3-dioxol-2-one, oxazol-2(3H)-one, 1,3-dihydro-2H-imidazol-2-one, furo-2,5-dione, 3,6-dihydropyridin-2(1H)-one, pyridin-2,6-(1H, 3H)-dione, 5,6-dihydro-2H-pyran-2-one, 3,6-dihydro-2H-pyran-2-one, 3,4-dihydro-2H-1,3-oxazine, 3,6-dihydro-2H-1,3-oxazine, and 1,2,3,4-tetrahydropyrimidine.

In an embodiment of the present invention, the fused 5- or 6-membered monocyclic heterocycloalkyl ring has a structure selected from:

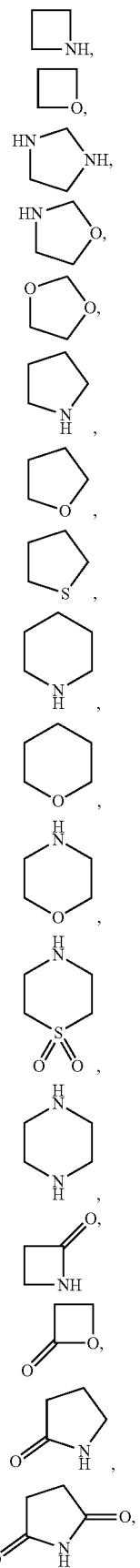

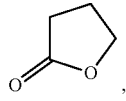,
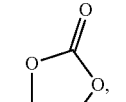,
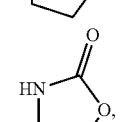,
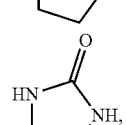,
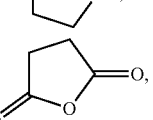,
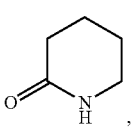,
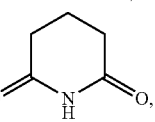,
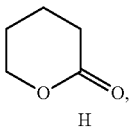,
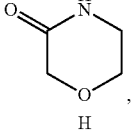,
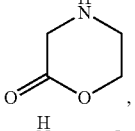,
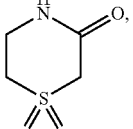,
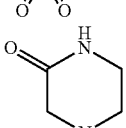,
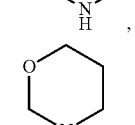,
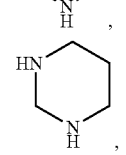,

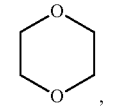,
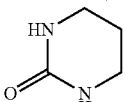,
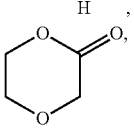,
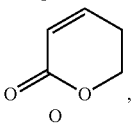,
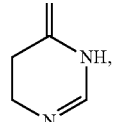,
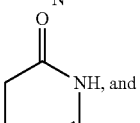 and
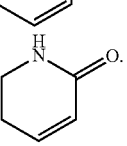.

In an embodiment of the present invention, in the above-mentioned groups (e.g., Ar, $R_O$), the 8- to 10-membered bicyclic heteroaryl is independently selected from benzoxazole, benzoisoxazole, benzoimidazole, benzothiazole, benzoisothiazole, benzotriazole, benzofuran, benzothiophene, indole, indazole, isoindole, quinoline, isoquinoline, quinazoline, quinoxaline, cinnoline, pyridopyrimidine, and naphthyridine.

In an embodiment of the present invention, in the above-mentioned groups (e.g., Ar, $R_O$), the 8- to 10-membered bicyclic heteroaryl is independently selected from benzo[d]isoxazole, H-indole, isoindole, 1H-benzo[d]imidazole, benzo[d]isothiazole, 1H-benzo[d][1,2,3]triazole, benzo[d]oxazole, benzo[d]thiazole, indazole, benzofuran, benzo[b]thiophene, quinoline, isoquinoline, quinazoline, quinoxaline, cinnoline, pyrido[3,2-d]pyrimidine, pyrido[2,3-d]pyrimidine, pyrido[3,4-d]pyrimidine, pyrido[4,3-d]pyrimidine, 1,8-naphthyridine, 1,7-naphthyridine, 1,6-naphthyridine, and 1,5-naphthyridine.

In an embodiment of the present invention, in the above-mentioned groups (e.g., Ar, $R_O$), the 8- to 10-membered bicyclic heteroaryl independently has a structure selected from:

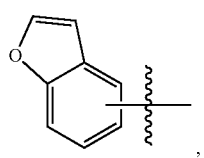,

-continued
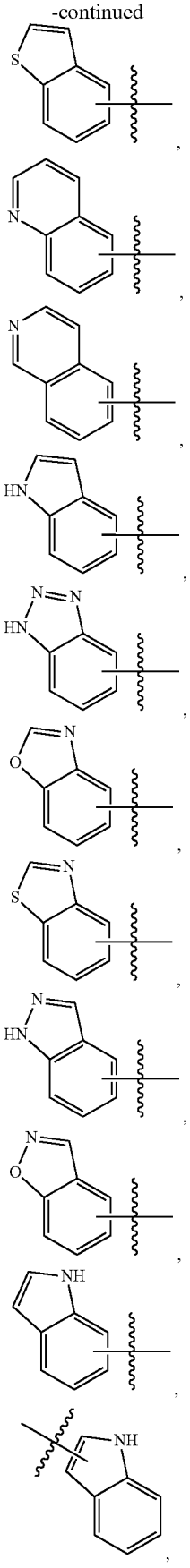
-continued
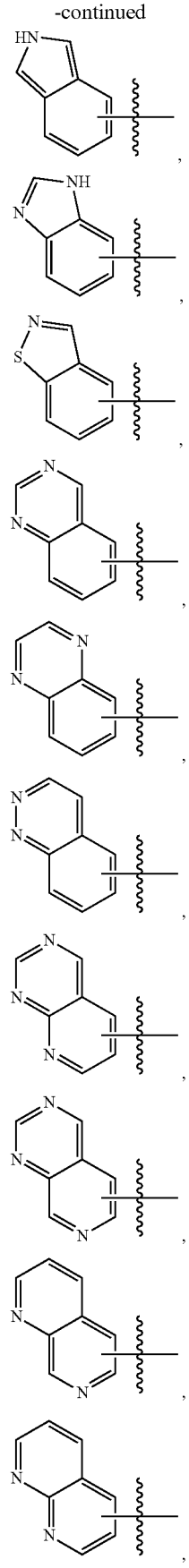

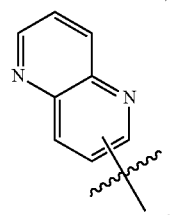

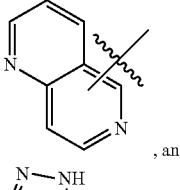

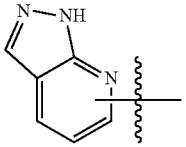, and

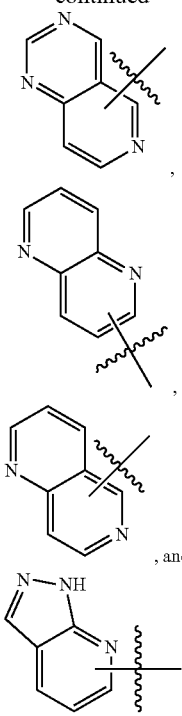

In an embodiment of the present invention, in the above-mentioned groups (e.g., Ar, $R_O$), the 8- to 10-membered bicyclic heteroaryl independently has a structure selected from:

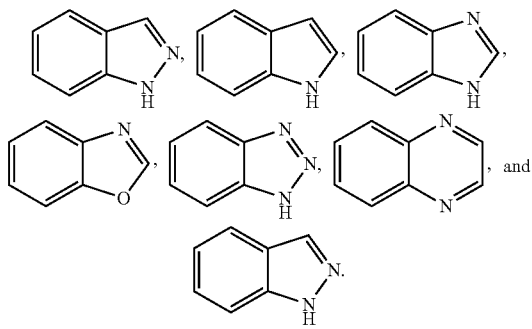, and

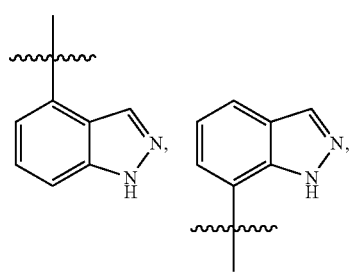

In an embodiment of the present invention, in the above-mentioned groups (e.g., Ar, $R_O$), the 8- to 10-membered bicyclic heteroaryl independently has a structure selected from:

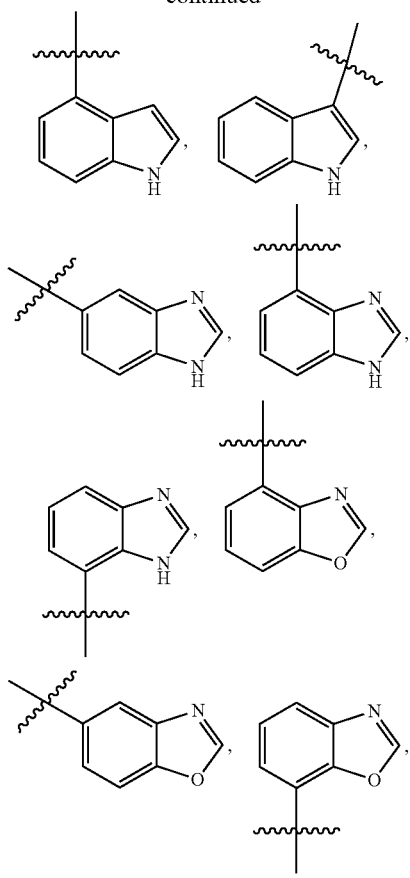

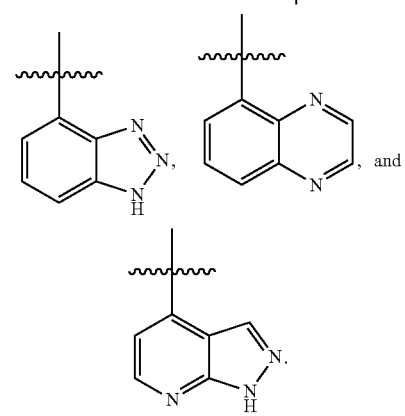

In an embodiment of the present invention,

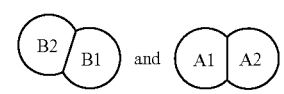 and 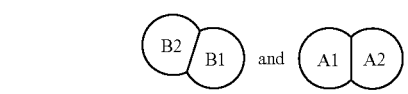

are each independently selected from:

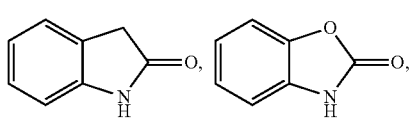

-continued
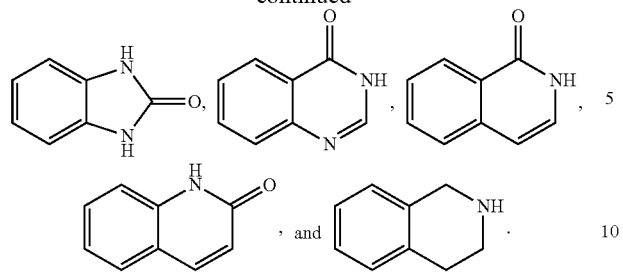
In an embodiment of the present invention, Formula (B) and Formula (A-1) are each independently selected from:
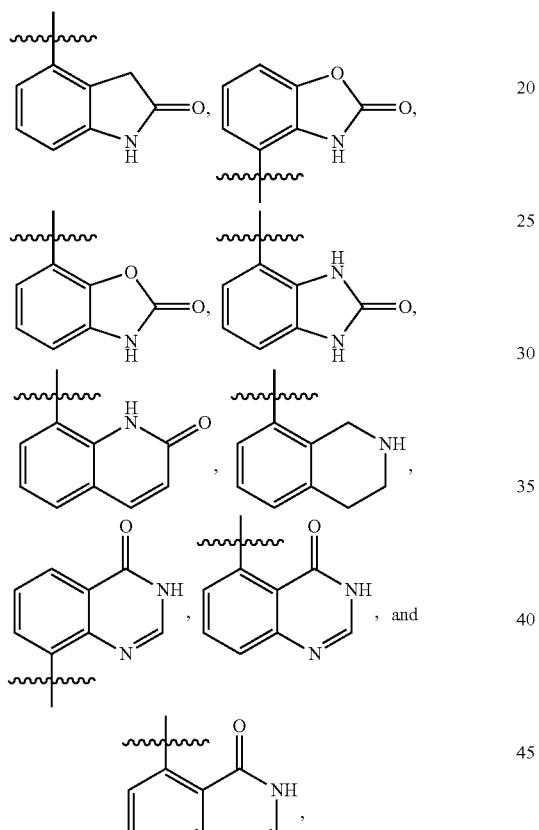
In an embodiment of the present invention, Ar and Ar' each independently have a structure selected from:
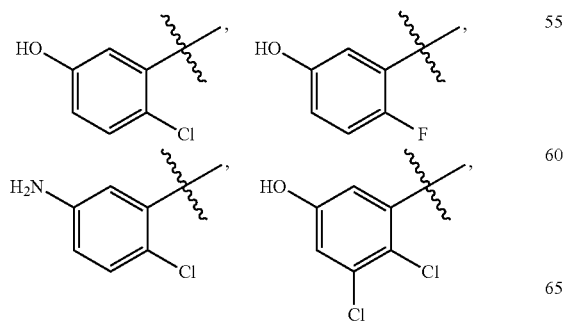
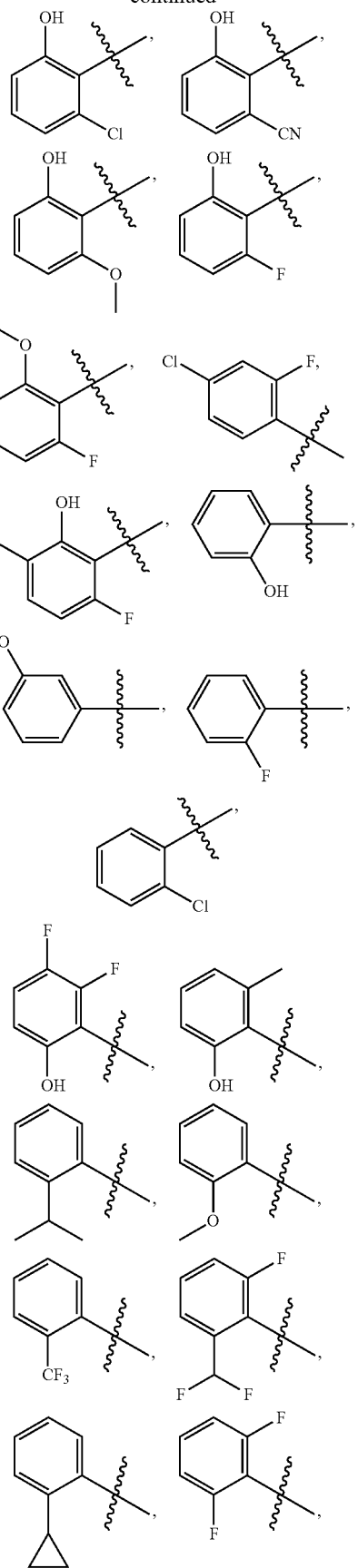

-continued
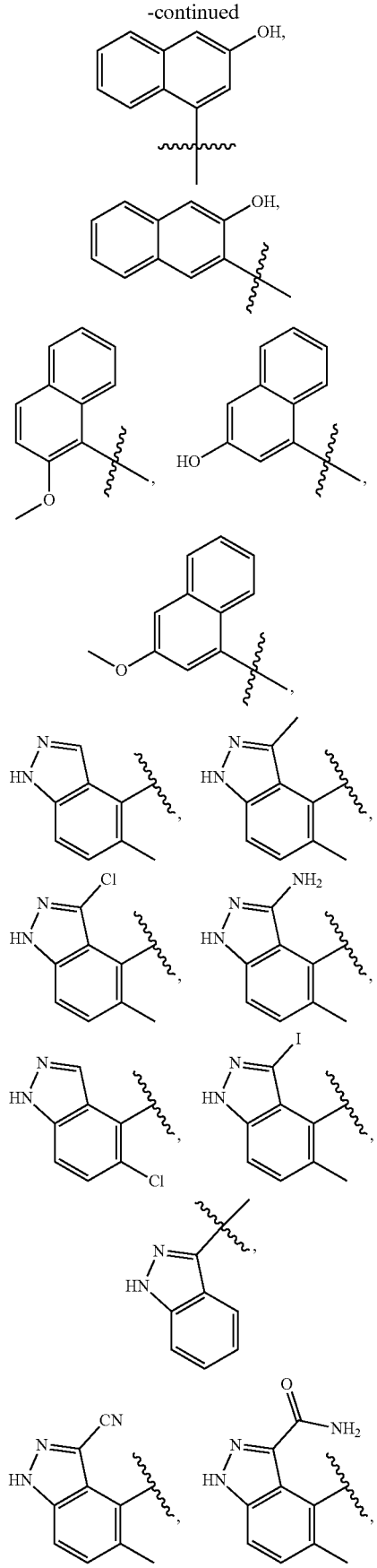
-continued
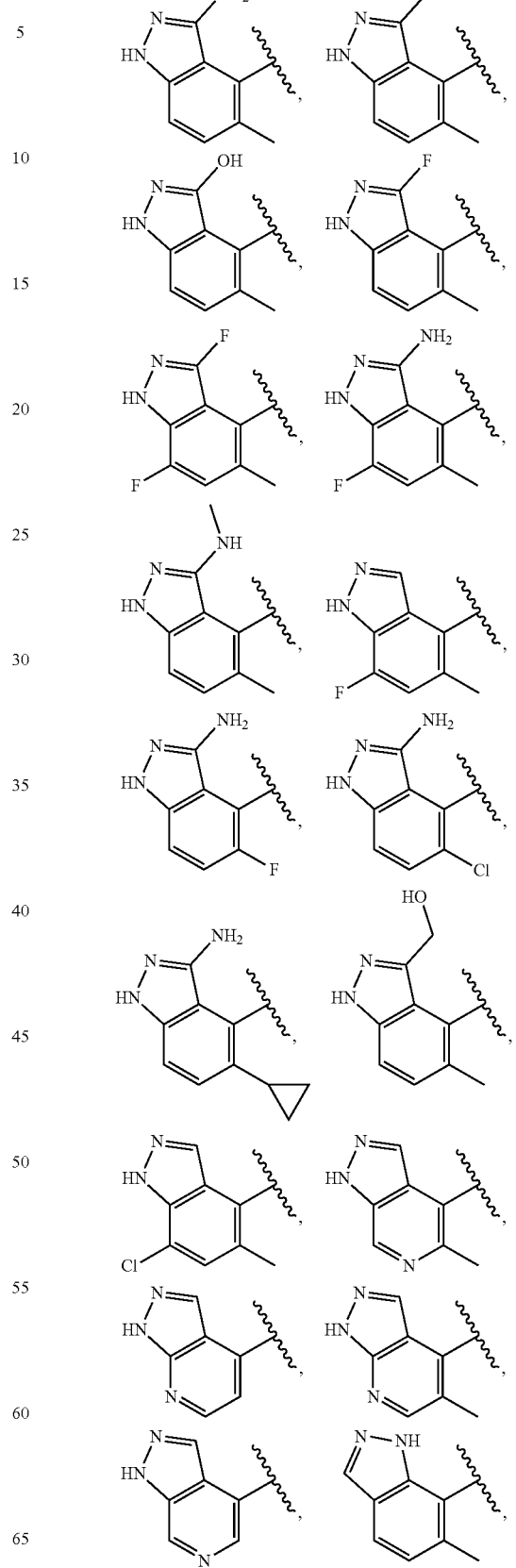

-continued
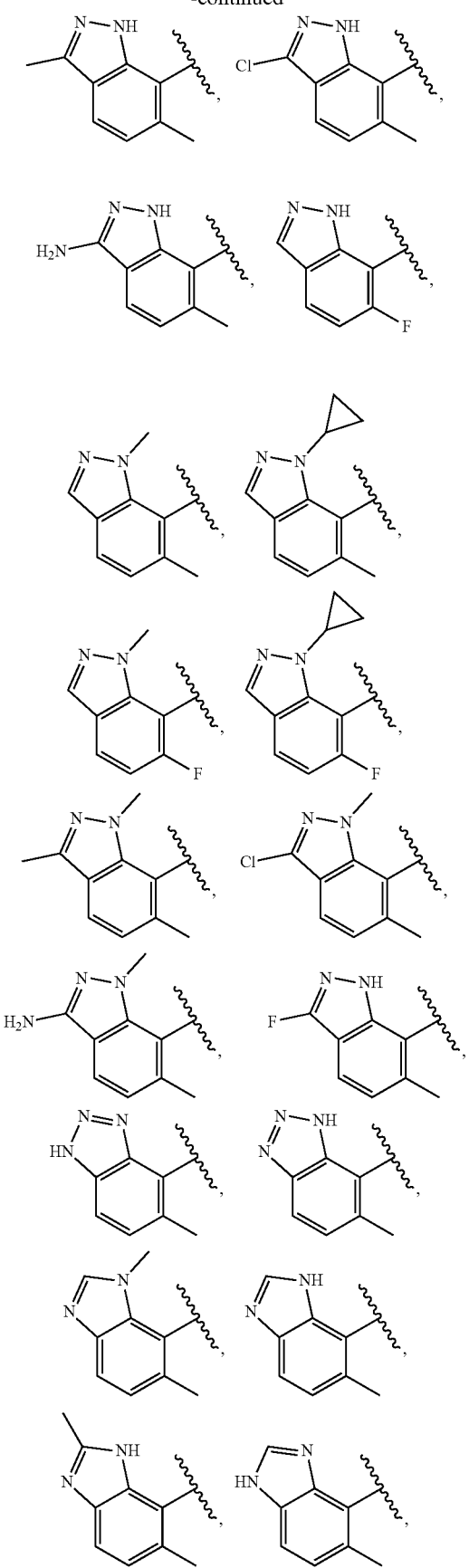
-continued
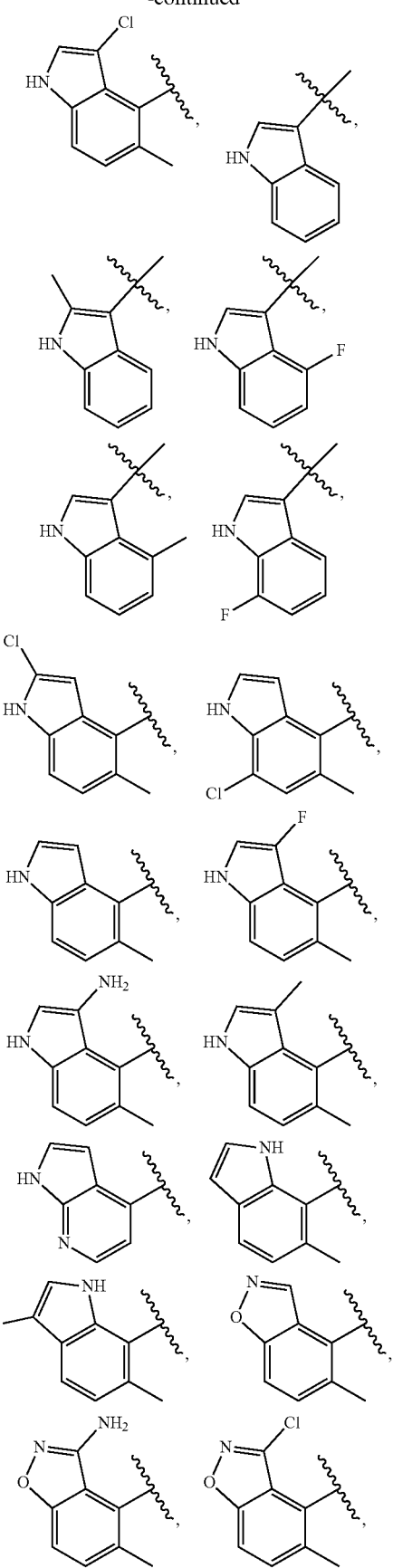

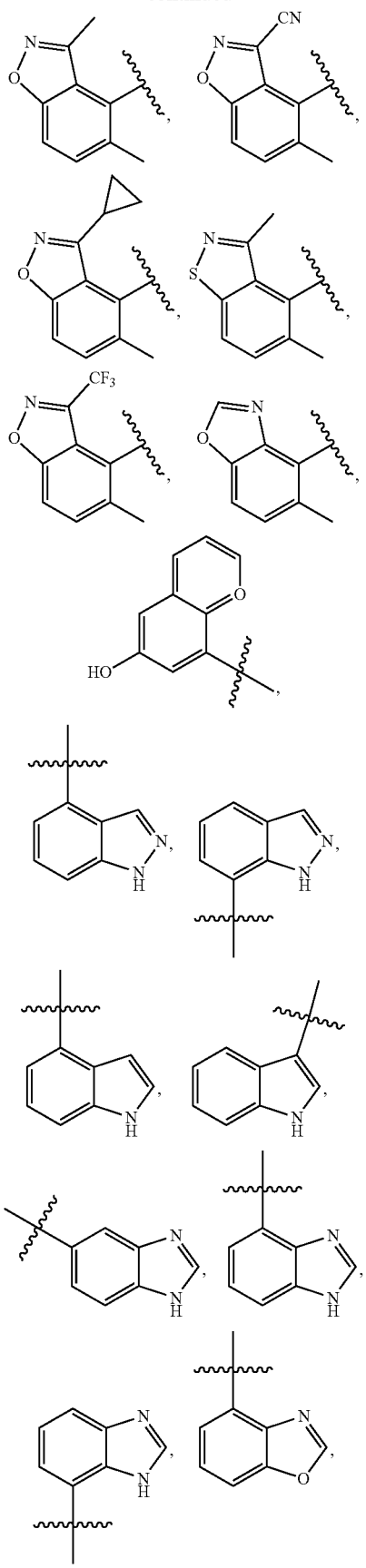
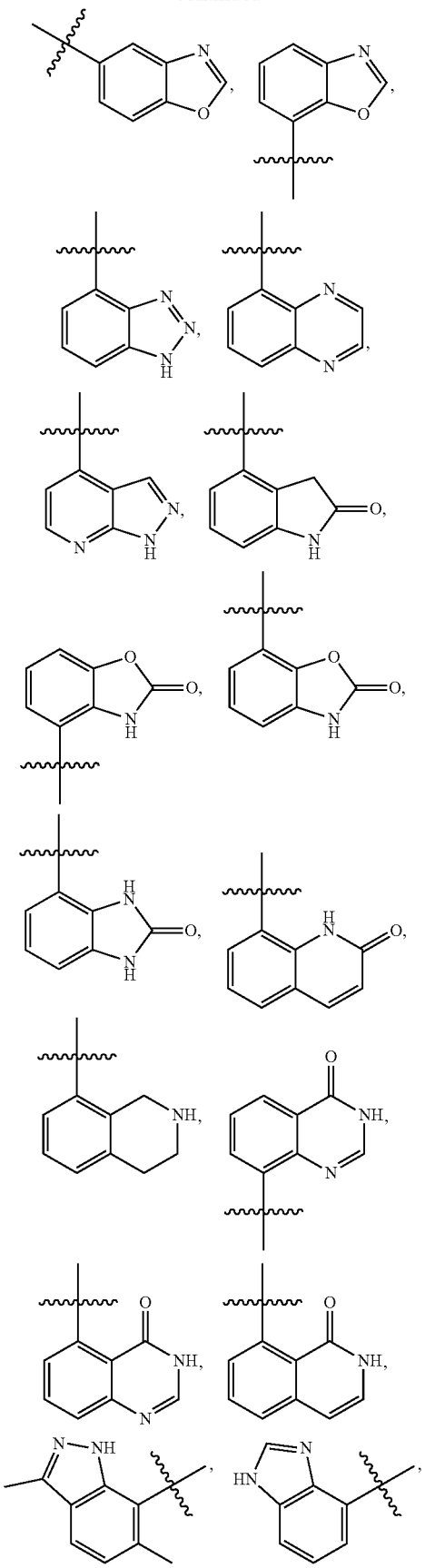

-continued
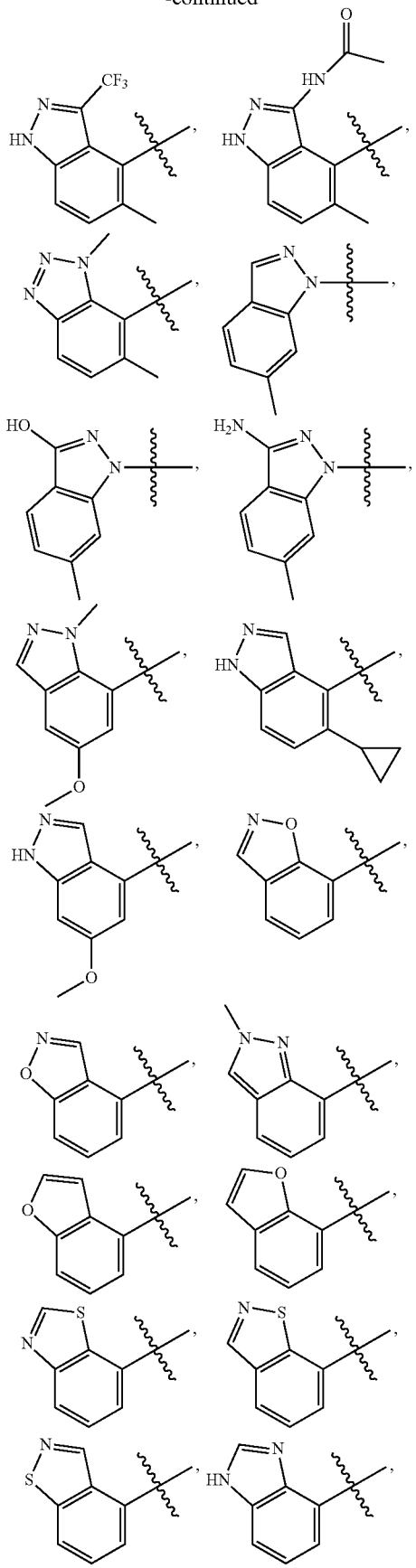
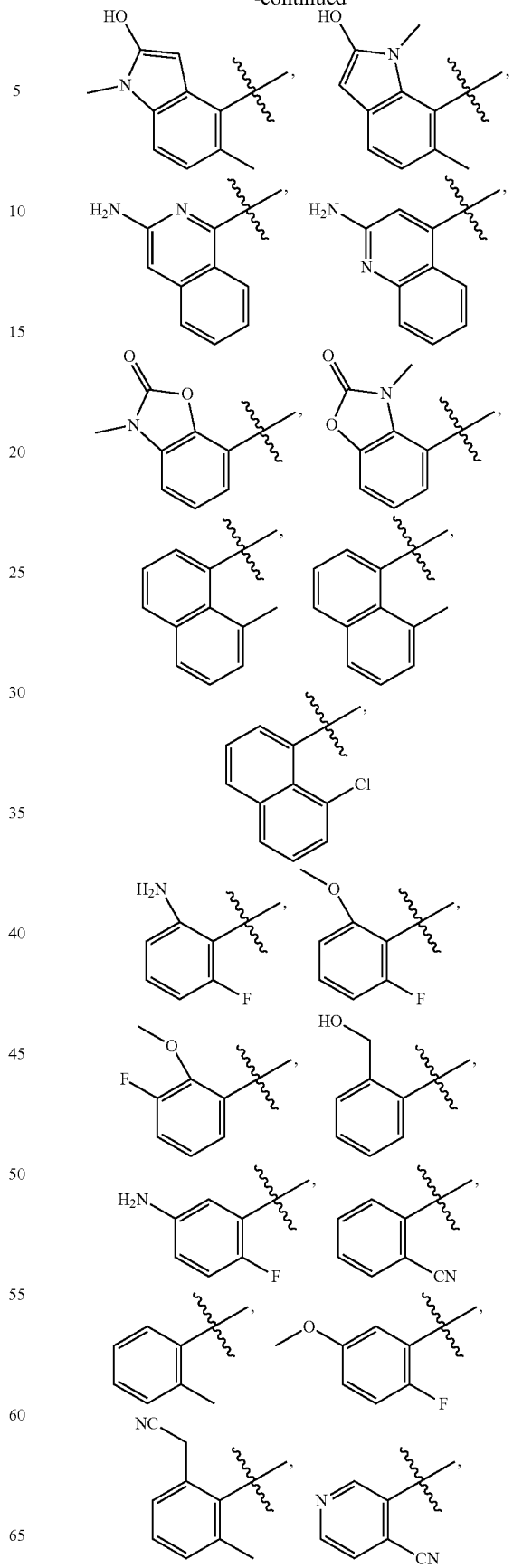

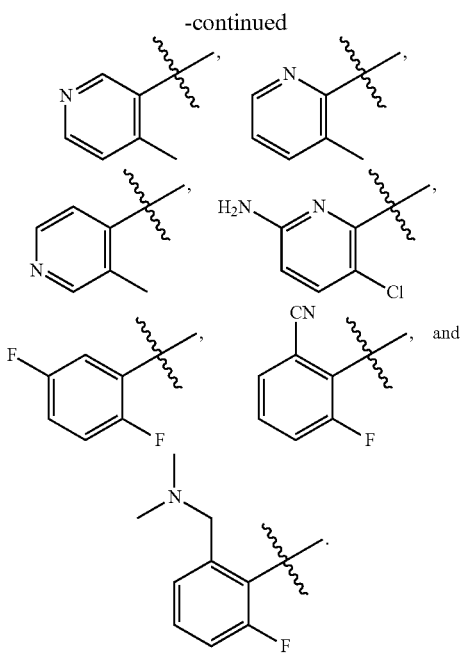

In an embodiment of the present invention, in the above-mentioned groups (e.g., $R_0$), the $C_{3-6}$ cycloalkyl is selected from cyclopropyl, cyclobutyl, cyclopentyl, cyclopentenyl, cyclohexyl, cyclohexenyl, cyclohexadienyl, cyclobutanone, cyclobutan-1,2-dione, cyclopentanone, cyclopentan-1,3-dione, cyclohexanone, and cyclohexan-1,3-dione.

In an embodiment of the present invention, in the above-mentioned groups (e.g., $R_0$), the 3- to 6-membered heterocycloalkyl is selected from aziridine, ethylene oxide, azetidine, oxetane, oxazolidine, 1,3-dioxolane, imidazolidine, tetrahydrofuran, tetrahydrothiophene, tetrahydropyrrole, piperidine, piperazine, morpholine, thiomorpholine, thiomorpholin-1,1-dioxide, tetrahydropyrane, 1,3-oxazinane, hexahydropyrimidine, and 1,4-dioxane.

In an embodiment of the present invention, in the above-mentioned groups (e.g., $R_0$), the 7- to 11-membered spirocycloalkyl is a monospirocycloalkyl containing one spiro-atom that is formed by any two monocyclic cycloalkyl groups each selected from a cyclopropyl ring, a cyclobutyl ring, a cyclopentyl ring, and a cyclohexyl ring.

In an embodiment of the present invention, $R_0$ is —$C_{1-6}$ alkyl, —$C_{3-6}$ cycloalkyl, 3- to 6-membered heterocycloalkyl, phenyl, 5- or 6-membered monocyclic heteroaryl, 8- to 10-membered bicyclic heteroaryl, 7- to 11-membered spirocycloalkyl, —$CH_2$-phenyl, —$CH(C_{1-2}$ alkyl)-phenyl, —$CH_2$-5- or 6-membered monocyclic heteroaryl, —CH($C_{1-2}$ alkyl)-5- or 6-membered monocyclic heteroaryl, —NH-phenyl, —N($C_{1-3}$ alkyl)-phenyl, —O-phenyl, —$CH_2$-3- to 6-membered heterocycloalkyl, —$CH_2$—$C_{3-6}$ cycloalkyl, —CH($C_{1-2}$ alkyl)-$C_{3-6}$ cycloalkyl, where the $C_{1-6}$ alkyl, the $C_{3-6}$ cycloalkyl, the 3- to 6-membered heterocycloalkyl, the phenyl, the 5- or 6-membered monocyclic heteroaryl, the 8- to 10-membered bicyclic heteroaryl, and the 7- to 11-membered spirocycloalkyl are unsubstituted or each substituted by 1, 2, 3, or 4 groups each independently selected from $R_{s3}$.

In an embodiment of the present invention, $R_0$ is phenyl, cyclopropyl, 5- or 6-membered monocyclic heteroaryl, —$CH_2$-5- or 6-membered monocyclic heteroaryl, —$CH_2$-phenyl, —CH($C_{1-2}$ alkyl)-phenyl, —NH-phenyl, —N($C_{1-3}$ alkyl)-phenyl, or —O-phenyl, where the 5- or 6-membered monocyclic heteroaryl is selected from thiophene, N-alkyl-cyclopyrrole, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine, and pyrazine; and the phenyl and the 5- or 6-membered monocyclic heteroaryl are unsubstituted or each substituted by 1, 2, 3, or 4 groups each independently selected from $R_{s3}$.

In an embodiment of the present invention, $R_0$ has a structure selected from:

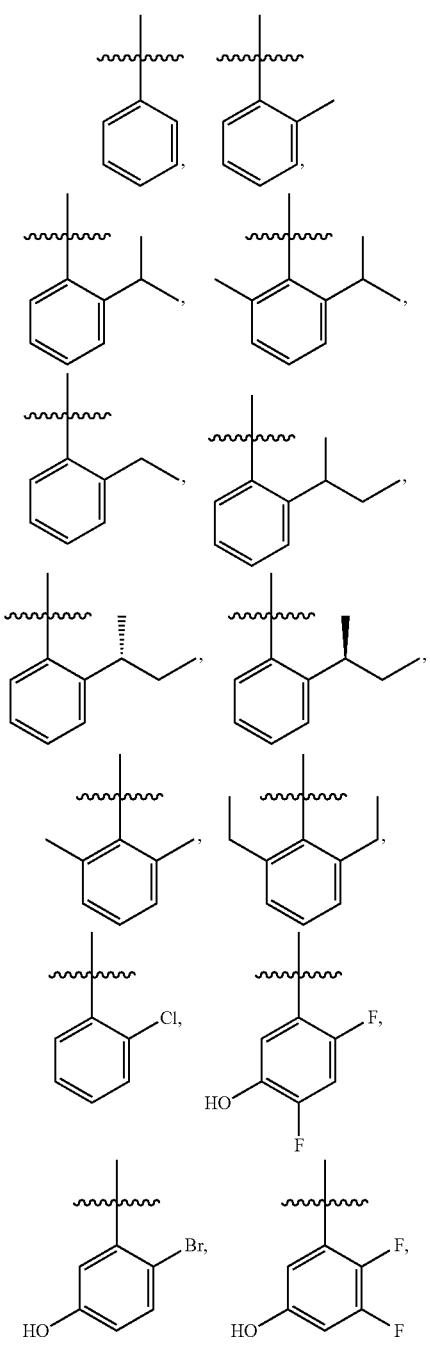

-continued
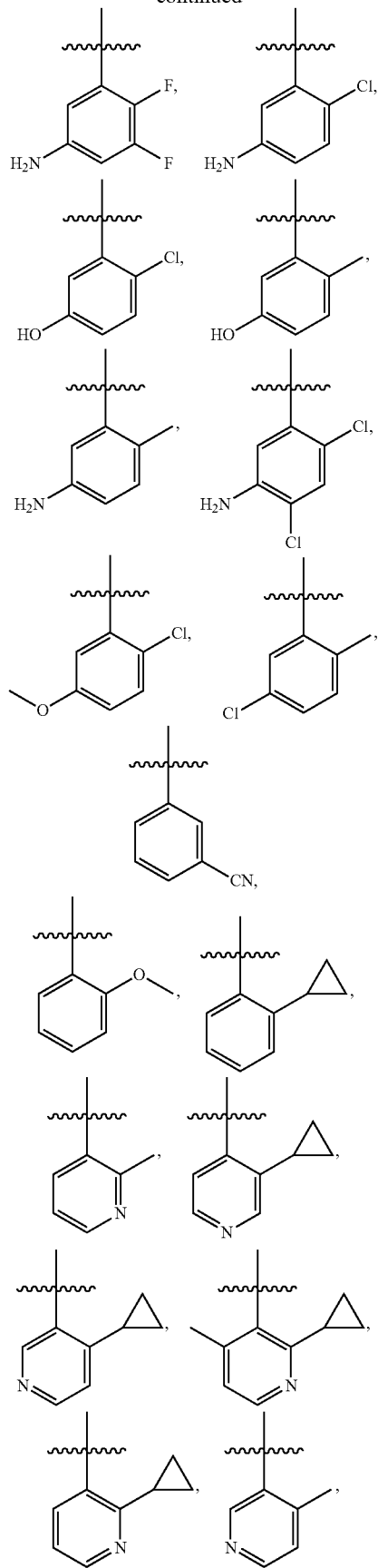
-continued
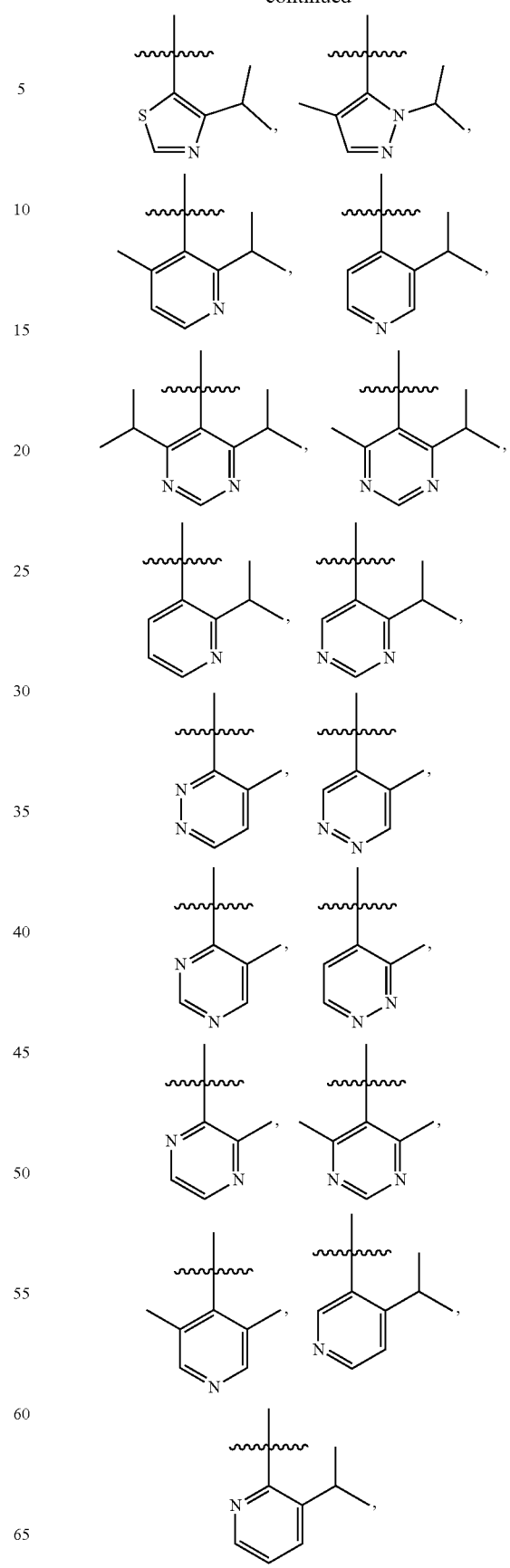

-continued
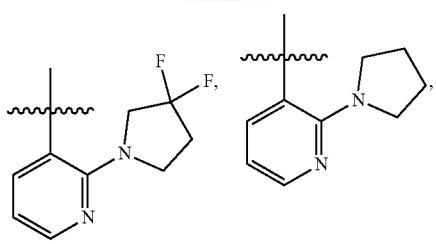
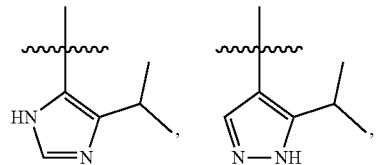
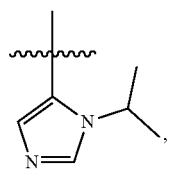
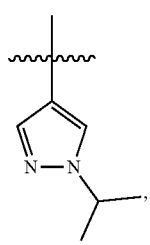
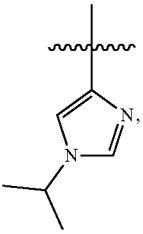
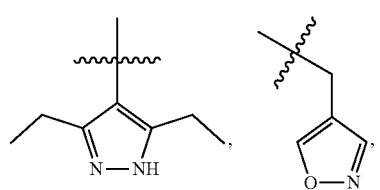
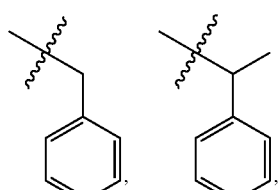
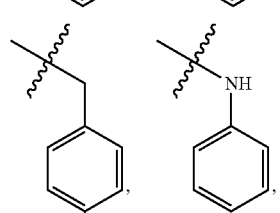
-continued
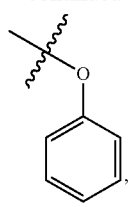
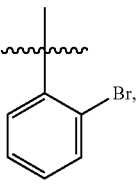
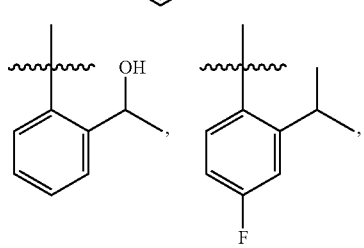
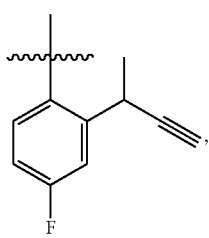
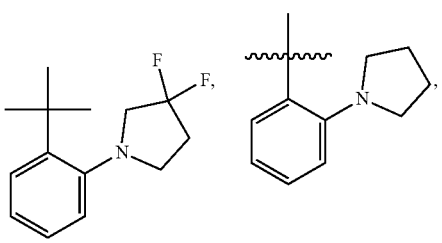
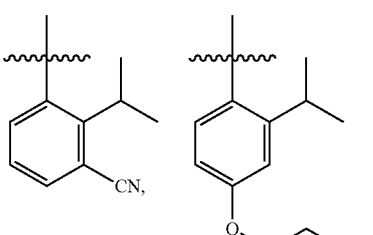
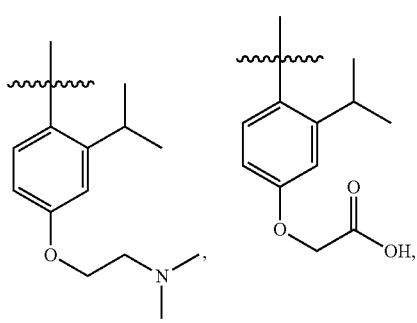

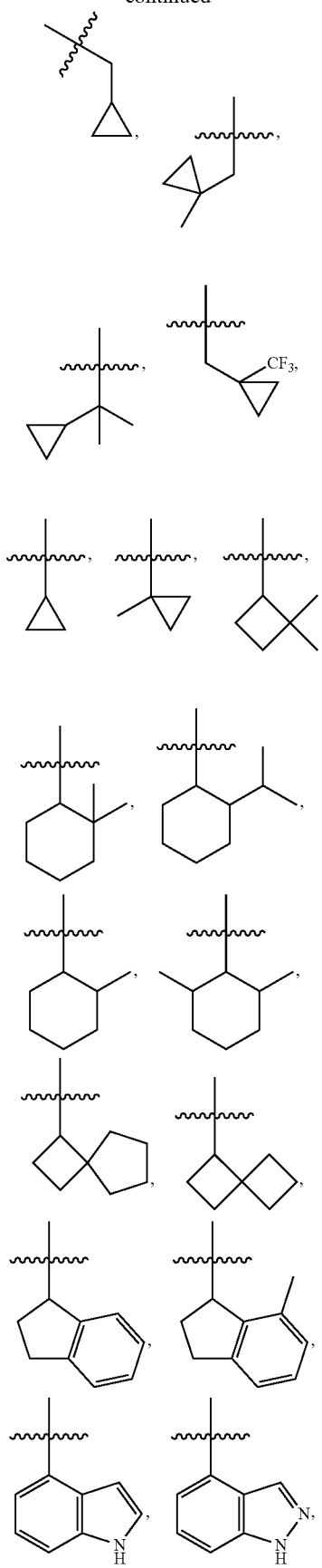

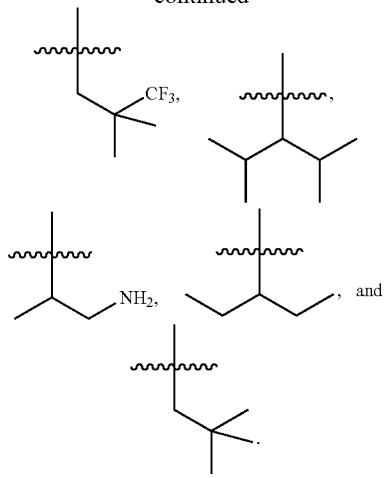

In an embodiment of the present invention, $R_{11}$ and $R_{12}$ are either identical or different and are each independently hydrogen, halogen, —$C_{1-3}$ alkyl, —$CH_2$-hydroxyl, —$CH_2$-cyano, —$CH_2$—$C_{1-3}$ alkoxy, —$CH_2$-halogenated $C_{1-3}$ alkyl, or —$CH_2$—$C_{1-3}$ haloalkoxy.

In an embodiment of the present invention, $R_1$ and $R_{12}$ are either identical or different and are each independently hydrogen, halogen, methyl, ethyl, n-propyl, isopropyl, —$CH_2$-hydroxyl, —$CH_2$-cyano, —$CH_2$-methoxy, —$CH_2$-ethoxy, —$CH_2$-propoxy (n-propoxy), —$CH_2$-isopropoxy, —$CH_2$-trifluoromethyl, —$CH_2$-difluoromethyl, —$CH_2$-difluoroethyl, —$CH_2$-trifluoromethoxy, or —$CH_2$-difluoromethoxy.

In an embodiment of the present invention, $R_{11}$ and $R_{12}$ are either identical or different and are each independently hydrogen or —$C_{1-3}$ alkyl.

In an embodiment of the present invention, $R_{11}$ and $R_{12}$ are either identical or different and are each independently hydrogen or methyl.

In an embodiment of the present invention, $R_{21}$ and $R_{22}$ are either identical or different and are each independently hydrogen, halogen, —$C_{1-3}$ alkyl, —$CH_2$-hydroxyl, —$CH_2$-cyano, —$CH_2$—$C_{1-3}$ alkoxy, —$CH_2$-halogenated $C_{1-3}$ alkyl, or —$CH_2$—$C_{1-3}$ haloalkoxy.

In an embodiment of the present invention, $R_{21}$ and $R_{22}$ are either identical or different and are each independently hydrogen, halogen, methyl, ethyl, n-propyl, isopropyl, —$CH_2$-hydroxyl, —$CH_2$-cyano, —$CH_2$-methoxy, —$CH_2$-ethoxy, —$CH_2$-propoxy (n-propoxy), —$CH_2$-isopropoxy, —$CH_2$-trifluoromethyl, —$CH_2$-difluoromethyl, —$CH_2$-difluoroethyl, —$CH_2$-trifluoromethoxy, or —$CH_2$-difluoromethoxy.

In an embodiment of the present invention, $R_2$, and $R_{22}$ are either identical or different and are each independently hydrogen or —$C_{1-3}$ alkyl.

In an embodiment of the present invention, $R_{21}$ and $R_{22}$ are either identical or different and are each independently hydrogen or methyl.

In an embodiment of the present invention, $R_{31}$ and $R_{32}$ are either identical or different and are each independently hydrogen, halogen, —$C_{1-3}$ alkyl, —$CH_2$-hydroxyl, —$CH_2$-cyano, —$CH_2$—$C_{1-3}$ alkoxy, —$CH_2$-halogenated $C_{1-3}$ alkyl, or —$CH_2$—$C_{1-3}$ haloalkoxy.

In an embodiment of the present invention, $R_{31}$ and $R_{32}$ are either identical or different and are each independently hydrogen, halogen, methyl, ethyl, n-propyl, isopropyl, —CH$_2$-hydroxyl, —CH$_2$-cyano, —CH$_2$-methoxy, —CH$_2$-ethoxy, —CH$_2$-propoxy (n-propoxy), —CH$_2$-isopropoxy, —CH$_2$-trifluoromethyl, —CH$_2$-difluoromethyl, —CH$_2$-difluoroethyl, —CH$_2$-trifluoromethoxy, or —CH$_2$-difluoromethoxy.

In an embodiment of the present invention, R$_{31}$ and R$_{32}$ are either identical or different and are each independently hydrogen or —C$_{1-3}$ alkyl.

In an embodiment of the present invention, R$_{31}$ and R$_{32}$ are either identical or different and are each independently hydrogen or methyl.

In an embodiment of the present invention, R$_{41}$ is hydrogen, halogen, —C$_{1-3}$ alkyl, —CH$_2$-hydroxyl, —CH$_2$-cyano, —CH$_2$—C$_{1-3}$ alkoxy, —CH$_2$-halogenated C$_{1-3}$ alkyl, or —CH$_2$—C$_{1-3}$ haloalkoxy.

In an embodiment of the present invention, R$_{41}$ is hydrogen, halogen, methyl, ethyl, n-propyl, isopropyl, —CH$_2$-hydroxyl, —CH$_2$-cyano, —CH$_2$-methoxy, —CH$_2$-ethoxy, —CH$_2$-propoxy (n-propoxy), —CH$_2$-isopropoxy, —CH$_2$-trifluoromethyl, —CH$_2$-difluoromethyl, —CH$_2$-difluoroethyl, —CH$_2$-trifluoromethoxy, or —CH$_2$-difluoromethoxy.

In an embodiment of the present invention, R$_{41}$ is hydrogen.

In an embodiment of the present invention, in Formula I, when the dashed line in $$\overset{R_{42}}{\underset{P}{\vdots}}$$

is a single bond, P is O; R$_{42}$ is —C$_{1-3}$ alkyl-, —C$_{1-3}$ alkyl (hydroxy)-, —C$_{1-3}$ alkyl (cyano)-, —C$_{1-3}$ alkyl (C$_{1-3}$alkyl), —C$_{1-3}$ alkyl (halogenated C$_{1-3}$ alkyl)-, —C$_{1-3}$ alkyl (C$_{1-3}$ alkyl-hydroxy)-, —C$_{1-3}$ alkyl (C$_{1-3}$ alkyl-cyano)-, —C$_{1-3}$ alkyl (C$_{1-3}$ alkoxy)-, or —C$_{1-3}$ alkyl (C$_{1-3}$ haloalkoxy)-, where C$_{1-3}$ alkyl is methyl, ethyl, or propyl (n-propyl or isopropyl); and C$_{1-3}$ alkoxy is methoxy, ethoxy, or propoxy (n-propoxy or isopropoxy).

In an embodiment of the present invention, in Formula I, when the dashed line in $$\overset{R_{42}}{\underset{P}{\vdots}}$$

is a single bond, P is NH or NR$^m$; R$^m$ is —C$_{1-3}$ alkyl, -halogenated C$_{1-3}$ alkyl, —C$_{1-3}$ alkyl-hydroxyl, —C$_{1-3}$ alkyl-cyano, —C$_{1-3}$ alkyl-C$_{1-3}$ alkoxy, or —C$_{1-3}$ alkyl-C$_{1-3}$ haloalkoxy; R$_{42}$ is —(C=O)—, —C$_{1-3}$ alkyl-, —C$_{1-3}$ alkyl (hydroxy)-, —C$_{1-3}$ alkyl (cyano)-, —C$_{1-3}$ alkyl (C$_{1-3}$ alkyl), —C$_{1-3}$ alkyl(halogenated C$_{1-3}$ alkyl)-, —C$_{1-3}$ alkyl (C$_{1-3}$ alkyl-hydroxy)-, —C$_{1-3}$ alkyl (C$_{1-3}$ alkyl-cyano)-, —C$_{1-3}$ alkyl (C$_{1-3}$ alkoxy)-, or —C$_{1-3}$ alkyl (C$_{1-3}$ haloalkoxy)-, where C$_{1-3}$ alkyl is methyl, ethyl, or propyl (n-propyl or isopropyl); and C$_{1-3}$ alkoxy is methoxy, ethoxy, or propoxy (n-propoxy or isopropoxy).

In an embodiment of the present invention, in Formula I, when the dashed line in $$\overset{R_{42}}{\underset{P}{\vdots}}$$

is a single bond, P is O, NH, or NR$^m$; R$^m$ is —C$_{1-6}$ alkyl; and R$_{42}$ is —(C=O)— or —C$_{1-3}$ alkyl-.

In an embodiment of the present invention, in Formula I, when the dashed line in $$\overset{R_{42}}{\underset{P}{\vdots}}$$

is a single bond, P is O, NH, or NR$^m$; R$^m$ is —C$_{1-3}$ alkyl; and R$_{42}$ is —(C=O)— or —C$_{1-3}$ alkyl-.

In an embodiment of the present invention, in Formula I, when the dashed line in $$\overset{R_{42}}{\underset{P}{\vdots}}$$

is a single bond, P is O, NH, or NR$^m$; R$^m$ is methyl, ethyl, n-propyl, or isopropyl; and R$_{42}$ is —(C=O)—, —CH$_2$—, —CH$_2$CH$_2$—, or —CH$_2$CH$_2$CH$_2$—.

In an embodiment of the present invention, in Formula I, when the dashed line in $$\overset{R_{42}}{\underset{P}{\vdots}}$$

is absent, P is hydrogen or halogen; and R$_{42}$ is hydrogen, halogen, —C$_{1-3}$ alkyl, —CH$_2$-hydroxyl, —CH$_2$-cyano, —CH$_2$—C$_{1-3}$ alkoxy, —CH$_2$-halogenated C$_{1-3}$ alkyl, or —CH$_2$—C$_{1-3}$ haloalkoxy.

In an embodiment of the present invention, in Formula I, when the dashed line in $$\overset{R_{42}}{\underset{P}{\vdots}}$$

is absent, P is hydrogen or halogen; and R$_{42}$ is hydrogen, halogen, methyl, ethyl, n-propyl, isopropyl, —CH$_2$-hydroxyl, —CH$_2$-cyano, —CH$_2$-methoxy, —CH$_2$-ethoxy, —CH$_2$-propoxy (n-propoxy), —CH$_2$-isopropoxy, —CH$_2$-trifluoromethyl, —CH$_2$-difluoromethyl, —CH$_2$-difluoroethyl, —CH$_2$-trifluoromethoxy, or —CH$_2$-difluoromethoxy.

In an embodiment of the present invention, in Formula I, X$_1$ is hydrogen, halogen, cyano, hydroxyl, amino, nitro, -substituted or unsubstituted C$_{1-3}$ alkyl, -substituted or unsubstituted C$_{3-6}$ cycloalkyl, -substituted or unsubstituted 3- to 6-membered heterocycloalkyl, —O-substituted or unsubstituted C$_{1-3}$ alkyl, —O-substituted or unsubstituted C$_{3-6}$ cycloalkyl, —O-substituted or unsubstituted 3- to 6-membered heterocycloalkyl, —NH-substituted or unsubstituted C$_{1-3}$ alkyl, —N(substituted or unsubstituted C$_{1-3}$ alkyl)$_2$, —NH-substituted or unsubstituted C$_{3-6}$ cycloalkyl, —NH-substituted or unsubstituted 3- to 6-membered heterocycloalkyl, —NH(C=O)-substituted or unsubstituted C$_{1-3}$ alkyl, —NH(C=O)— C$_{3-6}$ cycloalkyl, —NH(SO$_2$)-substituted or unsubstituted C$_{1-3}$ alkyl, —NH(SO$_2$)-substituted or unsubstituted C$_{3-6}$ cycloalkyl, —SO$_2$-substituted or unsubstituted C$_{1-3}$ alkyl, —SO$_2$-substituted or unsubstituted C$_{3-6}$ cycloalkyl, —(C=O)— NR$^j$R$^k$—, —(C=O)—O-substituted or unsubstituted C$_{1-3}$ alkyl, —(C=O)—O-substituted, or unsubstituted $C_{3-6}$ cycloalkyl; $R^j$ and $R^k$ are each independently hydrogen or $C_{1-3}$ alkyl; or $R^j$ and $R^k$ each form together with a nitrogen atom adjacent thereto substituted or unsubstituted 3- to 6-membered N-containing heterocycloalkyl; the 3- to 6-membered heterocycloalkyl has 1, 2, or 3 heteroatoms selected from N, O, and S as ring atoms; the 3- to 6-membered N-containing heterocycloalkyl has 3 to 6 ring atoms, and one of the ring atoms is nitrogen atom, while 0, 1 or 2 ring atoms among the rest of the ring atoms are optionally heteroatoms selected from N, O, and S; the "substituted" means 1, 2, 3, or 4 hydrogen atoms in a group being each independently substituted by a group-S substituent; and the $C_{1-3}$ alkyl is methyl, ethyl, or propyl (n-propyl or isopropyl), while the $C_{1-3}$ alkoxy is methoxy, ethoxy, or propoxy (n-propoxy or isopropoxy).

In an embodiment of the present invention, in Formula I, $Y_1$ is N; $E_1$ is C; and $E_2$ is C.

In an embodiment of the present invention, in Formula I, $Y_1$ is C; $E_1$ is N; and $E_2$ is C.

In an embodiment of the present invention, in Formula I, $Y_1$ is C; $E_1$ is C; and $E_2$ is N.

In an embodiment of the present invention, in Formula I, $Y_1$ is C; $E_1$ is N; and $E_2$ is N.

In an embodiment of the present invention, in Formula I, $Y_1$ is N; $E_1$ is N; and $E_2$ is C.

In an embodiment of the present invention, in Formula I, $Y_1$ is N; $E_1$ is N; and $E_2$ is C.

In an embodiment of the present invention, in Formula II, P is O.

In an embodiment of the present invention, in Formula II, P is NH or $NR^m$; and $R^m$ is $C_{1-3}$ alkyl, halogenated $C_{1-3}$ alkyl, —$C_{1-3}$ alkyl-hydroxyl, —$C_{1-3}$ alkyl-cyano, —$C_{1-3}$ alkyl-$C_{1-3}$ alkoxy, or —$C_{1-3}$ alkyl-$C_{1-3}$ haloalkoxy, where the $C_{1-3}$ alkyl is methyl, ethyl or propyl (n-propyl or isopropyl); and the $C_{1-3}$ alkoxy is methoxy, ethoxy, or propoxy (n-propoxy or isopropoxy).

In an embodiment of the present invention, in Formula II, $R_{42}$ is —(C=O)—, —$C_{1-3}$ alkyl, —$C_{1-3}$ alkyl (hydroxy)-, —$C_{1-3}$ alkyl (cyano)-, —$C_{1-3}$ alkyl ($C_{1-3}$ alkyl), —$C_{1-3}$ alkyl(halogenated $C_{1-3}$ alkyl)-, —$C_{1-3}$ alkyl ($C_{1-3}$ alkyl-hydroxy)-, —$C_{1-3}$alkyl ($C_{1-3}$ alkyl-cyano)-, —$C_{1-3}$ alkyl ($C_{1-3}$ alkoxy)-, or —$C_{1-3}$ alkyl($C_{1-3}$ haloalkoxy)-, where the $C_{1-3}$ alkyl is methyl, ethyl, or propyl (n-propyl or isopropyl); and the $C_{1-3}$alkoxy is methoxy, ethoxy, or propoxy (n-propoxy or isopropoxy).

In an embodiment of the present invention, in Formula II, $X_2$ and $Y_2$ are either identical or different and are each independently hydrogen, halogen, —$C_{1-3}$ alkyl, —$C_{1-3}$ alkyl-hydroxyl, —$C_{1-3}$ alkyl-cyano, —$C_{1-3}$ alkyl-$C_{1-3}$ alkoxy, —$C_{1-3}$ alkyl-halogenated $C_{1-3}$ alkyl, or —$C_{1-3}$ alkyl-$C_{1-3}$ haloalkoxy, where the $C_{1-3}$ alkyl is methyl, ethyl, or propyl (n-propyl or isopropyl); and the $C_{1-3}$ alkoxy is methoxy, ethoxy, or propoxy (n-propoxy or isopropoxy).

In an embodiment of the present invention, in Formula II, $X_2$ and $Y_2$ each form together with a carbon atom adjacent thereto substituted or unsubstituted $C_{3-6}$ cycloalkyl or substituted or unsubstituted 3- to 6-membered heterocycloalkyl; the 3- to 6-membered heterocycloalkyl has 1, 2 or 3 heteroatoms selected from N, O, and S as ring atoms; and the "substituted" means 1, 2, 3, or 4 hydrogen atoms in a group being each independently substituted by a group-S substituent.

In an embodiment of the present invention, in Formula II, L is a bond.

In an embodiment of the present invention, in Formula II, $R_5$ is hydrogen, halogen, hydroxyl, -substituted or unsubstituted $C_{1-3}$ alkyl, -substituted or unsubstituted $C_{3-6}$ cycloalkyl, -substituted or unsubstituted 3- to 6-membered heterocycloalkyl, —O-substituted or unsubstituted $C_{1-3}$ alkyl, —O-substituted or unsubstituted $C_{3-6}$ cycloalkyl, —O-substituted or unsubstituted 3- to 6-membered heterocycloalkyl, —$SO_2$-substituted or unsubstituted $C_{1-3}$ alkyl, —$SO_2$-substituted or unsubstituted $C_{3-6}$ cycloalkyl, —$SO_2$-substituted or unsubstituted 3- to 6-membered heterocycloalkyl, -substituted or unsubstituted 5- or 6-membered monocyclic heteroaryl, or $NR_{51}R_{52}$, where $R_{51}$ and $R_{52}$ are each independently hydrogen, substituted or unsubstituted $C_{1-3}$ alkyl, —$SO_2C_{1-3}$ alkyl, —$SO_2C_{3-6}$ cycloalkyl, —C(O)$C_{1-3}$ alkyl, or —C(O)halogenated $C_{1-3}$ alkyl; or $R_{51}$ and $R_{52}$ each form together with a nitrogen atom adjacent thereto substituted or unsubstituted 3- to 6-membered N-containing heterocycloalkyl; the 3- to 6-membered heterocycloalkyl and the 5- or 6-membered monocyclic heteroaryl each independently have 1, 2, or 3 heteroatoms selected from N, O, and S as ring atoms; the 3- to 6-membered N-containing heterocycloalkyl has 3 to 6 ring atoms, and one of the ring atoms is nitrogen atom, while 0, 1, or 2 ring atoms among the rest of the ring atoms are optionally heteroatoms selected from N, O, and S; the "substituted" means 1, 2, 3, or 4 hydrogen atoms in a group being each independently substituted by a group-S substituent; the $C_{1-3}$alkyl is methyl, ethyl, or propyl (n-propyl or isopropyl); and the $C_{1-3}$ alkoxy is methoxy, ethoxy, or propoxy (n-propoxy or isopropoxy).

In an embodiment of the present invention, $R_1$ and $R_2$ are each independently hydrogen, halogen, cyano, amino, $NHCH_3$, $N(CH_3)_2$, methyl, ethyl, n-propyl, isopropyl, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, —$CH_2$-hydroxyl, —$CH_2$-cyano, —$CH_2$-methoxy, —$CH_2$-ethoxy, —$CH_2$-propoxy (n-propoxy), —$CH_2$-isopropoxy, —$CH_2$—$NH_2$, —$CH_2$—$NHCH_3$, —$CH_2$—$N(CH_3)_2$, —$CH_2$-3- to 6-membered heterocycloalkyl, or —$CH_2$-5- or 6-membered monocyclic heteroaryl; the 3- to 6-membered heterocycloalkyl is selected from aziridine, ethylene oxide, azetidine, oxetane, tetrahydrofuran, tetrahydrothiophene, tetrahydropyrrole, piperidine, piperazine, morpholine, thiomorpholine, thiomorpholin-1,1-dioxide, and tetrahydropyrane; the 5- or 6-membered monocyclic heteroaryl is selected from thiophene, N-alkylcyclopyrrole, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine, and pyrazine; and the 3- to 6-membered heterocycloalkyl and the 5- or 6-membered monocyclic heteroaryl are each optionally substituted by 1 or 2 halogens or $C_{1-3}$ alkyl.

In an embodiment of the present invention, $R_3$ is hydrogen, halogen, methoxy, ethoxy, propoxy (n-propoxy), or isopropoxy.

In an embodiment of the present invention, $R_4$ is hydrogen, monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, —$CH_2$-hydroxyl, —$CH_2$-cyano, —$CH_2$-methoxy, —$CH_2$-ethoxy, —$CH_2$-propoxy (n-propoxy), or —$CH_2$-isopropoxy.

In an embodiment of the present invention, $R_1$, $R_2$, and $R_3$ are each independently hydrogen.

In an embodiment of the present invention, $E_1$ is N or $CR_5$, where $R_5$ is hydrogen.

In an embodiment of the present invention, $E_2$ is N or $CR_6$, where $R_6$ is hydrogen.

In an embodiment of the present invention, in the compound of Formula (I), $R_{11}$, $R_{12}$, $R_{21}$, $R_{22}$, $R_{31}$, $R_{32}$, $R_{41}$, $R_{42}$, Z, P, $R_0$, Ar, $E_1$, $E_2$, $X_1$, and $Y_1$ are each independently corresponding groups in different specific compounds in Examples.

In an embodiment of the present invention, the compound of Formula (I) is any one of compounds Z1, and Z3 to Z16 in Examples, or diastereoisomers thereof.

In an embodiment of the present invention, the representative compound of Formula (IA) includes structures shown in Table A-1 below, or a tautomer, a cis-trans isomer, a mesomer, a raceme, an enantiomer, a diastereoisomer, or an atropisomer of any structure in Table A-1, or a mixture of such isomers, or the structures in Table A-1 and pharmaceutically acceptable salts, solvates or prodrugs of such isomers.

TABLE A-1

Z1

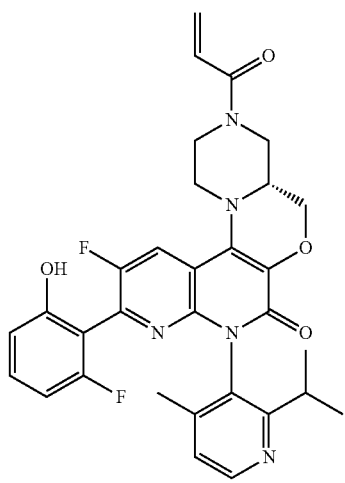 [SMILES: C=CC(=O)N1CCN2c3c(c(=O)n(-c4c(C)ccnc4C(C)C)c4nc(-c5c(O)cccc5F)c(F)cc34)OC[C@H]2C1]

Z3a

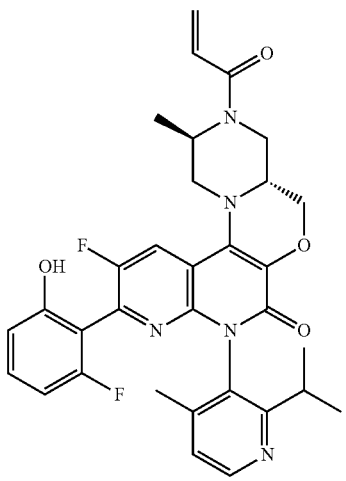 [SMILES: C=CC(=O)N1C[C@@H]2COc3c(c4cc(F)c(-c5c(O)cccc5F)nc4n(-c4c(C)ccnc4C(C)C)c3=O)N2C[C@H]1C]

TABLE A-1-continued

Z3

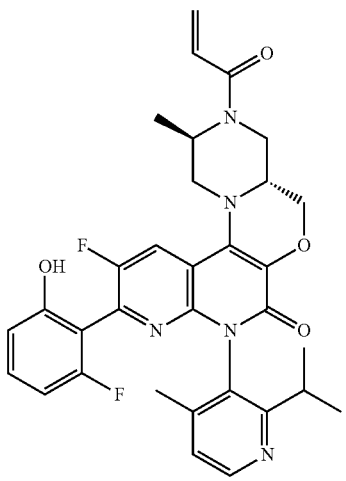 [SMILES: C=CC(=O)N1C[C@@H]2COc3c(c4cc(F)c(-c5c(O)cccc5F)nc4n(-c4c(C)ccnc4C(C)C)c3=O)N2C[C@H]1C]

Z4

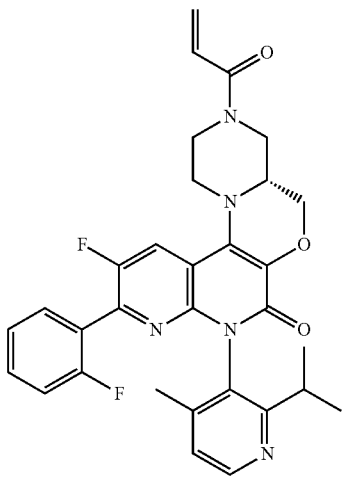 [SMILES: C=CC(=O)N1CCN2c3c(c(=O)n(-c4c(C)ccnc4C(C)C)c4nc(-c5ccccc5F)c(F)cc34)OC[C@H]2C1]

Z5

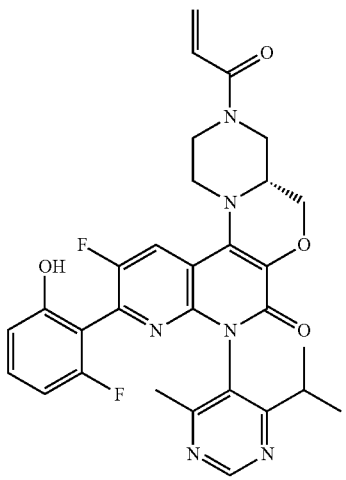

TABLE A-1-continued
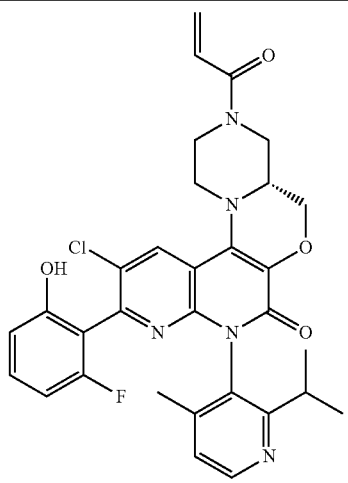
Z6
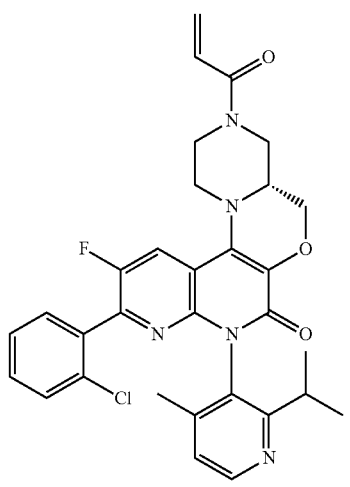 [SMILES: C=CC(=O)N1CCN2c3c(c(=O)n(-c4c(C)ccnc4C(C)C)c4nc(-c5ccccc5Cl)c(F)cc34)OC[C@H]2C1]
Z7
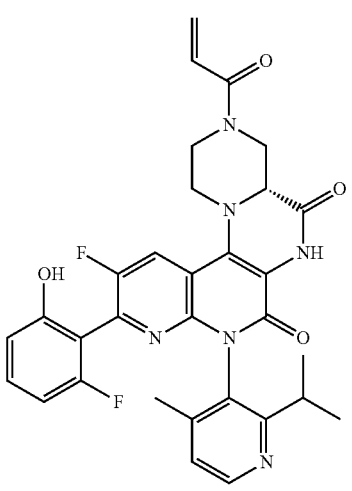 [SMILES: C=CC(=O)N1CCN2c3c(c(=O)n(-c4c(C)ccnc4C(C)C)c4nc(-c5c(O)cccc5F)c(F)cc34)NC(=O)[C@H]2C1]
Z8
TABLE A-1-continued
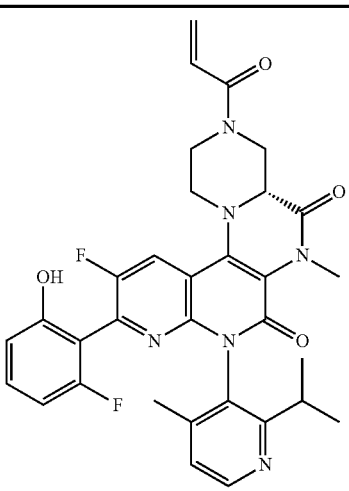
Z9
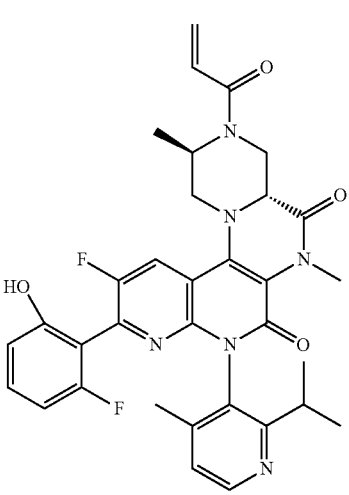 [SMILES: C=CC(=O)N1C[C@@H]2C(=O)N(C)c3c(c4cc(F)c(-c5c(O)cccc5F)nc4n(-c4c(C)ccnc4C(C)C)c3=O)N2C[C@H]1C]
Z10
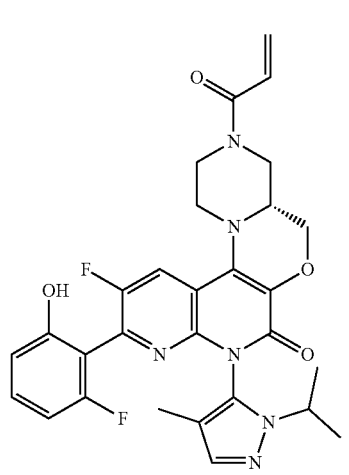 [SMILES: C=CC(=O)N1CCN2c3c(c(=O)n(-c4c(C)cnn4C(C)C)c4nc(-c5c(O)cccc5F)c(F)cc34)OC[C@H]2C1]
Z11

TABLE A-1-continued
Z12
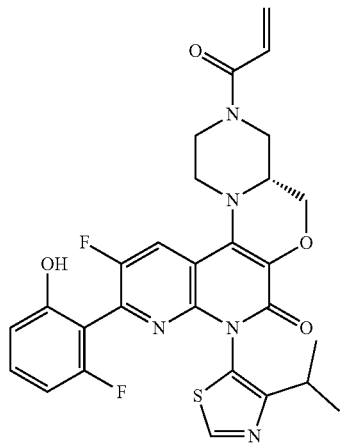 [SMILES: C=CC(=O)N1CCN2c3c(c(=O)n(-c4scnc4C(C)C)c4nc(-c5c(O)cccc5F)c(F)cc34)OC[C@H]2C1]
Z21
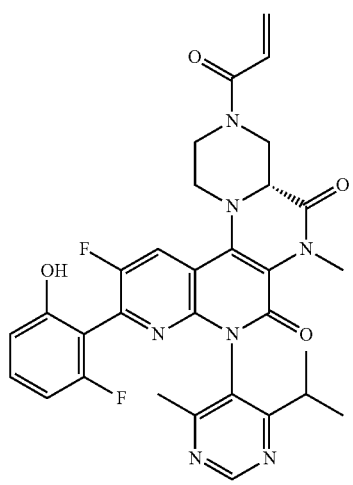 [SMILES: C=CC(=O)N1CCN2c3c(c(=O)n(-c4c(C)ncnc4C(C)C)c4nc(-c5c(O)cccc5F)c(F)cc34)N(C)C(=O)[C@H]2C1]
Z22
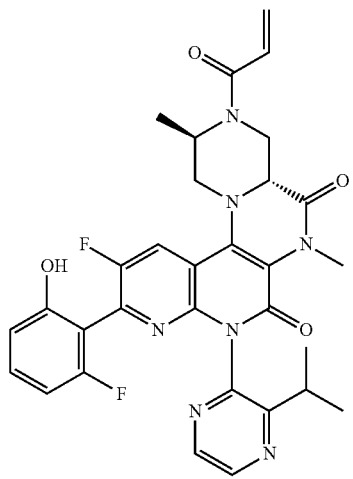 [SMILES: C=CC(=O)N1C[C@@H]2C(=O)N(C)c3c(c4cc(F)c(-c5c(O)cccc5F)nc4n(-c4nccnc4C(C)C)c3=O)N2C[C@H]1C]
TABLE A-1-continued
Z23
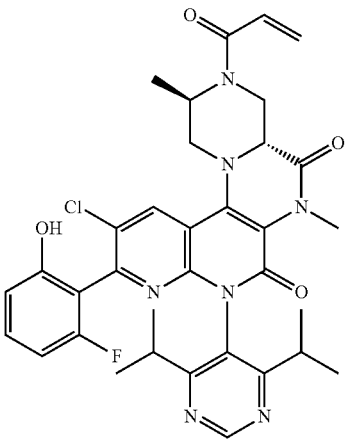 [SMILES: C=CC(=O)N1C[C@@H]2C(=O)N(C)c3c(c4cc(Cl)c(-c5c(O)cccc5F)nc4n(-c4c(C(C)C)ncnc4C(C)C)c3=O)N2C[C@H]1C]
Z24
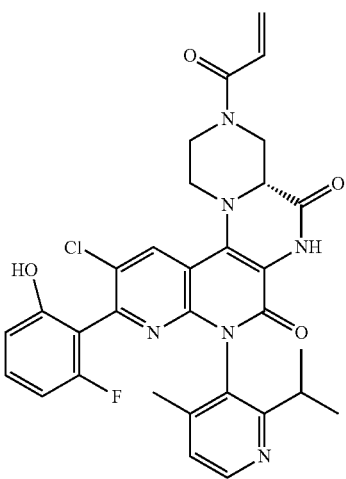 [SMILES: C=CC(=O)N1CCN2c3c(c(=O)n(-c4c(C)ccnc4C(C)C)c4nc(-c5c(O)cccc5F)c(Cl)cc34)NC(=O)[C@H]2C1]
Z25
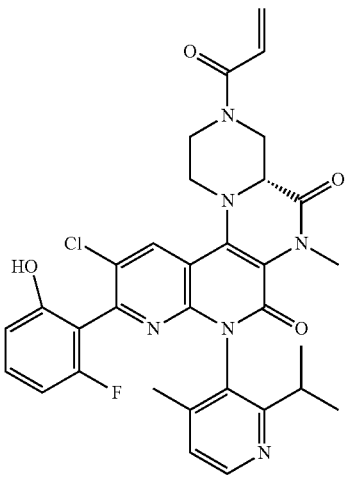 [SMILES: C=CC(=O)N1CCN2c3c(c(=O)n(-c4c(C)ccnc4C(C)C)c4nc(-c5c(O)cccc5F)c(Cl)cc34)N(C)C(=O)[C@H]2C1]

TABLE A-1-continued
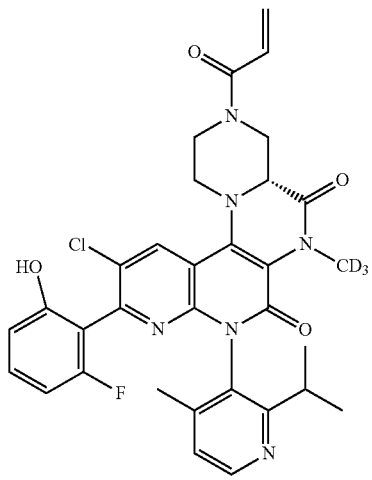 [SMILES: [2H]C([2H])([2H])N1C(=O)[C@H]2CN(C(=O)C=C)CCN2c2c1c(=O)n(-c1c(C)ccnc1C(C)C)c1nc(-c3c(O)cccc3F)c(Cl)cc21]
Z26
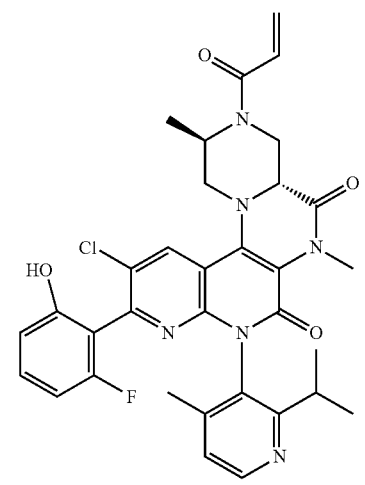 [SMILES: C=CC(=O)N1C[C@@H]2C(=O)N(C)c3c(c4cc(Cl)c(-c5c(O)cccc5F)nc4n(-c4c(C)ccnc4C(C)C)c3=O)N2C[C@H]1C]
Z27
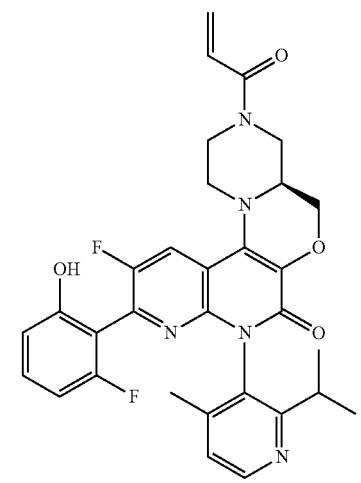 [SMILES: C=CC(=O)N1CCN2c3c(c(=O)n(-c4c(C)ccnc4C(C)C)c4nc(-c5c(O)cccc5F)c(F)cc34)OC[C@@H]2C1]
Z28
TABLE A-1-continued
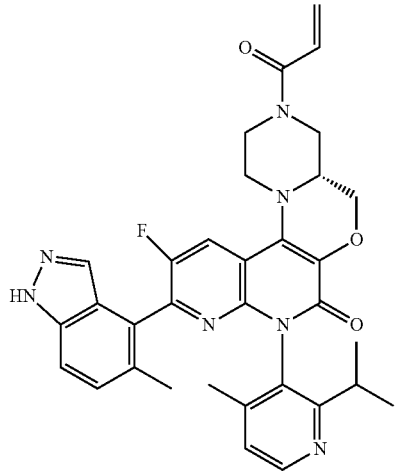 [SMILES: C=CC(=O)N1CCN2c3c(c(=O)n(-c4c(C)ccnc4C(C)C)c4nc(-c5c(C)ccc6[nH]ncc56)c(F)cc34)OC[C@H]2C1]
Z29
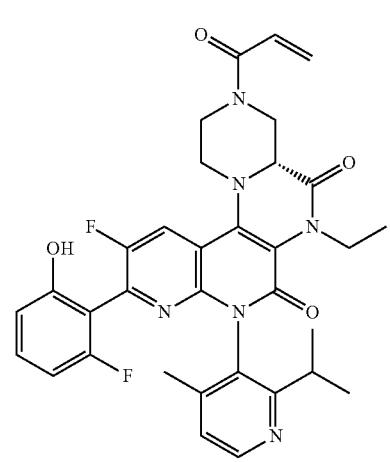 [SMILES: C=CC(=O)N1CCN2c3c(c(=O)n(-c4c(C)ccnc4C(C)C)c4nc(-c5c(O)cccc5F)c(F)cc34)N(CC)C(=O)[C@H]2C1]
Z30
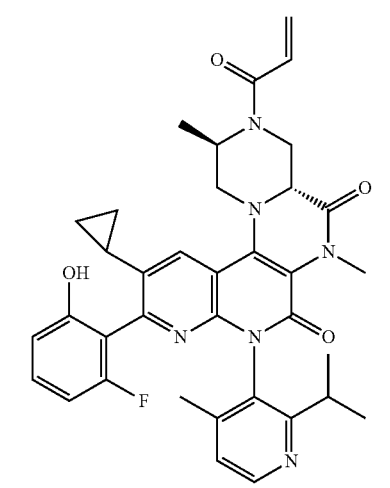 [SMILES: C=CC(=O)N1C[C@@H]2C(=O)N(C)c3c(c4cc(C5CC5)c(-c5c(O)cccc5F)nc4n(-c4c(C)ccnc4C(C)C)c3=O)N2C[C@H]1C]
Z31

TABLE A-1-continued
Z32
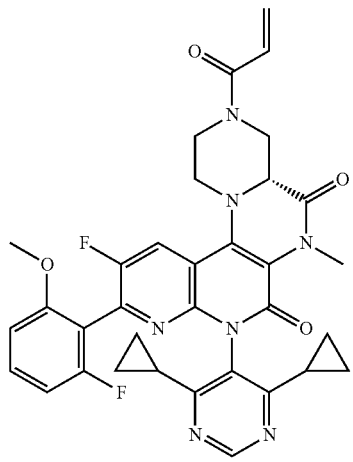 [SMILES: C=CC(=O)N1CCN2c3c(c(=O)n(-c4c(C5CC5)ncnc4C4CC4)c4nc(-c5c(F)cccc5OC)c(F)cc34)N(C)C(=O)[C@H]2C1]
Z33
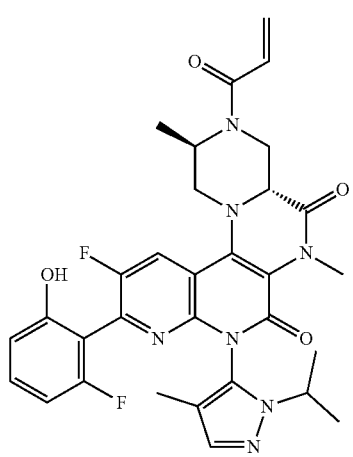 [SMILES: C=CC(=O)N1C[C@@H]2C(=O)N(C)c3c(c4cc(F)c(-c5c(O)cccc5F)nc4n(-c4c(C)cnn4C(C)C)c3=O)N2C[C@H]1C]
Z34
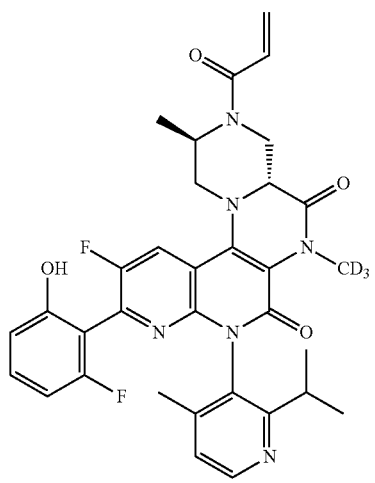 [SMILES: [2H]C([2H])([2H])N1C(=O)[C@H]2CN(C(=O)C=C)[C@H](C)CN2c2c1c(=O)n(-c1c(C)ccnc1C(C)C)c1nc(-c3c(O)cccc3F)c(F)cc21]
TABLE A-1-continued
Z35
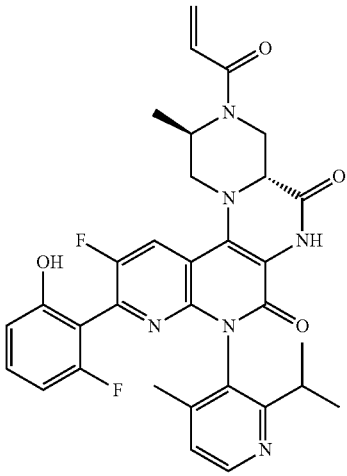 [SMILES: C=CC(=O)N1C[C@@H]2C(=O)Nc3c(c4cc(F)c(-c5c(O)cccc5F)nc4n(-c4c(C)ccnc4C(C)C)c3=O)N2C[C@H]1C]
Z36
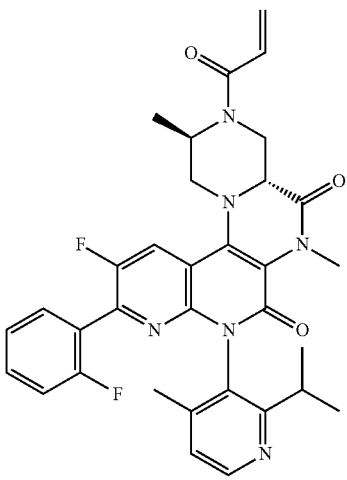 [SMILES: C=CC(=O)N1C[C@@H]2C(=O)N(C)c3c(c4cc(F)c(-c5ccccc5F)nc4n(-c4c(C)ccnc4C(C)C)c3=O)N2C[C@H]1C]
Z37
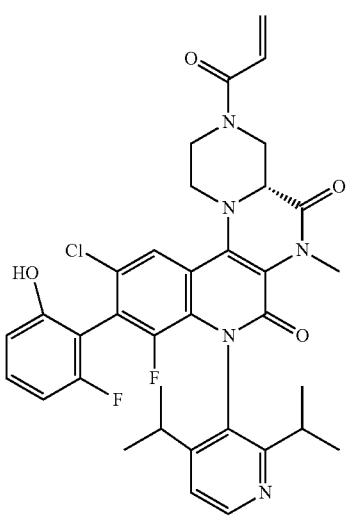 [SMILES: C=CC(=O)N1CCN2c3c(c(=O)n(-c4c(C(C)C)ccnc4C(C)C)c4c(F)c(-c5c(O)cccc5F)c(Cl)cc34)N(C)C(=O)[C@H]2C1]

TABLE A-1-continued
Z38
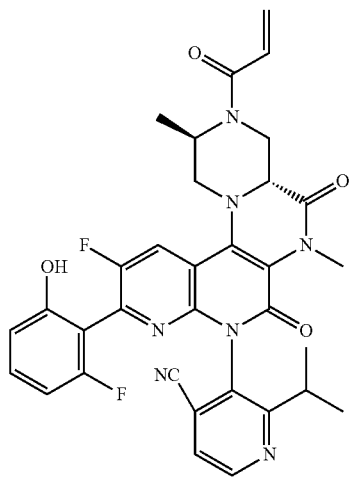 [SMILES: C=CC(=O)N1C[C@@H]2C(=O)N(C)c3c(c4cc(F)c(-c5c(O)cccc5F)nc4n(-c4c(C#N)ccnc4C(C)C)c3=O)N2C[C@H]1C]
Z39
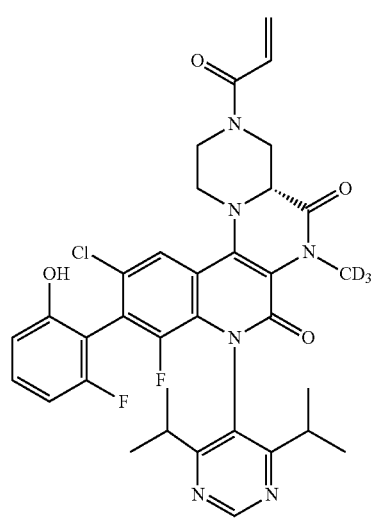 [SMILES: [2H]C([2H])([2H])N1C(=O)[C@H]2CN(C(=O)C=C)CCN2c2c1c(=O)n(-c1c(C(C)C)ncnc1C(C)C)c1c(F)c(-c3c(O)cccc3F)c(Cl)cc21]
Z40
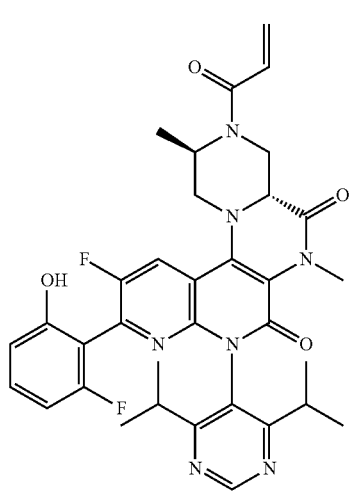 [SMILES: C=CC(=O)N1C[C@@H]2C(=O)N(C)c3c(c4cc(F)c(-c5c(O)cccc5F)nc4n(-c4c(C(C)C)ncnc4C(C)C)c3=O)N2C[C@H]1C]
TABLE A-1-continued
Z41
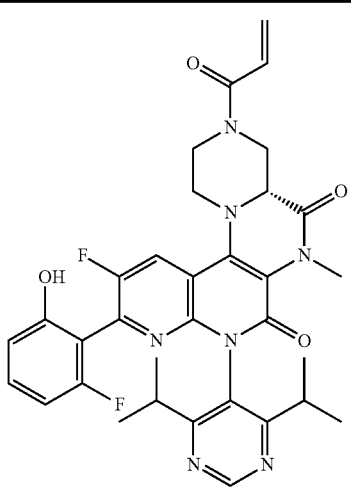
Z42
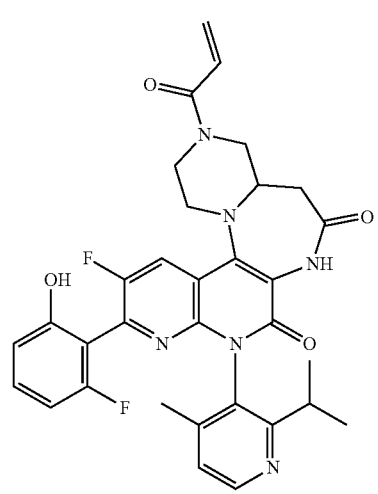 [SMILES: C=CC(=O)N1CCN2c3c(c(=O)n(-c4c(C)ccnc4C(C)C)c4nc(-c5c(O)cccc5F)c(F)cc34)NC(=O)CC2C1]
Z43
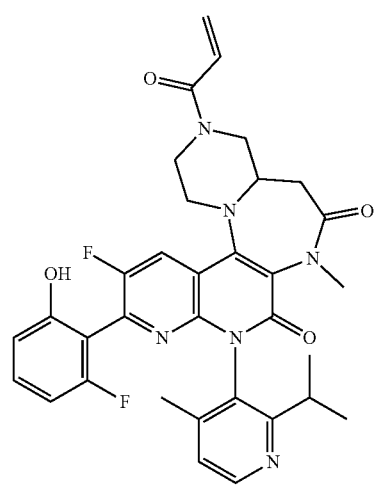 [SMILES: C=CC(=O)N1CCN2c3c(c(=O)n(-c4c(C)ccnc4C(C)C)c4nc(-c5c(O)cccc5F)c(F)cc34)N(C)C(=O)CC2C1]

TABLE A-1-continued
Z44
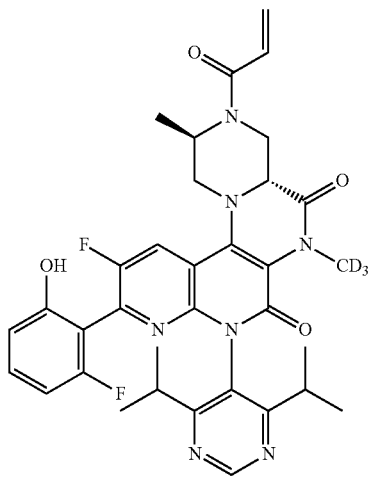 [SMILES: [2H]C([2H])([2H])N1C(=O)[C@H]2CN(C(=O)C=C)[C@H](C)CN2c2c1c(=O)n(-c1c(C(C)C)ncnc1C(C)C)c1nc(-c3c(O)cccc3F)c(F)cc21]
Z44a
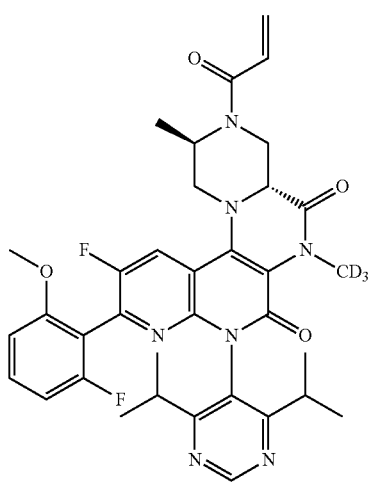 [SMILES: [2H]C([2H])([2H])N1C(=O)[C@H]2CN(C(=O)C=C)[C@H](C)CN2c2c1c(=O)n(-c1c(C(C)C)ncnc1C(C)C)c1nc(-c3c(F)cccc3OC)c(F)cc21]
Z45
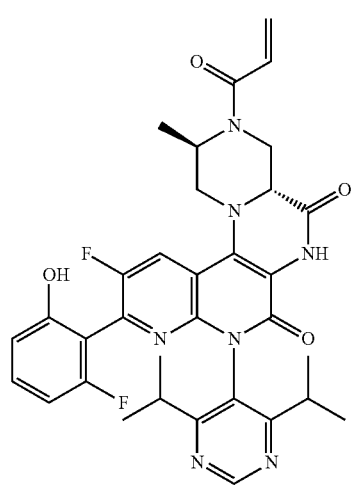 [SMILES: C=CC(=O)N1C[C@@H]2C(=O)Nc3c(c4cc(F)c(-c5c(O)cccc5F)nc4n(-c4c(C(C)C)ncnc4C(C)C)c3=O)N2C[C@H]1C]
Z46
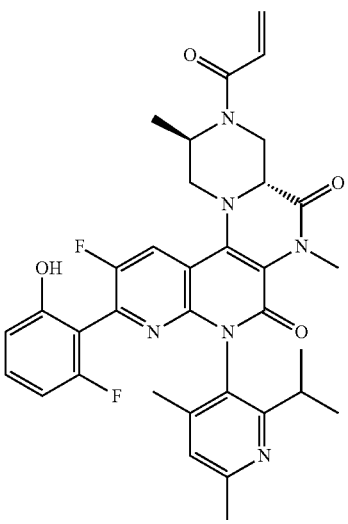 [SMILES: C=CC(=O)N1C[C@@H]2C(=O)N(C)c3c(c4cc(F)c(-c5c(O)cccc5F)nc4n(-c4c(C)cc(C)nc4C(C)C)c3=O)N2C[C@H]1C]
Z47
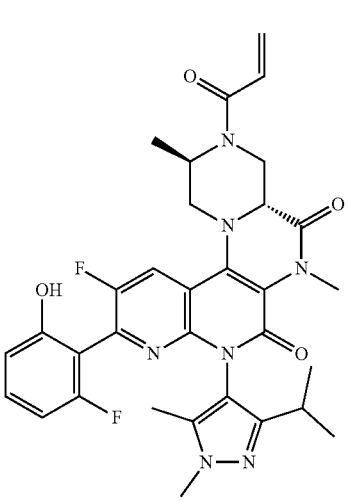 [SMILES: C=CC(=O)N1C[C@@H]2C(=O)N(C)c3c(c4cc(F)c(-c5c(O)cccc5F)nc4n(-c4c(C(C)C)nn(C)c4C)c3=O)N2C[C@H]1C]
Z48
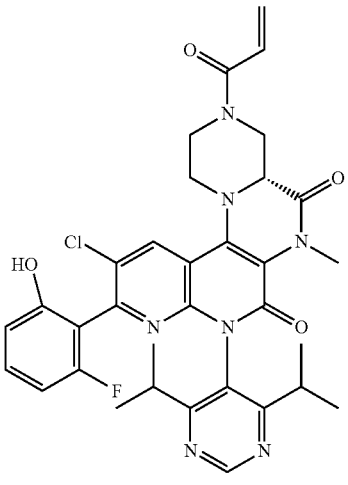 [SMILES: C=CC(=O)N1CCN2c3c(c(=O)n(-c4c(C(C)C)ncnc4C(C)C)c4nc(-c5c(O)cccc5F)c(Cl)cc34)N(C)C(=O)[C@H]2C1]

TABLE A-1-continued
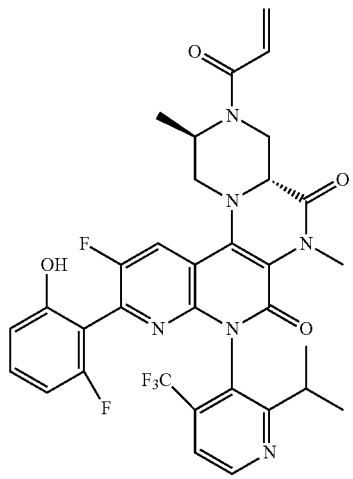 [SMILES: C=CC(=O)N1C[C@@H]2C(=O)N(C)c3c(c4cc(F)c(-c5c(O)cccc5F)nc4n(-c4c(C(F)(F)F)ccnc4C(C)C)c3=O)N2C[C@H]1C]
Z49
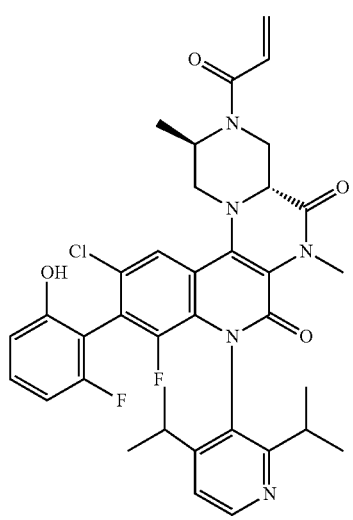 [SMILES: C=CC(=O)N1C[C@@H]2C(=O)N(C)c3c(c4cc(Cl)c(-c5c(O)cccc5F)c(F)c4n(-c4c(C(C)C)ccnc4C(C)C)c3=O)N2C[C@H]1C]
Z50
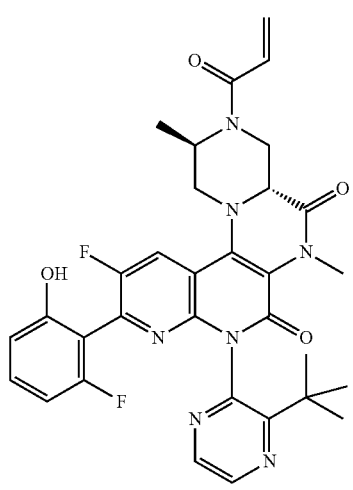 [SMILES: C=CC(=O)N1C[C@@H]2C(=O)N(C)c3c(c4cc(F)c(-c5c(O)cccc5F)nc4n(-c4nccnc4C(C)(C)C)c3=O)N2C[C@H]1C]
Z51
TABLE A-1-continued
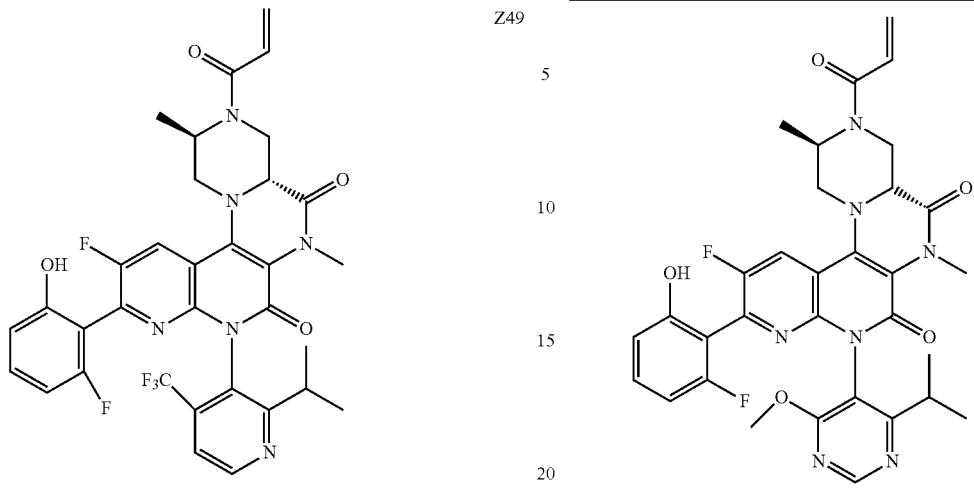
Z52
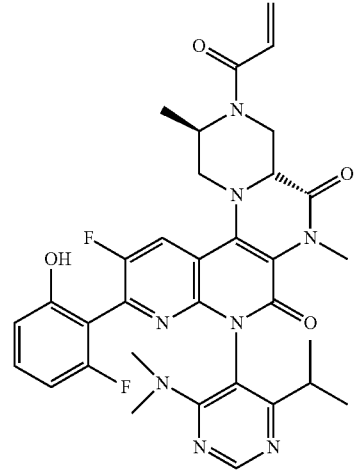
Z53
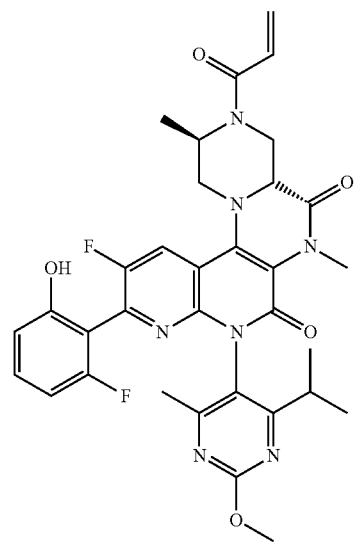
Z54

TABLE A-1-continued
Z55
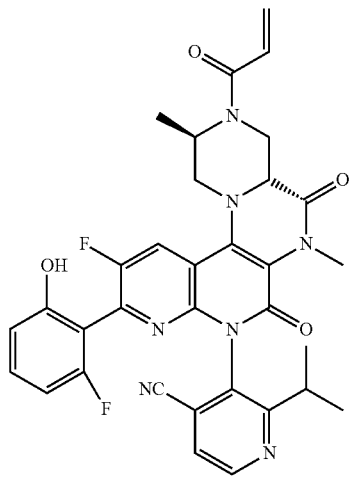
Z56
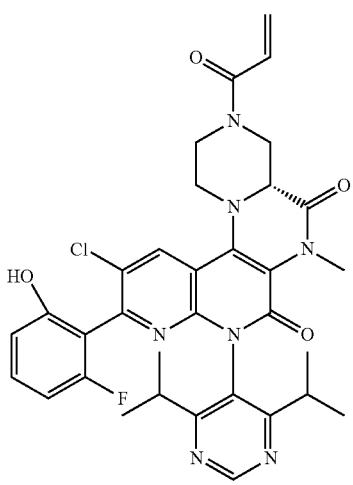 [SMILES: C=CC(=O)N1CCN2c3c(c(=O)n(-c4c(C(C)C)ncnc4C(C)C)c4nc(-c5c(O)cccc5F)c(Cl)cc34)N(C)C(=O)[C@H]2C1]
Z57
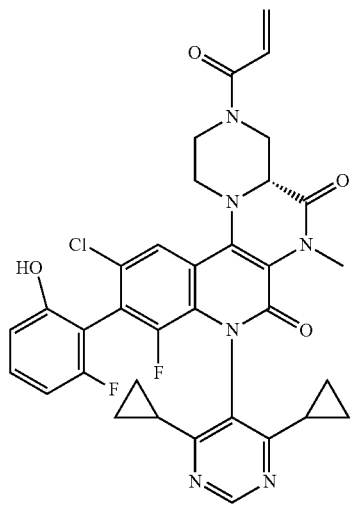 [SMILES: C=CC(=O)N1CCN2c3c(c(=O)n(-c4c(C5CC5)ncnc4C4CC4)c4c(F)c(-c5c(O)cccc5F)c(Cl)cc34)N(C)C(=O)[C@H]2C1]
TABLE A-1-continued
Z58
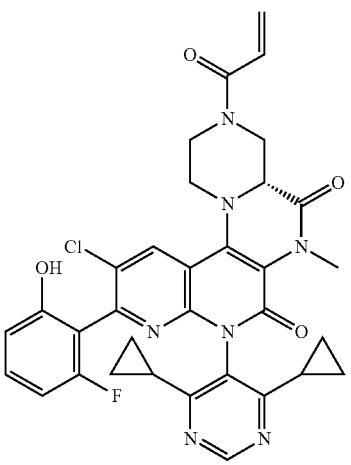 [SMILES: C=CC(=O)N1CCN2c3c(c(=O)n(-c4c(C5CC5)ncnc4C4CC4)c4nc(-c5c(O)cccc5F)c(Cl)cc34)N(C)C(=O)[C@H]2C1]
Z59
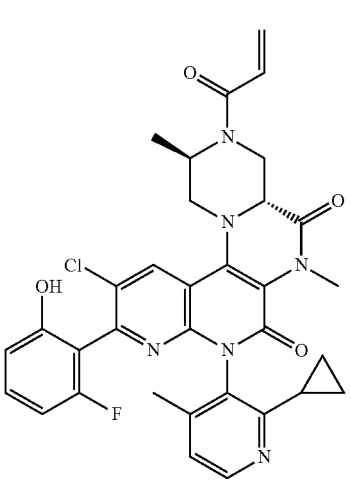 [SMILES: C=CC(=O)N1C[C@@H]2C(=O)N(C)c3c(c4cc(Cl)c(-c5c(O)cccc5F)nc4n(-c4c(C)ccnc4C4CC4)c3=O)N2C[C@H]1C]
Z60
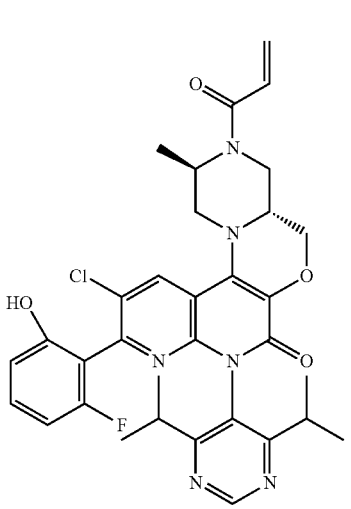 [SMILES: C=CC(=O)N1C[C@@H]2COc3c(c4cc(Cl)c(-c5c(O)cccc5F)nc4n(-c4c(C(C)C)ncnc4C(C)C)c3=O)N2C[C@H]1C]

TABLE A-1-continued
Z61
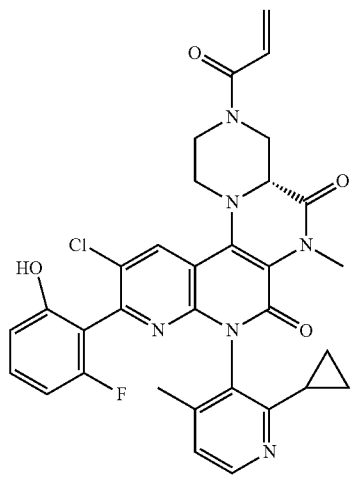 [SMILES: C=CC(=O)N1CCN2c3c(c(=O)n(-c4c(C)ccnc4C4CC4)c4nc(-c5c(O)cccc5F)c(Cl)cc34)N(C)C(=O)[C@H]2C1]
Z62
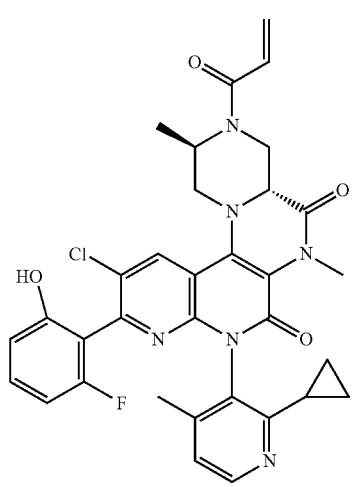 [SMILES: C=CC(=O)N1C[C@@H]2C(=O)N(C)c3c(c4cc(Cl)c(-c5c(O)cccc5F)nc4n(-c4c(C)ccnc4C4CC4)c3=O)N2C[C@H]1C]
Z63
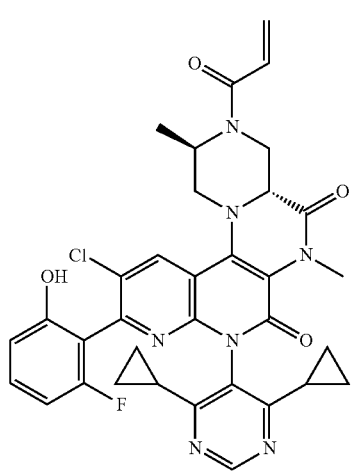 [SMILES: C=CC(=O)N1C[C@@H]2C(=O)N(C)c3c(c4cc(Cl)c(-c5c(O)cccc5F)nc4n(-c4c(C5CC5)ncnc4C4CC4)c3=O)N2C[C@H]1C]
TABLE A-1-continued
Z64
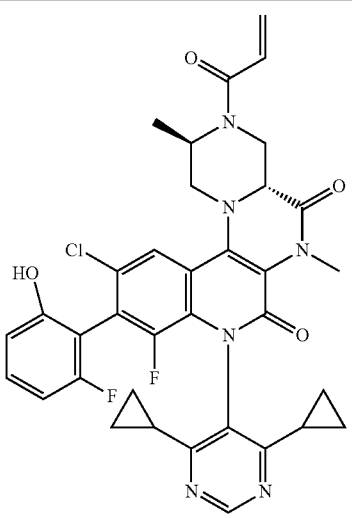 [SMILES: C=CC(=O)N1C[C@@H]2C(=O)N(C)c3c(c4cc(Cl)c(-c5c(O)cccc5F)c(F)c4n(-c4c(C5CC5)ncnc4C4CC4)c3=O)N2C[C@H]1C]
Z65
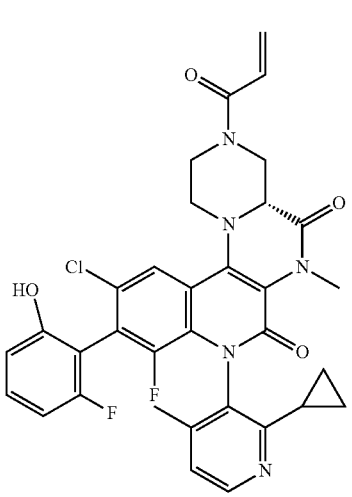 [SMILES: C=CC(=O)N1CCN2c3c(c(=O)n(-c4c(C)ccnc4C4CC4)c4c(F)c(-c5c(O)cccc5F)c(Cl)cc34)N(C)C(=O)[C@H]2C1]
Z67
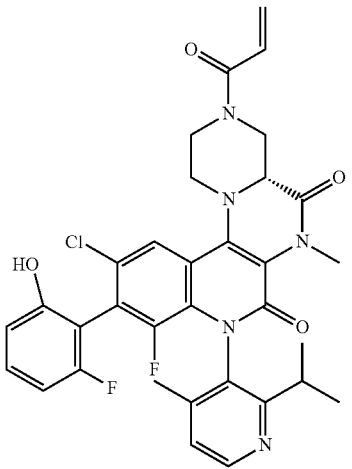 [SMILES: C=CC(=O)N1CCN2c3c(c(=O)n(-c4c(C)ccnc4C(C)C)c4c(F)c(-c5c(O)cccc5F)c(Cl)cc34)N(C)C(=O)[C@H]2C1]

TABLE A-1-continued
Z68
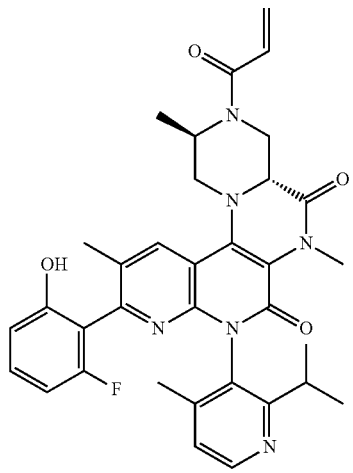 [SMILES: C=CC(=O)N1C[C@@H]2C(=O)N(C)c3c(c4cc(C)c(-c5c(O)cccc5F)nc4n(-c4c(C)ccnc4C(C)C)c3=O)N2C[C@H]1C]
Z69
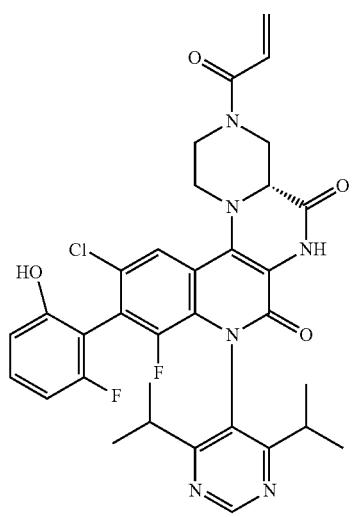 [SMILES: C=CC(=O)N1CCN2c3c(c(=O)n(-c4c(C(C)C)ncnc4C(C)C)c4c(F)c(-c5c(O)cccc5F)c(Cl)cc34)NC(=O)[C@H]2C1]
Z70
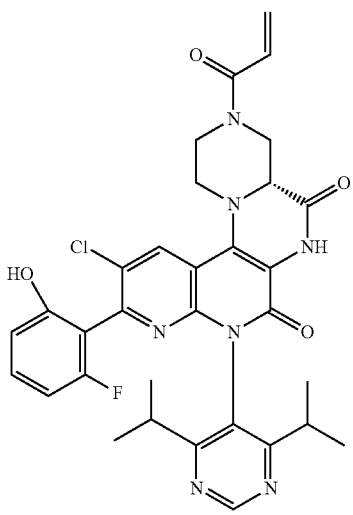 [SMILES: C=CC(=O)N1CCN2c3c(c(=O)n(-c4c(C(C)C)ncnc4C(C)C)c4nc(-c5c(O)cccc5F)c(Cl)cc34)NC(=O)[C@H]2C1]
TABLE A-1-continued
Z71
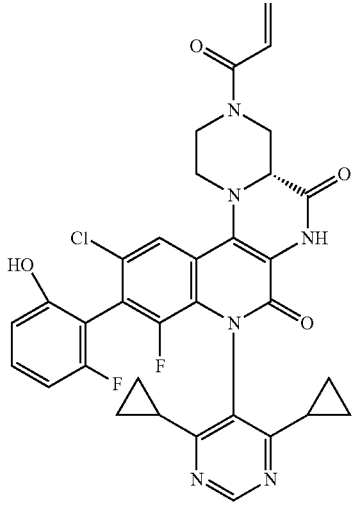 [SMILES: C=CC(=O)N1CCN2c3c(c(=O)n(-c4c(C5CC5)ncnc4C4CC4)c4c(F)c(-c5c(O)cccc5F)c(Cl)cc34)NC(=O)[C@H]2C1]
Z72
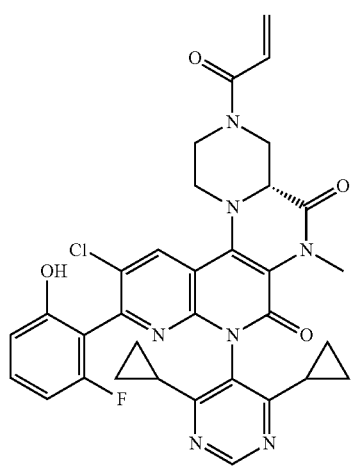 [SMILES: C=CC(=O)N1CCN2c3c(c(=O)n(-c4c(C5CC5)ncnc4C4CC4)c4nc(-c5c(O)cccc5F)c(Cl)cc34)N(C)C(=O)[C@H]2C1]
Z73
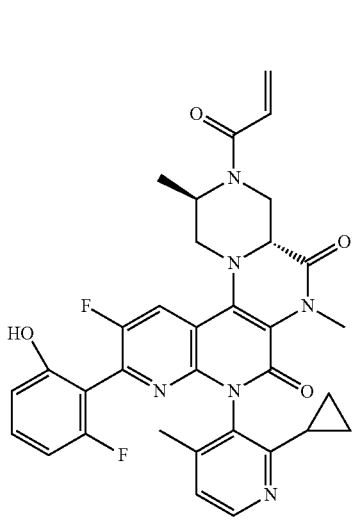

TABLE A-1-continued
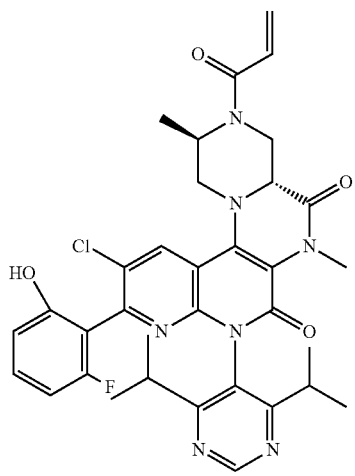 [SMILES: C=CC(=O)N1C[C@@H]2C(=O)N(C)c3c(c4cc(Cl)c(-c5c(O)cccc5F)nc4n(-c4c(C(C)C)ncnc4C(C)C)c3=O)N2C[C@H]1C]
Z74
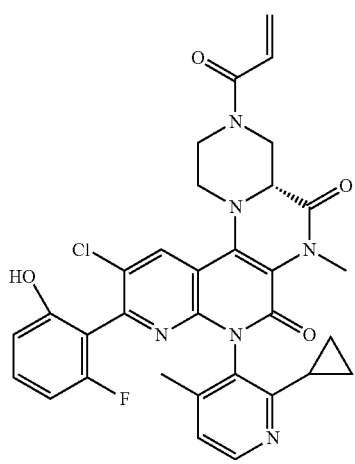 [SMILES: C=CC(=O)N1CCN2c3c(c(=O)n(-c4c(C)ccnc4C4CC4)c4nc(-c5c(O)cccc5F)c(Cl)cc34)N(C)C(=O)[C@H]2C1]
Z75
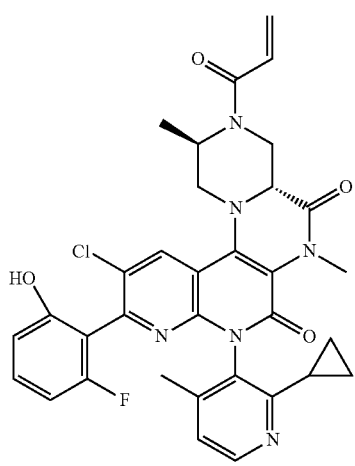 [SMILES: C=CC(=O)N1C[C@@H]2C(=O)N(C)c3c(c4cc(Cl)c(-c5c(O)cccc5F)nc4n(-c4c(C)ccnc4C4CC4)c3=O)N2C[C@H]1C]
Z76
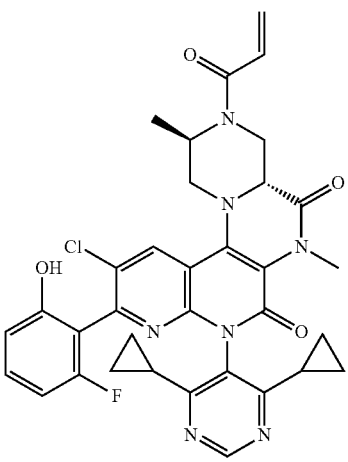 [SMILES: C=CC(=O)N1C[C@@H]2C(=O)N(C)c3c(c4cc(Cl)c(-c5c(O)cccc5F)nc4n(-c4c(C5CC5)ncnc4C4CC4)c3=O)N2C[C@H]1C]
Z77
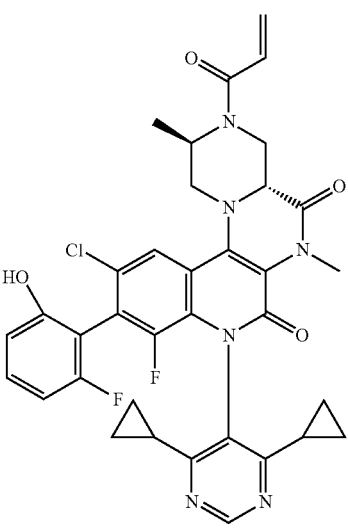 [SMILES: C=CC(=O)N1C[C@@H]2C(=O)N(C)c3c(c4cc(Cl)c(-c5c(O)cccc5F)c(F)c4n(-c4c(C5CC5)ncnc4C4CC4)c3=O)N2C[C@H]1C]
Z78
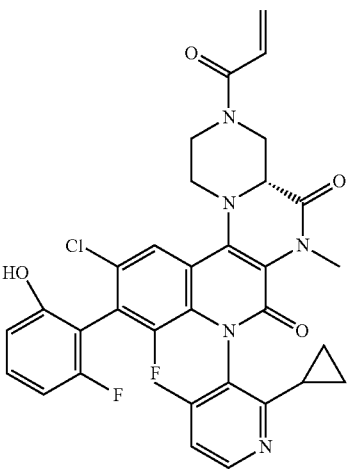 [SMILES: C=CC(=O)N1CCN2c3c(c(=O)n(-c4c(C)ccnc4C4CC4)c4c(F)c(-c5c(O)cccc5F)c(Cl)cc34)N(C)C(=O)[C@H]2C1]
Z79

TABLE A-1-continued
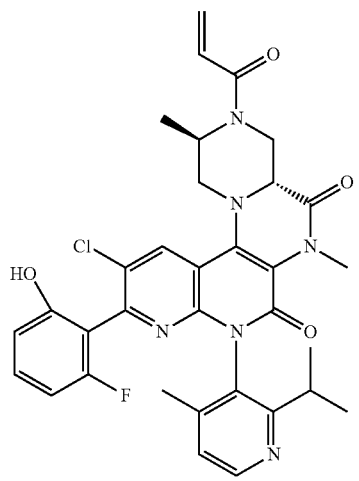 [SMILES: C=CC(=O)N1C[C@@H]2C(=O)N(C)c3c(c4cc(Cl)c(-c5c(O)cccc5F)nc4n(-c4c(C)ccnc4C(C)C)c3=O)N2C[C@H]1C]
Z80
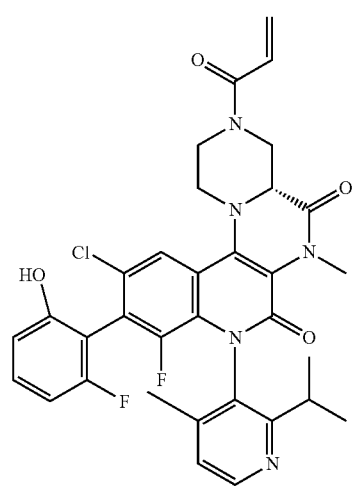 [SMILES: C=CC(=O)N1CCN2c3c(c(=O)n(-c4c(C)ccnc4C(C)C)c4c(F)c(-c5c(O)cccc5F)c(Cl)cc34)N(C)C(=O)[C@H]2C1]
Z81
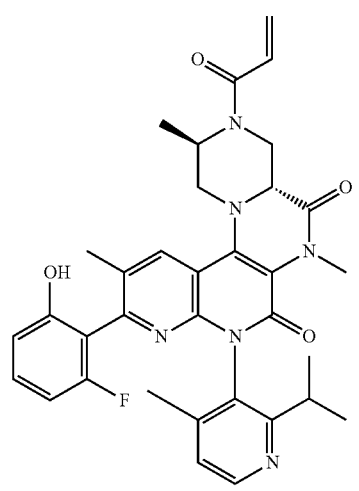 [SMILES: C=CC(=O)N1C[C@@H]2C(=O)N(C)c3c(c4cc(C)c(-c5c(O)cccc5F)nc4n(-c4c(C)ccnc4C(C)C)c3=O)N2C[C@H]1C]
Z82
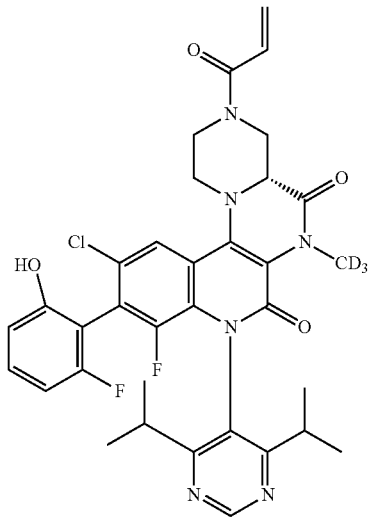 [SMILES: [2H]C([2H])([2H])N1C(=O)[C@H]2CN(C(=O)C=C)CCN2c2c1c(=O)n(-c1c(C(C)C)ncnc1C(C)C)c1c(F)c(-c3c(O)cccc3F)c(Cl)cc21]
Z83
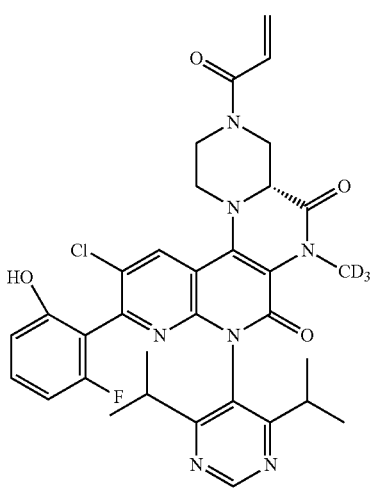 [SMILES: [2H]C([2H])([2H])N1C(=O)[C@H]2CN(C(=O)C=C)CCN2c2c1c(=O)n(-c1c(C(C)C)ncnc1C(C)C)c1nc(-c3c(O)cccc3F)c(Cl)cc21]
Z84
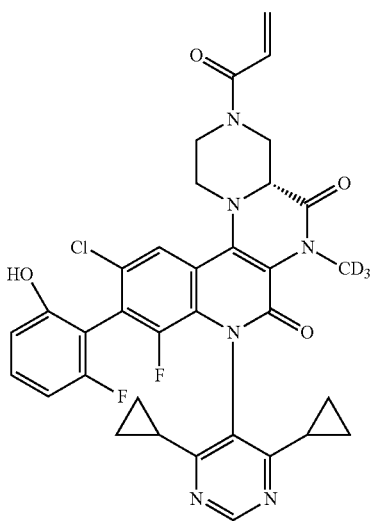 [SMILES: [2H]C([2H])([2H])N1C(=O)[C@H]2CN(C(=O)C=C)CCN2c2c1c(=O)n(-c1c(C3CC3)ncnc1C1CC1)c1c(F)c(-c3c(O)cccc3F)c(Cl)cc21]
Z85

TABLE A-1-continued
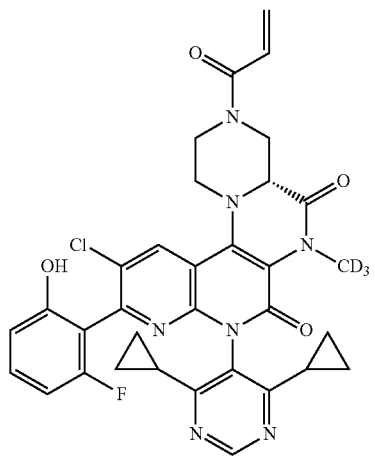 [SMILES: [2H]C([2H])([2H])N1C(=O)[C@H]2CN(C(=O)C=C)CCN2c2c1c(=O)n(-c1c(C3CC3)ncnc1C1CC1)c1nc(-c3c(O)cccc3F)c(Cl)cc21]
Z86
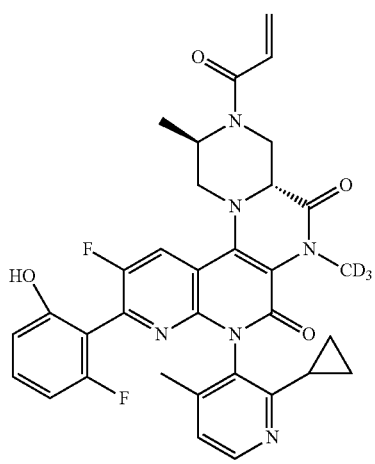 [SMILES: [2H]C([2H])([2H])N1C(=O)[C@H]2CN(C(=O)C=C)[C@H](C)CN2c2c1c(=O)n(-c1c(C)ccnc1C1CC1)c1nc(-c3c(O)cccc3F)c(F)cc21]
Z87
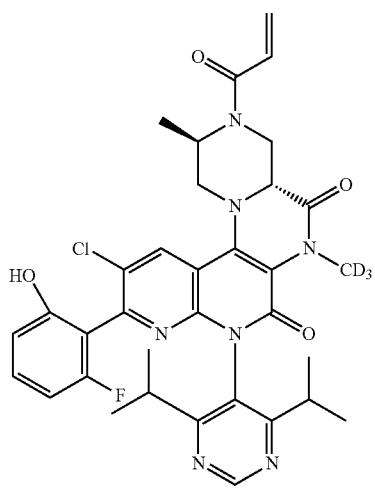 [SMILES: [2H]C([2H])([2H])N1C(=O)[C@H]2CN(C(=O)C=C)[C@H](C)CN2c2c1c(=O)n(-c1c(C(C)C)ncnc1C(C)C)c1nc(-c3c(O)cccc3F)c(Cl)cc21]
Z88
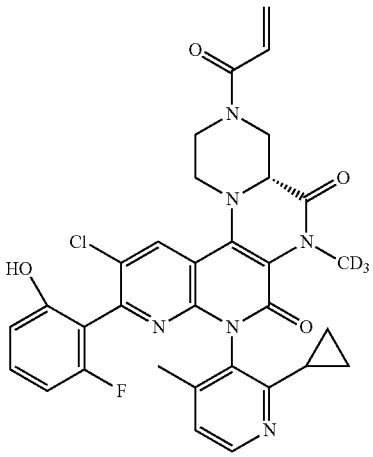 [SMILES: [2H]C([2H])([2H])N1C(=O)[C@H]2CN(C(=O)C=C)CCN2c2c1c(=O)n(-c1c(C)ccnc1C1CC1)c1nc(-c3c(O)cccc3F)c(Cl)cc21]
Z89
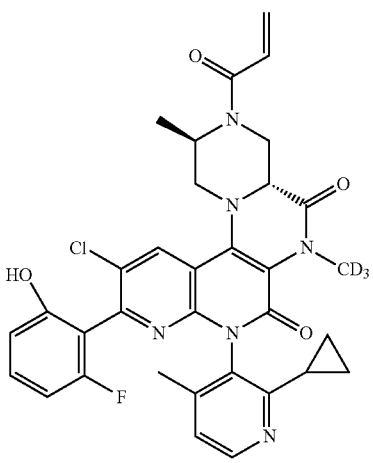
Z90
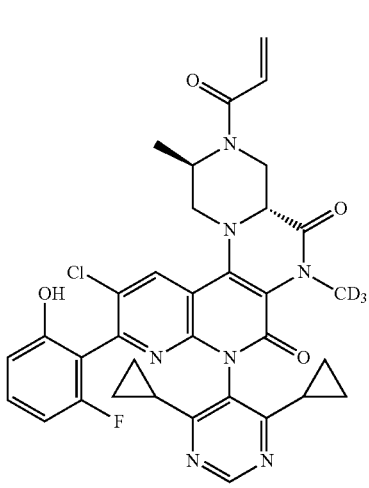 [SMILES: [2H]C([2H])([2H])N1C(=O)[C@H]2CN(C(=O)C=C)[C@H](C)CN2c2c1c(=O)n(-c1c(C3CC3)ncnc1C1CC1)c1nc(-c3c(O)cccc3F)c(Cl)cc21]
Z91

TABLE A-1-continued
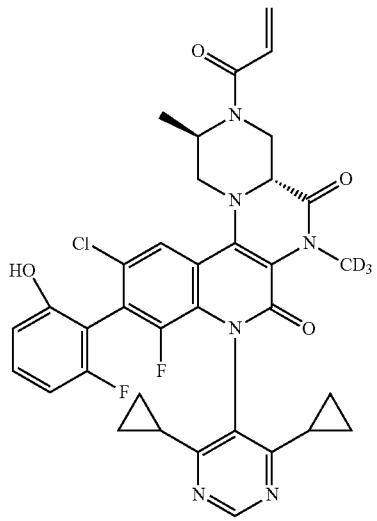 [SMILES: [2H]C([2H])([2H])N1C(=O)[C@H]2CN(C(=O)C=C)[C@H](C)CN2c2c1c(=O)n(-c1c(C3CC3)ncnc1C1CC1)c1c(F)c(-c3c(O)cccc3F)c(Cl)cc21]
Z92
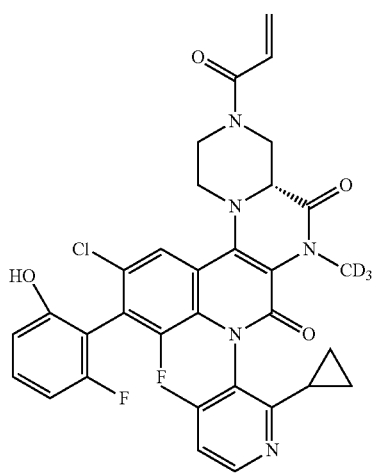 [SMILES: [2H]C([2H])([2H])N1C(=O)[C@H]2CN(C(=O)C=C)CCN2c2c1c(=O)n(-c1c(C)ccnc1C1CC1)c1c(F)c(-c3c(O)cccc3F)c(Cl)cc21]
Z93
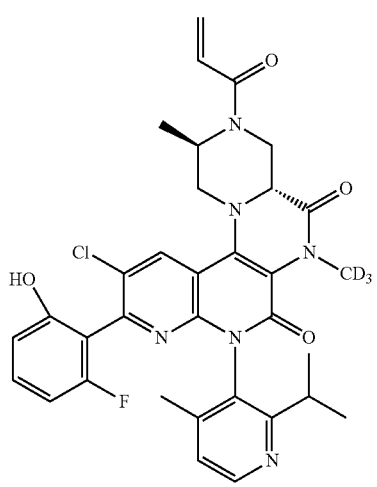 [SMILES: [2H]C([2H])([2H])N1C(=O)[C@H]2CN(C(=O)C=C)[C@H](C)CN2c2c1c(=O)n(-c1c(C)ccnc1C(C)C)c1nc(-c3c(O)cccc3F)c(Cl)cc21]
Z95
TABLE A-1-continued
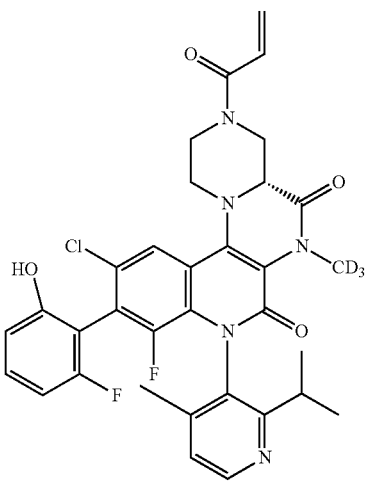 [SMILES: [2H]C([2H])([2H])N1C(=O)[C@H]2CN(C(=O)C=C)CCN2c2c1c(=O)n(-c1c(C)ccnc1C(C)C)c1c(F)c(-c3c(O)cccc3F)c(Cl)cc21]
Z96
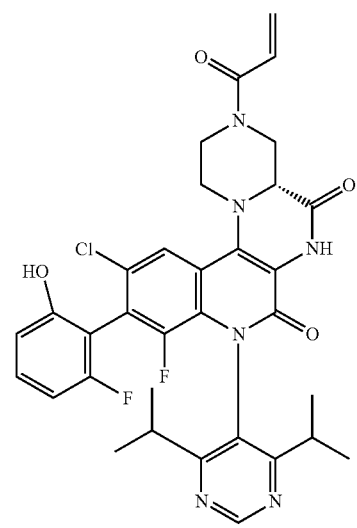 [SMILES: C=CC(=O)N1CCN2c3c(c(=O)n(-c4c(C(C)C)ncnc4C(C)C)c4c(F)c(-c5c(O)cccc5F)c(Cl)cc34)NC(=O)[C@H]2C1]
Z97
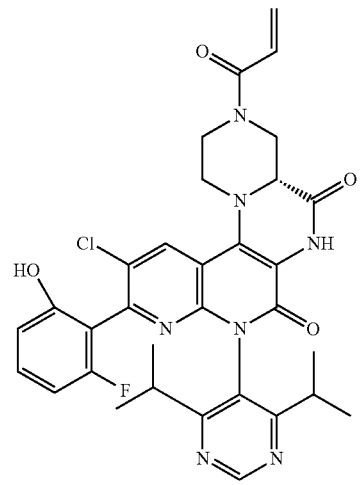 [SMILES: C=CC(=O)N1CCN2c3c(c(=O)n(-c4c(C(C)C)ncnc4C(C)C)c4nc(-c5c(O)cccc5F)c(Cl)cc34)NC(=O)[C@H]2C1]
Z98

TABLE A-1-continued
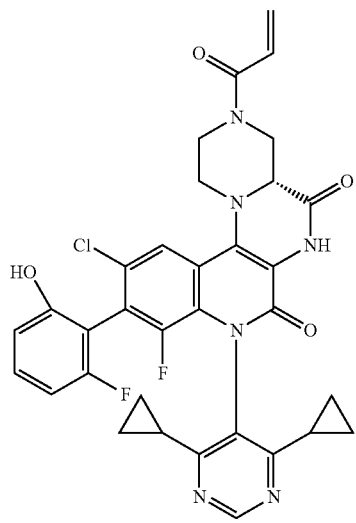 [SMILES: C=CC(=O)N1CCN2c3c(c(=O)n(-c4c(C5CC5)ncnc4C4CC4)c4c(F)c(-c5c(O)cccc5F)c(Cl)cc34)NC(=O)[C@H]2C1]
Z99
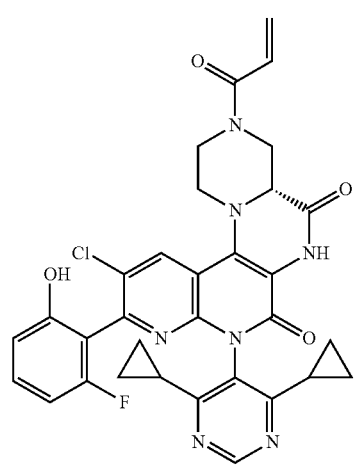 [SMILES: C=CC(=O)N1CCN2c3c(c(=O)n(-c4c(C5CC5)ncnc4C4CC4)c4nc(-c5c(O)cccc5F)c(Cl)cc34)NC(=O)[C@H]2C1]
Z100
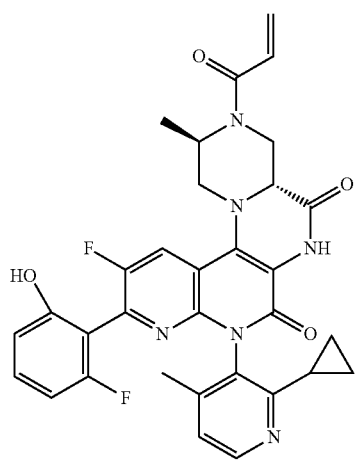 [SMILES: C=CC(=O)N1C[C@@H]2C(=O)Nc3c(c4cc(F)c(-c5c(O)cccc5F)nc4n(-c4c(C)ccnc4C4CC4)c3=O)N2C[C@H]1C]
Z101
TABLE A-1-continued
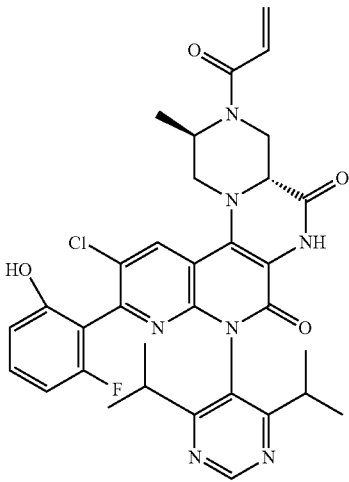 [SMILES: C=CC(=O)N1C[C@@H]2C(=O)Nc3c(c4cc(Cl)c(-c5c(O)cccc5F)nc4n(-c4c(C(C)C)ncnc4C(C)C)c3=O)N2C[C@H]1C]
Z102
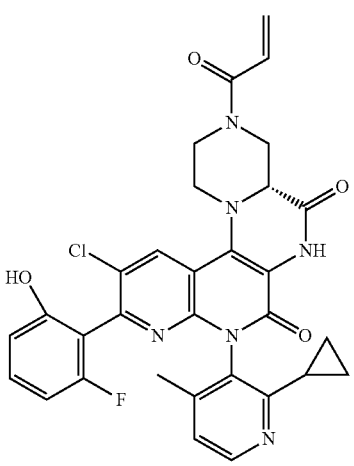 [SMILES: C=CC(=O)N1CCN2c3c(c(=O)n(-c4c(C)ccnc4C4CC4)c4nc(-c5c(O)cccc5F)c(Cl)cc34)NC(=O)[C@H]2C1]
Z103
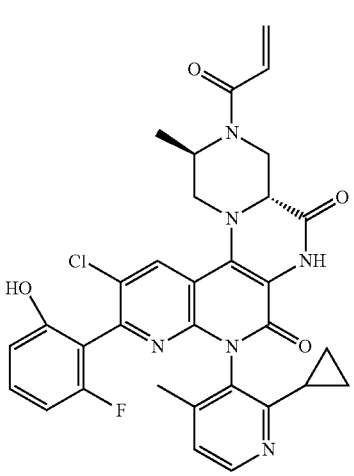 [SMILES: C=CC(=O)N1C[C@@H]2C(=O)Nc3c(c4cc(Cl)c(-c5c(O)cccc5F)nc4n(-c4c(C)ccnc4C4CC4)c3=O)N2C[C@H]1C]
Z104

TABLE A-1-continued
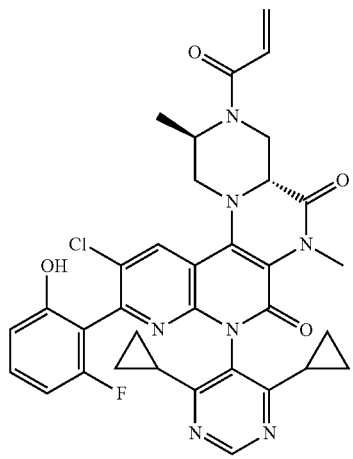 [SMILES: C=CC(=O)N1C[C@@H]2C(=O)N(C)c3c(c4cc(Cl)c(-c5c(O)cccc5F)nc4n(-c4c(C5CC5)ncnc4C4CC4)c3=O)N2C[C@H]1C]
Z105
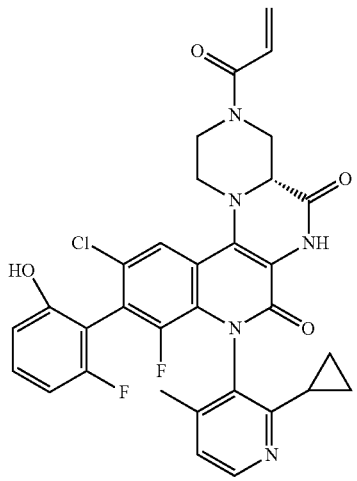
Z108
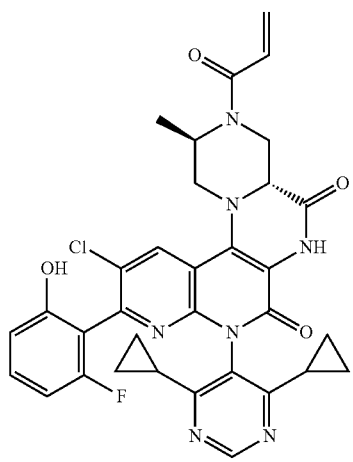 [SMILES: C=CC(=O)N1C[C@@H]2C(=O)Nc3c(c4cc(Cl)c(-c5c(O)cccc5F)nc4n(-c4c(C5CC5)ncnc4C4CC4)c3=O)N2C[C@H]1C]
Z106
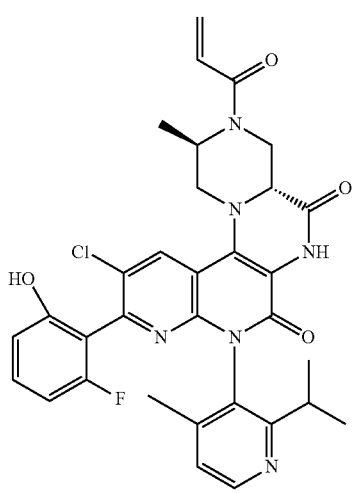
Z109
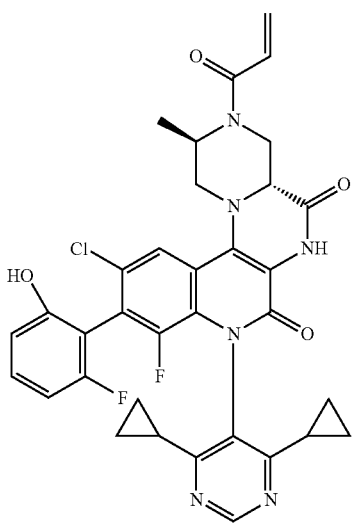 [SMILES: C=CC(=O)N1C[C@@H]2C(=O)Nc3c(c4cc(Cl)c(-c5c(O)cccc5F)c(F)c4n(-c4c(C5CC5)ncnc4C4CC4)c3=O)N2C[C@H]1C]
Z107
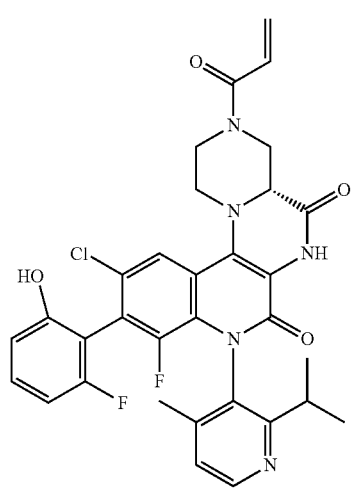 [SMILES: C=CC(=O)N1CCN2c3c(c(=O)n(-c4c(C)ccnc4C(C)C)c4c(F)c(-c5c(O)cccc5F)c(Cl)cc34)NC(=O)[C@H]2C1]
Z110

TABLE A-1-continued
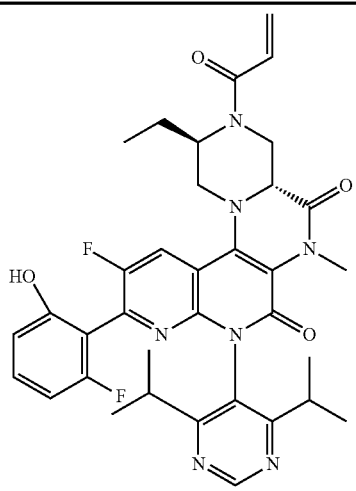
Z111
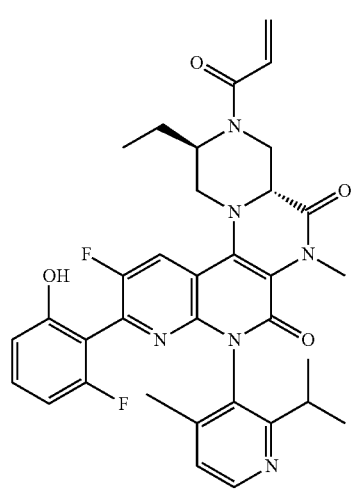 [SMILES: C=CC(=O)N1C[C@@H]2C(=O)N(C)c3c(c4cc(F)c(-c5c(O)cccc5F)nc4n(-c4c(C)ccnc4C(C)C)c3=O)N2C[C@H]1CC]
Z112
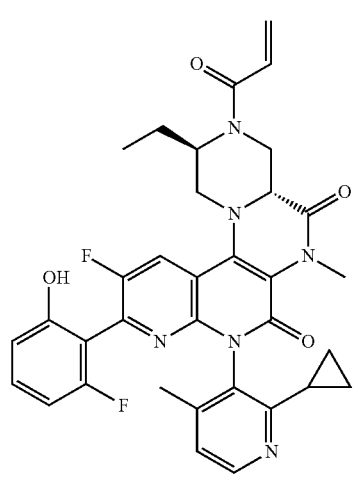 [SMILES: C=CC(=O)N1C[C@@H]2C(=O)N(C)c3c(c4cc(F)c(-c5c(O)cccc5F)nc4n(-c4c(C)ccnc4C4CC4)c3=O)N2C[C@H]1CC]
Z113
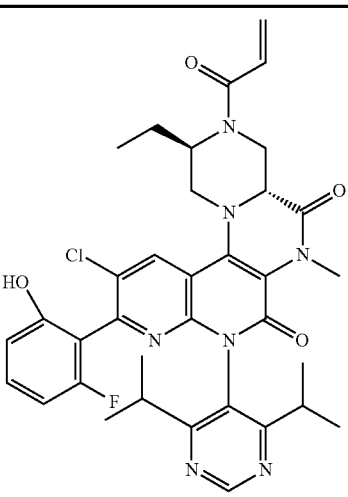
Z114
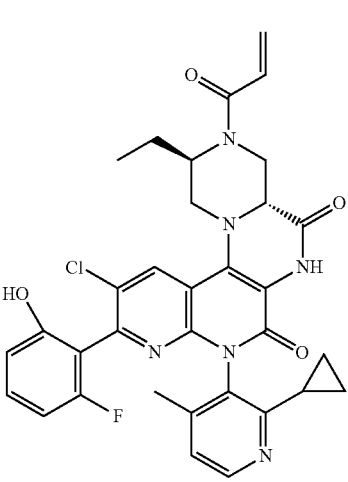 [SMILES: C=CC(=O)N1C[C@@H]2C(=O)Nc3c(c4cc(Cl)c(-c5c(O)cccc5F)nc4n(-c4c(C)ccnc4C4CC4)c3=O)N2C[C@H]1CC]
Z115
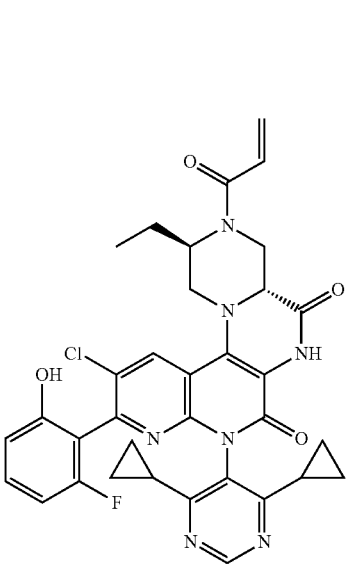 [SMILES: C=CC(=O)N1C[C@@H]2C(=O)Nc3c(c4cc(Cl)c(-c5c(O)cccc5F)nc4n(-c4c(C5CC5)ncnc4C4CC4)c3=O)N2C[C@H]1CC]
Z116

TABLE A-1-continued
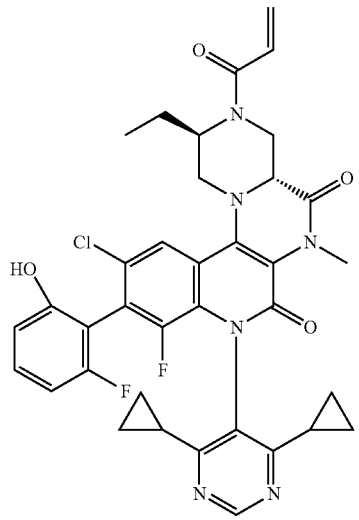 [SMILES: C=CC(=O)N1C[C@@H]2C(=O)N(C)c3c(c4cc(Cl)c(-c5c(O)cccc5F)c(F)c4n(-c4c(C5CC5)ncnc4C4CC4)c3=O)N2C[C@H]1CC]
Z117
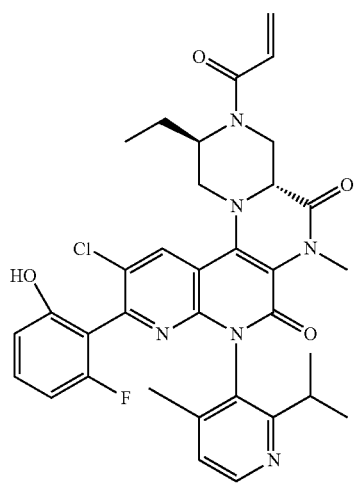 [SMILES: C=CC(=O)N1C[C@@H]2C(=O)N(C)c3c(c4cc(Cl)c(-c5c(O)cccc5F)nc4n(-c4c(C)ccnc4C(C)C)c3=O)N2C[C@H]1CC]
Z118
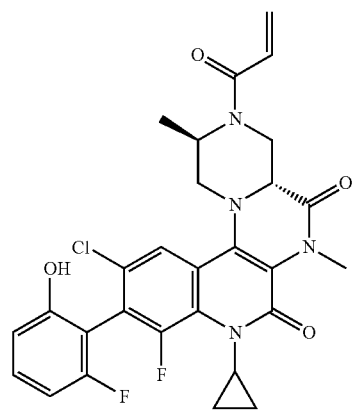 [SMILES: C=CC(=O)N1C[C@@H]2C(=O)N(C)c3c(c4cc(Cl)c(-c5c(O)cccc5F)c(F)c4n(C4CC4)c3=O)N2C[C@H]1C]
Z119
TABLE A-1-continued
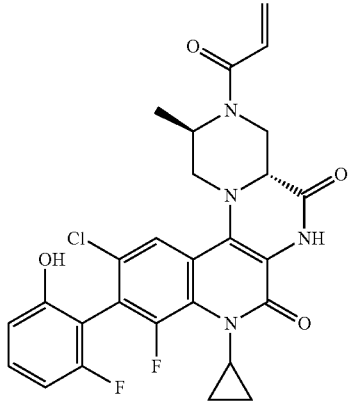 [SMILES: C=CC(=O)N1C[C@@H]2C(=O)Nc3c(c4cc(Cl)c(-c5c(O)cccc5F)c(F)c4n(C4CC4)c3=O)N2C[C@H]1C]
Z120
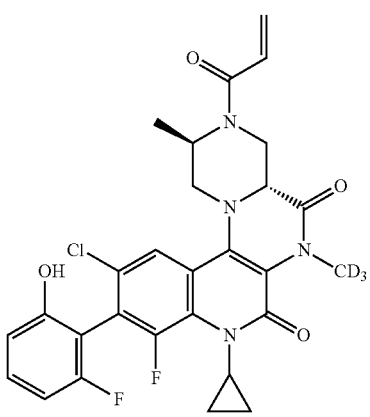 [SMILES: [2H]C([2H])([2H])N1C(=O)[C@H]2CN(C(=O)C=C)[C@H](C)CN2c2c1c(=O)n(C1CC1)c1c(F)c(-c3c(O)cccc3F)c(Cl)cc21]
Z121
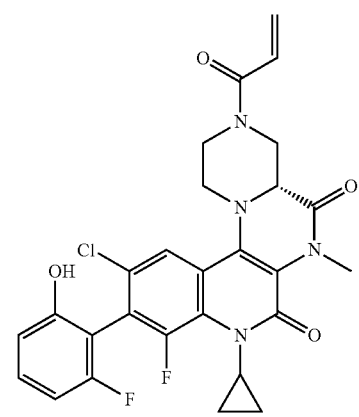 [SMILES: C=CC(=O)N1CCN2c3c(c(=O)n(C4CC4)c4c(F)c(-c5c(O)cccc5F)c(Cl)cc34)N(C)C(=O)[C@H]2C1]
Z122
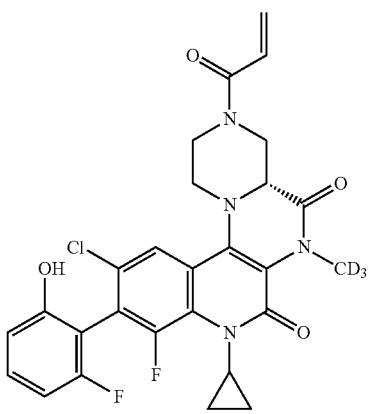 [SMILES: [2H]C([2H])([2H])N1C(=O)[C@H]2CN(C(=O)C=C)CCN2c2c1c(=O)n(C1CC1)c1c(F)c(-c3c(O)cccc3F)c(Cl)cc21]
Z123

TABLE A-1-continued
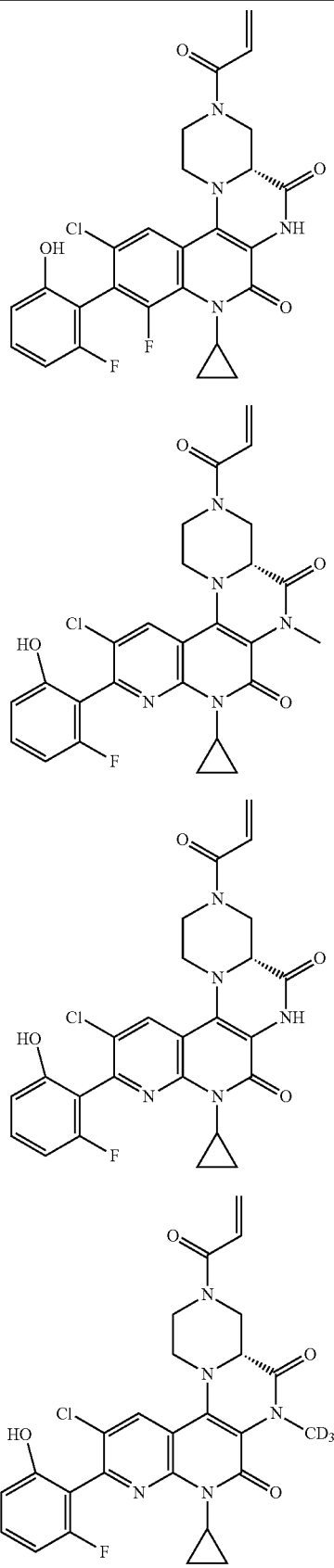
Z124
Z125
Z126
Z127
TABLE A-1-continued
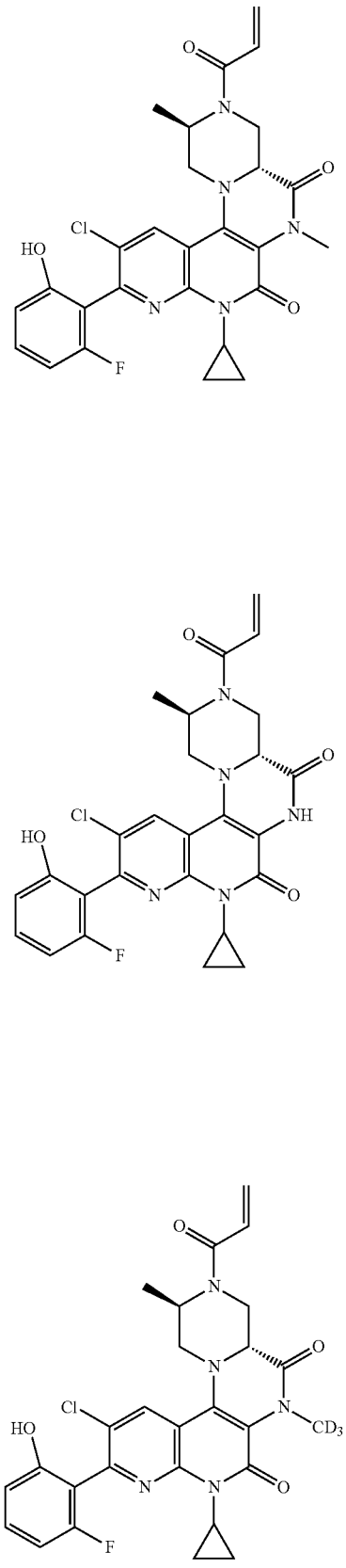
Z128
Z129
Z130

TABLE A-1-continued
Z131
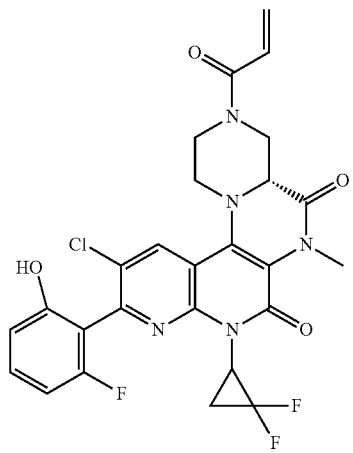 [SMILES: C=CC(=O)N1CCN2c3c(c(=O)n(C4CC4(F)F)c4nc(-c5c(O)cccc5F)c(Cl)cc34)N(C)C(=O)[C@H]2C1]
Z132
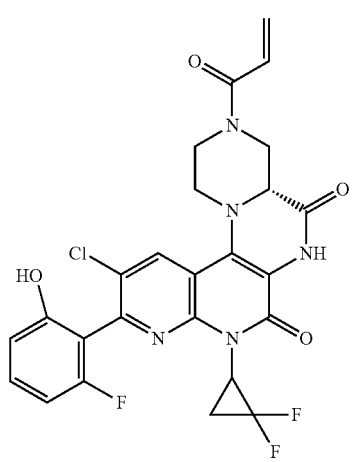 [SMILES: C=CC(=O)N1CCN2c3c(c(=O)n(C4CC4(F)F)c4nc(-c5c(O)cccc5F)c(Cl)cc34)NC(=O)[C@H]2C1]
Z133
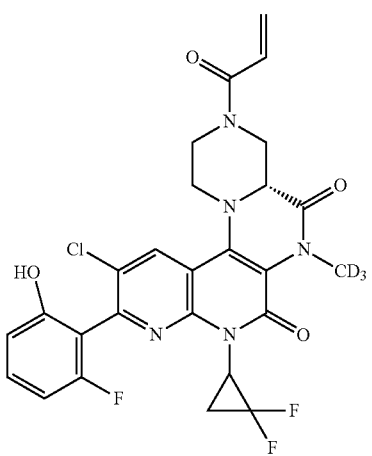 [SMILES: [2H]C([2H])([2H])N1C(=O)[C@H]2CN(C(=O)C=C)CCN2c2c1c(=O)n(C1CC1(F)F)c1nc(-c3c(O)cccc3F)c(Cl)cc21]
Z134
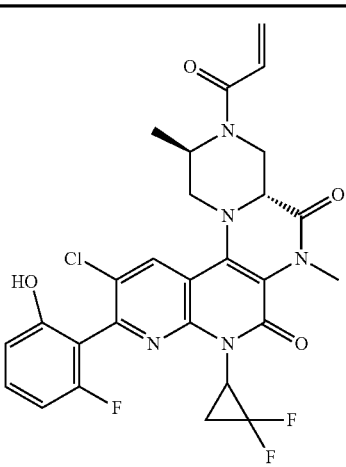
Z135
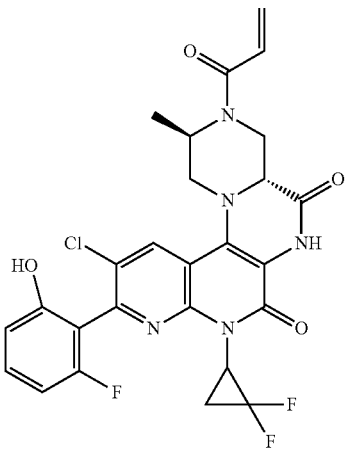 [SMILES: C=CC(=O)N1C[C@@H]2C(=O)Nc3c(c4cc(Cl)c(-c5c(O)cccc5F)nc4n(C4CC4(F)F)c3=O)N2C[C@H]1C]
Z136
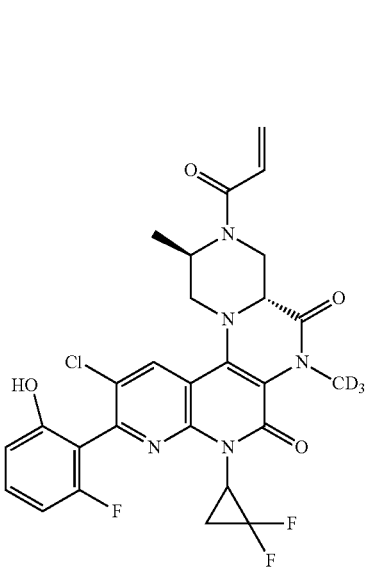 [SMILES: [2H]C([2H])([2H])N1C(=O)[C@H]2CN(C(=O)C=C)[C@H](C)CN2c2c1c(=O)n(C1CC1(F)F)c1nc(-c3c(O)cccc3F)c(Cl)cc21]

TABLE A-1-continued
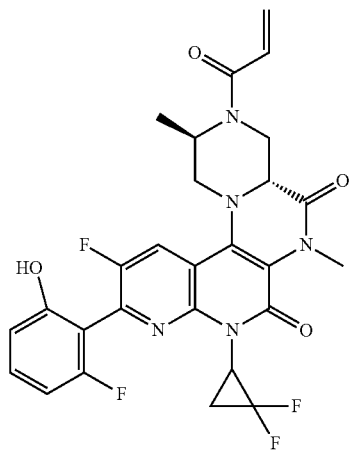 [SMILES: C=CC(=O)N1C[C@@H]2C(=O)N(C)c3c(c4cc(F)c(-c5c(O)cccc5F)nc4n(C4CC4(F)F)c3=O)N2C[C@H]1C]
Z137
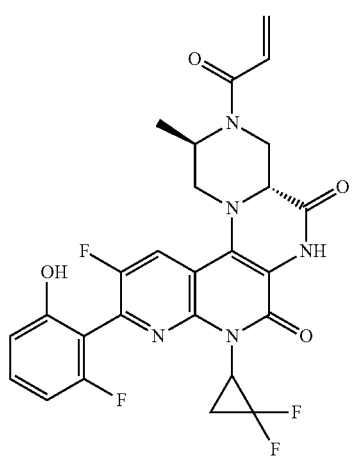 [SMILES: C=CC(=O)N1C[C@@H]2C(=O)Nc3c(c4cc(F)c(-c5c(O)cccc5F)nc4n(C4CC4(F)F)c3=O)N2C[C@H]1C]
Z138
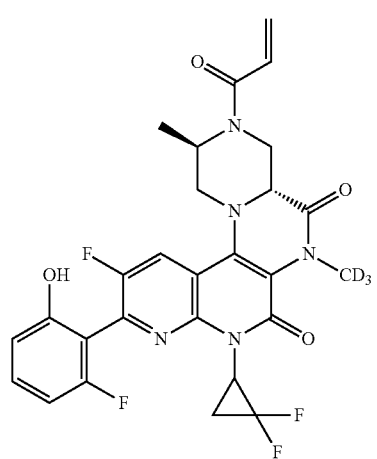 [SMILES: [2H]C([2H])([2H])N1C(=O)[C@H]2CN(C(=O)C=C)[C@H](C)CN2c2c1c(=O)n(C1CC1(F)F)c1nc(-c3c(O)cccc3F)c(F)cc21]
Z139
TABLE A-1-continued
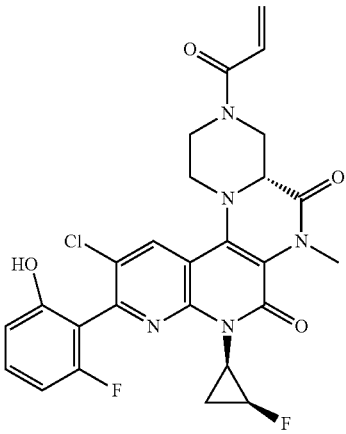 [SMILES: C=CC(=O)N1CCN2c3c(c(=O)n([C@@H]4C[C@@H]4F)c4nc(-c5c(O)cccc5F)c(Cl)cc34)N(C)C(=O)[C@H]2C1]
Z140
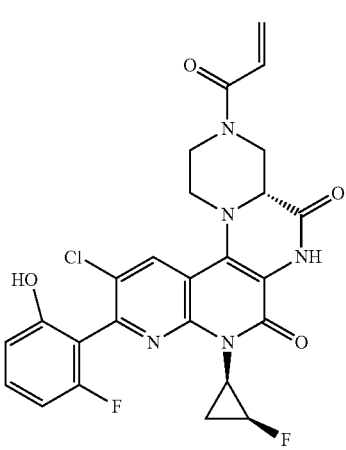 [SMILES: C=CC(=O)N1CCN2c3c(c(=O)n([C@@H]4C[C@@H]4F)c4nc(-c5c(O)cccc5F)c(Cl)cc34)NC(=O)[C@H]2C1]
Z141
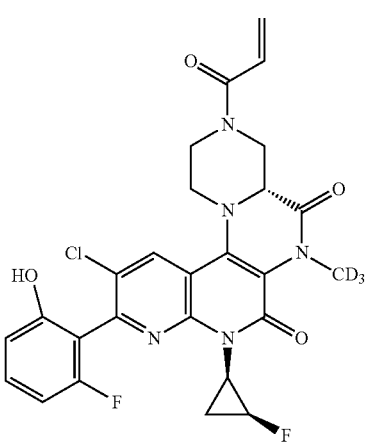 [SMILES: [2H]C([2H])([2H])N1C(=O)[C@H]2CN(C(=O)C=C)CCN2c2c1c(=O)n([C@@H]1C[C@@H]1F)c1nc(-c3c(O)cccc3F)c(Cl)cc21]
Z142

TABLE A-1-continued
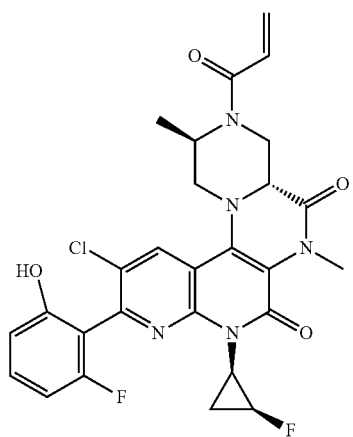 [SMILES: C=CC(=O)N1C[C@@H]2C(=O)N(C)c3c(c4cc(Cl)c(-c5c(O)cccc5F)nc4n([C@@H]4C[C@@H]4F)c3=O)N2C[C@H]1C]
Z143
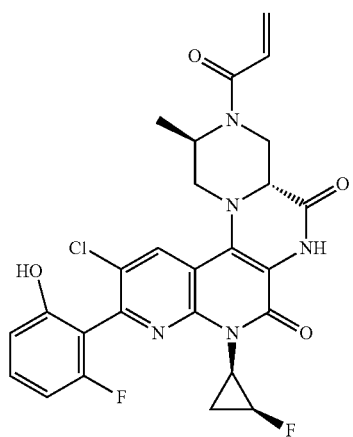 [SMILES: C=CC(=O)N1C[C@@H]2C(=O)Nc3c(c4cc(Cl)c(-c5c(O)cccc5F)nc4n([C@@H]4C[C@@H]4F)c3=O)N2C[C@H]1C]
Z144
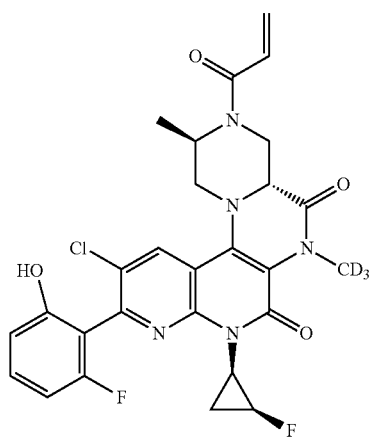 [SMILES: [2H]C([2H])([2H])N1C(=O)[C@H]2CN(C(=O)C=C)[C@H](C)CN2c2c1c(=O)n([C@@H]1C[C@@H]1F)c1nc(-c3c(O)cccc3F)c(Cl)cc21]
Z145
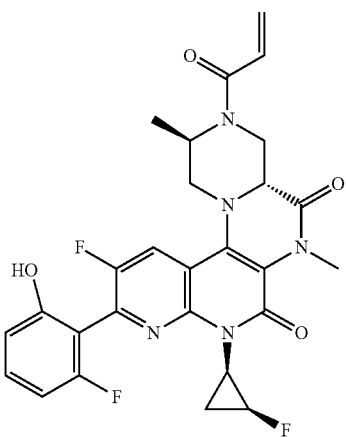 [SMILES: C=CC(=O)N1C[C@@H]2C(=O)N(C)c3c(c4cc(F)c(-c5c(O)cccc5F)nc4n([C@@H]4C[C@@H]4F)c3=O)N2C[C@H]1C]
Z146
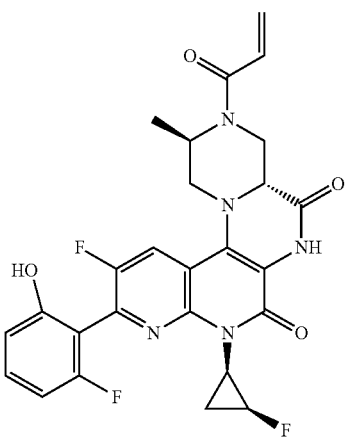 [SMILES: C=CC(=O)N1C[C@@H]2C(=O)Nc3c(c4cc(F)c(-c5c(O)cccc5F)nc4n([C@@H]4C[C@@H]4F)c3=O)N2C[C@H]1C]
Z147
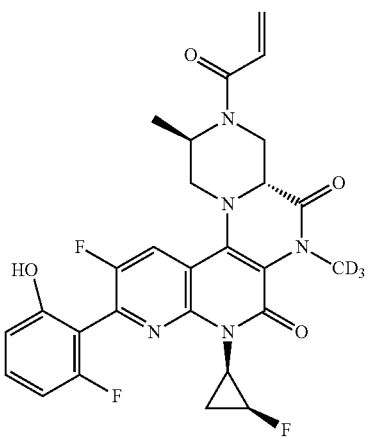 [SMILES: [2H]C([2H])([2H])N1C(=O)[C@H]2CN(C(=O)C=C)[C@H](C)CN2c2c1c(=O)n([C@@H]1C[C@@H]1F)c1nc(-c3c(O)cccc3F)c(F)cc21]
Z148

TABLE A-1-continued
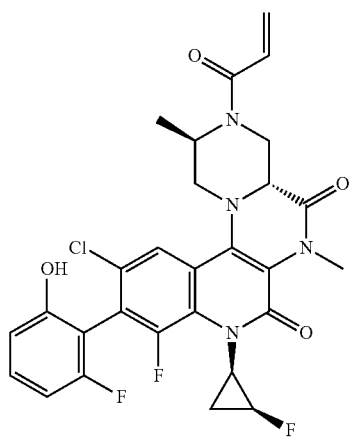 [SMILES: C=CC(=O)N1C[C@@H]2C(=O)N(C)c3c(c4cc(Cl)c(-c5c(O)cccc5F)c(F)c4n([C@@H]4C[C@@H]4F)c3=O)N2C[C@H]1C]
Z149
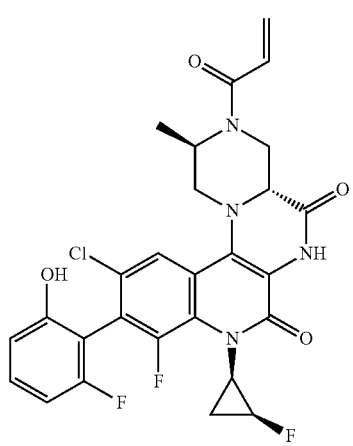 [SMILES: C=CC(=O)N1C[C@@H]2C(=O)Nc3c(c4cc(Cl)c(-c5c(O)cccc5F)c(F)c4n([C@@H]4C[C@@H]4F)c3=O)N2C[C@H]1C]
Z150
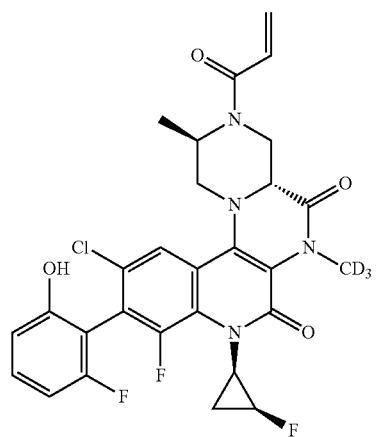 [SMILES: [2H]C([2H])([2H])N1C(=O)[C@H]2CN(C(=O)C=C)[C@H](C)CN2c2c1c(=O)n([C@@H]1C[C@@H]1F)c1c(F)c(-c3c(O)cccc3F)c(Cl)cc21]
Z151
TABLE A-1-continued
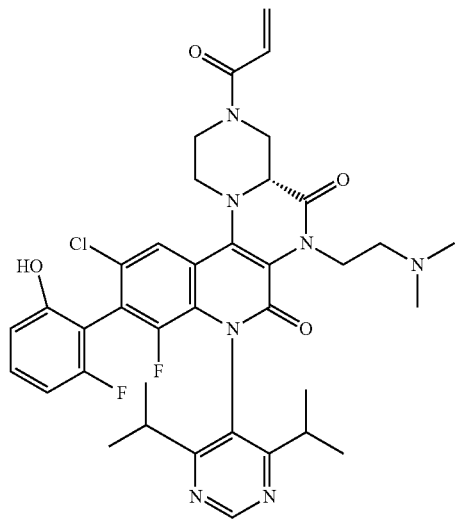 [SMILES: C=CC(=O)N1CCN2c3c(c(=O)n(-c4c(C(C)C)ncnc4C(C)C)c4c(F)c(-c5c(O)cccc5F)c(Cl)cc34)N(CCN(C)C)C(=O)[C@H]2C1]
Z152
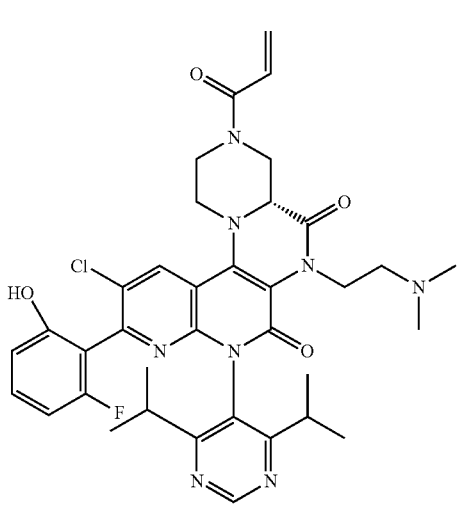 [SMILES: C=CC(=O)N1CCN2c3c(c(=O)n(-c4c(C(C)C)ncnc4C(C)C)c4nc(-c5c(O)cccc5F)c(Cl)cc34)N(CCN(C)C)C(=O)[C@H]2C1]
Z153
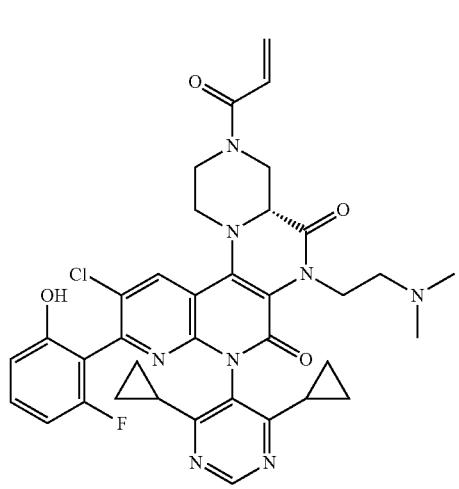 [SMILES: C=CC(=O)N1CCN2c3c(c(=O)n(-c4c(C5CC5)ncnc4C4CC4)c4nc(-c5c(O)cccc5F)c(Cl)cc34)N(CCN(C)C)C(=O)[C@H]2C1]
Z154

TABLE A-1-continued
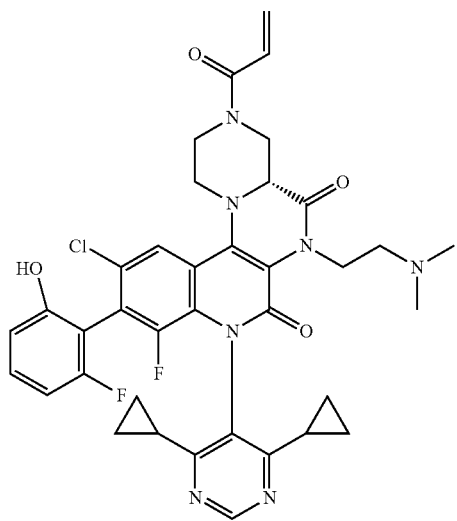 [SMILES: C=CC(=O)N1CCN2c3c(c(=O)n(-c4c(C5CC5)ncnc4C4CC4)c4c(F)c(-c5c(O)cccc5F)c(Cl)cc34)N(CCN(C)C)C(=O)[C@H]2C1]
Z155
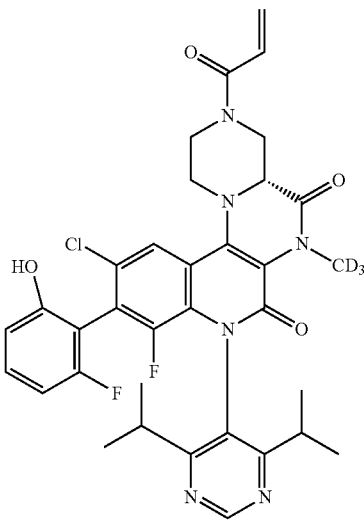 [SMILES: [2H]C([2H])([2H])N1C(=O)[C@H]2CN(C(=O)C=C)CCN2c2c1c(=O)n(-c1c(C(C)C)ncnc1C(C)C)c1c(F)c(-c3c(O)cccc3F)c(Cl)cc21]
Z158
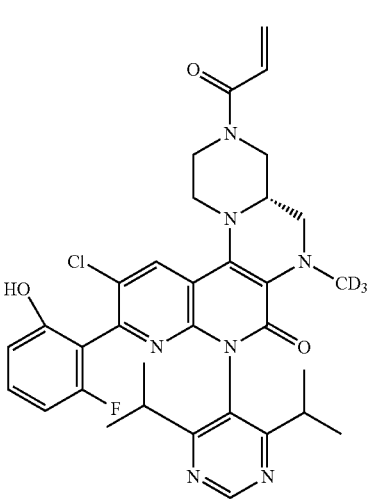 [SMILES: [2H]C([2H])([2H])N1C[C@H]2CN(C(=O)C=C)CCN2c2c1c(=O)n(-c1c(C(C)C)ncnc1C(C)C)c1nc(-c3c(O)cccc3F)c(Cl)cc21]
Z159
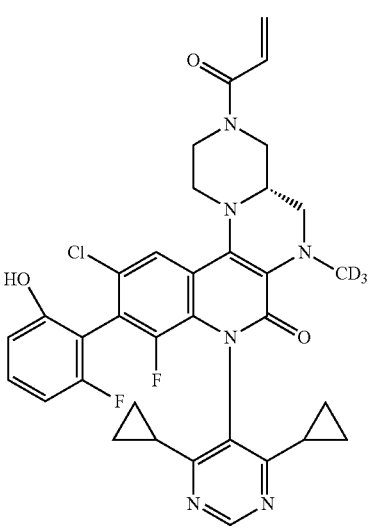 [SMILES: [2H]C([2H])([2H])N1C[C@H]2CN(C(=O)C=C)CCN2c2c1c(=O)n(-c1c(C3CC3)ncnc1C1CC1)c1c(F)c(-c3c(O)cccc3F)c(Cl)cc21]
Z160

TABLE A-1-continued
Z161
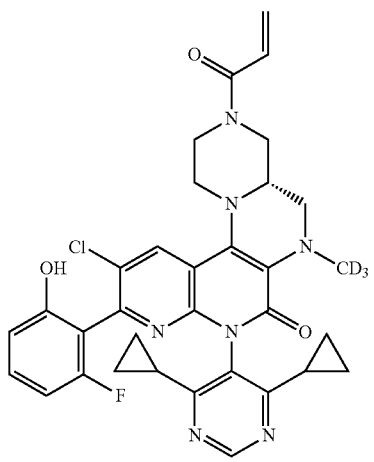 [SMILES: [2H]C([2H])([2H])N1C[C@H]2CN(C(=O)C=C)CCN2c2c1c(=O)n(-c1c(C3CC3)ncnc1C1CC1)c1nc(-c3c(O)cccc3F)c(Cl)cc21]
Z162
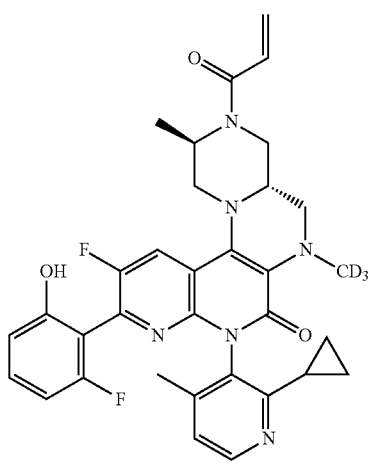 [SMILES: [2H]C([2H])([2H])N1C[C@H]2CN(C(=O)C=C)[C@H](C)CN2c2c1c(=O)n(-c1c(C)ccnc1C1CC1)c1nc(-c3c(O)cccc3F)c(F)cc21]
Z163
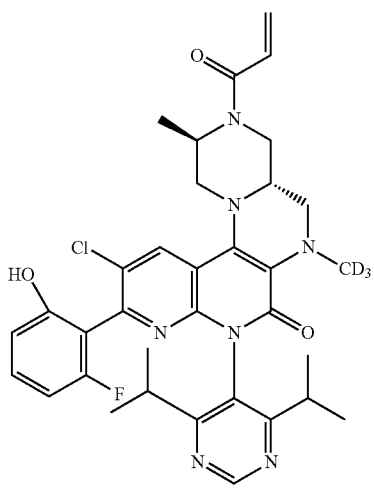 [SMILES: [2H]C([2H])([2H])N1C[C@H]2CN(C(=O)C=C)[C@H](C)CN2c2c1c(=O)n(-c1c(C(C)C)ncnc1C(C)C)c1nc(-c3c(O)cccc3F)c(Cl)cc21]
Z164
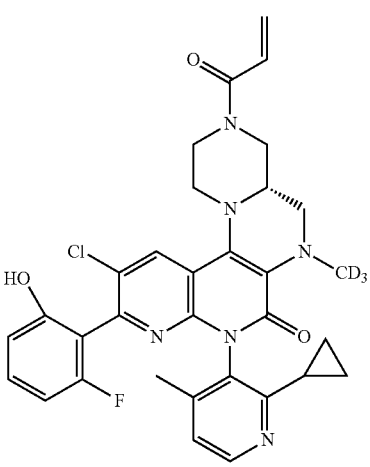 [SMILES: [2H]C([2H])([2H])N1C[C@H]2CN(C(=O)C=C)CCN2c2c1c(=O)n(-c1c(C)ccnc1C1CC1)c1nc(-c3c(O)cccc3F)c(Cl)cc21]
Z165
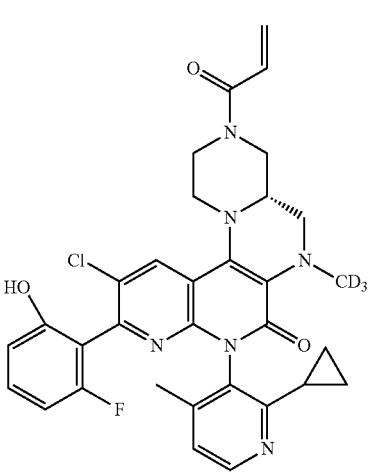
Z166
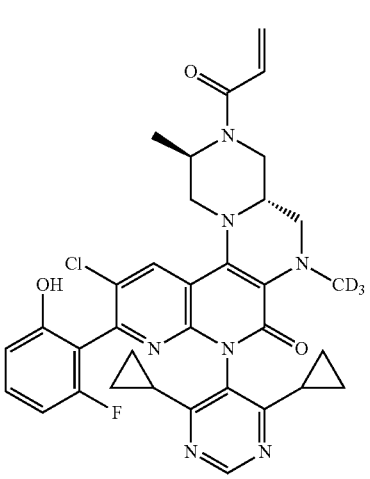 [SMILES: [2H]C([2H])([2H])N1C[C@H]2CN(C(=O)C=C)[C@H](C)CN2c2c1c(=O)n(-c1c(C3CC3)ncnc1C1CC1)c1nc(-c3c(O)cccc3F)c(Cl)cc21]

TABLE A-1-continued
Z167
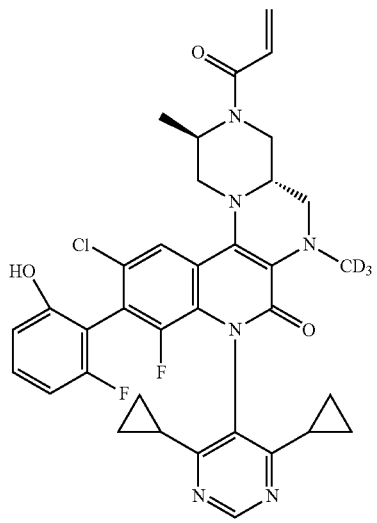 [SMILES: [2H]C([2H])([2H])N1C[C@H]2CN(C(=O)C=C)[C@H](C)CN2c2c1c(=O)n(-c1c(C3CC3)ncnc1C1CC1)c1c(F)c(-c3c(O)cccc3F)c(Cl)cc21]
Z168
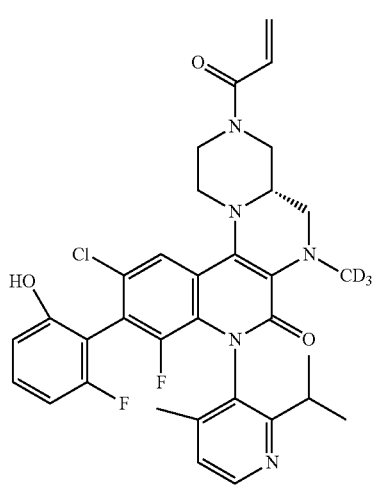 [SMILES: [2H]C([2H])([2H])N1C[C@H]2CN(C(=O)C=C)CCN2c2c1c(=O)n(-c1c(C)ccnc1C(C)C)c1c(F)c(-c3c(O)cccc3F)c(Cl)cc21]
Z169
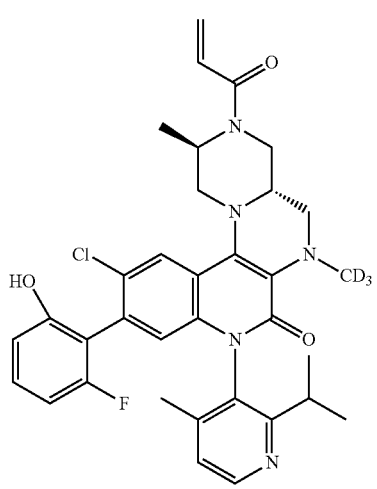 [SMILES: [2H]C([2H])([2H])N1C[C@H]2CN(C(=O)C=C)[C@H](C)CN2c2c1c(=O)n(-c1c(C)ccnc1C(C)C)c1cc(-c3c(O)cccc3F)c(Cl)cc21]
TABLE A-1-continued
Z170
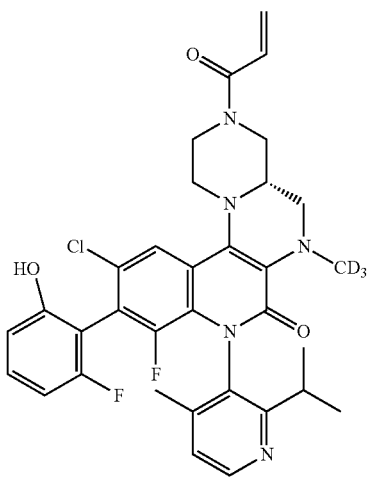 [SMILES: [2H]C([2H])([2H])N1C[C@H]2CN(C(=O)C=C)CCN2c2c1c(=O)n(-c1c(C)ccnc1C(C)C)c1c(F)c(-c3c(O)cccc3F)c(Cl)cc21]
Z171
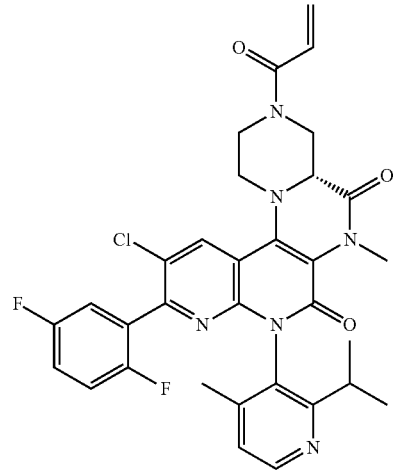 [SMILES: C=CC(=O)N1CCN2c3c(c(=O)n(-c4c(C)ccnc4C(C)C)c4nc(-c5cc(F)ccc5F)c(Cl)cc34)N(C)C(=O)[C@H]2C1]
Z172
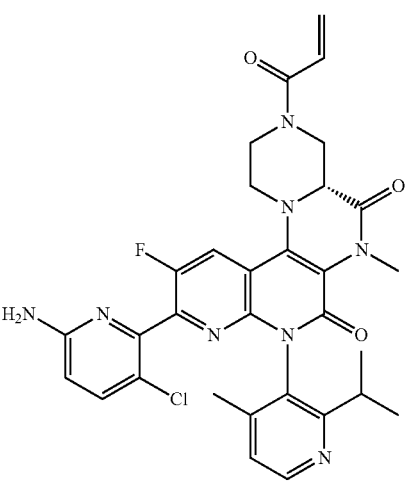 [SMILES: C=CC(=O)N1CCN2c3c(c(=O)n(-c4c(C)ccnc4C(C)C)c4nc(-c5nc(N)ccc5Cl)c(F)cc34)N(C)C(=O)[C@H]2C1]

TABLE A-1-continued
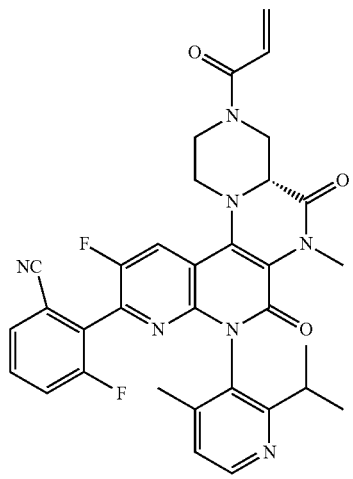 [SMILES: C=CC(=O)N1CCN2c3c(c(=O)n(-c4c(C)ccnc4C(C)C)c4nc(-c5c(F)cccc5C#N)c(F)cc34)N(C)C(=O)[C@H]2C1]
Z173
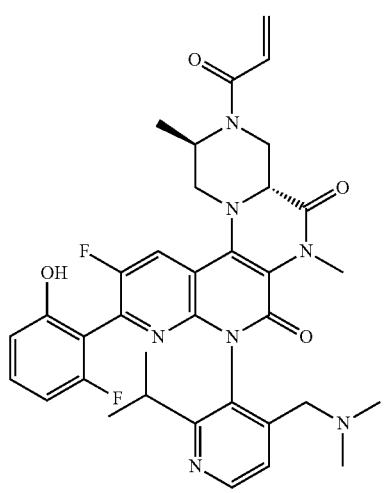 [SMILES: C=CC(=O)N1C[C@@H]2C(=O)N(C)c3c(c4cc(F)c(-c5c(O)cccc5F)nc4n(-c4c(CN(C)C)ccnc4C(C)C)c3=O)N2C[C@H]1C]
Z174
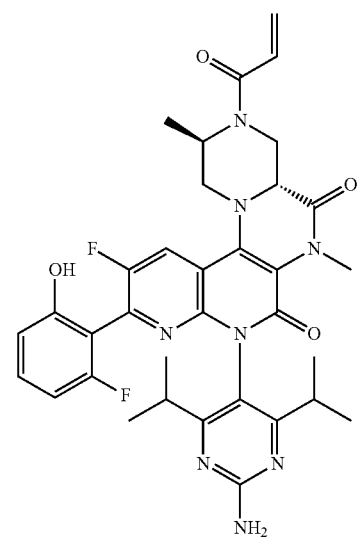 [SMILES: C=CC(=O)N1C[C@@H]2C(=O)N(C)c3c(c4cc(F)c(-c5c(O)cccc5F)nc4n(-c4c(C(C)C)nc(N)nc4C(C)C)c3=O)N2C[C@H]1C]
Z175
TABLE A-1-continued
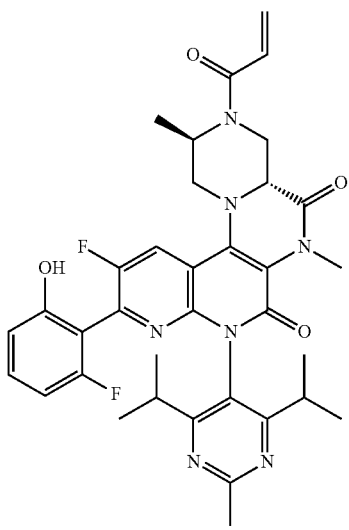 [SMILES: C=CC(=O)N1C[C@@H]2C(=O)N(C)c3c(c4cc(F)c(-c5c(O)cccc5F)nc4n(-c4c(C(C)C)nc(C)nc4C(C)C)c3=O)N2C[C@H]1C]
Z176
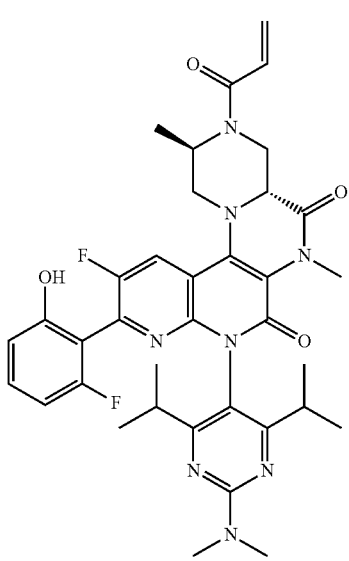 [SMILES: C=CC(=O)N1C[C@@H]2C(=O)N(C)c3c(c4cc(F)c(-c5c(O)cccc5F)nc4n(-c4c(C(C)C)nc(N(C)C)nc4C(C)C)c3=O)N2C[C@H]1C]
Z177
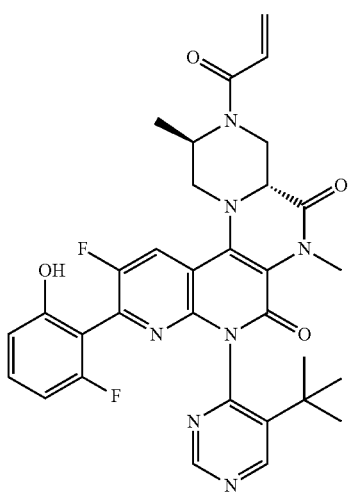 [SMILES: C=CC(=O)N1C[C@@H]2C(=O)N(C)c3c(c4cc(F)c(-c5c(O)cccc5F)nc4n(-c4ncncc4C(C)(C)C)c3=O)N2C[C@H]1C]
Z178

TABLE A-1-continued
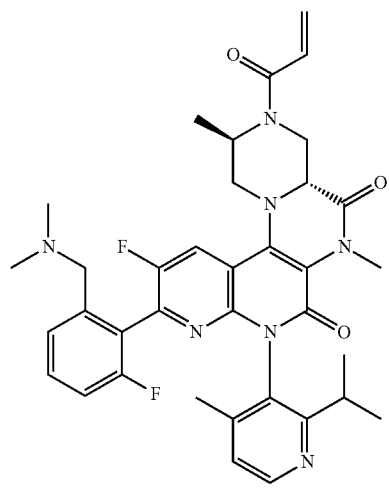 [SMILES: C=CC(=O)N1C[C@@H]2C(=O)N(C)c3c(c4cc(F)c(-c5c(F)cccc5CN(C)C)nc4n(-c4c(C)ccnc4C(C)C)c3=O)N2C[C@H]1C] Z179
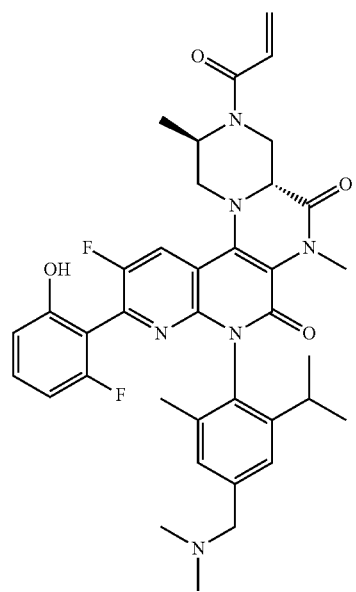 [SMILES: C=CC(=O)N1C[C@@H]2C(=O)N(C)c3c(c4cc(F)c(-c5c(O)cccc5F)nc4n(-c4c(C)cc(CN(C)C)cc4C(C)C)c3=O)N2C[C@H]1C] Z180
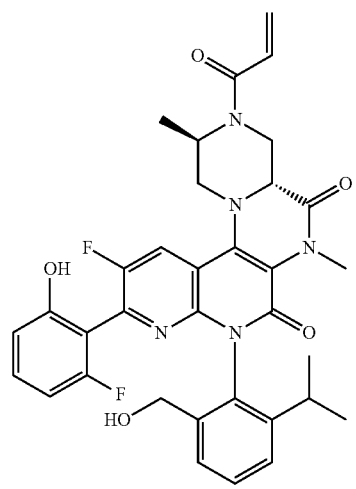 [SMILES: C=CC(=O)N1C[C@@H]2C(=O)N(C)c3c(c4cc(F)c(-c5c(O)cccc5F)nc4n(-c4c(CO)cccc4C(C)C)c3=O)N2C[C@H]1C] Z181
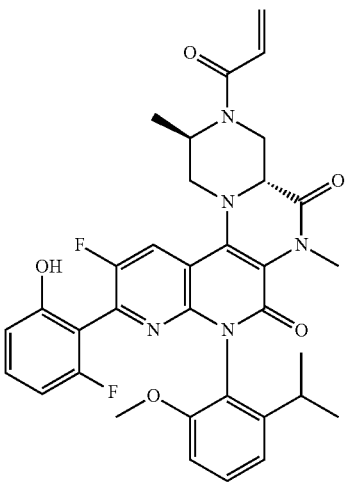 [SMILES: C=CC(=O)N1C[C@@H]2C(=O)N(C)c3c(c4cc(F)c(-c5c(O)cccc5F)nc4n(-c4c(OC)cccc4C(C)C)c3=O)N2C[C@H]1C] Z182
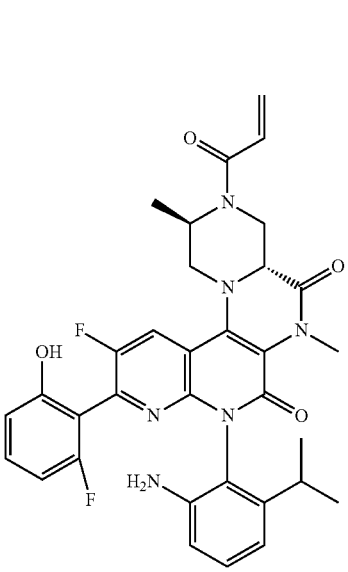 [SMILES: C=CC(=O)N1C[C@@H]2C(=O)N(C)c3c(c4cc(F)c(-c5c(O)cccc5F)nc4n(-c4c(N)cccc4C(C)C)c3=O)N2C[C@H]1C] Z183
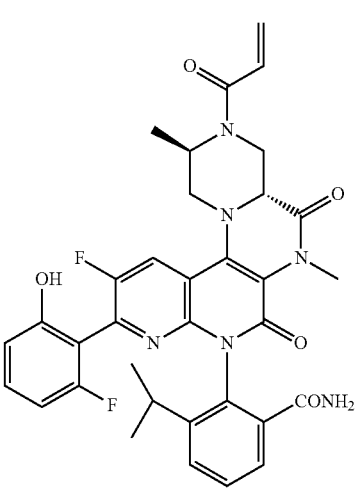 [SMILES: C=CC(=O)N1C[C@@H]2C(=O)N(C)c3c(c4cc(F)c(-c5c(O)cccc5F)nc4n(-c4c(C(N)=O)cccc4C(C)C)c3=O)N2C[C@H]1C] Z184

TABLE A-1-continued
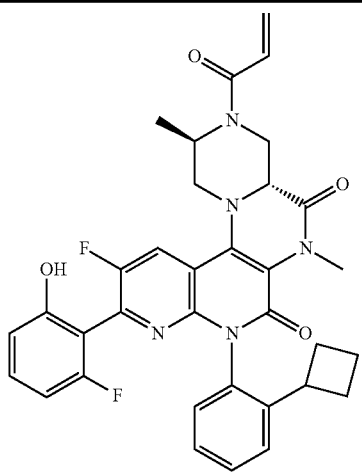
Z185
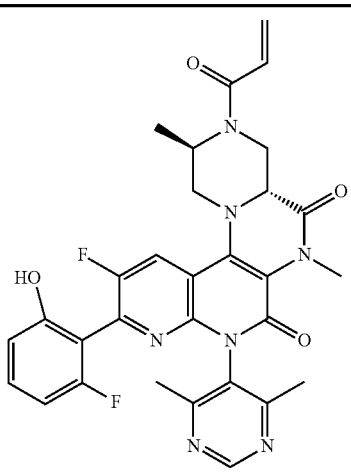
Z188
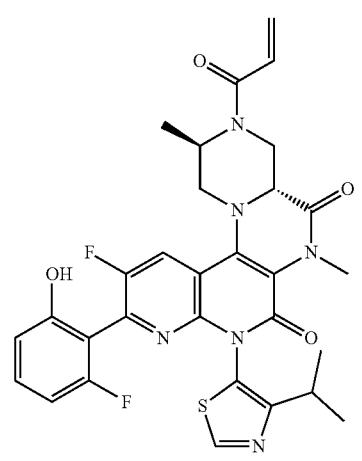 [SMILES: C=CC(=O)N1C[C@@H]2C(=O)N(C)c3c(c4cc(F)c(-c5c(O)cccc5F)nc4n(-c4scnc4C(C)C)c3=O)N2C[C@H]1C]
Z186
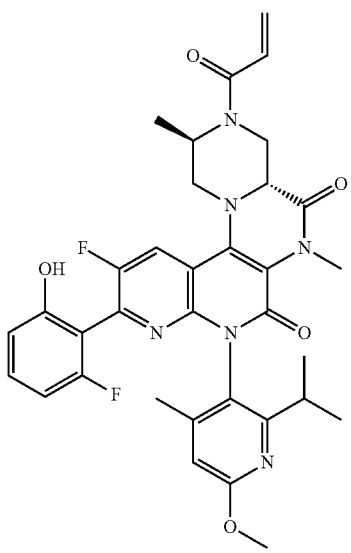
Z189
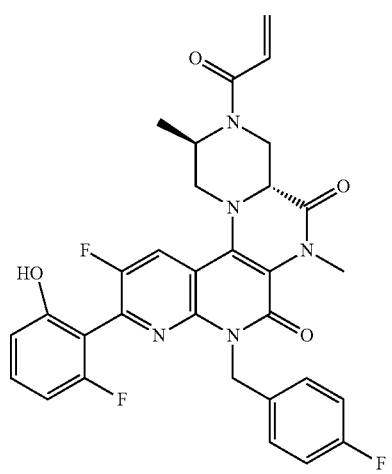 [SMILES: C=CC(=O)N1C[C@@H]2C(=O)N(C)c3c(c4cc(F)c(-c5c(O)cccc5F)nc4n(Cc4ccc(F)cc4)c3=O)N2C[C@H]1C]
Z187
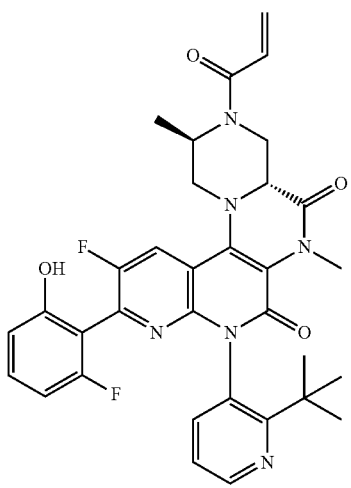 [SMILES: C=CC(=O)N1C[C@@H]2C(=O)N(C)c3c(c4cc(F)c(-c5c(O)cccc5F)nc4n(-c4cccnc4C(C)(C)C)c3=O)N2C[C@H]1C]
Z190

TABLE A-1-continued
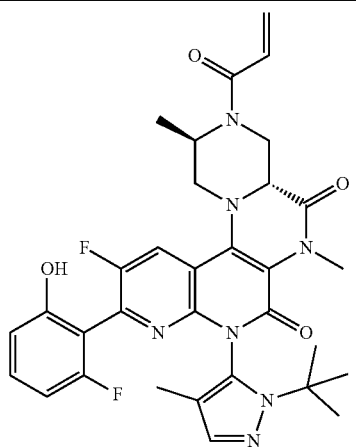
Z191
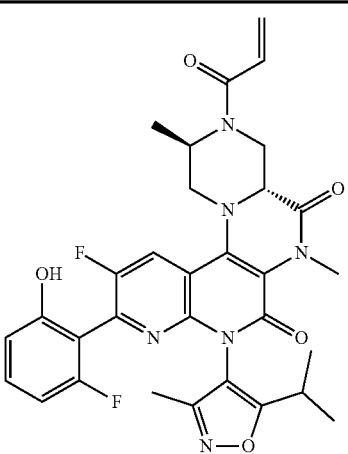
Z194
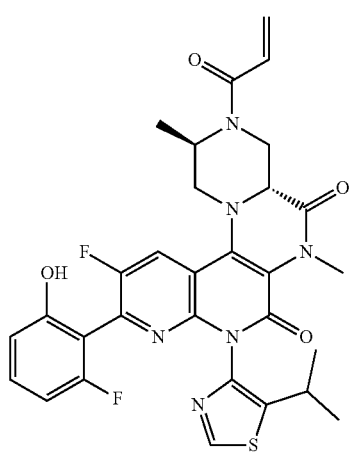 [SMILES: C=CC(=O)N1C[C@@H]2C(=O)N(C)c3c(c4cc(F)c(-c5c(O)cccc5F)nc4n(-c4ncsc4C(C)C)c3=O)N2C[C@H]1C]
Z192
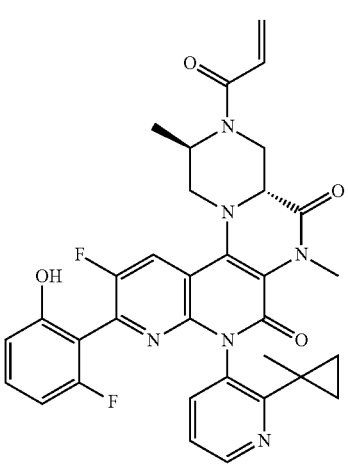
Z195
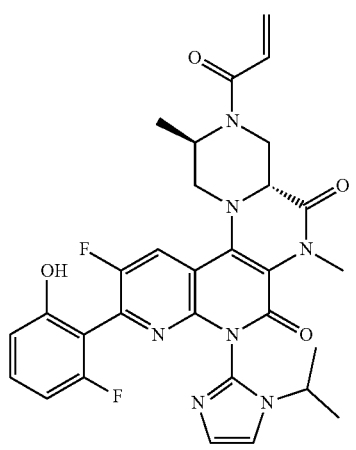 [SMILES: C=CC(=O)N1C[C@@H]2C(=O)N(C)c3c(c4cc(F)c(-c5c(O)cccc5F)nc4n(-c4nccn4C(C)C)c3=O)N2C[C@H]1C]
Z193
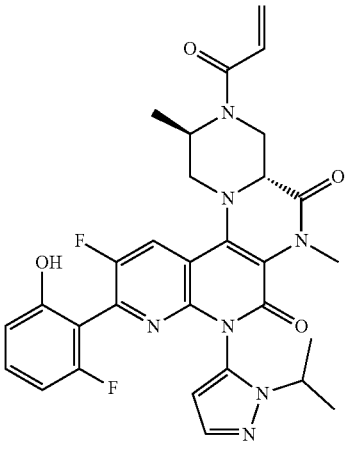 [SMILES: C=CC(=O)N1C[C@@H]2C(=O)N(C)c3c(c4cc(F)c(-c5c(O)cccc5F)nc4n(-c4ccnn4C(C)C)c3=O)N2C[C@H]1C]
Z196

TABLE A-1-continued
Z197
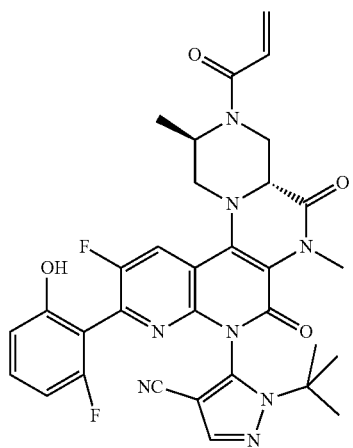 [SMILES: C=CC(=O)N1C[C@@H]2C(=O)N(C)c3c(c4cc(F)c(-c5c(O)cccc5F)nc4n(-c4c(C#N)cnn4C(C)(C)C)c3=O)N2C[C@H]1C]
Z200
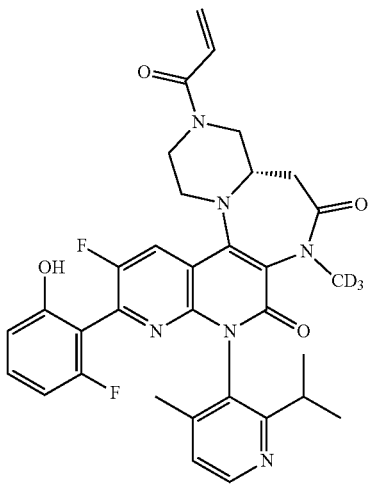
Z198
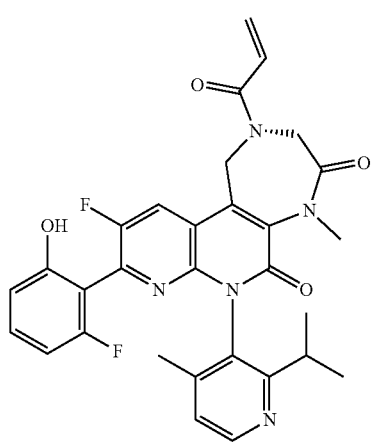
Z201
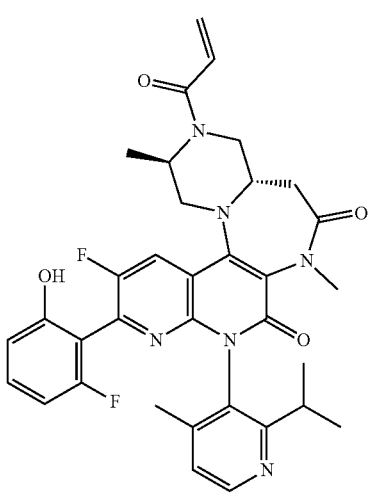
Z199
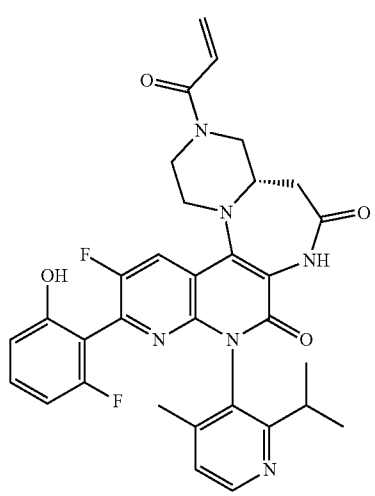 [SMILES: C=CC(=O)N1CCN2c3c(c(=O)n(-c4c(C)ccnc4C(C)C)c4nc(-c5c(O)cccc5F)c(F)cc34)NC(=O)C[C@H]2C1]
Z202
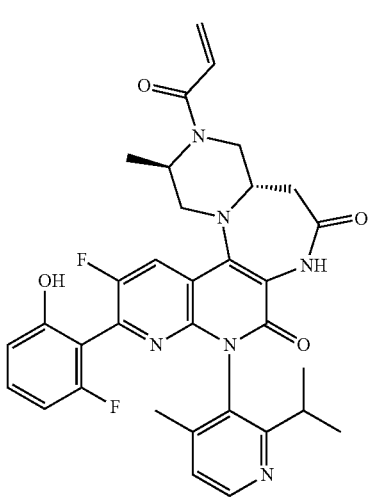 [SMILES: C=CC(=O)N1C[C@@H]2CC(=O)Nc3c(c4cc(F)c(-c5c(O)cccc5F)nc4n(-c4c(C)ccnc4C(C)C)c3=O)N2C[C@H]1C]

TABLE A-1-continued
Z203
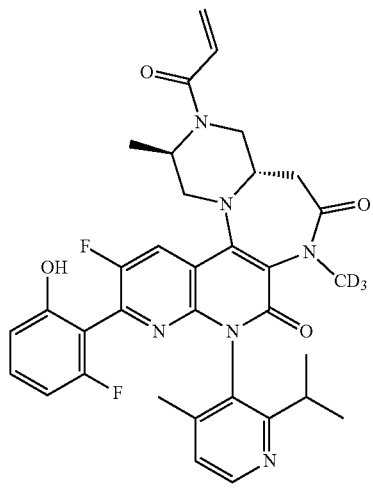 [SMILES: [2H]C([2H])([2H])N1C(=O)C[C@H]2CN(C(=O)C=C)[C@H](C)CN2c2c1c(=O)n(-c1c(C)ccnc1C(C)C)c1nc(-c3c(O)cccc3F)c(F)cc21]
Z206
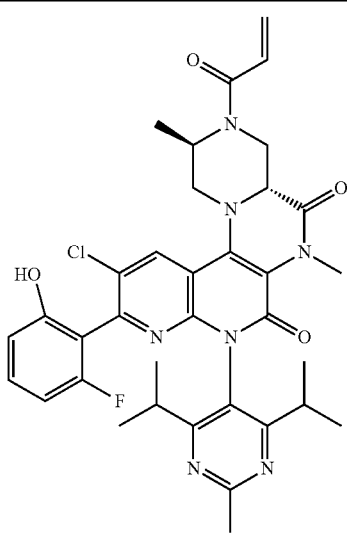
Z204
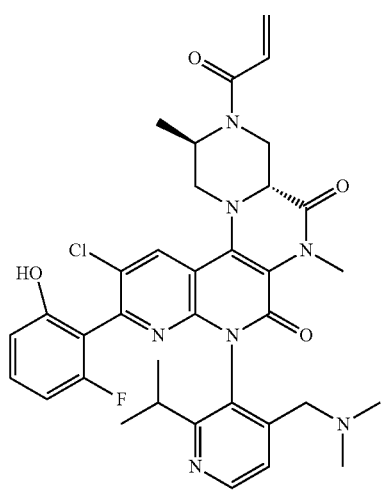 [SMILES: C=CC(=O)N1C[C@@H]2C(=O)N(C)c3c(c4cc(Cl)c(-c5c(O)cccc5F)nc4n(-c4c(CN(C)C)ccnc4C(C)C)c3=O)N2C[C@H]1C]
Z207
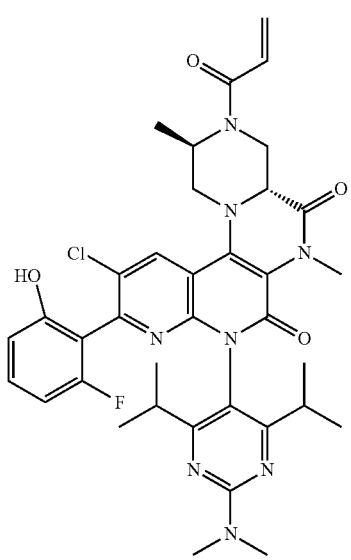
Z205
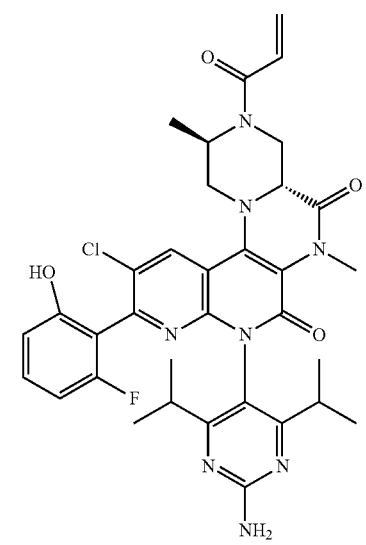 [SMILES: C=CC(=O)N1C[C@@H]2C(=O)N(C)c3c(c4cc(Cl)c(-c5c(O)cccc5F)nc4n(-c4c(C(C)C)nc(N)nc4C(C)C)c3=O)N2C[C@H]1C]
Z208
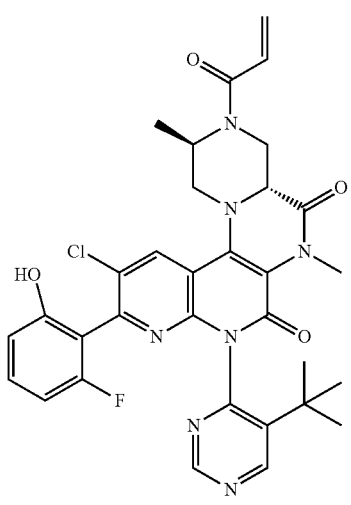 [SMILES: C=CC(=O)N1C[C@@H]2C(=O)N(C)c3c(c4cc(Cl)c(-c5c(O)cccc5F)nc4n(-c4ncncc4C(C)(C)C)c3=O)N2C[C@H]1C]

TABLE A-1-continued
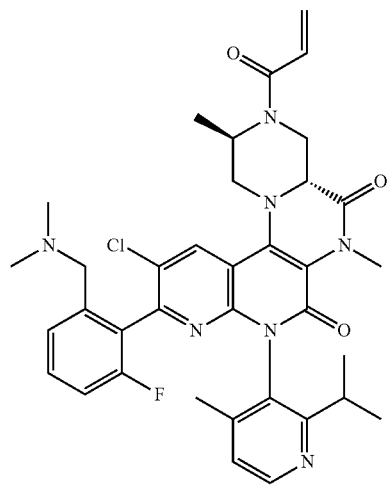 [SMILES: C=CC(=O)N1C[C@@H]2C(=O)N(C)c3c(c4cc(Cl)c(-c5c(F)cccc5CN(C)C)nc4n(-c4c(C)ccnc4C(C)C)c3=O)N2C[C@H]1C]
Z209
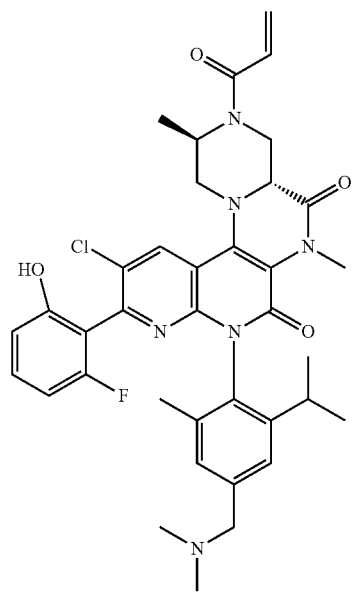 [SMILES: C=CC(=O)N1C[C@@H]2C(=O)N(C)c3c(c4cc(Cl)c(-c5c(O)cccc5F)nc4n(-c4c(C)cc(CN(C)C)cc4C(C)C)c3=O)N2C[C@H]1C]
Z210
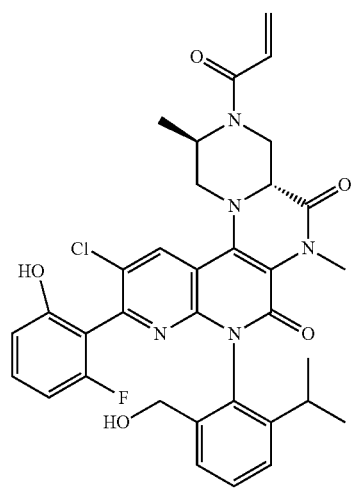 [SMILES: C=CC(=O)N1C[C@@H]2C(=O)N(C)c3c(c4cc(Cl)c(-c5c(O)cccc5F)nc4n(-c4c(CO)cccc4C(C)C)c3=O)N2C[C@H]1C]
Z211
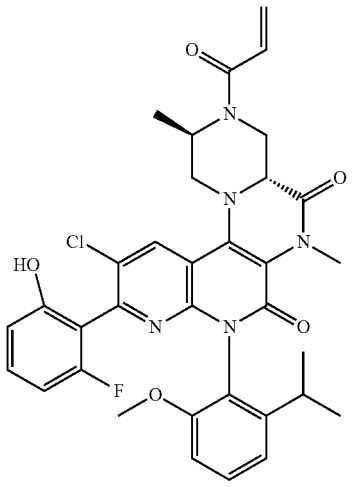 [SMILES: C=CC(=O)N1C[C@@H]2C(=O)N(C)c3c(c4cc(Cl)c(-c5c(O)cccc5F)nc4n(-c4c(OC)cccc4C(C)C)c3=O)N2C[C@H]1C]
Z212
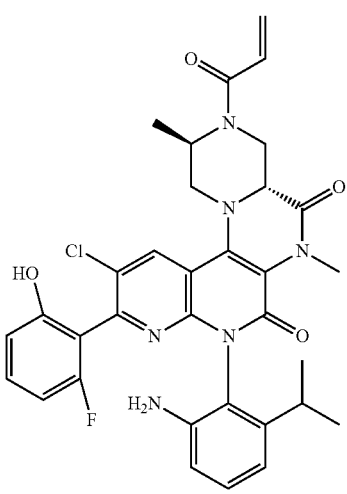 [SMILES: C=CC(=O)N1C[C@@H]2C(=O)N(C)c3c(c4cc(Cl)c(-c5c(O)cccc5F)nc4n(-c4c(N)cccc4C(C)C)c3=O)N2C[C@H]1C]
Z213
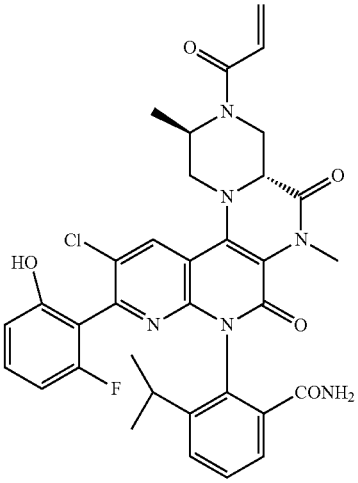 [SMILES: C=CC(=O)N1C[C@@H]2C(=O)N(C)c3c(c4cc(Cl)c(-c5c(O)cccc5F)nc4n(-c4c(C(N)=O)cccc4C(C)C)c3=O)N2C[C@H]1C]
Z214

TABLE A-1-continued
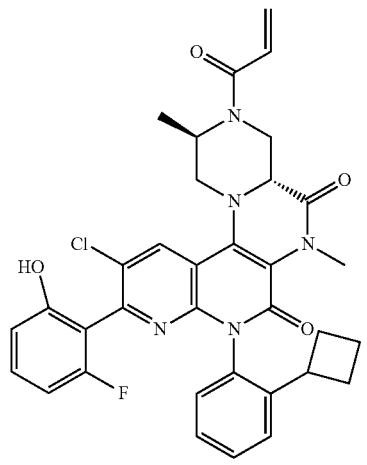 [SMILES: C=CC(=O)N1C[C@@H]2C(=O)N(C)c3c(c4cc(Cl)c(-c5c(O)cccc5F)nc4n(-c4ccccc4C4CCC4)c3=O)N2C[C@H]1C]
Z215
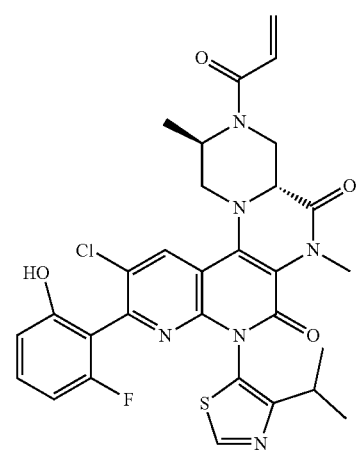 [SMILES: C=CC(=O)N1C[C@@H]2C(=O)N(C)c3c(c4cc(Cl)c(-c5c(O)cccc5F)nc4n(-c4scnc4C(C)C)c3=O)N2C[C@H]1C]
Z216
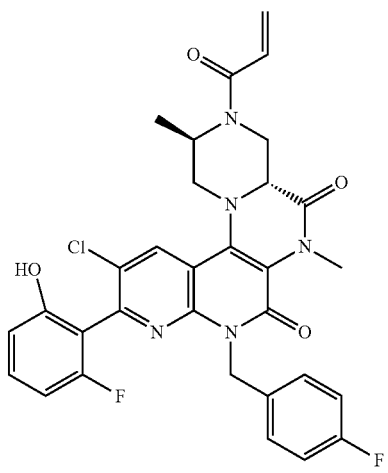 [SMILES: C=CC(=O)N1C[C@@H]2C(=O)N(C)c3c(c4cc(Cl)c(-c5c(O)cccc5F)nc4n(Cc4ccc(F)cc4)c3=O)N2C[C@H]1C]
Z217
TABLE A-1-continued
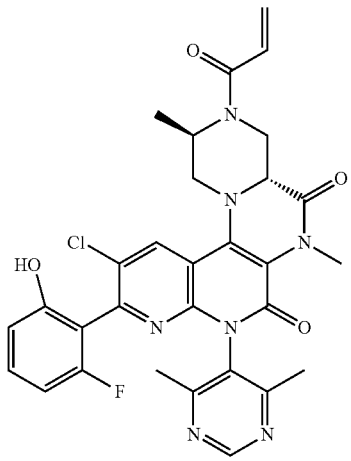 [SMILES: C=CC(=O)N1C[C@@H]2C(=O)N(C)c3c(c4cc(Cl)c(-c5c(O)cccc5F)nc4n(-c4c(C)ncnc4C)c3=O)N2C[C@H]1C]
Z218
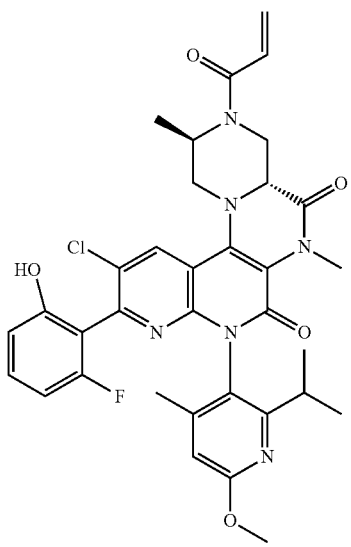 [SMILES: C=CC(=O)N1C[C@@H]2C(=O)N(C)c3c(c4cc(Cl)c(-c5c(O)cccc5F)nc4n(-c4c(C)cc(OC)nc4C(C)C)c3=O)N2C[C@H]1C]
Z219
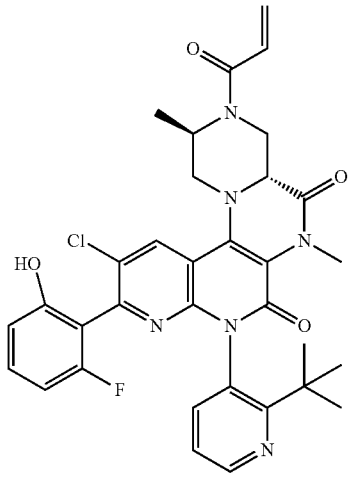 [SMILES: C=CC(=O)N1C[C@@H]2C(=O)N(C)c3c(c4cc(Cl)c(-c5c(O)cccc5F)nc4n(-c4cccnc4C(C)(C)C)c3=O)N2C[C@H]1C]
Z220

TABLE A-1-continued
Z221
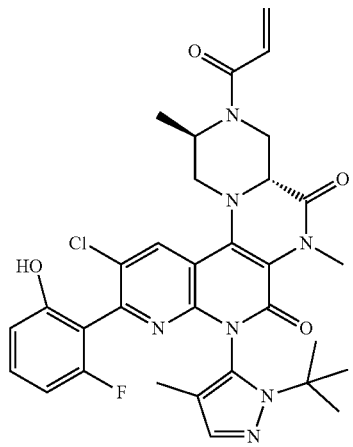 [SMILES: C=CC(=O)N1C[C@@H]2C(=O)N(C)c3c(c4cc(Cl)c(-c5c(O)cccc5F)nc4n(-c4c(C)cnn4C(C)(C)C)c3=O)N2C[C@H]1C]
Z222
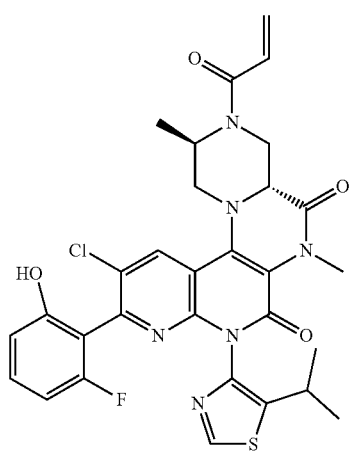 [SMILES: C=CC(=O)N1C[C@@H]2C(=O)N(C)c3c(c4cc(Cl)c(-c5c(O)cccc5F)nc4n(-c4ncsc4C(C)C)c3=O)N2C[C@H]1C]
Z223
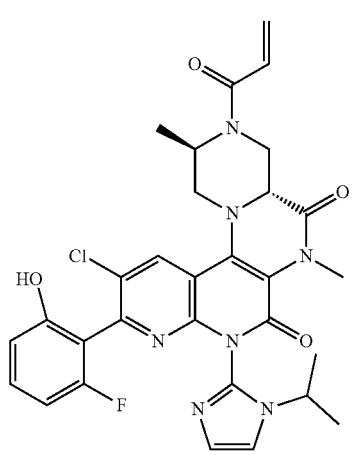 [SMILES: C=CC(=O)N1C[C@@H]2C(=O)N(C)c3c(c4cc(Cl)c(-c5c(O)cccc5F)nc4n(-c4nccn4C(C)C)c3=O)N2C[C@H]1C]
TABLE A-1-continued
Z224
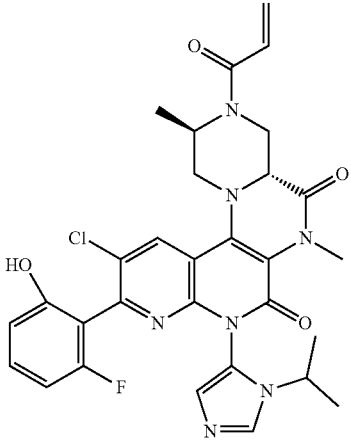 [SMILES: C=CC(=O)N1C[C@@H]2C(=O)N(C)c3c(c4cc(Cl)c(-c5c(O)cccc5F)nc4n(-c4cncn4C(C)C)c3=O)N2C[C@H]1C]
Z225
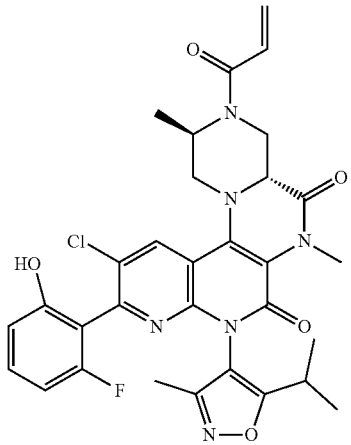 [SMILES: C=CC(=O)N1C[C@@H]2C(=O)N(C)c3c(c4cc(Cl)c(-c5c(O)cccc5F)nc4n(-c4c(C)noc4C(C)C)c3=O)N2C[C@H]1C]
Z226
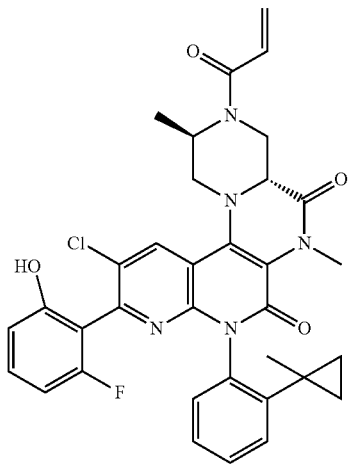 [SMILES: C=CC(=O)N1C[C@@H]2C(=O)N(C)c3c(c4cc(Cl)c(-c5c(O)cccc5F)nc4n(-c4ccccc4C4(C)CC4)c3=O)N2C[C@H]1C]

TABLE A-1-continued
Z227
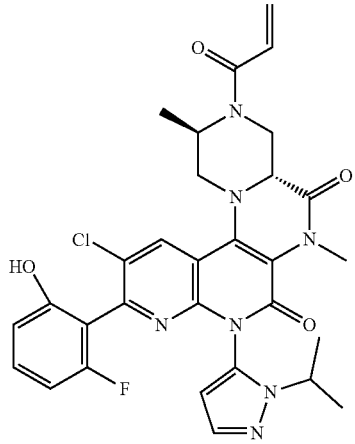 [SMILES: C=CC(=O)N1C[C@@H]2C(=O)N(C)c3c(c4cc(Cl)c(-c5c(O)cccc5F)nc4n(-c4ccnn4C(C)C)c3=O)N2C[C@H]1C]
Z228
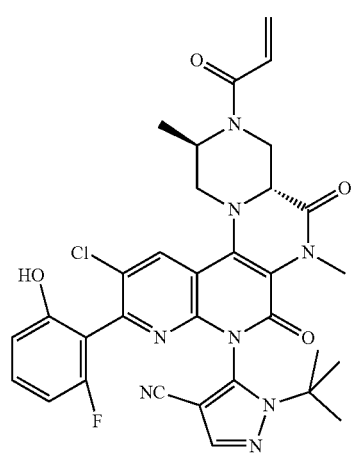 [SMILES: C=CC(=O)N1C[C@@H]2C(=O)N(C)c3c(c4cc(Cl)c(-c5c(O)cccc5F)nc4n(-c4c(C#N)cnn4C(C)(C)C)c3=O)N2C[C@H]1C]
Z229
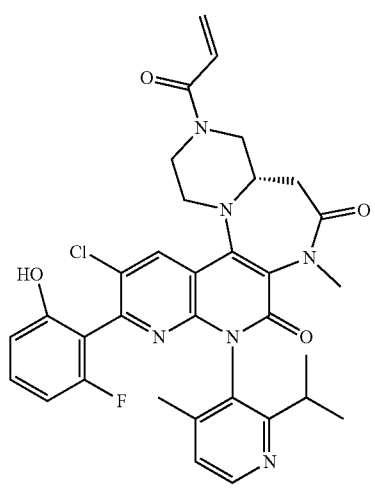 [SMILES: C=CC(=O)N1CCN2c3c(c(=O)n(-c4c(C)ccnc4C(C)C)c4nc(-c5c(O)cccc5F)c(Cl)cc34)N(C)C(=O)C[C@H]2C1]
TABLE A-1-continued
Z230
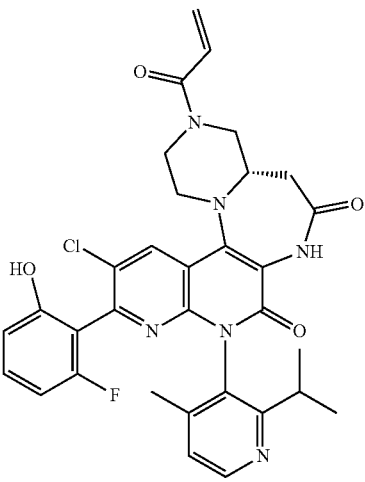 [SMILES: C=CC(=O)N1CCN2c3c(c(=O)n(-c4c(C)ccnc4C(C)C)c4nc(-c5c(O)cccc5F)c(Cl)cc34)NC(=O)C[C@H]2C1]
Z231
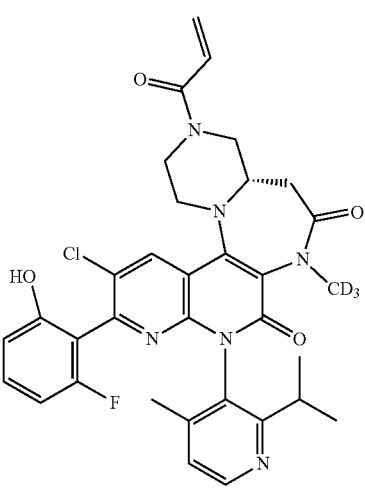 [SMILES: [2H]C([2H])([2H])N1C(=O)C[C@H]2CN(C(=O)C=C)CCN2c2c1c(=O)n(-c1c(C)ccnc1C(C)C)c1nc(-c3c(O)cccc3F)c(Cl)cc21]
Z232
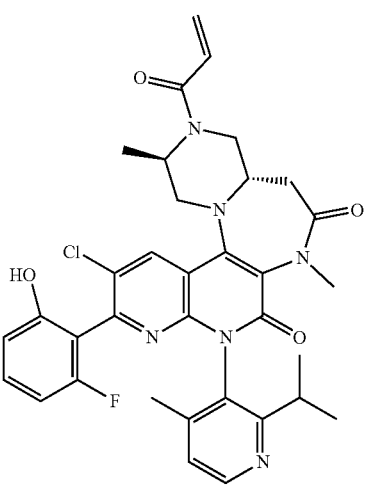 [SMILES: C=CC(=O)N1C[C@@H]2CC(=O)N(C)c3c(c4cc(Cl)c(-c5c(O)cccc5F)nc4n(-c4c(C)ccnc4C(C)C)c3=O)N2C[C@H]1C]

TABLE A-1-continued
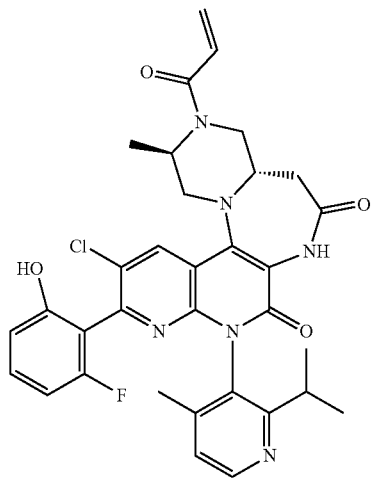 [SMILES: C=CC(=O)N1C[C@@H]2CC(=O)Nc3c(c4cc(Cl)c(-c5c(O)cccc5F)nc4n(-c4c(C)ccnc4C(C)C)c3=O)N2C[C@H]1C]
Z233
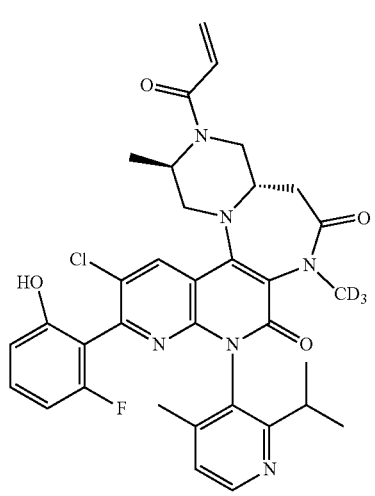 [SMILES: [2H]C([2H])([2H])N1C(=O)C[C@H]2CN(C(=O)C=C)[C@H](C)CN2c2c1c(=O)n(-c1c(C)ccnc1C(C)C)c1nc(-c3c(O)cccc3F)c(Cl)cc21]
Z234
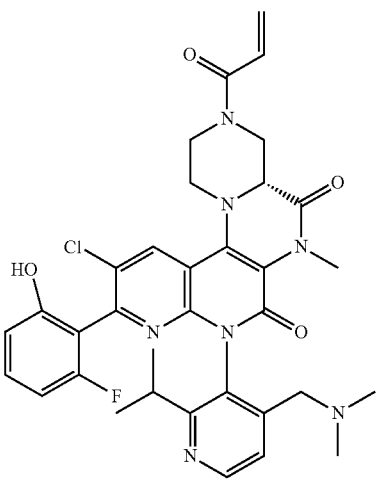 [SMILES: C=CC(=O)N1CCN2c3c(c(=O)n(-c4c(CN(C)C)ccnc4C(C)C)c4nc(-c5c(O)cccc5F)c(Cl)cc34)N(C)C(=O)[C@H]2C1]
Z235
TABLE A-1-continued
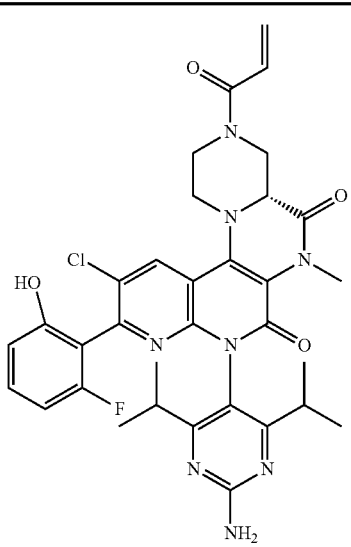
Z236
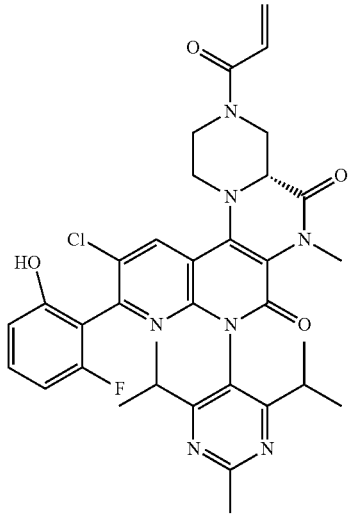 [SMILES: C=CC(=O)N1CCN2c3c(c(=O)n(-c4c(C(C)C)nc(C)nc4C(C)C)c4nc(-c5c(O)cccc5F)c(Cl)cc34)N(C)C(=O)[C@H]2C1]
Z237
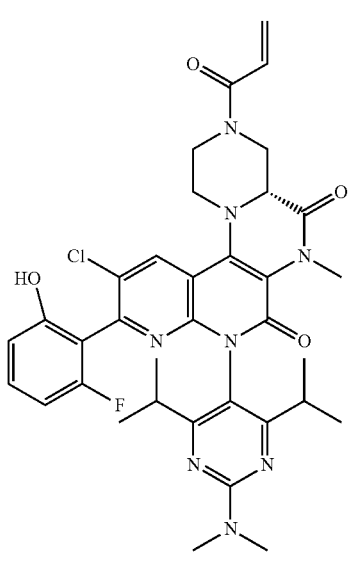 [SMILES: C=CC(=O)N1CCN2c3c(c(=O)n(-c4c(C(C)C)nc(N(C)C)nc4C(C)C)c4nc(-c5c(O)cccc5F)c(Cl)cc34)N(C)C(=O)[C@H]2C1]
Z238

TABLE A-1-continued
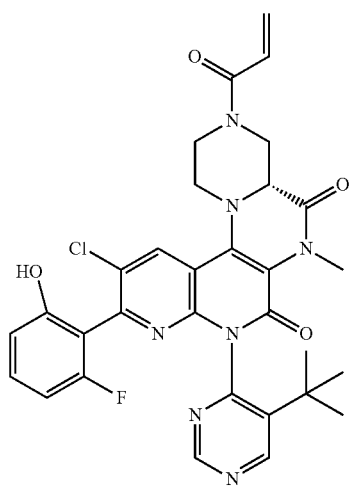 [SMILES: C=CC(=O)N1CCN2c3c(c(=O)n(-c4ncncc4C(C)(C)C)c4nc(-c5c(O)cccc5F)c(Cl)cc34)N(C)C(=O)[C@H]2C1]
Z239
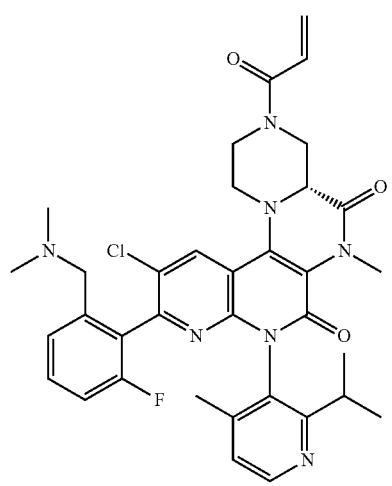 [SMILES: C=CC(=O)N1CCN2c3c(c(=O)n(-c4c(C)ccnc4C(C)C)c4nc(-c5c(F)cccc5CN(C)C)c(Cl)cc34)N(C)C(=O)[C@H]2C1]
Z240
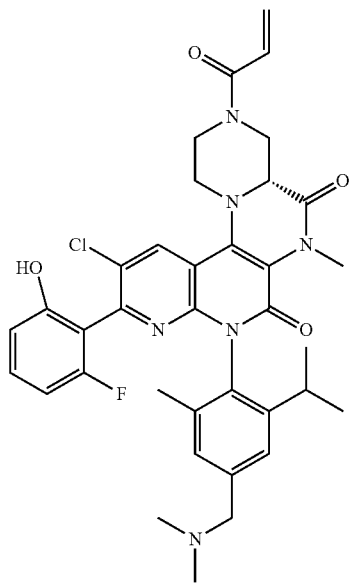 [SMILES: C=CC(=O)N1CCN2c3c(c(=O)n(-c4c(C)cc(CN(C)C)cc4C(C)C)c4nc(-c5c(O)cccc5F)c(Cl)cc34)N(C)C(=O)[C@H]2C1]
Z241
TABLE A-1-continued
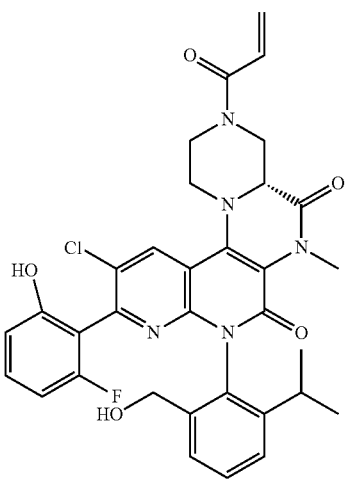 [SMILES: C=CC(=O)N1CCN2c3c(c(=O)n(-c4c(CO)cccc4C(C)C)c4nc(-c5c(O)cccc5F)c(Cl)cc34)N(C)C(=O)[C@H]2C1]
Z242
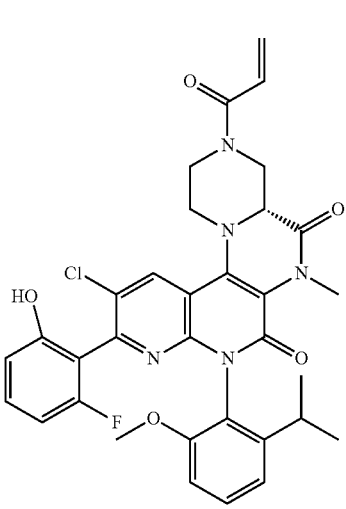 [SMILES: C=CC(=O)N1CCN2c3c(c(=O)n(-c4c(OC)cccc4C(C)C)c4nc(-c5c(O)cccc5F)c(Cl)cc34)N(C)C(=O)[C@H]2C1]
Z243
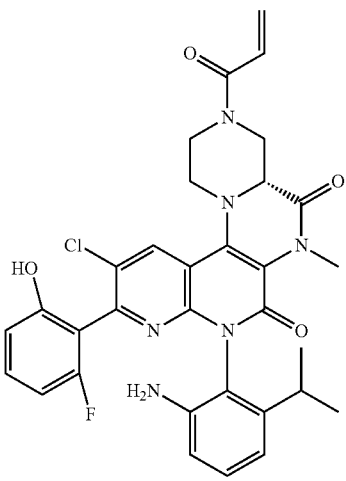 [SMILES: C=CC(=O)N1CCN2c3c(c(=O)n(-c4c(N)cccc4C(C)C)c4nc(-c5c(O)cccc5F)c(Cl)cc34)N(C)C(=O)[C@H]2C1]
Z244

TABLE A-1-continued
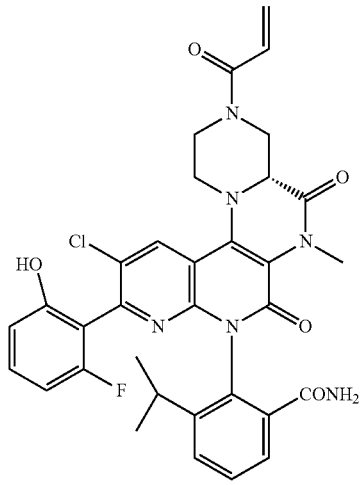 [SMILES: C=CC(=O)N1CCN2c3c(c(=O)n(-c4c(C(N)=O)cccc4C(C)C)c4nc(-c5c(O)cccc5F)c(Cl)cc34)N(C)C(=O)[C@H]2C1]
Z245
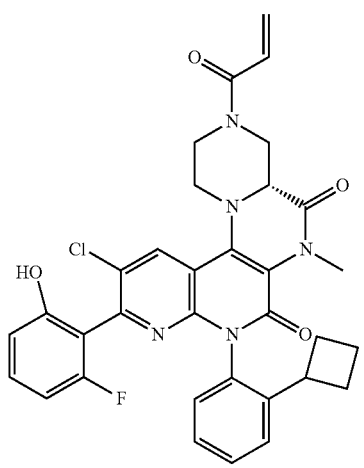 [SMILES: C=CC(=O)N1CCN2c3c(c(=O)n(-c4ccccc4C4CCC4)c4nc(-c5c(O)cccc5F)c(Cl)cc34)N(C)C(=O)[C@H]2C1]
Z246
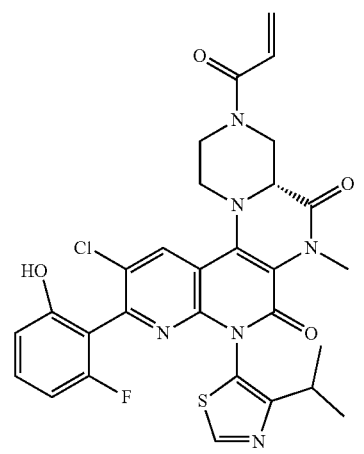 [SMILES: C=CC(=O)N1CCN2c3c(c(=O)n(-c4scnc4C(C)C)c4nc(-c5c(O)cccc5F)c(Cl)cc34)N(C)C(=O)[C@H]2C1]
Z247
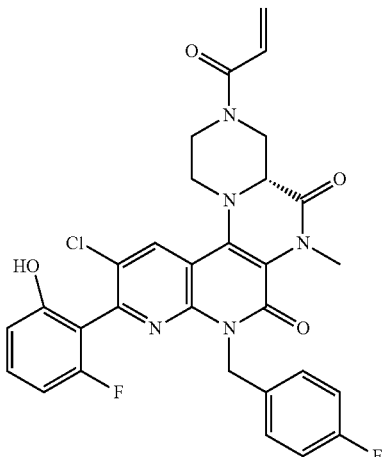
Z248
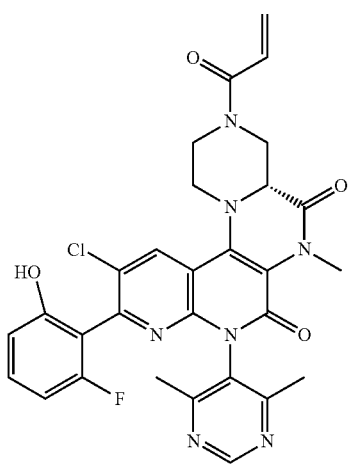 [SMILES: C=CC(=O)N1CCN2c3c(c(=O)n(-c4c(C)ncnc4C)c4nc(-c5c(O)cccc5F)c(Cl)cc34)N(C)C(=O)[C@H]2C1]
Z249
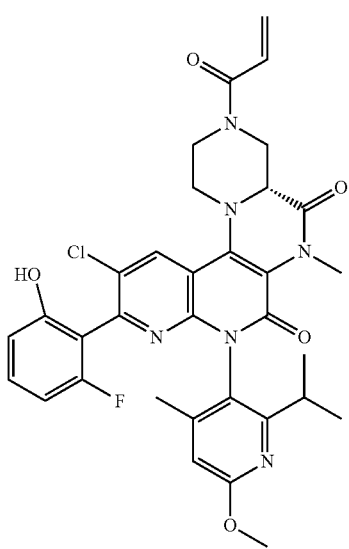 [SMILES: C=CC(=O)N1CCN2c3c(c(=O)n(-c4c(C)cc(OC)nc4C(C)C)c4nc(-c5c(O)cccc5F)c(Cl)cc34)N(C)C(=O)[C@H]2C1]
Z250

TABLE A-1-continued
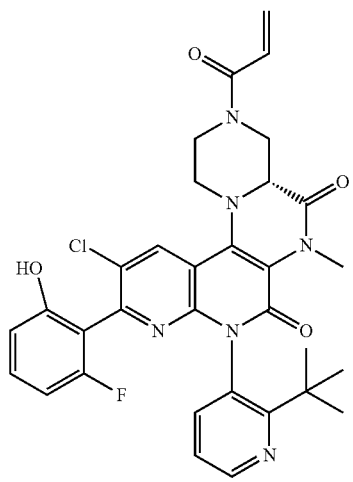 [SMILES: C=CC(=O)N1CCN2c3c(c(=O)n(-c4cccnc4C(C)(C)C)c4nc(-c5c(O)cccc5F)c(Cl)cc34)N(C)C(=O)[C@H]2C1]
Z251
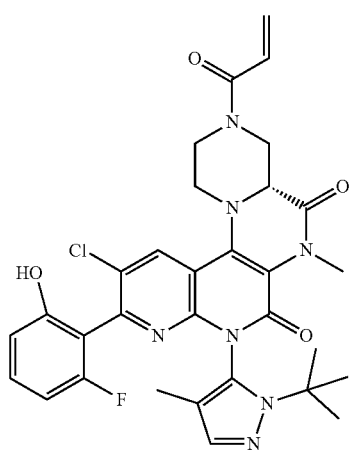
Z252
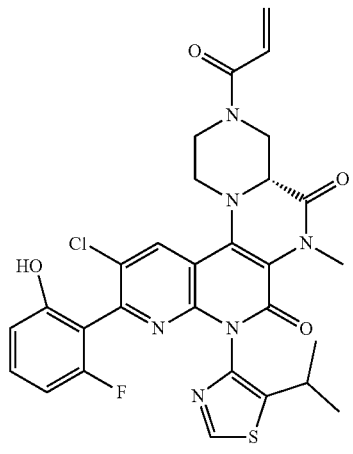 [SMILES: C=CC(=O)N1CCN2c3c(c(=O)n(-c4ncsc4C(C)C)c4nc(-c5c(O)cccc5F)c(Cl)cc34)N(C)C(=O)[C@H]2C1]
Z253
TABLE A-1-continued
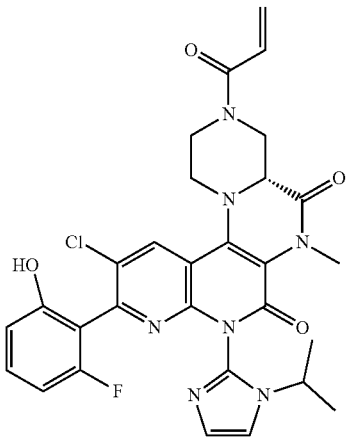 [SMILES: C=CC(=O)N1CCN2c3c(c(=O)n(-c4nccn4C(C)C)c4nc(-c5c(O)cccc5F)c(Cl)cc34)N(C)C(=O)[C@H]2C1]
Z254
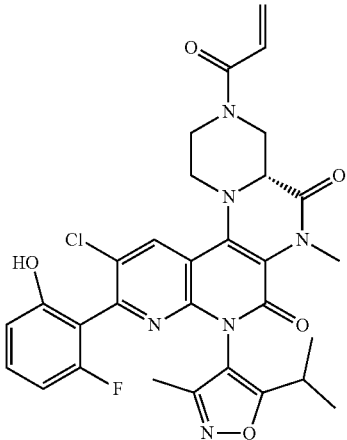 [SMILES: C=CC(=O)N1CCN2c3c(c(=O)n(-c4c(C)noc4C(C)C)c4nc(-c5c(O)cccc5F)c(Cl)cc34)N(C)C(=O)[C@H]2C1]
Z255
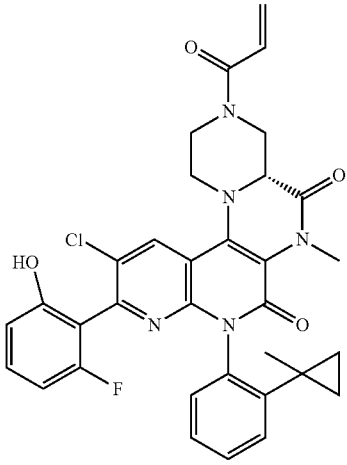 [SMILES: C=CC(=O)N1CCN2c3c(c(=O)n(-c4ccccc4C4(C)CC4)c4nc(-c5c(O)cccc5F)c(Cl)cc34)N(C)C(=O)[C@H]2C1]
Z256

TABLE A-1-continued
Z257
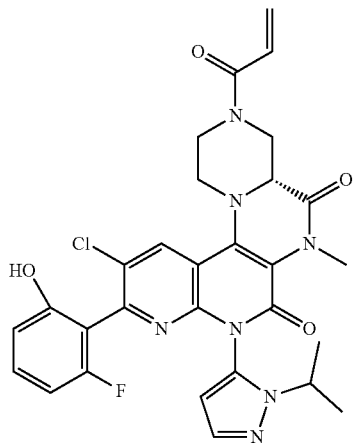 [SMILES: C=CC(=O)N1CCN2c3c(c(=O)n(-c4ccnn4C(C)C)c4nc(-c5c(O)cccc5F)c(Cl)cc34)N(C)C(=O)[C@H]2C1]
Z258
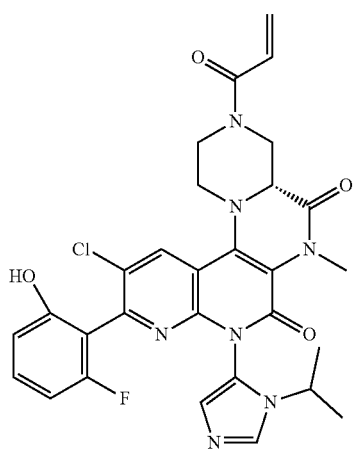 [SMILES: C=CC(=O)N1CCN2c3c(c(=O)n(-c4cncn4C(C)C)c4nc(-c5c(O)cccc5F)c(Cl)cc34)N(C)C(=O)[C@H]2C1]
Z259
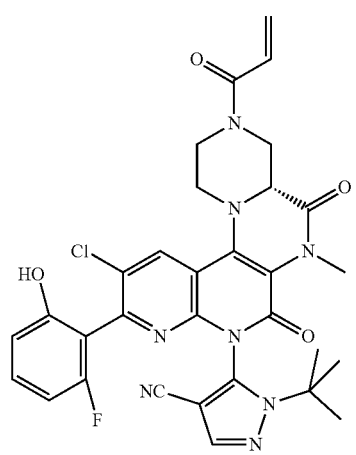 [SMILES: C=CC(=O)N1CCN2c3c(c(=O)n(-c4c(C#N)cnn4C(C)(C)C)c4nc(-c5c(O)cccc5F)c(Cl)cc34)N(C)C(=O)[C@H]2C1]
TABLE A-1-continued
Z260
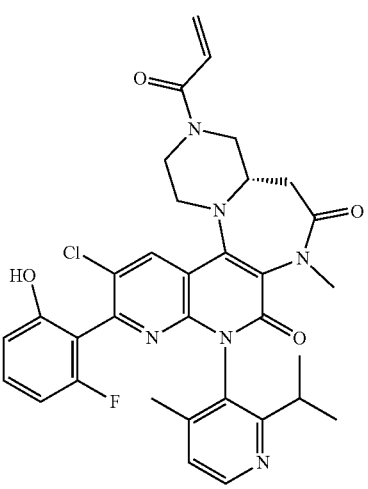 [SMILES: C=CC(=O)N1CCN2c3c(c(=O)n(-c4c(C)ccnc4C(C)C)c4nc(-c5c(O)cccc5F)c(Cl)cc34)N(C)C(=O)C[C@H]2C1]
Z261
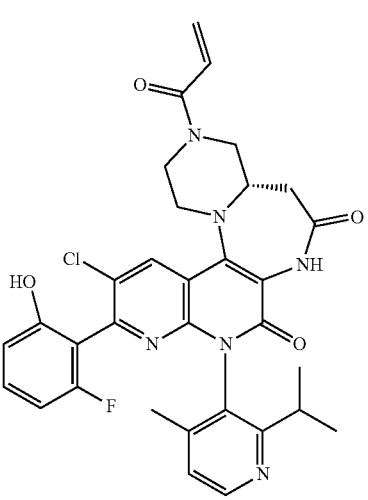 [SMILES: C=CC(=O)N1CCN2c3c(c(=O)n(-c4c(C)ccnc4C(C)C)c4nc(-c5c(O)cccc5F)c(Cl)cc34)NC(=O)C[C@H]2C1]
Z262
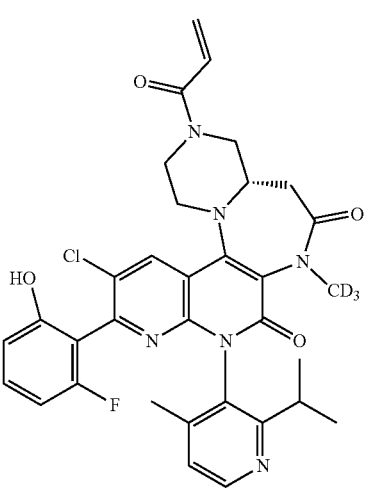 [SMILES: [2H]C([2H])([2H])N1C(=O)C[C@H]2CN(C(=O)C=C)CCN2c2c1c(=O)n(-c1c(C)ccnc1C(C)C)c1nc(-c3c(O)cccc3F)c(Cl)cc21]

TABLE A-1-continued
Z266
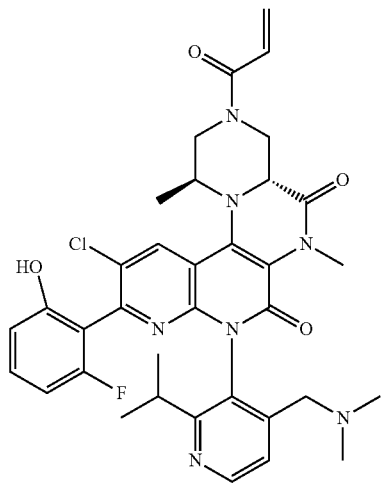 [SMILES: C=CC(=O)N1C[C@@H]2C(=O)N(C)c3c(c4cc(Cl)c(-c5c(O)cccc5F)nc4n(-c4c(CN(C)C)ccnc4C(C)C)c3=O)N2[C@@H](C)C1]
Z267
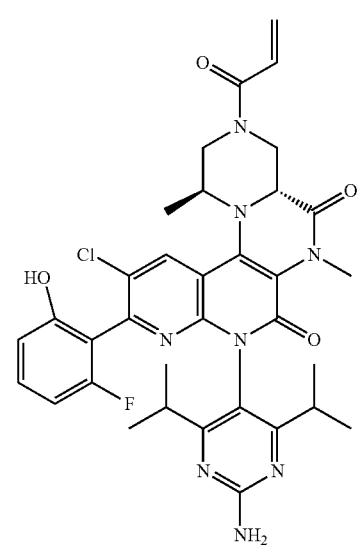 [SMILES: C=CC(=O)N1C[C@@H]2C(=O)N(C)c3c(c4cc(Cl)c(-c5c(O)cccc5F)nc4n(-c4c(C(C)C)nc(N)nc4C(C)C)c3=O)N2[C@@H](C)C1]
Z268
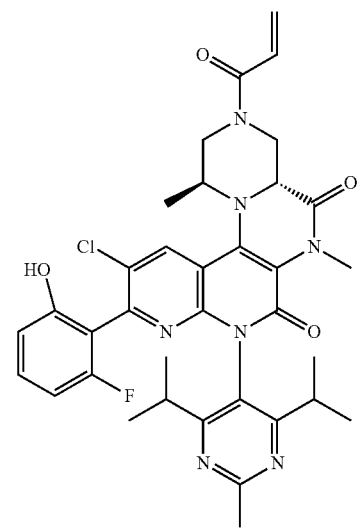 [SMILES: C=CC(=O)N1C[C@@H]2C(=O)N(C)c3c(c4cc(Cl)c(-c5c(O)cccc5F)nc4n(-c4c(C(C)C)nc(C)nc4C(C)C)c3=O)N2[C@@H](C)C1]
TABLE A-1-continued
Z269
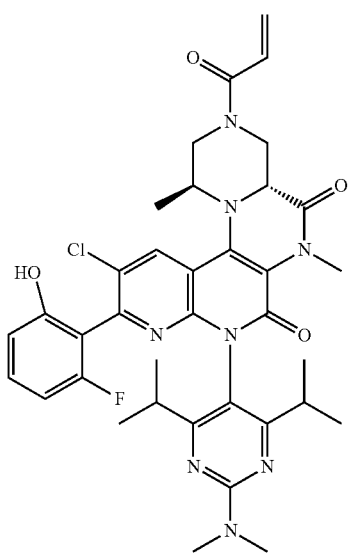 [SMILES: C=CC(=O)N1C[C@@H]2C(=O)N(C)c3c(c4cc(Cl)c(-c5c(O)cccc5F)nc4n(-c4c(C(C)C)nc(N(C)C)nc4C(C)C)c3=O)N2[C@@H](C)C1]
Z270
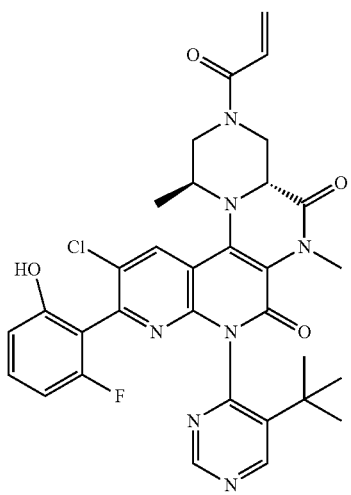 [SMILES: C=CC(=O)N1C[C@@H]2C(=O)N(C)c3c(c4cc(Cl)c(-c5c(O)cccc5F)nc4n(-c4ncncc4C(C)(C)C)c3=O)N2[C@@H](C)C1]
Z271
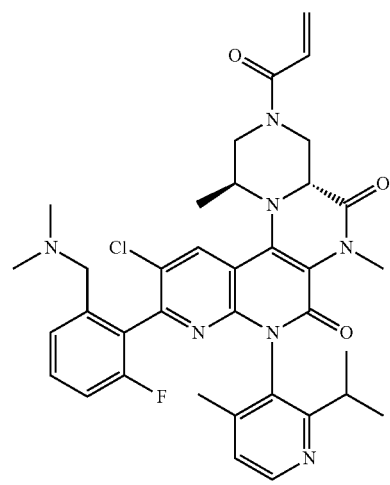 [SMILES: C=CC(=O)N1C[C@@H]2C(=O)N(C)c3c(c4cc(Cl)c(-c5c(F)cccc5CN(C)C)nc4n(-c4c(C)ccnc4C(C)C)c3=O)N2[C@@H](C)C1]

TABLE A-1-continued
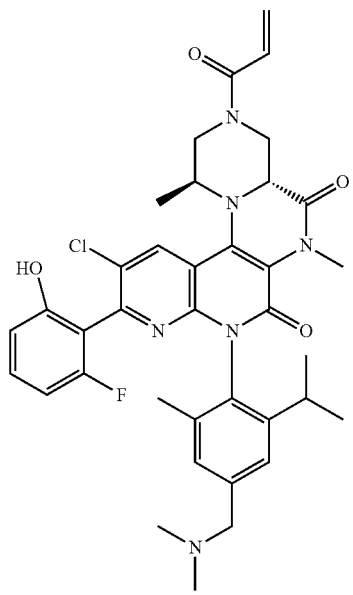 [SMILES: C=CC(=O)N1C[C@@H]2C(=O)N(C)c3c(c4cc(Cl)c(-c5c(O)cccc5F)nc4n(-c4c(C)cc(CN(C)C)cc4C(C)C)c3=O)N2[C@@H](C)C1] Z272
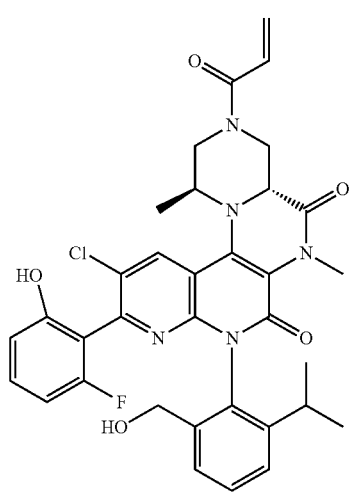 [SMILES: C=CC(=O)N1C[C@@H]2C(=O)N(C)c3c(c4cc(Cl)c(-c5c(O)cccc5F)nc4n(-c4c(CO)cccc4C(C)C)c3=O)N2[C@@H](C)C1] Z273
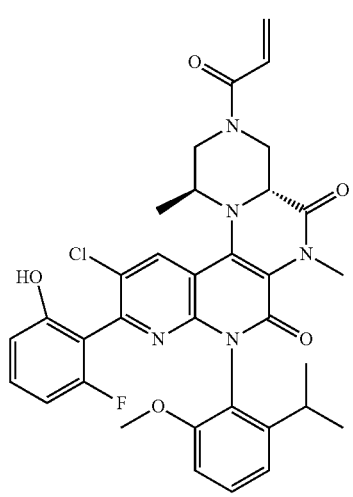 [SMILES: C=CC(=O)N1C[C@@H]2C(=O)N(C)c3c(c4cc(Cl)c(-c5c(O)cccc5F)nc4n(-c4c(OC)cccc4C(C)C)c3=O)N2[C@@H](C)C1] Z274
TABLE A-1-continued
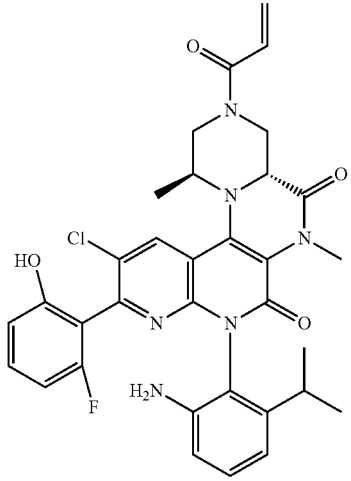 [SMILES: C=CC(=O)N1C[C@@H]2C(=O)N(C)c3c(c4cc(Cl)c(-c5c(O)cccc5F)nc4n(-c4c(N)cccc4C(C)C)c3=O)N2[C@@H](C)C1] Z275
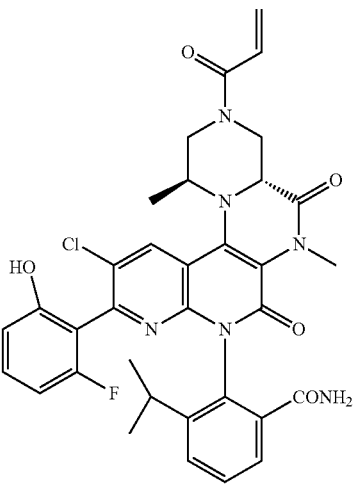 [SMILES: C=CC(=O)N1C[C@@H]2C(=O)N(C)c3c(c4cc(Cl)c(-c5c(O)cccc5F)nc4n(-c4c(C(N)=O)cccc4C(C)C)c3=O)N2[C@@H](C)C1] Z276
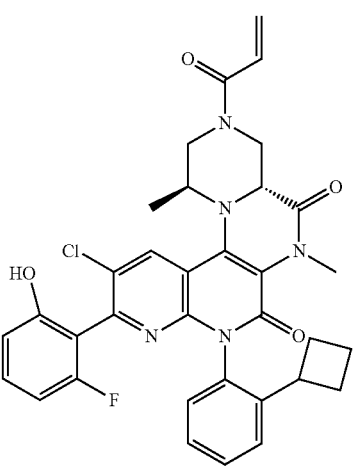 [SMILES: C=CC(=O)N1C[C@@H]2C(=O)N(C)c3c(c4cc(Cl)c(-c5c(O)cccc5F)nc4n(-c4ccccc4C4CCC4)c3=O)N2[C@@H](C)C1] Z277

TABLE A-1-continued
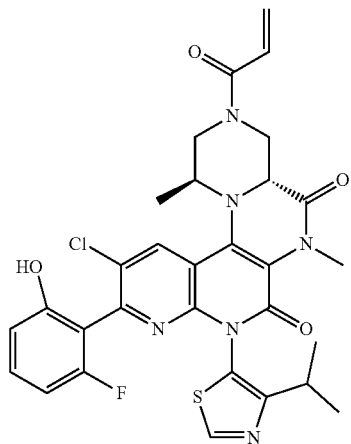 [SMILES: C=CC(=O)N1C[C@@H]2C(=O)N(C)c3c(c4cc(Cl)c(-c5c(O)cccc5F)nc4n(-c4scnc4C(C)C)c3=O)N2[C@@H](C)C1]
Z278
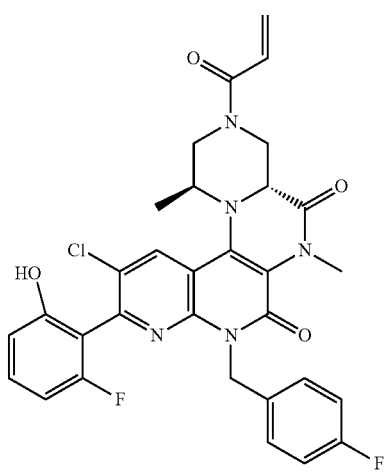 [SMILES: C=CC(=O)N1C[C@@H]2C(=O)N(C)c3c(c4cc(Cl)c(-c5c(O)cccc5F)nc4n(Cc4ccc(F)cc4)c3=O)N2[C@@H](C)C1]
Z279
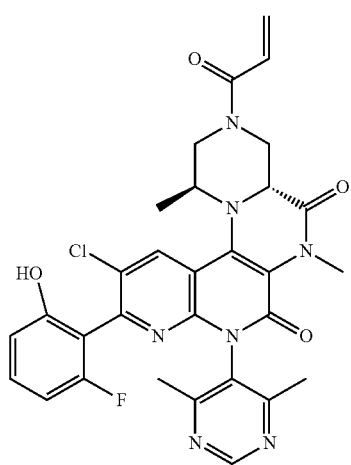 [SMILES: C=CC(=O)N1C[C@@H]2C(=O)N(C)c3c(c4cc(Cl)c(-c5c(O)cccc5F)nc4n(-c4c(C)ncnc4C)c3=O)N2[C@@H](C)C1]
Z280
TABLE A-1-continued
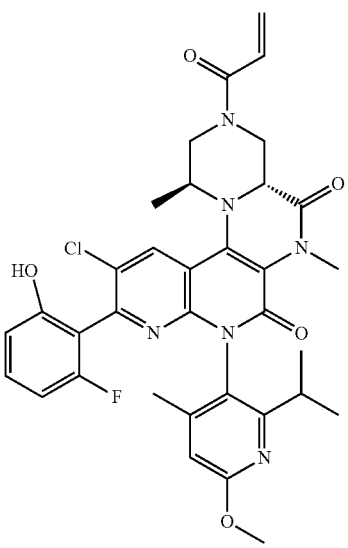 [SMILES: C=CC(=O)N1C[C@@H]2C(=O)N(C)c3c(c4cc(Cl)c(-c5c(O)cccc5F)nc4n(-c4c(C)cc(OC)nc4C(C)C)c3=O)N2[C@@H](C)C1]
Z281
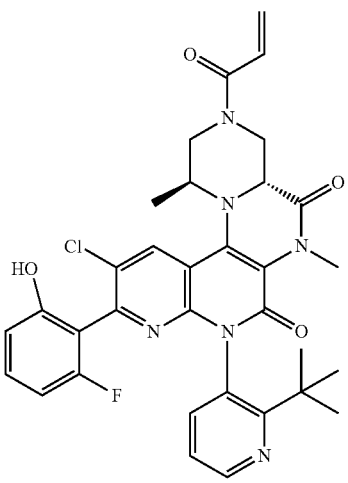 [SMILES: C=CC(=O)N1C[C@@H]2C(=O)N(C)c3c(c4cc(Cl)c(-c5c(O)cccc5F)nc4n(-c4cccnc4C(C)(C)C)c3=O)N2[C@@H](C)C1]
Z282
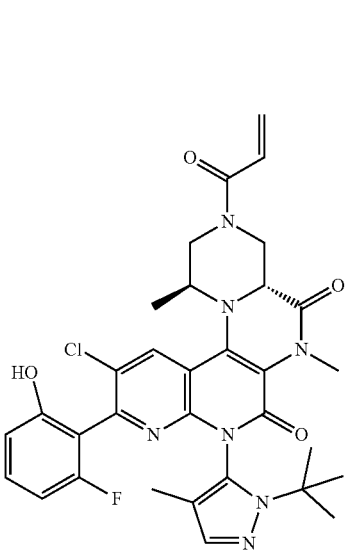 [SMILES: C=CC(=O)N1C[C@@H]2C(=O)N(C)c3c(c4cc(Cl)c(-c5c(O)cccc5F)nc4n(-c4c(C)cnn4C(C)(C)C)c3=O)N2[C@@H](C)C1]
Z283

TABLE A-1-continued
Z284
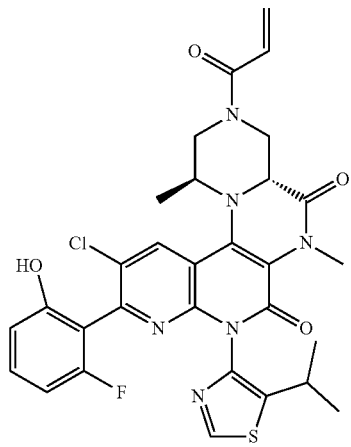 [SMILES: C=CC(=O)N1C[C@@H]2C(=O)N(C)c3c(c4cc(Cl)c(-c5c(O)cccc5F)nc4n(-c4ncsc4C(C)C)c3=O)N2[C@@H](C)C1]
Z285
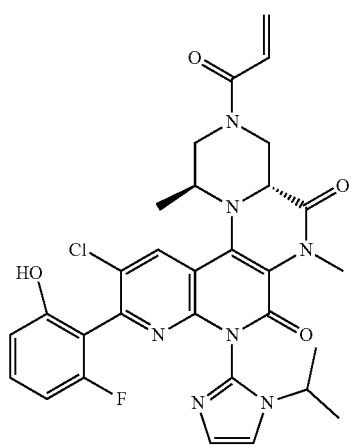 [SMILES: C=CC(=O)N1C[C@@H]2C(=O)N(C)c3c(c4cc(Cl)c(-c5c(O)cccc5F)nc4n(-c4nccn4C(C)C)c3=O)N2[C@@H](C)C1]
Z286
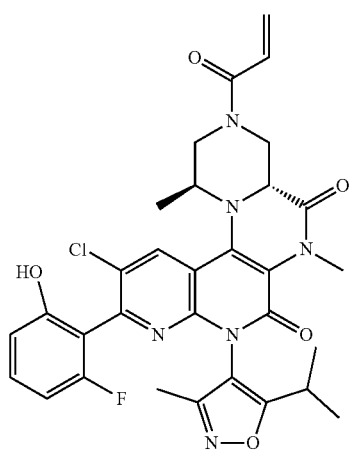 [SMILES: C=CC(=O)N1C[C@@H]2C(=O)N(C)c3c(c4cc(Cl)c(-c5c(O)cccc5F)nc4n(-c4c(C)noc4C(C)C)c3=O)N2[C@@H](C)C1]
TABLE A-1-continued
Z287
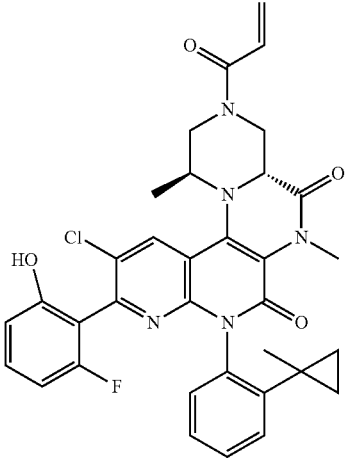 [SMILES: C=CC(=O)N1C[C@@H]2C(=O)N(C)c3c(c4cc(Cl)c(-c5c(O)cccc5F)nc4n(-c4ccccc4C4(C)CC4)c3=O)N2[C@@H](C)C1]
Z288
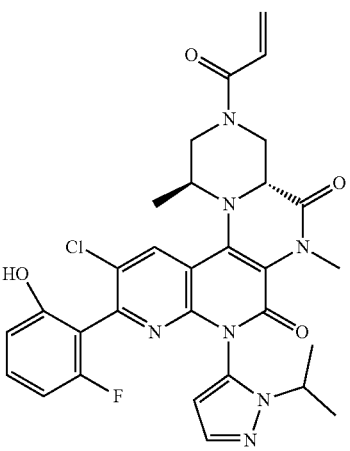 [SMILES: C=CC(=O)N1C[C@@H]2C(=O)N(C)c3c(c4cc(Cl)c(-c5c(O)cccc5F)nc4n(-c4ccnn4C(C)C)c3=O)N2[C@@H](C)C1]
Z289
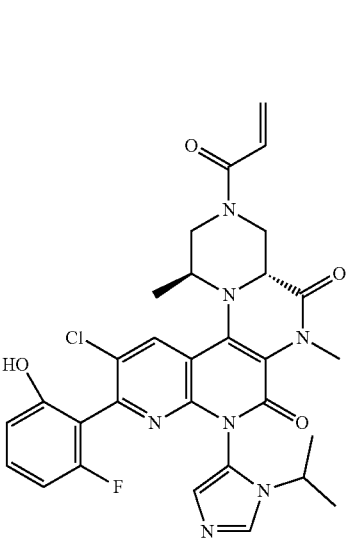 [SMILES: C=CC(=O)N1C[C@@H]2C(=O)N(C)c3c(c4cc(Cl)c(-c5c(O)cccc5F)nc4n(-c4cncn4C(C)C)c3=O)N2[C@@H](C)C1]

TABLE A-1-continued
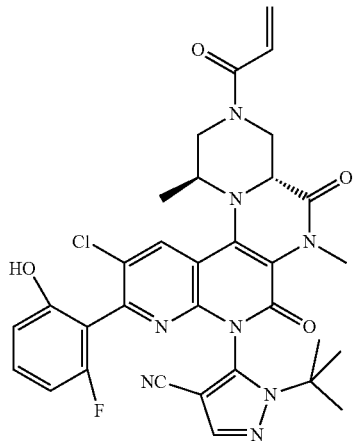 [SMILES: C=CC(=O)N1C[C@@H]2C(=O)N(C)c3c(c4cc(Cl)c(-c5c(O)cccc5F)nc4n(-c4c(C#N)cnn4C(C)(C)C)c3=O)N2[C@@H](C)C1]
Z290
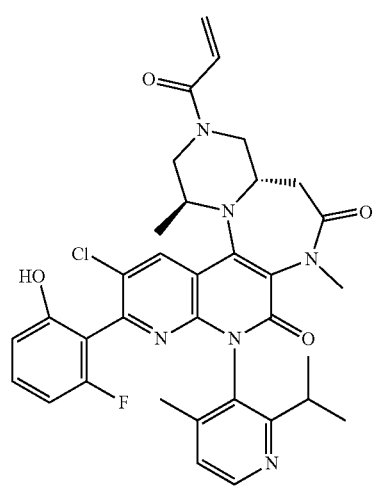 [SMILES: C=CC(=O)N1C[C@@H]2CC(=O)N(C)c3c(c4cc(Cl)c(-c5c(O)cccc5F)nc4n(-c4c(C)ccnc4C(C)C)c3=O)N2[C@@H](C)C1]
Z291
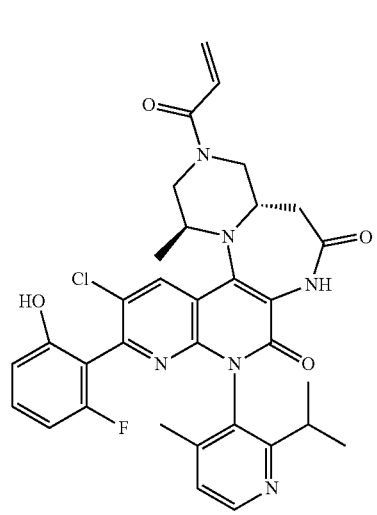 [SMILES: C=CC(=O)N1C[C@@H]2CC(=O)Nc3c(c4cc(Cl)c(-c5c(O)cccc5F)nc4n(-c4c(C)ccnc4C(C)C)c3=O)N2[C@@H](C)C1]
Z292
TABLE A-1-continued
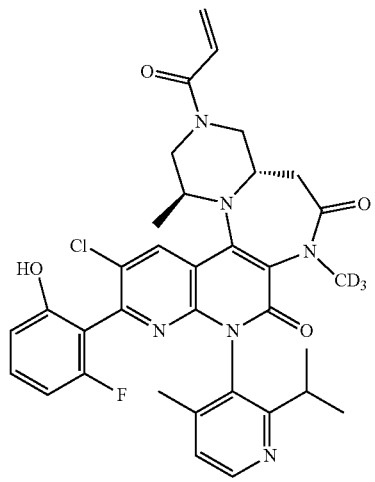 [SMILES: [2H]C([2H])([2H])N1C(=O)C[C@H]2CN(C(=O)C=C)C[C@H](C)N2c2c1c(=O)n(-c1c(C)ccnc1C(C)C)c1nc(-c3c(O)cccc3F)c(Cl)cc21]
Z293
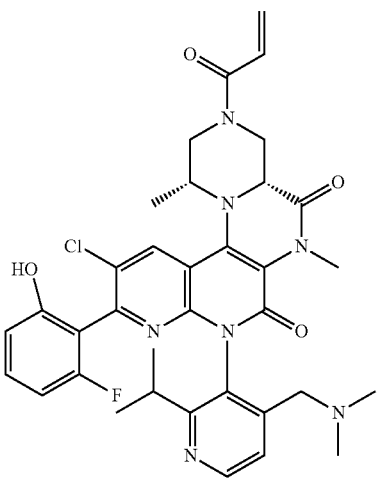 [SMILES: C=CC(=O)N1C[C@@H](C)N2c3c(c(=O)n(-c4c(CN(C)C)ccnc4C(C)C)c4nc(-c5c(O)cccc5F)c(Cl)cc34)N(C)C(=O)[C@H]2C1]
Z297
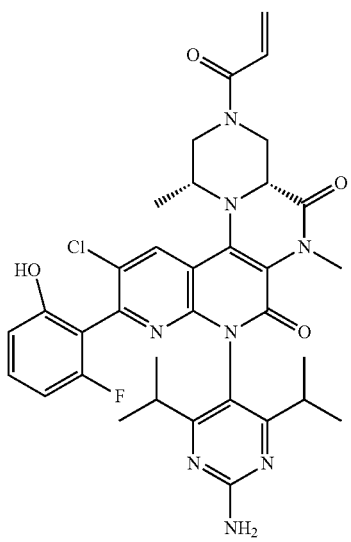 [SMILES: C=CC(=O)N1C[C@@H](C)N2c3c(c(=O)n(-c4c(C(C)C)nc(N)nc4C(C)C)c4nc(-c5c(O)cccc5F)c(Cl)cc34)N(C)C(=O)[C@H]2C1]
Z298

TABLE A-1-continued
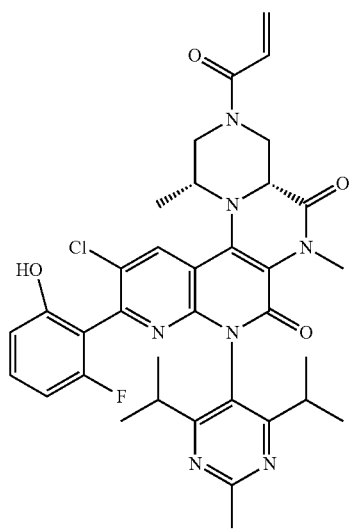 [SMILES: C=CC(=O)N1C[C@@H](C)N2c3c(c(=O)n(-c4c(C(C)C)nc(C)nc4C(C)C)c4nc(-c5c(O)cccc5F)c(Cl)cc34)N(C)C(=O)[C@H]2C1]
Z299
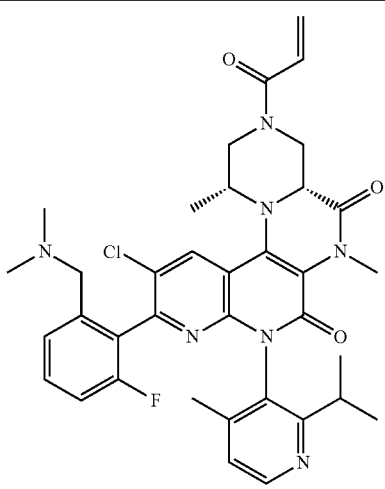
Z302
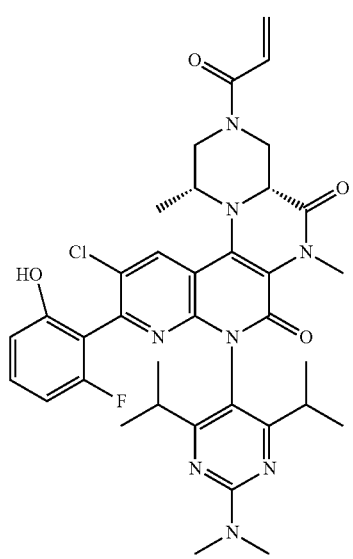 [SMILES: C=CC(=O)N1C[C@@H](C)N2c3c(c(=O)n(-c4c(C(C)C)nc(N(C)C)nc4C(C)C)c4nc(-c5c(O)cccc5F)c(Cl)cc34)N(C)C(=O)[C@H]2C1]
Z300
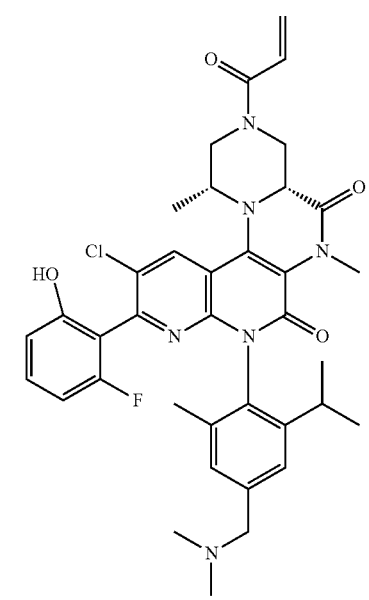
Z303
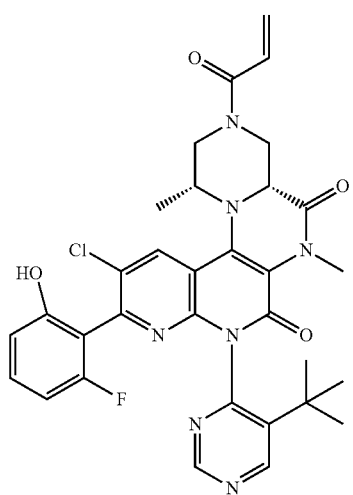 [SMILES: C=CC(=O)N1C[C@@H](C)N2c3c(c(=O)n(-c4ncncc4C(C)(C)C)c4nc(-c5c(O)cccc5F)c(Cl)cc34)N(C)C(=O)[C@H]2C1]
Z301
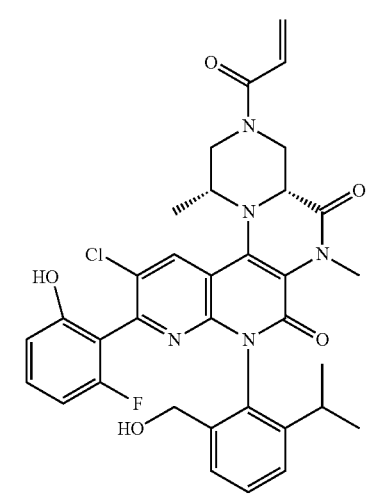 [SMILES: C=CC(=O)N1C[C@@H](C)N2c3c(c(=O)n(-c4c(CO)cccc4C(C)C)c4nc(-c5c(O)cccc5F)c(Cl)cc34)N(C)C(=O)[C@H]2C1]
Z304

TABLE A-1-continued
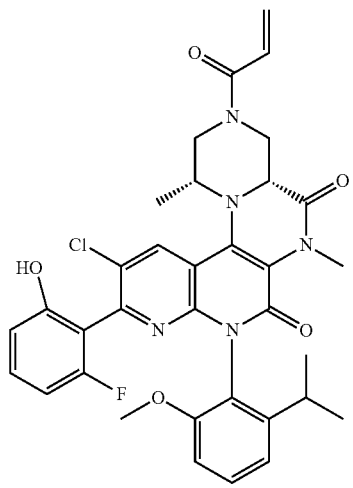 [SMILES: C=CC(=O)N1C[C@@H](C)N2c3c(c(=O)n(-c4c(OC)cccc4C(C)C)c4nc(-c5c(O)cccc5F)c(Cl)cc34)N(C)C(=O)[C@H]2C1]
Z305
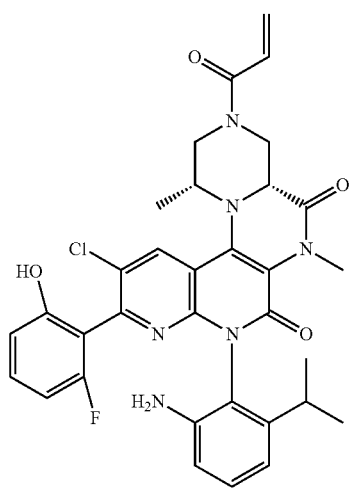 [SMILES: C=CC(=O)N1C[C@@H](C)N2c3c(c(=O)n(-c4c(N)cccc4C(C)C)c4nc(-c5c(O)cccc5F)c(Cl)cc34)N(C)C(=O)[C@H]2C1]
Z306
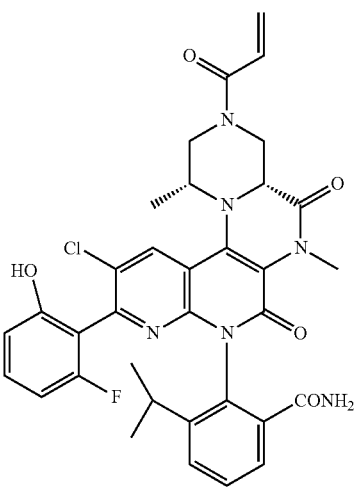 [SMILES: C=CC(=O)N1C[C@@H](C)N2c3c(c(=O)n(-c4c(C(N)=O)cccc4C(C)C)c4nc(-c5c(O)cccc5F)c(Cl)cc34)N(C)C(=O)[C@H]2C1]
Z307
TABLE A-1-continued
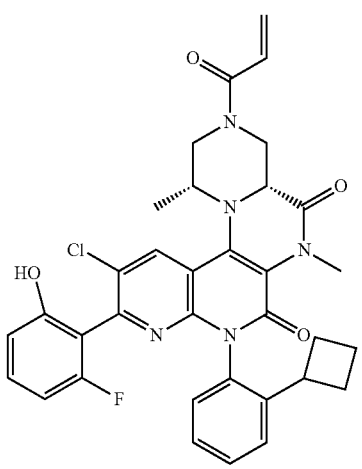 [SMILES: C=CC(=O)N1C[C@@H](C)N2c3c(c(=O)n(-c4ccccc4C4CCC4)c4nc(-c5c(O)cccc5F)c(Cl)cc34)N(C)C(=O)[C@H]2C1]
Z308
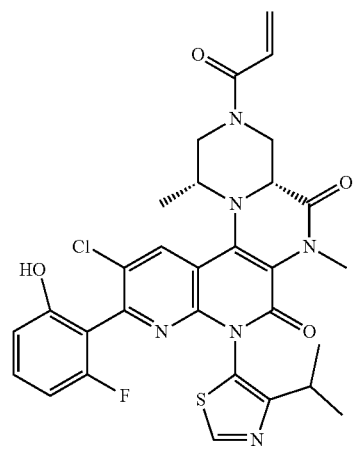 [SMILES: C=CC(=O)N1C[C@@H](C)N2c3c(c(=O)n(-c4scnc4C(C)C)c4nc(-c5c(O)cccc5F)c(Cl)cc34)N(C)C(=O)[C@H]2C1]
Z309
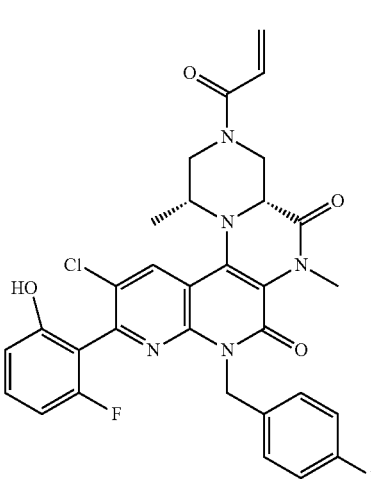
Z310

TABLE A-1-continued
Z311 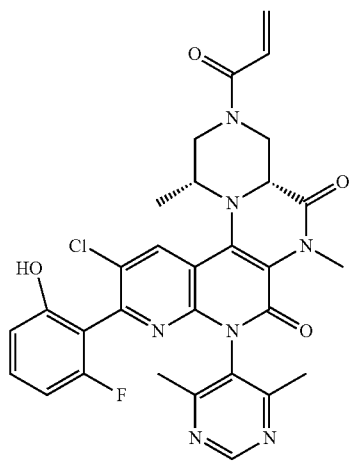 [SMILES: C=CC(=O)N1C[C@@H](C)N2c3c(c(=O)n(-c4c(C)ncnc4C)c4nc(-c5c(O)cccc5F)c(Cl)cc34)N(C)C(=O)[C@H]2C1]
Z312 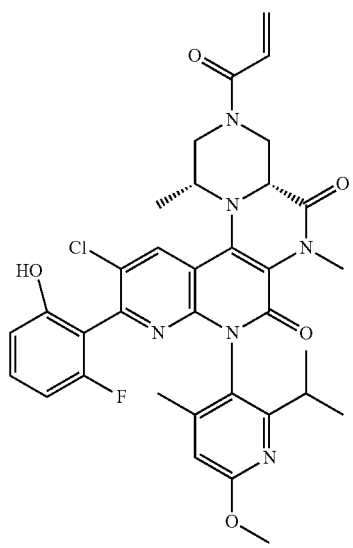 [SMILES: C=CC(=O)N1C[C@@H](C)N2c3c(c(=O)n(-c4c(C)cc(OC)nc4C(C)C)c4nc(-c5c(O)cccc5F)c(Cl)cc34)N(C)C(=O)[C@H]2C1]
Z313 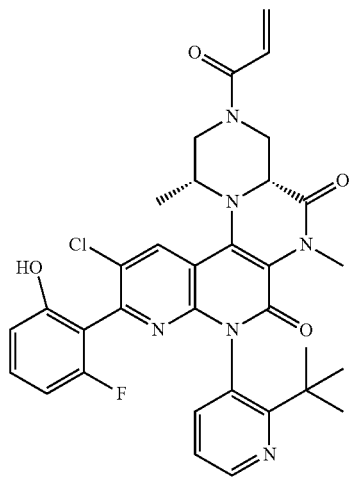 [SMILES: C=CC(=O)N1C[C@@H](C)N2c3c(c(=O)n(-c4cccnc4C(C)(C)C)c4nc(-c5c(O)cccc5F)c(Cl)cc34)N(C)C(=O)[C@H]2C1]
TABLE A-1-continued
Z314 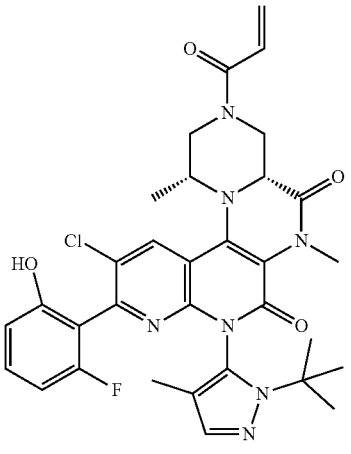 [SMILES: C=CC(=O)N1C[C@@H](C)N2c3c(c(=O)n(-c4c(C)cnn4C(C)(C)C)c4nc(-c5c(O)cccc5F)c(Cl)cc34)N(C)C(=O)[C@H]2C1]
Z315 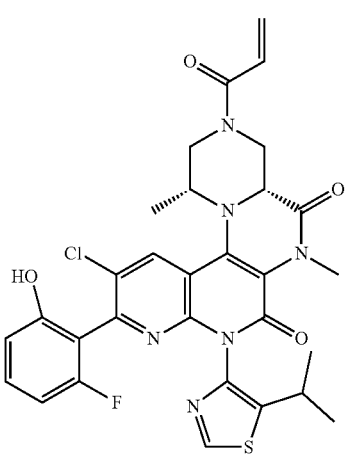 [SMILES: C=CC(=O)N1C[C@@H](C)N2c3c(c(=O)n(-c4ncsc4C(C)C)c4nc(-c5c(O)cccc5F)c(Cl)cc34)N(C)C(=O)[C@H]2C1]
Z316 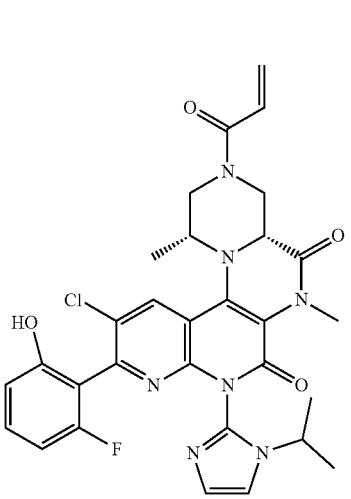 [SMILES: C=CC(=O)N1C[C@@H](C)N2c3c(c(=O)n(-c4nccn4C(C)C)c4nc(-c5c(O)cccc5F)c(Cl)cc34)N(C)C(=O)[C@H]2C1]

TABLE A-1-continued
Z317
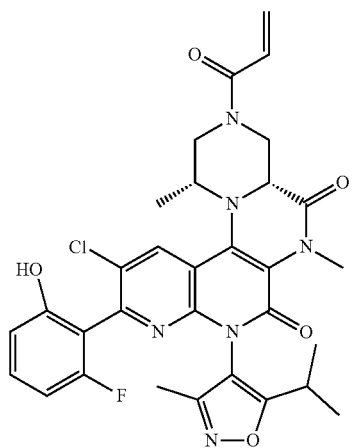 [SMILES: C=CC(=O)N1C[C@@H](C)N2c3c(c(=O)n(-c4c(C)noc4C(C)C)c4nc(-c5c(O)cccc5F)c(Cl)cc34)N(C)C(=O)[C@H]2C1]
Z318
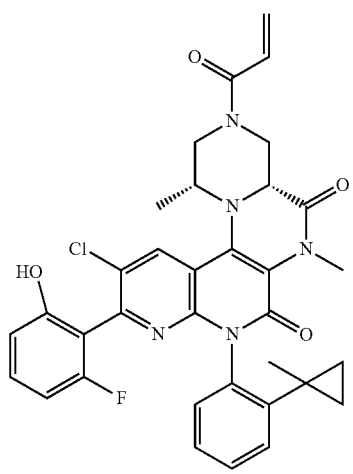 [SMILES: C=CC(=O)N1C[C@@H](C)N2c3c(c(=O)n(-c4ccccc4C4(C)CC4)c4nc(-c5c(O)cccc5F)c(Cl)cc34)N(C)C(=O)[C@H]2C1]
Z319
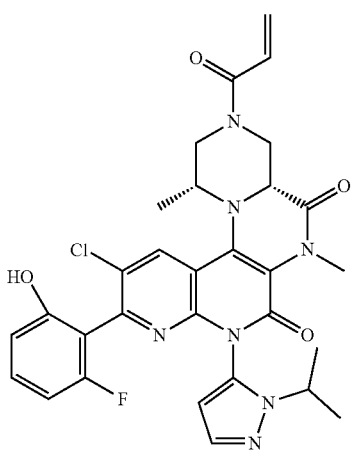 [SMILES: C=CC(=O)N1C[C@@H](C)N2c3c(c(=O)n(-c4ccnn4C(C)C)c4nc(-c5c(O)cccc5F)c(Cl)cc34)N(C)C(=O)[C@H]2C1]
TABLE A-1-continued
Z320
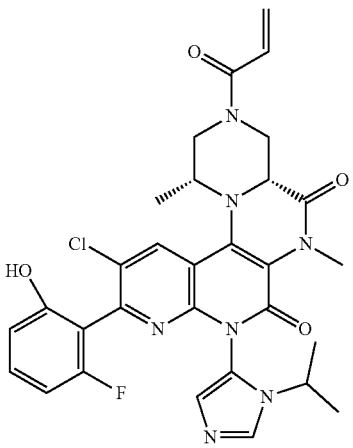 [SMILES: C=CC(=O)N1C[C@@H](C)N2c3c(c(=O)n(-c4cncn4C(C)C)c4nc(-c5c(O)cccc5F)c(Cl)cc34)N(C)C(=O)[C@H]2C1]
Z321
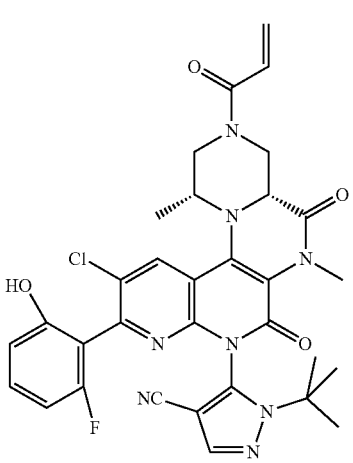 [SMILES: C=CC(=O)N1C[C@@H](C)N2c3c(c(=O)n(-c4c(C#N)cnn4C(C)(C)C)c4nc(-c5c(O)cccc5F)c(Cl)cc34)N(C)C(=O)[C@H]2C1]
Z322
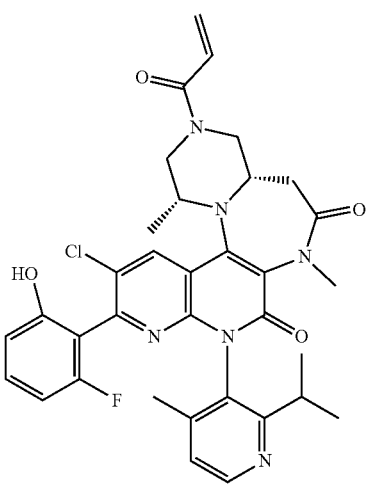 [SMILES: C=CC(=O)N1C[C@@H]2CC(=O)N(C)c3c(c4cc(Cl)c(-c5c(O)cccc5F)nc4n(-c4c(C)ccnc4C(C)C)c3=O)N2[C@H](C)C1]

TABLE A-1-continued
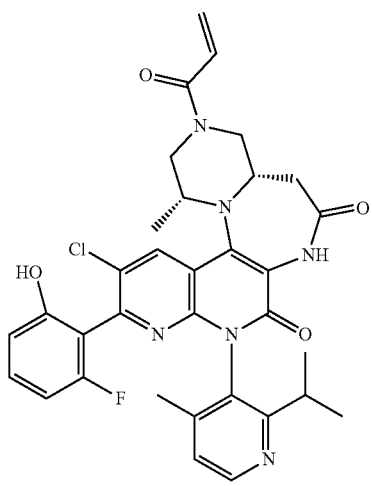 [SMILES: C=CC(=O)N1C[C@@H]2CC(=O)Nc3c(c4cc(Cl)c(-c5c(O)cccc5F)nc4n(-c4c(C)ccnc4C(C)C)c3=O)N2[C@H](C)C1]
Z323
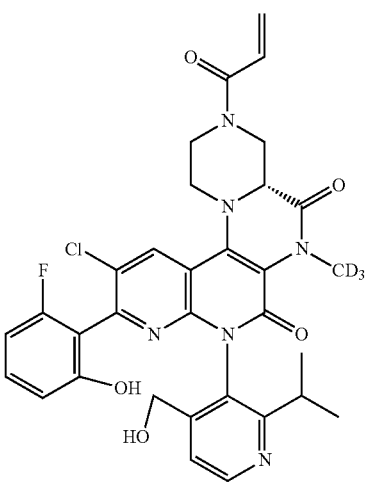
Z326
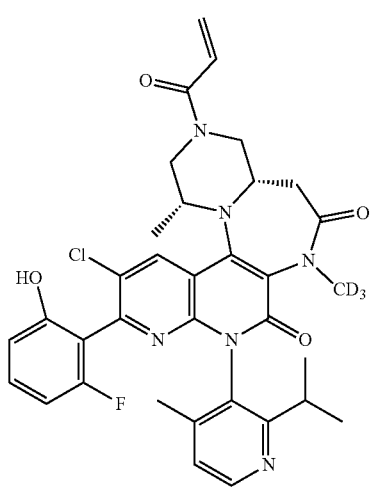 [SMILES: [2H]C([2H])([2H])N1C(=O)C[C@H]2CN(C(=O)C=C)C[C@@H](C)N2c2c1c(=O)n(-c1c(C)ccnc1C(C)C)c1nc(-c3c(O)cccc3F)c(Cl)cc21]
Z324
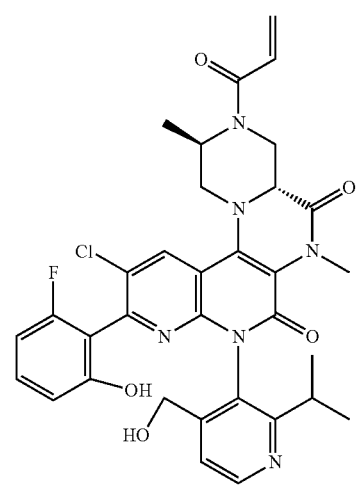
Z327
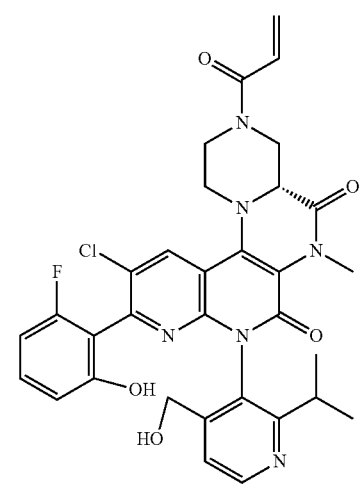 [SMILES: C=CC(=O)N1CCN2c3c(c(=O)n(-c4c(CO)ccnc4C(C)C)c4nc(-c5c(O)cccc5F)c(Cl)cc34)N(C)C(=O)[C@H]2C1]
Z325
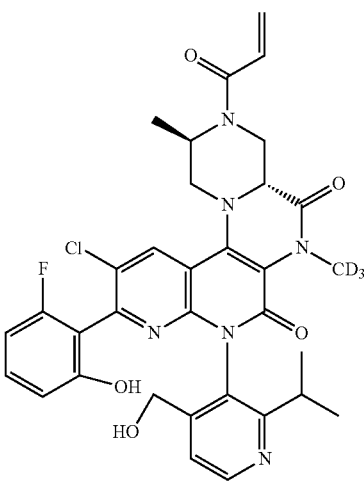 [SMILES: [2H]C([2H])([2H])N1C(=O)[C@H]2CN(C(=O)C=C)[C@H](C)CN2c2c1c(=O)n(-c1c(CO)ccnc1C(C)C)c1nc(-c3c(O)cccc3F)c(Cl)cc21]
Z328

TABLE A-1-continued
Z329
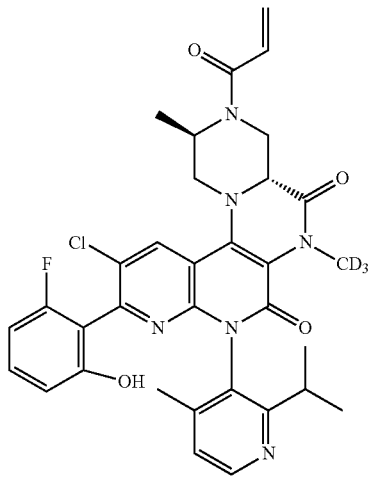 [SMILES: [2H]C([2H])([2H])N1C(=O)[C@H]2CN(C(=O)C=C)[C@H](C)CN2c2c1c(=O)n(-c1c(C)ccnc1C(C)C)c1nc(-c3c(O)cccc3F)c(Cl)cc21]
Z330
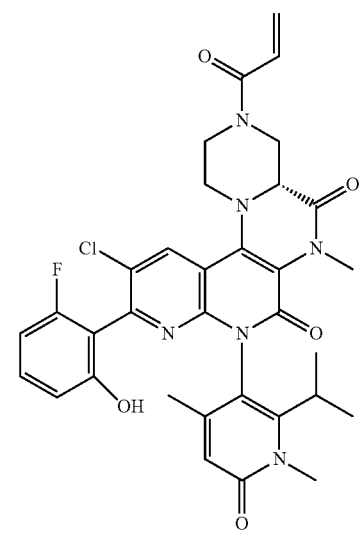 [SMILES: C=CC(=O)N1CCN2c3c(c(=O)n(-c4c(C)cc(=O)n(C)c4C(C)C)c4nc(-c5c(O)cccc5F)c(Cl)cc34)N(C)C(=O)[C@H]2C1]
Z331
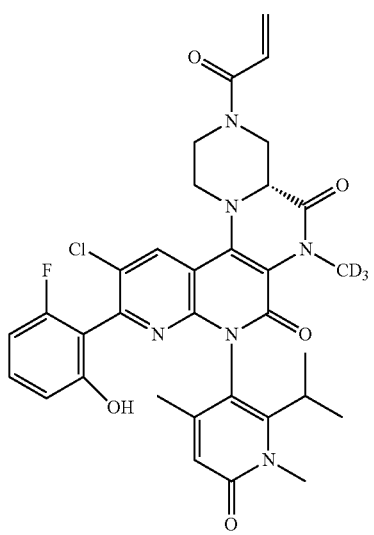 [SMILES: [2H]C([2H])([2H])N1C(=O)[C@H]2CN(C(=O)C=C)CCN2c2c1c(=O)n(-c1c(C)cc(=O)n(C)c1C(C)C)c1nc(-c3c(O)cccc3F)c(Cl)cc21]
TABLE A-1-continued
Z332
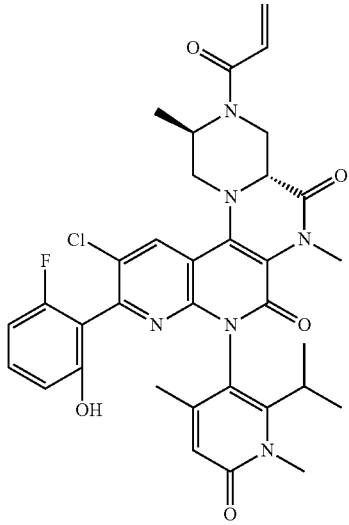 [SMILES: C=CC(=O)N1C[C@@H]2C(=O)N(C)c3c(c4cc(Cl)c(-c5c(O)cccc5F)nc4n(-c4c(C)cc(=O)n(C)c4C(C)C)c3=O)N2C[C@H]1C]
Z333
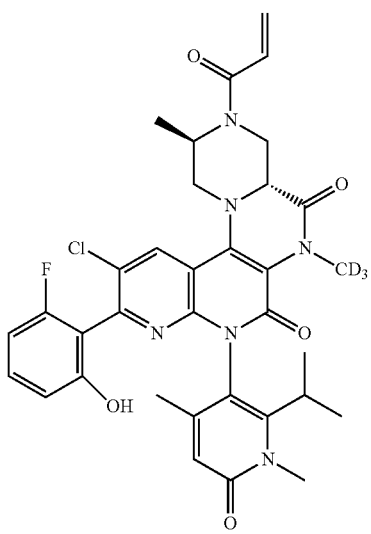 [SMILES: [2H]C([2H])([2H])N1C(=O)[C@H]2CN(C(=O)C=C)[C@H](C)CN2c2c1c(=O)n(-c1c(C)cc(=O)n(C)c1C(C)C)c1nc(-c3c(O)cccc3F)c(Cl)cc21]
Z334
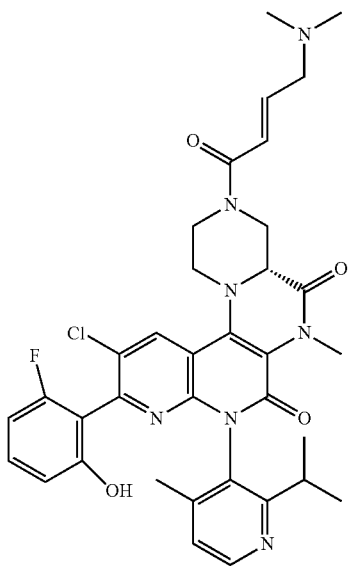 [SMILES: Cc1ccnc(C(C)C)c1-n1c(=O)c2c(c3cc(Cl)c(-c4c(O)cccc4F)nc31)N1CCN(C(=O)/C=C/CN(C)C)C[C@@H]1C(=O)N2C]

TABLE A-1-continued
Z335
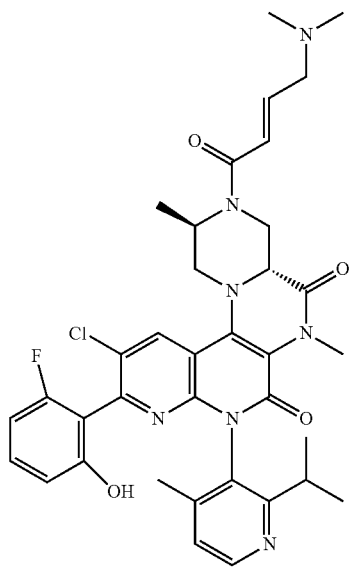 [SMILES: Cc1ccnc(C(C)C)c1-n1c(=O)c2c(c3cc(Cl)c(-c4c(O)cccc4F)nc31)N1C[C@@H](C)N(C(=O)/C=C/CN(C)C)C[C@@H]1C(=O)N2C]
Z94
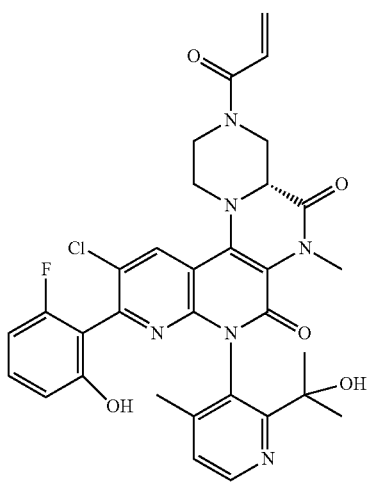 [SMILES: C=CC(=O)N1CCN2c3c(c(=O)n(-c4c(C)ccnc4C(C)(C)O)c4nc(-c5c(O)cccc5F)c(Cl)cc34)N(C)C(=O)[C@H]2C1]
Z263
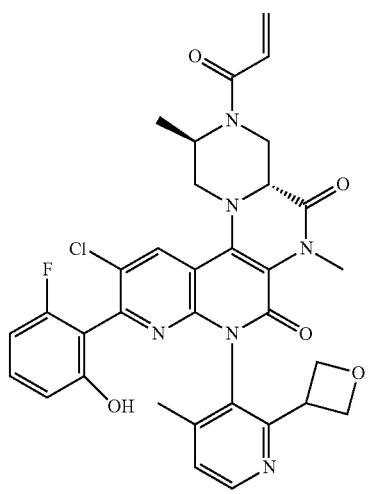 [SMILES: C=CC(=O)N1C[C@@H]2C(=O)N(C)c3c(c4cc(Cl)c(-c5c(O)cccc5F)nc4n(-c4c(C)ccnc4C4COC4)c3=O)N2C[C@H]1C]
TABLE A-1-continued
Z264
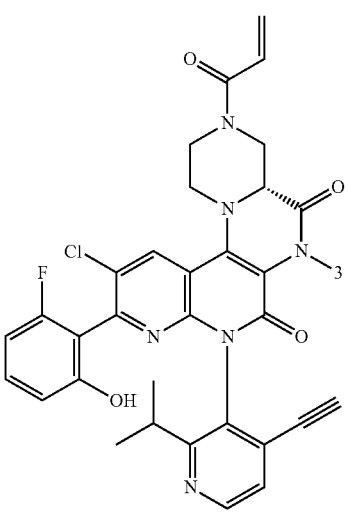
Z265
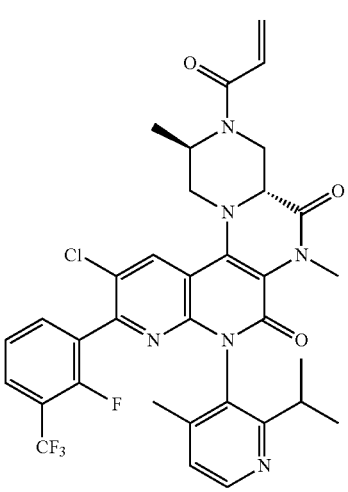 [SMILES: C=CC(=O)N1C[C@@H]2C(=O)N(C)c3c(c4cc(Cl)c(-c5cccc(C(F)(F)F)c5F)nc4n(-c4c(C)ccnc4C(C)C)c3=O)N2C[C@H]1C]
Z294
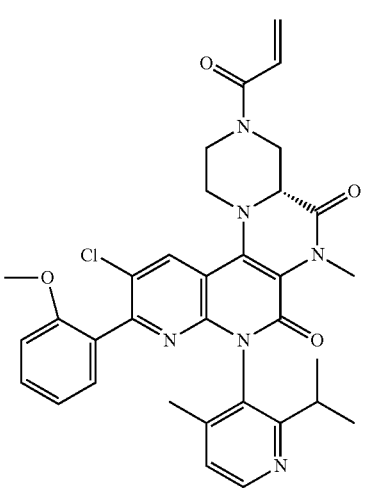 [SMILES: C=CC(=O)N1CCN2c3c(c(=O)n(-c4c(C)ccnc4C(C)C)c4nc(-c5ccccc5OC)c(Cl)cc34)N(C)C(=O)[C@H]2C1]

TABLE A-1-continued
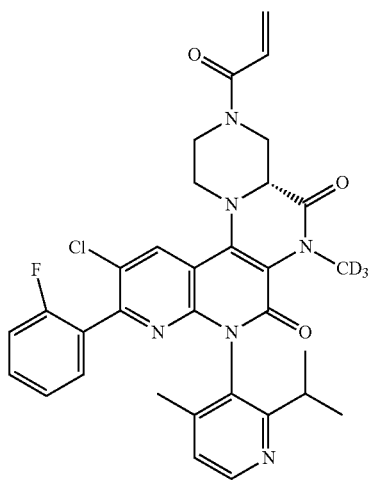 [SMILES: [2H]C([2H])([2H])N1C(=O)[C@H]2CN(C(=O)C=C)CCN2c2c1c(=O)n(-c1c(C)ccnc1C(C)C)c1nc(-c3ccccc3F)c(Cl)cc21]
Z295
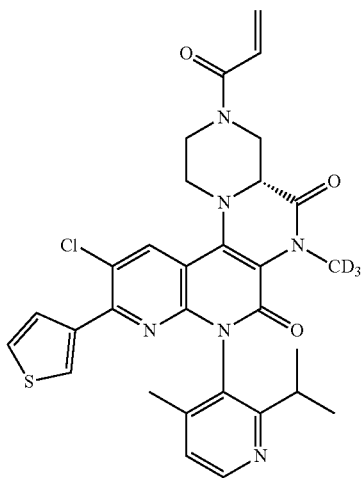
Z337
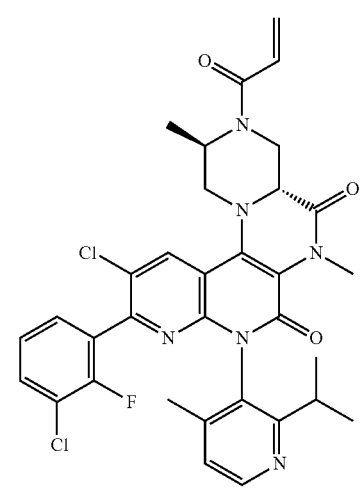 [SMILES: C=CC(=O)N1C[C@@H]2C(=O)N(C)c3c(c4cc(Cl)c(-c5cccc(Cl)c5F)nc4n(-c4c(C)ccnc4C(C)C)c3=O)N2C[C@H]1C]
Z296
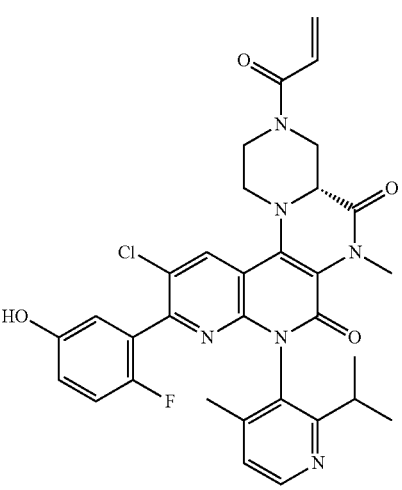
Z338
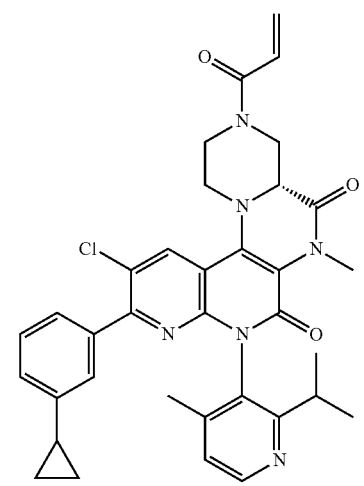 [SMILES: C=CC(=O)N1CCN2c3c(c(=O)n(-c4c(C)ccnc4C(C)C)c4nc(-c5cccc(C6CC6)c5)c(Cl)cc34)N(C)C(=O)[C@H]2C1]
Z336
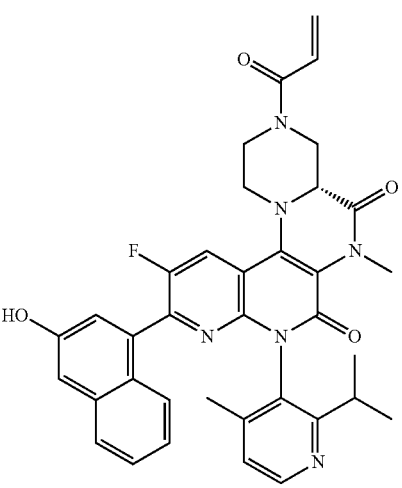 [SMILES: C=CC(=O)N1CCN2c3c(c(=O)n(-c4c(C)ccnc4C(C)C)c4nc(-c5cc(O)cc6ccccc56)c(F)cc34)N(C)C(=O)[C@H]2C1]
Z339

TABLE A-1-continued
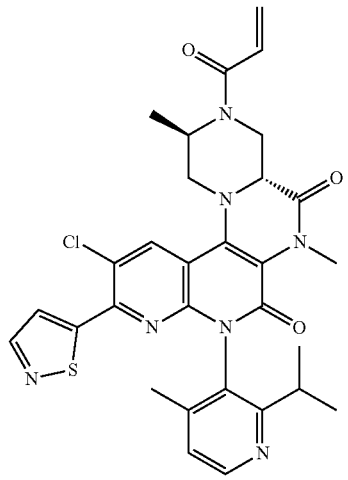 [SMILES: C=CC(=O)N1C[C@@H]2C(=O)N(C)c3c(c4cc(Cl)c(-c5ccns5)nc4n(-c4c(C)ccnc4C(C)C)c3=O)N2C[C@H]1C]
Z340
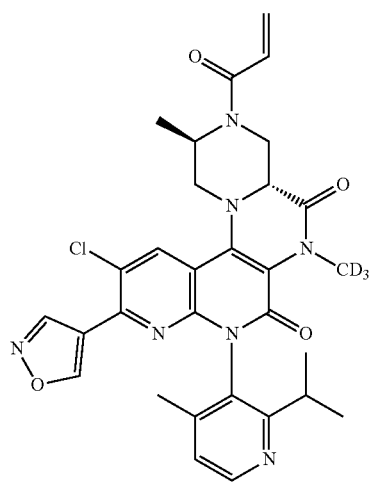 [SMILES: [2H]C([2H])([2H])N1C(=O)[C@H]2CN(C(=O)C=C)[C@H](C)CN2c2c1c(=O)n(-c1c(C)ccnc1C(C)C)c1nc(-c3cnoc3)c(Cl)cc21]
Z341
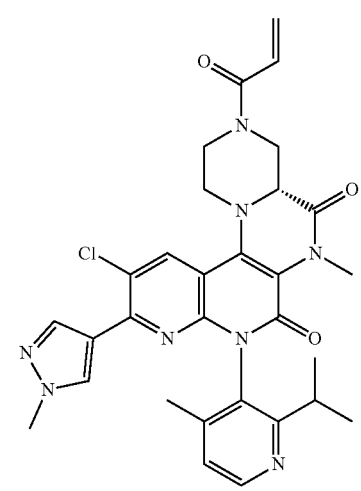 [SMILES: C=CC(=O)N1CCN2c3c(c(=O)n(-c4c(C)ccnc4C(C)C)c4nc(-c5cnn(C)c5)c(Cl)cc34)N(C)C(=O)[C@H]2C1]
Z342
TABLE A-2
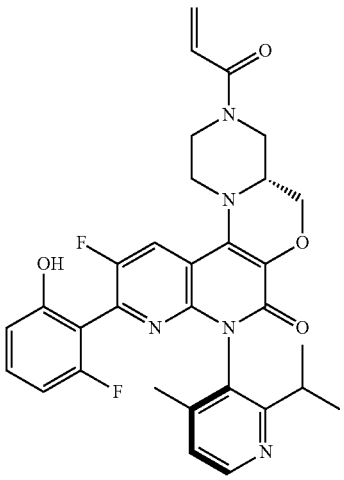
Z1-1
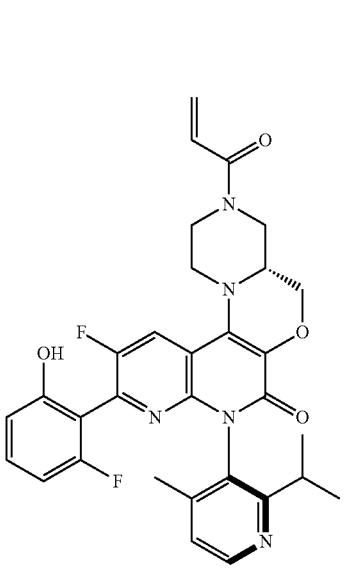
Z1-2
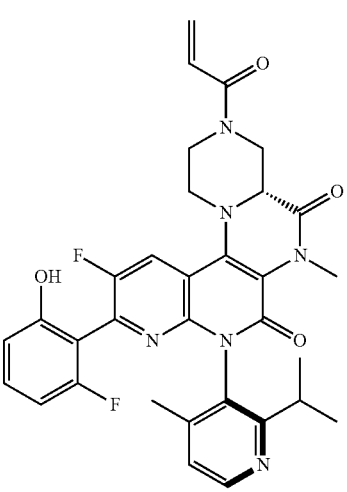
Z9-1
In an embodiment of the present invention, the representative compound of Formula (IA) includes but is not limited to structures shown in Table A-2 below, or pharmaceutically acceptable salts, solvates or prodrugs of such isomers of any structure in Table A-2.

TABLE A-2-continued
Z9-2
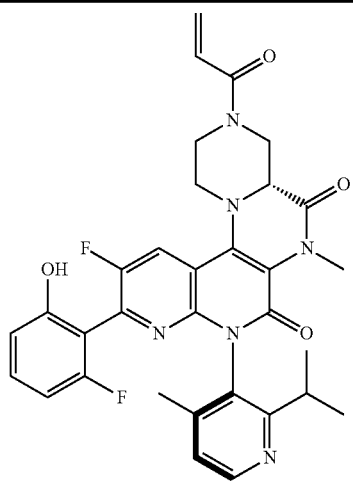
Z10-1
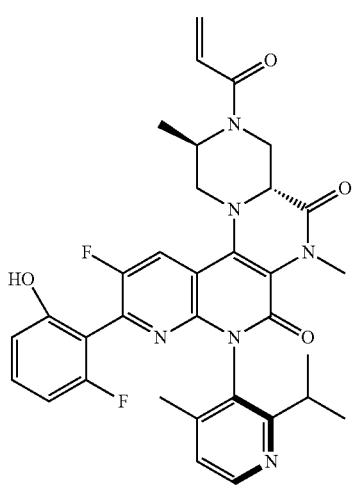
Z10-2
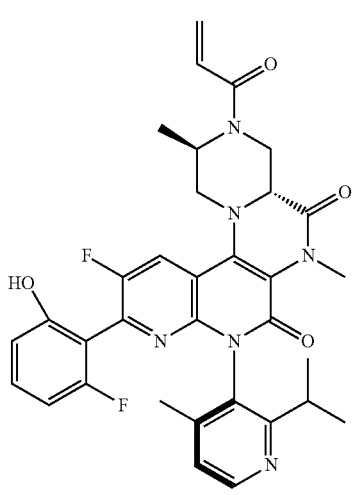
Z21-1
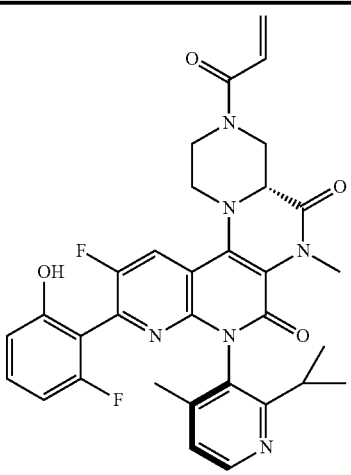
Z21-2
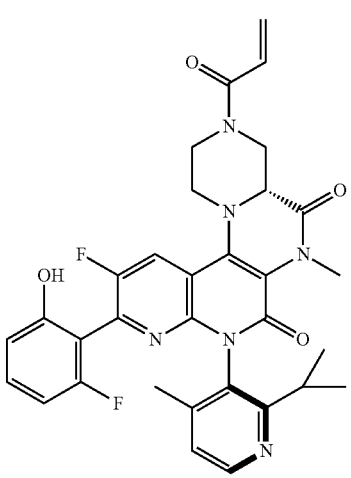
Z24-1
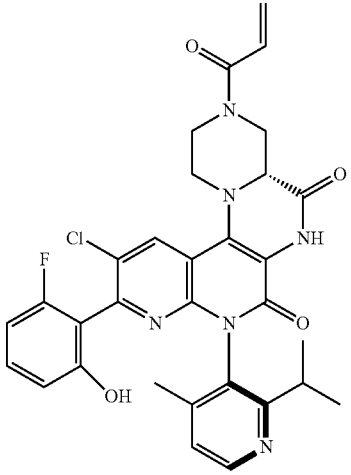

TABLE A-2-continued
Z24-2
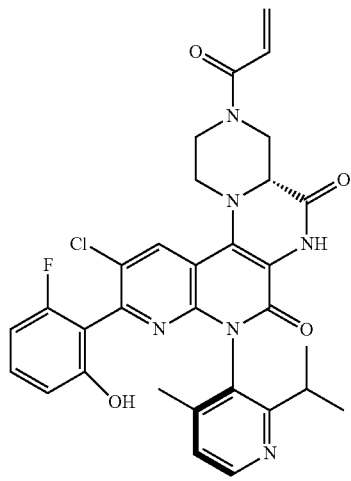
Z25-1
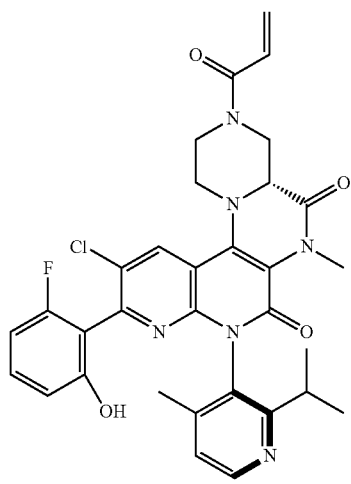
Z25-2
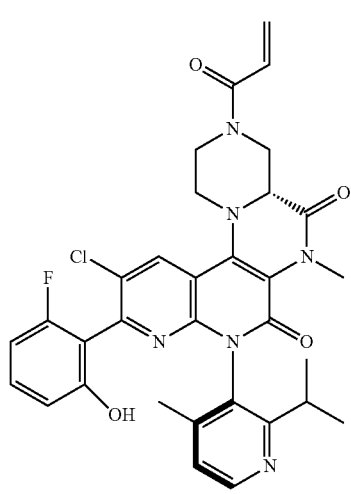
TABLE A-2-continued
Z26-1
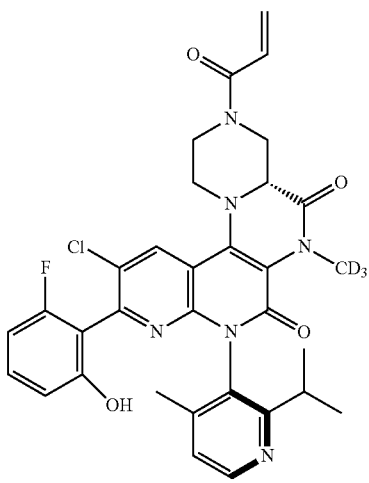
Z26-2
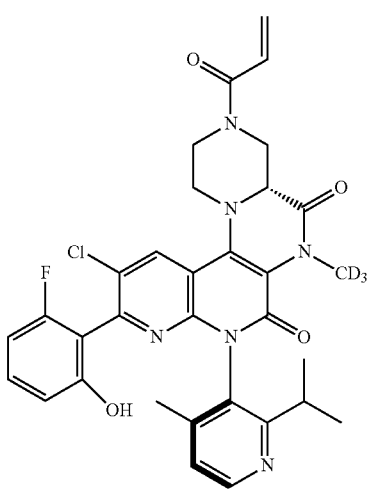
Z27-1
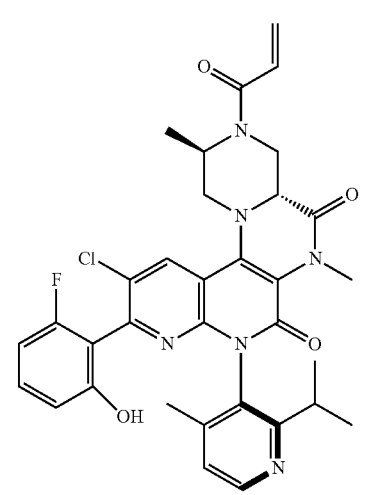

TABLE A-2-continued
Z27-2
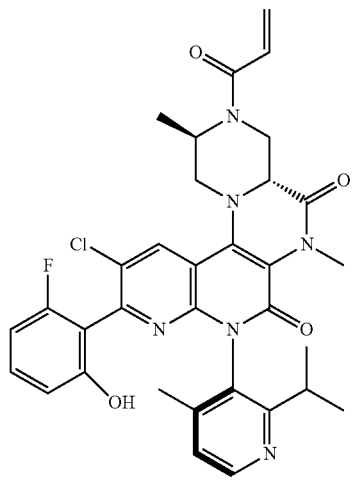
Z30-1
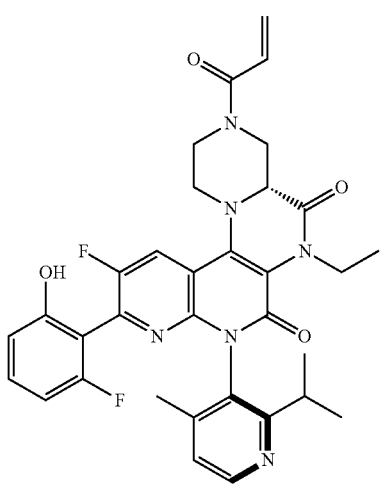
Z30-2
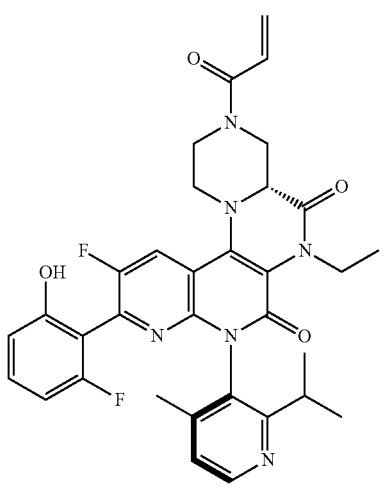
TABLE A-2-continued
Z33-1
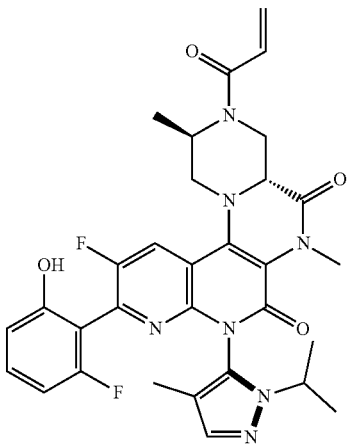
Z33-2
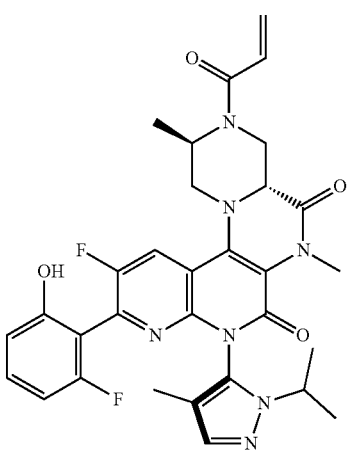
Z34-1
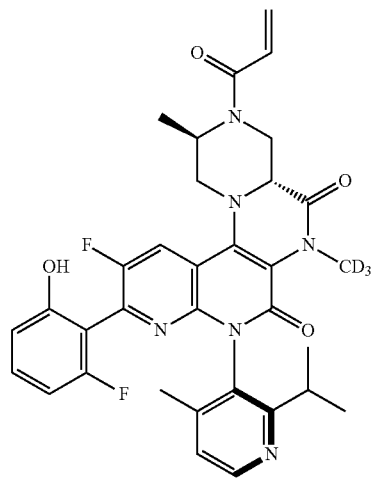

TABLE A-2-continued
Z34-2
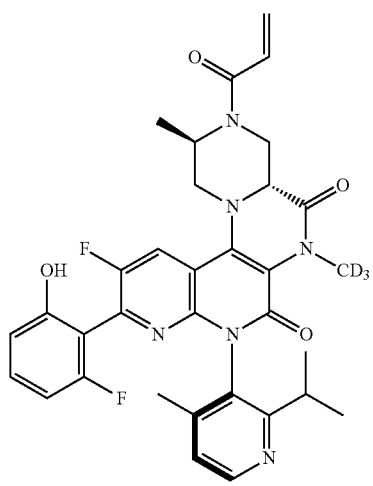
Z35-1
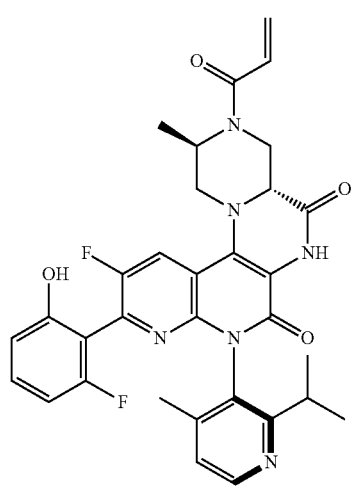
Z35-2
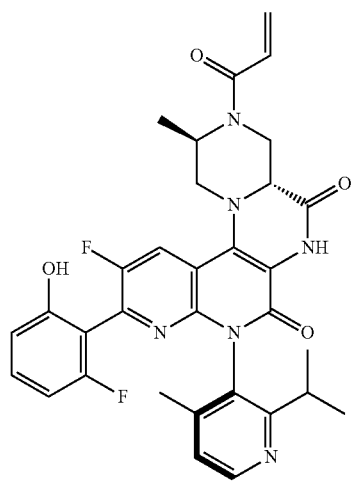
TABLE A-2-continued
Z36-1
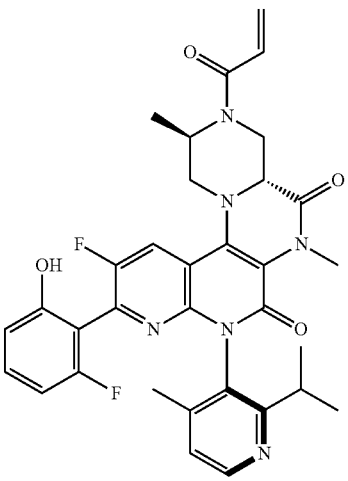
Z36-2
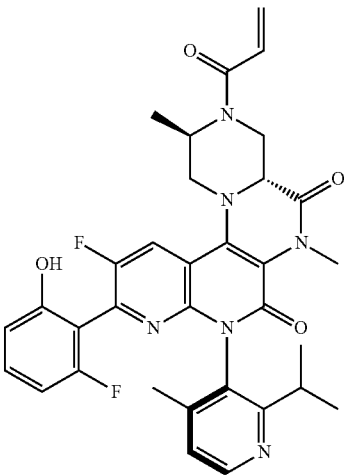
Z37-1
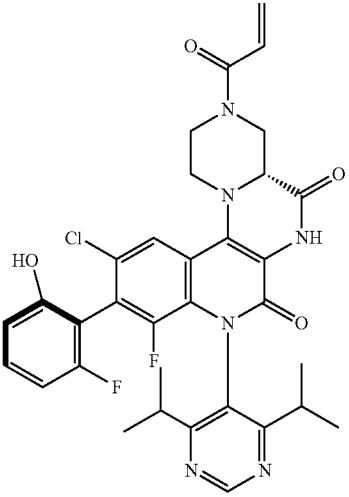

TABLE A-2-continued
Z37-2
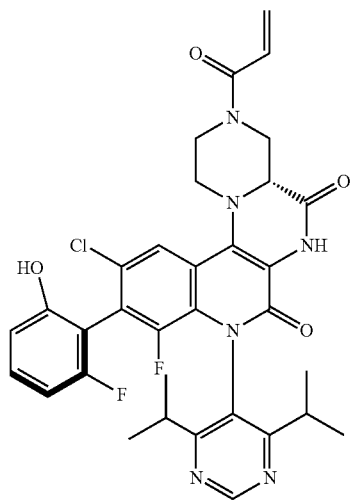
Z38-1
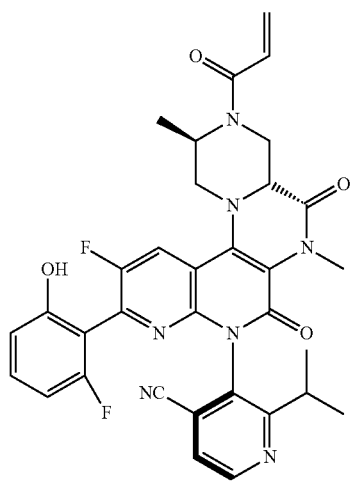
Z38-2
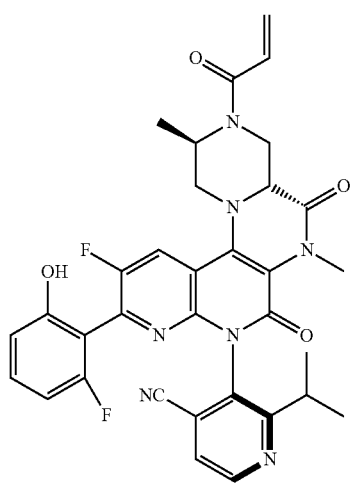
Z39-1
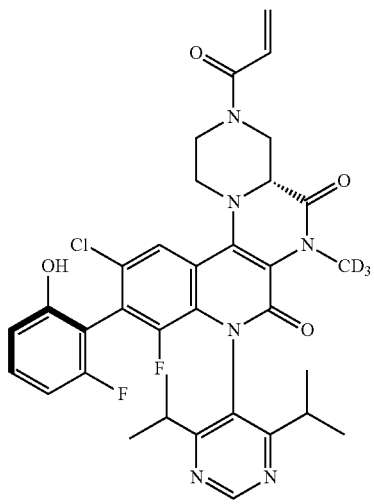
Z39-2
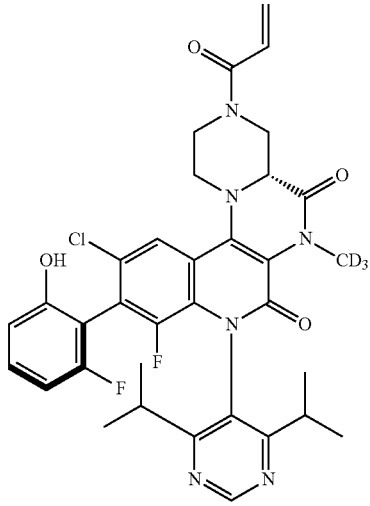
Z49-1
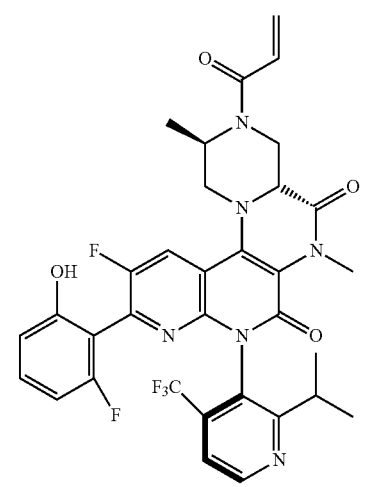

TABLE A-2-continued

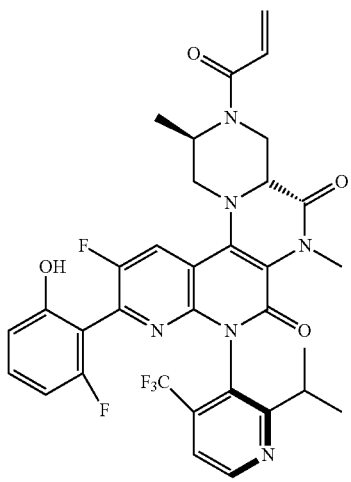

Z49-2

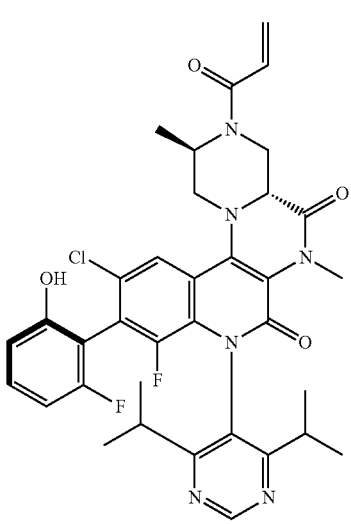

Z50-1

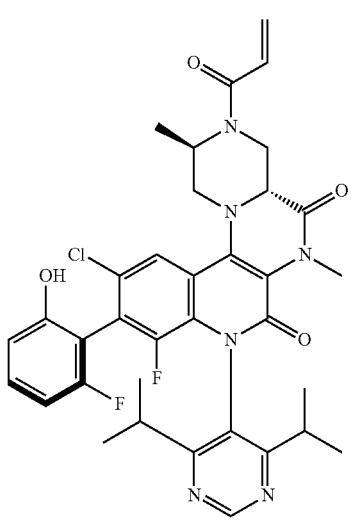

Z50-2

In an embodiment of the present invention, the representative compound of Formula (IA) includes but is not limited to any compound structure of example 51 to example 342, or pharmaceutically acceptable salts, solvates or prodrugs of such structures.

In an embodiment of the present invention, in the compound of Formula (II), $R_{11}$, $R_{12}$, $R_{21}$, $R_{22}$, $R_{31}$, $R_{32}$, $R_{41}$, $R_{42}$, Z, P, Ar, $E_3$, $E_4$, $X_2$, and $Y_2$ are each independently corresponding groups are each independently corresponding groups in different specific compounds in Examples.

In an embodiment of the present invention, the compound of Formula (II) is any one of compounds Z2, and Z17 to Z20 in Examples, or diastereoisomers thereof.

In another aspect, the present invention provides a pharmaceutical composition including a compound as described above, or a tautomer, a cis-trans isomer, a mesomer, a raceme, an enantiomer, a diastereoisomer, an atropisomer or a mixture thereof, or a pharmaceutically acceptable salt, a solvate or a prodrug thereof, and a pharmaceutically acceptable carrier.

As used herein, the term "pharmaceutically acceptable carrier" refers to any formulation capable of delivering an effective amount of the active substance of the present invention without interfering with the biological activity of the active substance and with no toxic side effects to a host or a subject, or a carrier representative of carrier media, including water, oils, vegetables and minerals, cream bases, lotion bases, ointment bases, and the like. Such bases include suspending agents, tackifiers, dermal penetration enhancer, and the like. Their formulations are well known to those skilled in the field of cosmetics or topical agents.

In embodiments of the present invention, the pharmaceutical composition can be administered in any way, such as orally, by spray inhalation, rectally, nasally, bucally, topically, parenterally, e.g., by subcutaneous, intravenous, intramuscular, intraperitoneal, intrathecal, intraventricular, intrasternal or intracranial injection or infusion, or with the aid of an explanted reservoir. When administered orally, the compounds of the present invention can be prepared into any orally acceptable formulation, including but not limited to tablets, capsules, aqueous solutions, or aqueous suspensions. Carriers for tablets typically include lactose and cornstarch. In addition, lubricants such as magnesium stearate may also be added. Diluents used in capsule formulations typically include lactose and dried cornstarch. Aqueous suspensions are usually prepared by mixing active ingredients with suitable emulsifiers and suspending agents. If desired, some sweeteners, flavoring agents, or colorants may also be added to the above-mentioned oral formulations. When administered topically, especially when to affected surfaces or organs that are easily accessible by topical application, such as eye, skin or lower intestinal neurological diseases, the compounds of the present invention can be prepared into different topical agents according to different affected surfaces or organs. When administered topically to eyes, the compounds of the present invention can be formulated into micronized suspensions or solutions with isotonic sterile salines at a certain pH with or without the addition of preservatives such as benzyl alkanol chlorides as carriers. For eye use, the compounds can also be prepared into ointments such as Vaseline ointments. When administered topically to the skin, the compounds of the present invention can be prepared into suitable ointment, lotion or cream formulations, with the active ingredients being suspended or dissolved in one or more carriers. Carriers that can be used in ointment formulations include but are not limited to mineral oils, liquid Vaseline, white Vaseline, propylene glycol, polyethylene oxide, polypropylene oxide, emulsified wax, and water. Carriers that can be used in lotions or creams include but are not limited to mineral oils, sorbitan monostearate, Tween 60, cetyl esters wax, hexadecen-aryl alcohol, 2-octyldodecanol, benzyl alcohol, and water. The compounds of the present invention may also be administered in the form of sterile injections, including sterile injectable water or oil suspensions or sterile injectable solutions. Carriers and solvents that can be used include water, Ringer's solution, and isotonic sodium chloride solution. In addition, sterile non-volatile oils can also be used as solvents or suspending media, e.g., monoglycerides or diglycerides.

In another aspect, the present invention provides use of the compounds as described above, or tautomers, cis-trans isomers, mesomers, racemes, enantiomers, diastereoisomers, atropisomers or mixtures thereof, or pharmaceutically acceptable salts, solvates or prodrugs thereof in preparing medicaments for preventing and/or treating a KRAS G12C mutation-induced disease. Preferably, the KRAS G12C mutation-induced disease is cancer.

In another aspect, the present invention provides use of the compounds as described above, or tautomers, cis-trans isomers, mesomers, racemes, enantiomers, diastereoisomers, atropisomers or mixtures thereof, or pharmaceutically acceptable salts, solvates or prodrugs thereof in preparing medicaments for preventing and/or treating cancer.

In an embodiment of the present invention, the cancer is pancreatic cancer, colorectal cancer, or lung cancer.

In an embodiment of the present invention, the cancer is lung cancer, preferably non-small-cell lung cancer (NSCLC).

In another aspect, the present invention provides use of the compounds as described above, or tautomers, cis-trans isomers, mesomers, racemes, enantiomers, diastereoisomers, atropisomers or mixtures thereof, or pharmaceutically acceptable salts, solvates or prodrugs thereof in preparing inhibitors for a KRAS mutation (preferably, the KRAS mutation is KRAS G12C mutation).

In another aspect, the present invention provides a method for treating cancer, including a Step of administering to a subject in need thereof a therapeutically effective amount of a compound, or a tautomer, a cis-trans isomer, a mesomer, a raceme, an enantiomer, a diastereoisomer, an atropisomer or a mixture thereof, or a pharmaceutically acceptable salt, a solvate or a prodrug thereof, as described above, or any combination thereof, or the above-mentioned pharmaceutical composition.

As used herein, the term "subject" refers to an animal, especially a mammal, preferably human.

As used herein, the term "effective amount" or "therapeutically effective amount" refers to a sufficient amount of a nontoxic drug or medicament that can achieve the expected effects. In embodiments of the present invention, when treating a patient according to the present invention, the amount of a drug is given depending on many factors, such as the specific dosage regimen, the disease or condition type and its severity, and the peculiarity (e.g., body weight) of the subject or host in need of treatment. However, in accordance with the particular ambient conditions, including, for example, the adopted specific drug and administration route, the treated condition, and the treated subject or host, the administered dosage may be conventionally determined by the known method in the art. Usually, for a dosage used for treating an adult, the administered dosage is typically in a range of 0.02-5000 mg/day, for example, about 1-1500 mg/day. The desired dosage can be conveniently shown as a single dose, or divided doses administered simultaneously (or in short time) or at appropriate intervals, for example, two, three, four or more divided doses each day. It will be understood by a person skilled in the art that although the above dosage range is given, the specific effective amount can be adjusted appropriately according to the patient's condition in combination with the doctor's diagnosis.

As used herein, the term "pharmaceutically acceptable salt" refers to a salt of a compound of the present invention that is pharmaceutically acceptable and has the pharmacological activity of the parent compound. Such salts include: acid addition salts formed with inorganic acids such as nitric acid, phosphoric acid, and carbonic acid, or organic acids such as propionic acid, hexanoic acid, cyclopentanoic acid, glycolic acid, pyruvic acid, gluconic acid, stearic acid, and muconic acid; or salts formed by replacing acidic protons present on the parent compounds with metal ions, such as alkali metal ions or alkaline earth metal ions; or coordination compounds formed with organic bases such as ethanolamine, diethanolamine, triethanolamine, and N-methylglucamine. The pharmaceutically acceptable salts of the present invention can be synthesized from the parent compounds containing acidic radicals or basic radicals by a conventional chemical method. In general, such salts are prepared by reacting these compounds in the form of free acids or bases with a stoichiometric amount of an appropriate base or acid in water or an organic solvent or a mixture thereof. In addition to the form of salts, the compounds provided herein also exist in the form of prodrugs. Prodrugs of the compounds described herein are prone to chemical changes under physiological conditions and thus transformed into the compounds of the present invention. In addition, prodrugs can be converted to the compounds of the present invention by a chemical or biochemical method in the in vivo environment.

As used herein, the terms "solvate" refer to a substrate formed by a compound of the present invention combined with a pharmaceutically acceptable solvent. Solvates include stoichiometric solvates and non-stoichiometric solvates.

Some compounds of the present invention can be present in a non-solvated or solvated form. In general, the solvated form and the non-solvated form are equivalent and both included in the scope of the present invention.

As used herein, the term "stereoisomer" includes a conformational isomer and a configurational isomer, where the configurational isomer mainly includes a cis-trans isomer and an optical isomer. The compounds of the present invention can be present in the form of stereoisomers and thus encompass all possible stereoisomer forms, including but not limited to cis-trans isomers, tautomers, enantiomers, diastereoisomers, atropisomers (or referred to as rotamers), etc. The compounds of the present invention can also be present in the form of any combination or any mixture of the aforementioned stereoisomers, for example, a mixture of equal amounts of a mesomer, a raceme, and an atropisomer. For example, each compound can be present as a single enantiomer, a single diastereoisomer or a mixture thereof, or a single atropisomer or a mixture thereof. When containing an olefinic double bond, the compounds of the present invention include cis isomers and trans isomer and any combination thereof unless specified otherwise. The atropisomers of the present invention are stereoisomers based on axial or planar chirality resulting from restricted intramolecular rotation. The compounds of the present invention each have two atropisomers originated from axial dissymmetry, which are derived from steric hindrance formed by restricting the rotation of the bond linkage between the substituent Ar' or $R_0$' and the substituted naphthyridinone ring, with the substituent being a cyclic group such as $C_{6-10}$ aryl, 5- or 6-membered heteroaryl, 8- to 10-membered bicyclic heteroaryl, or pyridonyl.

In regard to the atropisomers of the present invention, the compound have a structure of Formula (I), Formula (IA), or Formula (II), or the compound of Formula (I), Formula (IA), or Formula (II) has isomers derived from asymmetric carbon, which represent any one of a pair of atropisomers of each isocompound. As drugs, atropisomers having excellent activity are preferred. The compound of Formula (I), Formula (IA), or Formula (II) has optical isomers originated from asymmetric carbon, axial dissymmetry, etc, and a single isomer can be obtained by optical resolution when necessary. The atropisomers of the compounds of the present invention may be denoted as P- or M-configuration, and may also be denoted in other ways which are well-known and commonly used in the art.

As described above, the present invention provides the above-mentioned compounds of different structures, or tautomers, cis-trans isomers, mesomers, racemes, enantiomers, diastereoisomers, atropisomers or mixtures thereof, where the "mixture thereof" includes mixing in any form between any stereoisomer (e.g., a tautomer, a cis-trans isomer, an enantiomer, a diastereoisomer, or an atropisomer) and/or a mixture (a mesomer and a raceme), such as a mixture of cis-trans isomers, a mixture of an enantiomer and a diastereoisomer, a mixture of diastereoisomers, and a mixture of atropisomers, or mixing of a cis-trans isomer and a raceme, mixing of an enantiomer and a mixture of diastereoisomers, mixing of an atropisomer and a mixture of diastereoisomers, etc.

As used herein, the symbol "-" in a substituent in each group represents a bond for linking to other group or structure.

As used herein, the term "fused" refers to a structure in which two or more rings share one or more bonds.

As used herein, the term "alkyl" refers to a linear or branched saturated aliphatic hydrocarbyl group containing 1 to 20 carbon atoms. The term "$C_{1-10}$ alkyl" refers to linear or branched alkyl having 1 to 10 carbon atoms, more preferably linear or branched alkyl having 1, 2, 3, 4, 5, or 6 carbon atoms, namely $C_{1-6}$ alkyl, more preferably $C_{1-4}$ alkyl, and most preferably $C_{1-3}$ alkyl. Specific examples of alkyl include but are not limited to methyl, ethyl, n-propyl, isopropyl, n-butyl, isobutyl, tert-butyl, sec-butyl, n-amyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylamyl, 3-methylamyl, 4-methylamyl, 2,3-dimethylbutyl, and various branched isomers thereof, etc.

It needs to be noted that if propyl and isopropyl are present among parallel options, the propyl represents n-propyl unless specified otherwise. If only propyl is present among parallel options, the propyl represents n-propyl or isopropyl.

As used herein, "—$C_{1-3}$ alkyl-" and "$C_{1-3}$ alkylidene" can be used interchangeably, which refer to saturated linear or branched aliphatic hydrocarbyl having 2 residues derived by removing two hydrogen atoms from the same carbon atom or two different carbon atoms of the parent alkyl and is a linear or branched group having 1 to 3 carbon atoms.

Non-limiting examples of alkylidene include but are not limited to methylene (—$CH_2$—), 1,1-ethylidene (—CH($CH_3$)—), 1,2-ethylidene (—$CH_2CH_2$—), 1,1-propylidene (—CH($CH_2CH_3$)—), 1,2-propylidene (—$CH_2CH(CH_3)$—), 1,3-propylidene (—$CH_2CH_2CH_2$—), etc.

As used herein, "—$C_{1-3}$ alkyl (hydroxy)-, —$C_{1-3}$ alkyl (cyano)-, —$C_{1-3}$ alkyl ($C_{1-6}$ alkyl)-, —$C_{1-3}$ alkyl (halogenated $C_{1-6}$ alkyl)-, —$C_{1-3}$ alkyl ($C_{1-6}$ alkyl-hydroxy)-, —$C_{1-3}$ alkyl ($C_{1-6}$ alkyl-cyano)-, —$C_{1-3}$ alkyl ($C_{1-6}$ alkoxy)-, and —$C_{1-3}$ alkyl (halogenated $C_{1-6}$ alkoxy)-" refer to residues by substitution of one or more hydrogen atoms in "—$C_{1-3}$ alkyl-" by hydroxyl, cyano, $C_{1-6}$ alkyl, halogenated $C_{1-6}$ alkyl, —$C_{1-6}$ alkyl-hydroxyl, —$C_{1-6}$ alkyl-cyano, $C_{1-6}$ alkoxy, and halogenated $C_{1-6}$ alkoxy, respectively. Non-limiting examples include but are not limited to —CH(OH)—, —$CH_2CH(CN)$—, —$CH_2CH(CH_2CH_3)$—, —$CH_2CH(CF_3)$—, —CH($CH_2OH$)—, —$CH_2CH(CH_2CN)$—, —CH($OCH_3$)—, and —$CH_2CH(OCF_3)$—.

As used herein, the term "alkoxy" refers to a group having an —O-alkyl structure, where the alkyl is as defined above. The term "$C_{1-10}$ alkoxy" refers to alkoxy having 1 to 10 carbon atoms, preferably $C_{1-6}$ alkoxy, more preferably $C_{1-4}$ alkoxy, and further preferably $C_{1-3}$ alkoxy. Specific examples of alkoxy include but are not limited to methoxy, ethoxy, n-propoxy, isopropoxy, n-butoxy, tert-butoxy, isobutoxy, n-pentyloxy, etc.

It needs to be noted that if propoxy and isopropoxy are present among parallel options, the propoxy represents n-propoxy unless specified otherwise. If only propoxy is present among parallel options, the propoxy represents n-propoxy or isopropoxy.

As used herein, the term "thioalkyl" refers to a group having an —S-alkyl structure, where the alkyl is as defined above.

The term "$C_{1-10}$ thioalkyl" refers to thioalkyl having 1 to 10 carbon atoms, preferably $C_{1-6}$ thioalkyl, more preferably $C_{1-4}$ thioalkyl, and further preferably $C_{1-3}$ thioalkyl. Specific examples of thioalkyl include but are not limited to thiomethyl, thioethyl, thiopropyl, thioisopropyl, thiobutyl, thio-tert-butyl, thio-isobutyl, thioamyl, etc.

As used herein, the term "alkenyl" refers to alkyl having one or more C=C double bonds at any site of the chain as defined above, and the term "$C_{2-8}$ alkenyl" refers to alkenyl having 2 to 8 carbon atoms and at least one C=C double bond, preferably alkenyl having 2 to 6 carbon atoms and 1 to 2 C=C double bonds, namely $C_{2-6}$ alkenyl, more preferably alkenyl having 2 to 4 carbon atoms and 1 to 2 C=C double bonds, namely $C_{2-4}$ alkenyl. Specific examples of alkenyl include but are not limited to ethenyl, 1-propenyl, 2-propenyl, 1-, 2- or 3-butenyl, pentenyl, hexenyl, butadienyl, etc.

As used herein, the term "alkynyl" refers to alkyl having one or more C≡C triple bonds at any site of the chain as defined above, and the term "$C_{2-8}$ alkynyl" refers to alkynyl having 2 to 8 carbon atoms and at least one C≡C triple bond, preferably alkynyl having 2 to 6 carbon atoms and 1 to 2 C≡C triple bonds, namely $C_{2-6}$ alkynyl, more preferably alkynyl having 2 to 4 carbon atoms and 1 to 2 C≡C triple bonds, namely $C_{2-4}$ alkynyl. Specific examples of alkynyl include but are not limited to ethynyl, 1-propinyl, 2-propinyl, 1-, 2- or 3-butynyl, etc.

As used herein, the term "halogen" refers to fluorine, chlorine, bromine, and iodine.

As used herein, the term "haloalkyl" refers to alkyl substituted by one or more (e.g., 1, 2, 3, 4, or 5) halogens, where the alkyl is as defined above. The term "$C_{1-10}$ haloalkyl" refers to haloalkyl having 1 to 10 carbon atoms, preferably halogenated $C_{1-6}$ alkyl, more preferably Cia haloalkyl, and further preferably halogenated $C_{1-3}$ alkyl. Specific examples of haloalkyl include but are not limited to monochloromethyl, dichloromethyl, trichloromethyl, monochloroethyl, 1,2-dichloroethyl, trichloroethyl, monobromoethyl, monofluoromethyl, difluoromethyl, trifluoromethyl, monofluoroethyl, difluoroethyl, trifluoroethyl, etc.

As used herein, the term "deuteroalkyl" refers to alkyl substituted by one or more (e.g., 1, 2, 3, 4, or 5) deuterium atoms, where the alkyl is as defined above. The term "$C_{1-10}$ deuteroalkyl" refers to deuteroalkyl having 1 to 10 carbon atoms, preferably $C_{1-6}$ deuteroalkyl, more preferably Cia deuteroalkyl, and further preferably $C_{1-3}$ deuteroalkyl.

Specific examples of deuteroalkyl include but are not limited to monodeuteromethyl, dideuteromethyl, trideuteromethyl, monodeuteroethyl, 1,2-dideuteroethyl, trideuteroethyl, etc.

As used herein, the term "haloalkoxy" refers to alkoxy substituted by one or more (e.g., 1, 2, 3, 4, or 5) halogens, where the alkoxy is as defined above. The term "$C_{1-10}$ haloalkoxy" refers to haloalkoxy having 1 to 10 carbon atoms, preferably halogenated $C_{1-6}$ alkoxy, more preferably CIA haloalkoxy, and further preferably $C_{1-3}$ haloalkoxy. Specific examples of haloalkoxy include but are not limited to trifluoromethoxy, trifluoroethoxy, monofluoromethoxy, monofluoroethoxy, difluoromethoxy, difluoroethoxy, etc.

As used herein, the terms "cycloalkyl" and "cycloalkyl ring" can be used interchangeably, which refer to saturated monocyclic or polycyclic fused cyclohydrocarbyl. The term "$C_{3-20}$ cycloalkyl" refers to cycloalkyl having 3 to 20 carbon atoms, including monocyclic cycloalkyl, spirocycloalkyl, fused cycloalkyl, and bridged cycloalkyl, preferably $C_{3-12}$ cycloalkyl. The ring carbon atoms of the cycloalkyl in the present invention carbon atoms can be each optionally substituted by 1, 2, or 3 oxo groups to form cyclic ketone structures. The terms "$C_{3-8}$ monocyclic cycloalkyl" and "$C_{3-8}$ cycloalkyl" refer to saturated monocyclic cyclohydrocarbyl having 3 to 8 carbon atoms, preferably $C_{3-6}$ monocyclic cycloalkyl (i.e., $C_{3-6}$ cycloalkyl), more preferably $C_3$, $C_4$, $C_5$, or $C_6$ monocyclic cycloalkyl. Specific examples of monocyclic cycloalkyl include but are not limited to cyclopropyl, cyclobutyl, cyclopentyl, cyclohexyl, cycloheptyl, cyclooctyl, etc.

As used herein, the terms "spirocycloalkyl" and "spirocycloalkyl ring" refer to polycyclic cyclohydrocarbyl formed with two or more single rings sharing one carbon atom (called a spiro-atom). Spirocycloalkyl is classified as monospirocycloalkyl, bispirocycloalkyl, or polyspirocycloalkyl depending on the number of spiro-atoms shared between rings. The term "5- to 20-membered spirocycloalkyl" or "$C_{5-20}$ spirocycloalkyl" refers to polycyclic cyclohydrocarbyl having 5 to 20 ring carbon atoms, where the singe rings sharing a spiro-atom are 3- to 8-membered monocyclic cycloalkyl rings, preferably 6- to 14-membered ($C_{6-14}$) spirocycloalkyl, more preferably 6- to 14-membered monospirocycloalkyl, further preferably 7- to 11-membered ($C_{7-11}$) spirocycloalkyl, still further preferably 7- to 11-membered monospirocycloalkyl, and most preferably 7-membered (4-membered monocyclic cycloalkyl ring/4-membered monocyclic cycloalkyl ring), 8-membered (4-membered monocyclic cycloalkyl ring/5-membered monocyclic cycloalkyl ring), 9-membered (4-membered monocyclic cycloalkyl ring/6-membered monocyclic cycloalkyl ring, 5-membered monocyclic cycloalkyl ring/5-membered monocyclic cycloalkyl ring), 10-membered (5-membered monocyclic cycloalkyl ring/6-membered monocyclic cycloalkyl ring), or 11-membered (6-membered monocyclic cycloalkyl ring/6-membered monocyclic cycloalkyl ring) monospirocycloalkyl. Specific examples of spirocycloalkyl include but are not limited to:

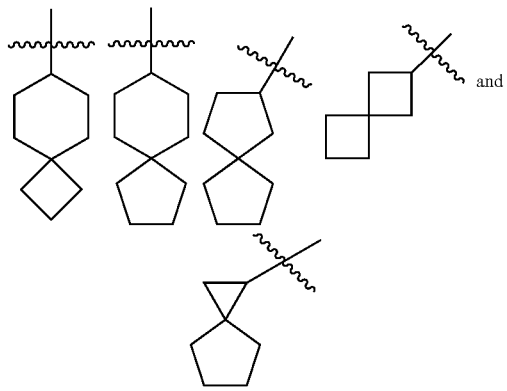

and

The cycloalkyl ring can be fused to an aryl, heteroaryl or heterocyclyl ring, where the ring linked to the parent structure is the cycloalkyl ring, and non-limiting examples thereof include indanyl, tetralyl, benzocycloheptyl, etc.

In the present invention, the above-mentioned cycloalkyl groups can be optionally substituted, and when such a cycloalkyl group is substituted, the substituent is preferably one or more substituent groups specified herein.

As used herein, the term "halocycloalkyl" refers to cycloalkyl substituted by one or more (e.g., 1, 2, 3, 4, or 5) halogens, where the cycloalkyl is as defined above. The term "$C_{3-8}$ halocycloalkyl" refers to halocycloalkyl having 3 to 8 ring carbon atoms, preferably $C_{3-6}$ halocycloalkyl, and more preferably $C_3$, $C_4$, $C_5$, or $C_6$ halocycloalkyl. Specific examples of halocycloalkyl include but are not limited to trifluorocyclopropyl, monofluorocyclopropyl, monofluorocyclohexyl, difluorocyclopropyl, difluorocyclohexyl, etc.

As used herein, the terms "heterocyclyl" and "heterocyclyl" can be used interchangeably, which refer to saturated or partially unsaturated monocyclic or polycyclic fused cyclohydrocarbyl, and the term "$C_{3-20}$ heterocyclyl" or "3- to 20-membered heterocyclyl" refers to saturated or partially unsaturated monocyclic or polycyclic fused cyclohydrocarbyl having 3 to 20 ring atoms, where one or more (preferably 1, 2, 3, or 4) ring atoms are heteroatoms selected from nitrogen, oxygen, or $S(O)_m$ (m is an integer ranging from 0 to 2), but not including the ring portion —O—O—, —O—S—, or —S—S—, and other ring atoms are C. When the ring atom is nitrogen atom, it may be substituted or unsubstituted (i.e., N or NR, R being hydrogen or other substituents already defined herein). The ring carbon atoms of the heterocyclyl in the present invention can be each optionally substituted by 1, 2, or 3 oxo groups to form cyclic ketone, cyclic lactone or cyclic lactam structures. The 3- to 20-membered heterocyclyl of the present invention includes monocyclic heterocyclyl, spiroheterocyclyl, fused heterocyclyl, and bridged heterocyclyl.

As used herein, the terms "$C_{3-8}$ monocyclic heterocyclyl", "3- to 8-membered monocyclic heterocyclyl" and "3- to 8-membered monocyclic heterocyclyl ring" refer to saturated or partially unsaturated monocyclic cyclohydrocarbyl having 3 to 8 ring atoms, with 1, 2, or 3 ring atoms being heteroatoms selected from nitrogen, oxygen, or $S(O)_m$ (m is an integer ranging from 0 to 2), preferably 3- to 6-membered monocyclic heterocyclyl having 3 to 6 ring atoms with 1 or 2 ring atoms being heteroatoms (i.e., $C_{3-6}$ monocyclic heterocyclyl), and more preferably 5- or 6-membered monocyclic heterocyclyl having 5 or 6 ring atoms with 1 or 2 ring atoms being heteroatoms. When the heteroatom is nitrogen atom, the nitrogen atom may be substituted or unsubstituted (i.e., N or NR, R being hydrogen or other substituents already defined herein). When the heteroatom is sulfur atom, the sulfur atom may be optionally oxidated (i.e., $S(O)_m$, m being an integer of 0 to 2). The ring carbon atoms of the monocyclic heterocyclyl can be each optionally substituted by 1, 2, or 3 oxo group to form cyclic ketone, cyclic lactone or cyclic lactam structures. Specific examples of monocyclic heterocyclyl include but are not limited to aziridine, ethylene oxide, azetidine, azetidin-2-one, oxetane, oxetan-2-one, oxazolidine, pyrrolidin-2-one, pyrrolidin-2,5-dione, 1,3-dioxolane, dihydrofuro-2(3H)-one, dihydrofuro-2,5-dione, piperidin-2-one, piperidin-2,6-dione, tetrahydro-2H-pyran-2-one, imidazolidine, tetrahydrofuran, tetrahydrothiophene, tetrahydropyrrole, 1,3-dioxolan-2-one, oxazolidin-2-one, imidazolidin-2-one, piperidine, piperazine, piperazin-2-one, morpholine, morpholin-3-one, morpholin-2-one, thiomorpholin-3-one1,1-dioxide, thiomorpholine, thiomorpholin-1, 1-dioxide, tetrahydropyrane, 1,2-dihydroazacyclobutadiene, 1,2-dihydrooxacyclobutadiene, 2,5-dihydro-1H-pyrrole, 2,5-dihydrofuran, 2,3-dihydrofuran, 2,3-dihydro-1H-pyrrole, 3,4-dihydro-2H-pyrane, 1,2,3,4-tetrahydropyridine, 3,6-dihydro-2H-pyrane, 1,2,3,6-tetrahydropyridine, 1,3-oxazinane, hexahydropyrimidine, 1,4-dioxane, tetrahydropyrimidin-2(1H)-one, 1,4-dioxan-2-one, 5,6-dihydro-2H-pyran-2-one, 5,6-dihydropyrimidin-4(3H)-one, 3,4-dihydropyridin-2(1H)-one, 5,6-dihydropyridin-2(1H)-one, 5,6-dihydropyrimidin-4(1H)-one, pyrimidin-4(3H)-one, pyrimidin-4(1H)-one, 4,5-dihydro-1H-imidazole, 2,3-dihydro-1H-imidazole, 2,3-dihydrooxazole, 1,3-dioxole, 2,3-dihydrothiophene, 2,5-dihydrothiophene, 3,4-dihydro-2H-1,4-oxazine, 3,4-dihydro-2H-1,4-thiazin1,1-dioxide, 1,2,3,4-tetrahydropyrazine, 1,3-dihydro-2H-pyrrol-2-one, 1,5-dihydro-2H-pyrrol-2-one, 1H-pyrrol-2,5-dione, furo-2(3H)-one, furo-2(5H)-one, 1,3-dioxol-2-one, oxazol-2(3H)-one, 1,3-dihydro-2H-imidazol-2-one, furo-2,5-dione, 3,6-dihydropyridin-2(1H)-one, pyridin-2,6-(I H, 3H)-dione, 5,6-dihydro-2H-pyran-2-one, 3,6-dihydro-2H-pyran-2-one, 3,4-dihydro-2H-1,3-oxazine, 3,6-dihydro-2H-1,3-oxazine, 1,2, 3,4-tetrahydropyrimidine, etc. The terms "$C_{3-8}$ heterocycloalkyl" and "3- to 8-membered heterocycloalkyl" refer to saturated monocyclic cyclohydrocarbyl having 3 to 8 ring atoms with 1 or 2 ring atoms being heteroatoms, preferably 3- to 6-membered heterocycloalkyl having 3 to 6 ring atoms with 1 or 2 ring atoms being heteroatoms. Specific examples of heterocycloalkyl include but are not limited to aziridinyl, an ethylene oxide group, azetidinyl, oxetanyl, oxazolidinyl, 1,3-dioxolanyl, dioxanyl, imidazolidinyl, tetrahydrofuryl, tetrahydrothienyl, tetrahydropyrrolyl, piperidinyl, piperazinyl, morpholinyl, thiomorpholinyl, a thiomorpholin-1,1-dioxide group, tetrahydropyranyl, 1,4-oxoazepanyl, 1,3-oxoazepanyl, 1,3-oxazinanyl, hexahydropyrimidinyl, and 1,4-dioxanyl.

Two linked ring atoms, including C—C and N—C, on the above-mentioned monocyclic heterocyclyl ring can be optionally fused with cycloalkyl such as a monocyclic cycloalkyl ring, a monocyclic heterocyclyl ring, a monoaryl ring, and a 5- or 6-membered monoheteroaryl ring, heterocyclyl, aryl or heteroaryl, as defined in the present invention, to form fused polycycles. The two linked ring atoms on the monocyclic heterocyclyl that forms a fused ring with other ring are preferably C—C.

As used herein, the terms "$C_{6-14}$ aryl", "$C_{6-14}$ aryl ring" and "$C_{6-14}$ aromatic ring" can be used interchangeably, which refer to an all-carbon monocyclic, all-carbon polycyclic (rings being linked by a covalent bond rather than fused) or all-carbon fused polycyclic (rings sharing a pair of adjoining atoms) group having 6 to 14 ring atoms, where the group has at least one aromatic ring, i.e., has a conjugated π electron system. $C_{6-10}$ aryl is preferred. $C_{6-14}$ aryl in the present invention includes monocyclic aryl, polycyclic aryl, and aromatic fused polycycles, where examples of monocyclic include phenyl, and examples of polycyclic aryl include biphenyl and the like.

In the present invention, when $C_{6-14}$ aryl is aromatic fused polycycles, the aromatic fused polycycles may be a polycyclic group formed by a monoaryl ring fused with one or more monoaryl rings, and non-limiting examples thereof include naphthyl, anthryl, etc.

In some embodiments of the present invention, the aromatic fused polycycles may also be a polycyclic group formed by a monoaryl ring (e.g., phenyl) fused with one or more non-aromatic rings, where the ring linked to the parent structure is an aromatic ring or a non-aromatic ring. The non-aromatic rings include but are not limited to 3- to 6-membered monocyclic heterocyclyl rings (preferably a 5- or 6-membered monocyclic heterocyclyl ring, where the ring carbon atoms of the monocyclic heterocyclyl ring can be substituted by 1 to 2 oxo groups, forming a cyclic lactam or cyclic lactone structure), and 3- to 6-membered monocyclic cycloalkyl rings (preferably a 5- or 6-membered monocyclic cycloalkyl ring, where the ring carbon atoms of the monocyclic cycloalkyl ring can be substituted by 1 or 2 oxo groups, forming a cyclic ketone structure). The above-mentioned polycyclic group formed by a monoaryl ring fused with one or more non-aromatic rings may be linked to other group or the parent structure by a nitrogen atom or a carbon atom, with the ring linked to the parent structure being a monoaryl ring or a non-aromatic ring.

Herein, fusing of a benzene ring with a single 5- or 6-membered monocyclic heterocyclyl ring to form 9- or 10-membered aromatic fused bicycles refers to forming a fused 5- or 6-membered monocyclic heterocyclyl ring by two adjacent substituent groups on phenyl together with a ring atom linked thereto, where the 5- or 6-membered monocyclic heterocyclyl ring is as defined above, and the resulting 9- or 10-membered aromatic fused bicycles may also be referred to as a 9- or 10-membered phenyl heterocyclyl ring.

Herein, fusing of a benzene ring with a single 5- or 6-membered monocyclic cycloalkyl ring to form 9- or 10-membered aromatic fused bicycles refers to forming a fused 5- or 6-membered monocyclic cycloalkyl ring by two adjacent substituent groups on phenyl together with a ring atom linked thereto, where the 5- or 6-membered monocyclic cycloalkyl ring is as defined above, and the resulting 9- or 10-membered aromatic fused bicycles may also be referred to as a 9- or 10-membered phenyl cycloalkyl ring. Non-limiting examples thereof include:

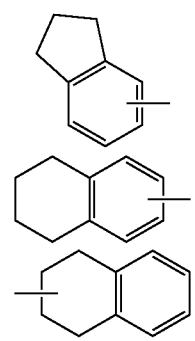

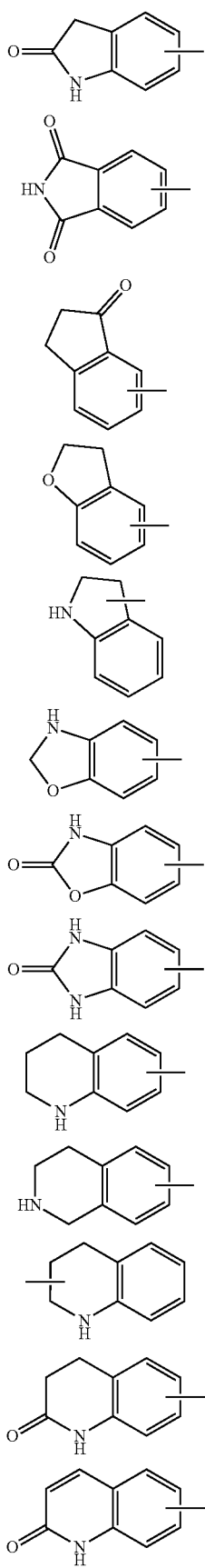

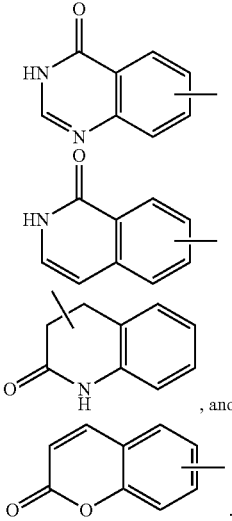

In the present invention, the above-mentioned aryl groups may be substituted or unsubstituted, and when such an aryl group is substituted, the substituent is preferably one or more substituent groups specified herein.

As used herein, the terms "heteroaryl", "heteroaryl ring" and "heteroaromatic ring" can be used interchangeably, which refer to a monocyclic or fused polycyclic (i.e., sharing a pair of adjoining ring atoms which may be C—C or N—C) group with a ring atom being substituted by at least one heteroatom independently selected from nitrogen, oxygen, or sulfur, where nitrogen and sulfur atoms can be each optionally oxidated, and the nitrogen atom can be optionally quaternized. The heteroaryl has shared 6, 10, or 14 π electrons, and at least one ring in the group is aromatic. The terms "$C_{5-14}$ heteroaryl" and "5- to 14-membered heteroaryl" refer to heteroaryl having 5 to 14 ring atoms with 1, 2, 3, or 4 ring atoms being heteroatoms, preferably 5- to 10-membered heteroaryl having 5 to 10 ring atoms with 1, 2, 3, or 4 ring atoms being heteroatoms. In the present invention, $C_{5-14}$ heteroaryl may be monoheteroaryl, fused bicyclic heteroaryl, or fused tricyclic heteroaryl.

As used herein, the terms "5- or 6-membered monoheteroaryl" and "5- or 6-membered monocyclic heteroaryl" can be used interchangeably, which refer to monocyclic heteroaryl having 5 or 6 ring atoms with 1, 2, or 3 ring atoms being heteroatoms. Specific examples of monoheteroaryl include but are not limited to thiophene, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyridazine, pyrimidine, pyrazine, etc.

As used herein, the terms "8- to 10-membered biheteroaryl" and "8- to 10-membered bicyclic heteroaryl" can be used interchangeably, which refer to fused bicyclic heteroaryl having 8 to 10 ring atoms with 1, 2, 3, 4, or 5 ring atoms being heteroatoms. The fused bicyclic heteroaryl may either a bicyclic group (preferably a 9- or 10-membered biheteroaryl ring) formed by a monoaryl ring (e.g., phenyl) fused with a monoheteroaryl ring (preferably a 5- or 6-membered monoheteroaryl ring), or a bicyclic group formed by a monoheteroaryl ring (preferably a 5- or 6-membered monoheteroaryl ring) fused with a monoheteroaryl ring (preferably a 5- or 6-membered monoheteroaryl ring).

Any two linked ring atoms, including C—C, N—C, and N—N, on the above-mentioned monoheteroaryl ring can be fused with cycloalkyl such as a monocyclic cycloalkyl ring, a monocyclic heterocyclyl ring, a monoaryl ring, and a 5- or 6-membered monoheteroaryl ring, heterocyclyl, aryl or heteroaryl, as defined in the present invention, to form fused polycycles. The two linked ring atoms on the monoheteroaryl ring that forms a fused ring with other ring are preferably C—C, non-restrictively including the following forms:

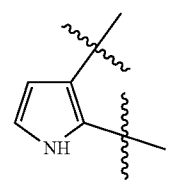,

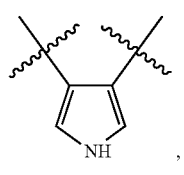,

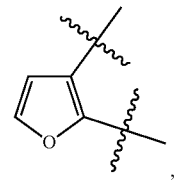,

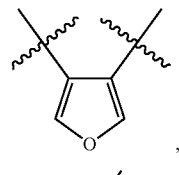,

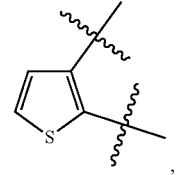,

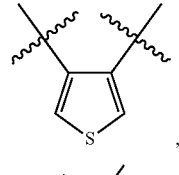,

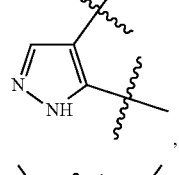,

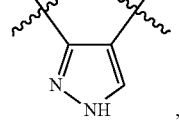,

-continued

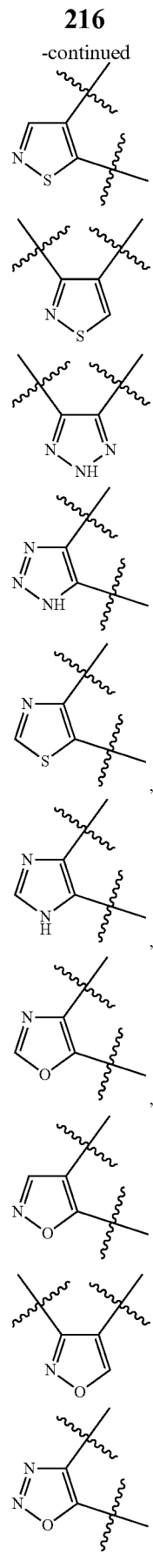

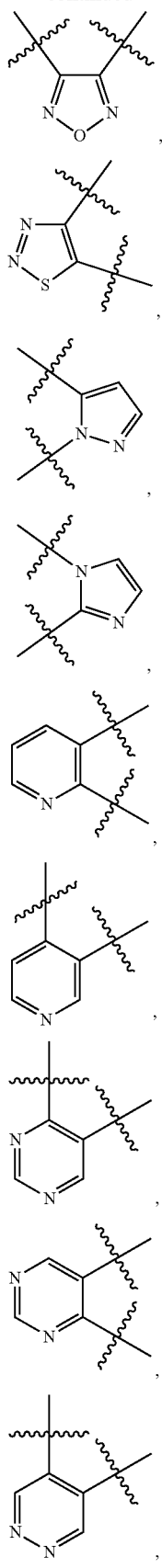

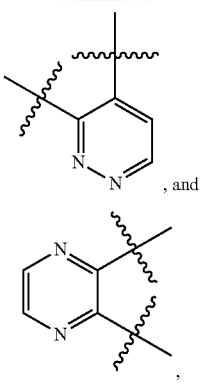, and

Non-limiting examples of 8- to 10-membered biheteroaryl include benzo[d]isoxazole, 1H-indole, isoindole, 1H-benzo[d]imidazole, benzo[d]isothiazole, 1H-benzo[d][1,2,3]triazole, benzo[d]oxazole, benzo[d]thiazole, indazole, benzofuran, benzo[b]thiophene, quinoline, isoquinoline, quinazoline, quinoxaline, cinnoline, pyrido[3,2-d]pyrimidine, pyrido[2,3-d]pyrimidine, pyrido[3,4-d]pyrimidine, pyrido[4,3-d]pyrimidine, 1,8-naphthyridine, 1,7-naphthyridine, 1,6-naphthyridine, 1,5-naphthyridine, pyrazolo[1,5-a]pyrimidine, imidazo[1,2-b]pyridazine, etc.

The above-mentioned monoheteroaryl, or biheteroaryl formed by a benzene ring fused with a monoheteroaryl ring, or biheteroaryl formed by a monoheteroaryl ring and a monoheteroaryl ring may be linked to other group or the parent structure by a nitrogen atom or a carbon atom. In case of biheteroaryl, the ring linked to the parent structure is a monoheteroaryl ring or a benzene ring, and the specific examples thereof include but are not limited to:

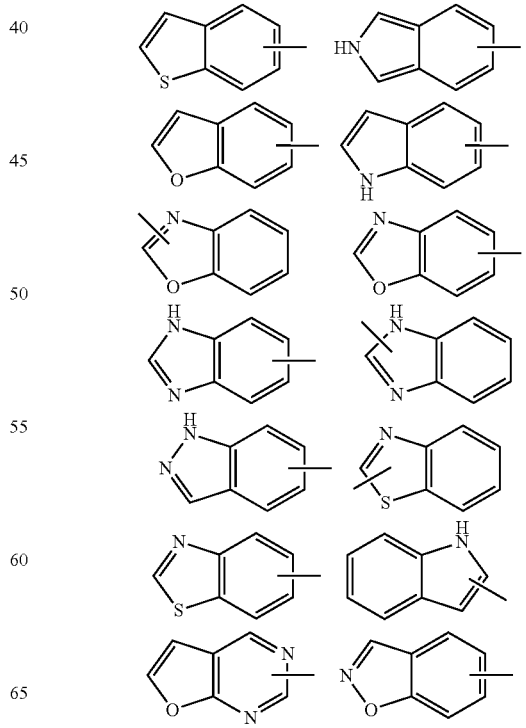

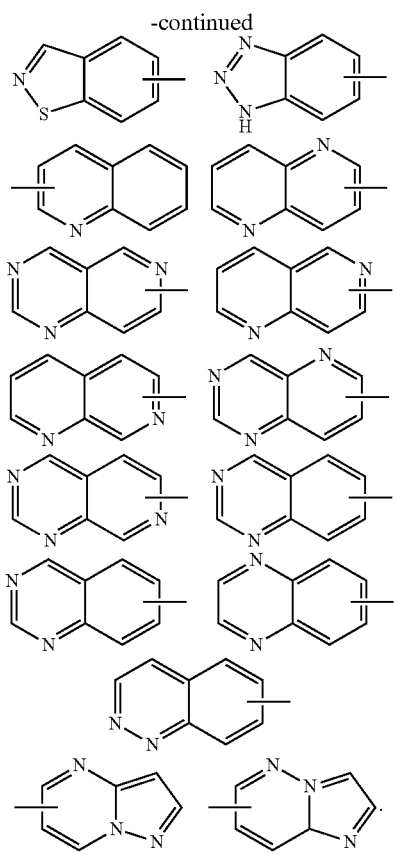

In some embodiments of the present invention, the fused bicyclic heteroaryl or the fused tricyclic heteroaryl may also be a polycyclic group formed by a monoheteroaryl ring (preferably a 5- or 6-membered monoheteroaryl ring) fused with one or more non-aromatic rings, where the ring linked to the parent structure is a monoheteroaryl ring or a non-aromatic ring. The non-aromatic rings include but are not limited to 3- to 6-membered monocyclic heterocyclyl rings (preferably a 5- or 6-membered monocyclic heterocyclyl ring, where the ring carbon atoms of the monocyclic heterocyclyl ring can be substituted by 1 to 2 oxo groups, forming a cyclic lactam or cyclic lactone structure), 3- to 6-membered monocyclic cycloalkyl rings (preferably a 5- or 6-membered monocyclic cycloalkyl ring, where the ring carbon atoms of the monocyclic cycloalkyl ring can be substituted by 1 or 2 oxo groups, forming a cyclic ketone structure), etc. The above-mentioned polycyclic group formed by a monoheteroaryl ring fused with one or more non-aromatic rings may be linked to other group or the parent structure by a nitrogen atom or a carbon atom, with the ring linked to the parent structure being a monoheteroaryl ring or a non-aromatic ring.

Herein, fusing of a 5- or 6-membered monoheteroaryl ring with a single 5- or 6-membered monocyclic heterocyclyl ring to form 8- to 10-membered fused bicyclic heteroaryl refers to forming a fused 5- or 6-membered monocyclic heterocyclyl ring by two adjacent substituent groups on 5- or 6-membered monoheteroaryl together with a ring atom adjacent thereto, where the 5- or 6-membered monocyclic heterocyclyl ring is as defined above, and the resulting 8- to 10-membered fused bicyclic heteroaryl may also be referred to as an 8- to 10-membered heteroaryl heterocyclyl ring.

Herein, fusing of a 5- or 6-membered monoheteroaryl ring with a single 5- or 6-membered monocyclic cycloalkyl ring to form 8- to 10-membered fused bicyclic heteroaryl refers to forming a fused 5- or 6-membered monocyclic cycloalkyl ring by two adjacent substituent groups on 5- or 6-membered monoheteroaryl together with a ring atom linked thereto, where the 5- or 6-membered monocyclic cycloalkyl ring is as defined above, and the resulting 8- to 10-membered fused bicyclic heteroaryl may also be referred to as an 8- to 10-membered heteroaryl cycloalkyl ring.

Non-limiting examples thereof include:

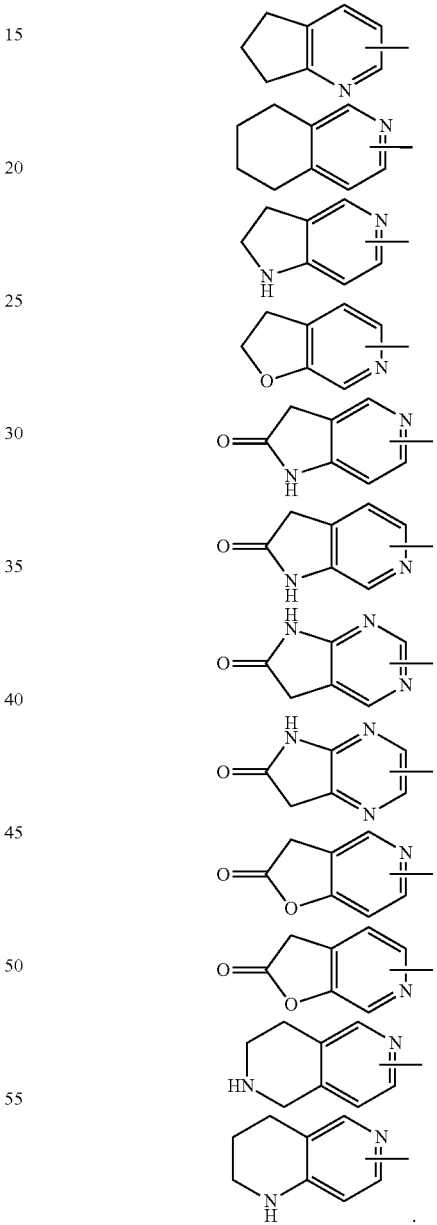

In the present invention, the above-mentioned heteroaryl groups may be substituted or unsubstituted, and when such a heteroaryl group is substituted, the substituent is preferably one or more substituent groups specified herein.

As used herein, the term "-alkyl-R" represents a substituent resulting from alkyl being substituted by one or more R groups, where "-alkyl-" represents alkylene or alkylidene formed after substitution. As specified herein, R may be hydroxyl, cyano, alkoxy, substituted amino, heterocycloalkyl, heteroaryl, haloalkyl, haloalkoxy, cycloalkyl, alkynyl or the like, and groups represented by R are as defined herein, preferably —$C_{1-6}$ alkyl-R, more preferably —$C_{1-4}$ alkyl-R, further preferably —$C_{1-3}$ alkyl-R, and still further preferably —$C_{1-2}$ alkyl-R, such as —$CH_2$—$CH(CH_3)$—R, —$CH_2$—$CH_2$—$CH_2$—R, —$CH_2$—$CH_2$—R, and —$CH_2$—R.

As used herein, the term "hydroxyl" refers to —OH.

As used herein, the term "hydroxymethyl" refers to —$CH_2OH$, and "hydroxyethyl" refers to —$CH_2CH_2OH$ or —$CH(OH)CH_3$.

As used herein, the term "cyanomethyl" refers to —$CH_2CN$, and "cyanoethyl" refers to —$CH_2CH_2CN$ or —$CHCNCH_3$.

As used herein, the term "amino" refers to —$NH_2$.

As used herein, the term "cyano" refers to —CN.

As used herein, the term "nitro" refers to —$NO_2$.

As used herein, the term "benzyl" refers to —$CH_2$-benzene.

As used herein, the term "oxo" refers to =O.

As used herein, the term "carboxyl" refers to —C(O)OH.

As used herein, the term "carboxylate group" refers to —C(O)O(alkyl) or —C(O)O(cycloalkyl).

As used herein, the term "acetyl" refers to —$COCH_3$.

Herein, $C_{1-10}$ may be preferably $C_{1-6}$, more preferably $C_{1-4}$, and further preferably $C_{1-3}$. For example, $C_{1-10}$ alkyl may be preferably $C_{1-6}$ alkyl, more preferably $C_{1-4}$ alkyl, and further preferably $C_{1-3}$ alkyl. For example, $C_{1-10}$ alkoxy may be preferably $C_{1-6}$ alkoxy, more preferably $C_{1-4}$ alkoxy, and further preferably $C_{1-3}$ alkoxy.

Herein, $C_{3-20}$ may be preferably $C_{3-10}$, more preferably $C_{3-8}$, further preferably $C_{3-6}$, and still further preferably $C_{3-5}$.

For example, $C_{3-20}$ cycloalkyl may be preferably $C_{3-8}$ cycloalkyl, more preferably $C_{3-6}$ cycloalkyl, and further preferably $C_{3-6}$ cycloalkyl.

In an embodiment of the present invention, in any group, the $C_{3-6}$ cycloalkyl is selected from cyclopropyl, cyclobutyl, cyclopentyl, and cyclohexyl.

In an embodiment of the present invention, in any group, the 3- to 6-membered heterocycloalkyl is selected from aziridine, ethylene oxide, azetidine, oxetane, tetrahydrofuran, tetrahydrothiophene, tetrahydropyrrole, piperidine, piperazine, morpholine, thiomorpholine, thiomorpholin-1,1-dioxide, and tetrahydropyrane.

In an embodiment of the present invention, in any group, the 5- or 6-membered monocyclic heteroaryl is selected from thiophene, N-alkylcyclopyrrole, furan, thiazole, isothiazole, imidazole, oxazole, pyrrole, pyrazole, triazole, 1,2,3-triazole, 1,2,4-triazole, 1,2,5-triazole, 1,3,4-triazole, tetrazole, isoxazole, oxadiazole, 1,2,3-oxadiazole, 1,2,4-oxadiazole, 1,2,5-oxadiazole, 1,3,4-oxadiazole, thiadiazole, pyridine, pyriazine, pyrimidine, and pyrazine.

In an embodiment of the present invention, in any group, the 8- to 10-membered bicyclic heteroaryl is selected from benzoxazole, benzoisoxazole, benzoimidazole, benzothiazole, benzoisothiazole, benzotriazole, benzofuran, benzothiophene, indole, indazole, isoindole, quinoline, isoquinoline, quinazoline, quinoxaline, cinnoline, pyridopyrimidine, and naphthyridine.

As used herein, the term "substituted" refers to any one or more hydrogen atoms at a particular atom being substituted by a substituent, which may include heavy hydrogen and variants of hydrogen as long as the valence state of the particular atom is normal and the substituted compound is stable. When the substituent is an oxo group (i.e., =O), two hydrogen atoms are substituted. The substitution of an oxo group will not occur on aryl. The term "optionally substituted" means that a group may be substituted and may also not be substituted. Unless stated otherwise, the types and the number of substituents can be chosen arbitrarily provided that they can be achieved chemically.

When any variable (e.g., R) occurs in the composition or structure of a compound once or more than once, it is independently defined at each occurrence. Therefore, for example, if a group is substituted by 0 to 2 R groups, the group can be optionally substituted by two R groups at most, and R can be independently selected in each case. In addition, combinations of substituents and/or variants thereof are allowable only when such combinations may result in stable compounds.

The compound of Formula (IA) or Formula (IB) in the present invention can be prepared by a known synthesis method in the art or the known synthesis method in the art in combination with a method described in the present invention. Solvents, temperatures and other reaction conditions given in the present invention are all exemplary and may vary according to well-known methods in the art. Example compounds specified in the present invention may be synthesized from appropriate starting materials by methods specified in respective Examples in accordance with their specific structures, and may also be synthesized by methods similar to those specified in the Examples. The starting materials used to synthesize the Example compounds of the present invention may be prepared by known synthesis methods or similar methods described in the literature, or obtained commercially. Example compounds may be further resolved by well-known methods in the art, such as crystallization and chromatography, to obtain their stereoisomers as required, and the resolution conditions are easily obtained by those skilled in the art through conventional means or limited experiments.

As a further illustration, the compounds of Formula (IB-1') and Formula (IB-2') of the present invention may be synthesized by methods below, where solvents, temperatures and other reaction conditions in each step can be identical or similar to those described in the following Examples, or reaction conditions known in the art may be used.

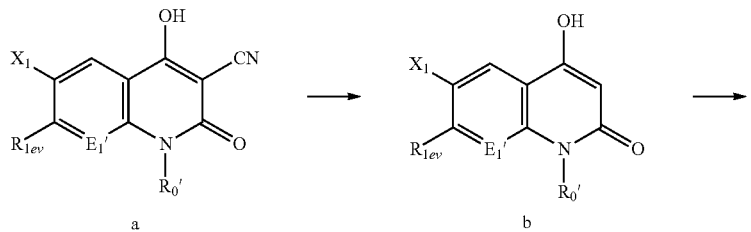

a     b 223
224
-continued
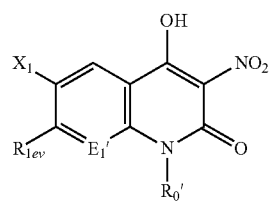

c → d
Ar'-boric acid or
Ar'-boric ester
Ar'-Potassium fluoborite
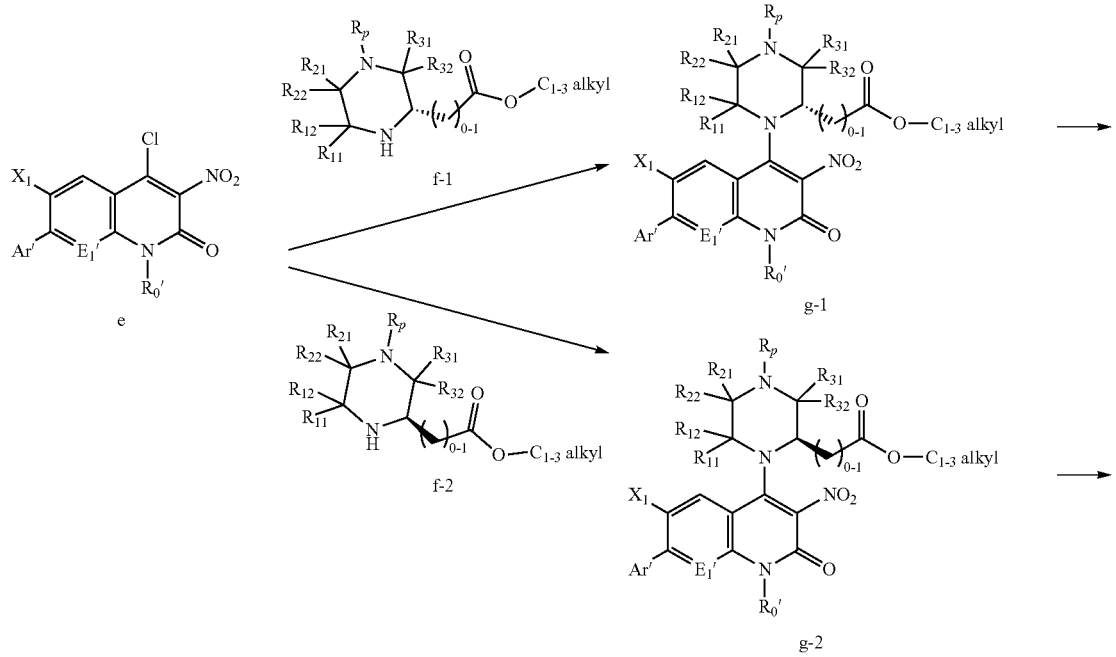
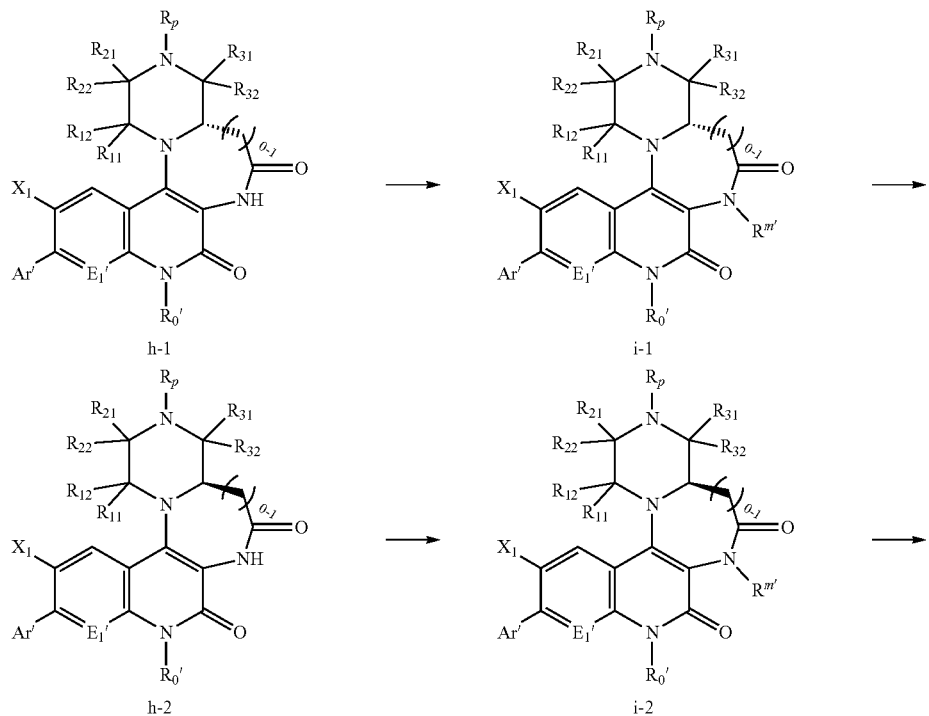

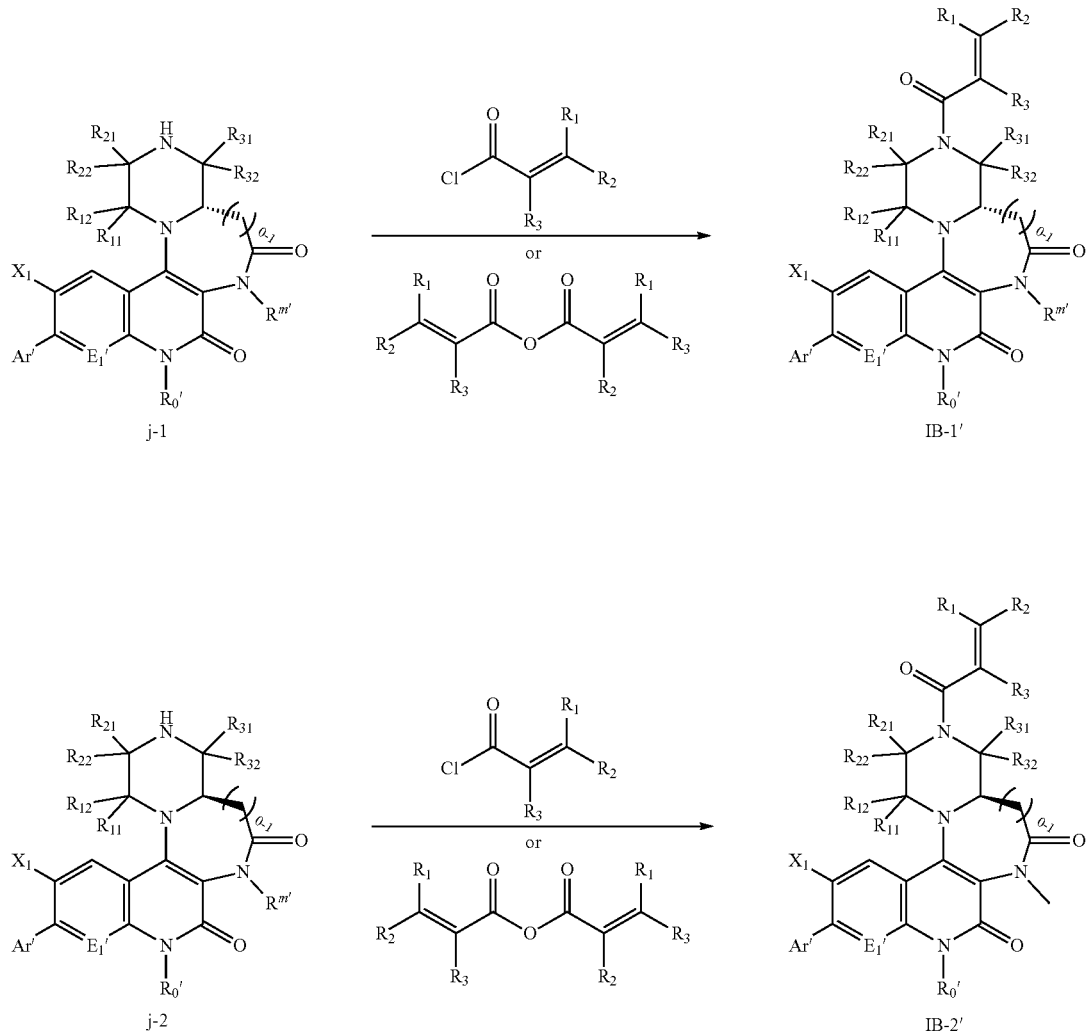
The compounds of Formula (IB-1') and Formula (IB-2') of the present invention may also be synthesized by methods below, where solvents, temperatures and other reaction conditions in each step can be identical or similar to those described in the following Examples, or reaction conditions known in the art may be used.
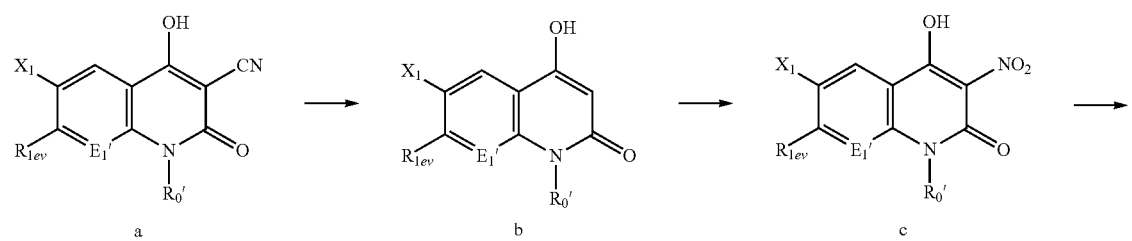

-continued
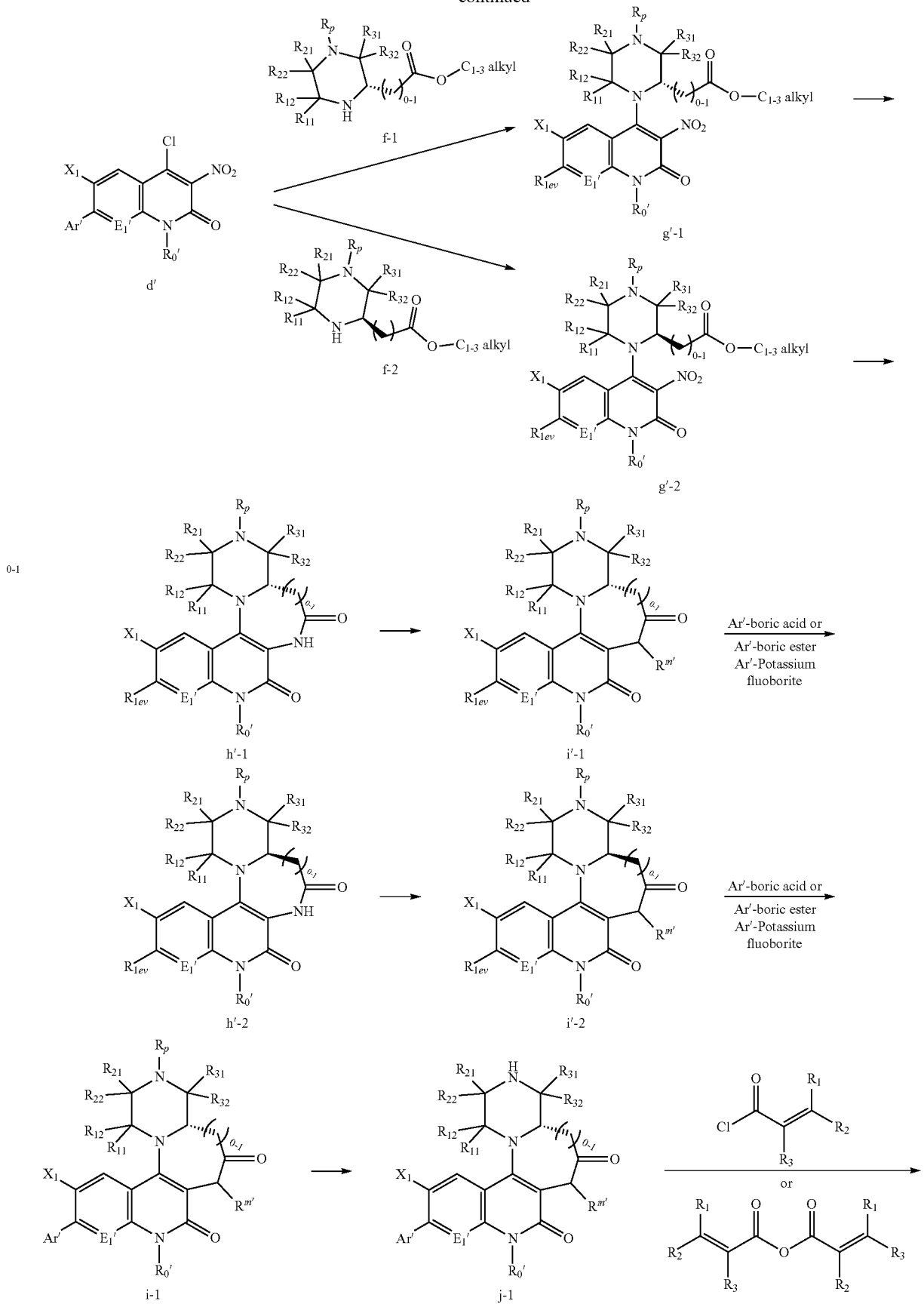

229

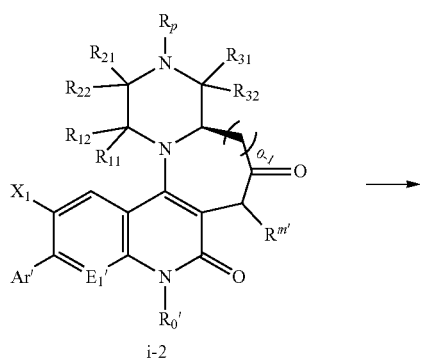

i-2

230

-continued

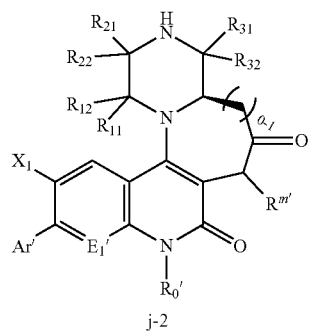

j-2

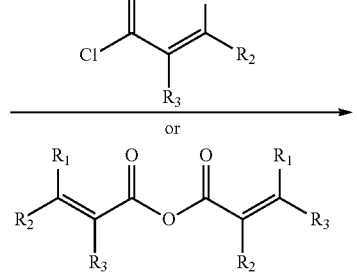

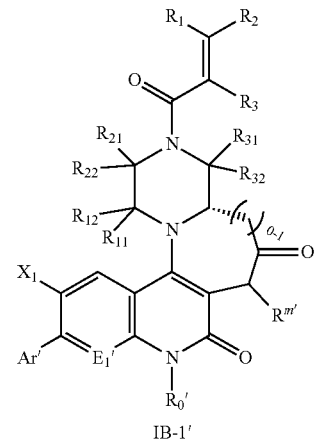

IB-1'

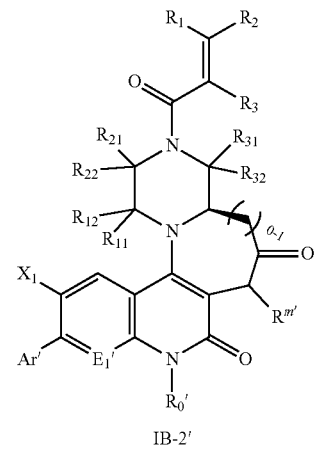

IB-2'

In the preparation routes of the compounds of Formula (IB-1') and Formula (IB-2'), in each Formula, $R_{lev}$ is a leaving group well known in the art, such as triflates, chlorine, bromine, iodine, sulfonate groups (such as mesylate, tosylate, and p-toluenesulfonate), and acyloxy groups (such as acetoxyl, and trifluoroacetoxyl). In each Formula, $R_p$ is an amino protecting group well known in the art, such as formyl, acyl (e.g., alkan-acyl, such as acetyl, trichloroacetyl, or trifluoroacetyl), alkoxycarbonyl (such as tert-butoxycarbonyl (Boc)), arylmethoxycarbonyl (such as carbobenzyloxy (Cbz) and 9-fluorenylmethyloxycarbonyl (Fmoc)), arylmethyl (such as benzyl (Bn), trityl (Tr), and 1,1-di-(4'-methoxyphenyl) methyl), and silyl (such as trimethylsilyl (TMS) and tert-butyldimethylsilyl (TBS)). $R_1$, $R_2$, $R_3$, $R_{21}$, $R_{22}$, $R_{12}$, $R_{11}$, $R_{31}$, $R_{32}$, $R^{m'}$, $R_{0'}$, $Ar'$, $E_{1'}$, and $X_1$ are as defined above (e.g., as defined as corresponding groups in Formula I or Formula IA).

The compounds of Formula (IB-1") and Formula (IB-2") of the present invention may be synthesized by methods below, where solvents, temperatures and other reaction conditions in each step can be identical or similar to those described in the following Examples, or reaction conditions known in the art may be used.

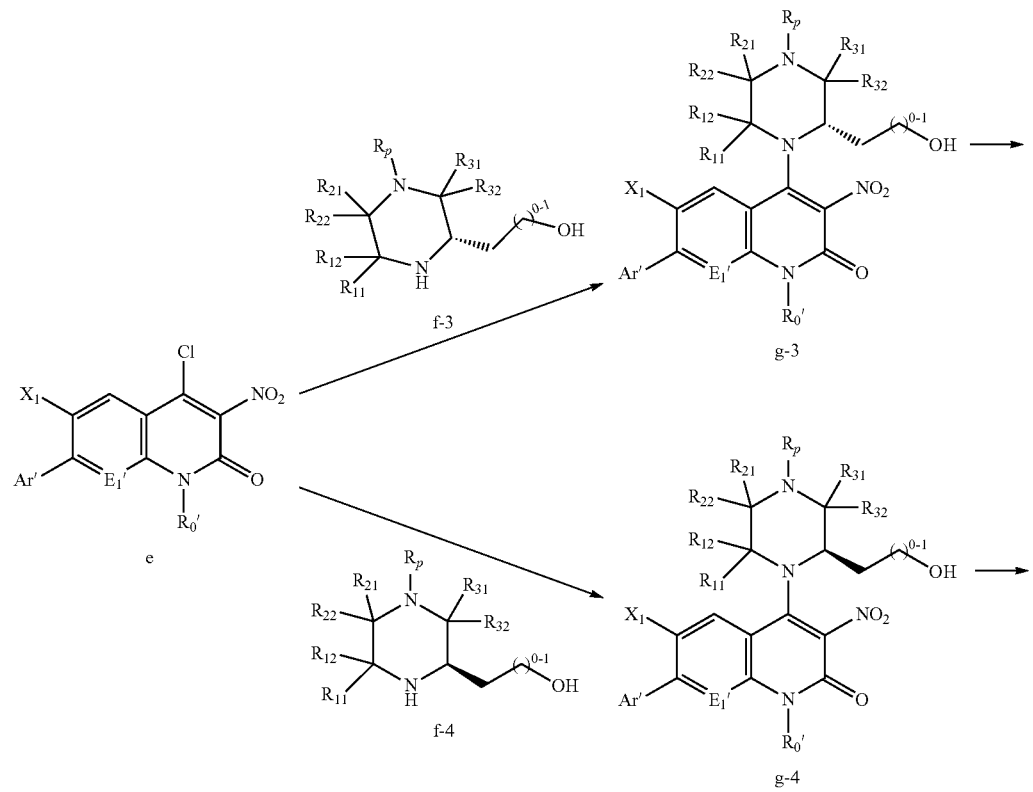
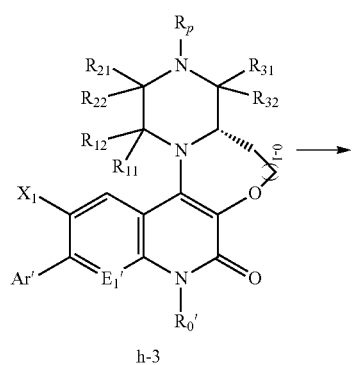
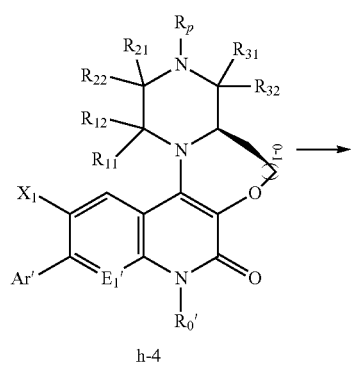

-continued

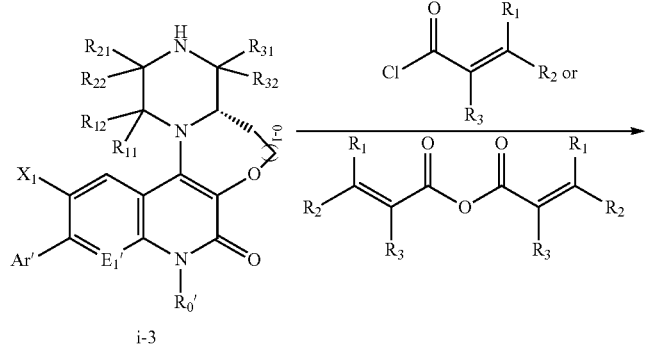

i-3

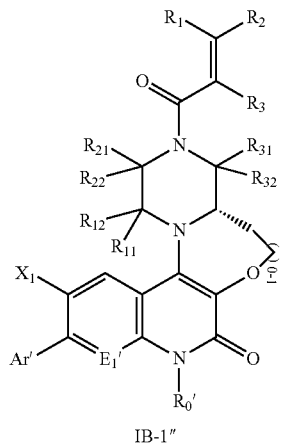

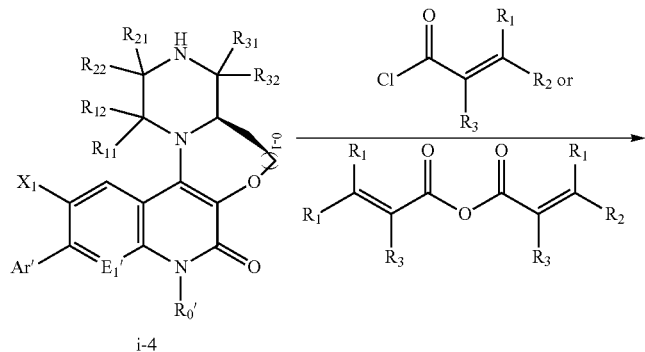

i-4

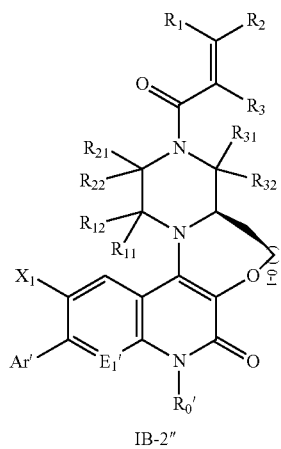

IB-1″

IB-2″

In the preparation routes of the compounds of Formula (IB-1″) and Formula (IB-2″), in each Formula, $R_p$ is an amino protecting group well known in the art, such as formyl, acyl (e.g., alkan-acyl, such as acetyl, trichloroacetyl, or trifluoroacetyl), alkoxycarbonyl (such as tert-butoxycarbonyl (Boc)), arylmethoxycarbonyl (such as carbobenzyloxy (Cbz) and 9-fluorenylmethyloxycarbonyl (Fmoc)), arylmethyl (such as benzyl (Bn), trityl (Tr), and 1,1-di-(4′-methoxyphenyl) methyl), and silyl (such as trimethylsilyl (TMS) and tert-butyldimethylsilyl (TBS)). $R_1$, $R_2$, $R_3$, $R_{21}$, $R_{22}$, $R_{12}$, $R_{11}$, $R_{31}$, $R_{32}$, $R_0'$, Ar′, $E_1'$, and $X_1$ are as defined above (e.g., as defined as corresponding groups in Formula I or Formula IA).

The compound of Formula e may also be synthesized by methods below, where solvents, temperatures and other reaction conditions in each step can be identical or similar to those described in the following Examples, or reaction conditions known in the art may be used.

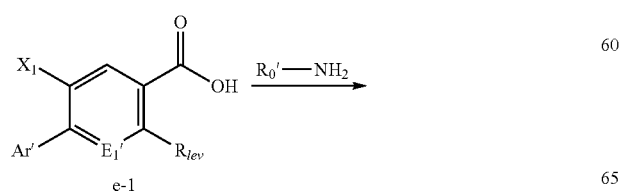

e-1

-continued

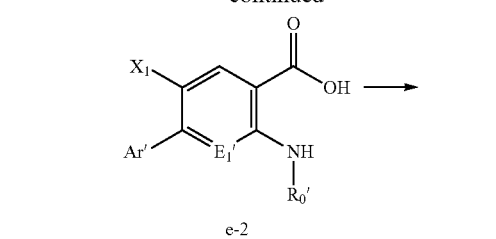

e-2

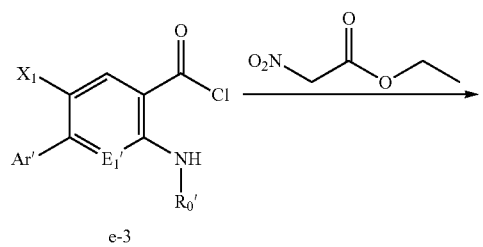

e-3

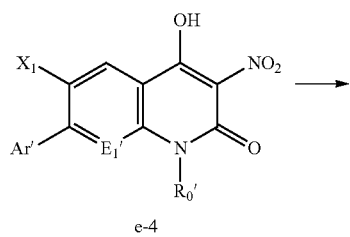

e-4

-continued

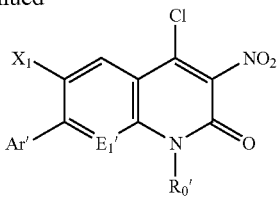

e

In the preparation route of the compound of Formula e, $R_{lev}$ is a leaving group well known in the art, such as triflates, chlorine, bromine, iodine, sulfonate groups (such as mesylate, tosylate, and p-toluenesulfonate), and acyloxy groups (such as acetoxyl, and trifluoroacetoxyl). $R_0$', Ar', $E_1$', and $X_1$ are as defined above (e.g., as defined as corresponding groups in Formula I or Formula IA).

DETAILED DESCRIPTION OF THE EMBODIMENTS

Figure 1:
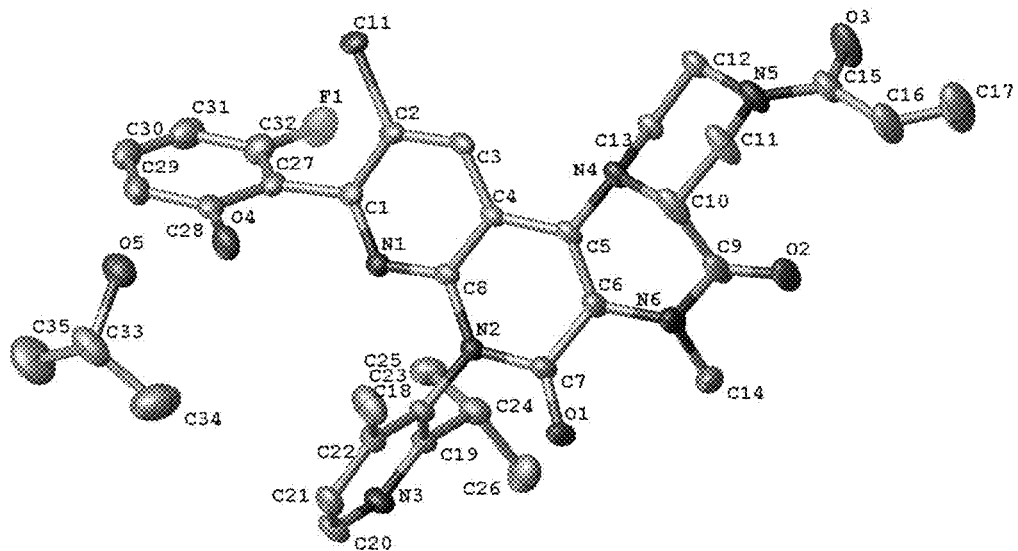
FIG. 1 is a three-dimensional molecular structure diagram of compound Z25-2 by single-crystal X-ray diffraction.

The compounds of the present invention can be prepared by a plurality of synthesis methods well known to those skilled in the art, including specific embodiments listed below, embodiments derived therefrom in combination with other chemical synthesis methods, and equivalent replacements well known to those skilled in the art. Preferred embodiments include but are not limited to the Examples of the present invention. The present invention will be described in detail below with reference to Examples, which, however, do not constitute any unfavorable limitation to the present invention. The present invention has been described in detail herein, and the specific embodiments thereof are also disclosed. It will be obvious for those skilled in the art that various changes and improvements can be made to the specific embodiments of the present invention without departing from the spirit and scope of the present invention. Where specific conditions are not indicated in Examples, conventional conditions or the conditions suggested by the manufacturer are adopted. For the used reagents or instruments that are not marked with the manufacturers, they are all conventional products that are commercially available.

List of abbreviations of reagents used in the following Examples: THF: tetrahydrofuran; DMSO: dimethyl sulfoxide; PE: petroleum ether; EtOAc: ethyl acetate; DCM: dichloromethane; MeOH: methanol; ACN: acetonitrile; IPA: isopropylamine; DMA: dimethylamine; TFA: trifluoroacetic acid; $NH_4Cl$: ammonium chloride; SPhos: 2-dicyclohexylphosphino-2',6'-dimethoxy-1,1'-biphenyl; SPhos-Pd-G2: chloro(2-dicyclohexylphosphino-2',6'-dimethoxy-1,1'-biphenyl)[2-(2'-amino-1,1'-biphenyl)]palladium (II); NaHMDS: sodium bis(trimethylsilyl)amide; and LiHMDS: lithium bis(trimethylsilyl)amide.

For the preparative high-performance liquid chromatography (HPLC) used in the following Examples, the following conditions may be adopted: column type: Waters XBridge C18, 190*250 mm, 5 m; mobile phase system: A: aqueous solution of 0.1% ammonium bicarbonate; B: preparative grade ACN; flow rate: 15 ml/min; B %=20%-100%; and column temperature: Room temperature.

If isomer compounds are tested by analytical scale HPLC, the following conditions may be adopted: column type: XBridge C18, 3.5 μm 4.6*150 mm; mobile phase: A: purified water (0.05% TFA); B: preparative grade ACN (0.05% TFA), gradient: 5%-95% B; run time: 15 min; flow rate: 1 ml/min; and column temperature=40° C.

Example 1 Preparation of Compounds Z1, Z1-1, and Z1-2

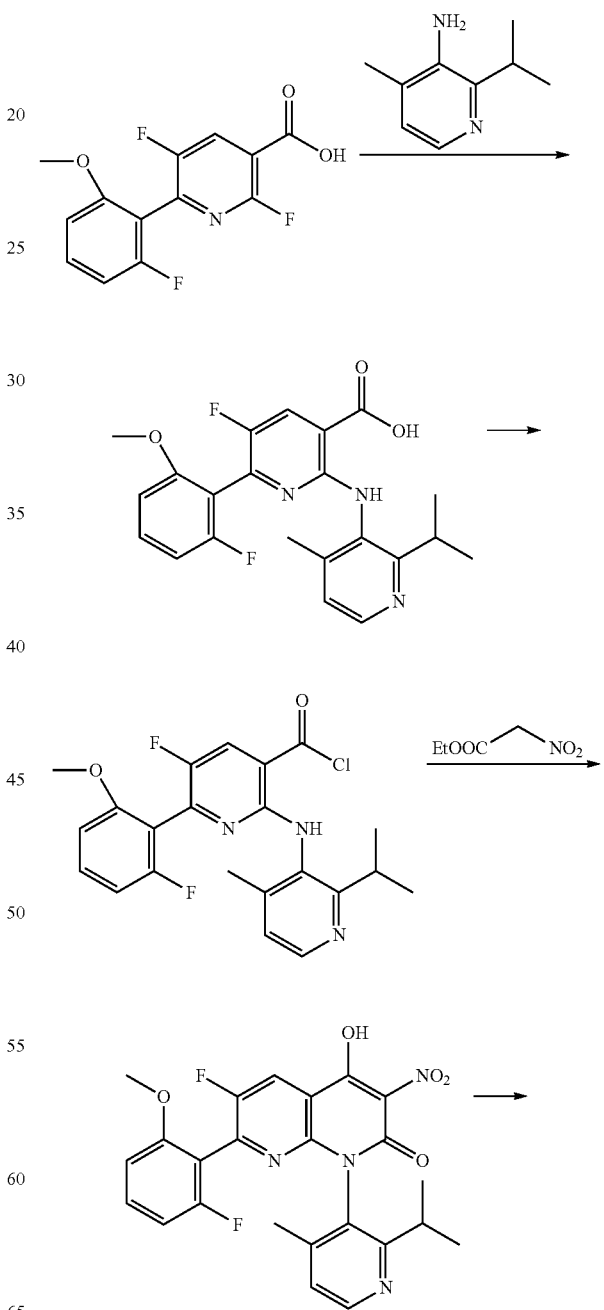

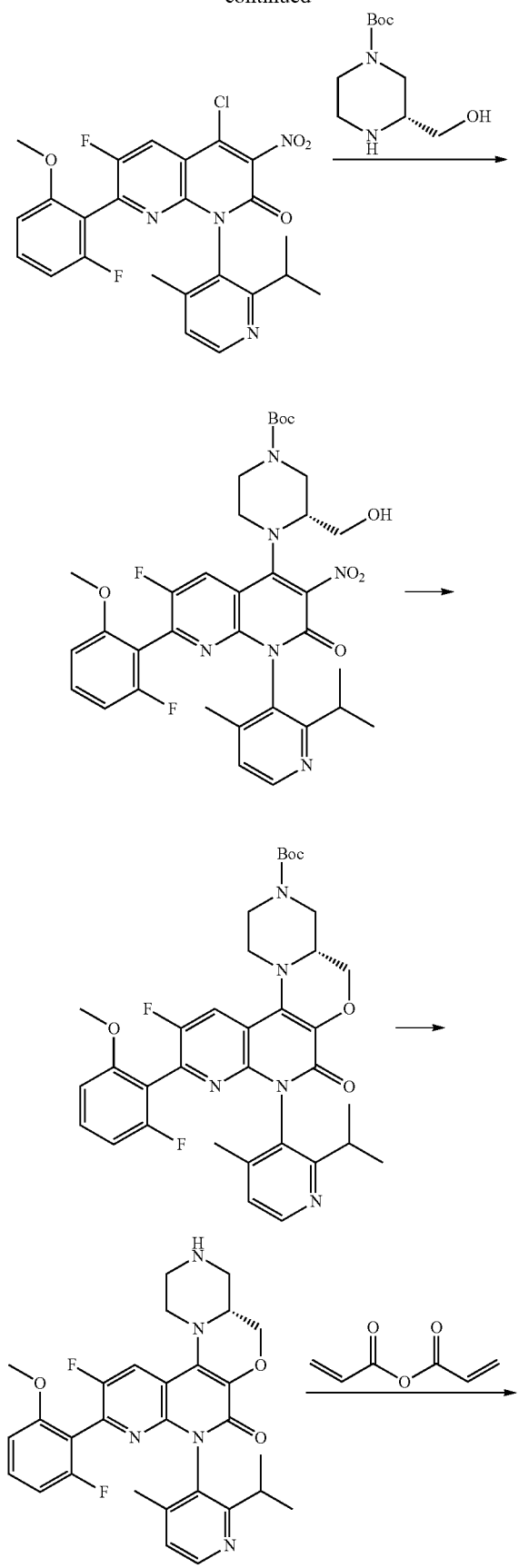
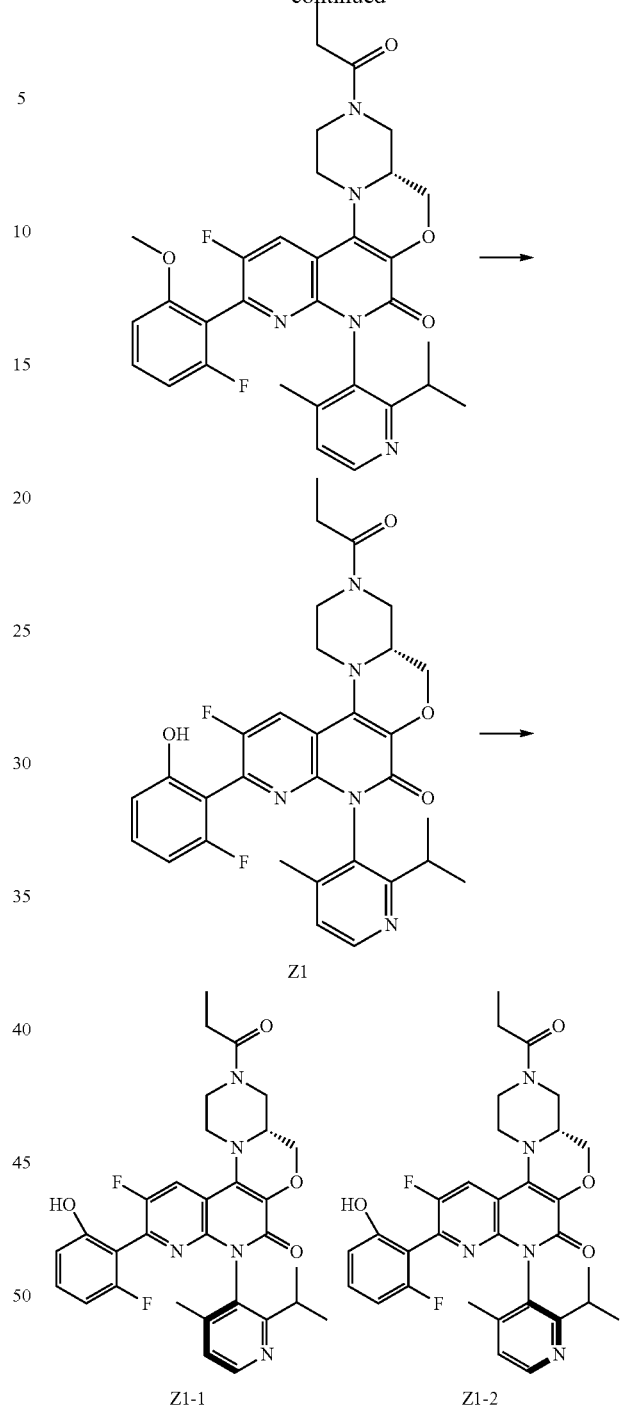

Step 1: 2-isopropyl-4-methylpyridin-3-amine (582 mg, 3.88 mmol) was dissolved in THF (20 mL), cooled to 0° C., added dropwise with NaHMDS (5.8 mL, 11.60 mmol, 2M in THF), stirred for 15 minutes to react, and then added dropwise with a solution of 2,5-difluoro-6-(2-fluoro-6-methoxyphenyl)nicotinic acid (1.0 g, 3.53 mmol) in THF (6 mL). The resulting mixture was stirred at room temperature for 3 hours to react. The resulting reaction liquid was poured into 30 mL of saturated NH$_4$Cl. The reaction liquid was extracted with 40 mL of EtOAc for 3 times. The resulting organic phase was dried and concentrated. The resulting crude product was purified by flash column chromatography on silica gel (0-5% MeOH/DCM) to obtain product 5-fluoro-6-(2-fluoro-6-methoxyphenyl)-2-((2-isopropyl-4-methylpyridin-3-yl)amino)nicotinic acid (850 mg, Y: 58.2%), which was yellow solid. ES-API: [M+H]$^+$=414.1.

Step 2: 5-fluoro-6-(2-fluoro-6-methoxyphenyl)-2-((2-isopropyl-4-methylpyridin-3-yl)amino)nicotinic acid (700 mg, 1.69 mmol) was dissolved in 1,2-dichloroethane (15 mL), added with SOCl$_2$ (2.0 g, 16.90 mmol), and stirred at 80° C. for 2 hours to react. By concentration after the reaction, product 5-fluoro-6-(2-fluoro-6-methoxyphenyl)-2-((2-isopropyl-4-methylpyridin-3-yl)amino)nicotinoyl chloride (721 mg, Y: 100%) was obtained, which was directly used in next step without being purified.

Step 3: a solution of ethyl nitroacetate (449 mg, 3.38 mmol) in THF (2 ml) was added dropwise to a THF (25 mL) suspension containing NaH (608 mg, 15.21 mmol) at 0° C., stirred at the temperature of 0° C. for half an hour to react, and then added dropwise with a solution of 5-fluoro-6-(2-fluoro-6-methoxyphenyl)-2-((2-isopropyl-4-methylpyridin-3-yl)amino)nicotinoyl chloride (721 mg, 1.69 mmol) in THF (15 mL). The ice bath was removed. The resulting reaction liquid was stirred at 70° C. overnight. The reaction liquid was poured into ice water, mixed with 3.0 M diluted hydrochloric acid such that the pH was adjusted to 3, and extracted with EtOAc for 3 times. The resulting organic phase was dried and concentrated to obtain product 6-fluoro-7-(2-fluoro-6-methoxyphenyl)-4-hydroxy-1-(2-isopropyl-4-methylpyridin-3-yl)-3-nitro-1,8-naphthyridin-2(1H)-one (1.05 g, crude), which was directed used in next step. ES-API: [M+H]$^+$=483.1.

Step 4: 6-fluoro-7-(2-fluoro-6-methoxyphenyl)-4-hydroxy-1-(2-isopropyl-4-methylpyridin-3-yl)-3-nitro-1,8-naphthyridin-2(1H)-one (1.05 g, 1.69 mmol) was dissolved in ACN (25 mL), then orderly added with POCl$_3$ (1.30 g, 8.45 mmol) and N,N-diisopropylethylamine (1.74 g, 13.52 mmol), and stirred at 80° C. for 1 hour to react. The resulting reaction liquid was concentrated, added with EtOAc, and washed orderly with ice water, water, and saturated salt water. After the resulting organic phase was dried and concentrated, the resulting crude product was purified by flash column chromatography on silica gel (EtOAc/PE: 0-50%) to obtain product 4-chloro-6-fluoro-7-(2-fluoro-6-methoxyphenyl)-1-(2-isopropyl-4-methylpyridin-3-yl)-3-nitro-1,8-naphthyridin-2(1H)-one (185 mg, Y: 21.9%), which was yellow solid. ES-API: [M+H]$^+$=500.1.

Step 5: 4-chloro-6-fluoro-7-(2-fluoro-6-methoxyphenyl)-1-(2-isopropyl-4-methylpyridin-3-yl)-3-nitro-1,8-naphthyridin-2(1H)-one (175 mg, 0.35 mmol) was dissolved in DMF (6 mL), added with tert-butyl (R)-3-(hydroxymethyl)piperazin-1-carboxylate (454 mg, 2.10 mmol), and stirred at 80° C. for 18 hours to react. The resulting reaction liquid was poured into 30 mL of water. The reaction liquid was extracted with 20 mL of EtOAc for 3 times.

The resulting organic phase was washed with saturated salt solution for 3 times, dried and concentrated, and the resulting crude product was purified by flash column chromatography on silica gel (EtOAc/PE: 0-70%) to obtain product tert-butyl (3R)-4-(6-fluoro-7-(2-fluoro-6-methoxyphenyl)-1-(2-isopropyl-4-methylpyridin-3-yl)-3-nitro-2-oxo-1,2-dihydro-1,8-naphthyridin-4-yl)-3-(hydroxymethyl)piperazin-1-carboxylate (85 mg, Y: 35.7%), which was yellow solid. ES-API: [M+H]$^+$=681.3.

Step 6: the tert-butyl (3R)-4-(6-fluoro-7-(2-fluoro-6-methoxyphenyl)-1-(2-isopropyl-4-methylpyridin-3-yl)-3-nitro-2-oxo-1,2-dihydro-1,8-naphthyridin-4-yl)-3-(hydroxymethyl)piperazin-1-carboxylate (73 mg, 0.11 mmol) was dissolved in DMA (4 mL), added with NaH (22 mg, 0.55 mmol), and stirred at 145° C. for 10 hours to react. Cooled reaction liquid was poured into 15 mL of water. The reaction liquid was extracted with 30 mL of EtOAc for 3 times.

The resulting organic phase was washed with saturated salt solution for 3 times, dried and concentrated, and the resulting crude product was subjected to thin-layer chromatography on a think plate (DCM/MeOH=20:1) to obtain product tert-butyl (4aR)-11-fluoro-10-(2-fluoro-6-methoxyphenyl)-8-(2-isopropyl-4-methylpyridin-3-yl)-7-oxo-1,2,4a,5,7,8-hexahydropyrazino[1',2':4,5][1,4]oxo-[2,3-c][1,8]naphthyridin-3(4H)-formate (35 mg, Y: 51.5%), which was yellow solid. ES-API: [M+H]$^+$=634.2.

Step 7: the tert-butyl (4aR)-11-fluoro-10-(2-fluoro-6-methoxyphenyl)-8-(2-isopropyl-4-methylpyridin-3-yl)-7-oxo-1,2,4a,5,7,8-hexahydropyrazino[1',2':4,5][1,4]oxo[-2,3-c][1,8]naphthyridin-3(4H)-formate (35 mg, 0.055 mmol) was dissolved in DCM (2.5 mL), and added with TFA (0.5 mL). The resulting mixture was stirred at room temperature for 0.5 hour, and the resulting reaction liquid was concentrated to obtain product (4aR)-11-fluoro-10-(2-fluoro-6-methoxyphenyl)-8-(2-isopropyl-4-methylpyridin-3-yl)-1,2,3,4,4a,5-hexahydropyrazino[1',2':4,5][1,4]oxazino[2,3-c][1,8]naphthyridin-7(8H)-one (40 mg, crude), which was directly used in next step. ES-API: [M+H]$^+$=534.3.

Step 8: the (4aR)-11-fluoro-10-(2-fluoro-6-methoxyphenyl)-8-(2-isopropyl-4-methylpyridin-3-yl)-1,2,3,4,4a,5-hexahydropyrazino[1',2':4,5][1,4]oxazino[2,3-c][1,8]naphthyridin-7(8H)-one (40 mg, 0.055 mmol) was dissolved in DCM (4 mL), and added with triethylamine (28 mg, 0.28 mmol). The resulting reaction liquid was cooled to 0° C., and added dropwise with a solution (0.5 mL) of acrylic anhydride (6 mg, 0.05 mmol) in DCM. The resulting mixture was stirred at 0° C. for 15 minutes to react. The resulting reaction liquid was added with 10 mL of saturated solution of NaHCO$_3$ and extracted with 10 mL of DCM for 3 times. The resulting organic phase was dried and concentrated, and the resulting crude product was subjected to thin-layer chromatography on a plate (DCM/MeOH=10:1) to obtain product (4aR)-3-acryloyl-11-fluoro-10-(2-fluoro-6-methoxyphenyl)-8-(2-isopropyl-4-methylpyridin-3-yl)-1,2,3,4,4a,5-hexahydropyrazino[1',2':4,5][1,4]oxazino[2,3-c][1,8]naphthyridin-7(8H)-one (17 mg, Y: 52.4%), which was faint yellow solid. ES-API: [M+H]$^+$=588.2.

Step 9: the (4aR)-3-acryloyl-11-fluoro-10-(2-fluoro-6-methoxyphenyl)-8-(2-isopropyl-4-methylpyridin-3-yl)-1,2,3,4,4a,5-hexahydropyrazino[1',2':4,5][1,4]oxazino[2,3-c][1,8]naphthyridin-7(8H)-one (15 mg, 0.025 mmol) was dissolved in DCM (1.5 mL). The resulting solution was cooled to 0° C., and then added dropwise with a solution (1 mL) of 17% boron tribromide in DCM. The resulting mixture was stirred at room temperature for 3 hours to react.

The resulting reaction liquid was poured into 20 mL of saturated solution of NaHCO$_3$ and extracted with 20 mL of DCM for 3 times. The resulting organic phase was dried and concentrated, and the resulting crude product was purified by preparative scale HPLC to obtain product (4aR)-3-acryloyl-11-fluoro-10-(2-fluoro-6-hydroxyphenyl)-8-(2-isopropyl-4-methylpyridin-3-yl)-1,2,3,4,4a,5-hexahydropyrazino[1',2':4,5][1,4]oxazino[2,3-c][1,8]naphthyridin-7(8H)-one (Z1, 10 mg, Y: 68.3%), which was white solid. $^1$H NMR (500 MHz, DMSO-d$_6$) δ 9.96 (s, 1H), 8.35 (d, J=4.8 Hz, 1H), 7.19-7.14 (m, 2H), 6.87-6.75 (m, 1H), 6.64 (d, J=8.5 Hz, 1H), 6.59 (t, J=8.5 Hz, 1H), 6.12 (d, J=15.9 Hz, 1H), 5.71-5.67 (m, 1H), 4.39-3.95 (m, 4H), 3.79-3.30 (m, 4H), 3.06-2.98 (m, 1H), 2.56-2.29 (m, 1H), 1.80-1.73 (m, 3H), 0.99-0.95 (m, 3H), 0.85-0.80 (m, 3H). ES-API: [M+H]$^+$=574.2.

Step 10: the compound Z1 was resolved by preparative scale chiral HPLC (column type: Chiralpak IC: 10 μm, 20*250 mm; mobile phase: ACN:isopropanol:aminomethanol=70:30:0.2; flow rate: 15 ml/min; and column temperature: room temperature) to obtain the following atropisomer compounds. One of the atropisomer compounds had a structure arbitrarily specified as Z1-1 (75 mg, peak 1, retention time: 3.94 min, Y: 15.4%), which was faint yellow solid. $^1$H NMR (400 MHz, DMSO-d$_6$) δ 10.04 (s, 1H), 8.42 (d, J=4.9 Hz, 1H), 8.22 (d, J=8.3 Hz, 1H), 7.28-7.20 (m, 2H), 6.96-6.81 (m, 1H), 6.75-6.58 (m, 2H), 6.18 (d, J=17.1 Hz, 1H), 5.82-5.69 (m, 1H), 4.49-4.00 (m, 4H), 3.90-3.43 (m, 4H), 3.08 (t, J=11.0 Hz, 1H), 2.64-2.55 (m, 1H), 1.80 (s, 3H), 1.05 (d, J=6.7 Hz, 3H), 0.91 (d, J=6.7 Hz, 3H). ES-API: [M+H]$^+$=574.2. The other atropisomer compound had a structure arbitrarily specified as Z1-2 (115 mg, peak 2, retention time: 5.04 min, Y: 23.6%), which was faint yellow solid. $^1$H NMR (400 MHz, DMSO-d$_6$) δ 10.05 (s, 1H), 8.42 (d, J=4.8 Hz, 1H), 8.22 (d, J=6.9 Hz, 1H), 7.28-7.20 (m, 2H), 6.96-6.81 (m, 1H), 6.74-6.59 (m, 2H), 6.19 (d, J=16.7 Hz, 1H), 5.83-5.68 (m, 1H), 4.49-4.00 (m, 4H), 3.94-3.44 (m, 4H), 3.08 (t, J=11.0 Hz, 1H), 2.49-2.41 (m, 1H), 1.87 (s, 3H), 1.03 (dd, J=6.3, 3.7 Hz, 3H), 0.88 (d, J=6.6 Hz, 3H). ES-API: [M+H]$^+$=574.2. The isomer compounds were detected by analytical scale chiral HPLC (column type: Chiralpak IC: 5 μm, 4.6*250 mm; mobile phase: ACN: isopropanol:aminomethanol=70:30:0.2; flow rate: 1 ml/min; and column temperature=30° C.).

Example 2 Preparation of Z2

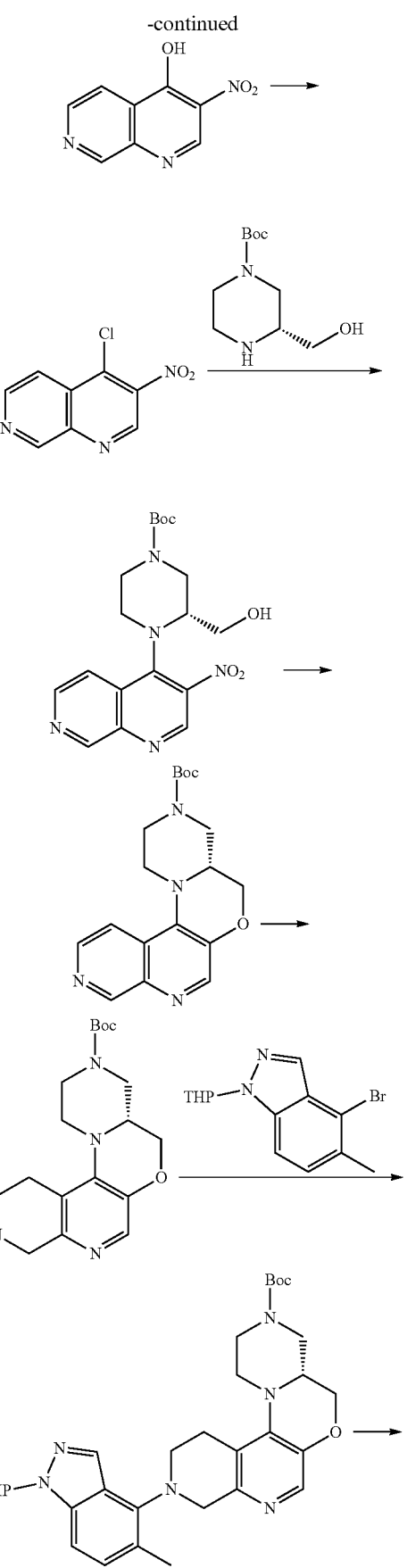

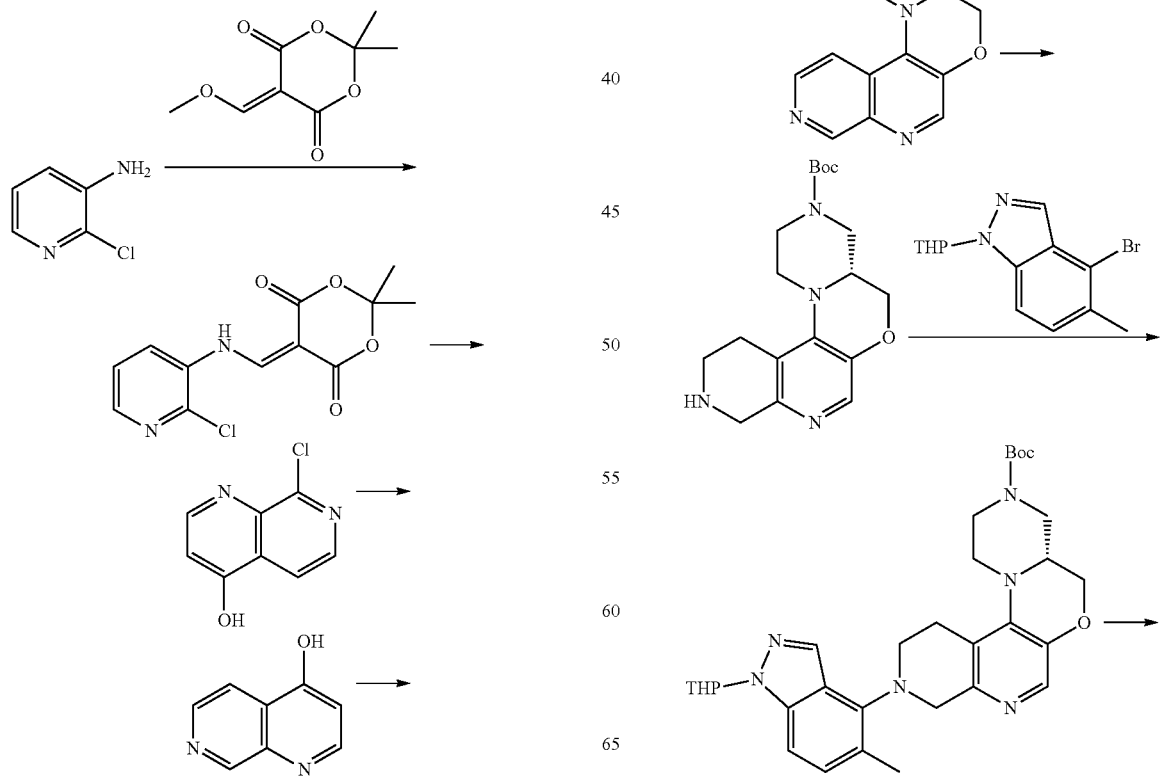

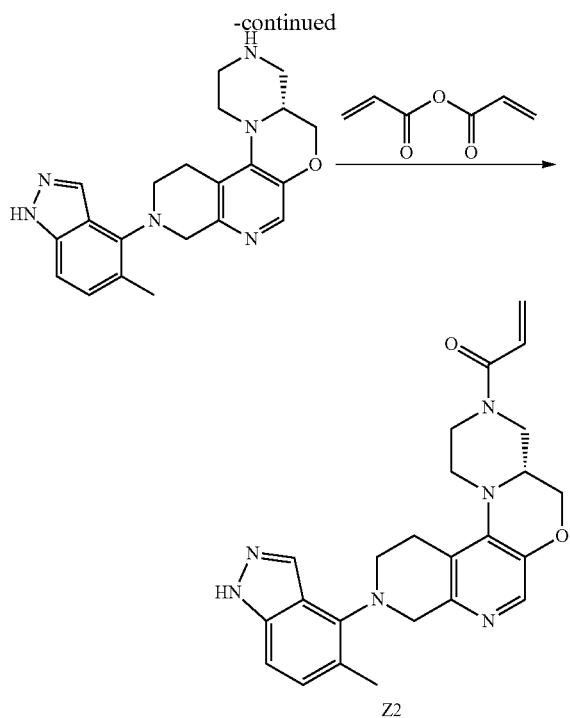

Z2

Step 1: at room temperature, 5-(methoxymethylene)-2,2-dimethyl-1,3-dioxan-4,6-dione (2.9 g, 15.62 mmol) and isopropanol (40 mL) were added to a 100 mL round-bottom flask, and 2-chloropyridin-3-amine (2.0 g, 15.62 mmol) was added thereto in batches. The resulting mixture was refluxed and stirred for 15 minutes to react. The resulting reaction liquid was cooled to room temperature. The precipitated solid was filtered. The filter cake was washed with a small amount of isopropanol and dried in vacuum to obtain product 5-((2-chloropyridin-3-yl)amino)methylene)-2,2-dimethyl-1,3-dioxan-4,6-dione (3.90 g, Y: 58.2%), which was white solid. ES-API: [M+H]$^+$=283.1.

Step 2: 200 mL of diphenyl ether was added to a 500 mL round-bottom flask, heated to 220° C., and the 5-((2-chloropyridin-3-yl)amino)methylene)-2,2-dimethyl-1,3-dioxan-4,6-dione (3.9 g, 13.83 mmol) was added thereto in batches, and stirred at 220° C. for 20 minutes to react. The resulting reaction liquid was cooled to room temperature and poured into PE. The precipitated solid was filtered. The filter cake was washed with PE and dried in vacuum to obtain product 8-chloro-1,7-naphthyridin-4-ol (1.5 g, Y: 60%), which was light brown solid. ES-API: [M+H]$^+$=181.0.

Step 3: the 8-chloro-1,7-naphthyridin-4-ol (500 mg, 2.78 mmol), sodium acetate (300 mg, 2.78 mmol), anhydrous ethanol (25 mL), and 5% Pd/C (250 mg) were added to a 50 mL round-bottom flask, and stirred at room temperature for 3 days to react with hydrogen supply from a hydrogen balloon. The resulting reaction liquid was filtered by using diatomite, and the filtrate was concentrated. The resulting crude product was purified by flash column chromatography on silica gel (DCM/MeOH: 0-10%) to obtain product 1,7-naphthyridin-4-ol (200 mg, Y: 49.3%), which was yellow solid. ES-API: [M+H]$^+$=147.1.

Step 4: the 1,7-naphthyridin-4-ol (550 mg, 3.77 mmol) was dissolved in concentrated sulfuric acid (4.5 mL), cooled to 0° C., slowly added dropwise with concentrated nitric acid (1.0 mL, 15.08 mmol), and stirred at 100° C. for 1 hour to react. Cooled reaction liquid was poured into ice water, and mixed with concentrated ammonia water such that the pH was adjusted to 6-7. The precipitated solid was filtered and dried in vacuum to obtain product 3-nitro-1,7-naphthyridin-4-ol (530 mg, Y: 73.7%), which was yellow solid. ES-API: [M+H]$^+$=192.1.

Step 5: the 3-nitro-1,7-naphthyridin-4-ol (480 mg, 2.51 mmol) and phosphorus oxychloride (4.68 mL, 50.20 mmol) were added to a 20 mL round-bottom flask, cooled to −15° C., slowly added dropwise with triethylamine (1.8 mL, 12.55 mmol), and stirred at room temperature for 1 hour to react. The resulting reaction liquid was poured into ice water, mixed with a cold saturated sodium bicarbonate solution such that the pH was adjusted to 8, and extracted with DCM for 3 times. The resulting organic phase was dried and concentrated to obtain product 4-chloro-3-nitro-1,7-naphthyridine (450 mg, Y: 85.7%), which was brown solid. ES-API: [M+H]$^+$=210.1.

Step 6: the 4-chloro-3-nitro-1,7-naphthyridine (450 mg, 2.15 mmol) was dissolved in 1, 4-dioxane (15 mL), orderly added with tert-butyl (R)-3-(hydroxymethyl)piperazin-1-carboxylate (1.02 g, 4.73 mmol) and N,N-diisopropylethylamine (832 mg, 6.45 mmol), and stirred at 80° C. for 3 hours to react. The resulting reaction liquid was concentrated, and the resulting crude product was purified by flash column chromatography on silica gel (EtOAc/PE: 50-100%) to obtain product tert-butyl (R)-3-(hydroxymethyl)-4-(3-nitro-1,7-naphthyridin-4-yl)piperazin-1-carboxylate (330 mg, Y: 39.4%), which was yellow solid. ES-API: [M+H]$^+$=390.2.

Step 7: the tert-butyl (R)-3-(hydroxymethyl)-4-(3-nitro-1,7-naphthyridin-4-yl)piperazin-1-carboxylate (310 mg, 0.80 mmol), DMF (18 mL), and NaH (96 mg, 2.40 mmol) were orderly added to a 50 mL sealing tube, and stirred at 95° C. for 3 days to react. Cooled reaction liquid was poured into water and extracted with EtOAc twice. The resulting organic phase was washed with saturated salt solution for 3 times, dried and concentrated, and the resulting crude product was subjected to thin-layer chromatography on a plate (DCM/MeOH=15:1) to obtain product tert-butyl (R)-8a,9,11,12-tetrahydropyrazino[1',2':4,5][1,4]oxazino[2,3-c][1,7]naphthyridin-10(8H)-carboxylate (175 mg, Y: 64%), which was yellow solid. ES-API: [M+H]$^+$=343.3.

Step 8: the tert-butyl (R)-8a,9,11,12-tetrahydropyrazino[1',2':4,5][1,4]oxazino[2,3-c][1,7]naphthyridin-10(8H)-carboxylate (100 mg, 0.29 mmol) was dissolved in acetic acid (4 mL), added with sodium cyanoborohydride (73 mg, 1.16 mmol), and stirred at room temperature overnight to react. The resulting reaction liquid was poured into ice water, mixed with a saturated sodium bicarbonate solution such that the pH was adjusted to 8, and extracted with DCM twice. The resulting organic phase was washed with saturated salt solution, dried and concentrated, and the resulting crude product was subjected to thin-layer chromatography on a plate (DCM/MeOH/ammonia water=100:8:1) to obtain product tert-butyl (R)-1,2,3,4,8a,9,11,12-octahydropyrazino[1',2':4,5][1,4]oxazino[2,3-c][1,7]naphthyridin-10(8H)-carboxylate (50 mg, Y: 49.4%), which was faint yellow solid. ES-API: [M+H]$^+$=390.2.

Step 9: the tert-butyl (R)-1,2,3,4,8a,9,11,12-octahydropyrazino[1',2':4,5][1,4]oxazino[2,3-c][1,7]naphthyridin-10(8H)-carboxylate (50 mg, 0.14 mmol), 4-bromo-5-methyl-1-(tetrahydro-2H-pyran-2-yl)-1H-indazole (83 mg, 0.28 mmol), cesium carbonate (136 mg, 0.42 mmol), Pd$_2$(dba)$_3$ (51 mg, 0.056 mmol), Ruphos (26 mg, 0.056 mmol) and toluene (6 mL) were added to a 5 mL microwave tube, subjected to nitrogen replacement, placed into a microwave reactor at 120° C., and stirred for 1 hour to react. The resulting reaction liquid was cooled to room temperature, and filtered. The filtrate was dried and concentrated. The resulting crude product was subjected to thin-layer chromatography on a plate (DCM/MeOH/ammonia water-100:5:1) to obtain tert-butyl (8aR)-3-(5-methyl-1-(tetrahydro-2H-pyran-2-yl)-1H-indazol-4-yl)-1,2,3,4,8a,9,11,12-octahydropyrazino[1',2':4,5][1,4]oxazino[2,3-c][1,7]naphthyridin-10(8H)-carboxylate (60 mg, Y: 74.1%). ES-API: [M+H]$^+$=561.3.

Step 10: the tert-butyl (8aR)-3-(5-methyl-1-(tetrahydro-2H-pyran-2-yl)-1H-indazol-4-yl)-1,2,3,4,8a,9,11,12-octahydropyrazino[1',2':4,5][1,4]oxazino[2,3-c][1,7]naphthyridin-10(8H)-carboxylate (60 mg, 0.11 mmol) was dissolved in DCM (3 mL), and added with TFA (0.8 mL). The resulting mixture was stirred at room temperature for 1 hour. The resulting reaction liquid was concentrated to obtain product (R)-3-(5-methyl-1H-indazol-4-yl)-1,2,3,4,8,8a,9,10,11,12-decahydropyrazino[1',2':4,5][1,4]oxazino[2,3-c][1,7]naphthyridine (60 mg, crude percent yield), which was directly used in next step without being purified. ES-API: [M+H]$^+$=377.1.

Step 11: the (R)-3-(5-methyl-1H-indazol-4-yl)-1,2,3,4,8,8a,9,10,11,12-decahydropyrazino[1',2':4,5][1,4]oxazino[2,3-c][1,7]naphthyridine (60 mg, 0.11 mmol) and N,N-diisopropylethylamine (71 mg, 0.55 mmol) were dissolved in DCM (5 mL), and cooled to 0° C. A solution (0.5 mL) of acrylic anhydride (13 mg, 0.10 mmol) in DCM was added dropwise to the resulting reaction liquid. The resulting mixture was stirred at 0° C. for 10 minutes to react. The resulting reaction liquid was added with 10 mL of saturated solution of NaHCO$_3$ and extracted with 10 mL of DCM for 3 times. The resulting organic phase was dried and concentrated, and the resulting crude product was purified by preparative scale HPLC to obtain product (R)-1-(3-(5-methyl-1H-indazol-4-yl)-1,2,3,4,8a,9,11,12-octahydropyrazino[1',2':4,5][1,4]oxazino[2,3-c][1,7]naphthyridin-10(8H)-yl)propyl-2-en-1-one (Z2, 12 mg, Y: 26.0%), which was white solid. $^1$H NMR (500 MHz, DMSO-d$_6$) δ 12.91 (s, 1H), 8.04 (s, 1H), 7.86 (s, 1H), 7.21-7.07 (m, 2H), 6.89-6.64 (m, 1H), 6.09 (d, J=16.6 Hz, 1H), 5.67 (m, 1H), 4.21-4.11 (m, 3H), 3.96 (t, J=10.0 Hz, 1H), 3.86-3.53 (m, 4H), 3.45-3.30 (m, 2H), 3.15-3.08 (m, 1H), 2.86-2.75 (m, 2H), 2.28 (s, 3H). ES-API: [M+H]$^+$=431.2.

Example 3 Preparation of Compounds Z3a and Z3

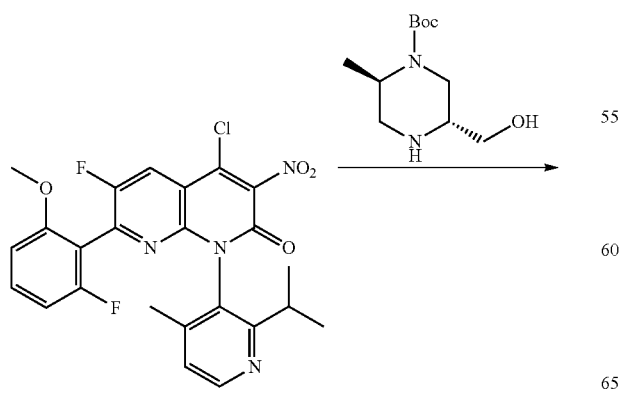

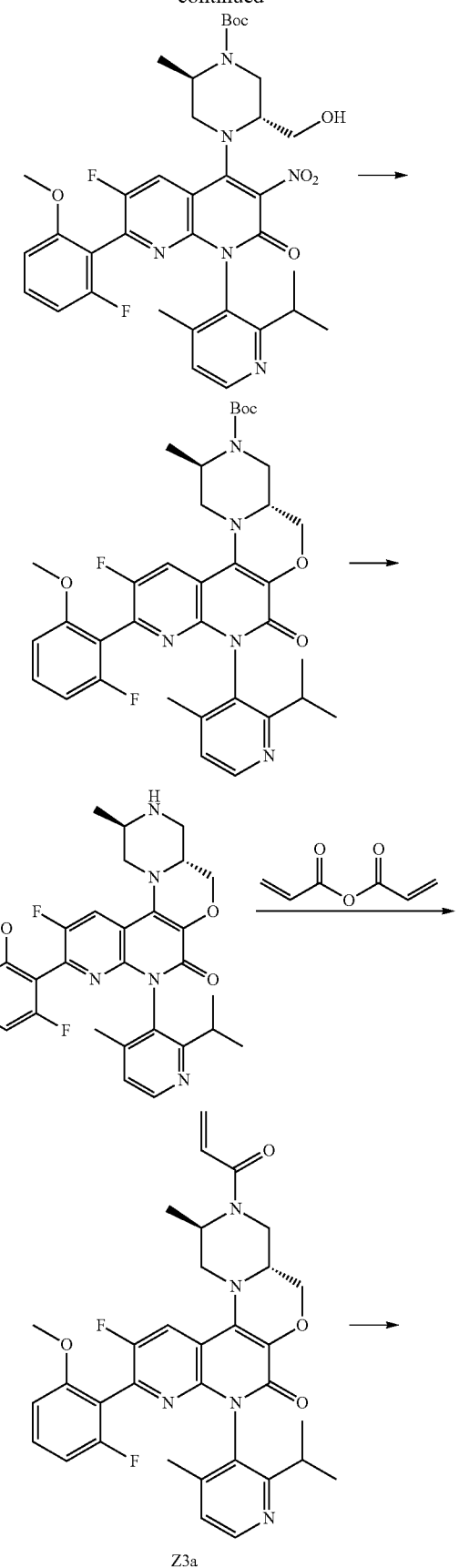

-continued

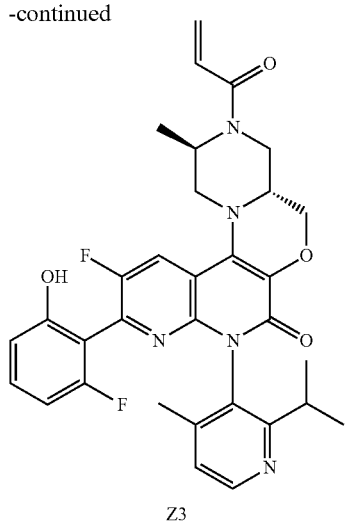

Z3

Step 1: 4-chloro-6-fluoro-7-(2-fluoro-6-methoxyphenyl)-1-(2-isopropyl-4-methylpyridin-3-yl)-3-nitro-1,8-naphthyridin-2(1H)-one (700 mg, 1.40 mmol) was dissolved in DMF (10 mL), added with tert-butyl (2R,5R)-5-(hydroxymethyl)-2-methylpiperazin-1-carboxylate (1.61 g, 7.0 mmol), and stirred at 80° C. for 1 hour to react. The resulting reaction liquid was poured into 30 mL of water. The reaction liquid was extracted with 20 mL of EtOAc for 3 times. The resulting organic phase was washed with saturated salt solution for 3 times, dried and concentrated, and the resulting crude product was purified by flash column chromatography on silica gel (EtOAc/PE: 0-70%) to obtain product tert-butyl (2R,5R)-4-(6-fluoro-7-(2-fluoro-6-methoxyphenyl)-1-(2-isopropyl-4-methylpyridin-3-yl)-3-nitro-2-oxo-1,2-dihydro-1,8-naphthyridin-4-yl)-5-(hydroxymethyl)-2-methylpiperazin-1-carboxylate (325 mg, Y: 33.4%), which was yellow solid. ES-API: [M+H]$^+$=695.2.

Step 2: the tert-butyl (2R,5R)-4-(6-fluoro-7-(2-fluoro-6-methoxyphenyl)-1-(2-isopropyl-4-methylpyridin-3-yl)-3-nitro-2-oxo-1,2-dihydro-1,8-naphthyridin-4-yl)-5-(hydroxymethyl)-2-methylpyridin-1-carboxylate (300 mg, 0.44 mmol) was dissolved in DMA (20 mL), added with NaH (52 mg, 1.32 mmol), and stirred at 125° C. for 20 hours to react. Cooled reaction liquid was poured into 15 mL of water. The reaction liquid was extracted with 30 mL of EtOAc for 3 times. The resulting organic phase was washed with saturated salt solution for 8 times, dried and concentrated, and the resulting crude product was purified by flash column chromatography on silica gel (EtOAc/PE: 0-100%) to obtain product tert-butyl (2R,4aR)-11-fluoro-10-(2-fluoro-6-methoxyphenyl)-8-(2-isopropyl-4-methylpyridin-3-yl)-2-methyl-7-oxo-1,2,4a,5,7,8-hexahydropyrazino[1',2':4,5][1,4]oxozino[2,3-c][1,8]naphthyridin-3(4H)-carboxylate (60 mg, Y: 21.4%), which was yellow solid. ES-API: [M+H]$^+$=648.3.

Step 3: the tert-butyl (2R,4aR)-11-fluoro-10-(2-fluoro-6-methoxyphenyl)-8-(2-isopropyl-4-methylpyridin-3-yl)-2-methyl-7-oxo-1,2,4a,5,7,8-hexahydropyrazino[1',2':4,5][1,4]oxozino[2,3-c][1,8]naphthyridin-3(4H)-carboxylate (60 mg, 0.093 mmol) was dissolved in DCM (3 mL), and added with TFA (0.7 mL). The resulting mixture was stirred at room temperature for 1 hour, and the resulting reaction liquid was concentrated to obtain product (2R,4aR)-11-fluoro-10-(2-fluoro-6-methoxyphenyl)-8-(2-isopropyl-4-methylpyridin-3-yl)-2-methyl-1,2,3,4,4a,5-hexahydropyrazino[1',2':4,5][1,4]oxazino[2,3-c][1,8]naphthyridin-7(8H)-one (61 mg, crude), which was directly used in next step. ES-API: [M+H]$^+$=548.2.

Step 4: the (2R,4aR)-11-fluoro-10-(2-fluoro-6-methoxyphenyl)-8-(2-isopropyl-4-methylpyridin-3-yl)-2-methyl-1,2,3,4,4a,5-hexahydropyrazino[1',2':4,5][1,4]oxazino[2,3-c][1,8]naphthyridin-7(8H)-one (61 mg, 0.093 mmol) was dissolved in DCM (5 mL), and added with triethylamine (47 mg, 0.46 mmol). The resulting reaction liquid was cooled to 0° C., and added dropwise with a solution (1 mL) of acrylic anhydride (17 mg, 0.14 mmol) in DCM. The resulting mixture was stirred at 0° C. for 15 minutes to react. The resulting reaction liquid was added with 10 mL of saturated solution of NaHCO$_3$ and extracted with 10 mL of DCM for 3 times. The resulting organic phase was dried and concentrated, and the resulting crude product was subjected to thin-layer chromatography on a plate (DCM/MeOH=10:1) to obtain product ((2R,4aR)-3-acryloyl-11-fluoro-10-(2-fluoro-6-methoxyphenyl)-8-(2-isopropyl-4-methylpyridin-3-yl)-2-methyl-1,2,3,4,4a,5-hexahydropyrazino[1',2':4,5][1,4]oxopyrazino[2,3-c][1,8]naphthyridin-7(8H)-one (Z3a, 32 mg, Y: 57.4%), which was white solid. ES-API: [M+H]$^+$=602.2. $^1$H NMR (500 MHz, DMSO-d$_6$) δ 8.42 (d, J=4.1 Hz, 1H), 7.87 (d, J=8.8 Hz, 1H), 7.43 (dd, J=15.4, 8.3 Hz, 1H), 7.21 (d, J=4.8 Hz, 1H), 6.99-6.78 (m, 3H), 6.17 (d, J=17.4 Hz, 1H), 5.75 (d, J=10.5 Hz, 1H), 4.80-4.15 (m, 4H), 3.94-3.35 (m, 6H), 3.13-2.97 (m, 1H), 2.62-2.40 (m, 1H), 1.90-1.73 (m, 3H), 1.66-1.48 (m, 3H), 1.08-0.95 (m, 3H), 0.91-0.77 (m, 3H).

Step 5: (6aR,9R)-8-acryloyl-3-fluoro-2-(2-fluoro-6-methoxyphenyl)-13-(2-isopropyl-4-methylpyridin-3-yl)-9-methyl-6,6a,7,8,9,10-hexahydropyrazino[1',2':4,5][1,4]oxopyrazino[3,2-c][1,8]naphthyridin-12(13H)-one (32 mg, 0.053 mmol) was dissolved in DCM (1.5 mL). The resulting solution was cooled to 0° C., and then added dropwise with a solution (1 mL) of 17% boron tribromide in DCM. The resulting mixture was stirred at room temperature for 3 hours to react. The resulting reaction liquid was poured into 20 mL of saturated solution of NaHCO$_3$ and extracted with 20 mL of DCM for 3 times. The resulting organic phase was dried and concentrated, and the resulting crude product was purified by preparative scale HPLC to obtain product (6aR,9R)-8-acryloyl-3-fluoro-2-(2-fluoro-6-hydroxyphenyl)-13-(2-isopropyl-4-methylpyridin-3-yl)-9-methyl-6,6a,7,8,9,10-hexahydropyrazino[1',2':4,5][1,4]oxopyrazino[3,2-c][1,8]naphthyridin-12(13H)-one (Z3, 18 mg, Y: 57.6%), which was white solid. ES-API: [M+H]$^+$=588.3.

Example 6 Preparation of Compound Z6

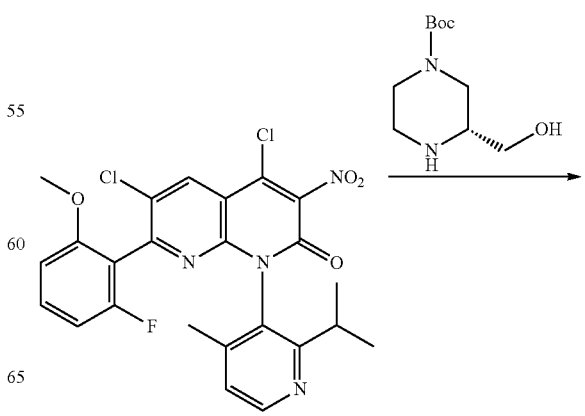

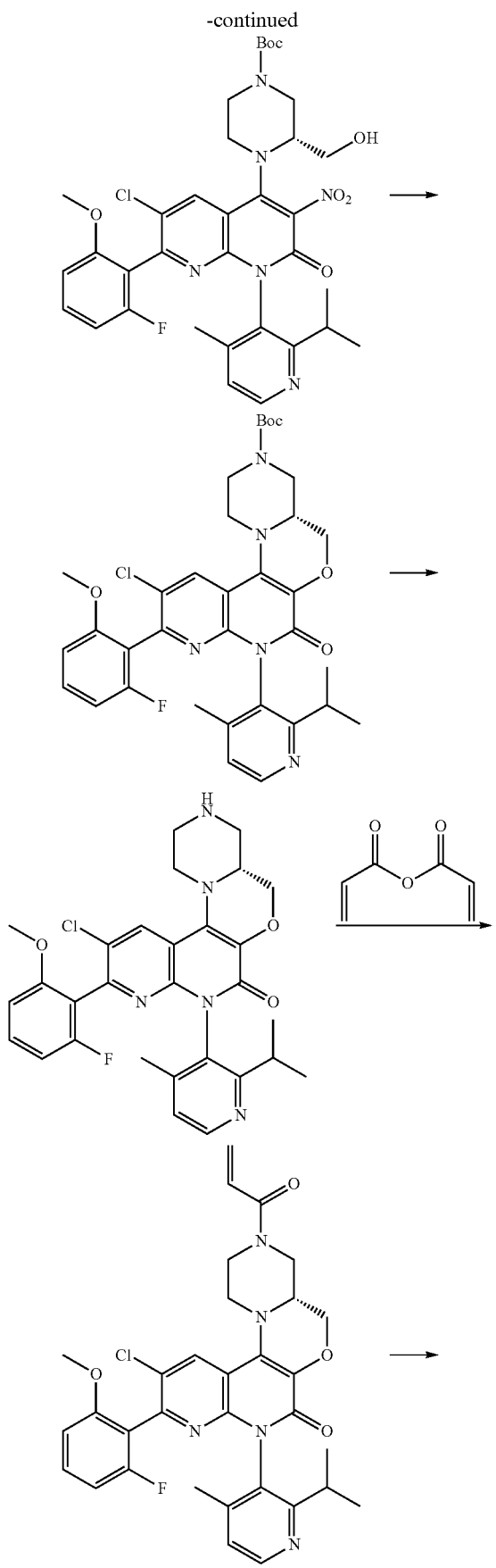

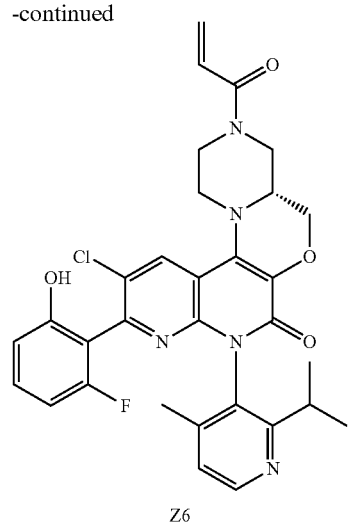

Z6

Step 1: 4,6-dichloro-7-(2-fluoro-6-methoxyphenyl)-1-(2-isopropyl-4-methylpyridin-3-yl)-3-nitro-1,8-naphthyridin-2(1H)-one (1.8 g, 3.48 mmol) was dissolved in DMF (15 mL), added with tert-butyl (R)-3-(hydroxymethyl)piperazin-1-carboxylate (3 g, 13.92 mmol), and stirred at 80° C. for 2 hours to react. The resulting reaction liquid was poured into 30 mL of water. The reaction liquid was extracted with 20 mL of EtOAc for 3 times. The resulting organic phase was washed with saturated salt solution for 3 times, dried and concentrated, and the resulting crude product was purified by flash column chromatography on silica gel (EtOAc/PE: 0-70%) to obtain product tert-butyl (3R)-4-(6-chloro-7-(2-fluoro-6-methoxyphenyl)-1-(2-isopropyl-4-methylpyridin-3-yl)-3-nitro-2-oxo-1,2-dihydro-1,8-naphthyridin-4-yl)-3-(hydroxymethyl)piperazin-1-formate (1.3 g, 54%), which was yellow solid. ES-API: [M+H]$^+$=697.2.

Step 2: the tert-butyl (3R)-4-(6-chloro-7-(2-fluoro-6-methoxyphenyl)-1-(2-isopropyl-4-methylpyridin-3-yl)-3-nitro-2-oxo-1,2-dihydro-1,8-naphthyridin-4-yl)-3-(hydroxymethyl)piperazin-1-formate (1.3 g, 1.86 mmol) was dissolved in DMA (10 mL), added with LHMDS (5.6 mmol, 5.6 mmol, 1 M tetrahydrofuran solution), and stirred at 140° C. for 20 hours to react. Cooled reaction liquid was poured into 15 mL of water. The reaction liquid was extracted with 30 mL of EtOAc for 3 times. The resulting organic phase was washed with saturated salt solution for 3 times, dried and concentrated, and the resulting crude product was purified by flash column chromatography on silica gel (MeOH/DCM: 0-10%) to obtain tert-butyl (4aR)-11-chloro-10-(2-fluoro-6-methoxyphenyl)-8-(2-isopropyl-4-methylpyridin-3-yl)-7-oxo-1,2,4a,5,7,8-hexahydropyrazino[1',2':4,5][1,4]oxazino[2,3-c][1,8]naphthyridin-3(4H)-carboxylate (0.24 g, 20%), which was yellow solid. ES-API: [M+H]$^+$=650.2.

Step 3: the tert-butyl (4aR)-11-chloro-10-(2-fluoro-6-methoxyphenyl)-8-(2-isopropyl-4-methylpyridin-3-yl)-7-oxo-1,2,4a,5,7,8-hexahydropyrazino[1',2':4,5][1,4]oxazino[2,3-c][1,8]naphthyridin-3(4H)-carboxylate (240 mg, 0.37 mmol) was dissolved in DCM (2 mL), and added with TFA (2 mL). The resulting mixture was stirred at room temperature for 0.5 hour, and the resulting reaction liquid was concentrated to obtain product (4aR)-11-chloro-10-(2-fluoro-6-methoxyphenyl)-8-(2-isopropyl-4-methylpyridin-3-yl)-1,2,3,4,4a,5-hexahydropyrazino[1',2':4,5][1,4]oxazino[2,3-c][1,8]naphthyridin-7(8H)-one (203 mg, crude), which was directly used in next step. ES-API: [M+H]$^+$=550.1.

Step 4: the (4aR)-11-chloro-10-(2-fluoro-6-methoxyphenyl)-8-(2-isopropyl-4-methylpyridin-3-yl)-1,2,3,4,4a,5-hexahydropyrazino[1',2':4,5][1,4]oxazino[2,3-c][1,8]naphthyridin-7(8H)-one (203 mg, 0.37 mmol) was dissolved in DCM (4 mL), and added with triethylamine (187 mg, 1.85 mmol). The resulting reaction liquid was cooled to 0° C., and added dropwise with a solution (0.5 mL) of acrylic anhydride (37 mg, 0.30 mmol) in DCM. The resulting mixture was stirred at 0° C. for 10 minutes to react. The resulting reaction liquid was added with 10 mL of saturated solution of NaHCO$_3$ and extracted with 10 mL of DCM for 3 times. The resulting organic phase was dried and concentrated, and the resulting crude product was subjected to thin-layer chromatography on a plate (DCM/MeOH=10:1) to obtain product (4aR)-3-acryloyl-11-chloro-10-(2-fluoro-6-methoxyphenyl)-8-(2-isopropyl-4-methylpyridin-3-yl)-1,2,3,4,4a,5-hexahydropyrazino[1',2':4,5][1,4]oxazino[2,3-c][1,8]naphthyridin-7(8H)-one (223 mg, crude), which was faint yellow solid. ES-API: [M+H]$^+$=604.2.

Step 5: the (4aR)-3-acryloyl-11-chloro-10-(2-fluoro-6-methoxyphenyl)-8-(2-isopropyl-4-methylpyridin-3-yl)-1,2,3,4,4a,5-hexahydropyrazino[1',2':4,5][1,4]oxazino[2,3-c][1,8]naphthyridin-7(8H)-one (223 mg, 0.37 mmol) was dissolved in DCM (1.5 mL). The resulting solution was cooled to 0° C., and then added dropwise with a solution (3 mL) of 17% boron tribromide in DCM. The resulting mixture was stirred at room temperature for 1 hour to react.

The resulting reaction liquid was poured into 20 mL of saturated solution of NaHCO$_3$ and extracted with 20 mL of DCM for 3 times. The resulting organic phase was dried and concentrated, and the resulting crude product was purified by preparative grade HPLC to obtain product (4aR)-3-acryloyl-11-chloro-10-(2-fluoro-6-hydroxyphenyl)-8-(2-isopropyl-4-methylpyridin-3-yl)-1,2,3,4,4a,5-hexahydropyrazino[1',2':4,5][1,4]oxazino[2,3-c][1,8]naphthyridin-7(8H)-one (Z6, 26.28 mg, 11%), which was white solid. $^1$H NMR (400 MHz, DMSO-d$_6$) δ 8.42-8.36 (m, 2H), 7.22-7.18 (m, 2H), 6.68-6.62 (m, 3H), 6.22-6.17 (m, 1H), 5.78-5.77 (m, 1H), 4.46-3.55 (m, 8H), 3.12-3.10 (m, 1H), 2.52-2.51 (m, 1H), 1.88-1.80 (m, 3H), 1.06-1.04 (m, 3H), 0.89-0.86 (m, 3H). ES-API: [M+H]$^+$=590.2.

Example 9 Preparation of Compounds Z9, Z9-1, and Z9-2

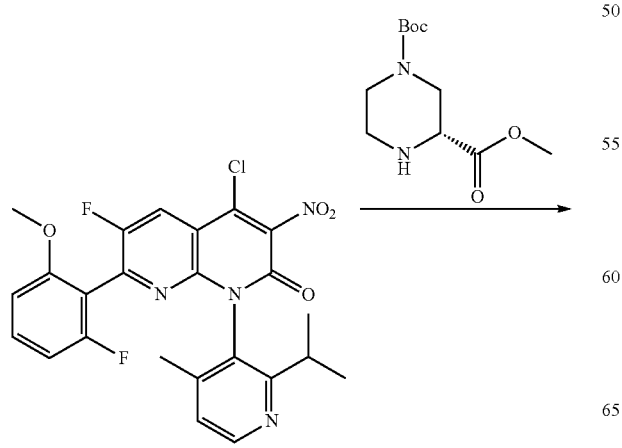

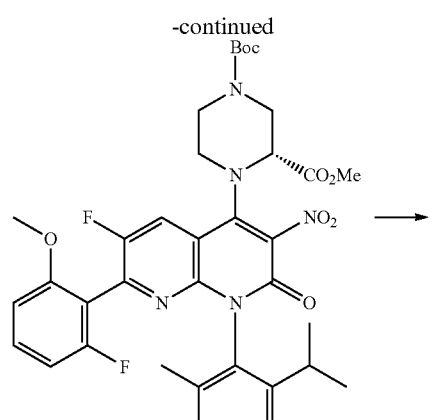

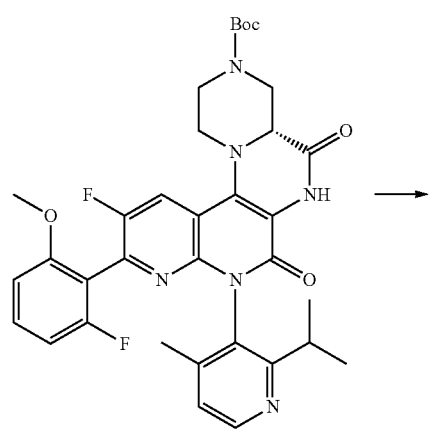

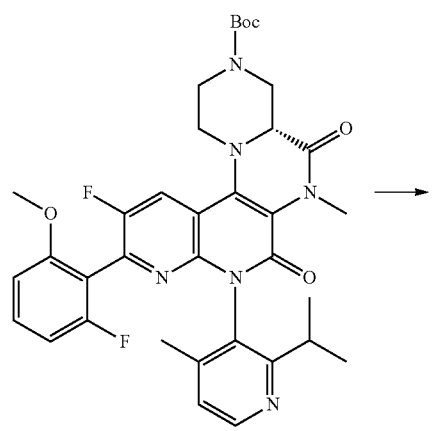

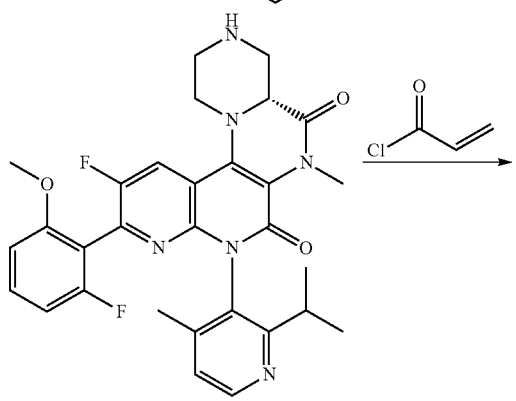

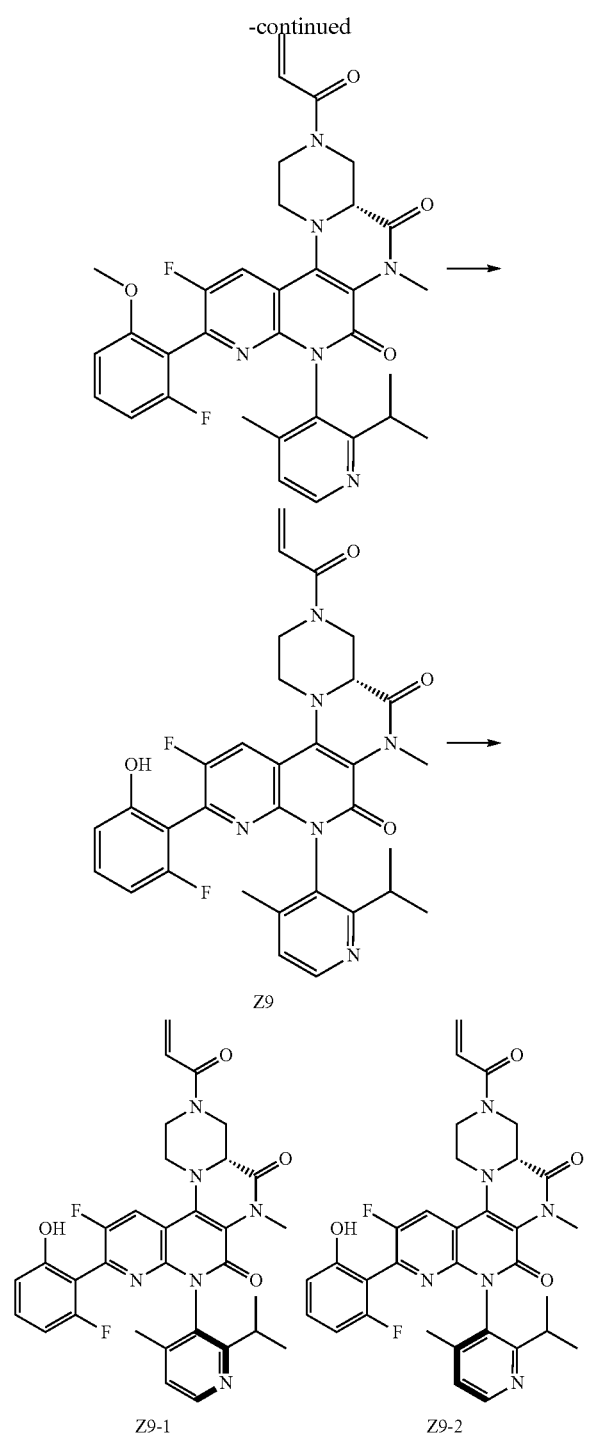

Z9

Z9-1    Z9-2

Step 1: 4-chloro-6-fluoro-7-(2-fluoro-6-methoxyphenyl)-1-(2-isopropyl-4-methylpyridin-3-yl)-3-nitro-1,8-naphthyridin-2(1H)-one (500 mg, 1.00 mmol) was dissolved in N,N-dimethylacetamide (6 mL), orderly added with (R)-1-(tert-butyl)3-methyl-piperazin-1,3-dicarboxylate (732 mg, 3.00 mmol) and N,N-diisopropylethylamine (387 mg, 3.00 mmol), and stirred at 120° C. for 2 hours to react. The resulting reaction liquid was added with 100 mL of EtOAc, washed with 30 mL of dilute brine for 4 times and then washed with 30 mL of saturated salt solution, dried and concentrated, and the resulting crude product was purified by flash column chromatography on silica gel (EtOAc/PE: 0-70%) to obtain product (3R)-1-(tert-butyl)-3-methyl-4-(6-fluoro-7-(2-fluoro-6-methoxyphenyl)-1-(2-isopropyl-4-methylpyridin-3-yl)-3-nitro-2-oxo-1,2-dihydro-1,8-naphthyridin-4-yl)piperazin-1,3-dicarboxylate (500 mg, Y: 70.6%), which was yellow solid. ES-API: [M+H]$^+$=709.2.

Step 2: the (3R)-1-(tert-butyl)-3-methyl-4-(6-fluoro-7-(2-fluoro-6-methoxyphenyl)-1-(2-isopropyl-4-methylpyridin-3-yl)-3-nitro-2-oxo-1,2-dihydro-1,8-naphthyridin-4-yl)piperazin-1,3-dicarboxylate (500 mg, 0.71 mmol) was dissolved in acetic acid (8 mL), added with iron powder (138 mg, 2.47 mmol), and stirred at 80° C. for 30 minutes to react. The resulting reaction liquid was concentrated, and orderly added with 50 mL of EtOAc and 30 mL of saturated sodium bicarbonate. The resulting suspension was filtered by using diatomite. The filter cake was washed with EtOAc.

The resulting organic phase was separated, washed orderly with 30 mL of saturated solution of sodium bicarbonate and 30 mL of saturated salt solution, dried and concentrated to obtain product tert-butyl (4aR)-11-fluoro-10-(2-fluoro-6-methoxyphenyl)-8-(2-isopropyl-4-methylpyridin-3-yl)-5,7-dioxo-1,2,4,4a,5,6,7,8-octahydro-3H-pyrazino[1',2':4,5]pyrazino[2,3-c][1,8]naphthyridin-3-carboxylate (450 mg, Y: 98.6%), which was faint yellow solid. ES-API: [M+H]$^+$=647.2.

Step 3: the tert-butyl (4aR)-11-fluoro-10-(2-fluoro-6-methoxyphenyl)-8-(2-isopropyl-4-methylpyridin-3-yl)-5,7-dioxo-1,2,4,4a,5,6,7,8-octahydro-3H-pyrazino[1',2':4,5]pyrazino[2,3-c][1,8]naphthyridin-3-carboxylate (450 mg, 0.70 mmol), 12 mL of acetone, anhydrous potassium carbonate (290 mg, 2.10 mmol), and iodomethane (596 mg, 4.20 mmol) were orderly added to a 15 mL sealing tube. The sealing tube was sealed, and the resulting mixture was stirred at 50° C. for 20 hours to react. The resulting reaction liquid was concentrated, added with 60 mL of EtOAc, washed orderly with 30 mL of water and 30 mL of saturated salt solution, dried and concentrated. The resulting crude product was purified by flash column chromatography on silica gel (EtOAc/PE: 0-70%) to obtain product tert-butyl (4aR)-11-fluoro-10-(2-fluoro-6-methoxyphenyl)-8-(2-isopropyl-4-methylpyridin-3-yl)-6-methyl-5,7-dioxy-1,2,4,4a,5,6,7,8-octahydro-3H-pyrazino[1',2':4,5]pyrazino[2,3-c][1,8]naphthyridin-3-carboxylate (390 mg, Y: 84.8%), which was orange solid. ES-API: [M+H]$^+$=661.3.

Step 4: the tert-butyl (4aR)-11-fluoro-10-(2-fluoro-6-methoxyphenyl)-8-(2-isopropyl-4-methylpyridin-3-yl)-6-methyl-5,7-dioxy-1,2,4,4a,5,6,7,8-octahydro-3H-pyrazino[1',2':4,5]pyrazino[2,3-c][1,8]naphthyridin-3-carboxylate (940 mg, 1.42 mmol) was dissolved in DCM (6 mL), and added with TFA (2 mL). After stirring at room temperature for 2 hours, the resulting reaction liquid was concentrated to obtain product (4aR)-11-fluoro-10-(2-fluoro-6-methoxyphenyl)-8-(2-isopropyl-4-methylpyridin-3-yl)-6-methyl-2,3,4,4a,6,8-hexahydro-1H-pyrazino[1',2':4,5]pyrazino[2,3-c][1,8]naphthyridin-5,7-dione (1.1 g, crude), which was directly used in next step. ES-API: [M+H]$^+$=561.3.

Step 5: the (4aR)-11-fluoro-10-(2-fluoro-6-methoxyphenyl)-8-(2-isopropyl-4-methylpyridin-3-yl)-6-methyl-2,3,4,4a,6,8-hexahydro-1H-pyrazino[1',2':4,5]pyrazino[2,3-c][1,8]naphthyridin-5,7-dione (1.1 g, crude) was dissolved in DCM (20 mL), and added with N,N-diisopropylethylamine (916 mg, 7.10 mmol). The resulting reaction liquid was cooled to 0° C., added with acryloyl chloride (256 mg, 2.84 mmol), and stirred at 0° C. for 15 minutes to react. The resulting reaction liquid was added with 30 mL of DCM, washed orderly with 15 mL of water, 15 mL of saturated solution of NaHCO$_3$ and 15 mL of saturated salt solution, dried and concentrated. The resulting crude product was purified by flash column chromatography on silica gel (EtOAc/PE: 0-100%) to obtain product (4aR)-3-acryloyl-11-fluoro-10-(2-fluoro-6-methoxyphenyl)-8-(2-isopropyl-4-methylpyridin-3-yl)-6-methyl-2,3,4,4a,6,8-hexahydro-1H-pyrazino[1',2':4,5]pyrazino[2,3-c][1,8]naphthyridin-5,7-dione (780 mg, Y: 88.3%), which was faint yellow solid. ES-API: [M+H]$^+$=615.3.

Step 6: the (4aR)-3-acryloyl-11-fluoro-10-(2-fluoro-6-methoxyphenyl)-8-(2-isopropyl-4-methylpyridin-3-yl)-6-methyl-2,3,4,4a,6,8-hexahydro-1H-pyrazino[1',2':4,5]pyrazino[2,3-c][1,8]naphthyridin-5,7-dione (390 mg, 0.64 mmol) was dissolved in DCM (9 mL). The resulting reaction liquid was cooled to 0° C., and then added dropwise with a solution (7 mL) of 17% boron tribromide in DCM. The resulting mixture was stirred at room temperature for 6 hours to react. The resulting reaction liquid was poured into 60 mL of saturated solution of NaHCO$_3$ and extracted with 80 mL of DCM twice. The resulting organic phase was washed orderly with 50 mL of saturated solution of NaHCO$_3$ and 80 mL of saturated salt solution, dried and concentrated to obtain product (4aR)-3-acryloyl-11-fluoro-10-(2-fluoro-6-hydroxyphenyl)-8-(2-isopropyl-4-methylpyridin-3-yl)-6-methyl-2,3,4,4a,6,8-hexahydro-1H-pyrazino[1',2':4,5]pyrazino[2,3-c][1,8]naphthyridin-5,7-dione (Z9, 375 mg, Y: 98.4%), which was faint yellow solid. ES-API: [M+H]$^+$=601.2.

Step 7: the (4aR)-3-acryloyl-11-fluoro-10-(2-fluoro-6-hydroxyphenyl)-8-(2-isopropyl-4-methylpyridin-3-yl)-6-methyl-2,3,4,4a,6,8-hexahydro-1H-pyrazino[1',2':4,5]pyrazino[2,3-c][1,8]naphthyridin-5,7-dione (750 mg, 1.25 mmol) was purified by preparative scale HPLC, and then resolved by preparative scale chiral HPLC (column type: IB: 10 μm, 30*250 mm; mobile phase: hexane:EtOH=65:35; flow rate: 25 ml/min; and column temperature: room temperature) to obtain the following atropisomer compounds. One of the atropisomer compounds had a structure arbitrarily specified as Z9-1 (250 mg, peak 1, retention time: 6.463 min, Y: 33.3%), which was faint yellow solid. $^1$H NMR (500 MHz, DMSO-d$_6$) δ 10.11 (d, J=1.3 Hz, 1H), 8.46-8.34 (m, 2H), 7.30-7.19 (m, 2H), 7.10-6.79 (m, 1H), 6.74-6.62 (m, 2H), 6.15 (d, J=16.9 Hz, 1H), 5.75 (d, J=12.0 Hz, 1H), 4.73 (d, J=13.3 Hz, 1H), 4.45 (d, J=12.7 Hz, 1H), 4.10-3.97 (m, 1H), 3.63-3.47 (m, 2H), 3.39-3.08 (m, 4H), 2.83-2.59 (m, 1H), 2.48-2.39 (m, 1H), 1.99 (s, 3H), 1.02 (d, J=6.7 Hz, 3H), 0.85 (d, J=6.7 Hz, 3H). ES-API: [M+H]$^+$=601.2. The other atropisomer compound had a structure arbitrarily specified as Z9-2 (350 mg, peak 2, retention time: 8.252 min, Y: 46.7%), which was faint yellow solid. $^1$H NMR (500 MHz, DMSO-d$_6$) δ 10.14 (s, 1H), 8.44 (d, J=4.9 Hz, 1H), 8.38 (d, J=9.0 Hz, 1H), 7.29-7.20 (m, 2H), 7.10-6.79 (m, 1H), 6.76-6.59 (m, 2H), 6.15 (d, J=16.9 Hz, 1H), 5.75 (d, J=11.1 Hz, 1H), 4.73 (d, J=14.0 Hz, 1H), 4.45 (d, J=12.4 Hz, 1H), 4.02-3.89 (m, 1H), 3.62-3.50 (m, 2H), 3.33-3.09 (m, 4H), 2.88-2.61 (m, 2H), 1.79 (s, 3H), 1.10 (d, J=6.7 Hz, 3H), 0.98 (d, J=6.7 Hz, 3H). ES-API: [M+H]$^+$=601.2. The isomer compounds were detected by analytical scale chiral HPLC (column type: IB: 5 μm, 4.6*250 mm; mobile phase: hexane:EtOH=65:35; flow rate: 1 ml/min; and column temperature=30° C.).

Example 10 Preparation of Compounds Z10, Z10-1, and Z10-2

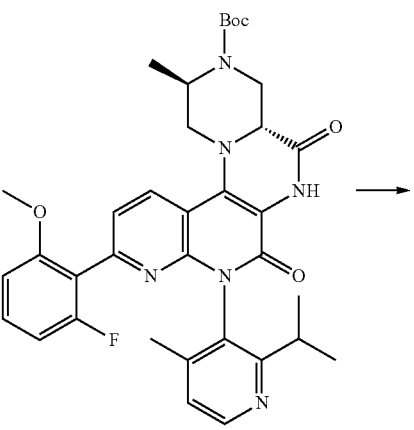

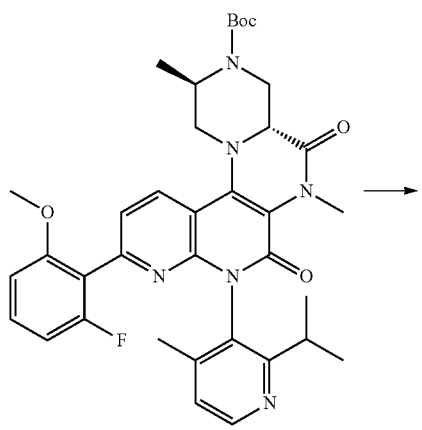

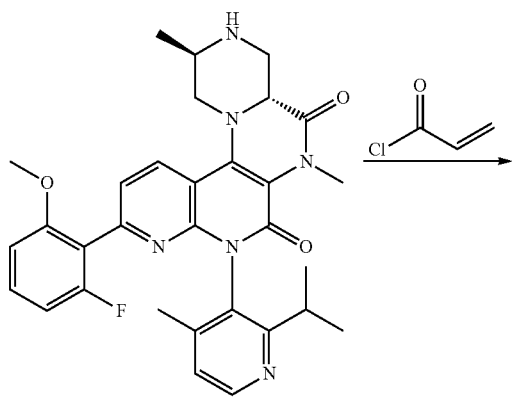

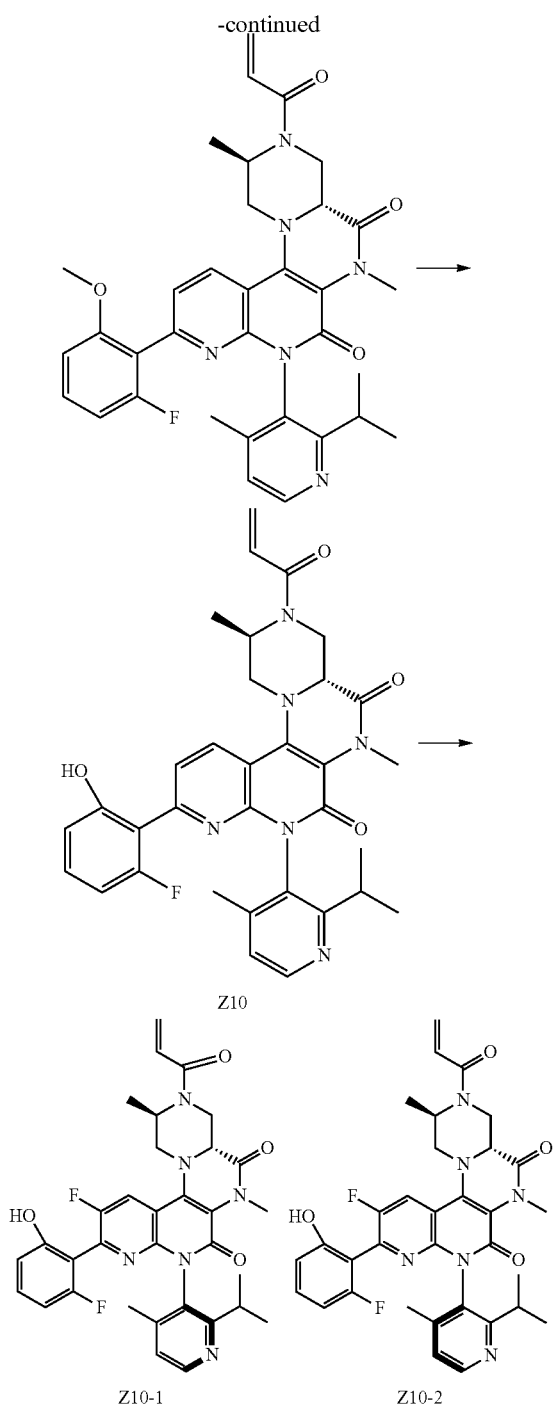

product was purified by flash column chromatography on silica gel (EtOAc/PE: 0-70%) to obtain product tert-butyl (2R,4aR)-11-fluoro-10-(2-fluoro-6-methoxyphenyl)-8-(2-isopropyl-4-methylpyridin-3-yl)-2,6-dimethyl-5,7-dioxo-1,2,4,4a,5,6,7,8-octyl-3H-pyrazino[1',2':4,5]pyrazino[2,3-c][1,8]naphthyridin-3-carboxylate (790 mg, Y: 96.7%), which was orange solid. ES-API: [M+H]$^+$=675.3.

Step 2: the tert-butyl (2R,4aR)-11-fluoro-10-(2-fluoro-6-methoxyphenyl)-8-(2-isopropyl-4-methylpyridin-3-yl)-2,6-dimethyl-5,7-dioxo-1,2,4,4a,5,6,7,8-octyl-3H-pyrazino[1',2':4,5]pyrazino[2,3-c][1,8]naphthyridin-3-carboxylate (790 mg, 1.42 mmol) was dissolved in DCM (6 mL), and added with TFA (2 mL). After stirring at room temperature for 2 hours, the resulting reaction liquid was concentrated to obtain product (2R,4aR)-11-fluoro-10-(2-fluoro-6-methoxyphenyl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin-5,7-dione (810 mg, crude), which was directly used in next step. ES-API: [M+H]$^+$=575.2.

Step 3: the (2R,4aR)-11-fluoro-10-(2-fluoro-6-methoxyphenyl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin-5,7-dione (810 mg, crude) was dissolved in DCM (15 mL), and added with N,N-diisopropylethylamine (755 mg, 5.85 mmol). The resulting reaction liquid was cooled to 0° C., added with acryloyl chloride (211 mg, 2.34 mmol), and stirred at 0° C. for 15 minutes to react. The resulting reaction liquid was added with 50 mL of DCM, washed orderly with 20 mL of water, 40 mL of saturated solution of NaHCO$_3$ and 20 mL of saturated salt solution, dried and concentrated. The resulting crude product was purified by flash column chromatography on silica gel (EtOAc/PE: 0-100%) to obtain product (2R,4aR)-3-acryloyl-11-fluoro-10-(2-fluoro-6-methoxyphenyl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin-5,7-dione (670 mg, Y: 91.0%), which was faint yellow solid. ES-API: [M+H]$^+$=629.2.

Step 4: the (2R,4aR)-3-acryloyl-11-fluoro-10-(2-fluoro-6-methoxyphenyl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin-5,7-dione (370 mg, 0.59 mmol) was dissolved in DCM (8 mL). The resulting reaction liquid was cooled to 0° C., and then added dropwise with a solution (7 mL) of 17% boron tribromide in DCM. The resulting mixture was stirred at room temperature for 3 hours to react. The resulting reaction liquid was poured into 60 mL of saturated solution of NaHCO$_3$ and extracted with 80 mL of DCM twice. The resulting organic phase was washed orderly with 50 mL of saturated solution of NaHCO$_3$ and 80 mL of saturated salt solution, dried and concentrated. The resulting crude product was purified by preparative scale HPLC to obtain product (2R,4aR)-3-acryloyl-11-fluoro-10-(2-fluoro-6-hydroxyphenyl)-8-(2-isopropyl-4-methylpyridin-3-yl)-2,6-dimethyl-2,3,4,4a,6-hexahydro-1H-pyrazino[1',2':4,5]pyrazino[2,3-c][1,8,8]naphthyridin-5-dione (Z10, 249 mg, Y: 68.7%), which was faint yellow solid. ES-API: [M+H]$^+$=615.2.

Step 5: the compound Z10 (450 mg, 1.06 mmol) was resolved by preparative scale chiral HPLC (column type: OD-H: 10 μm, 20*250 mm; mobile phase: hexane:EtOH=80:20; flow rate: 15 ml/min; and column temperature: room temperature) to obtain the following atropisomer compounds. One of the atropisomer compounds had a structure arbitrarily specified as Z10-1 (206 mg, peak 1, retention time: 8.321 min, Y: 45.7%), which was faint Step 1: tert-butyl (2R,4aR)-11-fluoro-10-(2-fluoro-6-methoxyphenyl)-8-(2-isopropyl-4-methylpyridin-3-yl)-2-methyl-5,7-dioxo-1,2,4,4a,5,6,7,8-octyl-3H-pyrazino[1',2':4,5]pyrazino[2,3-c][1,8]naphthyridin-3-carboxylate (800 mg, 1.21 mmol), 20 mL of acetone, anhydrous potassium carbonate (500 mg, 3.63 mmol), and iodomethane (1.03 g, 7.26 mmol) were orderly added to a 50 mL sealing tube. The sealing tube was sealed, and the resulting mixture was stirred at 50° C. for 18 hours to react. The resulting reaction liquid was concentrated, added with 60 mL of EtOAc, washed orderly with 20 mL of water and 30 mL of saturated salt solution, dried and concentrated. The resulting crude yellow solid. ¹H NMR (500 MHz, DMSO-d₆) δ 10.13 (d, J=1.3 Hz, 1H), 8.44 (d, J=4.9 Hz, 1H), 8.02-7.95 (m, 1H), 7.33-7.20 (m, 2H), 7.06-6.82 (m, 1H), 6.76-6.63 (m, 2H), 6.24-6.08 (m, 1H), 5.82-5.67 (m, 1H), 5.05-4.73 (m, 1H), 4.63-4.37 (m, 1H), 4.07-3.97 (m, 1H), 3.73 (dd, J=14.1, 4.2 Hz, 1H), 3.39-3.20 (m, 4H), 2.94-2.78 (m, 1H), 2.49-2.39 (m, 1H), 1.99 (s, 3H), 1.61-1.49 (m, 3H), 1.02 (d, J=6.7 Hz, 3H), 0.85 (d, J=6.7 Hz, 3H). ES-API: [M+H]⁺=615.2. The other atropisomer compound had a structure arbitrarily specified as Z10-2 (209 mg, peak 2, retention time: 10.183 min, Y: 46.4%), which was faint yellow solid. ¹H NMR (500 MHz, DMSO-d₆) δ10.15 (s, 1H), 8.45 (d, J=4.9 Hz, 1H), 8.03-7.95 (m, 1H), 7.30-7.18 (m, 2H), 7.06-6.82 (m, 1H), 6.75-6.61 (m, 2H), 6.21-6.09 (m, 1H), 5.80-5.65 (m, 1H), 5.05-4.72 (m, 1H), 4.63-4.37 (m, 1H), 4.01-3.92 (m, 1H), 3.74 (dd, J=14.2, 4.2 Hz, 1H), 3.43-3.21 (m, 4H), 2.95-2.82 (m, 1H), 2.80-2.72 (m, 1H), 1.80 (s, 3H), 1.60-1.48 (m, 3H), 1.11 (d, J=6.7 Hz, 3H), 0.98 (d, J=6.7 Hz, 3H). ES-API: [M+H]⁺=615.2. The isomer compounds were detected by analytical scale chiral HPLC (column type: OD-H: 5 μm, 4.6*250 mm; mobile phase: hexane:EtOH=80:20; flow rate: 1 ml/min; and column temperature=30° C.).

Examples 4-5, 7-8, and 11-20

Compounds Z4-Z5, Z7-Z8, and Z11-Z20 were prepared by similar methods to that for the compound Z1 or Z2, where starting materials for different compounds were commercially available or prepared by existing methods well known to those skilled in the art. Furthermore, it would be easy for a person skilled in the art to synthesize intermediates with reference to existing similar methods.

| Example No. | Compound No. | Compound Structure | MS [M + H] |
|---|---|---|---|
| 4 | Z4 | | 558.2 |
| 5 | Z5 | 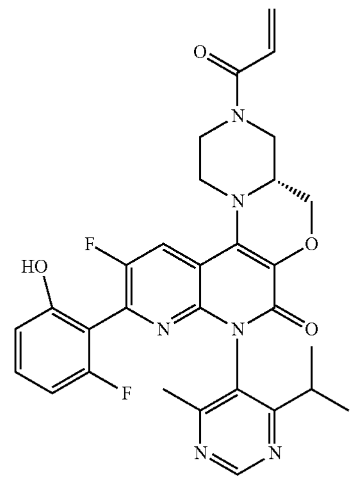 [SMILES: C=CC(=O)N1CCN2c3c(c(=O)n(-c4c(C)ncnc4C(C)C)c4nc(-c5c(O)cccc5F)c(F)cc34)OC[C@H]2C1] | 575.2 |
| 7 | Z7 | 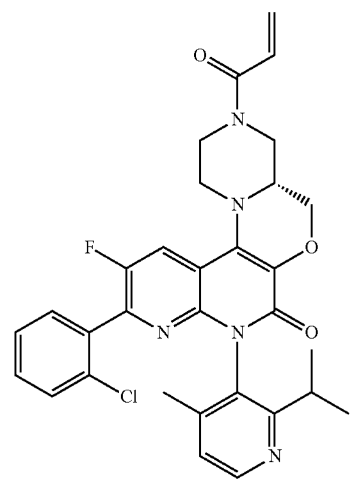 [SMILES: C=CC(=O)N1CCN2c3c(c(=O)n(-c4c(C)ccnc4C(C)C)c4nc(-c5ccccc5Cl)c(F)cc34)OC[C@H]2C1] | 574.2 |
| 8 | Z8 | 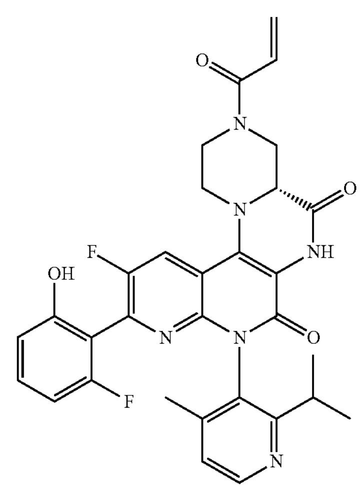 [SMILES: C=CC(=O)N1CCN2c3c(c(=O)n(-c4c(C)ccnc4C(C)C)c4nc(-c5c(O)cccc5F)c(F)cc34)NC(=O)[C@H]2C1] | 587.2 |

| Example No. | Compound No. | Compound Structure | MS [M + H] |
|---|---|---|---|
| 11 | Z11 | 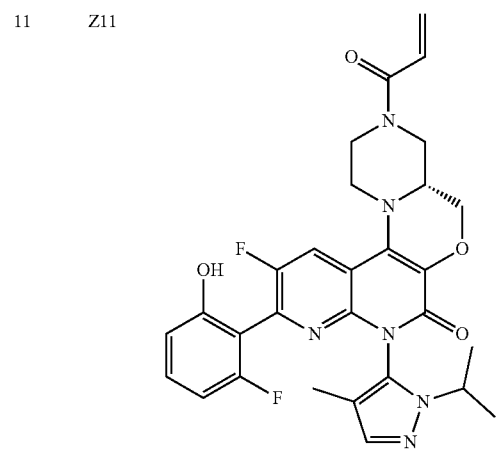 | 563.2 |
| 12 | Z12 | 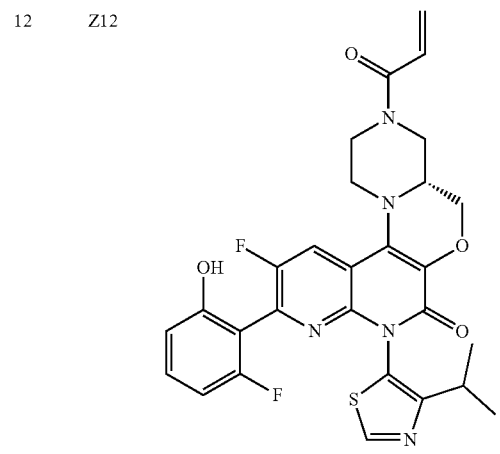 | 566.2 |
| 13 | Z13 | 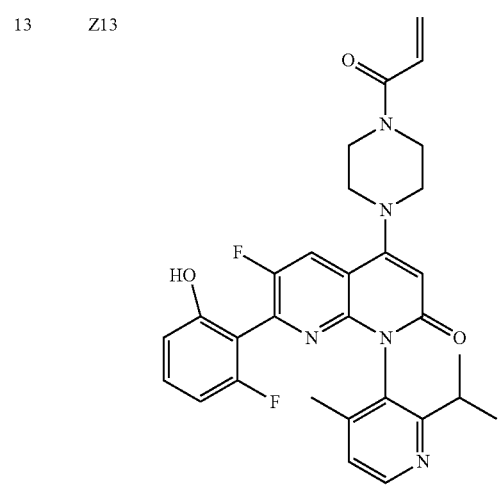 | 546.2 |
| Example No. | Compound No. | Compound Structure | MS [M + H] |
|---|---|---|---|
| 14 | Z14 | 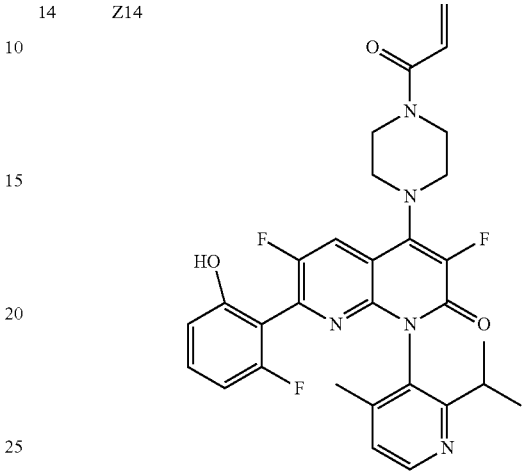 | 564.2 |
| 15 | Z15 | 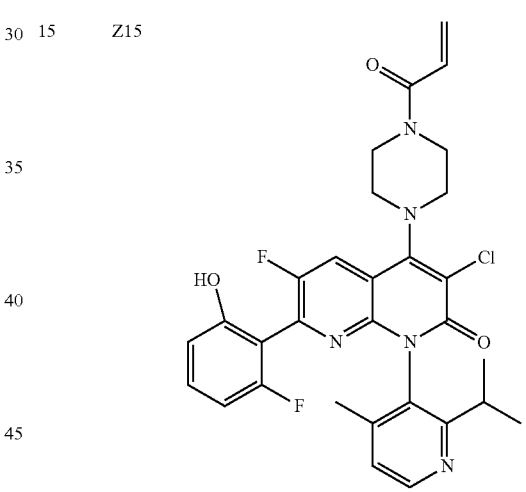 | 580.2 |
| 16 | Z16 | 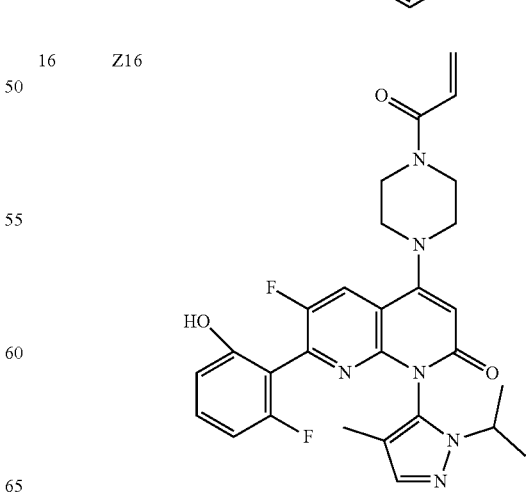 | 535.2 |

| Example No. | Compound No. | Compound Structure | MS [M + H] |
|---|---|---|---|
| 17 | Z17 | 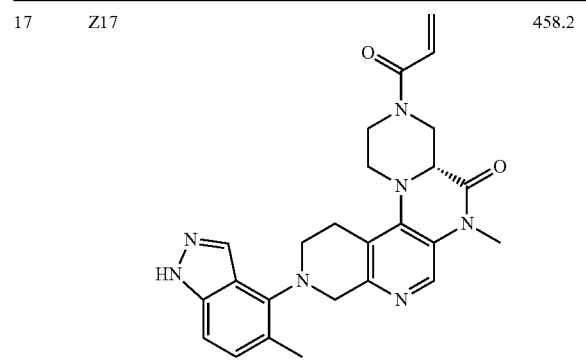 | 458.2 |
| 18 | Z18 | 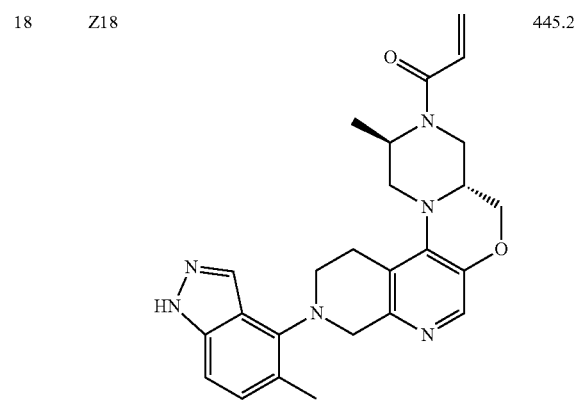 | 445.2 |
| 19 | Z19 | 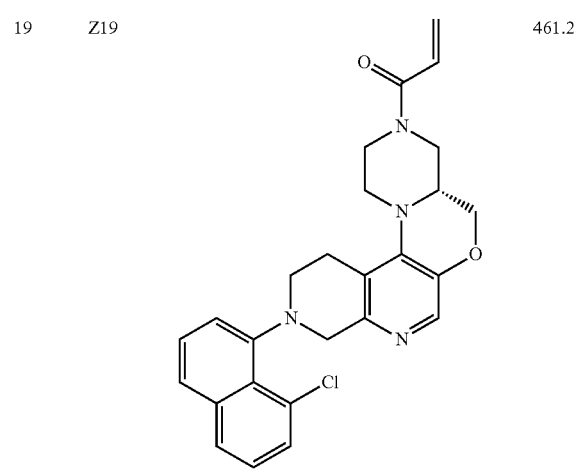 | 461.2 |
| Example No. | Compound No. | Compound Structure | MS [M + H] |
|---|---|---|---|
| 20 | Z20 | 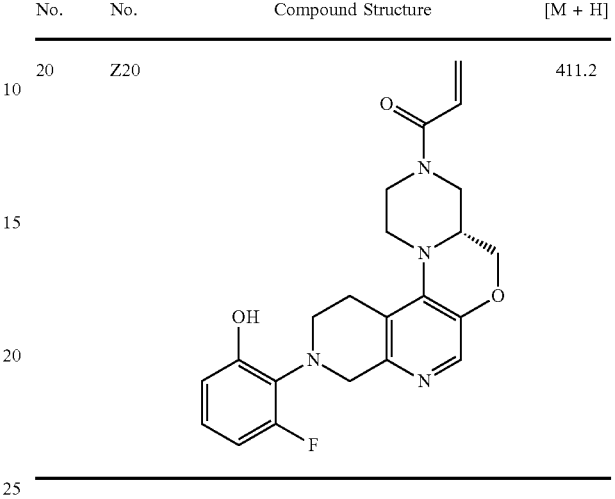 | 411.2 |
Example 21 Preparation of Compounds Z21, Z21-1 and Z21-2
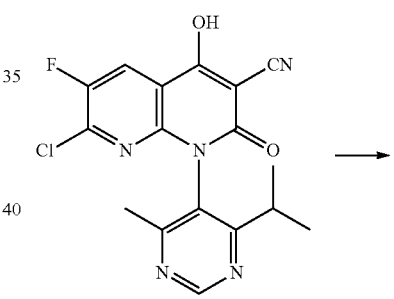
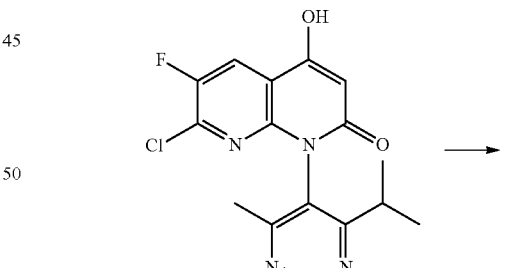
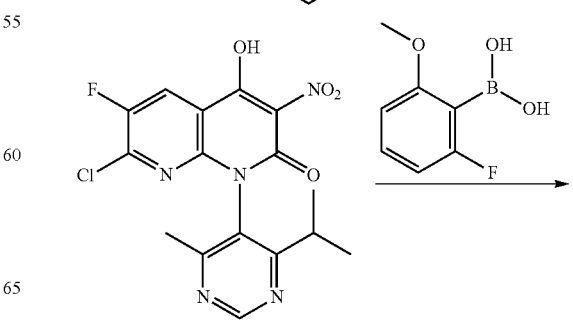

265
-continued
266
-continued
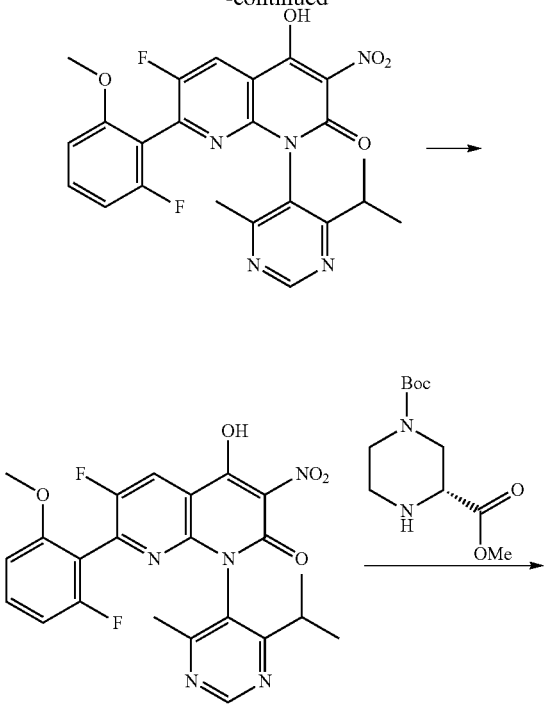
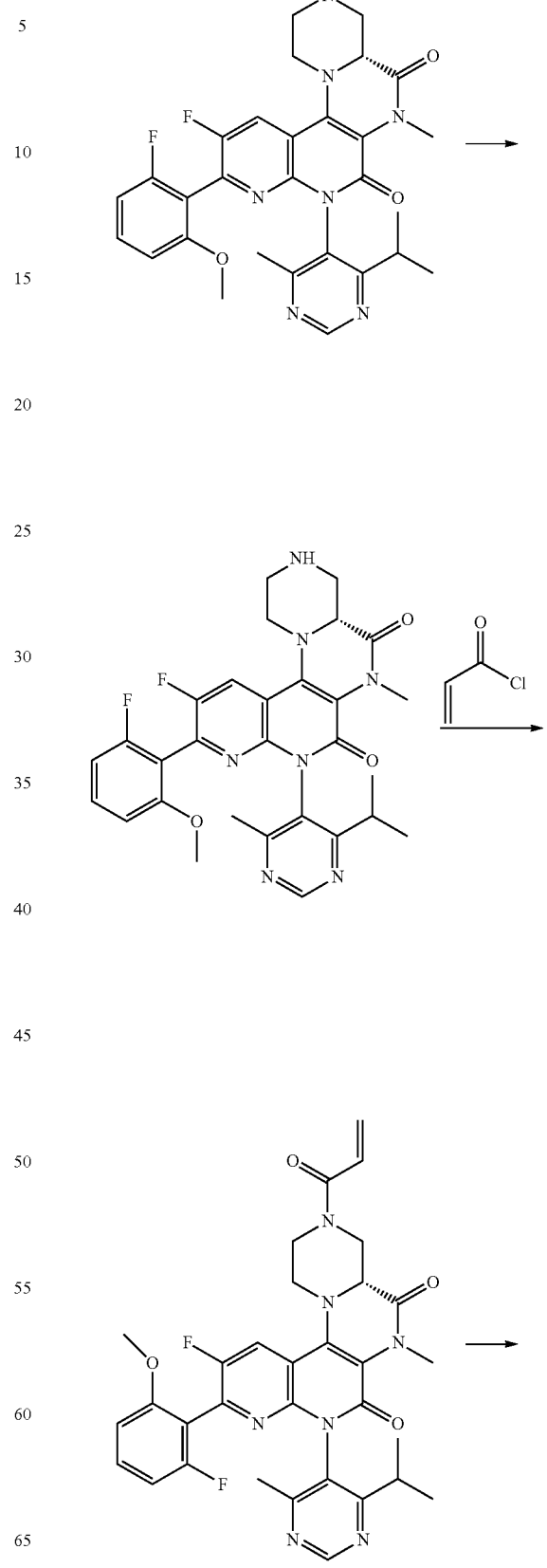

-continued

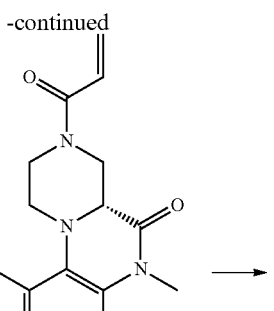

Z21

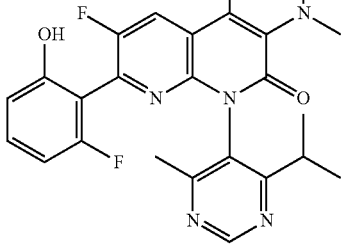

Z21-1

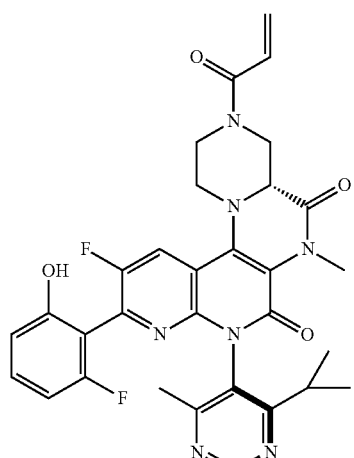

Z21-2

Step 1: 7-chloro-6-fluoro-4-hydroxy-1-(4-isopropyl-6-methylpyrimidin-5-yl)-2-oxo-1,2-dihydro-1,8-naphthyridin-3-nitrile (2 g, 5.34 mmol), 12 mL of water, and 12 mL of dioxane were added to a round-bottom flask. The resulting system was cooled to 0° C., and 12 mL of concentrated sulfuric acid was added dropwise to the resulting reaction liquid. After the completion of dropwise addition, the resulting mixture was stirred at 120° C. for 18 hours to react. After the completion of the reaction, a large amount of solid was precipitated. The resulting reaction mixture was filtered, and the filter cake was washed with water for 3 times. The filter cake was dried to obtain 7-chloro-6-fluoro-4-hydroxy-1-(4-isopropyl-6-methylpyrimidin-5-yl)-1,8-naphthyridin-2(1H)-one (1.4 g, 75%), which was white solid. The resulting crude product was directly used in next step. ES-API: [M+H]⁺=349.1.

Step 2: the 7-chloro-6-fluoro-4-hydroxy-1-(4-isopropyl-6-methylpyrimidin-5-yl)-1,8-naphthyridin-2(1H)-one (1.3 g, 3.72 mmol), sodium nitrite (26 mg, 0.37 mmol), and 8 mL of glacial acetic acid were added to a round-bottom flask. Concentrated nitric acid (700 mg, 11.1 mmol) was added dropwise to the resulting reaction liquid. The reaction liquid was placed into an oil bath at 30° C. to be heated for 2 hours. The reaction liquid was poured into ice water, and solid was precipitated. The resulting reaction mixture was filtered, and the filter cake was washed with water. The filter cake was collected and dried in vacuum to obtain 7-chloro-6-fluoro-4-hydroxy-1-(4-isopropyl-6-methylpyrimidin-5-yl)-3-nitro-1,8-naphthyridin-2(1H)-one (1.2 g, purity: 76%), which was yellow solid. The resulting crude product was directly used in next step. ES-API: [M+H]⁺=394.1.

Step 3: the 7-chloro-6-fluoro-4-hydroxy-1-(4-isopropyl-6-methylpyrimidin-5-yl)-3-nitro-1,8-naphthyridin-2(1H)-one (1.2 g, 3 mmol), 2-fluoro-6-methoxyphenylboronic acid (2 g, 12 mmol), 2-dicyclohexylphosphino-2',6'-dimethoxybiphenyl (123 mg, 0.3 mmol), SPhos-Pd-G2 (216 mg, 0.3 mmol), potassium phosphate (1.9 g, 9 mmol), 15 mL of dioxane, and 3 mL of water were added to a reaction flask. The resulting mixture was stirred in an oil bath at 110° C. for 1 hour to react under the protection of nitrogen, and then the reaction was terminated. The resulting reaction liquid was added with an aqueous solution (30 mL) of 1 M potassium carbonate, and extracted with 20 mL of EtOAc/PE (1:1) once to remove impurities. The water phase was then mixed with an aqueous solution of 6 M potassium carbonate such that the pH was adjusted to 4. Extraction was performed with EtOAc for 3 times. The resulting organic phase was dried by using sodium sulfate and concentrated to obtain 6-fluoro-7-(2-fluoro-6-methoxyphenyl)-4-hydroxy-1-(4-isopropyl-6-methylpyrimidin-5-yl)-3-nitro-1,8-naphthyridin-2(1H)-one (1.1 g, 75%), which was yellow solid. ES-API: [M+H]⁺=483.1.

Step 4: the 6-fluoro-7-(2-fluoro-6-methoxyphenyl)-4-hydroxy-1-(4-isopropyl-6-methylpyrimidin-5-yl)-3-nitro-1,8-naphthyridin-2(1H)-one (1.2 g, 2.48 mmol), diisopropylethylamine (3 g, 23.1 mmol), and ACN (20 mL) were added to a round-bottom flask. Phosphorus oxychloride (2.2 g, 14.5 mmol) was added thereto. The resulting mixture was stirred at 85° C. for 1 hour to react. Whether the reaction was completed was detected by liquid chromatography-mass spectrograph (LC-MS). The resulting reaction liquid was poured into ice water and extracted with EtOAc. The resulting organic phase was dried by using sodium sulfate and concentrated to obtain 4-chloro-6-fluoro-7-(2-fluoro-6-methoxyphenyl)-1-(4-isopropyl-6-methylpyrimidin-5-yl)-3-nitro-1,8-naphthyridin-2(1H)-one (1.1 g, purity: 83%). The resulting crude product was directly used in next step. ES-API: [M+H]⁺=502.1.

Step 5: the 4-chloro-6-fluoro-7-(2-fluoro-6-methoxyphenyl)-1-(4-isopropyl-6-methylpyrimidin-5-yl)-3-nitro-1,8-naphthyridin-2(1H)-one (1 g, 2 mmol), 1-(tert-butyl)3-methyl(R)-piperazin-1,3-dicarboxylate (1.94 g, 8 mmol), N,N-diisopropylethylamine (516 mg, 4 mmol), and N,N- dimethylacetamide (10 mL) were added to a round-bottom flask, and stirred at 120° C. for 2 hours to react. Whether the reaction was completed was detected by LC-MS. The resulting reaction liquid was poured into 30 mL of water. Extraction was performed with EtOAc for 3 times. The resulting organic phase was washed with saturated salt solution/water (v/v, 1:1) for 4 times, dried and concentrated. The resulting crude product was purified by flash column chromatography on silica gel (EtOAc/PE: 0-40%) to obtain 1-(tert-butyl)3-methyl(3R)-4-(6-fluoro-7-(2-fluoro-6-methoxyphenyl)-1-(4-isopropyl-6-methylpyrimidin-5-yl)-3-nitro-2-oxo-1,2-dihydro-1,8-naphthyridin-4-yl)piperazin-1,3-dicarboxylate (1 g, purity: 82%). ES-API: [M+H]$^+$=710.2.

Step 6: the 1-(tert-butyl)3-methyl(3R)-4-(6-fluoro-7-(2-fluoro-6-methoxyphenyl)-1-(4-isopropyl-6-methylpyrimidin-5-yl)-3-nitro-2-oxo-1,2-dihydro-1,8-naphthyridin-4-yl)piperazin-1,3-dicarboxylate (1 g, 1.4 mmol), iron powder (390 mg, 7 mmol), and 15 mL of glacial acetic acid were added to a reaction flask. The resulting mixture was stirred at 80° C. for 1 hour to react. Whether the reaction was completed was detected by LC-MS. The resulting reaction liquid was poured into 50 mL of aqueous solution of sodium bicarbonate and extracted with 30 mL of EtOAc for 3 times. The resulting organic phase was dried and concentrated to obtain tert-butyl (4aR)-11-fluoro-10-(2-fluoro-6-methoxyphenyl)-8-(4-isopropyl-6-methylpyrimidin-5-yl)-5,7-dioxo-1,2,4,4a,5,6,7,8-octahydro-3H-pyrazino[1',2':4,5]pyrazino[2,3-c][1,8]naphthyridin-3-carboxylate (850 mg, 93%), which was yellow solid. ES-API: [M+H]$^+$=648.3.

Step 7: the tert-butyl (4aR)-11-fluoro-10-(2-fluoro-6-methoxyphenyl)-8-(4-isopropyl-6-methylpyrimidin-5-yl)-5,7-dioxo-1,2,4,4a,5,6,7,8-octahydro-3H-pyrazino[1',2':4,5]pyrazino[2,3-c][1,8]naphthyridin-3-carboxylate (450 mg, 0.69 mmol), iodomethane (789 mg, 5.55 mmol), potassium carbonate (286 mg, 2.07 mmol), and 10 mL of acetone were added to a round-bottom flask. The resulting mixture was stirred at 50° C. for 16 hours to react in a sealing tube, and whether the reaction was completed was detected by LC-MS. The resulting reaction liquid was filtered by using diatomite. The filtrate was concentrated. The resulting crude product was purified by flash column chromatography on silica gel (EtOAc/PE: 0-60%) to obtain tert-butyl (4aR)-11-fluoro-10-(2-fluoro-6-methoxyphenyl)-8-(4-isopropyl-6-methylpyrimidin-5-yl)-6-methyl-5,7-dioxo-1,2,4,4a,5,6,7,8-octahydro-3H-pyrazino[1',2':4,5]pyrazino[2,3-c][1,8]naphthyridin-3-carboxylate (260 mg, 57%), which was yellow solid. ES-API: [M+H]$^+$=662.2.

Step 8: the tert-butyl (4aR)-11-fluoro-10-(2-fluoro-6-methoxyphenyl)-8-(4-isopropyl-6-methylpyrimidin-5-yl)-6-methyl-5,7-dioxo-1,2,4,4a,5,6,7,8-octahydro-3H-pyrazino[1',2':4,5]pyrazino[2,3-c][1,8]naphthyridin-3-carboxylate (260 mg, 0.39 mmol), 1 mL of DCM, and 3 mL of TFA were added to a round-bottom flask. The resulting mixture was stirred at room temperature for 1 hour, and whether the reaction was completed was detected by LC-MS. The resulting reaction liquid was concentrated to obtain (4aR)-11-fluoro-10-(2-fluoro-6-methoxyphenyl)-8-(4-isopropyl-6-methylpyrimidin-5-yl)-6-methyl-2,3,4,4a,6,8-hexahydro-1H-pyrazino[1',2':4,5]pyrazino[2,3-c][1,8]naphthyridin-5,7-dione (219 mg), which was yellow solid. The resulting crude product was directly used in next step. ES-API: [M+H]$^+$=562.2.

Step 9: the (4aR)-11-fluoro-10-(2-fluoro-6-methoxyphenyl)-8-(4-isopropyl-6-methylpyrimidin-5-yl)-6-methyl-2,3,4,4a,6,8-hexahydro-1H-pyrazino[1',2':4,5]pyrazino[2,3-c][1,8]naphthyridin-5,7-dione (219 mg, 0.39 mmol), 3 mL of DCM, and triethylamine (158 mg, 1.56 mmol) were added to a 50 mL round-bottom flask. The resulting reaction liquid was cooled to 0° C., and then added dropwise with a solution of acryloyl chloride in DCM (71 mg, 0.78 mmol, 0.5 mL). The resulting mixture was stirred at 0° C. for 10 minutes to react. The resulting reaction liquid was added with 40 mL of saturated solution of sodium bicarbonate and extracted with 20 mL of DCM for 3 times. The resulting organic phase was dried and concentrated to obtain (4aR)-3-acryloyl-11-fluoro-10-(2-fluoro-6-methoxyphenyl)-8-(4-isopropyl-6-methylpyrimidin-5-yl)-6-methyl-2,3,4,4a,6,8-hexahydro-1H-pyrazino[1',2':4,5]pyrazino[2,3-c][1,8]naphthyridin-5,7-dione (240 mg, purity: 87%), which was yellow solid. The resulting crude product was directly used in next step. ES-API: [M+H]$^+$=616.3.

Step 10: the (4aR)-3-acryloyl-11-fluoro-10-(2-fluoro-6-methoxyphenyl)-8-(4-isopropyl-6-methylpyrimidin-5-yl)-6-methyl-2,3,4,4a,6,8-hexahydro-1H-pyrazino[1',2':4,5]pyrazino[2,3-c][1,8]naphthyridin-5,7-dione (240 mg, 0.39 mmol) and 3 mL of DCM were added to a round-bottom flask. The resulting reaction liquid was cooled to 0° C., and then added dropwise with a solution (6 mL) of 17% boron tribromide in DCM. After the completion of dropwise addition, the resulting mixture was stirred at room temperature for 2 hours to react. The resulting reaction liquid was poured into 30 mL of glacial saturated solution of NaHCO$_3$ and extracted with 20 mL of DCM for 3 times. The resulting organic phase was dried and concentrated, and the resulting crude product was purified by preparative scale HPLC to obtain product (4aR)-3-acryloyl-11-fluoro-10-(2-fluoro-6-hydroxyphenyl)-8-(4-isopropyl-6-methylpyrimidin-5-yl)-6-methyl-2,3,4,4a,6,8-hexahydro-1H-pyrazino[1',2':4,5]pyrazino[2,3-c][1,8]naphthyridin-5,7-dione (Z21, 130 mg, 55%), which was yellow solid. ES-API: [M+H]$^+$=602.2.

Step 11: the compound (4aR)-3-acryloyl-11-fluoro-10-(2-fluoro-6-hydroxyphenyl)-8-(4-isopropyl-6-methylpyrimidin-5-yl)-6-methyl-2,3,4,4a,6,8-hexahydro-1H-pyrazino[1',2':4,5]pyrazino[2,3-c][1,8]naphthyridin-5,7-dione (130 mg) was resolved by preparative scale chiral HPLC (column type: Chiralpak IE: 10 μm, 20*250 mm; mobile phase: hexane:EtOH:diethylamine=70:30:0.2; flow rate: 15 ml/min; and column temperature: room temperature) to obtain the following atropisomer compounds. One of the atropisomer compounds had a structure arbitrarily specified as Z21-1 (peak 2, retention time: 12.33 min, 47 mg), which was yellow solid. ES-API: [M+H]$^+$=602.2. $^1$HNMR (500 MHz, DMSO-d$_6$): 10.17 (s, 1H), 9.03 (s, 1H), 8.41 (d, J=9 Hz, 1H), 7.26-7.25 (m, 1H), 7.08-7.05 (m, 1H), 6.68-6.66 (m, 2H), 6.17-6.14 (m, 1H), 5.77-5.75 (m, 1H), 4.75-4.73 (m, 1H), 4.46-4.44 (m, 1H), 4.0-3.95 (m, 1H), 3.55-3.54 (m, 2H), 3.41 (s, 3H), 3.20-3.18 (m, 1H), 2.85-2.83 (m, 1H), 2.68-2.65 (m, 1H), 2.00 (s, 3H), 1.13 (d, J=6.5 Hz, 3H), 1.06 (d, J=6.5 Hz, 3H). The other atropisomer compound had a structure arbitrarily specified as Z21-2 (peak 1, retention time: 10.58 min, 48 mg), which was yellow solid. ES-API: [M+H]$^+$=602.2. $^1$HNMR (500 MHz, DMSO-d$_6$): 10.16 (s, 1H), 9.03 (s, 1H), 8.41 (d, J=9 Hz, 1H), 7.26-7.25 (m, 1H), 7.08-7.05 (m, 1H), 6.68-6.66 (m, 2H), 6.17-6.14 (m, 1H), 5.77-5.75 (m, 1H), 4.75-4.73 (m, 1H), 4.46-4.44 (m, 1H), 4.0-3.95 (m, 1H), 3.55-3.54 (m, 2H), 3.41 (s, 3H), 3.20-3.18 (m, 1H), 2.65-2.60 (m, 1H), 2.52-2.51 (m, 1H), 2.20 (s, 3H), 1.06 (d, J=6.5 Hz, 3H), 0.86 (d, J=6.5 Hz, 3H). The isomer compounds were detected by analytical scale chiral HPLC (column type: Chiralpak IE: 5 μm, 4.6*250 mm; mobile phase: hexane:EtOH:aminomethanol=70:30:0.2; flow rate: 1 ml/min; and column temperature=30° C.).

Example 22 Preparation of Compound Z22
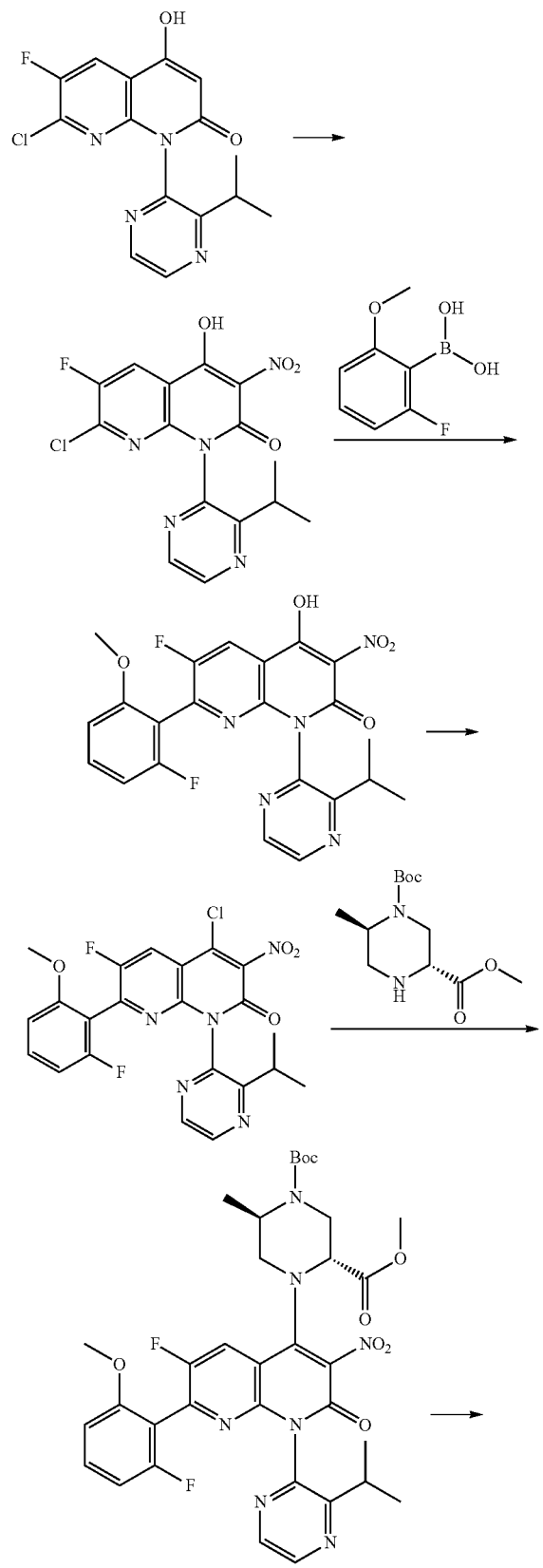
-continued
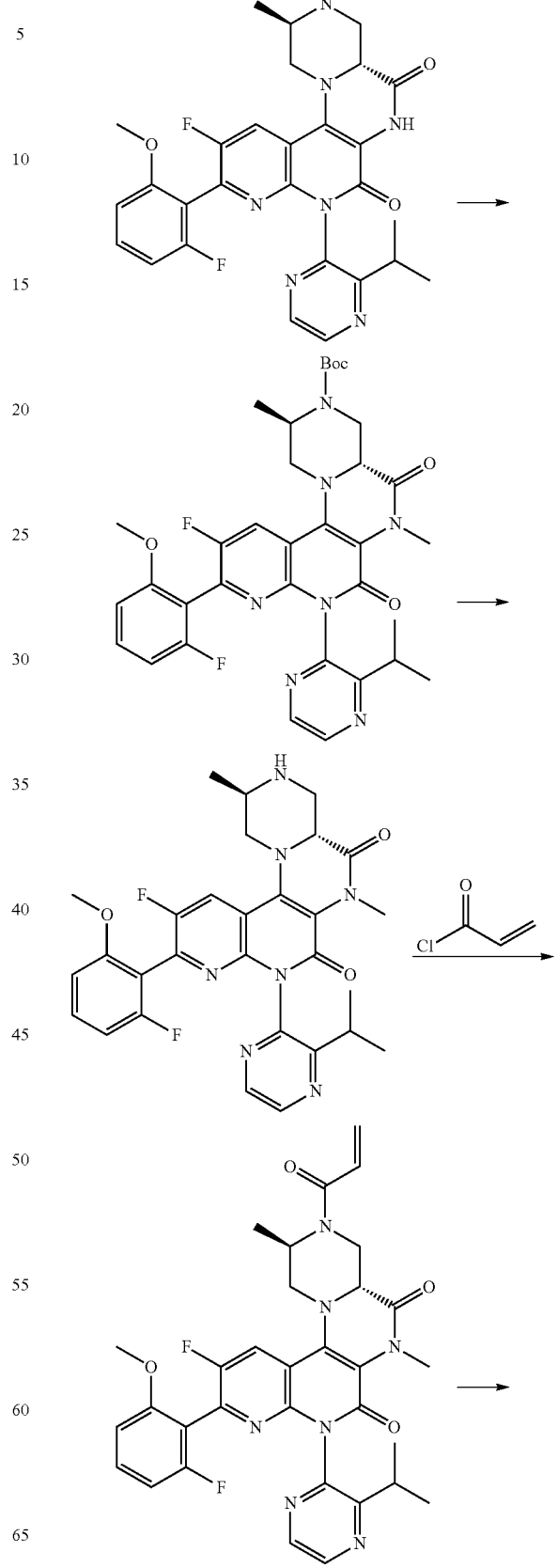

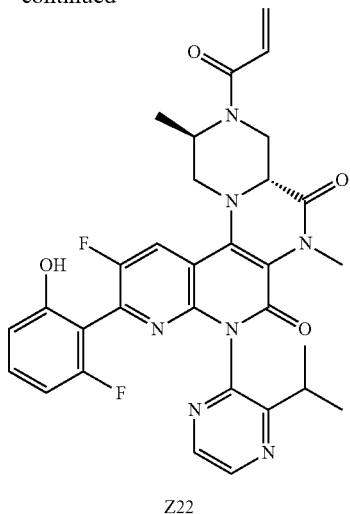

Z22

Step 1: 7-chloro-6-fluoro-4-hydroxy-1-(3-isopropylpyrazin-2-yl)-1,8-naphthyridin-2(1H)-one (2 g, 6 mmol) was dissolved in acetic acid (5 mL), orderly added with sodium nitrite (41 mg, 0.6 mmol) and concentrated nitric acid (1.5 g, 24 mmol), and stirred at room temperature for 30 minutes to react. The resulting reaction liquid was slowly poured into 100 mL of ice water. The precipitated solid was filtered. The filter cake was washed with 20 ml of ice water and dried in vacuum to obtain product 7-chloro-6-fluoro-4-hydroxy-1-(3-isopropylpyrazin-2-yl)-3-nitro-1,8-naphthyridin-2(1H)-one (1.5 g, 65%), which was yellow solid. ES-API: [M+H]$^+$=380.2.

Step 2: the 7-chloro-6-fluoro-4-hydroxy-1-(3-isopropylpyrazin-2-yl)-3-nitro-1,8-naphthyridin-2(1H)-one (1.5 g, 3.94 mmol), (2-fluoro-6-methoxyphenyl)boric acid (2.04 g, 12 mmol), SPhos-Pd-G2 (288 mg, 0.4 mmol), 2-dicyclohexylphosphino-2',6'-dimethoxybiphenyl (164 mg, 0.4 mmol), potassium phosphate (2.5 g, 12 mmol), 10 mL of water, and 40 mL of dioxane were added to a 100 mL three-necked round-bottom flask. The resulting mixture was stirred at 100° C. for 2-3 hours to react under the protection of nitrogen. After the completion of the reaction, the resulting reaction liquid was cooled to room temperature, added with 80 mL of water and 100 mL of methyl tert-butyl ether extracted once. The water phase was then mixed with 1M hydrochloric acid solution such that the pH was adjusted to a range of 3 to 5, and extracted with EtOAc (200 mL*2). The resulting combined EtOAc phase was dried by using anhydrous sodium sulfate, and filtered. The filtrate was dried in vacuum to obtain product 6-fluoro-7-(2-fluoro-6-methoxyphenyl)-4-hydroxy-1-(3-isopropylpyrazin-2-yl)-3-nitro-1,8-naphthyridin-2(1H)-one (1.6 g, crude), which was faint yellow solid. ES-API: [M+H]$^+$=470.1.

Step 3: the 6-fluoro-7-(2-fluoro-6-methoxyphenyl)-4-hydroxy-1-(3-isopropylpyrazin-2-yl)-3-nitro-1,8-naphthyridin-2(1H)-one (1.6 g, 3.4 mmol) was dissolved in ACN (30 mL), orderly added with phosphorus oxychloride (2.6 g, 17 mmol) and N,N-diisopropylethylamine (3 g, 23.8 mmol), and gradually heated to 80° C. and stirred for 30 minutes to react. The resulting reaction liquid was concentrated, added with 30 mL of cold ACN, then added dropwise to 150 mL of saturated sodium bicarbonate solution in an ice water bath, and extracted with EtOAc (200 mL*2). The resulting combined organic phase was washed with 200 mL of saturated salt solution once. The organic phase was then dried by using anhydrous sodium sulfate, filtered, dried and concentrated, and the resulting crude product was purified by flash column chromatography on silica gel (EtOAc/PE: 0-50%) to obtain 4-chloro-6-fluoro-7-(2-fluoro-6-methoxyphenyl)-1-(3-isopropylpyrazin-2-yl)-3-nitro-1,8-naphthyridin-2(1H)-one (340 mg, Y: 20%), which was yellow solid. ES-API: [M+H]$^+$=488.2.

Step 4: the 4-chloro-6-fluoro-7-(2-fluoro-6-methoxyphenyl)-1-(3-isopropylpyrazin-2-yl)-3-nitro-1,8-naphthyridin-2(1H)-one (310 mg, 0.64 mmol) was dissolved in N,N-dimethylacetamide (5 mL), orderly added with 1-(tert-butyl)3-methyl(3R,6R)-6-methylpiperazin-1,3-dicarboxylic acid (247 mg, 0.96 mmol) and N,N-diisopropylethylamine (250 mg, 1.92 mmol), and stirred at 120° C. for 2 hours to react. The resulting reaction liquid was added with 50 mL of EtOAc, and washed with 30 mL of saturated salt solution for 3 times. The EtOAc phase was dried and concentrated, and the resulting crude product was purified by flash column chromatography on silica gel (EtOAc/PE: 0-80%) to obtain product 1-(tert-butyl)3-methyl(3R,6R)-4-(6-fluoro-7-(2-fluoro-6-methoxyphenyl)-1-(3-isopropylpyrazin-2-yl)-3-nitro-2-oxo-1,2-dihydro-1,8-naphthyridin-4-yl)-6-methylpiperazin-1,3-dicarboxylate (317 mg, Y: 70%), which was yellow solid. ES-API: [M+H]$^+$=710.2.

Step 5: the 1-(tert-butyl)3-methyl(3R,6R)-4-(6-fluoro-7-(2-fluoro-6-methoxyphenyl)-1-(3-isopropylpyrazin-2-yl)-3-nitro-2-oxo-1,2-dihydro-1,8-naphthyridin-4-yl)-6-methylpiperazin-1,3-dicarboxylate (280 mg, 0.4 mmol) was dissolved in acetic acid (4 mL), added with iron powder (78 mg, 1.4 mmol), and stirred at 80° C. for 30 minutes to react. The resulting reaction liquid was orderly added with 50 mL of EtOAc and 30 mL of saturated sodium bicarbonate solution. The resulting suspension was filtered by using diatomite. The filter cake was washed with EtOAc. The resulting organic phase was separated, washed orderly with 100 mL of saturated sodium bicarbonate and 30 mL of saturated salt solution, dried and concentrated to obtain product tert-butyl (2R,4aR)-11-fluoro-10-(2-fluoro-6-methoxyphenyl)-8-(3-isopropylpyrazin-2-yl)-2-methyl-5,7-dioxo-1,2,4,4a,5,6,7,8-octahydro-3H-pyrazino[1',2':4,5]pyrazino[2,3-c][1,8]naphthyridin-3-carboxylate (312 mg, crude), which was yellow solid. ES-API: [M+H]$^+$=648.1.

Step 6: the tert-butyl (2R,4aR)-11-fluoro-10-(2-fluoro-6-methoxyphenyl)-8-(3-isopropylpyrazin-2-yl)-2-methyl-5,7-dioxo-1,2,4,4a,5,6,7,8-octahydro-3H-pyrazino[1',2':4,5]pyrazino[2,3-c][1,8]naphthyridin-3-carboxylate (295 mg, 0.46 mmol), 3 mL of acetone, anhydrous potassium carbonate (1 g, 6.9 mmol), and iodomethane (253 mg, 1.84 mmol) were added to a 15 mL sealing tube. The sealing tube was sealed, and the resulting mixture was stirred at 55° C. for 18 hours to react. The resulting reaction liquid was added with 50 mL of EtOAc, washed with 20 mL of saturated salt solution for 3 times, dried and concentrated to obtain product tert-butyl (2R,4aR)-11-fluoro-10-(2-fluoro-6-methoxyphenyl)-8-(3-isopropylpyrazin-2-yl)-2,6-dimethyl-5,7-dioxo-1,2,4,4a,5,6,7,8-octahydro-3H-pyrazino[1',2':4,5]pyrazino[2,3-c][1,8]naphthyridin-3-carboxylate (356 mg, crude), which was yellow solid. ES-API: [M+H]$^+$=662.2.

Step 7: the tert-butyl (2R,4aR)-11-fluoro-10-(2-fluoro-6-methoxyphenyl)-8-(3-isopropylpyrazin-2-yl)-2,6-dimethyl-5,7-dioxo-1,2,4,4a,5,6,7,8-octahydro-3H-pyrazino[1',2':4,5]pyrazino[2,3-c][1,8]naphthyridin-3-carboxylate (356 mg, 0.54 mmol) was dissolved in DCM (8 mL), and added with TFA (4 mL). The resulting mixture was stirred at room temperature for 2 hours. The resulting reaction liquid was concentrated to obtain product (2R,4aR)-11-fluoro-10-(2-fluoro-6-methoxyphenyl)-8-(3-isopropylpyrazin-2-yl)-2,6- dimethyl-2,3,4,4a,6,8-hexahydro-1H-pyrazino[1',2':4,5]
pyrazino[2,3-c][1,8]naphthyridin-5,7-dione (415 mg, crude), which was directly used in next step. ES-API: [M+H]⁺=562.2.

Step 8: the (2R,4aR)-11-fluoro-10-(2-fluoro-6-methoxyphenyl)-8-(3-isopropylpyrazin-2-yl)-2,6-dimethyl-2,3,4,4a,6,8-hexahydro-1H-pyrazino[1',2':4,5]pyrazino[2,3-c][1,8]naphthyridin-5,7-dione (415 mg, 0.74 mmol) was dissolved in DCM (15 mL), and added with triethylamine (3.0 mL, 21.62 mmol). The resulting reaction liquid was cooled to 0° C., and then added dropwise with acryloyl chloride (115 mg, 1.28 mmol). The resulting mixture was stirred at 0° C. for 5 minutes to react. The resulting reaction liquid was added with 50 mL of DCM, washed with 50 mL of saturated solution of NaHCO₃ and 80 mL of saturated salt solution, dried and concentrated. The resulting crude product was purified by flash column chromatography on silica gel (EtOAc/PE: 0-60%) to obtain product (2R,4aR)-3-acryloyl-11-fluoro-10-(2-fluoro-6-methoxyphenyl)-8-(3-isopropylpyrazin-2-yl)-2,6-dimethyl-2,3,4,4a,6,8-hexahydro-1H-pyrazino[1',2':4,5]pyrazino[2,3-c][1,8]naphthyridin-5,7-dione (201 mg, Y: 44%), which was yellow solid. ES-API: [M+H]⁺=616.2.

Step 9: under the condition of an ice water bath, the (2R,4aR)-3-acryloyl-11-fluoro-10-(2-fluoro-6-methoxyphenyl)-8-(3-isopropylpyrazin-2-yl)-2,6-dimethyl-2,3,4,4a,6,8-hexahydro-1H-pyrazino[1',2':4,5]pyrazino[2,3-c][1,8]naphthyridin-5,7-dione (201 mg, 0.33 mmol) was added to dry DCM (3.0 mL), and then added with boron tribromide (5.0 mL) to react at room temperature for 30 minutes. Under the condition of the ice water bath, the above reaction liquid was added dropwise to saturated sodium bicarbonate solution, extracted with DCM (50 mL) twice, dried and concentrated. The resulting crude product was purified by preparative scale HPLC to obtain product (2R,4aR)-3-acryloyl-11-fluoro-10-(2-fluoro-6-hydroxyphenyl)-8-(3-isopropylpyrazin-2-yl)-2,6-dimethyl-2,3,4,4a,6,8-hexahydro-1H-pyrazino[1',2':4,5]pyrazino[2,3-c][1,8]naphthyridin-5,7-dione (Z22, 65 mg, Y: 33%) ES-API: [M+H]⁺=602.2. ¹H NMR (500 MHz, DMSO-d₆) δ 10.17 (s, 1H), 8.75 (dd, J=4.0, 2.6 Hz, 1H), 8.55 (dd, J=15.5, 2.4 Hz, 1H), 8.05-7.98 (m, 1H), 7.26 (dd, J=15.0, 8.2 Hz, 1H), 7.03 (dd, J=16.8, 10.0 Hz, 1H), 6.73 (d, J=8.4 Hz, 1H), 6.67 (t, J=8.8 Hz, 1H), 6.16 (t, J=12.4 Hz, 1H), 5.74 (dd, J=20.0, 11.8 Hz, 1H), 4.78 (s, 1H), 4.65-4.56 (m, 1H), 4.00 (t, J=28.0 Hz, 1H), 3.80-3.70 (m, 1H), 3.36 (d, J=2.4 Hz, 3H), 3.05-2.62 (m, 2H), 1.63-1.48 (m, 3H), 1.18 (d, J=6.8 Hz, 2H), 1.10 (d, J=6.8 Hz, 3H), 1.00 (d, J=6.7 Hz, 2H).

Example 23 Preparation of Compound Z23

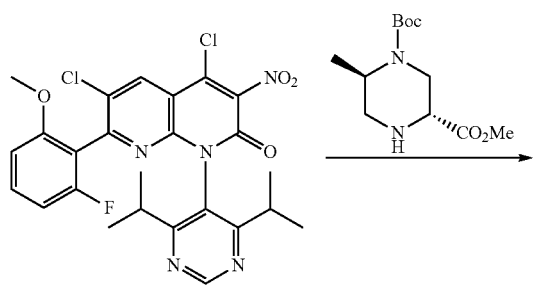

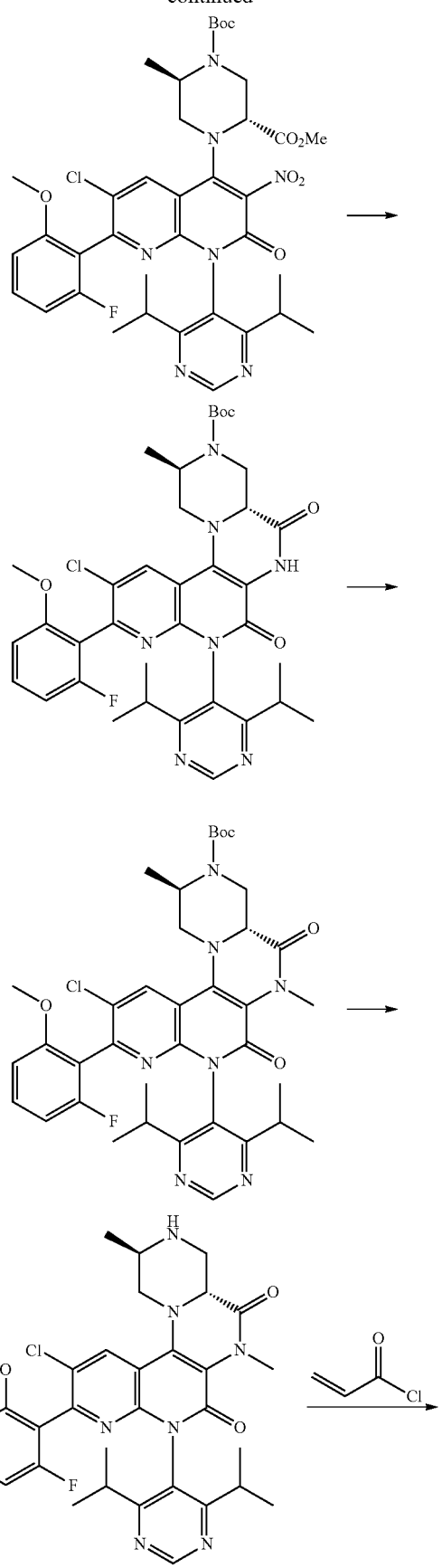

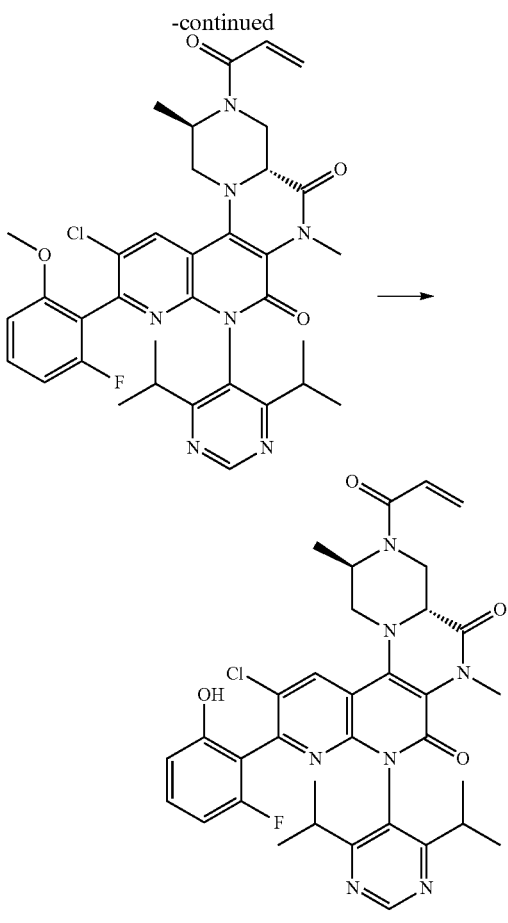

Z23

Step 1: 4-chloro-6-fluoro-7-(2-fluoro-6-methoxyphenyl)-1-(4-isopropyl-6-methylpyrimidin-5-yl)-3-nitro-1,8-naphthyridin-2(1H)-one (0.8 g, 1.46 mmol), 1-(tert-butyl)3-methyl(3R,6R)-6-methylpiperazin-1,3-dicarboxylate (567 mg, 2.2 mmol), N,N-diisopropylethylamine (565 mg, 4.38 mmol), and N,N-dimethylacetamide (10 mL) were added to a round-bottom flask, and stirred at 120° C. for 1 hour to react. Whether the reaction was completed was detected by LC-MS. The resulting reaction liquid was poured into 30 mL of water. Extraction was performed with EtOAc for 3 times. The resulting organic phase was washed with saturated salt solution/water (v/v, 1:1) for 4 times, dried and concentrated to obtain 1-(tert-butyl)3-methyl(3R,6R)-4-(6-chloro-1-(4,6-diisopropylpyrimidin-5-yl)-7-(2-fluoro-6-methoxyphenyl)-3-nitro-2-oxo-1,2-dihydro-1,8-naphthyridin-4-yl)-6-methylpiperazin-1,3-dicarboxylate (1 g, yield: 89%). ES-API: [M+H]⁺=768.3.

Step 2: the 1-(tert-butyl)3-methyl(3R,6R)-4-(6-chloro-1-(4,6-diisopropylpyrimidin-5-yl)-7-(2-fluoro-6-methoxyphenyl)-3-nitro-2-oxo-1,2-dihydro-1,8-naphthyridin-4-yl)-6-methylpiperazin-1,3-dicarboxylate (1 g, 1.3 mmol), iron powder (300 mg, 5.3 mmol), and 8 mL of glacial acetic acid was added to a reaction flask. The resulting mixture was stirred at 80° C. for 0.5 hour to react. Whether the reaction was completed was detected by LC-MS. The resulting reaction liquid was poured into 50 mL of aqueous solution of sodium bicarbonate and extracted with 30 mL of EtOAc for 3 times. The resulting organic phase was dried and concentrated to obtain crude product tert-butyl (2R,4aR)-11-chloro-8-(4,6-diisopropylpyrimidin-5-yl)-10-(2-fluoro-6-methoxyphenyl)-2-methyl-5,7-dioxo-1,2,4,4a,5,6,7,8-octahydro-3H-pyrazino[1',2':4,5]pyrazino[2,3-c][1,8]naphthyridin-3-carboxylate (761 mg, 83%), which was yellow solid. ES-API: [M+H]⁺=706.3.

Step 3: the tert-butyl (2R,4aR)-11-chloro-8-(4,6-diisopropylpyrimidin-5-yl)-10-(2-fluoro-6-methoxyphenyl)-2-methyl-5,7-dioxo-1,2,4,4a,5,6,7,8-octahydro-3H-pyrazino[1',2':4,5]pyrazino[2,3-c][1,8]naphthyridin-3-carboxylate (761 mg, 1.08 mmol), iodomethane (1.5 g, 10.79 mmol), potassium carbonate (596 mg, 4.32 mmol), and 15 mL of acetone were added to a round-bottom flask. The resulting mixture was stirred at 50° C. for 16 hours to react in a sealing tube, and whether the reaction was completed was detected by LC-MS. The resulting reaction liquid was filtered by using diatomite. The filtrate was concentrated to obtain crude product tert-butyl (2R,4aR)-11-chloro-8-(4,6-diisopropylpyrimidin-5-yl)-10-(2-fluoro-6-methoxyphenyl)-2,6-dimethyl-5,7-dioxo-1,2,4,4a,5,6,7,8-octahydro-3H-pyrazino[1',2':4,5]pyrazino[2,3-c][1,8]naphthyridin-3-carboxylate (738 mg, 95%), which was yellow solid. ES-API: [M+H]⁺=720.3.

Step 4: the tert-butyl (2R,4aR)-11-chloro-8-(4,6-diisopropylpyrimidin-5-yl)-10-(2-fluoro-6-methoxyphenyl)-2,6-dimethyl-5,7-dioxo-1,2,4,4a,5,6,7,8-octahydro-3H-pyrazino[1',2':4,5]pyrazino[2,3-c][1,8]naphthyridin-3-carboxylate (738 mg, 1.02 mmol), 2 mL of DCM, and 5 mL of TFA were added to a round-bottom flask. The resulting mixture was stirred at room temperature for 1 hour, and whether the reaction was completed was detected by LC-MS. The resulting reaction liquid was concentrated to obtain (2R,4aR)-11-chloro-8-(4,6-diisopropylpyrimidin-5-yl)-10-(2-fluoro-6-methoxyphenyl)-2,6-dimethyl-2,3,4,4a,6,8-hexahydro-1H-pyrazino[1',2':4,5]pyrazino[2,3-c][1,8]naphthyridin-5,7-dione (632 mg, 100%), which was yellow solid. The resulting crude product was directly used in next step. ES-API: [M+H]⁺=620.3.

Step 5: the (2R,4aR)-11-chloro-8-(4,6-diisopropylpyrimidin-5-yl)-10-(2-fluoro-6-methoxyphenyl)-2,6-dimethyl-2,3,4,4a,6,8-hexahydro-1H-pyrazino[1',2':4,5]pyrazino[2,3-c][1,8]naphthyridin-5,7-dione (632 mg, 1.02 mmol), 3 mL of DCM, and triethylamine (677 mg, 6.7 mmol) were added to a 50 mL round-bottom flask. The resulting reaction liquid was cooled to 0° C., and then added dropwise with a solution of acryloyl chloride in DCM (249 mg, 2.77 mmol, 0.5 mL). The resulting mixture was stirred at 0° C. for 10 minutes to react. The resulting reaction liquid was added with 40 mL of saturated solution of sodium bicarbonate and extracted with 20 mL of DCM for 3 times. The resulting organic phase was dried and concentrated, and the resulting crude product was purified by flash column chromatography on silica gel (EtOAc/PE: 0-60%) to obtain (2R,4aR)-3-acryloyl-11-chloro-8-(4,6-diisopropylpyrimidin-5-yl)-10-(2-fluoro-6-methoxyphenyl)-2,6-dimethyl-2,3,4,4a,6,8-hexahydro-1H-pyrazino[1',2':4,5]pyrazino[2,3-c][1,8]naphthyridin-5,7-dione (500 mg, 72%), which was yellow solid. The crude product was directly used in next step. ES-API: [M+H]⁺=674.2.

Step 6: the (2R,4aR)-3-acryloyl-11-chloro-8-(4,6-diisopropylpyrimidin-5-yl)-10-(2-fluoro-6-methoxyphenyl)-2,6-dimethyl-2,3,4,4a,6,8-hexahydro-1H-pyrazino[1',2':4,5]pyrazino[2,3-c][1,8]naphthyridin-5,7-dione (500 mg, 0.74 mmol) and 3 mL of DCM were added to a round-bottom flask. The resulting reaction liquid was cooled to 0° C., and then added dropwise with a solution (12 mL) of 17% boron tribromide in DCM. After the completion of dropwise addition, the resulting mixture was stirred at 25° C. for 25 hours to react. The resulting reaction liquid was poured into 30 mL of glacial saturated solution of NaHCO$_3$ and extracted with 20 mL of DCM for 3 times. The resulting organic phase was dried and concentrated, and the resulting crude product was purified by preparative scale HPLC to obtain product (2R, 4aR)-3-acryloyl-11-chloro-8-(4,6-diisopropylpyrimidin-5-yl)-10-(2-fluoro-6-hydroxyphenyl)-2,6-dimethyl-2,3,4,4a,6,8-hexahydro-1H-pyrazino[1',2':4,5]pyrazino[2,3-c][1,8]naphthyridin-5,7-dione (Z23, 200 mg, 40%), which was yellow solid. $^1$HNMR (500 MHz, DMSO-d$_6$): δ 10.10-10.5 (m, 1H), 9.11 (s, 1H), 8.25-8.23 (m 1H), 7.22-7.21 (m, 1H), 6.86-6.74 (m, 1H), 6.67-6.64 (m, 2H), 6.17-6.14 (m, 1H), 5.75-5.71 (m, 1H), 5.04-5.01 (m, 1H), 4.62-4.42 (m, 1H), 4.03-3.98 (m, 1H), 3.74-3.72 (m, 1H), 3.42-3.33 (m, 5H), 2.77-2.64 (m, 2H), 1.56-1.52 (m, 3H), 1.05-0.97 (m, 9H), 0.86-0.84 (m, 3H). ES-API: [M+H]$^+$=660.3.

Example 24 Preparation of Compounds Z24, Z24-1, and Z24-2

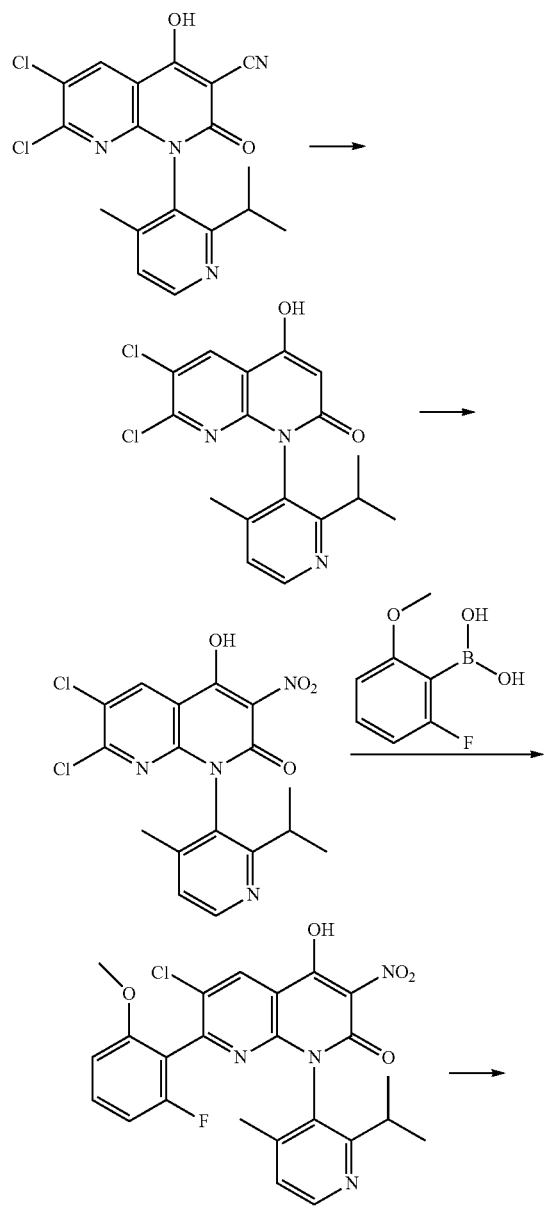

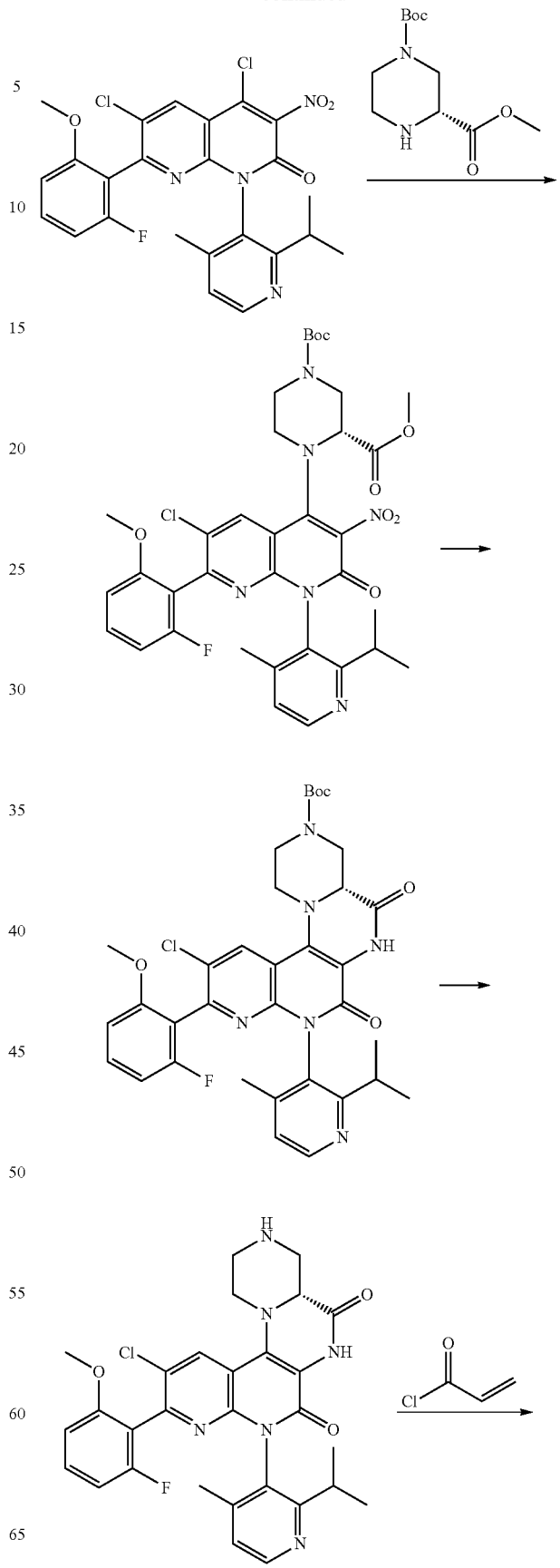

-continued

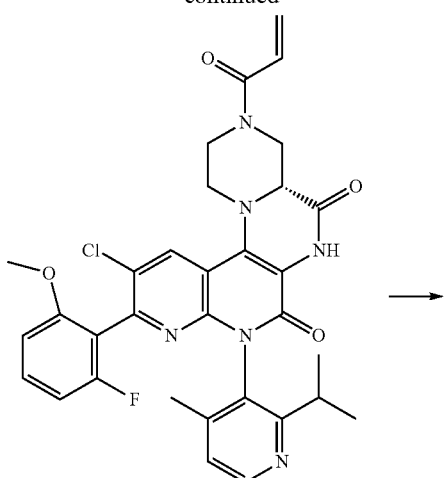

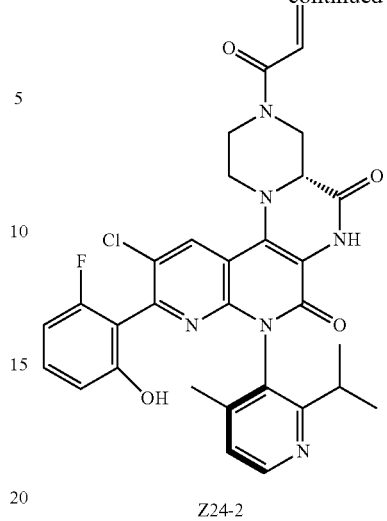

Z24-2

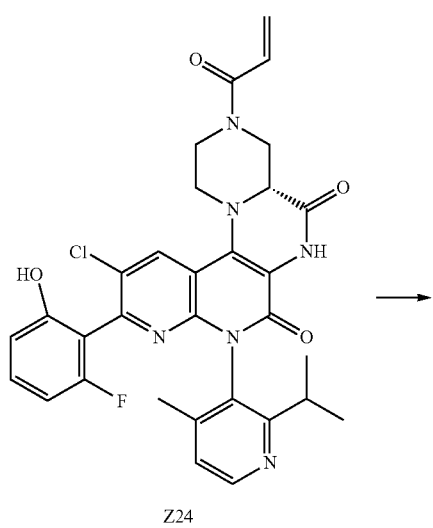

Z24

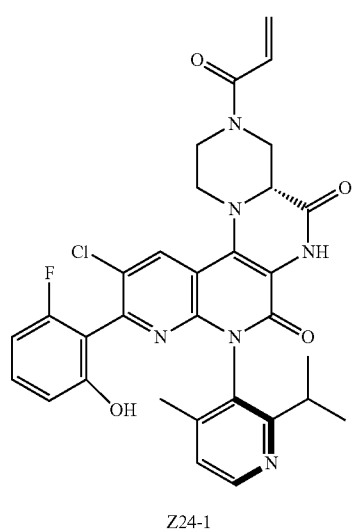

Z24-1

Step 1: 6,7-dichloro-4-hydroxy-1-(2-isopropyl-4-methylpyridin-3-yl)-2-oxo-1,2-dihydro-1,8-naphthyridin-3-carbonitrile (30.0 g, 77.319 mmol) was suspended in a mixed solution of 1, 4-dioxane (120 mL) and water (120 mL), and slowly added with concentrated sulfuric acid (120 mL). The resulting mixture was stirred at 120° C. for 36 hours to react. Cooled reaction liquid was poured into 200 mL of ice water, mixed with sodium carbonate to adjust the pH to a range of 2 to 3, and extracted with EtOAc (1000 mL*2). The resulting combined EtOAc phase was dried by anhydrous sodium sulfate, and filtered. The filtrate was dried in vacuum to obtain product 6,7-dichloro-4-hydroxy-1-(2-isopropyl-4-methylpyridin-3-yl)-1,8-naphthyridin-2(1H)-one (24 g, Y: 85.7%), which was light brown solid. ES-API: [M+H]$^+$= 364.1.

Step 2: the 6,7-dichloro-4-hydroxy-1-(2-isopropyl-4-methylpyridin-3-yl)-3,8-naphthyridin-2(1H)-one (3.16 g, 8.705 mmol) was dissolved in acetic acid (15 mL), orderly added with sodium nitrite (100 mg, 1.58 mmol) and concentrated nitric acid (5.0 mL, 74.52 mmol), and stirred at room temperature for 30 minutes to react. The resulting reaction liquid was slowly poured into 100 mL ice water. The precipitated solid was filtered. The filter cake was washed with 20 ml of ice water and dried in vacuum to obtain product 6,7-dichloro-4-hydroxy-1-(2-isopropyl-4-methylpyridin-3-yl)-3-nitro-1,8-naphthyridin-2(1H)-one (3.5 g, Y: 92%), which was yellow solid. ES-API: [M+H]$^+$= 409.1.

Step 3: the 6,7-dichloro-4-hydroxy-1-(2-isopropyl-4-methylpyridin-3-yl)-3-nitro-1,8-naphthyridin-2(1H)-one (3.5 g, 8.570 mmol), (2-fluoro-6-methoxyphenyl)boric acid (5.8 g, 34.10 mmol), tetrakis(triphenylphosphine)palladium (1.15 g, 0.9956 mmol), sodium carbonate (3.5 g, 33.02 mmol), 10 mL of water, and 40 mL of dioxane were added to a 100 mL three-necked round-bottom flask. The resulting mixture was stirred at 100° C. for 2-3 hours to react under the protection of nitrogen. After the completion of the reaction, the resulting reaction liquid was cooled to room temperature, added with 80 mL of water and 100 mL of methyl tert-butyl ether, and extracted once. The water phase was then mixed with 1M hydrochloric acid solution to adjust the pH to a range of 3 to 5, and extracted with EtOAc (200 mL*2). The resulting combined EtOAc phase was dried by anhydrous sodium sulfate, and filtered. The filtrate was dried in vacuum to obtain product 6-chloro-7-(2-fluoro-6-methoxyphenyl)-4-hydroxy-1-(2-isopropyl-4-methylpyridin-3-yl)-3-nitro-1,8-naphthyridin-2(1H)-one (4.5 g, crude), which was faint yellow solid. ES-API: [M+H]$^+$=499.1.

Step 4: the 6-chloro-7-(2-fluoro-6-methoxyphenyl)-4-hydroxy-1-(2-isopropyl-4-methylpyridin-3-yl)-3-nitro-1,8-naphthyridin-2(1H)-one (4.6 g, 8.57 mmol) was dissolved in ACN (30 mL), orderly added with phosphorus oxychloride (7.5 g, 48.92 mmol) and N,N-diisopropylethylamine (10.5 g, 81.24 mmol), and gradually warmed to 80° C. and stirred for 30 minutes to react. The resulting reaction liquid was concentrated, added with 30 mL of cold ACN, added dropwise to 150 mL of saturated sodium bicarbonate solution in an ice water bath, and extracted with EtOAc (200 mL*2). The resulting combined EtOAc phase was washed with 200 mL of saturated salt solution once, dried by anhydrous sodium sulfate, and filtered. After the organic phase was dried and concentrated, the resulting crude product was purified by flash column chromatography on silica gel (EtOAc/PE: 0-50%) to obtain 4,6-dichloro-7-(2-fluoro-6-methoxyphenyl)-1-(2-isopropyl-4-methylpyridin-3-yl)-3-nitro-1,8-naphthyridin-2(1H)-one (3.05 g, Y: 76%), which was yellow solid. ES-API: [M+H]$^+$=517.2.

Step 5: the 4,6-dichloro-7-(2-fluoro-6-methoxyphenyl)-1-(2-isopropyl-4-methylpyridin-3-yl)-3-nitro-1,8-naphthyridin-2(1H)-one (2.5 g, 4.843 mmol) was dissolved in N,N-dimethylacetamide (25 mL), orderly added with 1-(tert-butyl)3-methyl(R)-piperazin-1,3-dicarboxylate (3.5 g, 14.34 mmol) and N,N-diisopropylethylamine (2.0 g, 15.47 mmol), and stirred at 120° C. for 2 hours to react. The resulting reaction liquid was added with 80 mL of EtOAc, and washed with 80 mL of saturated salt solution for 3 times. The EtOAc phase was dried and concentrated, and the resulting crude product was purified by flash column chromatography on silica gel (EtOAc/PE: 0-80%) to obtain product 1-(tert-butyl)3-methyl(3R)-4-(6-chloro-7-(2-fluoro-6-methoxyphenyl)-1-(2-isopropyl-4-methylpyridin-3-yl)-3-nitro-2-oxo-1,2-dihydro-1,8-naphthyridin-4-yl)piperazin-1,3-dicarboxylate (2.7 g, Y: 77%), which was yellow solid. ES-API: [M+H]$^+$=725.2.

Step 6: the 1-(tert-butyl)3-methyl(3R)-4-(6-chloro-7-(2-fluoro-6-methoxyphenyl)-1-(2-isopropyl-4-methylpyridin-3-yl)-3-nitro-2-oxo-1,2-dihydro-1,8-naphthyridin-4-yl)piperazin-1,3-dicarboxylate (2.7 g, 3.728 mmol) was dissolved in acetic acid (30 mL), added with iron powder (835 mg, 14.91 mmol), and stirred at 80° C. for 30 minutes to react. The resulting reaction liquid was concentrated, orderly added with 200 mL of EtOAc and 100 mL of saturated sodium bicarbonate solution. The resulting suspension was filtered by diatomite. The filter cake was washed with EtOAc. The resulting organic phase was separated, washed orderly with 100 mL of saturated sodium bicarbonate solution and 150 mL of saturated salt solution, dried and concentrated to obtain product tert-butyl (4aR)-11-chloro-10-(2-fluoro-6-methoxyphenyl)-8-(2-isopropyl-4-methylpyridin-3-yl)-5,7-dioxo-1,2,4,4a,5,6,7,8-octahydro-3H-pyrazino[1',2':4,5]pyrazino[2,3-c][1,8]naphthyridin-3-carboxylate (2.70 g, crude), which was yellow solid. ES-API: [M+H]$^+$=663.2.

Step 7: the tert-butyl (4aR)-11-chloro-10-(2-fluoro-6-methoxyphenyl)-8-(2-isopropyl-4-methylpyridin-3-yl)-5,7-dioxo-1,2,4,4a,5,6,7,8-octahydro-3H-pyrazino[1',2':4,5]pyrazino[2,3-c][1,8]naphthyridin-3-carboxylate (250 mg, 0.3774 mmol), 4 mL of DCM, and 4 mL of TFA were orderly added to a 100 mL single-necked flask, stirred at room temperature for 2 hours. The resulting reaction liquid was concentrated to obtain product (4aR)-11-chloro-10-(2-fluoro-6-methoxyphenyl)-8-(2-isopropyl-4-methylpyridin-3-yl)-2,3,4,4a,6,8-hexahydro-1H-pyrazino[1',2':4,5]pyrazino[2,3-c][1,8]naphthyridin-5,7-dione (300 mg, crude), which was directly used in next step. ES-API: [M+H]$^+$=563.2.

Step 8: the (4aR)-11-chloro-10-(2-fluoro-6-methoxyphenyl)-8-(2-isopropyl-4-methylpyridin-3-yl)-2,3,4,4a,6,8-hexahydro-1H-pyrazino[1',2':4,5]pyrazino[2,3-c][1,8]naphthyridin-5,7-dione (300 mg, 0.3774 mmol) was dissolved in DCM (10 mL), and added with triethylamine (3.0 mL, 21.62 mmol). The resulting reaction liquid was cooled to 0° C., and added dropwise with acryloyl chloride (50 mg, 0.5524 mmol). The resulting mixture was stirred at 0° C. for 15 minutes to react. The resulting reaction liquid was added with 80 mL of DCM, washed with 100 mL of saturated solution of NaHCO$_3$ and 80 mL of saturated salt solution, dried and concentrated. The resulting crude product was purified by flash column chromatography on silica gel (MeOH/DCM: 0-20%) to obtain product (4aR)-3-acryloyl-11-chloro-10-(2-fluoro-6-methoxyphenyl)-8-(2-isopropyl-4-methylpyridin-3-yl)-2,3,4,4a,6,8-hexahydro-1H-pyrazino[1',2':4,5]pyrazino[2,3-c][1,8]naphthyridin-5,7-dione (243 mg, crude), which was yellow solid. ES-API: [M+H]$^+$=617.2.

Step 9: under the condition of an ice water bath, the (4aR)-3-acryloyl-11-chloro-10-(2-fluoro-6-methoxyphenyl)-8-(2-isopropyl-4-methylpyridin-3-yl)-2,3,4,4a,6,8-hexahydro-1H-pyrazino[1',2':4,5]pyrazino[2,3-c][1,8]naphthyridin-5,7-dione (243 mg, 0.3774 mmol) was added to dry DCM (6.0 mL), then added with boron tribromide (5.0 mL, 5.0 mmol), and warmed to room temperature to react overnight. Under the condition of the ice water bath, the above reaction liquid was added dropwise to saturated sodium bicarbonate solution, extracted with DCM (80 mL) twice, dried, concentrated, and purified by preparative scale HPLC to obtain (4aR)-3-acryloyl-11-chloro-10-(2-fluoro-6-hydroxyphenyl)-8-(2-isopropyl-4-methylpyridin-3-yl)-2,3,4,4a,6,8-hexahydro-1H-pyrazino[1',2':4,5]pyrazino[2,3-c][1,8]naphthyridin-5,7-dione (Z24, 76 mg, Y: 32%). [M+H]$^+$=603.2.

Step 10: the compound Z24 (76.0 mg, 0.1262 mmol) was resolved by preparative scale chiral HPLC (column type: IA: 10 µm, 30*250 mm; mobile phase: hexane:EtOH=40:60; flow rate: 25 ml/min; and column temperature: room temperature) to obtain the following atropisomer compounds. One of the atropisomer compounds had a structure arbitrarily specified as Z24-1 (13.7 mg, peak 1, retention time: 2.612 min, Y: 18%), ES-API: [M+H]$^+$=603.2. The other atropisomer compound had a structure arbitrarily specified as Z24-2 (21.4 mg, peak 2, retention time: 3.985 min, Y: 28%), ES-API: [M+H]$^+$=603.2. The isomer compounds were detected by analytical scale chiral HPLC (column type IA: 5 µm, 4.6*150 mm; mobile phase: hexane:EtOH=40:60; flow rate: 1 ml/min; and column temperature=30° C.).

Example 25 Preparation of Compounds Z25, Z25-1, and Z25-2
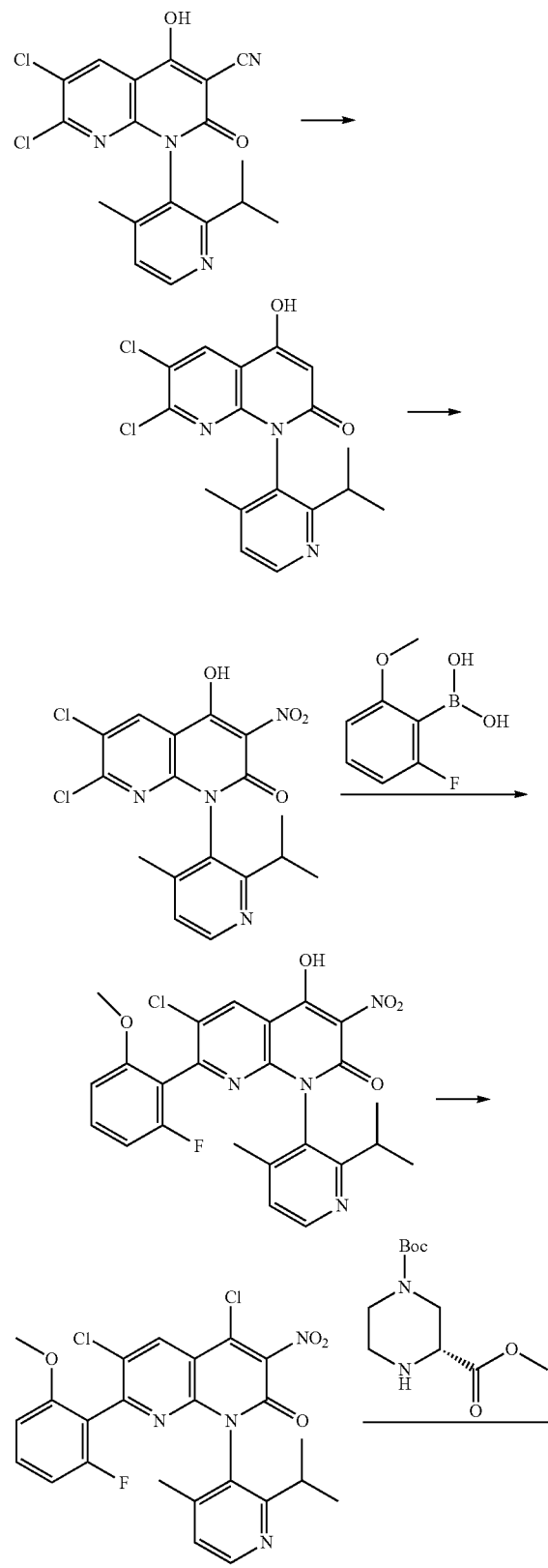
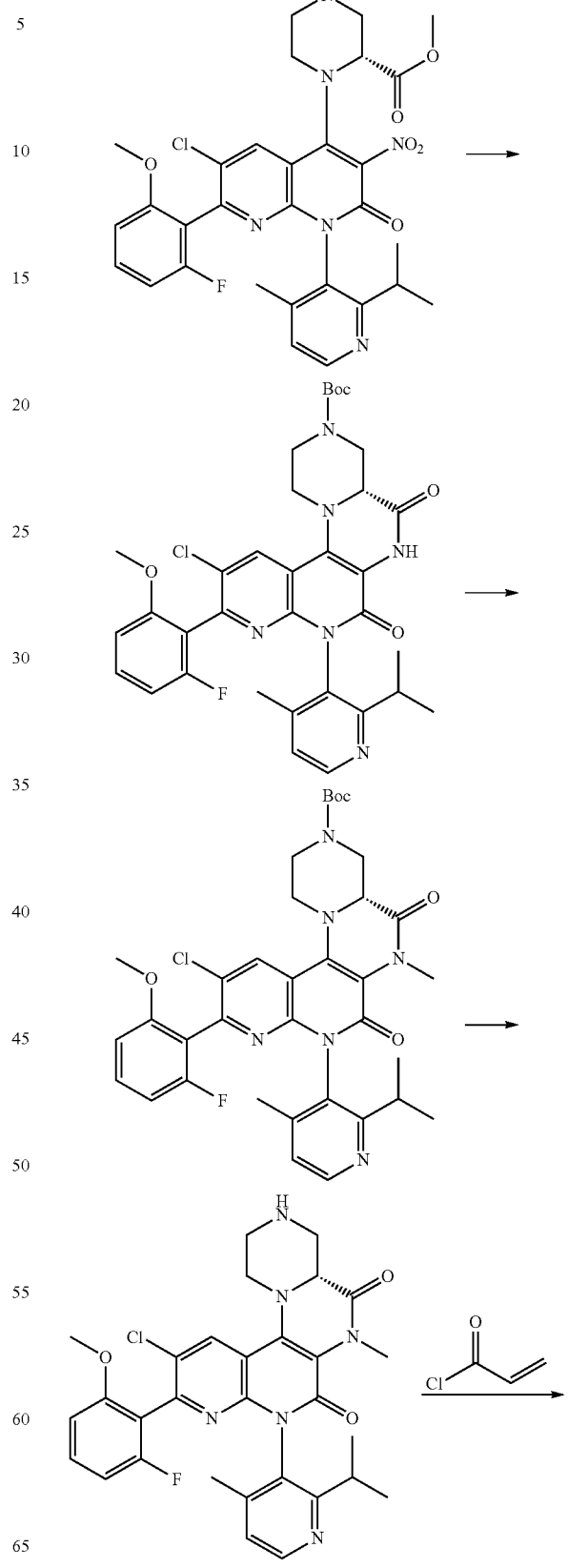

-continued

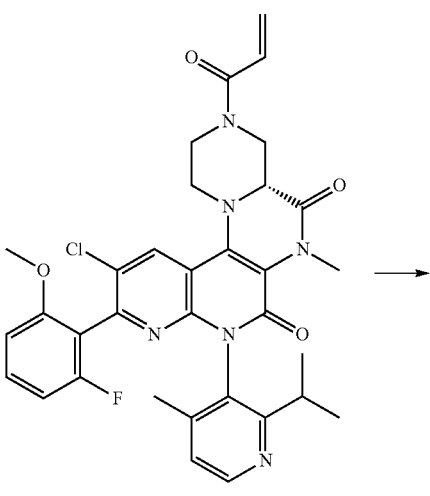

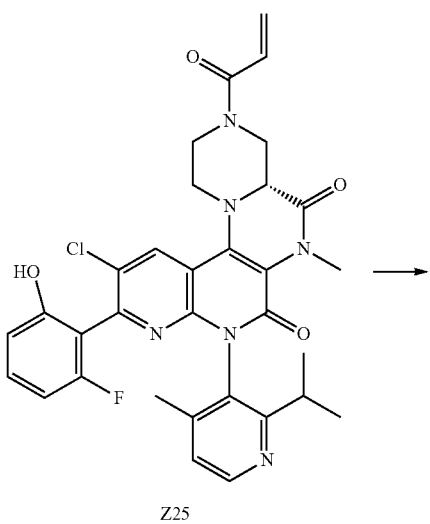

Z25

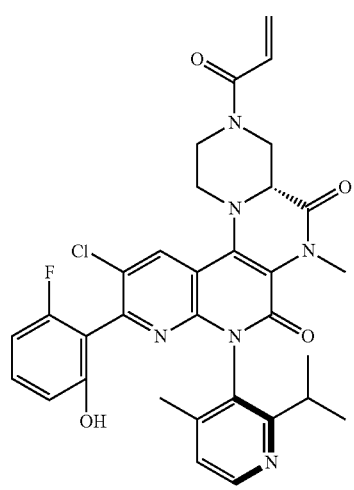

Z25-1

-continued

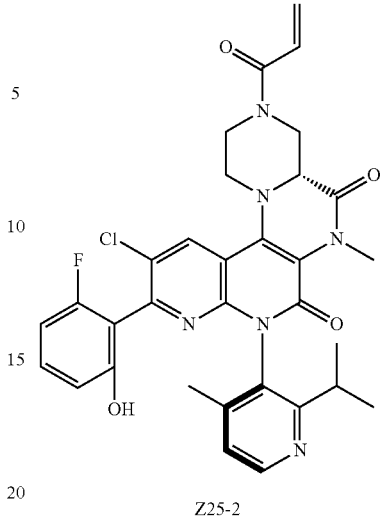

Z25-2

Step 1: 6,7-dichloro-4-hydroxy-1-(2-isopropyl-4-methylpyridin-3-yl)-2-oxo-1,2-dihydro-1,8-naphthyridin-3-carbonitrile (30.0 g, 77.319 mmol) was suspended in a mixed solution of 1, 4-dioxane (120 mL) and water (120 mL), and slowly added with concentrated sulfuric acid (120 mL). The resulting mixture was stirred at 120° C. for 36 hours to react. Cooled reaction liquid was poured into 200 mL of ice water, mixed with sodium carbonate to adjust the pH to a range of 2 to 3, and extracted with EtOAc (1000 mL*2). The resulting combined EtOAc phase was dried by anhydrous sodium sulfate, and filtered. The filtrate was dried in vacuum to obtain product 6,7-dichloro-4-hydroxy-1-(2-isopropyl-4-methylpyridin-3-yl)-1,8-naphthyridin-2(1H)-one (24 g, Y: 85.7%), which was light brown solid. ES-API: [M+H]$^+$= 364.1.

Step 2: the 6,7-dichloro-4-hydroxy-1-(2-isopropyl-4-methylpyridin-3-yl)-1,8-naphthyridin-2(1H)-one (3.16 g, 8.705 mmol) was dissolved in acetic acid (15 mL), order added with sodium nitrite (100 mg, 1.58 mmol) and concentrated nitric acid (5.0 mL, 74.52 mmol), and stirred at room temperature for 30 minutes to react. The resulting reaction liquid was slowly poured into 100 mL ice water. The precipitated solid was filtered. The filter cake was washed with 20 ml of ice water and dried in vacuum to obtain product 6,7-dichloro-4-hydroxy-1-(2-isopropyl-4-methylpyridin-3-yl)-3-nitro-1,8-naphthyridin-2(1H)-one (3.5 g, Y: 92%), which was yellow solid. ES-API: [M+H]$^+$= 409.1.

Step 3: the 6,7-dichloro-4-hydroxy-1-(2-isopropyl-4-methylpyridin-3-yl)-3-nitro-1,8-naphthyridin-2(1H)-one (3.5 g, 8.570 mmol), (2-fluoro-6-methoxyphenyl)boric acid (5.8 g, 34.10 mmol), tetrakis(triphenylphosphine)palladium (1.15 g, 0.9956 mmol), sodium carbonate (3.5 g, 33.02 mmol), 10 mL of water, and 40 mL of dioxane were added to a 100 mL three-necked round-bottom flask. The resulting mixture was stirred at 100° C. for 2-3 hours to react under the protection of nitrogen. After the completion of the reaction, the resulting reaction liquid was cooled to room temperature, added with 80 mL of water and 100 mL of methyl tert-butyl ether, and extracted once. The water phase was then mixed with 1M hydrochloric acid solution to adjust the pH to a range of 3 to 5, and extracted with EtOAc (200 mL*2). The resulting combined EtOAc phase was dried by anhydrous sodium sulfate, and filtered. The filtrate was dried in vacuum to obtain product 6-chloro-7-(2-fluoro-6-methoxyphenyl)-4-hydroxy-1-(2-isopropyl-4-methylpyridin-3-yl)-3-nitro-1,8-naphthyridin-2(1H)-one (4.5 g, crude), which was faint yellow solid. ES-API: [M+H]⁺=499.1.

Step 4: the 6-chloro-7-(2-fluoro-6-methoxyphenyl)-4-hydroxy-1-(2-isopropyl-4-methylpyridin-3-yl)-3-nitro-1,8-naphthyridin-2(1H)-one (4.6 g, 8.57 mmol) was dissolved in ACN (30 mL), orderly added with phosphorus oxychloride (7.5 g, 48.92 mmol) and N,N-diisopropylethylamine (10.5 g, 81.24 mmol), and gradually heated to 80° C. and stirred for 30 minutes to react. The resulting reaction liquid was concentrated, added with 30 mL of cold ACN, added dropwise to 150 mL of saturated sodium bicarbonate solution in an ice water bath, and extracted with EtOAc (200 mL*2). The resulting combined EtOAc phase was washed with 200 mL of saturated salt solution once, dried by anhydrous sodium sulfate, and filtered. After the organic phase was dried and concentrated, the resulting crude product was purified by flash column chromatography on silica gel (EtOAc/PE: 0-50%) to obtain 4,6-dichloro-7-(2-fluoro-6-methoxyphenyl)-1-(2-isopropyl-4-methylpyridin-3-yl)-3-nitro-1,8-naphthyridin-2(1H)-one (3.05 g, Y: 76%), which was yellow solid. ES-API: [M+H]⁺=517.2.

Step 5: the 4,6-dichloro-7-(2-fluoro-6-methoxyphenyl)-1-(2-isopropyl-4-methylpyridin-3-yl)-3-nitro-1,8-naphthyridin-2(1H)-one (2.5 g, 4.843 mmol) was dissolved in N,N-dimethylacetamide (25 mL), orderly added with 1-(tert-butyl)3-methyl(R)-piperazin-1,3-dicarboxylate (3.5 g, 14.34 mmol) and N,N-diisopropylethylamine (2.0 g, 15.47 mmol), and stirred at 120° C. for 2 hours to react. The resulting reaction liquid was added with 80 mL of EtOAc, and washed with 80 mL of saturated salt solution for 3 times. The EtOAc phase was dried and concentrated, and the resulting crude product was purified by flash column chromatography on silica gel (EtOAc/PE: 0-80%) to obtain product 1-(tert-butyl)3-methyl(3R)-4-(6-chloro-7-(2-fluoro-6-methoxyphenyl)-1-(2-isopropyl-4-methylpyridin-3-yl)-3-nitro-2-oxo-1,2-dihydro-1,8-naphthyridin-4-yl)piperazin-1,3-dicarboxylate (2.7 g, Y: 77%), which was yellow solid. ES-API: [M+H]⁺=725.2.

Step 6: the 1-(tert-butyl)3-methyl(3R)-4-(6-chloro-7-(2-fluoro-6-methoxyphenyl)-1-(2-isopropyl-4-methylpyridin-3-yl)-3-nitro-2-oxo-1,2-dihydro-1,8-naphthyridin-4-yl)piperazin-1,3-dicarboxylate (2.7 g, 3.728 mmol) was dissolved in acetic acid (30 mL), added with iron powder (835 mg, 14.91 mmol), and stirred at 80° C. for 30 minutes to react. The resulting reaction liquid was concentrated, orderly added with 200 mL of EtOAc and 100 mL of saturated sodium bicarbonate solution. The resulting suspension was filtered by diatomite. The filter cake was washed with EtOAc. The resulting organic phase was separated, washed orderly with 100 mL of saturated sodium bicarbonate solution and 150 mL of saturated salt solution, dried and concentrated to obtain product tert-butyl (4aR)-11-chloro-10-(2-fluoro-6-methoxyphenyl)-8-(2-isopropyl-4-methylpyridin-3-yl)-5,7-dioxo-1,2,4,4a,5,6,7,8-octahydro-3H-pyrazino[1',2':4,5]pyrazino[2,3-c][1,8]naphthyridin-3-carboxylate (2.70 g, crude), which was yellow solid. ES-API: [M+H]⁺=663.2.

Step 7: the tert-butyl (4aR)-11-chloro-10-(2-fluoro-6-methoxyphenyl)-8-(2-isopropyl-4-methylpyridin-3-yl)-5,7-dioxo-1,2,4,4a,5,6,7,8-octahydro-3H-pyrazino[1',2':4,5]pyrazino[2,3-c][1,8]naphthyridin-3-carboxylate (2.7 g, 3.728 mmol), 30 mL of acetone, anhydrous potassium carbonate (2.2 g, 15.94 mmol), and iodomethane (5.4 g, 38.03 mmol) were orderly added to a 150 mL sealing tube. The sealing tube was sealed, and the resulting mixture was stirred at 55° C. for 18 hours to react. The resulting reaction liquid was added with 150 mL of EtOAc, washed with 100 mL of saturated salt solution for 3 times, dried and concentrated. The resulting crude product was purified by flash column chromatography on silica gel (EtOAc/PE: 0-80%) to obtain product tert-butyl (4aR)-11-chloro-10-(2-fluoro-6-methoxyphenyl)-8-(2-isopropyl-4-methylpyridin-3-yl)-6-methyl-5,7-dioxo-1,2,4,4a,5,6,7,8-octahydro-3H-pyrazino[1',2':4,5]pyrazino[2,3-c][1,8]naphthyridin-3-carboxylate (2.2 g, Y: 87%), which was yellow solid. ES-API: [M+H]⁺=677.2.

Step 8: the tert-butyl (4aR)-11-chloro-10-(2-fluoro-6-methoxyphenyl)-8-(2-isopropyl-4-methylpyridin-3-yl)-6-methyl-5,7-dioxo-1,2,4,4a,5,6,7,8-octahydro-3H-pyrazino[1',2':4,5]pyrazino[2,3-c][1,8]naphthyridin-3-carboxylate (517 mg, 0.7549 mmol) was dissolved in DCM (8 mL), and added with TFA (2 mL). The resulting mixture was stirred at room temperature for 2 hours. The resulting reaction liquid was concentrated to obtain product (4aR)-11-chloro-10-(2-fluoro-6-methoxyphenyl)-8-(2-isopropyl-4-methylpyridin-3-yl)-6-methyl-2,3,4,4a,6,8-hexahydro-1H-pyrazino[1',2':4,5]pyrazino[2,3-c][1,8]naphthyridin-5,7-dione (530 mg, crude), which was directly used in next step.

ES-API: [M+H]⁺=577.2.

Step 9: the (4aR)-11-chloro-10-(2-fluoro-6-methoxyphenyl)-8-(2-isopropyl-4-methylpyridin-3-yl)-6-methyl-2,3,4,4a,6,8-hexahydro-1H-pyrazino[1',2':4,5]pyrazino[2,3-c][1,8]naphthyridin-5,7-dione (530 mg, 0.7549 mmol) was dissolved in DCM (15 mL), and added with triethylamine (3.0 mL, 21.62 mmol). The resulting reaction liquid was cooled to 0° C., and added dropwise with acryloyl chloride (100 mg, 1.1048 mmol). The resulting mixture was stirred at 0° C. for 15 minutes to react. The resulting reaction liquid was added with 80 mL of DCM, washed with 100 mL of saturated solution of NaHCO₃ and 80 mL of saturated salt solution, dried and concentrated. The resulting crude product was purified by flash column chromatography on silica gel (EtOAc/PE: 0-60%) to obtain product (4aR)-3-acryloyl-11-chloro-10-(2-fluoro-6-methoxyphenyl)-8-(2-isopropyl-4-methylpyridin-3-yl)-6-methyl-2,3,4,4a,6,8-hexahydro-1H-pyrazino[1',2':4,5]pyrazino[2,3-c][1,8]naphthyridin-5,7-dione (280 mg, Y: 59%), which was yellow solid. ES-API: [M+H]⁺=631.2.

Step 10: under the condition of an ice water bath, the (4aR)-3-acryloyl-11-chloro-10-(2-fluoro-6-methoxyphenyl)-8-(2-isopropyl-4-methylpyridin-3-yl)-6-methyl-2,3,4,4a,6,8-hexahydro-H-pyrazino[1',2':4,5]pyrazino[2,3-c][1,8]naphthyridin-5,7-dione (280 mg, 0.444 mmol) was added to dry DCM (6.0 mL), then added with boron tribromide (5.0 mL, 5.0 mmol), and warmed to room temperature to react overnight. Under the condition of the ice water bath, the above reaction liquid was added dropwise to saturated sodium bicarbonate solution, extracted with DCM (80 mL) twice, dried and concentrated. The resulting crude product was purified by flash column chromatography on silica gel (EtOAc/PE: 0-60%) to obtain product (4aR)-3-acryloyl-11-chloro-10-(2-fluoro-6-hydroxyphenyl)-8-(2-isopropyl-4-methylpyridin-3-yl)-6-methyl-2,3,4,4a,6,8-hexahydro-1H-pyrazino[1',2':4,5]pyrazino[2,3-c][1,8]naphthyridin-5,7-dione (Z25, 233 mg, Y: 85%).

Step 11: the compound Z25 was resolved by preparative scale chiral HPLC (column type: IA: 10 μm, 30*250 mm; mobile phase: hexane:EtOH=60:40; flow rate: 25 ml/min; and column temperature: room temperature) to obtain the following atropisomer compounds. One of the atropisomer compounds had a structure arbitrarily specified as Z25-1 (76.8 mg, peak 1, retention time: 2.531 min, Y: 34%). ¹H NMR (500 MHz, DMSO-d$_6$) δ 10.03 (d, J=18.4 Hz, 1H), 8.52 (d, J=7.3 Hz, 1H), 8.43 (d, J=4.7 Hz, 1H), 7.23 (d, J=9.6 Hz, 2H), 7.08 (dd, J=16.6, 10.5 Hz, 1H), 6.74-6.62 (m, 2H), 6.15 (d, J=16.8 Hz, 1H), 5.75 (d, J=10.7 Hz, 1H), 4.73 (d, J=14.2 Hz, 1H), 4.46 (d, J=12.9 Hz, 1H), 4.00 (s, 1H), 3.61 (d, J=10.0 Hz, 1H), 3.51 (s, 1H), 3.34 (s, 3H), 3.22 (s, 1H), 2.64 (t, J=11.5 Hz, 1H), 2.48-2.42 (m, 1H), 1.98 (d, J=5.1 Hz, 3H), 1.03 (t, J=6.9 Hz, 3H), 0.86 (t, J=7.9 Hz, 3H). ES-API: [M+H]$^+$=617.2. The other atropisomer compound had a structure arbitrarily specified as Z25-2 (70 mg, peak 2, retention time: 3.683 min, Y: 31%). $^1$H NMR (500 MHz, CDCl$_3$) δ 8.64-8.59 (m, 1H), 8.35 (s, 1H), 8.07 (s, 1H), 7.27-7.20 (m, 2H), 7.14-7.02 (m, 1H), 6.75-6.63 (m, 2H), 6.39 (dd, J=17.0, 2.0 Hz, 1H), 5.88-5.77 (m, 1H), 4.91 (d, J=14.0 Hz, 1H), 4.83 (d, J=13.0 Hz, 1H), 3.72-3.58 (m, 2H), 3.50 (s, 3H), 3.43 (d, J=12.0 Hz, 1H), 3.16 (t, J=13.0 Hz, 1H), 2.91 (t, J=12.0 Hz, 1H), 2.82-2.73 (m, 1H), 1.93 (s, 3H), 1.24 (d, J=7.0 Hz, 3H), 1.12 (d, J=7.0 Hz, 3H). ES-API: [M+H]$^+$=617.2. The isomer compounds were detected by analytical scale chiral HPLC (column type: IA: 5 m, 4.6*150 mm; mobile phase: hexane:EtOH=60:40; flow rate: 1 ml/min; and column temperature=30° C.).

Example 26 Preparation of Compounds Z26, Z26-1, and Z26-2

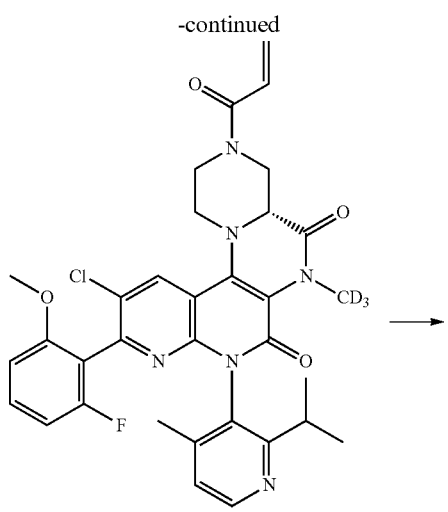

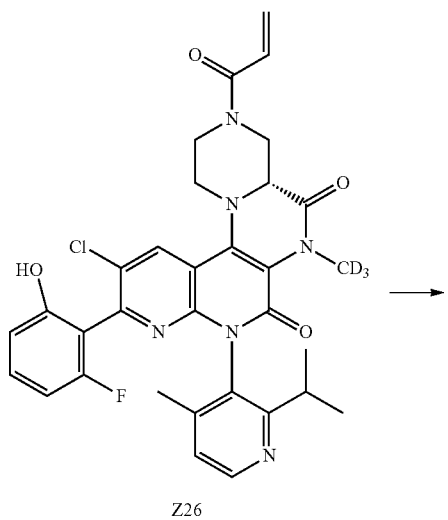

Z26

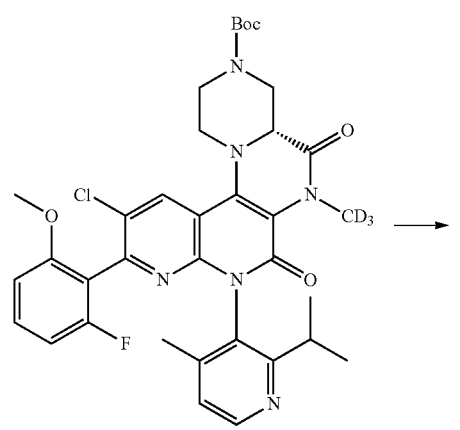

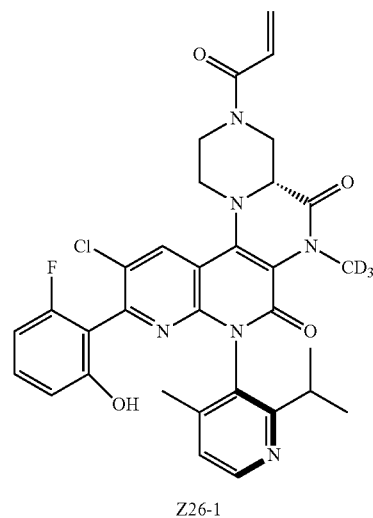

Z26-1

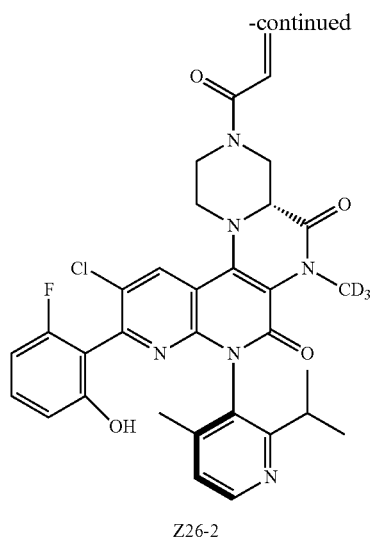

Z26-2

Step 1: tert-butyl (4aR)-11-chloro-10-(2-fluoro-6-methoxyphenyl)-8-(2-isopropyl-4-methylpyridin-3-yl)-6-(methyl-d3)-5,7-dioxo-1,2,4,4a,5,6,7,8-octahydro-3H-pyrazino[1',2':4,5]pyrazino[2,3-c][1,8]naphthyridin-3-carboxylate (511 mg, 0.7549 mmol) was dissolved in DCM (8 mL), and added with TFA (2 mL). The resulting mixture was stirred at room temperature for 2 hours. The resulting reaction liquid was concentrated to obtain product (4aR)-11-chloro-10-(2-fluoro-6-methoxyphenyl)-8-(2-isopropyl-4-methylpyridin-3-yl)-6-(methyl-d3)-2,3,4,4a,6,8-hexahydro-1H-pyrazino[1',2':4,5]pyrazino[2,3-c][1,8]naphthyridin-5,7-dione (520 mg, crude), which was directly used in next step. ES-API: [M+H]$^+$=580.3.

Step 2: the (4aR)-11-chloro-10-(2-fluoro-6-methoxyphenyl)-8-(2-isopropyl-4-methylpyridin-3-yl)-6-(methyl-d3)-2,3,4,4a,6,8-hexahydro-1H-pyrazino[1',2':4,5]pyrazino[2,3-c][1,8]naphthyridin-5,7-dione (520 mg, 0.7549 mmol) was dissolved in DCM (10 mL), and added with triethylamine (3.0 mL, 21.62 mmol). The resulting reaction liquid was cooled to 0° C., and added dropwise with acryloyl chloride (100 mg, 1.1048 mmol). The resulting mixture was stirred at 0° C. for 15 minutes to react. The resulting reaction liquid was added with 80 mL of DCM, washed with 100 mL of saturated solution of NaHCO$_3$ and 80 mL of saturated salt solution, dried and concentrated. The resulting crude product was purified by flash column chromatography on silica gel (EtOAc/PE: 0-60%) to obtain product (4aR)-3-acryloyl-11-chloro-10-(2-fluoro-6-methoxyphenyl)-8-(2-isopropyl-4-methylpyridin-3-yl)-6-(methyl-d3)-2,3,4,4a,6,8-hexahydro-1H-pyrazino[1',2':4,5]pyrazino[2,3-c][1,8]naphthyridin-5,7-dione (232 mg, Y: 48%), which was yellow solid. ES-API: [M+H]$^+$=634.2.

Step 3: under the condition of an ice water bath, the (4aR)-3-acryloyl-11-chloro-10-(2-fluoro-6-methoxyphenyl)-8-(2-isopropyl-4-methylpyridin-3-yl)-6-(methyl-d3)-2,3,4,4a,6,8-hexahydro-1H-pyrazino[1',2':4,5]pyrazino[2,3-c][1,8]naphthyridin-5,7-dione (240 mg, 0.3791 mmol) was added to dry DCM (6.0 mL), then added with boron tribromide (5.0 mL, 5.0 mmol), and warmed to room temperature to react overnight. Under the condition of the ice water bath, the above reaction liquid was added dropwise to saturated sodium bicarbonate solution, extracted with DCM (80 mL) twice, dried and concentrated. The resulting crude product was purified by flash column chromatography on silica gel (EtOAc/PE: 0-60%) to obtain product (4aR)-3-acryloyl-11-chloro-10-(2-fluoro-6-hydroxyphenyl)-8-(2-isopropyl-4-methylpyridin-3-yl)-6-(methyl-d3)-2,3,4,4a,6,8-hexahydro-1H-pyrazino[1',2':4,5]pyrazino[2,3-c][1,8]naphthyridin-5,7-dione (Z26, 187 mg, Y: 79%). [M+H]$^+$=620.3.

Step 4: the compound Z26 (187 mg, 0.302 mmol) was resolved by preparative scale chiral HPLC (column type: IA: 10 μm, 30*250 mm; mobile phase: hexane:EtOH=60:40; flow rate: 25 ml/min; and column temperature: room temperature) to obtain the following atropisomer compounds. One of the atropisomer compounds had a structure arbitrarily specified as Z26-1 (68.8 mg, peak 1, retention time: 2.525 min, Y: 36.7%). $^1$H NMR (500 MHz, DMSO-d$_6$) δ 10.03 (d, J=17.9 Hz, 1H), 8.51 (d, J=7.4 Hz, 1H), 8.43 (d, J=4.7 Hz, 1H), 7.29-7.18 (m, 2H), 7.08 (dd, J=17.0, 10.6 Hz, 1H), 6.74-6.61 (m, 2H), 6.15 (d, J=16.6 Hz, 1H), 5.75 (d, J=11.5 Hz, 1H), 4.73 (d, J=13.5 Hz, 1H), 4.46 (d, J=12.3 Hz, 1H), 4.00 (s, 1H), 3.61 (d, J=10.5 Hz, 1H), 3.50 (s, 1H), 3.22 (s, 1H), 2.65 (t, J=12.5 Hz, 1H), 2.49-2.42 (m, 1H), 1.98 (d, J=5.0 Hz, 3H), 1.02 (d, J=7.0 Hz, 3H), 0.86 (t, J=7.9 Hz, 3H). ES-API: [M+H]$^+$=620.3. The other atropisomer compound had a structure arbitrarily specified as Z26-2 (63.2 mg, peak 2, retention time: 3.683 min, Y: 33.79%). $^1$H NMR (400 MHz, CDCl$_3$) δ 8.62 (d, J=4.8 Hz, 11H), 8.35 (s, 1H), 8.07 (s, 1H), 7.24-7.20 (m, 2H), 7.16-7.01 (m, 1H), 6.74-6.63 (m, 2H), 6.39 (dd, J=16.8, 2.0 Hz, 1H), 5.82 (dd, J=10.4, 2.0 Hz, 1H), 4.91 (d, J=13.6 Hz, 1H), 4.83 (d, J=13.6 Hz, 1H), 3.71-3.57 (m, 2H), 3.42 (d, J=12.0 Hz, 1H), 3.16 (t, J=12.8 Hz, 1H), 2.91 (t, J=12.0 Hz, 1H), 2.81-2.70 (m, 1H), 1.92 (s, 3H), 1.22 (d, J=6.8 Hz, 3H), 1.10 (d, J=6.8 Hz, 3H). ES-API: [M+H]$^+$=620.3. The isomer compounds were detected by analytical scale chiral HPLC (column type: IA: 5 μm, 4.6*150 mm; mobile phase: hexane:EtOH=60:40; flow rate: 1 ml/min; and column temperature=30° C.).

Example 27 Preparation of Compounds Z27, Z27-1 and Z27-2

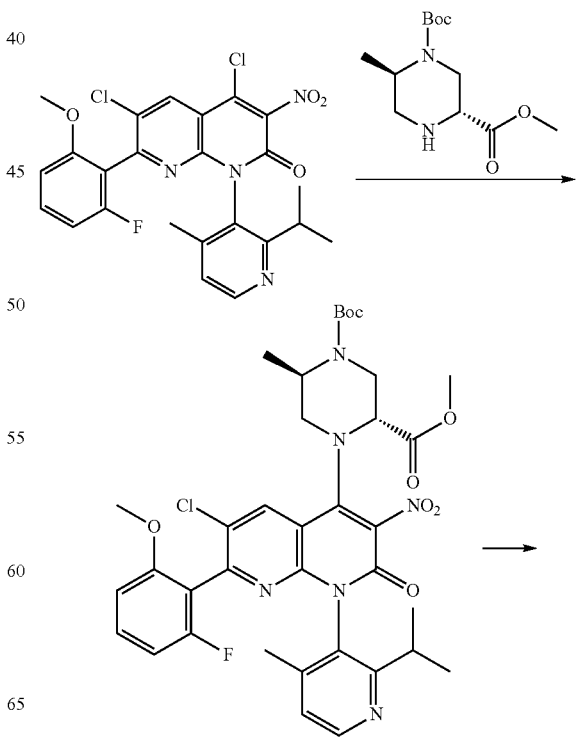

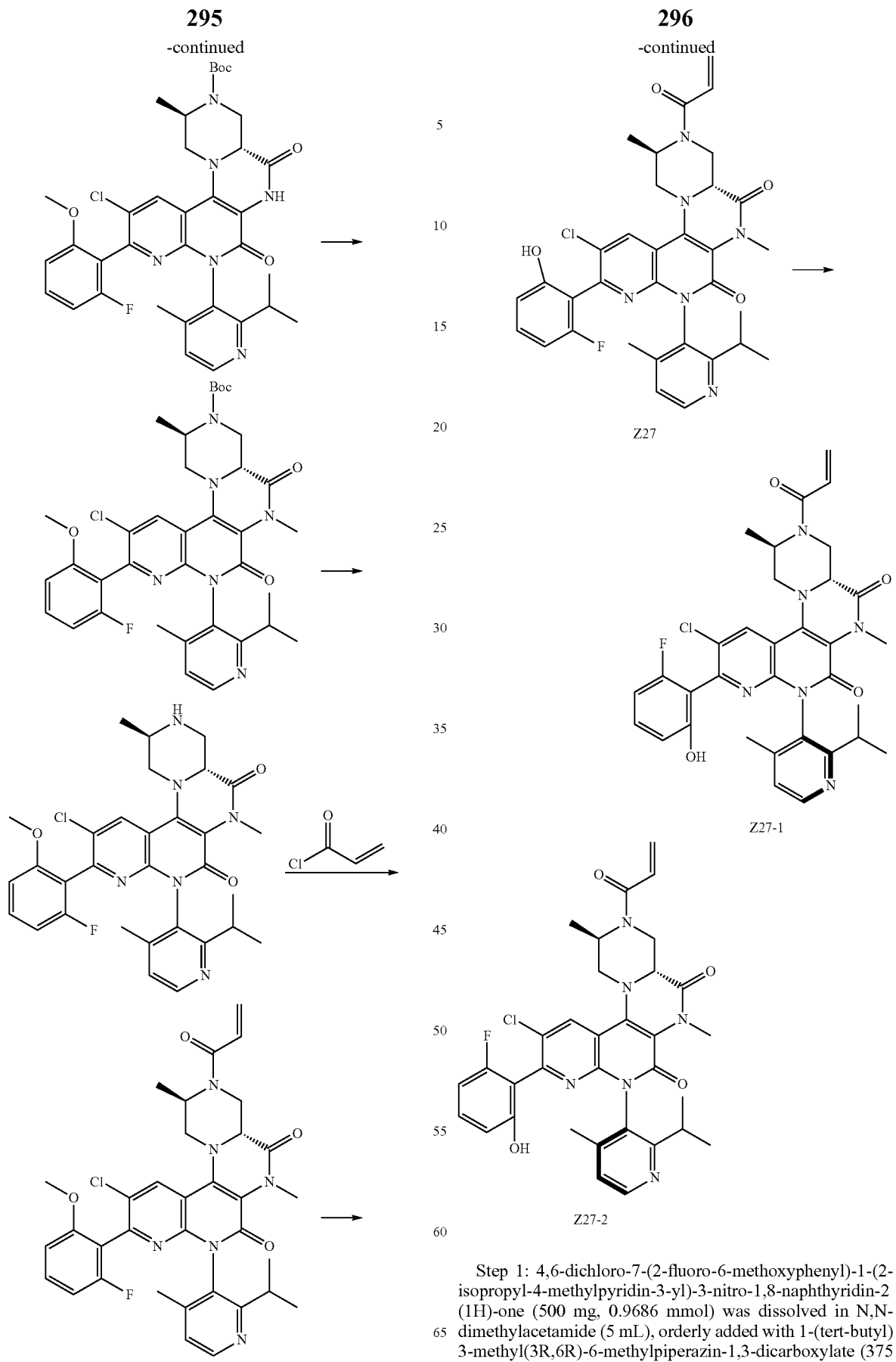
Step 1: 4,6-dichloro-7-(2-fluoro-6-methoxyphenyl)-1-(2-isopropyl-4-methylpyridin-3-yl)-3-nitro-1,8-naphthyridin-2(1H)-one (500 mg, 0.9686 mmol) was dissolved in N,N-dimethylacetamide (5 mL), orderly added with 1-(tert-butyl) 3-methyl(3R,6R)-6-methylpiperazin-1,3-dicarboxylate (375 mg, 1.452 mmol) and N,N-diisopropylethylamine (375 mg, 2.907 mmol), and stirred at 120° C. for 2 hours to react. The resulting reaction liquid was added with 80 mL of EtOAc, and washed with 80 mL of saturated salt solution for 3 times. The EtOAc phase was dried and concentrated, and the resulting crude product was purified by flash column chromatography on silica gel (EtOAc/PE: 0-80%) to obtain product 1-(tert-butyl)3-methyl(3R,6R)-4-(6-chloro-7-(2-fluoro-6-methoxyphenyl)-1-(2-isopropyl-4-methylpyridin-3-yl)-3-nitro-2-oxo-1,2-dihydro-1,8-naphthyridin-4-yl)-6-methylpiperazin-1,3-dicarboxylate (535 mg, Y: 74.5%), which was yellow solid. ES-API: [M+H]$^+$=739.2.

Step 2: the 1-(tert-butyl)3-methyl(3R,6R)-4-(6-chloro-7-(2-fluoro-6-methoxyphenyl)-1-(2-isopropyl-4-methylpyridin-3-yl)-3-nitro-2-oxo-1,2-dihydro-1,8-naphthyridin-4-yl)-6-methylpiperazin-1,3-dicarboxylate (530 mg, 0.7179 mmol) was dissolved in acetic acid (6 mL), added with iron powder (200 mg, 3.571 mmol), and stirred at 80° C. for 30 minutes to react. The resulting reaction liquid was concentrated and orderly added with 200 mL of EtOAc and 100 mL of saturated sodium bicarbonate. The resulting suspension was filtered by diatomite. The filter cake was washed with EtOAc. The resulting organic phase was separated, washed orderly with 100 mL of saturated sodium bicarbonate and 150 mL of saturated salt solution, dried and concentrated to obtain product tert-butyl (2R,4aR)-11-chloro-10-(2-fluoro-6-methoxyphenyl)-8-(2-isopropyl-4-methylpyridin-3-yl)-2-methyl-5,7-dioxo-1,2,4,4a,5,6,7,8-octahydro-3H-pyrazino[1',2':4,5]pyrazino[2,3-c][1,8]naphthyridin-3-carboxylate (452 mg, Y: 92%), which was yellow solid. ES-API: [M+H]$^+$=677.2.

Step 3: the tert-butyl (2R,4aR)-11-chloro-10-(2-fluoro-6-methoxyphenyl)-8-(2-isopropyl-4-methylpyridin-3-yl)-2-methyl-5,7-dioxo-1,2,4,4a,5,6,7,8-octahydro-3H-pyrazino[1',2':4,5]pyrazino[2,3-c][1,8]naphthyridin-3-carboxylate (445 mg, 0.6583 mmol), 10 mL of acetone, anhydrous potassium carbonate (500 mg, 2.633 mmol), and iodomethane (1.20 g, 6.5828 mmol) were orderly added to a 150 mL sealing tube. The sealing tube was sealed, and the resulting mixture was stirred at 55° C. for 18 hours to react. The resulting reaction liquid was added with 150 mL of EtOAc, washed with 100 mL of saturated salt solution for 3 times, dried and concentrated. The resulting crude product was purified by flash column chromatography on silica gel (EtOAc/PE: 0-80%) to obtain product tert-butyl (2R,4aR)-11-chloro-10-(2-fluoro-6-methoxyphenyl)-8-(2-isopropyl-4-methylpyridin-3-yl)-2,6-dimethyl-5,7-dioxo-1,2,4,4a,5,6,7,8-octahydro-3H-pyrazino[1',2':4,5]pyrazino[2,3-c][1,8]naphthyridin-3-carboxylate (455 mg, crude), which was yellow solid. ES-API: [M+H]$^+$=691.3.

Step 4: the tert-butyl (2R,4aR)-11-chloro-10-(2-fluoro-6-methoxyphenyl)-8-(2-isopropyl-4-methylpyridin-3-yl)-2,6-dimethyl-5,7-dioxo-1,2,4,4a,5,6,7,8-octahydro-3H-pyrazino[1',2':4,5]pyrazino[2,3-c][1,8]naphthyridin-3-carboxylate (511 mg, 0.7549 mmol) was dissolved in DCM (8 mL), and added with TFA (2 mL). After stirring at room temperature for 2 hours, the resulting reaction liquid was concentrated to obtain product (2R,4aR)-11-chloro-10-(2-fluoro-6-methoxyphenyl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin-5,7-dione (462 mg, crude), which was directly used in next step. ES-API: [M+H]$^+$=591.3.

Step 5: the (2R,4aR)-11-chloro-10-(2-fluoro-6-methoxyphenyl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin-5,7-dione (462 mg, 0.6283 mmol) was dissolved in DCM (8 mL), and added with triethylamine (2.0 mL, 14.41 mmol). The resulting reaction liquid was cooled to 0° C., and added dropwise with acryloyl chloride (100 mg, 1.1048 mmol). The resulting mixture was stirred at 0° C. for 15 minutes to react. The resulting reaction liquid was added with 80 mL of DCM, washed with 100 mL of saturated solution of NaHCO$_3$ and 80 mL of saturated salt solution, dried and concentrated. The resulting crude product was purified by flash column chromatography on silica gel (EtOAc/PE: 0-60%) to obtain product (2R,4aR)-3-acryloyl-11-chloro-10-(2-fluoro-6-methoxyphenyl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin-5,7-dione (290 mg, Y: 68%), which was yellow solid. ES-API: [M+H]$^+$=645.2.

Step 6: under the condition of an ice water bath, the (2R,4aR)-3-acryloyl-11-chloro-10-(2-fluoro-6-methoxyphenyl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin-5,7-dione (290 mg, 0.4503 mmol) was added to dry DCM (6.0 mL), then added with boron tribromide (6.0 mL, 6.0 mmol), and warmed to room temperature to react overnight. Under the condition of an ice water bath, the above reaction liquid was added dropwise to saturated sodium bicarbonate solution, extracted with DCM (80 mL) twice, dried and concentrated. The resulting crude product was purified by flash column chromatography on silica gel (EtOAc/PE: 0-60%) to obtain product (2R,4aR)-3-acryloyl-11-chloro-10-(2-fluoro-6-hydroxyphenyl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin-5,7-dione (Z27, 307 mg, crude). [M+H]$^+$=631.2.

Step 7: the compound Z27 was resolved by preparative scale chiral HPLC (column type: IA*: 10 μm, 30*250 mm; mobile phase: hexane:EtOH=60:40; flow rate: 25 ml/min; and column temperature: room temperature) to obtain the following atropisomer compounds. One of the atropisomer compounds had a structure arbitrarily specified as Z27-1 (67.7 mg, peak 1, retention time: 2.394 min, Y: 23.4%). $^1$H NMR (500 MHz, DMSO-d$_6$) δ 10.05 (d, J=17.8 Hz, 1H), 8.43 (d, J=4.8 Hz, 1H), 8.23 (d, J=9.9 Hz, 1H), 7.23 (d, J=9.9 Hz, 2H), 7.02 (dd, J=16.8, 10.6 Hz, 1H), 6.74-6.63 (m, 2H), 6.15 (dd, J=16.8, 2.3 Hz, 1H), 5.76 (dd, J=10.5, 2.3 Hz, 1H), 4.78 (s, 1H), 4.60 (d, J=13.8 Hz, 1H), 4.00 (d, J=3.5 Hz, 1H), 3.75 (dd, J=14.1, 3.9 Hz, 1H), 3.41-3.33 (m, 1H), 3.34 (s, 3H), 2.81 (d, J=12.1 Hz, 1H), 2.48-2.42 (m, 1H), 1.98 (s, 3H), 1.53 (d, J=6.7 Hz, 3H), 1.03 (d, J=5.5 Hz, 3H), 0.85 (t, J=6.2 Hz, 3H). ES-API: [M+H]$^+$=631.2. The other atropisomer compound had a structure arbitrarily specified as Z27-2 (64.6 mg, peak 2, retention time: 3.382 min, Y: 23.2%). $^1$H NMR (400 MHz, CDCl$_3$) δ 8.57 (d, J=4.8 Hz, 1H), 8.36 (s, 1H), 8.28 (s, 1H), 7.25-7.15 (m, 2H), 7.03 (dd, J=16.8, 10.8 Hz, 1H), 6.72-6.61 (m, 2H), 6.34 (dd, J=16.8, 2.0 Hz, 1H), 5.80 (dd, J=10.8, 2.0 Hz, 1H), 5.11-5.01 (m, 1H), 4.77 (d, J=14.0 Hz, 1H), 3.82 (dd, J=14.0, 4.4 Hz, 1H), 3.61 (d, J=4.4 Hz, 1H), 3.49 (s, 3H), 3.30-3.17 (m, 1H), 3.03 (dd, J=12.0, 3.6 Hz, 1H), 2.80-2.68 (m, 1H), 1.91 (s, 3H), 1.66 (d, J=6.8 Hz, 3H), 1.22 (d, J=6.8 Hz, 3H), 1.08 (d, J=6.8 Hz, 3H). ES-API: [M+H]$^+$=631.2. The isomer compounds were detected by analytical scale chiral HPLC (column type: IA: 5 μm, 4.6*150 mm; mobile phase: hexane:EtOH=60:40; flow rate: 1 ml/min; and column temperature=30° C.).

Example 28 Preparation of Compound Z28

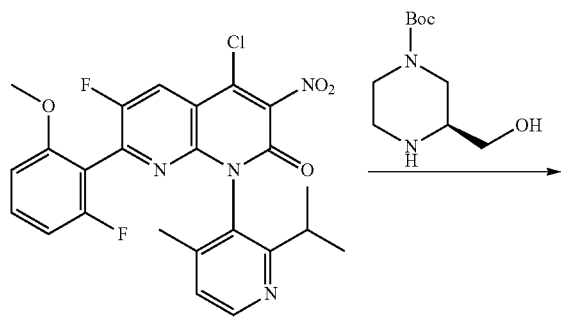
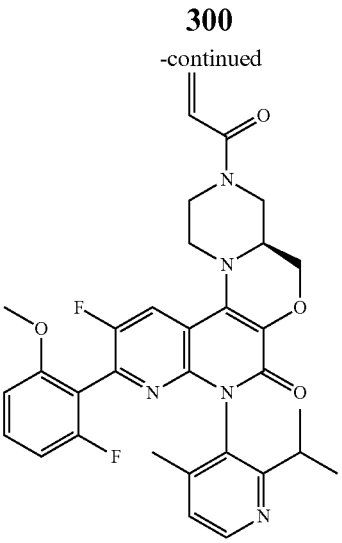
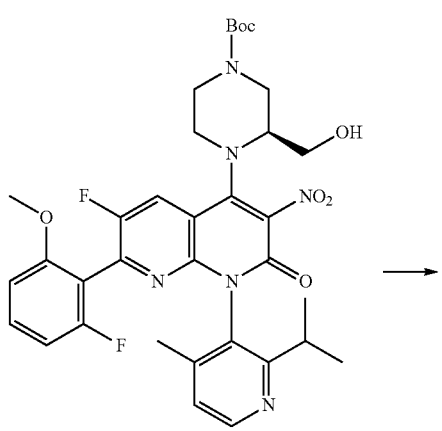
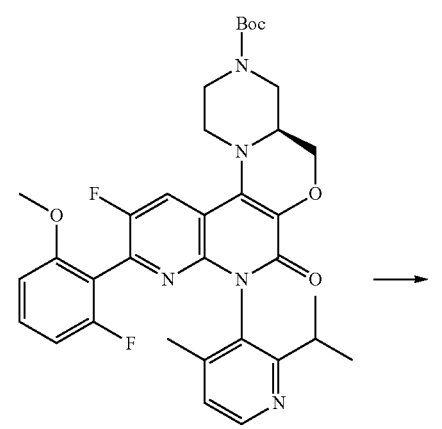
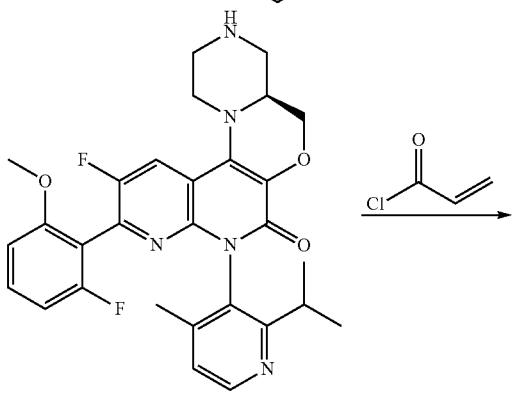
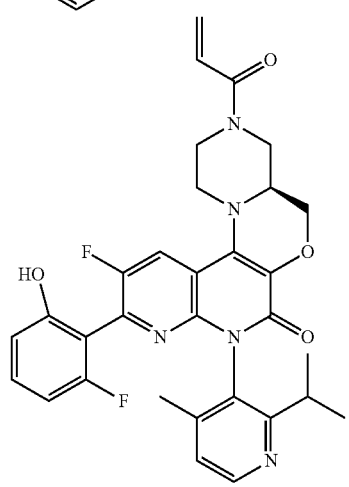

Z28

Step 1: 4-chloro-6-fluoro-7-(2-fluoro-6-methoxyphenyl)-1-(2-isopropyl-4-methylpyridin-3-yl)-3-nitro-1,8-naphthyridin-2(1H)-one (400 mg, 0.80 mmol) was dissolved in DMF (5 mL), added with tert-butyl (S)-3-(hydroxymethyl) piperazin-1I-carboxylate (432 mg, 2.00 mmol) and N,N-diisopropylethylamine (310 mg, 2.40 mmol), and stirred at 75° C. for 2 hours to react. The resulting reaction liquid was diluted by 100 mL of EtOAc, washed with 40 mL of saturated salt solution for 5 times, dried and concentrated. The resulting crude product was purified by flash column chromatography on silica gel (EtOAc/PE: 0-70%) to obtain product tert-butyl (3S)-4-(6-fluoro-7-(2-fluoro-6-methoxyphenyl)-1-(2-isopropyl-4-methylpyridin-3-yl)-3-nitro-2-oxo-1,2-dihydro-1,8-naphthyridin-4-yl)-3-(hydroxymethyl) piperazin-1-carboxylate (420 mg, Y: 77.2%), which was yellow solid. ES-API: [M+H]⁺=681.3.

Step 2: the tert-butyl (3S)-4-(6-fluoro-7-(2-fluoro-6-methoxyphenyl)-1-(2-isopropyl-4-methylpyridin-3-yl)-3-nitro-2-oxo-1,2-dihydro-1,8-naphthyridin-4-yl)-3-(hydroxymethyl)piperazin-1-carboxylate (420 mg, 0.62 mmol) was dissolved in DMA (20 mL), added with LiHMDS (1.55 mL, 1.55 mmol, 1.0 M in THF), and then slowly heated to 140° C. and stirred for 24 hours to react. The resulting reaction liquid was diluted by 100 mL of EtOAc, washed with 40 mL of dilute brine for 4 times and then with 40 mL of saturated salt solution once, dried and concentrated. The resulting crude product was purified by flash column chromatography on silica gel (EtOAc/PE: 0-100%) to obtain product tert-butyl (4aS)-11-fluoro-10-(2-fluoro-6-methoxyphenyl)-8-(2-isopropyl-4-methylpyridin-3-yl)-7-oxo-1,2,4a,5,7,8-hexahydropyrazino[1',2':4,5][1,4]oxazino[2,3-c][1,8]naphthyridin-3(4H)-carboxylate (180 mg, Y: 46.0%), which was yellow solid. ES-API: [M+H]$^+$=634.3.

Step 3: (4aS)-11-fluoro-10-(2-fluoro-6-methoxyphenyl)-8-(2-isopropyl-4-methylpyridin-3-yl)-7-oxo-1,2,4a,5,7,8-hexahydropyrazino[1',2':4,5][1,4]oxo[2,3-c][1,8]naphthyridin-3(4H)-carboxylate (35 mg, 0.055 mmol) was dissolved in DCM (4 mL), and added with TFA (1 mL). After stirring at room temperature for 1 hour, the resulting reaction liquid was concentrated to obtain product (4aS)-11-fluoro-10-(2-fluoro-6-methoxyphenyl)-8-(2-isopropyl-4-methylpyridin-3-yl)-1,2,3,4,4a, 5-hexahydropyrazino[1',2':4,5][1,4]oxazino[2,3-c][1,8]naphthyridin-7(8H)-one (185 mg, crude), which was directly used in next step. ES-API: [M+H]$^+$=534.3.

Step 4: the (4aS)-11-fluoro-10-(2-fluoro-6-methoxyphenyl)-8-(2-isopropyl-4-methylpyridin-3-yl)-1,2,3,4,4a,5-hexahydropyrazino[1',2':4,5][1,4]oxazino[2,3-c][1,8]naphthyridin-7(8H)-one (185 mg, crude) was dissolved in DCM (6 mL), and added with N,N-diisopropylethylamine (180 mg, 1.40 mmol). The resulting liquid was cooled to 0° C., and then added dropwise with a solution (0.5 mL) of acryloyl chloride (50 mg, 0.56 mmol) in DCM. The resulting mixture was stirred at 0° C. for 15 minutes to react. The resulting reaction liquid was added with 50 mL of DCM, washed orderly with 15 mL of water, with 15 mL of saturated solution of NaHCO$_3$ twice and then with 15 mL of saturated salt solution. The resulting organic phase was dried and concentrated to obtain product (4aS)-3-acryloyl-11-fluoro-10-(2-fluoro-6-methoxyphenyl)-8-(2-isopropyl-4-methylpyridin-3-yl)-1,2,3,4,4a, 5-hexahydropyrazino[1',2':4,5][1,4]oxazino[2,3-c][1,8]naphthyridin-7(8H)-one (160 mg, Y: 95.8%), which was yellow solid. ES-API: [M+H]$^+$=588.3.

Step 5: the (4aS)-3-acryloyl-11-fluoro-10-(2-fluoro-6-methoxyphenyl)-8-(2-isopropyl-4-methylpyridin-3-yl)-1,2,3,4,4a, 5-hexahydropyrazino[1',2':4,5][1,4]oxazino[2,3-c][1,8]naphthyridin-7(8H)-one (160 mg, 0.27 mmol) was dissolved in DCM (4 mL). The resulting solution was cooled to 0° C., and then added dropwise with a solution (3 mL) of 17% boron tribromide in DCM. The resulting mixture was stirred at room temperature for 3 hours to react. The resulting reaction liquid was poured into 25 mL of cold saturated solution of NaHCO$_3$ and extracted with 50 mL of DCM. The resulting organic phase was washed orderly with 25 mL of saturated solution of NaHCO$_3$ and 25 mL of saturated salt solution, dried and concentrated. The resulting crude product was purified by preparative scale HPLC to obtain product (4aS)-3-acryloyl-11-fluoro-10-(2-fluoro-6-hydroxyphenyl)-8-(2-isopropyl-4-methylpyridin-3-yl)-1,2,3,4,4a,5-hexahydropyrazino[1',2':4,5][1,4]oxazino[2,3-c][1,8]naphthyridin-7(8H)-one (Z28, 90 mg, Y: 57.6%), which was faint yellow solid. $^1$H NMR (400 MHz, DMSO-d$_6$) δ 10.04 (s, 1H), 8.42 (d, J=4.8 Hz, 1H), 8.22 (d, J=7.4 Hz, 1H), 7.27-7.17 (m, 2H), 7.01-6.78 (m, 1H), 6.77-6.58 (m, 2H), 6.18 (d, J=16.3 Hz, 1H), 5.87-5.66 (m, 1H), 4.51-3.97 (m, 4H), 3.91-3.39 (m, 4H), 3.14-3.01 (m, 1H), 2.62-2.41 (m, 1H), 1.91-1.76 (m, 3H), 1.12-0.98 (m, 3H), 0.94-0.83 (m, 3H). ES-API: [M+H]$^+$=574.2.

Example 29 Preparation of Compound Z29

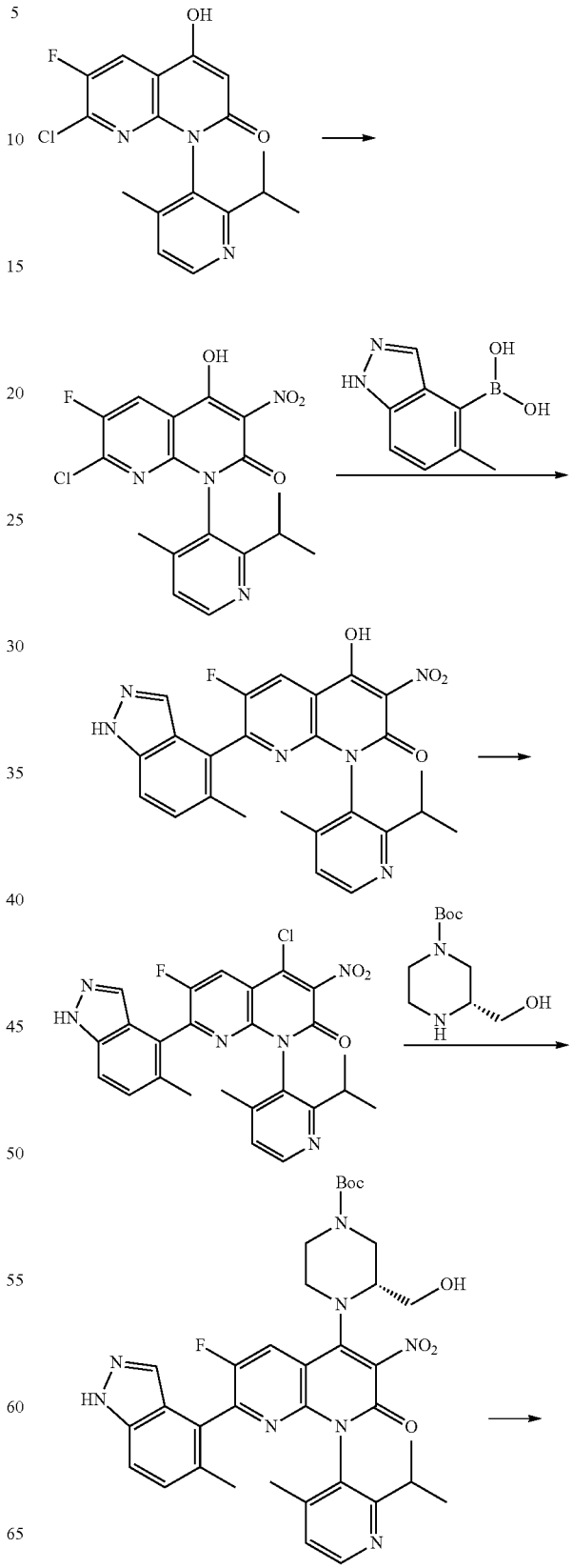

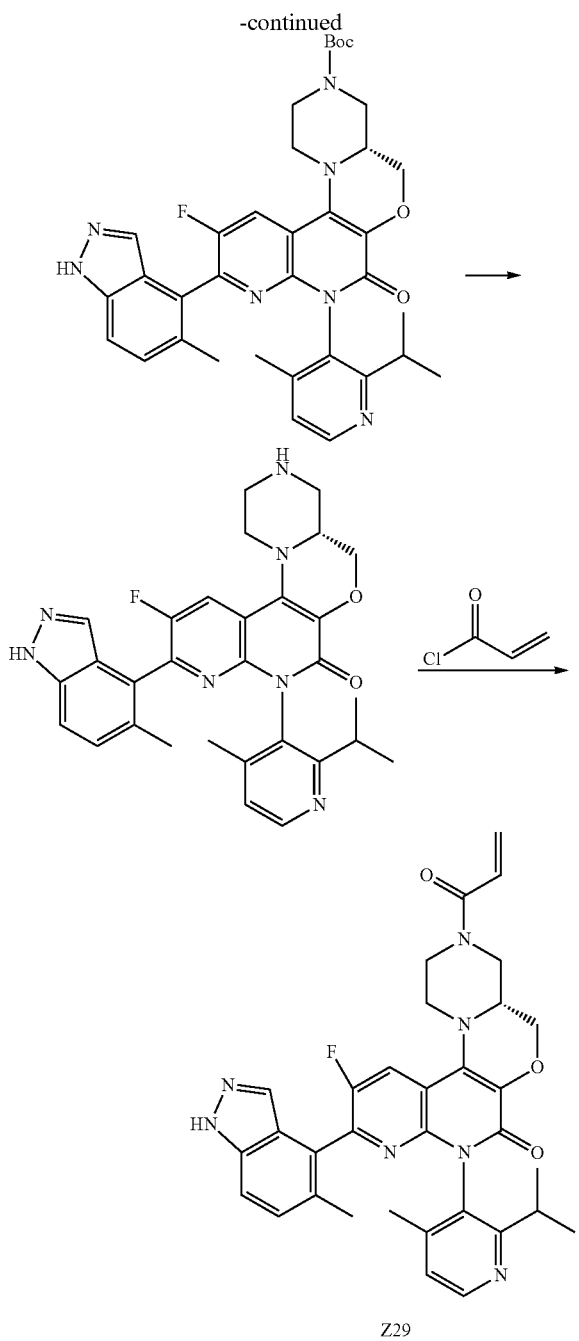

Z29

Step 1: 7-chloro-6-fluoro-4-hydroxy-1-(2-isopropyl-4-methylpyridin-3-yl)-1,8-naphthyridin-2(1H)-one (4.0 g, 11.53 mmol) was dissolved in acetic acid (9 mL), orderly added with sodium nitrite (79 mg, 1.15 mmol) and concentrated nitric acid (2.3 mL, 34.6 mmol), and stirred at room temperature for 30 minutes to react. The resulting reaction liquid was slowly poured into 100 mL of ice water. The precipitated solid was filtered. The filter cake was washed with 20 ml of ice water and dried in vacuum to obtain product 7-chloro-6-fluoro-4-hydroxy-1-(2-isopropyl-4-methylpyridin-3-yl)-3-nitro-1,8-naphthyridin-2(1H)-one (3.1 g, Y: 80%), which was yellow solid. ES-API: [M+H]$^+$=393.1.

Step 2: the 7-chloro-6-fluoro-4-hydroxy-1-(2-isopropyl-4-methylpyridin-3-yl)-3-nitro-1,8-naphthyridin-2(1H)-one (1.0 g, 2.55 mmol), (5-methyl-1H-indazol-4-yl)boric acid (1.8 g, 10.2 mmol), tetrakis(triphenylphosphine)palladium (589 mg, 0.51 mmol), potassium carbonate (1.76 g, 12.75 mmol), 2 mL of water, and 8 mL of dioxane were added to a 100 mL three-necked round-bottom flask. The resulting mixture was stirred at 110° C. for 1 hour to react under the protection of nitrogen. After the completion of the reaction, the resulting reaction liquid was cooled to room temperature, added with 80 mL of water and 100 mL of methyl tert-butyl ether, and extracted once. The water phase was then mixed with 1 M hydrochloric acid solution to adjust the pH to a range of 3 to 4. Solid was precipitated and filtered to obtain a solid product which was dried in vacuum to obtain product 6-fluoro-7-(5-methyl-1H-indazol-4-yl)-4-hydroxy-1-(2-isopropyl-4-methylpyridin-3-yl)-3-nitro-1,8-naphthyridin-2(1H)-one (0.8 g, 50%), which was faint yellow solid. ES-API: [M+H]$^+$=489.2.

Step 3: the 6-fluoro-7-(5-methyl-1H-indazol-4-yl)-4-hydroxy-1-(2-isopropyl-4-methylpyridin-3-yl)-3-nitro-1,8-naphthyridin-2(1H)-one (0.6 g, 1.23 mmol) was dissolved in ACN (20 mL), orderly added with phosphorus oxychloride (0.94 g, 6.15 mmol) and N,N-diisopropylethylamine (1.27 g, 9.84 mmol), and gradually heated to 80° C. and stirred for 24 hours to react. The resulting reaction liquid was concentrated, added with 30 mL of cold ACN, added dropwise to 30 mL of saturated sodium bicarbonate solution under the condition of an ice water bath, and extracted with EtOAc, and then combine the ethyl acetate phase (200 mL*2). The resulting combined EtOAc phase was washed with 50 mL of saturated salt solution once, dried by anhydrous sodium sulfate and filtered. After the resulting organic phase was dried and concentrated, the resulting crude product was purified by flash column chromatography on silica gel (EtOAc/PE: 0-80%) to obtain 4-chloro-6-fluoro-7-(5-methyl-1H-indazol-4-yl)-1-(2-isopropyl-4-methylpyridin-3-yl)-3-nitro-1,8-naphthyridin-2(1H)-one (0.3 g, Y: 50%), which was yellow solid. ES-API: [M+H]$^+$=507.0.

Step 4: the tert-butyl 4-chloro-6-fluoro-7-(5-methyl-1H-indazol-4-yl)-1-(2-isopropyl-4-methylpyridin-3-yl)-3-nitro-1,8-naphthyridin-2(1H)-one (150 mg, 0.296 mmol) was dissolved in N,N-dimethylacetamide (25 mL), subsequently added with tert-butyl (R)-3-(hydroxymethyl)piperazin-1-formate (1.48 g, 320 mmol), and stirred at 80° C. for 1.5 hours to react. The resulting reaction liquid was added with 80 mL of EtOAc, and washed with 80 mL of saturated salt solution for 3 times. The EtOAc phase was dried and concentrated, and the resulting crude product was purified by flash column chromatography on silica gel (EtOAc/PE: 0-80%) to obtain product tert-butyl (3R)-4-(6-fluoro-1-(2-isopropyl-4-methylpyridin-3-yl)-7-(5-methyl-1H-indazol-4-yl)-3-nitro-2-oxo-1,2-dihydro-1,8-naphthyridin-4-yl)-3-(hydroxymethyl)piperazin-1-carboxylate (10 mg, Y: 40%), which was yellow solid. ES-API: [M+H]$^+$=787.3.

Step 5: the tert-butyl (3R)-4-(6-fluoro-1-(2-isopropyl-4-methylpyridin-3-yl)-7-(5-methyl-1H-indazol-4-yl)-3-nitro-2-oxo-1,2-dihydro-1,8-naphthyridin-4-yl)-3-(hydroxymethyl)piperazin-1-carboxylate (90 mg, 0.13 mmol) was dissolved in was dissolved in N,N-dimethylacetamide (25 mL), added with sodium hydride (15.7 mg, 0.39 mmol), and stirred at 130° C. for 18 hours to react. The resulting reaction liquid was cooled to room temperature, poured into ice water, mixed with 3 M hydrochloric acid to adjust the pH to 7, and added with 30 mL of EtOAc. The organic phase was separated, washed orderly with 30 mL of water and 30 mL of saturated salt solution, dried and concentrated to obtain product tert-butyl (4aR)-11-fluoro-8-(2-isopropyl-4-methylpyridin-3-yl)-10-(5-methyl-1H-indazol-4-yl)-7-oxo-1,2, 4a,5,7,8-hexahydropyrazino[1',2':4,5][1,4]oxazino[2,3-c][1,8]naphthyridin-3(4H)-carboxylate (60 mg, Y: 70%), which was yellow solid. ES-API: [M+H]⁺=640.3.

Step 6: the tert-butyl (4aR)-11-fluoro-8-(2-isopropyl-4-methylpyridin-3-yl)-10-(5-methyl-1H-indazol-4-yl)-7-oxo-1,2,4a,5,7,8-hexahydropyrazino[1',2':4,5][1,4]oxazino[2,3-c][1,8]naphthyridin-3(4H)-carboxylate (60 mg, 0.094 mmol) was dissolved in DCM (4 mL), and added with TFA (2 mL). After stirring at room temperature for 2 hours, the resulting reaction liquid was concentrated to obtain product (4aR)-11-fluoro-8-(2-isopropyl-4-methylpyridin-3-yl)-10-(5-methyl-1H-indazol-4-yl)-1,2,3,4,4a, 5-hexahydropyrazino[1',2':4,5][1,4]oxazino[2,3-c][1,8]naphthyridin7(8H)-one (50 mg, crude), which was directly used in next step. ES-API: [M+H]⁺=540.2.

Step 7: the (4aR)-11-fluoro-8-(2-isopropyl-4-methylpyridin-3-yl)-10-(5-methyl-H-indazol-4-yl)-1,2,3,4,4a, 5-hexahydropyrazino[1',2':4,5][1,4]oxazino[2,3-c][1,8]naphthyridin7(8H)-one (50 mg, 0.093 mmol) was dissolved in DCM (5 mL), and added with triethylamine (60 mg, 0.465 mmol). The resulting reaction liquid was cooled to 0° C., and then added dropwise with acryloyl chloride (10.5 mg, 0.083 mmol). The resulting mixture was stirred at 0° C. for 15 minutes to react. The resulting reaction liquid was added with 20 mL of DCM, washed with 20 mL of saturated solution of NaHCO₃ and 20 mL of saturated salt solution, dried and concentrated, and purified by preparative scale HPLC to obtain product (4aR)-3-acryloyl-11-fluoro-8-(2-isopropyl-4-methylpyridin-3-yl)-10-(5-methyl-1H-indazol-4-yl)-1,2,3,4,4a,5-hexahydropyrazino[1',2':4,5][1,4]oxazino[2,3-c][1,8]naphthyridin-7(8H)-one (Z29, 15 mg, Y: 28%). ES-API: [M+H]⁺=594.2. ¹H NMR (500 MHz, DMSO-d₆) δ 13.08 (s, 1H), 8.37 (d, J=4.8 Hz, 1H), 8.32 (d, J=9.4 Hz, 1H), 7.49 (d, J=8.1 Hz, 2H), 7.24 (d, J=8.5 Hz, 1H), 7.20 (d, J=5.0 Hz, 1H), 6.90 (s, 1H), 6.20 (d, J=16.7 Hz, 1H), 5.78 (s, 1H), 4.45 (d, J=46.5 Hz, 1H), 4.35-4.20 (m, 2H), 4.05 (s, 1H), 3.85 (d, J=51.4 Hz, 1H), 3.75-3.57 (m, 2H), 3.48 (s, 1H), 3.15 (s, 1H), 2.05 (s, 3H), 1.90 (d, J=33.7 Hz, 3H), 1.03 (t, J=6.7 Hz, 3H), 0.81 (dd, J=20.9, 6.4 Hz, 3H).

Example 30 Preparation of Compounds Z30, Z30-1, and Z30-2

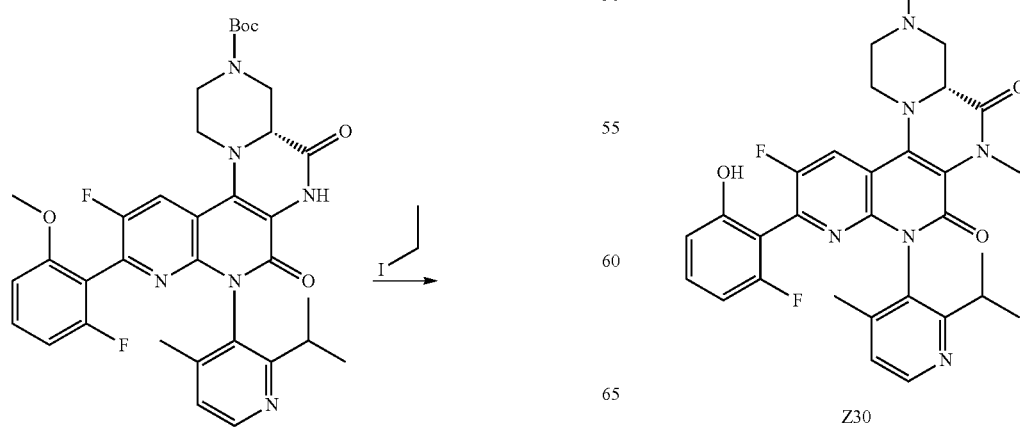

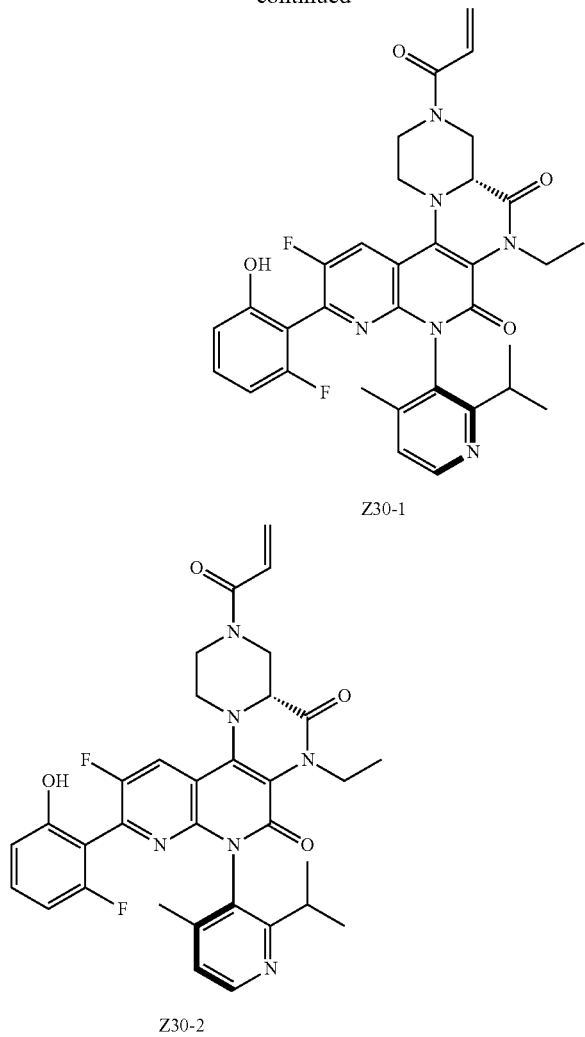

Z30-1

Z30-2

Step 1: tert-butyl (4aR)-11-fluoro-10-(2-fluoro-6-methoxyphenyl)-8-(2-isopropyl-4-methylpyridin-3-yl)-5,7-dioxo-1,2,4,4a,5,6,7,8-octahydro-3H-pyrazino[1',2':4,5]pyrazino[2,3-c][1,8]naphthyridin-3-carboxylate (310 mg, 0.48 mmol), 10 mL of acetone, anhydrous potassium carbonate (265 mg, 1.92 mmol), and iodoethane (599 mg, 3.84 mmol) were orderly added to a 15 mL sealing tube. The sealing tube was sealed, and the resulting mixture was stirred at 55° C. for 18 hours to react. The resulting reaction liquid was concentrated, added with 60 mL of EtOAc, washed orderly with 30 mL of water and 30 mL of saturated salt solution, dried and concentrated. The resulting crude product was purified by flash column chromatography on silica gel (EtOAc/PE: 0-70%) to obtain product tert-butyl (4aR)-6-ethyl-11-fluoro-10-(2-fluoro-6-methoxyphenyl)-8-(2-isopropyl-4-methylpyridin-3-yl)-5,7-dioxo-1,2,4,4a,5,6,7,8-octyl-3H-pyrazino[1',2':4,5]pyrazino[2,3-c][1,8]naphthyridin-3-carboxylate (290 mg, Y: 89.7%), which was orange solid. ES-API: [M+H]⁺=675.3.

Step 2: the tert-butyl (4aR)-6-ethyl-11-fluoro-10-(2-fluoro-6-methoxyphenyl)-8-(2-isopropyl-4-methylpyridin-3-yl)-5,7-dioxo-1,2,4,4a,5,6,7,8-octyl-3H-pyrazino[1',2':4,5]pyrazino[2,3-c][1,8]naphthyridin-3-carboxylate (290 mg, 0.43 mmol) was dissolved in DCM (4 mL), and added with TFA (1 mL). After stirring at room temperature for 2 hours, the resulting reaction liquid was concentrated to obtain product (4aR)-6-ethyl-11-fluoro-10-(2-fluoro-6-methoxyphenyl)-8-(2-isopropyl-4-methylpyridin-3-yl)-2,3,4,4a,6,8-hexahydro-1H-pyrazino[1',2':4,5]pyrazino[2,3-c][1,8]naphthyridin-5,7-dione (300 mg, crude), which was directly used in next step. ES-API: [M+H]⁺=575.2.

Step 3: the (4aR)-6-ethyl-11-fluoro-10-(2-fluoro-6-methoxyphenyl)-8-(2-isopropyl-4-methylpyridin-3-yl)-2,3,4,4a,6,8-hexahydro-1H-pyrazino[1',2':4,5]pyrazino[2,3-c][1,8]naphthyridin-5,7-dione (300 mg, crude) was dissolved in DCM (15 mL), and added with N,N-diisopropylethylamine (464 mg, 3.60 mmol). The resulting reaction liquid was cooled to 0° C., added with acryloyl chloride (130 mg, 1.44 mmol), and stirred at 0° C. for 15 minutes to react. The reaction liquid was added with 45 mL of DCM, washed orderly with 25 mL of water, 25 mL of saturated solution of NaHCO₃ and 25 mL of saturated salt solution, dried and concentrated. The resulting crude product was purified by flash column chromatography on silica gel (EtOAc/PE: 0-90%) to obtain product (4aR)-3-acryloyl-6-ethyl-11-fluoro-10-(2-fluoro-6-methoxyphenyl)-8-(2-isopropyl-4-methylpyridin-3-yl)-2,3,4,4a,6,8-hexahydro-1H-pyrazino[1',2':4,5]pyrazino[2,3-c][1,8]naphthyridin-5,7-dione (2450 mg, Y: 90.7%), which was faint yellow solid. ES-API: [M+H]⁺=615.3.

Step 4: the (4aR)-3-acryloyl-6-ethyl-11-fluoro-10-(2-fluoro-6-methoxyphenyl)-8-(2-isopropyl-4-methylpyridin-3-yl)-2,3,4,4a,6,8-hexahydro-1H-pyrazino[1',2':4,5]pyrazino[2,3-c][1,8]naphthyridin-5,7-dione (245 mg, 0.39 mmol) was dissolved in DCM (5 mL). The resulting solution was cooled to 0° C., and then added dropwise with a solution (5 mL) of 17% boron tribromide in DCM. The resulting mixture was stirred at room temperature for 3 hours to react.

The resulting reaction liquid was poured into 60 mL of saturated solution of NaHCO₃ and extracted with 50 mL of DCM twice. The resulting organic phase was washed orderly with 30 mL of saturated solution of NaHCO₃ and 30 mL of saturated salt solution, dried and concentrated to obtain product (4aR)-3-acryloyl-6-ethyl-11-fluoro-10-(2-fluoro-6-hydroxyphenyl)-8-(2-isopropyl-4-methylpyridin-3-yl)-2,3,4,4a,6,8-hexahydro-1H-pyrazino[1',2':4,5]pyrazino[2,3-c][1,8]naphthyridin-5,7-dione (Z30, 240 mg, Y: 100%), which was faint yellow solid. ES-API: [M+H]⁺=615.3.

Step 5: the compound Z30 (240 mg, 0.39 mmol) was purified by preparative scale HPLC and then resolved by preparative scale chiral HPLC (column type: IB: 10 μm, 30*250 mm; mobile phase: hexane:EtOH=70:30; flow rate: 25 m/min; and column temperature: room temperature) to obtain the following atropisomer compounds. One of the atropisomer compounds had a structure arbitrarily specified as Z30-1 (71 mg, peak 1, retention time: 6.342 min, Y: 29.6%), which was faint yellow solid. ¹H NMR (500 MHz, DMSO-d₆) δ 10.11 (d, J=1.1 Hz, 1H), 8.45 (d, J=4.9 Hz, 1H), 8.40 (d, J=8.8 Hz, 1H), 7.32-7.18 (m, 2H), 7.12-6.80 (m, 1H), 6.75-6.62 (m, 2H), 6.15 (dd, J=16.8, 2.0 Hz, 1H), 5.75 (d, J=12.2 Hz, 1H), 4.72 (d, J=13.5 Hz, 1H), 4.46 (d, J=11.9 Hz, 1H), 4.18-3.93 (m, 3H), 3.63-3.50 (m, 2H), 3.26-3.06 (m, 1H), 2.80-2.55 (m, 1H), 2.50-2.39 (m, 1H), 1.97 (s, 3H), 1.10-0.95 (m, 6H), 0.86 (d, J=6.7 Hz, 3H). ES-API: [M+H]⁺=615.2. The other atropisomer compound had a structure arbitrarily specified as Z30-2 (73 mg, peak 2, retention time: 7.970 min, Y: 30.5%), which was faint yellow solid. ¹H NMR (500 MHz, DMSO-d₆) δ 10.13 (s, 1H), 8.45 (d, J=4.9 Hz, 1H), 8.39 (d, J=8.8 Hz, 1H), 7.31-7.19 (m, 2H), 7.12-6.80 (m, 1H), 6.77-6.62 (m, 2H), 6.15 (dd, J=16.8, 2.1 Hz, 1H), 5.75 (d, J=12.3 Hz, 1H), 4.73

(d, J=14.1 Hz, 1H), 4.46 (d, J=13.0 Hz, 1H), 4.20-4.02 (m, 2H), 4.00-3.91 (m, 1H), 3.65-3.53 (m, 2H), 3.26-3.06 (m, 1H), 2.82-2.58 (m, 2H), 1.80 (s, 3H), 1.15-0.93 (m, 9H). $^1$ES-API: [M+H]$^+$=615.2. The isomer compounds were detected by analytical scale chiral HPLC (column type: IB: 5 μm, 4.6*250 mm; mobile phase: hexane:EtOH=70:30; flow rate: 1 ml/min; and column temperature=30° C.).
Example 31 Preparation of Compound Z31
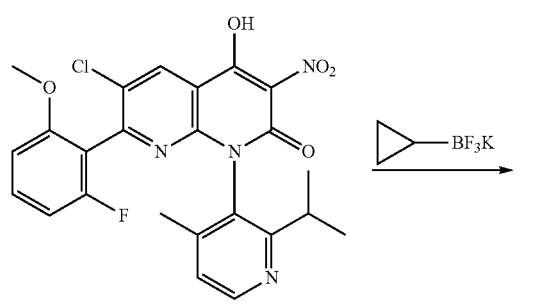
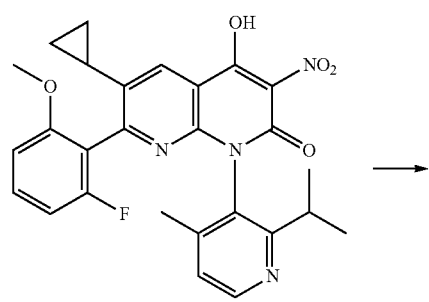
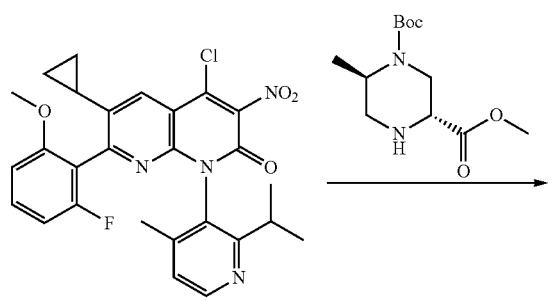
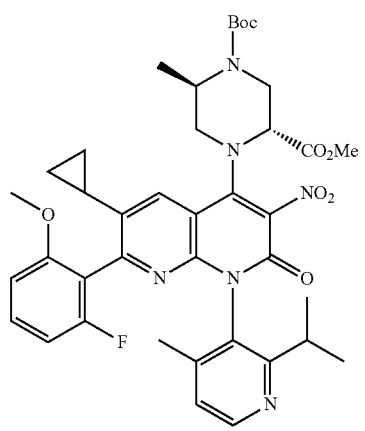
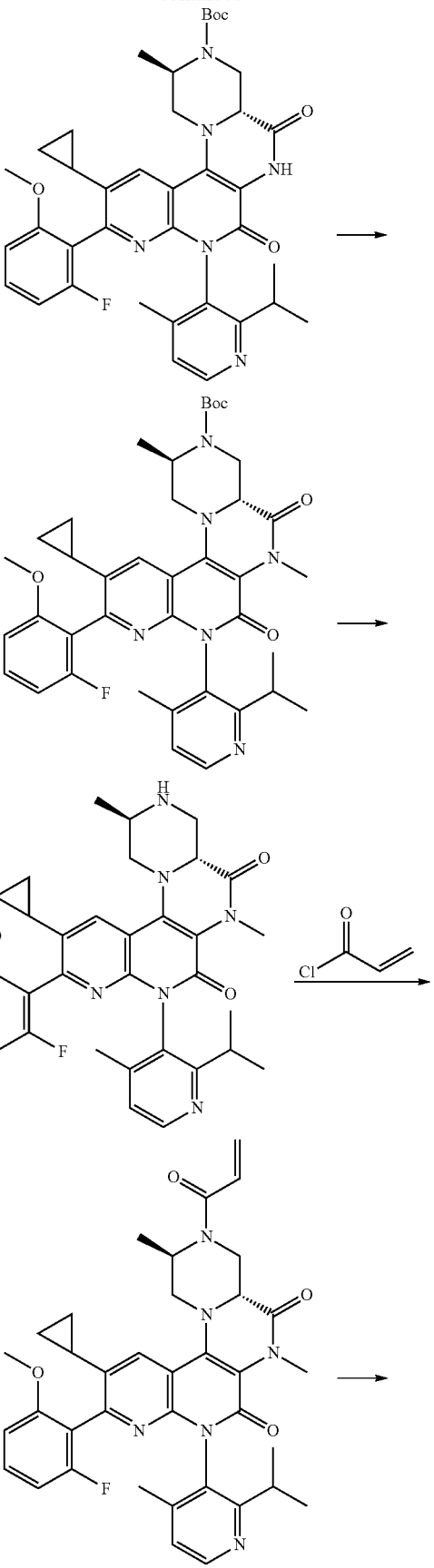

-continued

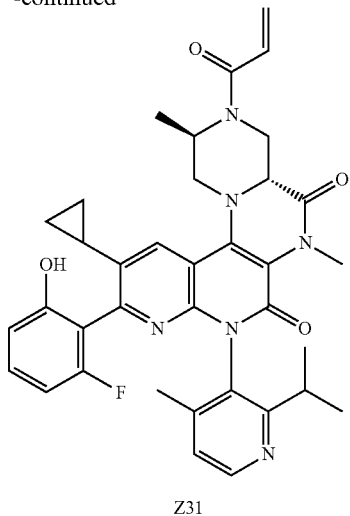

Z31

Step 1: 6-chloro-7-(2-fluoro-6-methoxyphenyl)-4-hydroxy-1-(2-isopropyl-4-methylpyridin-3-yl)-3-nitro-1,8-naphthyridin-2(1H)-one (1.0 g, 2.0 mmol), potassium cyclopropyltrifluoroborate (1.48 g, 10.0 mmol), SPhos-Pd-G2 (144 mg, 0.20 mmol), SPhos (82 mg, 0.20 mmol), potassium carbonate (1.66 g, 12.0 mmol), 2 mL of water, and 20 mL of toluene were added to a 250 mL round-bottom flask. The resulting mixture was stirred at 125° C. for 18 hours to react under the protection of nitrogen. The resulting reaction liquid was concentrated, added with 50 mL of DCM twice. The resulting organic phase was dried and concentrated to obtain product 6-cyclopropyl-7-(2-fluoro-6-methoxyphenyl)-4-hydroxy-1-(2-isopropyl-4-methylpyridin-3-yl)-3-nitro-1,8-naphthyridin-2(1H)-one (850 mg, crude) which was brown solid. ES-API: [M+H]$^+$=505.2.

Step 2: the 6-cyclopropyl-7-(2-fluoro-6-methoxyphenyl)-4-hydroxy-1-(2-isopropyl-4-methylpyridin-3-yl)-3-nitro-1,8-naphthyridin-2(1H)-one (1.6 g, crude) was dissolved in ACN (50 mL), orderly added with phosphorus oxychloride (2.43 g, 15.85 mmol) and N,N-diisopropylethylamine (3.27 g, 25.36 mmol), and stirred at 85° C. for 1 hour to react. The resulting reaction liquid was concentrated, added with 120 mL of EtOAc, and washed orderly with 60 mL of water, with 60 mL of saturated sodium bicarbonate solution twice and then with 60 mL saturated salt solution. After the resulting organic phase was dried and concentrated, the resulting crude product was purified by flash column chromatography on silica gel (EtOAc/PE: 0-35%) to obtain product 4-chloro-6-cyclopropyl-7-(2-fluoro-6-methoxyphenyl)-1-(2-isopropyl-4-methylpyridin-3-yl)-3-nitro-1,8-naphthyridin-2(1H)-one (520 mg, Y: 24.8%), which was faint yellow solid. ES-API: [M+H]$^+$=523.2.

Step 3: the 4-chloro-6-cyclopropyl-7-(2-fluoro-6-methoxyphenyl)-1-(2-isopropyl-4-methylpyridin-3-yl)-3-nitro-1,8-naphthyridin-2(1H)-one (490 mg, 0.94 mmol) was dissolved in N,N-dimethylacetamide (6 mL), orderly added with methyl (3R,6R)-1-N-BOC-6-methylpiperazin-3-formate (485 mg, 1.88 mmol) and N,N-diisopropylethylamine (364 mg, 2.82 mmol), and stirred at 125° C. for 3 hours to react. The resulting reaction liquid was added with 100 mL of EtOAc washed, with 30 mL of dilute brine for 4 times and then with 30 mL saturated salt solution, dried and concentrated. The resulting crude product was purified by flash column chromatography on silica gel (EtOAc/PE: 0-50%) to obtain product methyl (3R,6R)-1-N-BOC-4-(6-cyclopropyl-7-(2-fluoro-6-methoxyphenyl)-1-(2-isopropyl-4-methylpyridin-3-yl)-3-nitro-2-oxo-1,2dihydro-1,8-naphthyridin-4-yl)-6-methylpiperazin-3-formate (485 mg, Y: 69.4%), which was orange solid. ES-API: [M+H]$^+$=745.3.

Step 4: the methyl (3R,6R)-1-N-BOC-4-(6-cyclopropyl-7-(2-fluoro-6-methoxyphenyl)-1-(2-isopropyl-4-methylpyridin-3-yl)-3-nitro-2-oxo-1,2-dihydro-1,8-naphthyridin-4-yl)-6-methylpiperazin-3-formate (455 mg, 0.61 mmol) was dissolved in acetic acid (8 mL), added with iron powder (120 mg, 2.14 mmol), and stirred at 80° C. for 30 minutes to react. The resulting reaction liquid was concentrated, and orderly added with 80 mL of EtOAc and 50 mL of saturated sodium bicarbonate solution. The resulting suspension was filtered by diatomite. The filter cake was washed with EtOAc. The resulting organic phase was separated, washed orderly with 25 mL of saturated sodium bicarbonate solution and 25 mL of saturated salt solution, dried and concentrated to obtain product tert-butyl (2R,4aR)-11-cyclopropyl-10-(2-fluoro-6-methoxyphenyl)-8-(2-isopropyl-4-methylpyridin-3-yl)-2-methyl-5,7-dioxo-1,2,4,4a,5,6,7,8-octyl-3H-pyrazino[1',2':4,5]pyrazino[2,3-c][1,8]naphthyridin-3-carboxylate (415 mg, Y: 99.5%), which was faint yellow solid. ES-API: [M+H]$^+$=683.3.

Step 5: the tert-butyl (2R,4aR)-11-cyclopropyl-10-(2-fluoro-6-methoxyphenyl)-8-(2-isopropyl-4-methylpyridin-3-yl)-2-methyl-5,7-dioxo-1,2,4,4a,5,6,7,8-octyl-3H-pyrazino[1',2':4,5]pyrazino[2,3-c][1,8]naphthyridin-3-carboxylate (415 mg, 0.61 mmol), 12 mL of acetone, anhydrous potassium carbonate (337 mg, 2.44 mmol), and iodomethane (693 mg, 4.88 mmol) were orderly added to a 50 mL sealing tube. The sealing tube was sealed, and the resulting mixture was stirred at 50° C. for 18 hours to react. The resulting reaction liquid was added with 60 mL of EtOAc, washed orderly with 15 mL of water and 15 mL of saturated salt solution, dried and concentrated. The resulting crude product was purified on a preparative thin-layer chromatographic plate (DCM/MeOH=25:1) to obtain product tert-butyl (2R,4aR)-11-cyclopropyl-10-(2-fluoro-6-methoxyphenyl)-8-(2-isopropyl-4-methylpyridin-3-yl)-2,6-dimethyl-5,7-dioxo-1,2,4,4a,5,6,7,8-octyl-3H-pyrazino[1',2':4,5]pyrazino[2,3-c][1,8]naphthyridin-3-carboxylate (160 mg, Y: 37.8%), which was faint yellow solid. ES-API: [M+H]$^+$=697.3.

Step 6: the tert-butyl (2R,4aR)-11-cyclopropyl-10-(2-fluoro-6-methoxyphenyl)-8-(2-isopropyl-4-methylpyridin-3-yl)-2,6-dimethyl-5,7-dioxo-1,2,4,4a,5,6,7,8-octyl-3H-pyrazino[1',2':4,5]pyrazino[2,3-c][1,8]naphthyridin-3-carboxylate (160 mg, 0.23 mmol) was dissolved in DCM (3.5 mL), and added with TFA (0.8 mL). After stirring at room temperature for 2 hours, the resulting reaction liquid was concentrated to obtain product (2R,4aR)-11-cyclopropyl-10-(2-fluoro-6-methoxyphenyl)-8-(2-isopropyl-4-methylpyridin-3-yl)-2,6-dimethyl-,2,4,4a, 6,8-hexahydro-3l2-pyrazino[4', 3': 4,5]pyrazino[2,3-c][1,8]naphthyridin-5,7-dione (165 mg, crude), which was directly used in next step. ES-API: [M+H]$^+$=597.2.

Step 7: the (2R,4aR)-11-cyclopropyl-10-(2-fluoro-6-methoxyphenyl)-8-(2-isopropyl-4-methylpyridin-3-yl)-2,6-dimethyl-1,2,4,4a, 6,8-hexahydro-3l2-pyrazino[4', 3: 4,5] pyrazino[2,3-c][1,8]naphthyridin-5,7-dione (165 mg, crude) was dissolved in DCM (10 mL), and added with N,N-diisopropylethylamine (148 mg, 1.15 mmol). The resulting reaction liquid was cooled to 0° C., and added dropwise with acryloyl chloride (41 mg, 0.46 mmol). The resulting mixture was stirred at 0° C. for 15 minutes to react. The resulting reaction liquid was added with 30 mL of DCM, washed orderly with 15 mL of water, 15 mL of saturated solution of NaHCO₃ and 15 mL of saturated salt solution, dried and concentrated. The resulting crude product was purified by flash column chromatography on silica gel (DCM/MeOH: 0-5%) to obtain product (2R,4aR)-3-acryloyl-11-cyclopropyl-10-(2-fluoro-6-methoxyphenyl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin-5,7-dione (140 mg, Y: 93.7%), which was faint yellow solid. ES-API: [M+H]⁺=651.3.

Step 8: the (2R,4aR)-3-acryloyl-11-cyclopropyl-10-(2-fluoro-6-methoxyphenyl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin-5,7-dione (130 mg, 0.20 mmol) was dissolved in DCM (3 mL). The resulting solution was cooled to 0° C., and then added dropwise with a solution (3 mL) of 17% boron tribromide in DCM. The resulting mixture was stirred at room temperature for 3 hours to react. The resulting reaction liquid was poured into 40 mL of saturated solution of NaHCO₃ and extracted with 25 mL of DCM twice. The resulting organic phase was dried and concentrated, and the resulting crude product was purified by preparative scale HPLC to obtain product (2R,4aR)-3-acryloyl-11-cyclopropyl-10-(2-fluoro-6-hydroxyphenyl)-8-(2-isopropyl-4-methylpyridin-3-yl)-2,6-dimethyl-2,3,4,4a,6,8-hexahydro-1H-pyrazino[1',2':4,5]pyrazino[2,3-c][1,8]naphthyridin-5,7-dione (Z31, 65 mg, Y: 51.1%), which was white solid. ¹H NMR (500 MHz, DMSO-d₆) δ 9.90 (s, 1H), 8.42 (d, J=4.8 Hz, 1H), 7.75-7.73 (m, 1H), 7.22-7.17 (m, 2H), 7.03 (dd, J=16.8, 10.5 Hz, 1H), 6.74-6.60 (m, 2H), 6.22-6.08 (m, 1H), 5.81-5.69 (m, 1H), 5.05-4.81 (m, 1H), 4.62-4.41 (m, 1H), 4.03-3.90 (m, 1H), 3.75 (dd, J=14.1, 4.2 Hz, 1H), 3.39-3.25 (m, 4H), 2.83-2.67 (m, 1H), 2.48-2.37 (m, 1H), 2.01-1.75 (m, 3H), 1.70-1.46 (m, 4H), 1.14-0.55 (m, 10H). ES-API: [M+H]⁺=637.3.

Example 32 Preparation of Compound Z32

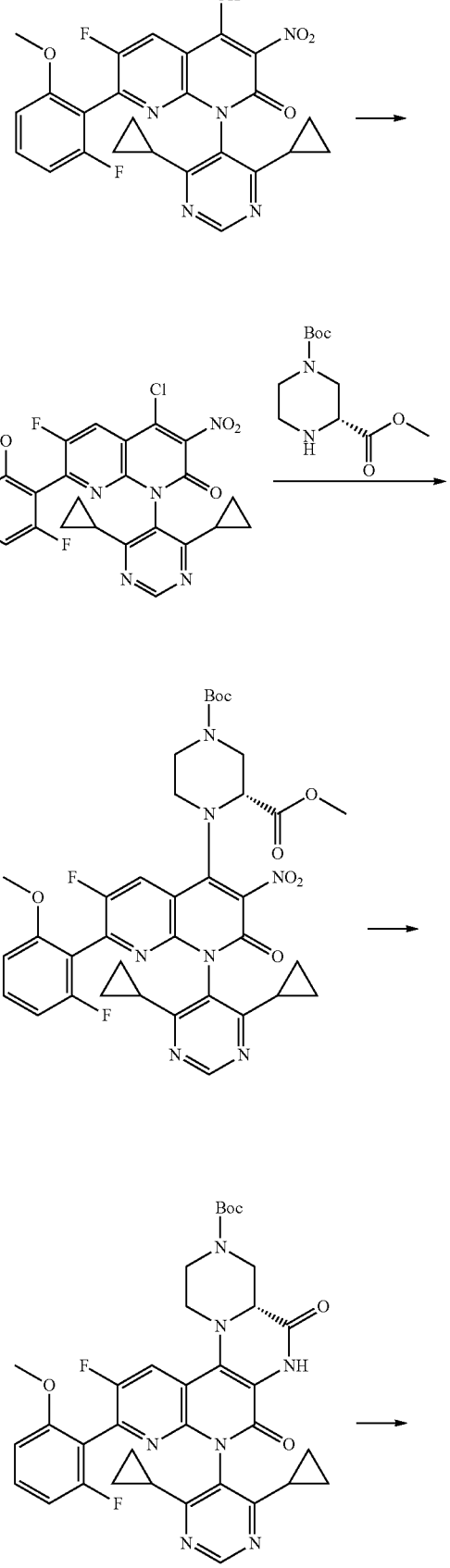
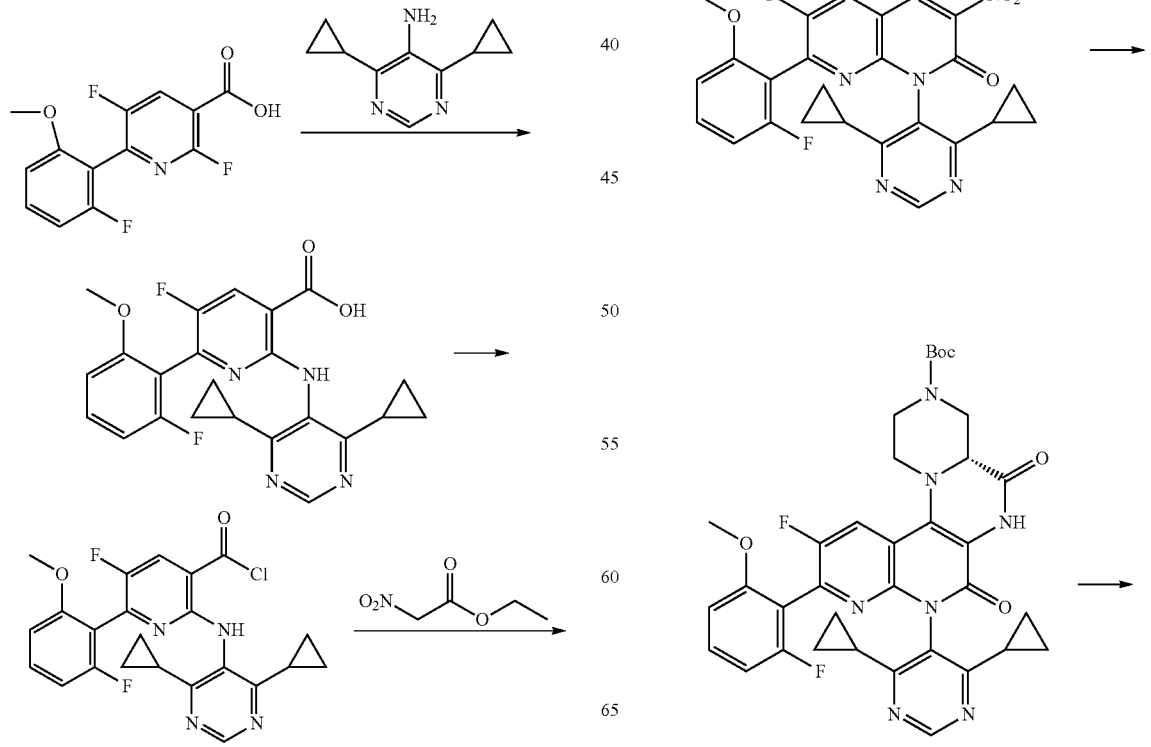

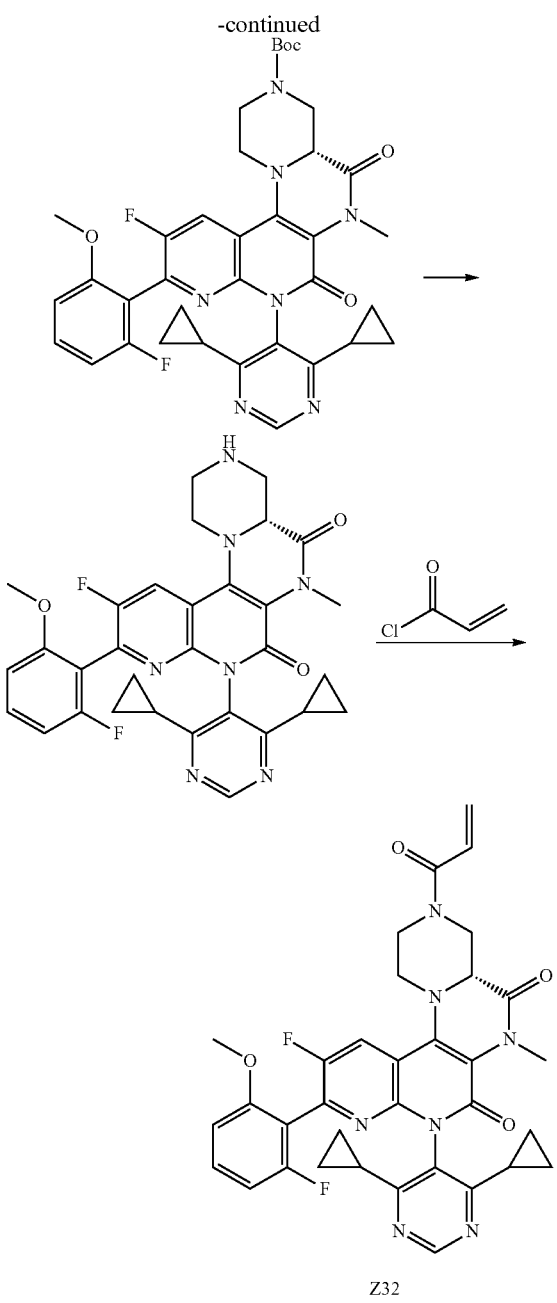

Z32

Step 1: 4,6-bicyclopropylpyrimidin-5-amine (742 mg, 4.24 mmol) was dissolved in dry tetrahydrofuran (20 mL), added with 2 M NaHMDS (8.48 mL, 16.96 mmol) under the condition of an ice water bath, and stirred for 20 minutes under the condition of the ice water bath. The resulting mixture was added with 2,5-difluoro-6-(2-fluoro-6-methoxyphenyl)nicotinic acid (1.2 g, 4.24 mmol), and stirred at room temperature for 3 hours. The resulting reaction liquid was slowly poured into 30 mL of ice water, mixed with diluted hydrochloric acid (3M) to adjust the pH to a range of 5 to 6, extracted with EtOAc, washed with 50 mL of saturated salt solution once, dried by anhydrous sodium sulfate, and filtered. After the resulting organic phase was dried and concentrated, the resulting crude product was purified by flash column chromatography on silica gel (EtOAc/PE: 20-40%) to obtain product 2-((4,6-bicyclopropylpyrimidin-5-yl)amino)-5-fluoro-6-(2-fluoro-6-methoxyphenyl)nicotinic acid (1.8 g, Y: 98%), which was yellow solid. ES-API: [M+H]$^+$=439.1.

Step 2: the 2-((4,6-bicyclopropylpyrimidin-5-yl)amino)-5-fluoro-6-(2-fluoro-6-methoxyphenyl)nicotinic acid (1.5 g, 3.42 mmol) was dissolved in dichloroethane, and added with thionyl chloride (4.07 g, 34.2 mmol). The resulting mixture was stirred at 80° C. for 2 hours to react. After the completion of the reaction, the resulting reaction liquid was cooled to room temperature, concentrated, and dried in 50 degrees of vacuum for 4 hours to obtain product 2-((4,6-dicyclopropylpyrimidin-5-yl)amino)-5-fluoro-6-(2-fluoro-6-methoxyphenyl)nicotinoyl chloride (1.57 g, crude), which was faint yellow solid. MeOH was used to detect ES-API: [M+H]$^+$=453.2.

Step 3: under the condition of the ice water bath, sodium hydride (1.97 g, 49.35 mmol) was added to a solution of ethyl nitroacetate (1.31 g, 9.86 mmol) in tetrahydrofuran, stirred for 30 minutes, subsequently added with the 2-((4,6-bicyclopropylpyrimidin-5-yl)amino)-5-fluoro-6-(2-fluoro-6-methoxyphenyl)nicotinoyl chloride (1.57 g, 3.29 mmol), stirred at room temperature for 1 hour, and then heated to 80° C. to react for 2 hours. The resulting reaction liquid was poured into ice water, mixed with 3 M hydrochloric acid to adjust the pH to 34, extracted with EtOAc, dried by anhydrous sodium sulfate, and filtered. The resulting organic phase was dried and concentrated to obtain product 1-(4,6-bicyclopropylpyrimidin-5-yl)-6-fluoro-7-(2-fluoro-6-methoxyphenyl)-4-hydroxy-3-nitro-1,8-naphthyridin-2(1H)-one (110 mg, Y: 20%). ES-API: [M+H]$^+$=508.1.

Step 4: the 1-(4,6-bicyclopropylpyrimidin-5-yl)-6-fluoro-7-(2-fluoro-6-methoxyphenyl)-4-hydroxy-3-nitro-1,8-naphthyridin-2(1H)-one (110 mg, 0.20 mmol) was dissolved in ACN (10 mL), orderly added with phosphorus oxychloride (153 mg, 1.0 mmol) and N,N-diisopropylethylamine (77 g, 0.6 mmol), and gradually heated to 80° C. and stirred for 3 hours to react. The resulting reaction liquid was concentrated, added with 30 mL of cold ACN, added dropwise to 30 mL of saturated sodium bicarbonate solution under the condition of the ice water bath, and extracted with EtOAc (50 mL*2). The resulting combined organic phase was washed with 30 mL of saturated salt solution, dried by anhydrous sodium sulfate, and filtered. After the resulting organic phase was dried and concentrated, the resulting crude product was purified by flash column chromatography on silica gel (EtOAc/PE: 0-80%) to obtain 4-chloro-6-fluoro-7-(2-fluoro-6-methoxyphenyl)-1-(4,6-bicyclopropylpyrimidin-5-yl)-3-nitro-1,8-naphthyridin-2(1H)-one (110 mg, Y: 68%), which was yellow solid. ES-API: [M+H]$^+$=526.2.

Step 5: the 4-chloro-6-fluoro-7-(2-fluoro-6-methoxyphenyl)-1-(4,6-bicyclopropylpyrimidin-5-yl)-3-nitro-1,8-naphthyridin-2(1H)-one (110 mg, 0.296 mmol) was dissolved in N,N-dimethylacetamide (3 mL), subsequently added with 1-(tert-butyl)3-methyl(R)-piperazin-1,3-dicarboxylate (54 mg, 0.22 mmol), and stirred at 120° C. for 2 hours to react. After the completion of the reaction, the resulting product was added with 30 mL of EtOAc and washed with 30 mL of saturated salt solution for 3 times. The EtOAc phase was dried and concentrated to obtain a crude product, namely target product (3R)-1-tert-butyl3-methyl4-(1-(4,6-bicyclopropylpyrimidin-5-yl)-6-fluoro-7-(2-fluoro-6-methoxyphenyl)-3-nitro-2-oxo-1,2-dihydro-1,8-naphthyridin-4-yl)piperazin-1,3-dione (50 mg, Y: 46%), which was yellow solid. ES-API: [M+H]$^+$=734.3.

Step 6: the (3R)-1-tert-butyl3-methyl4-(1-(4,6-bicyclopropylpyrimidin-5-yl)-6-fluoro-7-(2-fluoro-6-methoxyphenyl)-3-nitro-2-oxo-1,2-dihydro-1,8-naphthyridin-4-yl)piperazin-1,3-dione (50 mg, 0.068 mmol) was dissolved in acetic acid (25 mL), added with iron powder (11.5 mg, 0.204 mmol), and stirred at 80° C. for 30 minutes to react. The resulting reaction liquid was concentrated, and orderly added with 30 mL of EtOAc and 30 mL of saturated sodium bicarbonate solution. The resulting suspension was filtered by diatomite. The filter cake was washed with EtOAc. The resulting organic phase was separated, washed orderly with 30 mL of saturated sodium bicarbonate solution and 30 mL of saturated salt solution, dried and concentrated to obtain product tert-butyl (4aR)-8-(4,6-bicyclopropylpyrimidin-5-yl)-11-fluoro-10-(2-fluoro-6-methoxyphenyl)-5,7-dioxo-4, 4a,5,6,7,8-hexahydro-1H-pyrazino[1',2':4,5]pyrazino[2,3-c][1,8]naphthyridin-3(2H)-carboxylate (40 mg, crude), which was yellow solid. ES-API: [M+H]$^+$=672.2.

Step 7: the tert-butyl (4aR)-8-(4,6-bicyclopropylpyrimidin-5-yl)-11-fluoro-10-(2-fluoro-6-methoxyphenyl)-5,7-dioxo-4,4a,5,6,7,8-hexahydro-1H-pyrazino[1',2':4,5]pyrazino[2,3-c][1,8]naphthyridin-3(2H)-carboxylate (40 mg, 0.059 mmol), 30 mL of acetone, anhydrous potassium carbonate (33 mg, 0.24 mmol), and iodomethane (85 mg, 0.59 mmol) were sealed in a sealing tube, and stirred at 50° C. for 18 hours to react. The resulting reaction liquid was added with 20 mL of EtOAc, washed with 20 mL of saturated salt solution, dried and concentrated. The resulting crude product was purified by flash column chromatography on silica gel (EtOAc/PE: 0-80%) to obtain product (4aR)-tert-butyl8-(4,6-bicyclopropylpyrimidin-5-yl)-11-fluoro-10-(2-fluoro-6-methoxyphenyl)-6-methyl-5,7-dioxo-4,4a,5,6,7,8-hexahydro-1H-pyrazino[1',2':4,5]pyrazino[2,3-c][1,8]naphthyridin-3(2H)-one (40 mg, Y: 90%), which was yellow solid. ES-API: [M+H]$^+$=686.2.

Step 8: the (4aR)-tert-butyl8-(4,6-bicyclopropylpyrimidin-5-yl)-11-fluoro-10-(2-fluoro-6-methoxyphenyl)-6-methyl-5,7-dioxo-4,4a,5,6,7,8-hexahydro-1H-pyrazino[1',2':4,5]pyrazino[2,3-c][1,8]naphthyridin-3(2H)-one (44 mg) was dissolved in DCM (3 mL), and added with TFA (1 mL). After stirring at room temperature for 2 hours, the resulting reaction liquid was concentrated to obtain product (4aR)-8-(4,6-bicyclopropylpyrimidin-5-yl)-11-fluoro-10-(2-fluoro-6-methoxyphenyl)-6-methyl-2,3,4,4a-tetrahydro-1H-pyrazino[1',2':4,5]pyrazino[2,3-c][1,8]naphthyridin-5,7(6H, 8H)-dione (40 mg, crude), which was directly used in next step. ES-API: [M+H]$^+$=586.2.

Step 9: the (4aR)-8-(4,6-bicyclopropylpyrimidin-5-yl)-11-fluoro-10-(2-fluoro-6-methoxyphenyl)-6-methyl-2,3,4,4a-tetrahydro-1H-pyrazino[1',2':4,5]pyrazino[2,3-c][1,8]naphthyridin-5,7(6H, 8H)-dione (40 mg, 0.068 mmol) was dissolved in DCM (5 mL), and added with diisopropylethylamine (53 mL, 0.408 mmol). The resulting reaction liquid was cooled to 0° C., and added dropwise with acryloyl chloride (12.4 mg, 0.137 mmol). The resulting mixture was stirred at 0° C. for 15 minutes to react. The resulting reaction liquid was added with 20 mL of DCM, washed with 20 mL of saturated solution of NaHCO$_3$ and 20 mL of saturated salt solution, dried and concentrated. The resulting crude product was purified by preparative scale HPLC to obtain product (4aR)-3-acryloyl-11-fluoro-10-(2-fluoro-6-methoxyphenyl)-8-(4,6-bicyclopropylpyrimidin-5-yl)-6-methyl-2,3,4,4a,6,8-hexahydro-1H-pyrazino[1',2':4,5]pyrazino[2,3-c][1,8]naphthyridin-5,7-dione (Z32, 10 mg, Y: 22%), which was yellow solid. ES-API: [M+H]$^+$=640.2.

Example 33 Preparation of Compounds Z33, Z33-1, and Z33-2

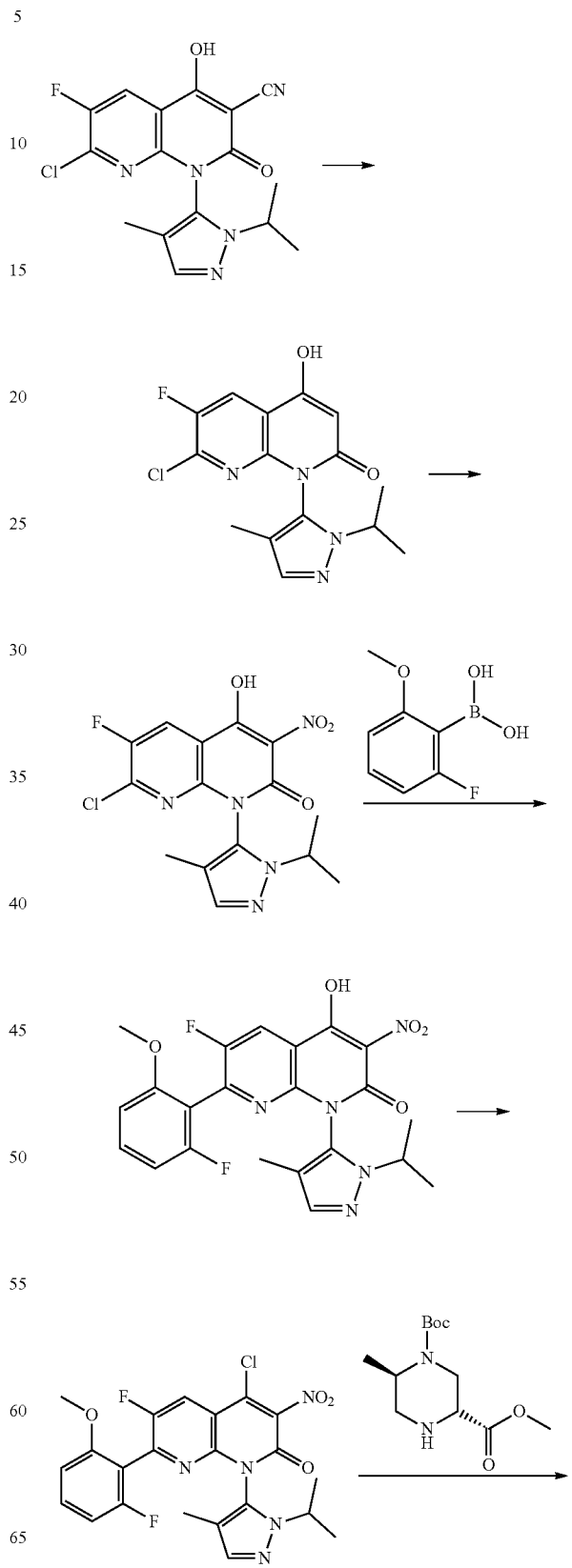

319
-continued
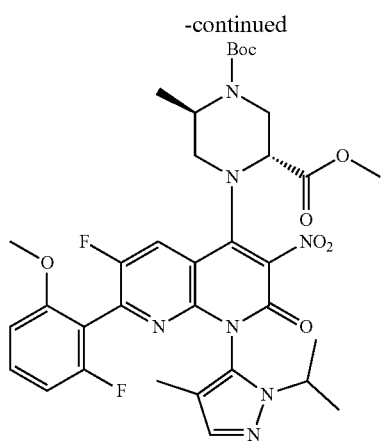
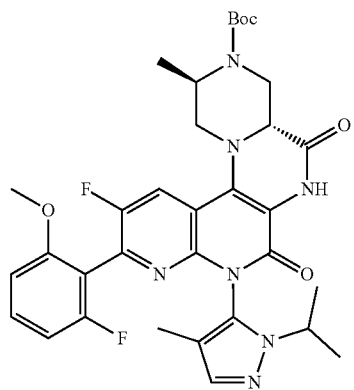
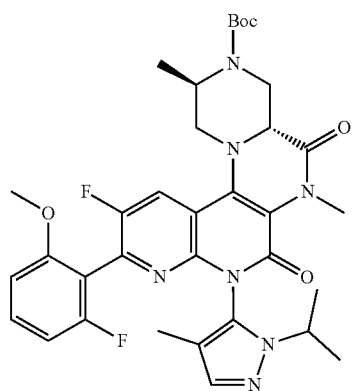
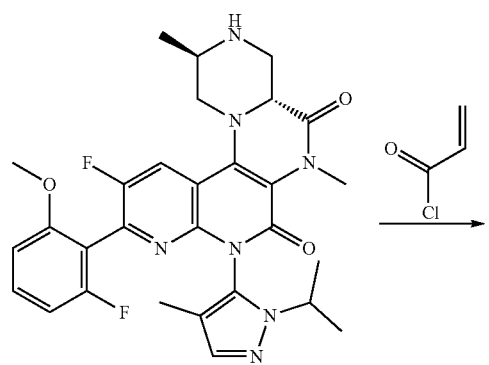
320
-continued
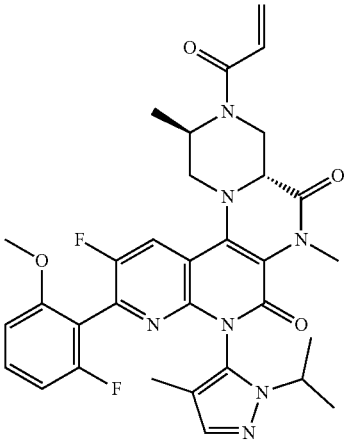
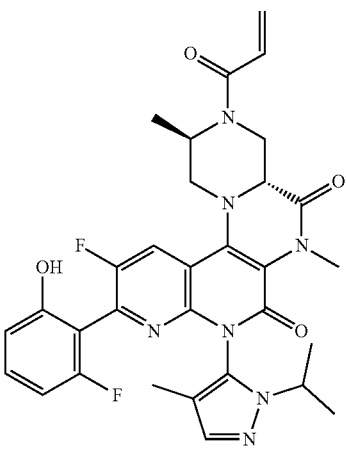
Z33
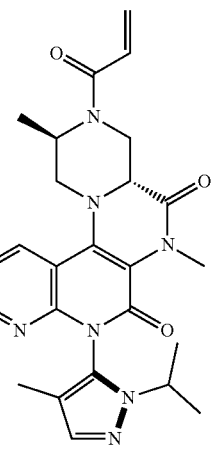
Z33-1

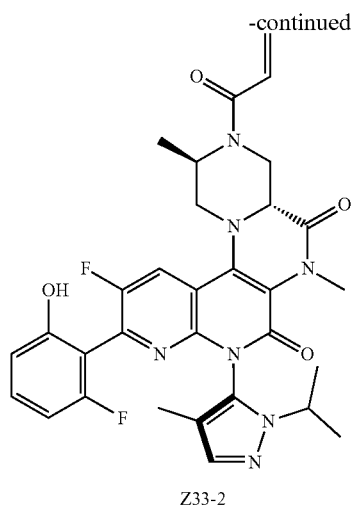

Z33-2

Step 1: 7-chloro-6-fluoro-4-hydroxy-1-(1-isopropyl-4-methyl-1H-pyrazol-5-yl)-2-oxo-1,2-dihydro-1,8-naphthyridin-3-nitrile (3.6 g, 10.0 mmol) was suspended in a mixed solution of 1, 4-dioxane (10 mL) and water (120 mL), and slowly added with concentrated sulfuric acid (10 mL). The resulting mixture was stirred at 120° C. for 18 hours to react. Cooled reaction liquid was poured into 20 mL of ice water, mixed with sodium carbonate to adjust the pH to a range of 2 to 3, and extracted with EtOAc (1000 mL*2). The resulting combined EtOAc phase was dried by anhydrous sodium sulfate, and filtered. The filtrate was dried in vacuum to obtain product 7-chloro-6-fluoro-4-hydroxy-1-(1-isopropyl-4-methyl-1H-pyrazol-5-yl)-1,8-naphthyridin-2(1H)-one (3.36 g, Y: 92%), which was light brown solid. ES-API: [M+H]$^+$=337.1.

Step 2: the 7-chloro-6-fluoro-4-hydroxy-1-(1-isopropyl-4-methyl-1H-pyrazol-5-yl)-1,8-naphthyridin-2(1H)-one (3.36 g, 10 mmol) was dissolved in acetic acid (7 mL), orderly added with sodium nitrite (69 mg, 1.0 mmol) and concentrated nitric acid (2.0 mL, 30 mmol), and stirred at room temperature for 30 minutes to react. The resulting reaction liquid was slowly added into 21 mL of ice water. The precipitated solid was filtered. The filter cake was washed with 10 ml of ice water and dried in vacuum to obtain product 7-chloro-6-fluoro-4-hydroxy-1-(1-isopropyl-4-methyl-1H-pyrazol-5-yl)3-nitro-1,8-naphthyridin-2(1H)-one (3.0 g, Y: 90%), which was yellow solid. ES-API: [M+H]$^+$=382.1.

Step 3: the 7-chloro-6-fluoro-4-hydroxy-1-(1-isopropyl-4-methyl-1H-pyrazol-5-yl)3-nitro-1,8-naphthyridin-2(1H)-one (1.5 g, 3.93 mmol), (2-fluoro-6-methoxyphenyl)boric acid (2.67 g, 15.72 mmol), tetrakis(triphenylphosphine)palladium (908 mg, 0.786 mmol), potassium carbonate (2.72 g, 19.65 mmol), 4 mL of water, and 20 mL of dioxane were added to a 100 mL three-necked round-bottom flask. The resulting mixture was stirred at 100° C. for 3 hours to react under the protection of nitrogen. After the completion of the reaction, the resulting reaction liquid was cooled to room temperature, added with 20 mL of water and 50 mL of methyl tert-butyl ether, and extracted once. The water phase was then mixed with 1 M hydrochloric acid solution to adjust the pH to a range of 3 to 5, and extracted with EtOAc (50 mL*2). The resulting combined EtOAc phase was dried by anhydrous sodium sulfate, and filtered. The filtrate was dried in vacuum to obtain product 6-fluoro-7-(2-fluoro-6-methoxyphenyl)-4-hydroxy-1-(1-isopropyl-4-methyl-1H-pyrazol-5-yl)-3-nitro-1,8-naphthyridin-2(1H)-one (1.5 g, crude), which was faint yellow solid. ES-API: [M+H]$^+$=472.1.

Step 4: the 6-fluoro-7-(2-fluoro-6-methoxyphenyl)-4-hydroxy-1-(1-isopropyl-4-methyl-1H-pyrazol-5-yl)-3-nitro-1,8-naphthyridin-2(1H)-one (1.5 g, 3.18 mmol) was dissolved in ACN (15 mL), orderly added with phosphorus oxychloride (2.4 ml, 25.5 mmol) and N,N-diisopropylethylamine (2.6 ml, 15.9 mmol), and gradually heated to 80° C. and stirred for 30 minutes to react. The resulting reaction liquid was concentrated, added with 10 mL of cold ACN, added dropwise to 20 mL of saturated sodium bicarbonate solution in an ice water bath, and extracted with EtOAc (20 mL*2). The resulting combined EtOAc phase was washed with 20 mL of saturated salt solution once, dried by anhydrous sodium sulfate, and filtered. After the resulting organic phase was dried and concentrated, the resulting crude product was purified by flash column chromatography on silica gel (EtOAc/PE: 0-50%) to obtain 4-chloro-6-fluoro-7-(2-fluoro-6-methoxyphenyl)-1-(1-isopropyl-4-methyl-1H-pyrazol-5-yl)-3-nitro-1,8-naphthyridin-2(1H)-one (0.9 g, Y: 65%), which was yellow solid. ES-API: [M+H]$^+$=490.1.

Step 5: the 4-chloro-6-fluoro-7-(2-fluoro-6-methoxyphenyl)-1-(1-isopropyl-4-methyl-1H-pyrazol-5-yl)-3-nitro-1,8-naphthyridin-2(1H)-one (490 mg, 1.0 mmol) was dissolved in N,N-dimethylacetamide (5 mL), orderly added with (3R, 6R)-1-tert-butyl3-methyl6-methylpiperazin-1,3-dicarboxylic acid (310 mg, 1.2 mmol) and N,N-diisopropylethylamine (390 mg, 3 mmol), and stirred at 120° C. for 2 hours to react. The resulting reaction liquid was added with 20 mL of EtOAc, and washed with 20 mL of saturated salt solution for 3 times. The EtOAc phase was dried and concentrated to obtain product (3R,6R)-1-tert-butyl-3-methyl4-(6-fluoro-7-(2-fluoro-6-methoxyphenyl)-1-(1-isopropyl-4-methyl-1H-pyrazol-5-yl)-3-nitro-2-oxo-1,2-dihydro-1,8-naphthyridin-4-yl)piperazin-1,3-dione (620 mg, crude), which was yellow solid. ES-API: [M+H]$^+$=712.2.

Step 6: the (3R,6R)-1-tert-butyl-3-methyl4-(6-fluoro-7-(2-fluoro-6-methoxyphenyl)-1-(1-isopropyl-4-methyl-1H-pyrazol-5-yl)-3-nitro-2-oxo-1,2-dihydro-1,8-naphthyridin-4-yl)piperazin-1,3-dione (620 mg, 0.872 mmol) was dissolved in acetic acid (8 mL), added with iron powder (146 mg, 2.62 mmol), and stirred at 80° C. for 30 minutes to react. The resulting reaction liquid was concentrated, and orderly added with 30 mL of EtOAc and 30 mL of saturated sodium bicarbonate solution. The resulting suspension was filtered by using diatomite. The filter cake was washed with EtOAc. The resulting organic phase was separated, washed orderly with 30 mL of saturated sodium bicarbonate solution and 30 mL of saturated salt solution, dried and concentrated to obtain product tert-butyl (2R,4aR)-tert-butyl11-fluoro-10-(2-fluoro-6-methoxyphenyl)-8-(1-isopropyl-4-methyl-1H-pyrazol-5-yl)-2-methyl-5,7-dioxo-4,4a,5,6,7,8-hexahydro-1H-pyrazino[1',2':4,5]pyrazino[2,3-c][1,8]naphthyridin-3 (2H)-carboxylate (300 mg, crude), which was yellow solid. ES-API: [M+H]$^+$=650.3.

Step 7: the tert-butyl (2R,4aR)-tert-butyl11-fluoro-10-(2-fluoro-6-methoxyphenyl)-8-(1-isopropyl-4-methyl-1H-pyrazol-5-yl)-2-methyl-5,7-dioxo-4,4a,5,6,7,8-hexahydro-1H-pyrazino[1',2':4,5]pyrazino[2,3-c][1,8]naphthyridin-3 (2H)-carboxylate (300 mg, 0.462 mmol), 6 mL of acetone, anhydrous potassium carbonate (255 mg, 1.84 mmol), and iodomethane (656 mg, 4.62 mmol) were sealed in a sealing tube, and stirred at 50° C. for 18 hours to react. The resulting reaction liquid was added with 20 mL of EtOAc, washed with 20 mL of saturated salt solution, dried and concentrated. The resulting crude product was purified by flash column chromatography on silica gel (EtOAc/PE: 0-80%) to obtain product tert-butyl (2R,4aR)-11-fluoro-10-(2-fluoro-6-methoxyphenyl)-8-(1-isopropyl-4-methyl-1H-pyrazol-5-yl)-2,6-dimethyl-5,7-dioxo-4,4a,5,6,7,8-hexahydro-1H-pyrazino[1',2':4,5]pyrazino[2,3-c][1,8]naphthyridin-3(2H)-carboxylate (350 mg, Y: 95%), which was yellow solid. ES-API: [M+H]⁺=664.3.

Step 8: the tert-butyl (2R,4aR)-11-fluoro-10-(2-fluoro-6-methoxyphenyl)-8-(1-isopropyl-4-methyl-1H-pyrazol-5-yl)-2,6-dimethyl-5,7-dioxo-4,4a,5,6,7,8-hexahydro-1H-pyrazino[1',2':4,5]pyrazino[2,3-c][1,8]naphthyridin-3(2H)-carboxylate (350 mg) was dissolved in DCM (4 mL), and added with TFA (2 mL). After stirring at room temperature for 2 hours, the resulting reaction liquid was concentrated to obtain product (2R,4aR)-11-fluoro-10-(2-fluoro-6-methoxyphenyl)-8-(1-isopropyl-4-methyl-1H-pyrazol-5-yl)-2,6-dimethyl-2,3,4,4a-tetrahydro-1H-pyrazino[1',2':4,5]pyrazino[2,3-c][1,8]naphthyridin-5,7(6H, 8H)-dione (40 mg, crude), which was directly used in next step. ES-API: [M+H]⁺=564.2.

Step 9: the (2R,4aR)-11-fluoro-10-(2-fluoro-6-methoxyphenyl)-8-(1-isopropyl-4-methyl-1H-pyrazol-5-yl)-2,6-dimethyl-2,3,4,4a-tetrahydro-1H-pyrazino[1',2':4,5]pyrazino[2,3-c][1,8]naphthyridin-5,7(6H, 8H)-dione (350 mg, 0.62 mmol) was dissolved in DCM (6 mL), and added with diisopropylethylamine (480 mg, 3.72 mmol). The resulting reaction liquid was cooled to 0° C., and added dropwise with acryloyl chloride (112.5 mg, 1.24 mmol). The resulting mixture was stirred at 0° C. for 15 minutes to react. The resulting reaction liquid was added with 20 mL of DCM, washed with 20 mL of saturated solution of NaHCO₃ and 20 mL of saturated salt solution, dried and concentrated. The resulting crude product was purified by preparative scale chromatography to obtain product (2R,4aR)-3-acryloyl-11-fluoro-10-(2-fluoro-6-methoxyphenyl)-8-(1-isopropyl-4-methyl-1H-pyrazol-5-yl)-2,6-dimethyl-2,3,4,4a-tetrahydro-1H-pyrazino[1',2':4,5]pyrazino[2,3-c][1,8]naphthyridin-5,7 (6H, 8H)-dione (250 mg, Y: 60%), which was yellow solid. ES-API: [M+H]⁺=618.3.

Step 10: under the condition of the ice water bath, the (2R,4aR)-3-acryloyl-11-fluoro-10-(2-fluoro-6-methoxyphenyl)-8-(1-isopropyl-4-methyl-1H-pyrazol-5-yl)-2,6-dimethyl-2,3,4,4a-tetrahydro-1H-pyrazino[1',2':4,5]pyrazino[2,3-c][1,8]naphthyridin-5,7(6H, 8H)-dione (250 mg, 0.405 mmol) was added to dry DCM (6.0 mL), then added with boron tribromide (4.0 mL, 4.0 mmol), and warmed to room temperature to react for 1 hour. Under the condition of the ice water bath, the above reaction liquid was added dropwise to saturated sodium bicarbonate solution, extracted with DCM (30 mL) twice, dried and concentrated to obtain product (2R,4aR)-3-acryloyl-11-fluoro-10-(2-fluoro-6-hydroxyphenyl)-8-(1-isopropyl-4-methyl-1H-pyrazol-5-yl)-2,6-dimethyl-2,3,4,4a-tetrahydro-1H-pyrazino[1',2':4,5]pyrazino[2,3-c][1,8]naphthyridin-5,7(6H, 8H)-dione (Z33).

Step 11: the compound Z33 was purified by preparative scale HPLC to obtain the following atropisomer compounds. One of the atropisomer compounds had a structure arbitrarily specified as Z33-1 (peak 1, 30 mg, retention time: 9.576 min, Y: 50%). ¹H NMR (500 MHz, DMSO-d₆) δ 10.17 (s, 1H), 7.98 (dd, J=8.4, 5.5 Hz, 1H), 7.40 (d, J=5.5 Hz, 1H), 7.29 (q, J=7.9 Hz, 1H), 7.02 (dd, J=16.8, 10.6 Hz, 1H), 6.81-6.68 (m, 2H), 6.20-6.11 (m, 1H), 5.81-5.69 (m, 1H), 4.77 (s, 1H), 4.61 (d, J=14.7 Hz, 1H), 4.01-3.83 (m, 2H), 3.73 (dd, J=14.2, 4.2 Hz, 1H), 3.35 (d, J=5.8 Hz, 3H), 2.86 (dd, J=48.2, 12.0 Hz, 1H), 1.76-1.59 (m, 3H), 1.55 (dd, J=16.6, 6.7 Hz, 3H), 1.26 (dd, J=32.6, 6.6 Hz, 3H), 1.21-1.10 (m, 3H). The other atropisomer compound had a structure arbitrarily specified as Z33-2 (peak 2, 15 mg, retention time: 9.663 min, Y: 25%). ¹H NMR (500 MHz, DMSO-d₆) δ 10.17 (s, 1H), 7.96 (m, 1H), 7.40 (d, J=5.5 Hz, 1H), 7.29 (q, J=7.9 Hz, 1H), 7.02 (m, 1H), 6.81-6.68 (m, 2H), 6.20-6.11 (m, 1H), 5.81-5.69 (m, 1H), 4.77 (s, 1H), 4.61 (d, J=14.7 Hz, 1H), 4.01-3.83 (m, 2H), 3.73 (dd, J=14.2, 4.2 Hz, 1H), 3.35 (d, J=5.8 Hz, 3H), 2.86 (m, 1H), 1.76-1.59 (m, 3H), 1.55 (m, 3H), 1.30 (dd, J=32.6, 6.6 Hz, 3H), 1.23-1.15 (m, 3H). The isomer compounds were detected by analytical scale HPLC.

Example 34 Preparation of Compounds Z34, Z34-1, and Z34-2

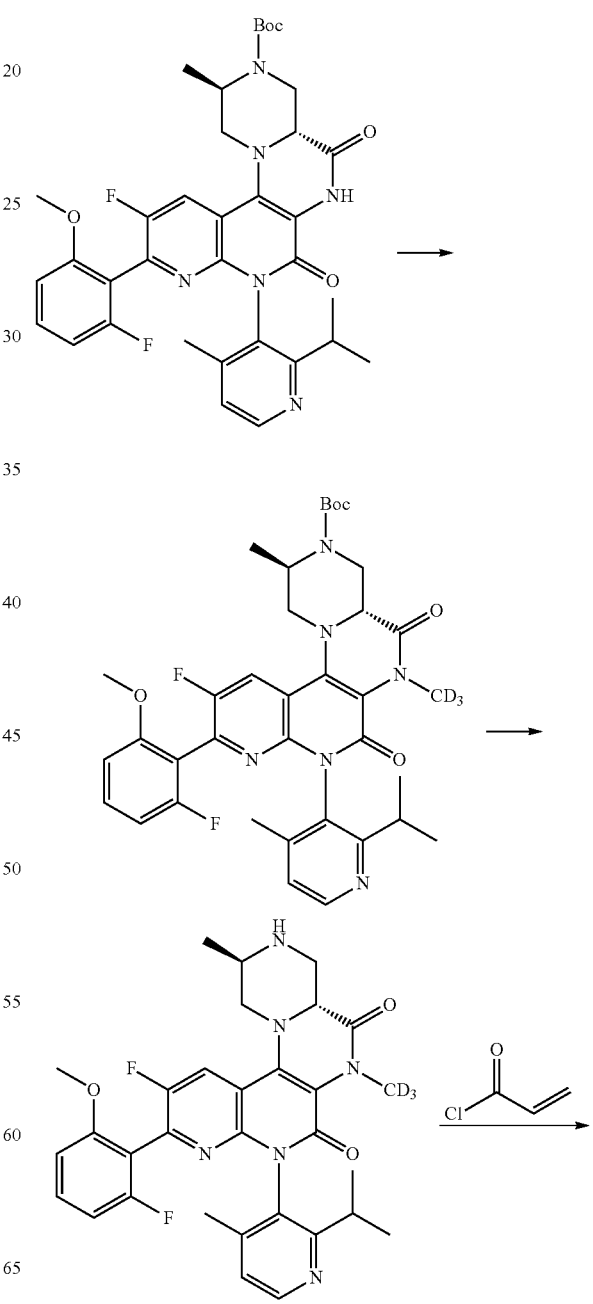

-continued

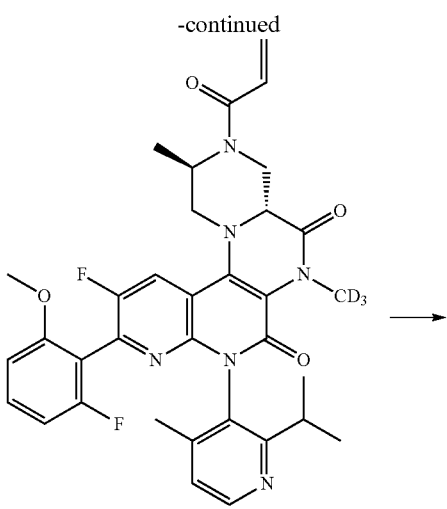

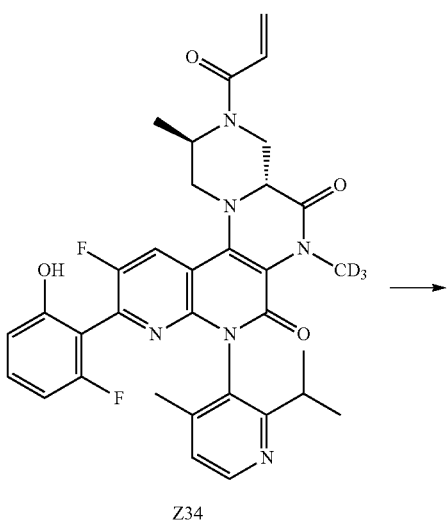

Z34

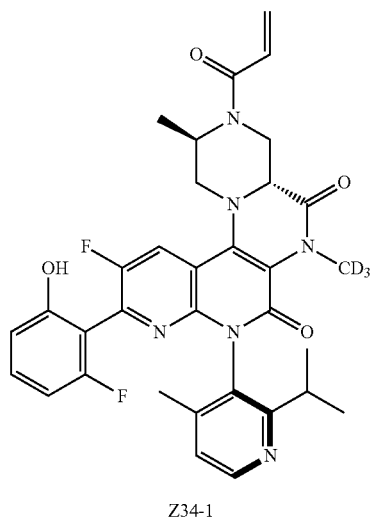

Z34-1

-continued

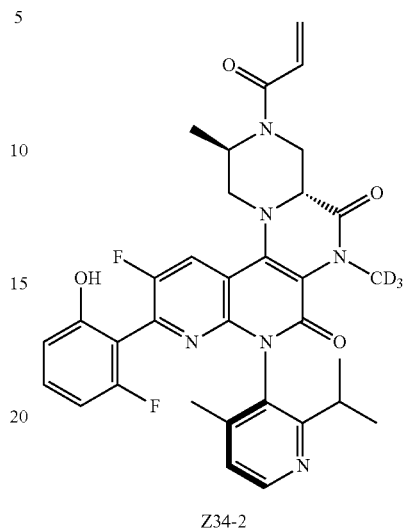

Z34-2

Step 1: tert-butyl (2R,4aR)-11-fluoro-10-(2-fluoro-6-methoxyphenyl)-8-(2-isopropyl-4-methylpyridin-3-yl)-2-methyl-5,7-dioxo-1,2,4,4a,5,6,7,8-octyl-3H-pyrazion[1',2':4,5]pyrazino[2,3-c][1,8]naphthyridin-3-carboxylate (115 mg, 0.17 mmol), 4 mL of acetone, anhydrous potassium carbonate (94 mg, 0.68 mmol), and deuteroiodomethane (246 mg, 1.70 mmol) were added to a 15 mL sealing tube. The sealing tube was sealed, and the resulting mixture was stirred at 50° C. for 18 hours to react. The resulting reaction liquid was added with 30 mL of EtOAc, washed orderly with 12 mL of water and 15 mL of saturated salt solution, dried and concentrated to obtain product tert-butyl (2R,4aR)-11-fluoro-10-(2-fluoro-6-methoxyphenyl)-8-(2-isopropyl-4-methylpyridin-3-yl)-2-methyl-6-(methyl-d3)-5,7-dioxo-1,2,4,4a,5,6,7,8-octyl-3H-pyrazino[1',2':4,5]pyrazino[2,3-c][1,8]naphthyridin-3-carboxylate (118 mg, Y: 100.0%), which was yellow solid. ES-API: [M+H]$^+$=678.3.

Step 2: the tert-butyl (2R,4aR)-11-fluoro-10-(2-fluoro-6-methoxyphenyl)-8-(2-isopropyl-4-methylpyridin-3-yl)-2-methyl-6-(methyl-d3)-5,7-dioxo-1,2,4,4a,5,6,7,8-octyl-3H-pyrazino[1',2':4,5]pyrazino[2,3-c][1,8]naphthyridin-3-carboxylate (118 mg, 0.17 mmol) was dissolved in DCM (3 mL), and added with TFA (0.7 mL). After stirring at room temperature for 2 hours, the resulting reaction liquid was concentrated to obtain product (2R,4aR)-11-fluoro-10-(2-fluoro-6-methoxyphenyl)-8-(2-isopropyl-4-methylpyridin-3-yl)-2-methyl-6-(methyl-d3)-2,3,4,4a,6,8-hexahydro-1H-pyrazino[1',2':4,5]pyrazino[2,3-c][1,8]naphthyridin-5,7-dione (120 mg, crude), which was directly used in next step. ES-API: [M+H]$^+$=578.2.

Step 3: the (2R,4aR)-11-fluoro-10-(2-fluoro-6-methoxyphenyl)-8-(2-isopropyl-4-methylpyridin-3-yl)-2-methyl-6-(methyl-d3)-2,3,4,4a,6,8-hexahydro-1H-pyrazino[1',2':4,5]pyrazino[2,3-c][1,8]naphthyridin-5,7-dione (120 mg, crude) was dissolved in DCM (5 mL), and added with N,N-diisopropylethylamine (110 mg, 0.85 mmol). The resulting reaction liquid was cooled to 0° C., and added dropwise with acryloyl chloride (31 mg, 0.34 mmol). The resulting mixture was stirred at 0° C. for 15 minutes to react. The resulting reaction liquid was added with 25 mL of DCM, washed orderly with 15 mL of water, 15 mL of saturated solution of NaHCO$_3$ and 15 mL of saturated salt solution, dried and concentrated. The resulting crude product was purified by flash column chromatography on silica gel (EtOAc/PE: 0-100%) to obtain product (2R,4aR)-3-acryloyl-11-fluoro-10-(2-fluoro-6-methoxyphenyl)-8-(2-isopropyl-4-methylpyridin-3-yl)-2-methyl-6-(methyl-d3)-2,3,4,4a,6,8-hexahydro-1H-pyrazino[1',2':4,5]pyrazino[2,3-c][1,8]naphthyridin-5,7-dione (85 mg, Y: 77.3%), which was faint yellow solid. ES-API: [M+H]$^+$=632.2.

Step 4: the (2R,4aR)-3-acryloyl-11-fluoro-10-(2-fluoro-6-methoxyphenyl)-8-(2-isopropyl-4-methylpyridin-3-yl)-2-methyl-6-(methyl-d3)-2,3,4,4a,6,8-hexahydro-1H-pyrazino[1',2':4,5]pyrazino[2,3-c][1,8]naphthyridin-5,7-dione (85 mg, 0.13 mmol) was dissolved in DCM (1.5 mL). The resulting solution was cooled to 0° C., and then added dropwise with a solution (1.5 mL) of 17% boron tribromide in DCM. The resulting mixture was stirred at room temperature for 4 hours to react. The resulting reaction liquid was poured into 40 mL of saturated solution of NaHCO$_3$ and extracted with 25 mL of DCM twice. The resulting organic phase was dried and concentrated, and the resulting crude product was purified by preparative scale HPLC to obtain product (2R,4aR)-3-acryloyl-11-fluoro-10-(2-fluoro-6-methoxyphenyl)-8-(2-isopropyl-4-methylpyridin-3-yl)-2-methyl-6-(methyl-d3)-2,3,4,4a,6,8-hexahydro-1H-pyrazino[1',2':4,5]pyrazino[2,3-c][1,8]naphthyridin-5,7-dione (Z34).

Step 5: the compound Z34 was resolved by preparative scale chiral HPLC (column type: OD-H: 10 μm, 20*250 mm; mobile phase: hexane:EtOH=80:20; flow rate: 15 ml/min; and column temperature: room temperature) and purified to obtain the following atropisomer compounds. One of the atropisomer compounds had a structure arbitrarily specified as Z34-1 (23 mg, peak 1, retention time: 11.056 min, Y: 28.7%), which was faint yellow solid. $^1$H NMR (500 MHz, DMSO-d$_6$) δ 10.14 (s, 1H), 8.44 (d, J=4.9 Hz, 1H), 8.01-7.97 (m, 1H), 7.28-7.23 (m, 2H), 7.05-6.84 (m 1H), 6.77-6.64 (m, 2H), 6.18-6.13 (m, 1H), 5.77-5.71 (m, 1H), 5.03-4.77 (m, 1H), 4.61-4.41 (m, 1H), 4.06-4.00 (m, 1H), 3.73 (dd, J=14.1, 4.2 Hz, 1H), 3.39-3.20 (m, 1H), 2.92-2.79 (m, 1H), 2.47-2.36 (m, 1H), 1.99 (s, 3H), 1.58-1.53 (m, 3H), 1.03 (d, J=6.7 Hz, 3H), 0.85 (d, J=6.7 Hz, 3H). ES-API: [M+H]$^+$=618.2. the other atropisomer compound had a structure arbitrarily specified as Z34-2 (25 mg, peak 2, retention time: 14.067 min, Y: 31.2%), which was faint yellow solid. $^1$H NMR (500 MHz, DMSO-d$_6$) δ 10.15 (s, 1H), 8.45 (d, J=4.9 Hz, 1H), 8.01-7.97 (m, 1H), 7.28-7.23 (m, 2H), 7.05-6.85 (m 1H), 6.74-6.63 (m, 2H), 6.18-6.13 (m, 1H), 5.77-5.71 (m, 1H), 5.04-4.77 (m, 1H), 4.62-4.41 (m, 1H), 4.00-3.94 (m, 1H), 3.73 (dd, J=14.1, 4.2 Hz, 1H), 3.43-3.25 (m, 1H), 2.95-2.83 (m, 1H), 2.79-2.74 (m, 1H), 1.80 (s, 3H), 1.58-1.53 (m, 3H), 1.11 (d, J=6.7 Hz, 3H), 0.98 (d, J=6.7 Hz, 3H). ES-API: [M+H]$^+$=618.2. The isomer compounds were detected by analytical scale chiral HPLC (column type: OD-H: 5 μm, 4.6*250 mm; mobile phase: hexane:EtOH=80:20; flow rate: 1 ml/min; and column temperature=30° C.).

Example 35 Preparation of Compounds Z35, Z35-1, and Z35-2

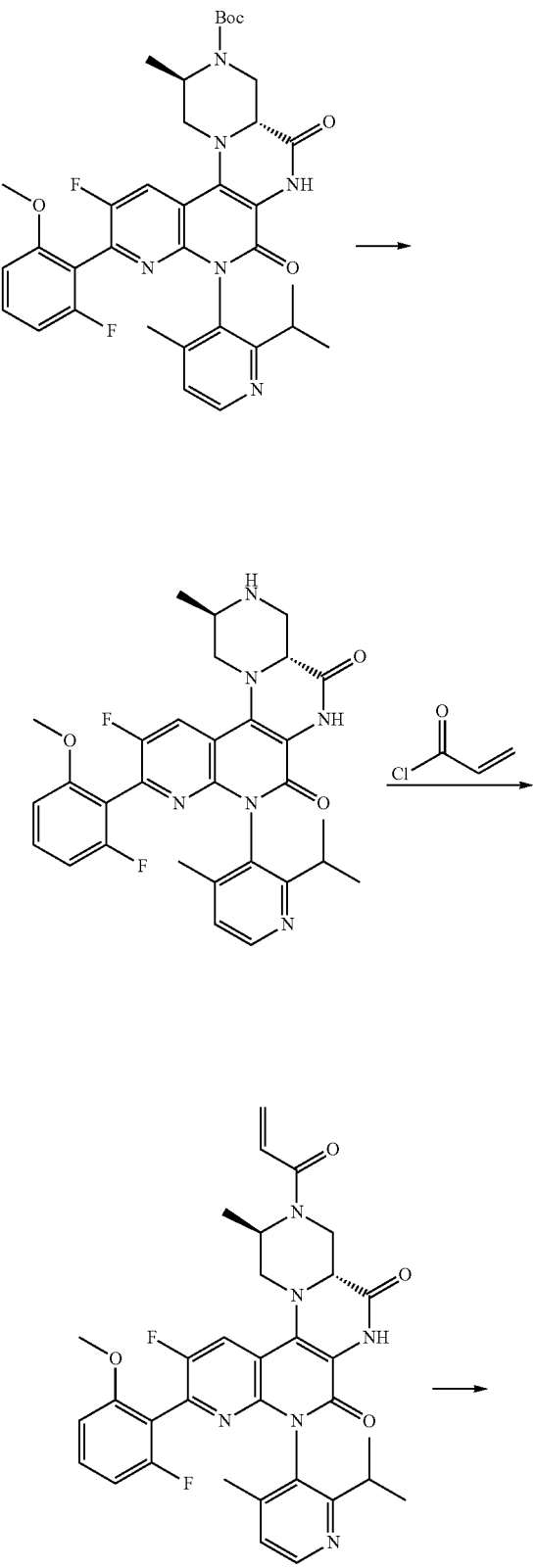

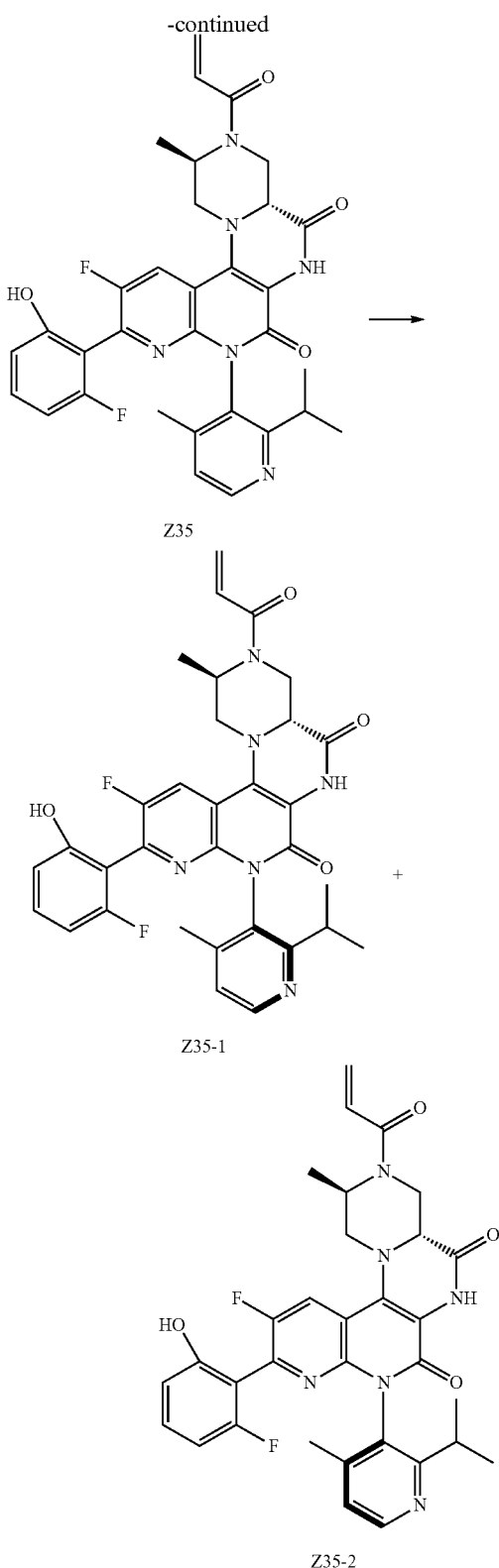

Z35

Z35-1

Z35-2

Step 1: tert-butyl (2R,4aR)-11-fluoro-10-(2-fluoro-6-methoxyphenyl)-8-(2-isopropyl-4-methylpyridin-3-yl)-2-methyl-5,7-dioxo-1,2,4,4a,5,6,7,8-octyl-3H-pyrazino[1',2':4,5]pyrazino[2,3-c][1,8]naphthyridin-3-carboxylate (200 mg, 0.30 mmol) was dissolved in DCM (4 mL), and added with TFA (1 mL). After stirring at room temperature for 2 hours, the resulting reaction liquid was concentrated to obtain product (2R,4aR)-11-fluoro-10-(2-fluoro-6-methoxyphenyl)-8-(2-isopropyl-4-methylpyridin-3-yl)-2-methyl-2,3,4,4a,6,8-hexahydro-1H-pyrazino[1',2':4,5]pyrazino[2,3-c][1,8]naphthyridin-5,7-dione (210 mg, crude), which was directly used in next step. ES-API: [M+H]$^+$=561.3.

Step 2: the (2R,4aR)-11-fluoro-10-(2-fluoro-6-methoxyphenyl)-8-(2-isopropyl-4-methylpyridin-3-yl)-2-methyl-2,3,4,4a,6,8-hexahydro-1H-pyrazino[1',2':4,5]pyrazino[2,3-c][1,8]naphthyridin-5,7-dione (210 mg, crude) was dissolved in DCM (10 mL), and added with N,N-diisopropylethylamine (194 mg, 1.50 mmol). The resulting reaction liquid was cooled to 0° C., and added dropwise with acryloyl chloride (54 mg, 0.60 mmol). The resulting mixture was stirred at 0° C. for 15 minutes to react. The resulting reaction liquid was added with 30 mL of DCM, washed orderly with 15 mL of water, 15 mL of saturated solution of NaHCO$_3$ and 15 mL of saturated salt solution, dried and concentrated to obtain product (2R,4aR)-3-acryloyl-11-fluoro-10-(2-fluoro-6-methoxyphenyl)-8-(2-isopropyl-4-methylpyridin-3-yl)-2-methyl-2,3,4,4a,6,8-hexahydro-1H-pyrazino[1',2':4,5]pyrazino[2,3-c][1,8]naphthyridin-5,7-dione (175 mg, Y: 95.0%), which was faint yellow solid. ES-API: [M+H]$^+$=615.3.

Step 3: the (2R,4aR)-3-acryloyl-11-fluoro-10-(2-fluoro-6-methoxyphenyl)-8-(2-isopropyl-4-methylpyridin-3-yl)-2-methyl-2,3,4,4a,6,8-hexahydro-1H-pyrazino[1',2':4,5]pyrazino[2,3-c][1,8]naphthyridin-5,7-dione (175 mg, 0.28 mmol) was dissolved in DCM (4 mL). The resulting solution was cooled to 0° C., and then added dropwise with a solution (4 mL) of 17% boron tribromide in DCM. The resulting mixture was stirred at room temperature for 3 hours to react. The resulting reaction liquid was poured into 80 mL of saturated solution of NaHCO$_3$ and extracted with 30 mL of DCM twice. The resulting organic phase was dried and concentrated to obtain product (2R,4aR)-3-acryloyl-11-fluoro-10-(2-fluoro-6-hydroxyphenyl)-8-(2-isopropyl-4-methylpyridin-3-yl)-2-methyl-2,3,4,4a,6,8-hexahydro-1H-pyrazino[1',2':4]pyrazino[2,3,3-c][1,8,8]naphthyridin-5-dione (Z35, 170 mg, Y: 99.4%), which was faint yellow solid. ES-API: [M+H]$^+$=601.2.

Step 4: the compound Z35 (170 mg, 0.28 mmol) was purified by preparative scale HPLC and then resolved by preparative scale chiral HPLC (column type: IA: 10 μm, 30*250 mm; mobile phase: hexane:EtOH=40:60; flow rate: 25 m/min; and column temperature: room temperature) to obtain the following atropisomer compounds. One of the atropisomer compounds had a structure arbitrarily specified as Z35-1 (19 mg, peak 1, retention time: 2.905 min, Y: 11.1%), which was faint yellow solid. $^1$H NMR (500 MHz, DMSO-d$_6$) δ 10.60-10.46 (m, 1H), 10.12 (s, 1H), 8.45 (d, J=4.8 Hz, 1H), 8.01-7.91 (m, 1H), 7.31-7.18 (m, 2H), 7.03-6.82 (m, 1H), 6.75-6.63 (m, 2H), 6.20-6.10 (m, 1H), 5.79-5.70 (m, 1H), 5.08-4.70 (m, 1H), 4.67-4.39 (m, 1H), 4.09-3.97 (m, 1H), 3.72 (dd, J=14.1, 4.0 Hz, 1H), 3.31-3.18 (m, 1H), 3.02-2.87 (m, 1H), 2.57-2.50 (m, 1H), 1.89 (s, 3H), 1.58-1.44 (m, 3H), 1.05 (d, J=6.7 Hz, 3H), 0.89 (d, J=6.7 Hz, 3H). ES-API: [M+H]$^+$=601.2. The other atropisomer compound had a structure arbitrarily specified as Z35-2 (19 mg, peak 2, retention time: 8.769 min, Y: 11.1%), which was faint yellow solid. $^1$H NMR (500 MHz, DMSO-d$_6$) δ 10.60-10.46 (m, 1H), 10.12 (s, 1H), 8.45 (d, J=4.9 Hz, 1H), 8.01-7.91 (m, 1H), 7.31-7.18 (m, 2H), 7.03-6.82 (m, 1H), 6.75-6.63 (m, 2H), 6.20-6.08 (m, 1H), 5.78-5.67 (m, 1H), 5.10-4.70 (m, 1H), 4.67-4.39 (m, 1H), 4.09-3.97 (m, 1H), 3.72 (dd, J=14.1, 3.8 Hz, 1H), 3.31-3.18 (m, 1H), 3.06-2.92 (m, 1H), 2.66-2.57 (m, 1H), 1.83 (s, 3H), 1.58-1.44 (m, 3H),

331
1.08 (d, J=6.7 Hz, 3H), 0.91 (d, J=6.7 Hz, 3H). ES-API: [M+H]+=601.2. The isomer compounds were detected by analytical scale chiral HPLC (column type: IA: 5 μm, 4.6*150 mm; mobile phase: hexane:EtOH=40:60; flow rate: 1 ml/min; and column temperature=30° C.).
Example 36 Preparation of Compounds Z36, Z36-1, and Z36-2
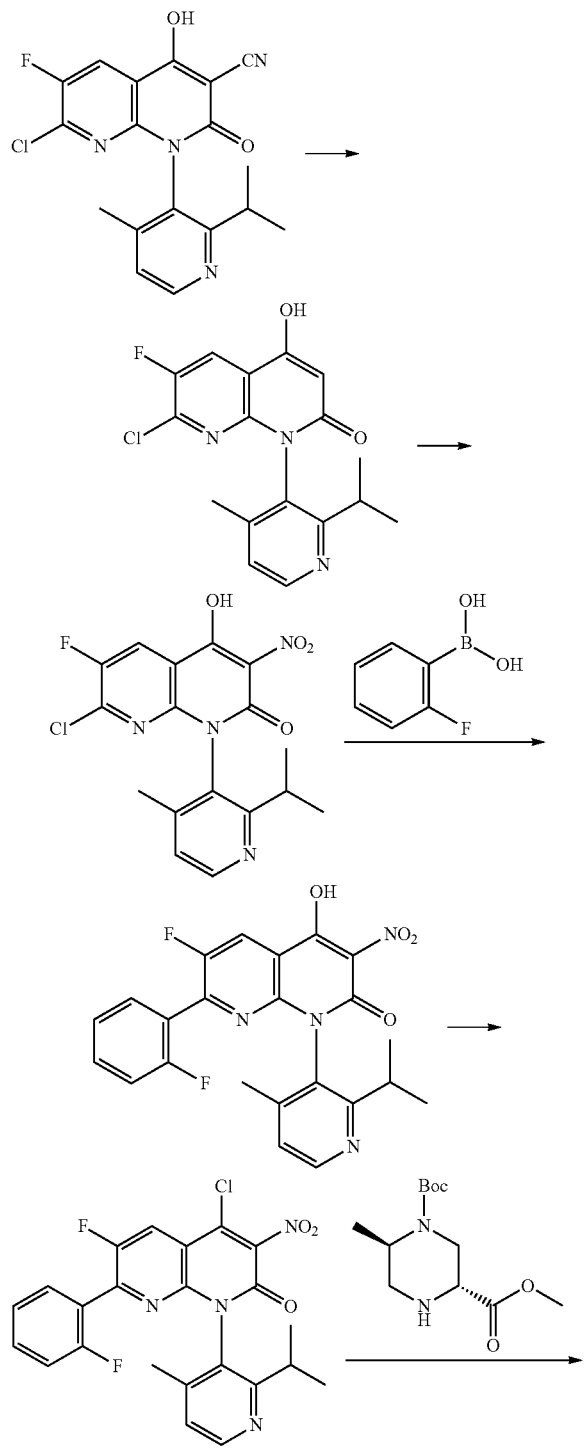
332
-continued
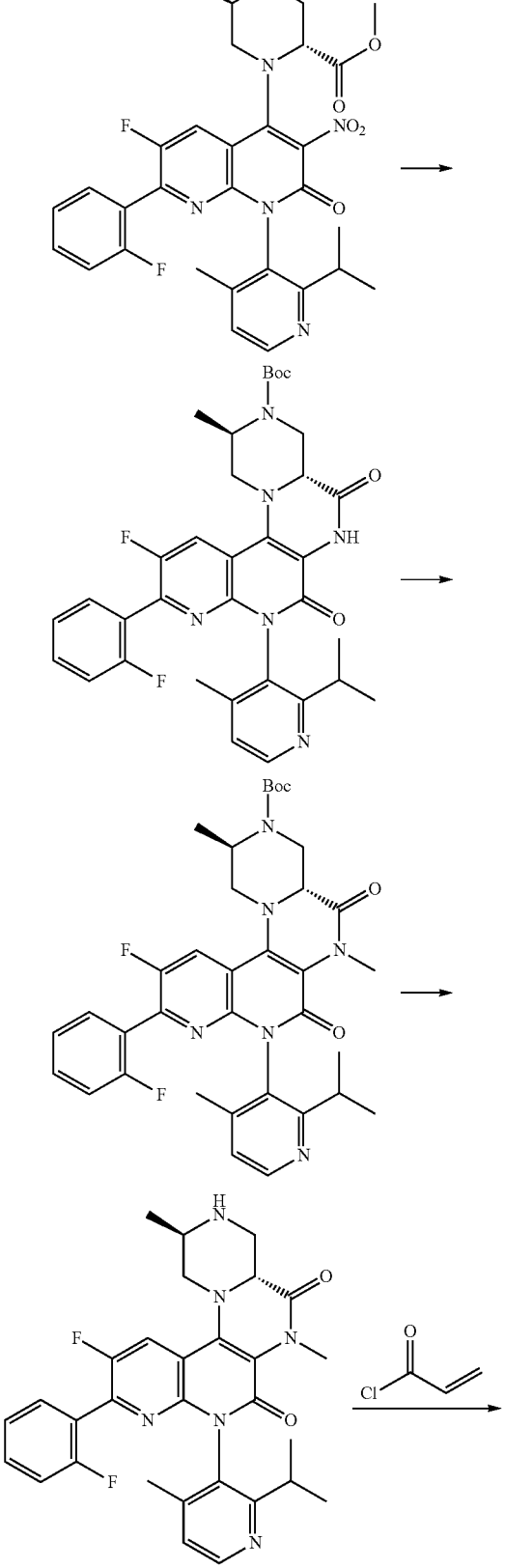

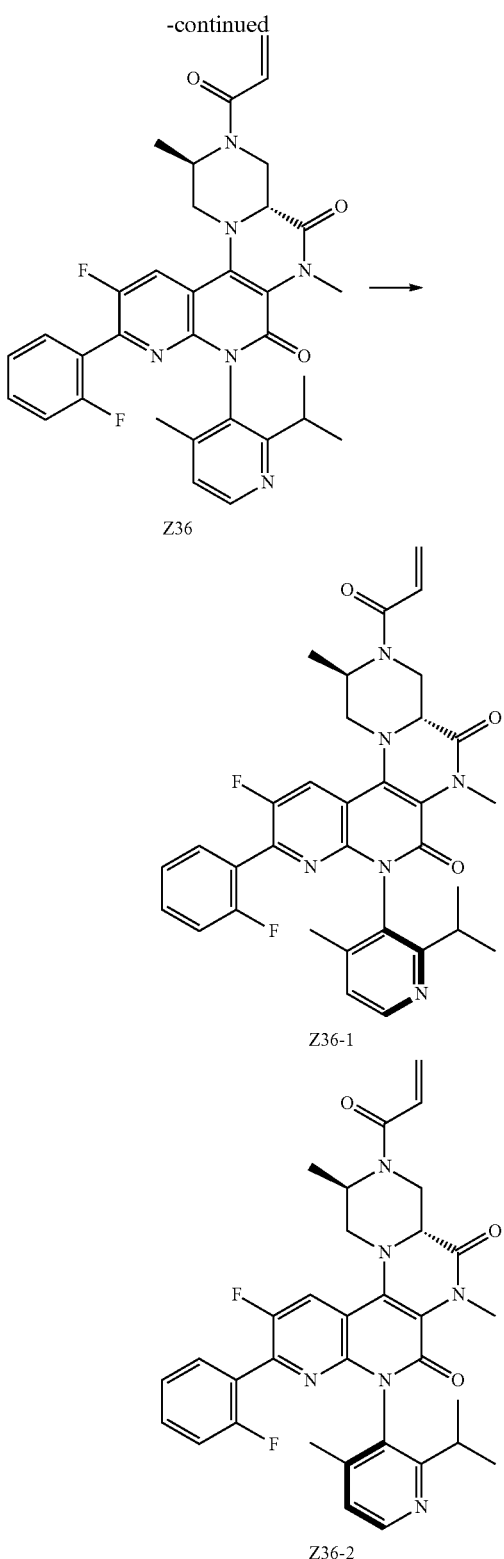

Z36

Z36-1

Z36-2

Step 1: 7-chloro-6-fluoro-4-hydroxy-1-(2-isopropyl-4-methylpyridin-3-yl)-2-oxo-1,2-dihydro-1,8-naphthyridin-3-carbonitrile (3.6 g, 10.0 mmol) was suspended in a mixed solution of 1, 4-dioxane (10 mL) and water (120 mL), and slowly added with concentrated sulfuric acid (10 mL). The resulting mixture was stirred at 120° C. for 18 hours to react. Cooled reaction liquid was poured into 20 mL of ice water, mixed with sodium carbonate to adjust the pH to a range of 2 to 3, and extracted with EtOAc (1000 mL*2). The resulting combined EtOAc phase was dried by anhydrous sodium sulfate, and filtered. The filtrate was dried in vacuum to obtain product 7-chloro-6-fluoro-4-hydroxy-1-(2-isopropyl-4-methylpyridin-3-yl)-1,8-naphthyridin-2(1H)-one (3.36 g, Y: 90%), which was light brown solid. ES-API: [M+H]$^+$=348.1.

Step 2: the 7-chloro-6-fluoro-4-hydroxy-1-(2-isopropyl-4-methylpyridin-3-yl)-1,8-naphthyridin-2(1H)-one (3.36 g, 10 mmol) was dissolved in acetic acid (7 mL), orderly added with sodium nitrite (69 mg, 1.0 mmol) and concentrated nitric acid (2.0 mL, 30 mmol), and stirred at room temperature for 30 minutes to react. The resulting reaction liquid was slowly poured into 21 mL of ice water. The precipitated solid was filtered. The filter cake was washed with 10 ml of ice water and dried in vaccum to obtain product 7-chloro-6-fluoro-4-hydroxy-1-(2-isopropyl-4-methylpyridin-3-yl)3-nitro-1,8-naphthyridin-2(1H)-one (3.0 g, Y: 90%), which was yellow solid. ES-API: [M+H]$^+$=393.1.

Step 3: the 7-chloro-6-fluoro-4-hydroxy-1-(2-isopropyl-4-methylpyridin-3-yl)3-nitro-1,8-naphthyridin-2(1H)-one (1.5 g, 3.93 mmol), (2-fluorophenyl)boric acid (2.67 g, 15.72 mmol), tetrakis(triphenylphosphine)palladium (908 mg, 0.786 mmol), potassium carbonate (2.72 g, 19.65 mmol), 4 mL of water, and 20 mL of dioxane were added to a 100 mL three-necked round-bottom flask. The resulting mixture was stirred at 100° C. for 3 hours to react under the protection of nitrogen. After the completion of the reaction, the resulting reaction liquid was cooled to room temperature, added with 20 mL of water and 50 mL of methyl tert-butyl ether, and extracted once. The water phase was then mixed with 1 M hydrochloric acid solution to adjust the pH to a range of 3 to 5, and extracted with EtOAc (50 mL*2). The resulting combined EtOAc phase was dried by anhydrous sodium sulfate, and filtered. The filtrate was dried in vacuum to obtain product 6-fluoro-7-(2-fluorophenyl)-4-hydroxy-1-(2-isopropyl-4-methylpyridin-3-yl)-3-nitro-1,8-naphthyridin-2(1H)-one (1.5 g, Y: 65%), which was faint yellow solid. ES-API: [M+H]$^+$=453.1.

Step 4: the 6-fluoro-7-(2-fluorophenyl)-4-hydroxy-1-(2-isopropyl-4-methylpyridin-3-yl)-3-nitro-1,8-naphthyridin-2(1H)-one (1.5 g, 3.18 mmol) was dissolved in ACN (15 mL), orderly added with phosphorus oxychloride (2.4 ml, 25.5 mmol) and N,N-diisopropylethylamine (2.6 ml, 15.9 mmol), and gradually heated to 80° C. and stirred for 30 minutes to react. The resulting reaction liquid was concentrated, added with 10 mL of cold ACN, added dropwise to 20 mL of saturated sodium bicarbonate solution in an ice water bath, and extracted with EtOAc (20 mL*2). The resulting combined EtOAc phase was washed with 20 mL of saturated salt solution once, dried by anhydrous sodium sulfate, and filtered. After the resulting organic phase was dried and concentrated, the resulting crude product was purified by flash column chromatography on silica gel (EtOAc/PE: 0-50%) to obtain 4-chloro-6-fluoro-7-(2-fluorophenyl)-1-(2-isopropyl-4-methylpyridin-3-yl)-3-nitro-1,8-naphthyridin-2(1H)-one (0.9 g, Y: 65%), which was yellow solid. ES-API: [M+H]$^+$=471.1.

Step 5: the 4-chloro-6-fluoro-7-(2-fluorophenyl)-1-(2-isopropyl-4-methylpyridin-3-yl)-3-nitro-1,8-naphthyridin-2(1H)-one (490 mg, 1.0 mmol) was dissolved in N,N-dimethylacetamide (5 mL), orderly added with (3R,6R)-1-tert-butyl3-methyl 6-methylpiperazin-1,3-dicarboxylic acid (310 mg, 1.2 mmol) and N,N-diisopropylethylamine (390 mg, 3 mmol), and stirred at 120° C. for 1 hour to react. The resulting reaction liquid was added with 20 mL of EtOAc, and washed with 20 mL of saturated salt solution for 3 times. The EtOAc phase was dried and concentrated to obtain product (3R,6R)-1-tert-butyl-3-methyl4-(6-fluoro-7-(2-fluorophenyl)-1-(1-isopropyl-4-methyl-1H-pyrazol-5-yl)-3-nitro-2-oxo-1,2-dihydro-1,8-naphthyridin-4-yl)piperazin-1,3-dione (620 mg, Y: 50%), which was yellow solid. ES-API: [M+H]$^+$=692.2.

Step 6: the (3R,6R)-1-tert-butyl-3-methyl4-(6-fluoro-7-(2-fluorophenyl)-1-(1-isopropyl-4-methyl-1H-pyrazol-5-yl)-3-nitro-2-oxo-1,2-dihydro-1,8-naphthyridin-4-yl)piperazin-1,3-dione (620 mg, 0.872 mmol) was dissolved in acetic acid (8 mL), added with iron powder (146 mg, 2.62 mmol), and stirred at 80° C. for 30 minutes to react. The resulting reaction liquid was concentrated, and orderly added with 30 mL of EtOAc and 30 mL of saturated sodium bicarbonate solution. The resulting suspension was filtered by diatomite. The filter cake was washed with EtOAc. The resulting organic phase was separated, washed orderly with 30 mL of saturated sodium bicarbonate and 30 mL of saturated salt solution, dried and concentrated to obtain product tert-butyl (2R,4aR)-11-fluoro-10-(2-fluorophenyl)-8-(2-isopropyl-4-methylpyridin-3-yl)-2-methyl-5,7-dioxo-4,4a,5,6,7,8-hexahydro-1H-pyrazino[1',2':4,5]pyrazino[2,3-c][1,8]naphthyridin-3(2H)-carboxylate (300 mg, Y: 80%), which was yellow solid. ES-API: [M+H]$^+$=631.3.

Step 7: the tert-butyl (2R,4aR)-11-fluoro-10-(2-fluorophenyl)-8-(2-isopropyl-4-methylpyridin-3-yl)-2-methyl-5,7-dioxo-4,4a,5,6,7,8-hexahydro-1H-pyrazino[1',2':4,5]pyrazino[2,3-c][1,8]naphthyridin-3(2H)-carboxylate (300 mg, 0.462 mmol), 6 mL of acetone, anhydrous potassium carbonate (255 mg, 1.84 mmol), and iodomethane (656 mg, 4.62 mmol) were sealed in a sealing tube, and stirred at 50° C. for 18 hours to react. The resulting reaction liquid was added with 20 mL of EtOAc, washed with 20 mL of saturated salt solution, dried and concentrated. The resulting crude product was purified by flash column chromatography on silica gel (EtOAc/PE: 0-80%) to obtain product tert-butyl (2R,4aR)-11-fluoro-10-(2-fluorophenyl)-8-(2-isopropyl-4-methylpyridin-3-yl)-2,6-dimethyl-5,7-dioxo-4,4a,5,6,7,8-hexahydro-1H-pyrazino[1',2':4,5]pyrazino[2,3-c][1,8]naphthyridin-3(2H)-carboxylate (350 mg, Y: 95%), which was yellow solid. ES-API: [M+H]$^+$=645.2.

Step 8: the tert-butyl (2R,4aR)-11-fluoro-10-(2-fluorophenyl)-8-(2-isopropyl-4-methylpyridin-3-yl)-2,6-dimethyl-5,7-dioxo-4,4a,5,6,7,8-hexahydro-1H-pyrazino[1',2':4,5]pyrazino[2,3-c][1,8]naphthyridin-3(2H)-carboxylate (350 mg) was dissolved in DCM (4 mL), and added with TFA (2 mL). After stirring at room temperature for 2 hours, the resulting reaction liquid was concentrated to obtain product (2R,4aR)-11-fluoro-10-(2-fluorophenyl)-8-(2-isopropyl-4-methylpyridin-3-yl)-2,6-dimethyl-2,3,4,4a-tetrahydro-1H-pyrazino[1',2':4,5]pyrazino[2,3-c][1,8]naphthyridin-5,7(6H, 8H)-dione (40 mg, crude), which was directly used in next step. ES-API: [M+H]$^+$=545.2.

Step 9: the (2R,4aR)-11-fluoro-10-(2-fluorophenyl)-8-(2-isopropyl-4-methylpyridin-3-yl)-2,6-dimethyl-2,3,4,4a-tetrahydro-1H-pyrazino[1',2':4,5]pyrazino[2,3-c][1,8]naphthyridin-5,7(6H, 8H)-dione (350 mg, 0.62 mmol) was dissolved in DCM (6 mL), and added with diisopropylethylamine (480 mg, 3.72 mmol). The resulting reaction liquid was cooled to 0° C., and added dropwise with acryloyl chloride (112.5 mg, 1.24 mmol). The resulting mixture was stirred at 0° C. for 15 minutes to react. The resulting reaction liquid was added with 20 mL of DCM, washed with 20 mL of saturated solution of NaHCO$_3$ and 20 mL of saturated salt solution, dried and concentrated. The resulting crude product was purified by preparative scale HPLC to obtain product (2R, 4aR)-3-acryloyl-11-fluoro-10-(2-fluorophenyl)-8-(2-isopropyl-4-methylpyridin-3-yl)-2,6-dimethyl-2,3,4,4a-tetrahydro-1H-pyrazino[1',2':4,5]pyrazino[2,3-c][1,8] naphthyridin-5,7(6H, 8H)-dione (Z36, 60 mg, Y: 18%), which was yellow solid. ES-API: [M+H]$^+$=698.3. $^1$H NMR (500 MHz, DMSO-d$_6$) δ 8.49 (d, J=4.9 Hz, 1H), 8.04 (dd, J=14.3, 9.2 Hz, 1H), 7.52 (tdd, J=7.7, 5.3, 1.9 Hz, 1H), 7.36-7.26 (m, 3H), 7.23 (td, J=7.5, 2.0 Hz, 1H), 6.95-6.77 (m, 1H), 6.21-6.09 (m, 1H), 5.80-5.69 (m, 1H), 5.07-4.75 (m, 1H), 4.64-4.39 (m, 1H), 4.03 (dd, J=27.3, 4.3 Hz, 1H), 3.74 (dd, J=4.2, 4.3 Hz, 1H), 3.39 (d, J=2.1 Hz, 4H), 2.95-2.80 (m, 1H), 2.45 (q, J=6.7 Hz, 1H), 2.02 (d, J=2.5 Hz, 3H), 1.56 (dd, J=17.1, 6.7 Hz, 3H), 1.04 (d, J=6.6 Hz, 3H), 0.87 (d, J=6.7 Hz, 3H).

Step 10: the compound Z36 was resolved by preparative scale chiral HPLC (column: Chiralpak TB: 10 μm, 30*250 mm; mobile phase: hexane:EtOH:aminomethanol=50:50:0.2; flow rate: 25 ml/min; and column temperature: room temperature) to obtain the following atropisomer compounds. One of the atropisomer compounds had a structure arbitrarily specified as Z36-1 (peak 1, 22 mg, retention time: 10.211 min, Y: 38%), ES-API: [M+H]$^+$=599.2; $^1$H NMR (500 MHz, DMSO-d$_6$) δ 8.49 (d, J=4.9 Hz, 1H), 8.04 (dd, J=14.3, 9.2 Hz, 1H), 7.52 (t, J=7.7, 5.3, 1.9 Hz, 1H), 7.36-7.26 (m, 3H), 7.23 (t, J=7.5, 2.0 Hz, 1H), 6.95-6.70 (m, 1H), 6.21-6.09 (m, 1H), 5.80-5.69 (m, 1H), 5.07-4.75 (m, 1H), 4.64-4.39 (m, 1H), 4.03-3.70 (m, 1H), 3.74 (dd, J=14.2, 4.3 Hz, 1H), 3.39 (d, J=2.1 Hz, 4H), 2.95-2.80 (m, 1H), 2.45 (q, J=6.7 Hz, 1H), 2.02 (d, J=2.5 Hz, 3H), 1.56 (dd, J=17.1, 6.7 Hz, 3H), 1.04 (d, J=6.6 Hz, 3H), 0.87 (d, J=6.7 Hz, 3H). The other atropisomer compound had a structure arbitrarily specified as Z36-2 (peak 2, 20 mg, retention time: 12.534 min, Y: 34%), ES-API: [M+H]$^+$=599.2; $^1$H NMR (500 MHz, DMSO-d$_6$) δ 8.49 (d, J=4.9 Hz, 1H), 8.03 (dd, J=14.5, 9.2 Hz, 1H), 7.52-7.44 (m, 1H), 7.36-7.22 (m, 4H), 6.95-6.77 (m, 1H), 6.20-6.11 (m, 1H), 5.78-5.70 (m, 1H), 4.77 (s, 1H), 4.61 (d, J=14.1 Hz, 1H), 4.02-3.93 (m, 1H), 3.74 (dd, J=14.2, 4.2 Hz, 1H), 3.35 (s, 4H), 2.92-2.76 (m, 2H), 1.82 (s, 3H), 1.56-1.45 (m, 3H), 1.11 (d, J=6.9 Hz, 3H), 0.99 (dd, J=6.8, 2.9 Hz, 3H). The isomer compounds were detected by analytical scale chiral HPLC (column: Chiralpak IB: 5 μm, 4.6*250 mm; mobile phase: hexane:EtOH:aminomethanol=50:50:0.2; flow rate: 1 ml/min; column temperature=30° C.).

Example 37 Preparation of Compounds Z37, Z37-1 and Z37-2

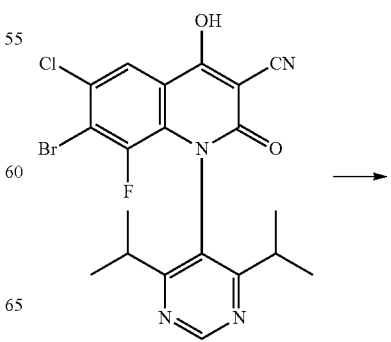

337
-continued
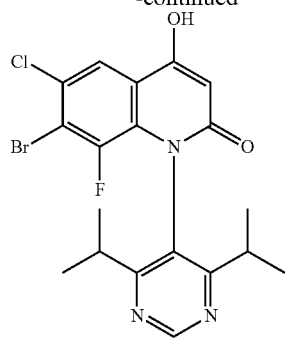
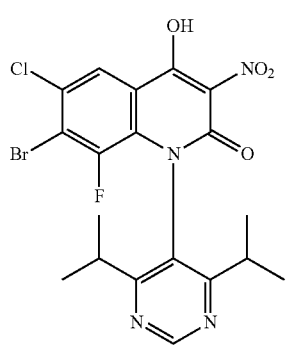
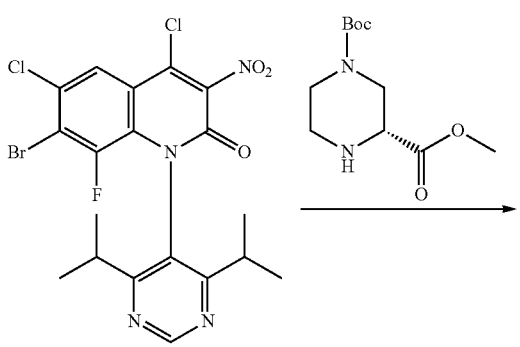
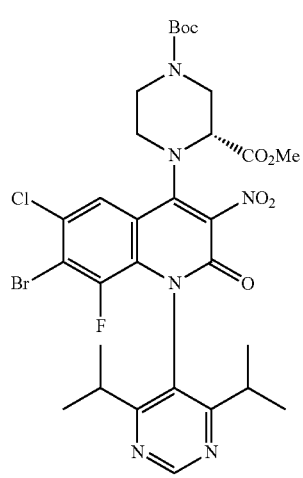
338
-continued
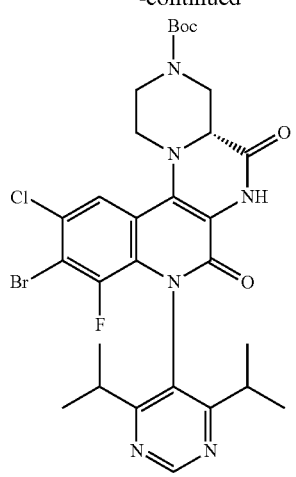
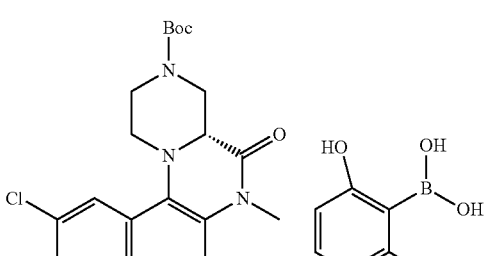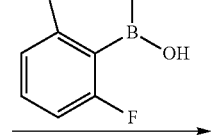
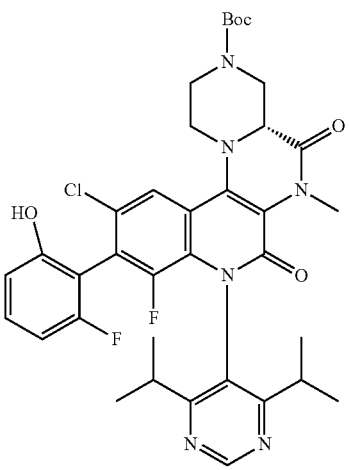

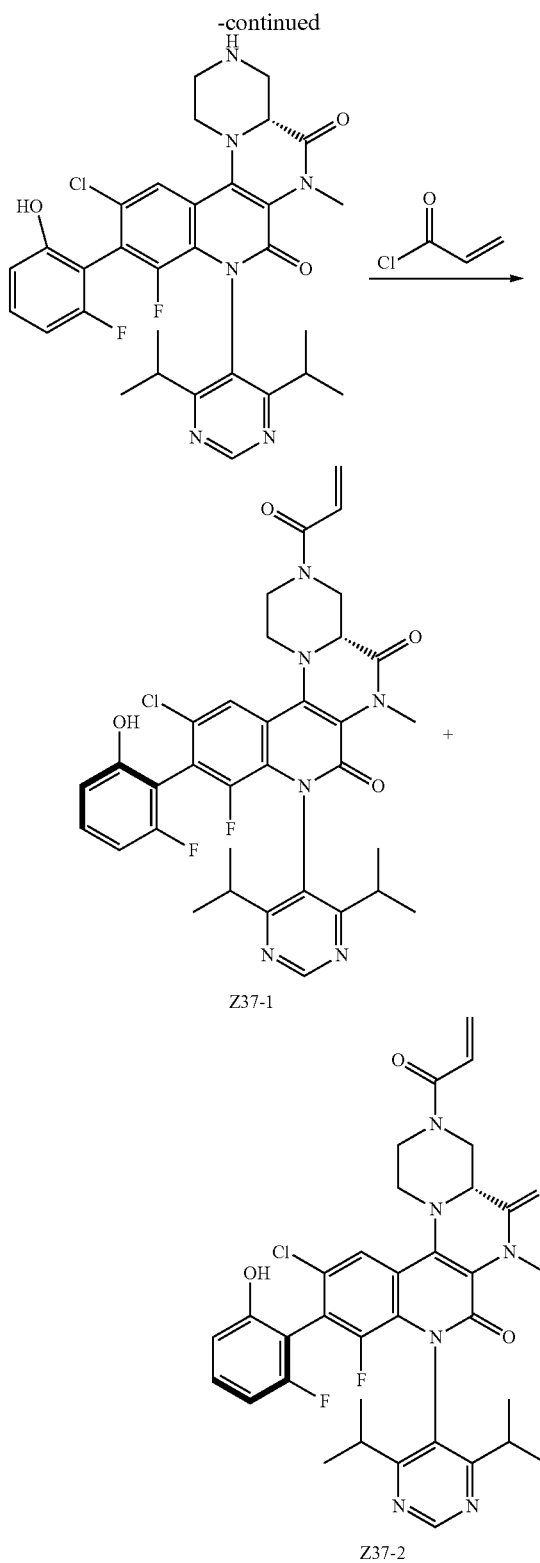

Z37-1

Z37-2

Step 1: 7-bromo-6-chloro-1-(4,6-diisopropylpyrimidin-5-yl)-8-fluoro-4-hydroxy-2-oxo-1,2-dihydroquinolin-3-carbonitrile (2.0 g, 4.17 mmol) was suspended in 1, 4-dioxane (10 mL), and slowly added with a mixed liquid of concentrated sulfuric acid (10 mL) and water (10 mL). The resulting mixture was stirred at 120° C. for 18 hours to react. Cooled reaction liquid was poured into 50 mL of ice water. The precipitated solid was filtered. The filter cake was washed with a small amount of water and dried in vacuum to obtain product 7-bromo-6-chloro-1-(4,6-diisopropylpyrimidin-5-yl)-8-fluoro-4-hydroxylquinolin-2(1H)-one (1.5 g, Y: 79.1%), which was light brown solid. ES-API: [M+H]⁺= 454.0, 456.1.

Step 2: the 7-bromo-6-chloro-1-(4,6-diisopropylpyrimidin-5-yl)-8-fluoro-4-hydroxylquinolin-2(1H)-one (1.4 g, 3.08 mmol) was dissolved in acetic acid (4 mL), orderly added with sodium nitrite (21 mg, 0.31 mmol) and concentrated nitric acid (0.62 mL, 9.24 mmol), and stirred at room temperature for 30 minutes to react. The resulting reaction liquid was poured into 10 mL of ice water. The precipitated solid was filtered. The filter cake was washed with 6 mL of water and dried in vacuum to obtain product 7-bromo-6-chloro-1-(4,6-diisopropylpyrimidin-5-yl)-8-fluoro-4-hydroxy-3-nitroquinolin-2(1H)-one (1.25 g, Y: 81.2%), which was yellow solid. ES-API: [M+H]⁺=499.0, 501.0.

Step 3: the 7-bromo-6-chloro-1-(4,6-diisopropylpyrimidin-5-yl)-8-fluoro-4-hydroxy-3-nitroquinolin-2(1H)-one (1.25 g, 2.50 mmol) was dissolved in ACN (25 mL), orderly added with phosphorus oxychloride (1.15 mL, 12.50 mmol) and N,N-diisopropylethylamine (3.48 mL, 20.0 mmol), and stirred at 85° C. for 30 minutes to react. The resulting reaction liquid was concentrated, added with 100 mL of EtOAc, and washed with 30 mL of water, with 30 mL saturated sodium bicarbonate solution twice and then with 30 mL of saturated salt solution. After the resulting organic phase was dried and concentrated, the resulting crude product was purified by flash column chromatography on silica gel (EtOAc/PE: 0-15%) to obtain product 7-bromo-4,6-dichloro-1-(4,6-diisopropylpyrimidin-5-yl)-8-fluoro-3-nitroquinolin-2(1H)-one (650 mg, Y: 50.1%), which was yellow solid. ES-API: [M+H]1=517.0, 519.0.

Step 4: the 7-bromo-4,6-dichloro-1-(4,6-diisopropylpyrimidin-5-yl)-8-fluoro-3-nitroquinolin-2(1H)-one (370 mg, 0.71 mmol) was dissolved in N,N-dimethylacetamide (5 mL), orderly added with (R)-1-(tert-butyl)3-methyl-piperazin-1,3-dicarboxylate (520 mg, 2.13 mmol) and N,N-diisopropylethylamine (275 mg, 2.13 mmol), and stirred at 120° C. for 2 hours to react. The resulting reaction liquid was added with 80 mL of EtOAc, washed with 30 mL of dilute brine for 4 times and then with 30 mL saturated salt solution, dried and concentrated. The resulting crude product was purified by flash column chromatography on silica gel (EtOAc/PE: 0-25%) to obtain product (R)-1-(tert-butyl)-3-methyl-4-(7-bromo-6-chloro-1-(4,6-diisopropylpyrimidin-5-yl)-8-fluoro-3-nitro-2-oxo-1,2-dihydroquinolin-4-yl)piperazin-1,3-dicarboxylate (400 mg, Y: 77.1%), which was orange solid. ES-API: [M+H]⁺=725.0, 727.2.

Step 5: the (R)-1-(tert-butyl)-3-methyl-4-(7-bromo-6-chloro-1-(4,6-diisopropylpyrimidin-5-yl)-8-fluoro-3-nitro-2-oxo-1,2-dihydroquinolin-4-yl)piperazin-1,3-dicarboxylate (380 mg, 0.52 mmol) was dissolved in acetic acid (7 mL), added with iron powder (103 mg, 1.83 mmol), and stirred at 80° C. for 30 minutes to react. The resulting reaction liquid was concentrated, and orderly added with 100 mL of EtOAc and 60 mL of saturated sodium bicarbonate. The resulting suspension was filtered by using diatomite. The filter cake was washed with EtOAc. The resulting organic phase was separated, washed orderly with 40 mL of saturated sodium bicarbonate solution and 40 mL of saturated salt solution, then dried and concentrated to obtain product tert-butyl (R)-10-bromo-11-chloro-8-(4,6-diisopropylpyrimidin-5-yl)-9-fluoro-5,7-dioxo-1,2,4,4a,5,6,7,8-octahydro-3H-pyrazino[1',2':4,5]pyrazino[2,3-c]quinolin- 3-carboxylate (347 mg, Y: 100%), which was yellow solid. ES-API: [M+H]$^+$=663.2, 665.2.

Step 6: the tert-butyl (R)-10-bromo-11-chloro-8-(4,6-diisopropylpyrimidin-5-yl)-9-fluoro-5,7-dioxo-1,2,4,4a,5,6,7,8-octahydro-3H-pyrazino[1',2':4,5]pyrazino[2,3-c]quinolin-3-carboxylate (317 mg, 0.48 mmol), 12 mL of acetone, anhydrous potassium carbonate (265 mg, 1.92 mmol), and iodomethane (678 mg, 4.80 mmol) were orderly added to a 50 mL sealing tube. The sealing tube was sealed, and the resulting mixture was stirred at 50° C. for 18 hours to react. The resulting reaction liquid was added with 60 mL of EtOAc, washed orderly with 25 mL of water and 25 mL of saturated salt solution, dried and concentrated. The resulting crude product was purified by flash column chromatography on silica gel (EtOAc/PE: 0-30%) to obtain product tert-butyl (R)-10-bromo-11-chloro-8-(4,6-diisopropylpyrimidin-5-yl)-9-fluoro-6-methyl-5,7-dioxo-1,2,4,4a,5,6,7,8-octyl-3H-pyrazino[1',2':4,5]pyrazino[2,3-c]quinolin-3-carboxylate (310 mg, Y: 95.8%), which was yellow solid. ES-API: [M+H]$^+$=677.1, 679.2.

Step 7: the tert-butyl (R)-10-bromo-11-chloro-8-(4,6-diisopropylpyrimidin-5-yl)-9-fluoro-6-methyl-5,7-dioxo-1,2,4,4a,5,6,7,8-octyl-3H-pyrazino[1',2':4,5]pyrazino[2,3-c]quinolin-3-carboxylate (285 mg, 0.42 mmol), (2-fluoro-6-hydroxyphenyl)boric acid (262 mg, 1.68 mmol), SPhos-Pd-G2 (30 mg, 0.042 mmol), 2-dicyclohexylphosphino-2',6'-dimethoxybiphenyl (17 mg, 0.042 mmol), potassium phosphate (356 mg, 1.68 mmol), 3 mL of water, and 15 mL of dioxane were added to a 100 mL round-bottom flask. The resulting mixture was stirred at 90° C. for 2 hours to react under the protection of nitrogen. The resulting reaction liquid was concentrated, and the resulting crude product was purified by flash column chromatography on silica gel (EtOAc/PE: 0-50%) to obtain product tert-butyl (4aR)-11-chloro-8-(4,6-diisopropylpyrimidin-5-yl)-9-fluoro-10-(2-fluoro-6-hydroxyphenyl)-6-methyl-5,7-dioxo-1,2,4,4a,5,6,7,8-octahydro-3H-pyrazino[1',2':4,5]pyrazino[2,3-c]quinolin-3-carboxylate (230 mg, Y: 77.2%), which was directly used in next step. ES-API: [M+H]$^+$=709.2.

Step 8: the tert-butyl (4aR)-11-chloro-8-(4,6-diisopropylpyrimidin-5-yl)-9-fluoro-10-(2-fluoro-6-hydroxyphenyl)-6-methyl-5,7-dioxo-1,2,4,4a,5,6,7,8-octahydro-3H-pyrazino[1',2':4,5]pyrazino[2,3-c]quinolin-3-carboxylate (230 mg, 0.32 mmol) was dissolved in DCM (3 mL), and added with TFA (0.8 mL). After stirring at room temperature for 1 hour, the resulting reaction liquid was concentrated to obtain product (4aR)-11-chloro-8-(4,6-diisopropylpyrimidin-5-yl)-9-fluoro-10-(2-fluoro-6-hydroxyphenyl)-6-methyl-2,3,4,4a,6,8-hexahydro-1H-pyrazino[1', 2', 5]pyrazino[2,3-c]quinolin-5,7-dione (270 mg, crude), which was directly used in next step. ES-API: [M+H]$^+$=609.2.

Step 9: the (4aR)-11-chloro-8-(4,6-diisopropylpyrimidin-5-yl)-9-fluoro-10-(2-fluoro-6-hydroxyphenyl)-6-methyl-2,3,4,4a,6,8-hexahydro-1H-pyrazino[1', 2', 5]pyrazino[2,3-c]quinolin-5,7-dione (270 mg, crude) was dissolved in DCM (12 mL), and added with N,N-diisopropylethylamine (206 mg, 1.60 mmol). The resulting reaction liquid was cooled to 0° C., and added dropwise with acryloyl chloride (26 mg, 0.29 mmol). The resulting mixture was stirred at 0° C. for 15 minutes to react. The resulting reaction liquid was added with 30 mL of DCM, washed orderly with 10 mL of water, 10 mL of saturated solution of NaHCO$_3$ and 10 mL of saturated salt solution, dried and concentrated. The resulting crude product was purified by preparative scale HPLC to obtain the following atropisomer compounds. One of the atropisomer compounds had a structure arbitrarily specified as Z37-1 (retention time: 10.095 min; 40 mg, Y: 18.6%), which was white solid. $^1$H NMR (400 MHz, DMSO-d$_6$) δ 9.13 (s, 1H), 8.02 (s, 1H), 7.27 (dd, J=15.4, 8.1 Hz, 1H), 7.07 (dd, J=16.4, 10.6 Hz, 1H), 6.77-6.67 (m, 2H), 6.15 (d, J=16.7 Hz, 1H), 5.76 (d, J=11.1 Hz, 1H), 4.72 (d, J=13.4 Hz, 1H), 4.48 (d, J=13.0 Hz, 1H), 4.07-3.97 (m, 1H), 3.67-3.41 (m, 2H), 3.31-3.11 (m, 4H), 3.00-2.89 (m, 1H), 2.74-2.56 (m, 2H), 1.30-0.72 (m, 12H). ES-API: [M+H]$^+$=663.2. The other atropisomer compound had a structure arbitrarily specified as Z37-2 (retention time: 10.424 min; 50 mg, Y: 23.2%), which was white solid. $^1$H NMR (400 MHz, DMSO-d$_6$) δ 10.21 (s, 1H), 9.13 (s, 1H), 8.03 (s, 1H), 7.27 (dd, J=15.4, 8.3 Hz, 1H), 7.07 (dd, J=16.7, 10.7 Hz, 1H), 6.77-6.65 (m, 2H), 6.15 (dd, J=16.8, 2.2 Hz, 1H), 5.75 (d, J=10.2 Hz, 1H), 4.72 (d, J=13.9 Hz, 1H), 4.48 (d, J=13.8 Hz, 1H), 4.07-3.97 (m, 1H), 3.66-3.41 (m, 2H), 3.30-3.10 (m, 4H), 3.00-2.89 (m, 1H), 2.70-2.54 (m, 2H), 1.21-0.84 (m, 12H). ES-API: [M+H]$^+$=663.2. The isomer compounds were detected by analytical scale HPLC.

Example 38 Preparation of Compounds Z38, Z38-1 and Z38-2

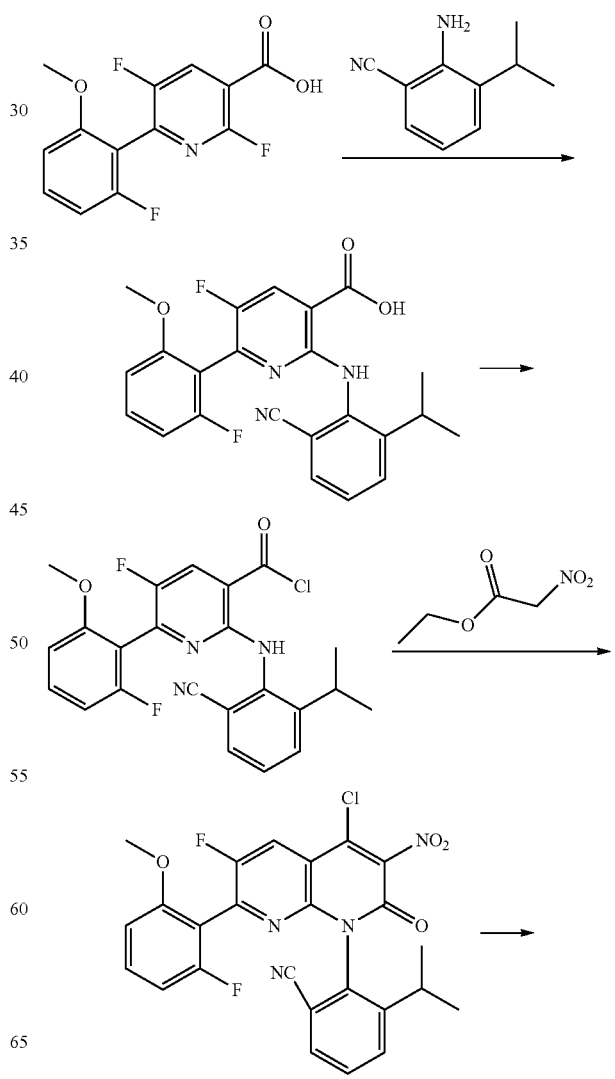

343
-continued
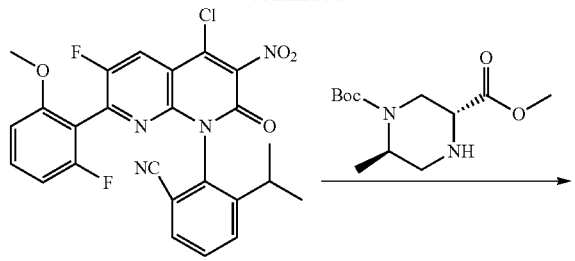
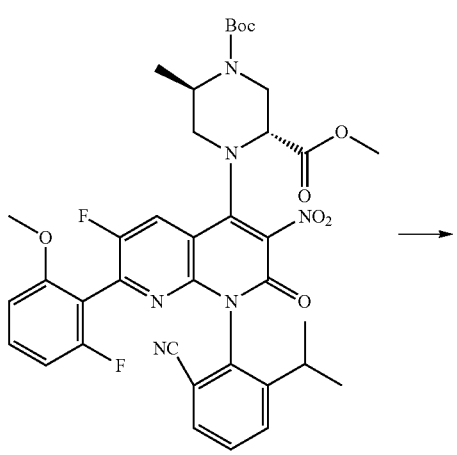
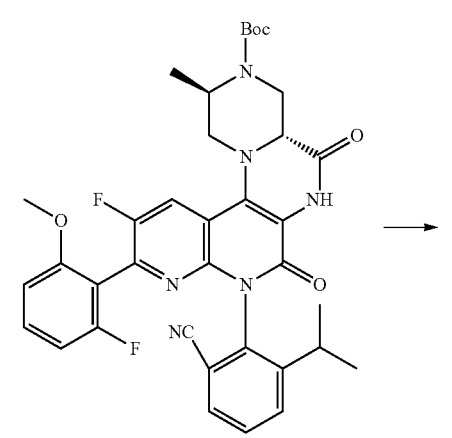
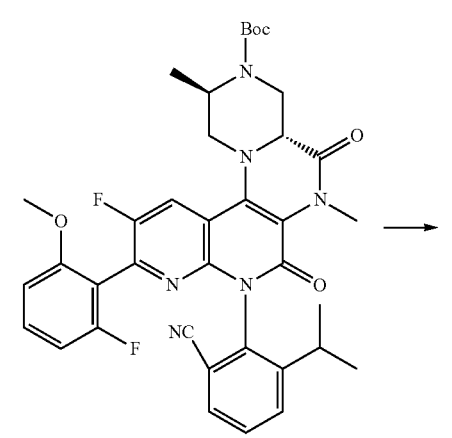
344
-continued
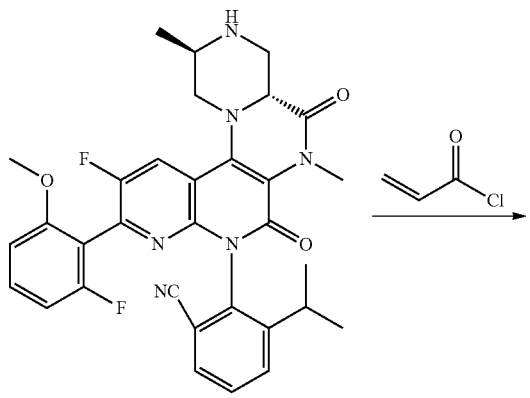
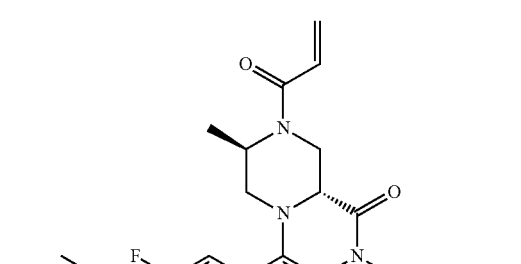
Z38

-continued

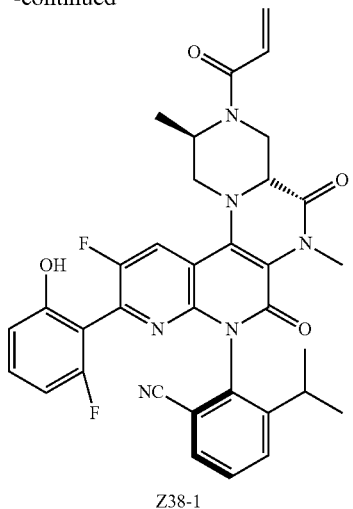

Z38-1

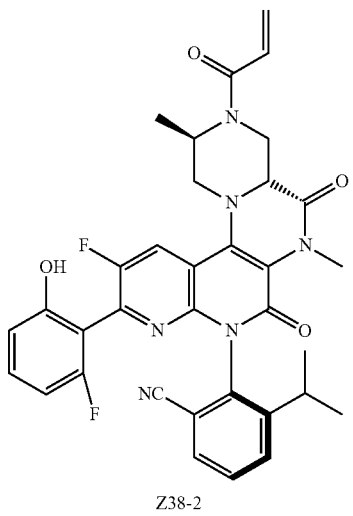

Z38-2

Step 1: 2-cyano-6-isopropylphenyl-3-amine (742 mg, 4.24 mmol) was dissolved in dry tetrahydrofuran (20 mL), added with 2 M NaHMDS (8.48 mL, 16.96 mmol) under the condition of an ice water bath, and stirred for 20 minutes under the condition of the ice water bath. The resulting mixture was added with 2,5-difluoro-6-(2-fluoro-6-methoxyphenyl)nicotinic acid (1.2 g, 4.24 mmol), and stirred at room temperature for 3 hours. The resulting reaction liquid was slowly poured into 30 mL of ice water, mixed with diluted hydrochloric acid (3 M) to adjust the pH to a range of 5 to 6, extracted with EtOAc, washed with 50 mL of saturated salt solution once, dried by anhydrous sodium sulfate, and filtered. After the resulting organic phase was dried and concentrated, the resulting crude product was purified by flash column chromatography on silica gel (EtOAc/PE: 20-40%) to obtain product 2-((2-cyano-6-isopropylphenyl)amino)-5-fluoro-6-(2-fluoro-6-methoxyphenyl)nicotinic acid (1.8 g, Y: 98%), which was yellow solid. ES-API: [M+H]$^+$=424.1.

Step 2: the 2-((2-cyano-6-isopropylphenyl)amino)-5-fluoro-6-(2-fluoro-6-methoxyphenyl)nicotinic acid (1.5 g, 3.42 mmol) was dissolved in dichloroethane, and added with thionyl chloride (4.07 g, 34.2 mmol). The resulting mixture was stirred at 80° C. for 2 hours to react. After the completion of the reaction, the resulting reaction liquid was cooled to room temperature, concentrated, and dried in 50 degrees of vacuum for 4 hours to obtain product 2-((2-cyano-6-isopropylphen-3-yl)amino)-5-fluoro-6-(2-fluoro-6-methoxyphenyl)nicotinoyl chloride (1.57 g, crude), which was faint yellow solid. MeOH was used to detect ES-API: [M+H]$^+$=438.1 (MeOH).

Step 3: under the condition of the ice water bath, sodium hydride (1.97 g, 49.35 mmol) was added to a solution of ethyl nitroacetate (1.31 g, 9.86 mmol) in tetrahydrofuran, stirred for 30 minutes, subsequently added with the 2-((2-cyano-6-isopropylphen-3-yl)amino)-5-fluoro-6-(2-fluoro-6-methoxyphenyl)nicotinoyl chloride (1.57 g, 3.29 mmol), stirred at room temperature for 1 hour, and then heated to 80° C. to react for 2 hours. The resulting reaction liquid was poured into ice water, mixed with 3 M hydrochloric acid to adjust the pH to a range of 3 to 4, extracted with EtOAc, dried by anhydrous sodium sulfate, and filtered. The resulting organic phase was dried and concentrated to obtain product 1-(2-cyano-6-isopropylphen-3-yl)-6-fluoro-7-(2-fluoro-6-methoxyphenyl)-4-hydroxy-3-nitro-1,8-naphthyridin-2(1H)-one (110 mg, Y: 20%). ES-API: [M+H]$^+$=493.1.

Step 4: the 1-(2-cyano-6-isopropylphen-3-yl)-6-fluoro-7-(2-fluoro-6-methoxyphenyl)-4-hydroxy-3-nitro-1,8-naphthyridin-2(1H)-one (110 mg, 0.20 mmol) was dissolved in ACN (10 mL), orderly added with phosphorus oxychloride (153 mg, 1.0 mmol) and N,N-diisopropylethylamine (77 g, 0.6 mmol), and gradually heated to 80° C. and stirred for 3 hours to react. The resulting reaction liquid was concentrated, added with 30 mL of cold ACN, added dropwise to 30 mL of saturated sodium bicarbonate solution under the condition of the ice water bath, and extracted with EtOAc (50 mL*2). The resulting combined organic phase was washed with 30 mL of saturated salt solution, dried by anhydrous sodium sulfate, and filtered. After the resulting organic phase was dried and concentrated, the resulting crude product was purified by flash column chromatography on silica gel (EtOAc/PE: 0-80%) to obtain 4-chloro-6-fluoro-7-(2-fluoro-6-methoxyphenyl)-1-(2-cyano-6-isopropylphen-3-yl)-3-nitro-1,8-naphthyridin-2(1H)-one (110 mg, Y: 68%), which was yellow solid. ES-API: [M+H]$^+$=511.1.

Step 5: the 4-chloro-6-fluoro-7-(2-fluoro-6-methoxyphenyl)-1-(2-cyano-6-isopropylphen-3-yl)-3-nitro-1,8-naphthyridin-2(1H)-one (110 mg, 0.296 mmol) was dissolved in N,N-dimethylacetamide (3 mL), subsequently added with (3R,6R)-1-tert-butyl3-methyl6-methylpiperazin-1,3-dicarboxylic acid (54 mg, 0.22 mmol), and stirred at 120° C. for 2 hours to react. After the completion of the reaction, the resulting product was added with 30 mL of EtOAc and washed with 30 mL of saturated salt solution for 3 times. The EtOAc phase was dried and concentrated to obtain a crude product, namely target product (3R,6R)-1-tert-butyl3-methyl4-(1-(2-cyano-6-isopropylphenyl)-6-fluoro-7-(2-fluoro-6-methoxyphenyl)-3-nitro-2-oxo-1,2-dihydro-1,8-naphthyridin-4-yl)-6-methylpiperazin-1,3-dicarboxylic acid (50 mg, Y: 46%), which was yellow solid. ES-API: [M+H]$^+$=733.3.

Step 6: the (3R,6R)-1-tert-butyl3-methyl4-(1-(2-cyano-6-isopropylphenyl)-6-fluoro-7-(2-fluoro-6-methoxyphenyl)-3-nitro-2-oxo-1,2-dihydro-1,8-naphthyridin-4-yl)-6-methylpiperazin-1,3-dicarboxylic acid (50 mg, 0.068 mmol) was dissolved in acetic acid (25 mL), added with iron powder (11.5 mg, 0.204 mmol), and stirred at 80° C. for 30 minutes to react. The resulting reaction liquid was concentrated, and orderly added with 30 mL of EtOAc and 30 mL of saturated sodium bicarbonate solution. The resulting suspension was filtered by diatomite. The filter cake was washed with EtOAc. The resulting organic phase was separated, washed orderly with 30 mL of saturated sodium bicarbonate and 30 mL of saturated salt solution, dried and concentrated to obtain product (2R,4aR)-tert-butyl8-(2-cyano-6-isopropylphenyl)-11-fluoro-10-(2-fluoro-6-methoxyphenyl)-2-methyl-5,7-dioxo-4,4a, 5,6,7,8-hexahydro-1H-pyrazino[1',2':4,5]pyrazino[2,3-c][1,8]naphthyridin-3(2H)-carboxylate (40 mg, crude), which was yellow solid. ES-API: [M+H]⁺=671.2.

Step 7: the (2R,4aR)-tert-butyl8-(2-cyano-6-isopropylphenyl)-11-fluoro-10-(2-fluoro-6-methoxyphenyl)-2-methyl-5,7-dioxo-4,4a, 5,6,7,8-hexahydro-1H-pyrazino[1',2':4,5]pyrazino[2,3-c][1,8]naphthyridin-3(2H)-carboxylate (40 mg, 0.059 mmol), 30 mL of acetone, anhydrous potassium carbonate (33 mg, 0.24 mmol), and iodomethane (85 mg, 0.59 mmol) were sealed in a sealing tube, and stirred at 50° C. for 18 hours to react. The resulting reaction liquid was added with 20 mL of EtOAc, washed with 20 mL of saturated salt solution, dried and concentrated. The resulting crude product was purified by flash column chromatography on silica gel (EtOAc/PE: 0-80%) to obtain product (2R,4aR)-tert-butyl8-(2-cyano-6-isopropylphenyl)-11-fluoro-10-(2-fluoro-6-methoxyphenyl)-2,6-dimethyl-5,7-dioxo-4,4a,5,6,7,8-hexahydro-1H-pyrazino[1',2':4,5]pyrazino[2,3-c][1,8]naphthyridin-3(2H)-carboxylate (40 mg, Y: 90%), which was yellow solid. ES-API: [M+H]⁺=685.2.

Step 8: the (2R,4aR)-tert-butyl8-(2-cyano-6-isopropylphenyl)-11-fluoro-10-(2-fluoro-6-methoxyphenyl)-2,6-dimethyl-5,7-dioxo-4,4a,5,6,7,8-hexahydro-1H-pyrazino[1',2':4,5]pyrazino[2,3-c][1,8]naphthyridin-3(2H)-carboxylate (44 mg) was dissolved in DCM (3 mL), and added with TFA (1 mL). After stirring at room temperature for 2 hours, the resulting reaction liquid was concentrated to obtain product 2-((2R,4aR)-11-fluoro-10-(2-fluoro-6-methoxyphenyl)-2,6-dimethyl-5,7-dioxo-2,3,4,4a,5,6-hexahydro-1H-pyrazino[1',2':4,5]pyrazino[2,3-c][1,8]naphthyridin-8(7H)-yl)-3-isopropylbenzonitrile (40 mg, crude), which was directly used in next step. ES-API: [M+H]⁺=585.2.

Step 9: the 2-((2R,4aR)-11-fluoro-10-(2-fluoro-6-methoxyphenyl)-2,6-dimethyl-5,7-dioxo-2,3,4,4a,5,6-hexahydro-1H-pyrazino[1',2':4,5]pyrazino[2,3-c][1,8]naphthyridin-8(7H)-yl)-3-isopropylbenzonitrile (40 mg, 0.068 mmol) was dissolved in DCM (5 mL), and added with diisopropylethylamine (53 mL, 0.408 mmol). The resulting reaction liquid was cooled to 0° C., and added dropwise with acryloyl chloride (12.4 mg, 0.137 mmol). The resulting mixture was stirred at 0° C. for 15 minutes to react. The resulting reaction liquid was added with 20 mL of DCM, washed with 20 mL of saturated solution of NaHCO₃ and 20 mL of saturated salt solution, dried and concentrated. The resulting crude product was purified by preparative scale chromatography to obtain product 2-((2R,4aR)-3-acryloyl-11-fluoro-10-(2-fluoro-6-methoxyphenyl)-2,6-dimethyl-5,7-dioxo-2,3,4,4a,5,6-hexahydro-1H-pyrazino[1',2':4,5]pyrazino[2,3-c][1,8]naphthyridin-8(7H)-yl)-3-isopropylbenzonitrile (32 mg, Y: 70%), which was yellow solid. ES-API: [M+H]⁺=639.3.

Step 10: the 2-((2R,4aR)-3-acryloyl-11-fluoro-10-(2-fluoro-6-methoxyphenyl)-2,6-dimethyl-5,7-dioxo-2,3,4,4a,5,6-hexahydro-1H-pyrazino[1',2':4,5]pyrazino[2,3-c][1,8]naphthyridin-8(7H)-yl)-3-isopropylbenzonitrile (32 mg, 0.068 mmol) was added to dry DCM (4.0 mL), then added with boron tribromide (4.0 mL, 4.0 mmol), and warmed to room temperature to react for 1 hour. Under the condition of the ice water bath, the above reaction liquid was added dropwise to saturated sodium bicarbonate solution, extracted with DCM (30 mL) twice, dried and concentrated. The resulting crude product was purified by preparative scale thin-layer chromatography (DCM/MeOH: 10/1) to obtain product 2-((2R,4aR)-3-acryloyl-11-fluoro-10-(2-fluoro-6-hydroxyphenyl)-2,6-dimethyl-5,7-dioxo-2,3,4,4a,5,6-hexahydro-1H-pyrazino[1',2':4,5]pyrazino[2,3-c][1,8]naphthyridin-8(7H)-yl)-3-isopropylbenzonitrile (Z38, 25 mg, Y: 80%), which was yellow solid. ES-API: [M+H]⁺=625.2.

Step 11: the compound Z38 was resolved by preparative scale chiral HPLC (column type: Chiralpak IB: 10 μm, 30*250 mm; mobile phase: hexane:EtOH:aminomethanol=50:50:0.2; flow rate: 25 ml/min; and column temperature: room temperature) to obtain the following atropisomer compounds. One of the atropisomer compounds had a structure arbitrarily specified as Z38-1 (peak 1, 7 mg, retention time: 10.117 min, Y: 28%), ES-API: [M+H]⁺=625.2. The other atropisomer compound had a structure arbitrarily specified as Z38-2 (peak 2, 9 mg, retention time: 12.237 min, Y: 39%), ES-API: [M+H]⁺=625.2. The isomer compounds were detected by analytical scale chiral HPLC (column: Chiralpak IB: 5 μm, 4.6*250 mm; mobile phase: hexane:EtOH:aminomethanol=50:50:0.2; flow rate: 1 ml/min; and column temperature=30° C.).

Example 39 Preparation of Compounds Z39 Z39-1 and Z39-2

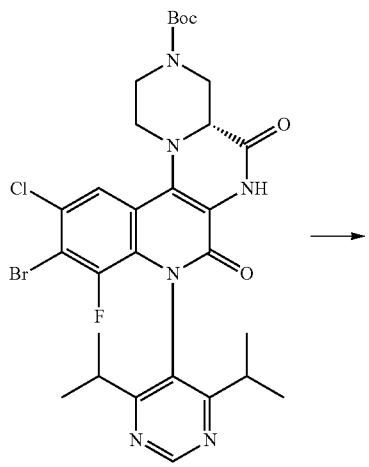

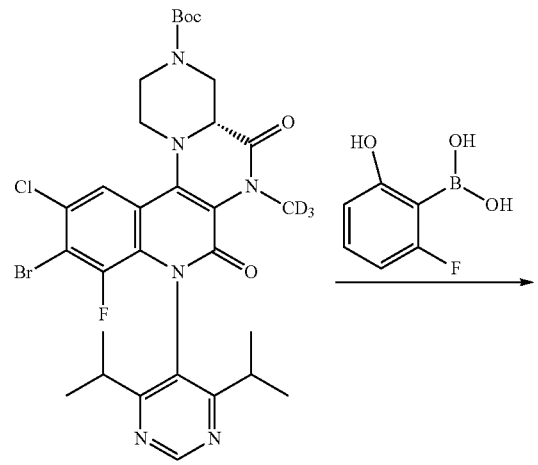

349
-continued

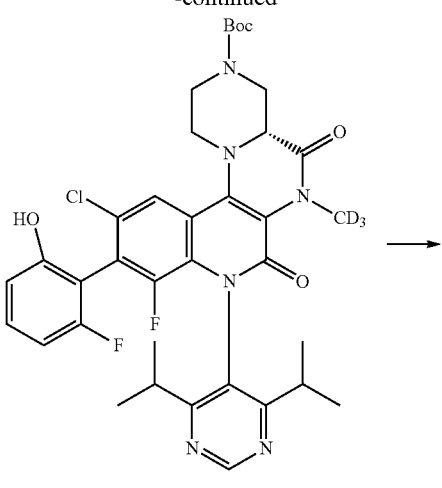

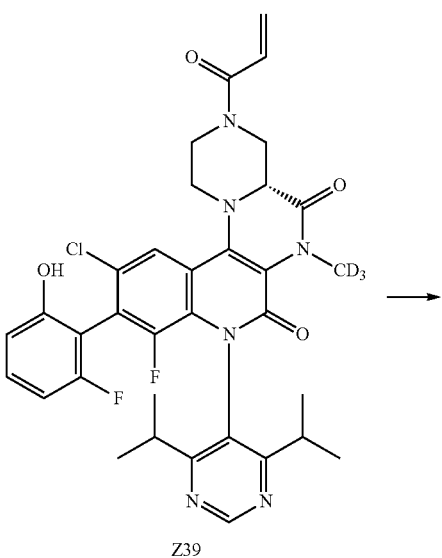

350
-continued

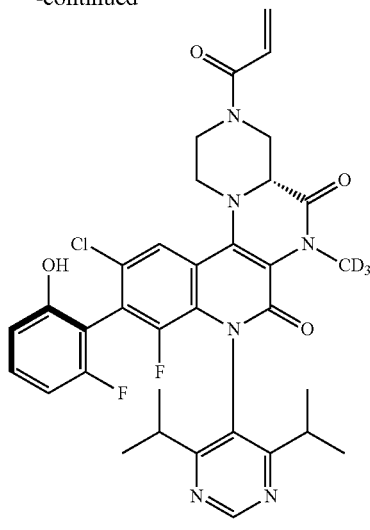

Z39-1

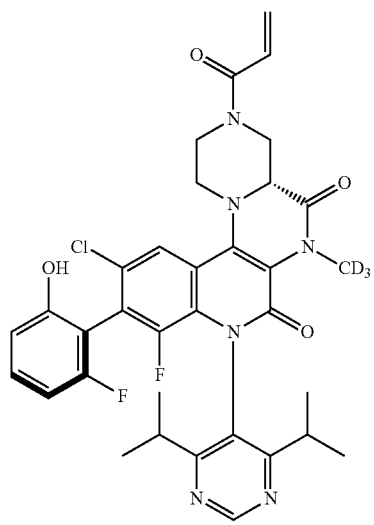

Z39-2

Step 1: tert-butyl (R)-10-bromo-11-chloro-8-(4,6-diisopropylpyrimidin-5-yl)-9-fluoro-5,7-dioxo-1,2,4,4a,5,6,7,8-octahydro-3H-pyrazino[1',2':4,5]pyrazino[2,3-c]quinolin-3-carboxylate (230 mg, 0.35 mmol), 8 mL of acetone, anhydrous potassium carbonate (193 mg, 1.40 mmol), and deuteroiodomethane (507 mg, 3.50 mmol) were orderly added to a 15 mL sealing tube. The sealing tube was sealed, and the resulting mixture was stirred at 50° C. for 18 hours to react. The resulting reaction liquid was added with 60 mL of EtOAc, washed orderly with 25 mL of water and 25 mL of saturated salt solution, dried and concentrated. The resulting crude product was purified by flash column chromatography on silica gel (EtOAc/PE: 0-30%) to obtain product tert-butyl (R)-10-bromo-11-chloro-8-(4,6-diisopropylpyrimidin-5-yl)-9-fluoro-6-(deuteromethyl-d$_3$)-5,7-dioxo-1,2, 4,4a,5,6,7,8-octyl-3H-pyrazino[1',2':4,5]pyrazino[2,3-c] quinolin-3-carboxylate (185 mg, Y: 78.5%), which was faint yellow solid. ES-API: [M+H]$^+$=680.2, 682.2.

Step 2: tert-butyl (R)-10-bromo-11-chloro-8-(4,6-diisopropylpyrimidin-5-yl)-9-fluoro-6-deuteromethyl-5,7-dioxo-1,2,4,4a,5,6,7,8-octyl-3H-pyrazino[1',2':4,5]pyrazino[2,3-c] quinolin-3-carboxylate (185 mg, 0.27 mmol), (2-fluoro-6- hydroxyphenyl)boric acid (262 mg, 1.35 mmol), SPhos-Pd-G2 (19 mg, 0.027 mmol), 2-dicyclohexylphosphino-2',6'-dimethoxybiphenyl (11 mg, 0.027 mmol), potassium phosphate (229 mg, 1.08 mmol), 2 mL of water, and 10 mL of dioxane were added to a 100 mL round-bottom flask. The resulting mixture was stirred at 90° C. for 4 hours to react under the protection of nitrogen. The resulting reaction liquid was concentrated, and the resulting crude product was purified by flash column chromatography on silica gel (EtOAc/PE: 0-50%) to obtain product tert-butyl (4aR)-11-chloro-8-(4,6-diisopropylpyrimidin-5-yl)-9-fluoro-10-(2-fluoro-6-hydroxyphenyl)-6-(deuteromethyl-$d_3$)-5,7-dioxo-1,2,4,4a,5,6,7,8-octahydro-3H-pyrazino[1',2':4,5]pyrazino[2,3-c]quinolin-3-carboxylate (140 mg, Y: 72.4%), which was yellow solid. ES-API: $[M+H]^+$=712.3.

Step 3: the tert-butyl (4aR)-11-chloro-8-(4,6-diisopropylpyrimidin-5-yl)-9-fluoro-10-(2-fluoro-6-hydroxyphenyl)-6-(deuteromethyl-$d_3$)-5,7-dioxo-1,2,4,4a,5,6,7,8-octahydro-3H-pyrazino[1',2':4,5]pyrazino[2,3-c]quinolin-3-carboxylate (140 mg, 0.20 mmol) was dissolved in DCM (3 mL), and added with TFA (0.8 mL). After stirring at room temperature for 1 hour, the resulting reaction liquid was concentrated to obtain product (4aR)-11-chloro-8-(4,6-diisopropylpyrimidin-5-yl)-9-fluoro-10-(2-fluoro-6-hydroxyphenyl)-6-(deuteromethyl-$d_3$)-2,3,4,4a,6,8-hexahydro-1H-pyrazino[1', 2', 5]pyrazino[2,3-c]quinolin-5,7-dione (165 mg, crude), which was directly used in next step. ES-API: $[M+H]^+$=612.3.

Step 4: the (4aR)-11-chloro-8-(4,6-diisopropylpyrimidin-5-yl)-9-fluoro-10-(2-fluoro-6-hydroxyphenyl)-6-(deuteromethyl-$d_3$)-2,3,4,4a,6,8-hexahydro-1H-pyrazino[1', 2', 5]pyrazino[2,3-c]quinolin-5,7-dione (165 mg, crude) was dissolved in DCM (8 mL), and added with N,N-diisopropylethylamine (129 mg, 1.0 mmol). The resulting reaction liquid was cooled to 0° C., and added dropwise with acryloyl chloride (16 mg, 0.18 mmol). The resulting mixture was stirred at 0° C. for 15 minutes to react. The resulting reaction liquid was added with 30 mL of DCM, washed orderly with 10 mL of water, 10 mL of saturated solution of $NaHCO_3$ and 10 mL of saturated salt solution, dried and concentrated to obtain product (4aR) -3-acryloyl-11-chloro-8-(4,6-diisopropylpyrimidin-5-yl)-9-fluoro-10-(2-fluoro-6-hydroxyphenyl)-6-(deuteromethyl-$d_3$)-2,3,4,4a,6,8-hexahydro-1H-pyrazino[1',2',5]pyrazino[2,3-c]quinolin-5,7-dione (Z39).

Step 5: the compound Z39 was purified by preparative scale HPLC to obtain the following atropisomer compounds. One of the atropisomer compounds had a structure arbitrarily specified as Z39-1 (retention time: 10.088 min; 23 mg, Y: 17.6%), which was white solid. $^1$H NMR (500 MHz, DMSO-$d_6$) δ 10.19 (d, J=1.5 Hz, 1H), 9.13 (s, 1H), 8.02 (s, 1H), 7.27 (dd, J=15.5, 8.2 Hz, 1H), 7.07 (dd, J=16.7, 10.7 Hz, 1H), 6.77-6.69 (m, 2H), 6.15 (d, J=16.8 Hz, 1H), 5.75 (d, J=11.2 Hz, 1H), 4.72 (d, J=14.4 Hz, 1H), 4.48 (d, J=12.2 Hz, 1H), 3.99 (s, 1H), 3.62 (d, J=10.5 Hz, 1H), 3.46 (d, J=11.1 Hz, 1H), 3.19 (t, J=12.1 Hz, 1H), 3.00-2.90 (m, 1H), 2.70-2.54 (m, 2H), 1.14-0.95 (m, 12H). ES-API: $[M+H]^+$=666.2. The other atropisomer compound had a structure arbitrarily specified as Z39-2 (retention time: 10.420 min; 30 mg, Y: 22.9%), which was white solid. $^1$H NMR (500 MHz, DMSO-$d_6$) δ 10.20 (d, J=1.4 Hz, 1H), 9.13 (s, 1H), 8.03 (s, 1H), 7.27 (dd, J=15.4, 8.2 Hz, 1H), 7.07 (dd, J=16.7, 10.2 Hz, 1H), 6.79-6.66 (m, 2H), 6.15 (d, J=16.7 Hz, 1H), 5.75 (d, J=10.9 Hz, 1H), 4.72 (d, J=13.7 Hz, 1H), 4.49 (d, J=13.3 Hz, 1H), 4.00 (s, 1H), 3.63-3.44 (m, 2H), 3.19 (t, J=12.1 Hz, 1H), 3.00-2.90 (m, 1H), 2.73-2.55 (m, 2H), 1.25-0.78 (m, 12H). ES-API: $[M+H]^+$=666.2. The isomer compounds were detected by analytical scale HPLC.

Example 40 Preparation of Compound Z40

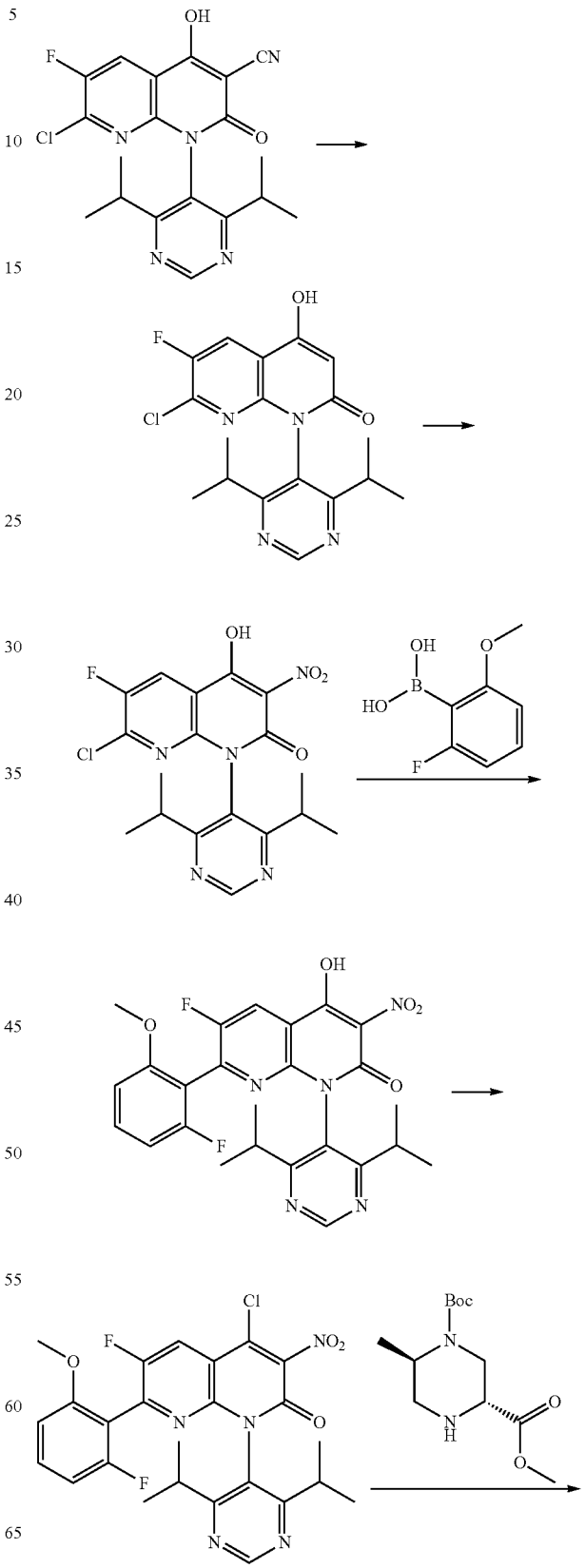

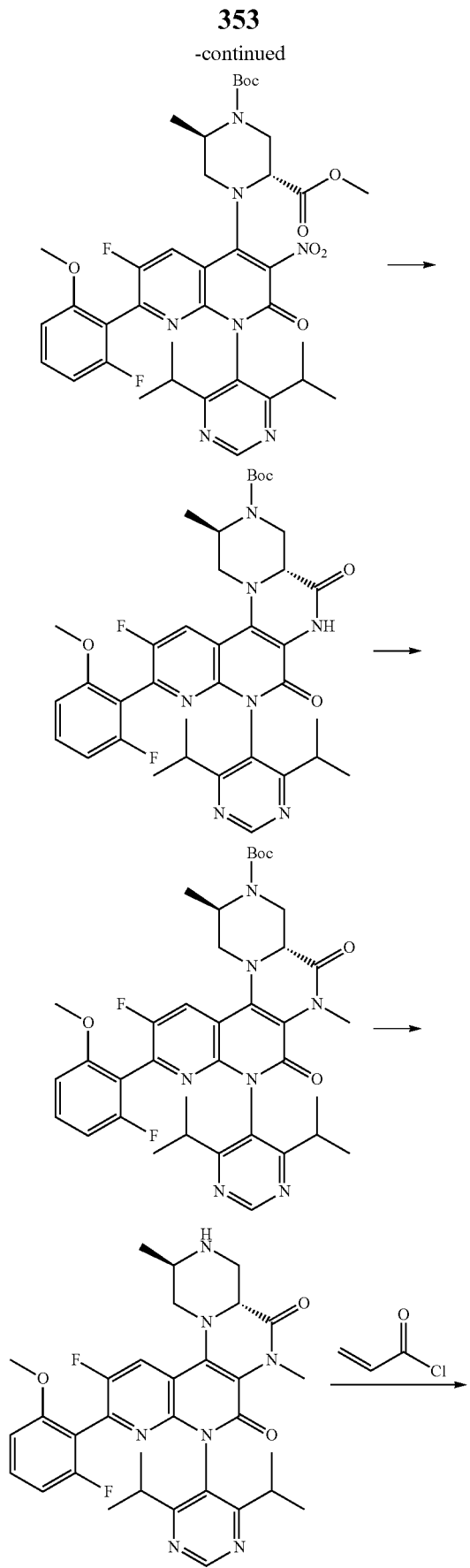
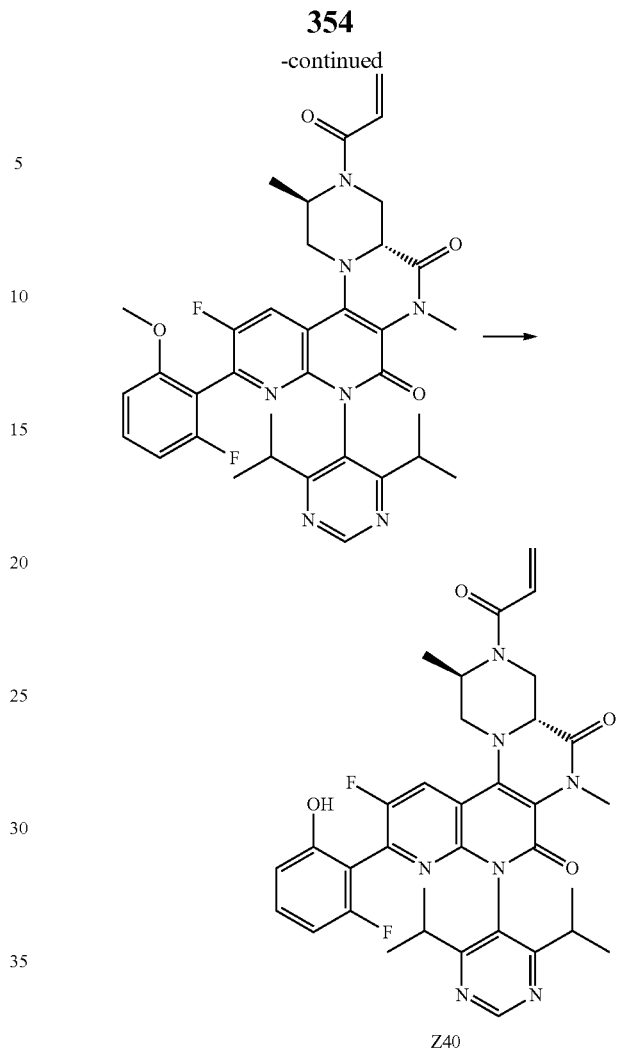

Step 1: 7-chloro-1-(4,6-diisopropylpyrimidin-5-yl)-6-fluoro-4-hydroxy-2-oxo-1,2-dihydro-1,8-naphthyridin-3-carbonitrile (2 g, 5 mmol) was suspended in 1,4-dioxane (12 mL), and slowly added with a mixed liquid of concentrated sulfuric acid (12 mL) and water (12 mL). The resulting mixture was stirred at 120° C. to react overnight. The resulting reaction liquid was cooled and poured into ice water (50 mL), and extracted with EtOAc (50 mL*3). The resulting organic phase was dried and concentrated to obtain product 7-chloro-1-(4,6-diisopropylpyrimidin-5-yl)-6-fluoro-4-hydroxy-1,8-naphthyridin-2(1H)-one (1.8 g, Y: 96%), which was faint yellow solid. ES-API: [M+H]$^+$= 377.2.

Step 2: the 7-chloro-1-(4,6-diisopropylpyrimidin-5-yl)-6-fluoro-4-hydroxy-1,8-naphthyridin-2(1H)-one (1.56 g, 4.14 mmol) was dissolved in acetic acid (5.46 mL), orderly added with sodium nitrite (29 mg, 0.42 mmol) and concentrated nitric acid (780 mg, 12.42 mmol), and stirred at room temperature for 20 minutes. The resulting reaction liquid was poured into 6 mL of water. Yellow solid was precipitated and then filtered. The filter cake was washed with 6 mL of water and dried in vacuum to obtain product 7-chloro-1-(4,6-diisopropylpyrimidin-5-yl)-6-fluoro-4-hydroxy-3-nitro-1,8-naphthyridin-2(1H)-one (1.6 g, Y: 91%), which was faint yellow solid. ES-API: [M+H]$^+$=422.0.

Step 3: a mixed solution of the 7-chloro-1-(4,6-diisopropylpyrimidin-5-yl)-6-fluoro-4-hydroxy-3-nitro-1,8-naphthyridin-2(1H)-one (1.56 g, 3.70 mmol), (2-fluoro-6-methoxyphenyl)boric acid (3.14 g, 18.49 mmol), chloro(2-dicyclohexylphosphino-2',6'-dimethoxy-1,1'-biphenyl)(2'-amino-1,1'-biphen-2-yl)palladium(II) (266 mg, 0.37 mmol), 2-dicyclohexylphosphino-2',6'-dimethoxybiphenyl (152 mg, 0.37 mmol), and potassium phosphate (2.36 g, 11.09 mmol) in 8 mL of water and 40 mL of dioxane was replaced with nitrogen for 3 times and allowed to react at 100° C. for 2 hours. The resulting reaction liquid was poured into 50 mL of water, and washed with methyl tert-butyl ether (30 mL*2). The water phase was mixed with 1.0 M diluted hydrochloric acid to adjust the pH to 6.0, and extracted with EtOAc (30 mL*2). The resulting organic phase was dried and concentrated to obtain crude product 1-(4,6-diisopropylpyrimidin-5-yl)-6-fluoro-7-(2-fluoro-6-methoxyphenyl)-4-hydroxy-3-nitro-1,8-naphthyridin-2(1H)-one (1.55 g, Y: 82%), which was yellow solid. ES-API: [M+H]$^+$=512.2.

Step 4: phosphorus oxychloride (2.29 g, 14.96 mmol) and N,N-diisopropylethylamine (3.09 g, 23.93 mmol) were orderly added to a solution of the 1-(4,6-diisopropylpyrimidin-5-yl)-6-fluoro-7-(2-fluoro-6-methoxyphenyl)-4-hydroxy-3-nitro-1,8-naphthyridin-2(1H)-one (1.53 g, 2.99 mmol) in ACN (20 mL). The resulting mixture was stirred at 80° C. for 1 hour to react. The resulting reaction liquid was concentrated, added with 50 mL of EtOAc, and washed orderly with 30 mL of saturated sodium bicarbonate twice and then with 30 mL of water and 30 mL of saturated salt solution. After the resulting organic phase was dried and concentrated, the resulting crude product was purified by flash column chromatography on silica gel (EtOAc/PE: 0-50%) to obtain product 4-chloro-1-(4,6-diisopropylpyrimidin-5-yl)-6-fluoro-7-(2-fluoro-6-methoxyphenyl)-3-nitro-1,8-naphthyridin-2(1H)-one (800 mg, Y: 50%), which was faint yellow solid. ES-API: [M+H]$^+$=530.2.

Step 5: the 4-chloro-1-(4,6-diisopropylpyrimidin-5-yl)-6-fluoro-7-(2-fluoro-6-methoxyphenyl)-3-nitro-1,8-naphthyridin-2(1H)-one (800 mg, 1.51 mmol) was dissolved in N,N-dimethylacetamide (8 mL), orderly added with 1-(tert-butyl)3-methyl(3R,6R)-6-methylpiperazin-1,3-dicarboxylic acid (390 mg, 1.51 mmol) and N,N-diisopropylethylamine (585 mg, 4.53 mmol), and stirred at 120° C. for 2 hours. Cooled reaction liquid was added with 30 mL of EtOAc, washed with 30 mL of sodium bicarbonate twice, with 30 mL of dilute brine twice, with 30 mL of water once and with 30 mL of saturated salt solution once, dried and concentrated, and purified by flash column chromatography on silica gel (EtOAc/PE: 0-100%) to obtain 1-(tert-butyl)3-methyl(3R,6R)-4-(1-(4,6-diisopropylpyrimidin-5-yl)-6-fluoro-7-(2-fluoro-6-methoxyphenyl)-3-nitro-2-oxo-1,2-dihydro-1,8-naphthyridin-4-yl)-6-methylpiperazin-1,3-dicarboxylic acid (540 mg, Y: 47%). ES-API: [M+H]$^+$=752.2.

Step 6: the 1-(tert-butyl)3-methyl(3R,6R)-4-(1-(4,6-diisopropylpyrimidin-5-yl)-6-fluoro-7-(2-fluoro-6-methoxyphenyl)-3-nitro-2-oxo-1,2-dihydro-1,8-naphthyridin-4-yl)-6-methylpiperazin-1,3-dicarboxylic acid (540 mg, 0.72 mmol) was dissolved in acetic acid (5 mL), added with iron powder (140 mg, 2.51 mmol), and stirred at 80° C. for 1 hour. The resulting reaction liquid was concentrated, added with 50 mL of EtOAc, and mixed with saturated sodium bicarbonate solution to adjust the pH to 8. The resulting suspension was filtered by diatomite. The filter cake was washed with EtOAc. The resulting organic phase was separated, washed orderly with 25 mL of saturated sodium bicarbonate and 25 mL of saturated salt solution, dried and concentrated to obtain crude product tert-butyl (2R,4aR)-8-(4,6-diisopropylpyrimidin-5-yl)-11-fluoro-10-(2-fluoro-6-methoxyphenyl)-2-methyl-5,7-dioxo-1,2,4,4a,5,6,7,8-octahydro-3H-pyrazino[1',2':4,5]pyrazino[2,3-c][1,8]naphthyridin-3-carboxylate (540 mg), which was yellow solid. ES-API: [M+H]$^+$=690.3.

Step 7: the tert-butyl (2R,4aR)-8-(4,6-diisopropylpyrimidin-5-yl)-11-fluoro-10-(2-fluoro-6-methoxyphenyl)-2-methyl-5,7-dioxo-1,2,4,4a,5,6,7,8-octahydro-3H-pyrazino[1',2':4,5]pyrazino[2,3-c][1,8]naphthyridin-3-carboxylate (540 mg, 0.78 mmol), acetone (10 mL), anhydrous potassium carbonate (433 mg, 3.13 mmol), and iodomethane (1.11 g, 7.83 mmol) were orderly added to a 50 mL sealing tube. The sealing tube was sealed, and the resulting mixture was stirred at 50° C. to react overnight. The resulting reaction liquid was filtered, concentrated, dissolved in DCM (10 mL), and washed with water (10 mL). The resulting organic phase was dried and concentrated to obtain crude product tert-butyl (2R,4aR)-8-(4,6-diisopropylpyrimidin-5-yl)-11-fluoro-10-(2-fluoro-6-methoxyphenyl)-2,6-dimethyl-5,7-dioxo-1,2,4,4a,5,6,7,8-octahydro-3H-pyrazino[1',2':4,5]pyrazino[2,3-c][1,8]naphthyridin-3-carboxylate (420 mg), which was yellow solid. ES-API: [M+H]$^+$=704.3.

Step 8: the tert-butyl (2R,4aR)-8-(4,6-diisopropylpyrimidin-5-yl)-11-fluoro-10-(2-fluoro-6-methoxyphenyl)-2,6-dimethyl-5,7-dioxo-1,2,4,4a,5,6,7,8-octahydro-3H-pyrazino[1',2':4,5]pyrazino[2,3-c][1,8]naphthyridin-3-carboxylate (420 mg, 0.60 mmol) was dissolved in DCM (20 mL), and added with TFA (4 mL). After stirring at room temperature for 2 hours, the resulting reaction liquid was concentrated to obtain crude product (2R,4aR)-8-(4,6-diisopropylpyrimidin-5-yl)-11-fluoro-10-(2-fluoro-6-methoxyphenyl)-2,6-dimethyl-2,3,4,4a,6,8-hexahydro-1H-pyrazino[1',2':4,5]pyrazino[2,3-c][1,8]naphthyridin-5,7-dione (360 mg), which was directly used in next step. ES-API: [M+H]$^+$=604.3.

Step 9: the (2R,4aR)-8-(4,6-diisopropylpyrimidin-5-yl)-11-fluoro-10-(2-fluoro-6-methoxyphenyl)-2,6-dimethyl-2,3,4,4a,6,8-hexahydro-1H-pyrazino[1',2':4,5]pyrazino[2,3-c][1,8]naphthyridin-5,7-dione (360 mg, 0.60 mmol) was dissolved in DCM (5 mL), and added with N,N-diisopropylethylamine (385 mg, 2.98 mmol). The resulting reaction liquid was cooled to 0° C., and added dropwise with acryloyl chloride (108 mg, 1.19 mmol). The reaction liquid was stirred at 0° C. for 5 minutes, and concentrated. The resulting crude product was purified by flash column chromatography on silica gel (0-80% EtOAc/PE) to obtain product (2R,4aR)-3-acryloyl-8-(4,6-diisopropylpyrimidin-5-yl)-11-fluoro-10-(2-fluoro-6-methoxyphenyl)-2,6-dimethyl-2,3,4,4a,6,8-hexahydro-1H-pyrazino[1',2':4,5]pyrazino[2,3-c][1,8]naphthyridin-5,7-dione (220 mg, Y: 56%), which was faint yellow solid. ES-API: [M+H]$^+$=658.2.

Step 10: the (2R,4aR)-3-acryloyl-8-(4,6-diisopropylpyrimidin-5-yl)-11-fluoro-10-(2-fluoro-6-methoxyphenyl)-2,6-dimethyl-2,3,4,4a,6,8-hexahydro-1H-pyrazino[1',2':4,5]pyrazino[2,3-c][1,8]naphthyridin-5,7-dione (220 mg, 0.33 mmol) was dissolved in DCM (3 mL). The resulting solution was cooled to 0° C., added dropwise with a solution (3 mL) of 17% boron tribromide in DCM, and stirred at room temperature overnight. The resulting reaction liquid was poured into 40 mL of saturated solution of sodium bicarbonate and extracted with 25 mL of DCM twice. The resulting organic phase was dried and concentrated, and the resulting crude product was purified by preparative scale HPLC to obtain product (2R,4aR)-3-acryloyl-8-(4,6-diisopropylpyrimidin-5-yl)-11-fluoro-10-(2-fluoro-6-hydroxyphenyl)-2,6-dimethyl-2,3,4,4a,6,8-hexahydro-1H-pyrazino[1',2':4,5]pyrazino[2,3-c][1,8]naphthyridin-5,7-dione (Z40, 115 mg, Y: 53%), which was faint yellow solid. $^1$H NMR (500 MHz, DMSO-$d_6$) δ 10.14 (s, 1H), 9.12 (s, 1H), 8.02 (dd, J=14.8, 8.5 Hz, 1H), 7.26 (dd, J=15.4, 8.2 Hz, 1H), 6.95 (ddd, J=75.5, 16.8, 10.6 Hz, 1H), 6.73 (d, J=8.3 Hz, 1H), 6.68 (t, J=8.8 Hz, 1H), 6.22-6.09 (m, 1H), 5.79-5.61 (m, 1H), 5.13-4.55 (m, 1H), 4.77-4.42 (m, 1H), 4.02 (dd, J=28.2, 3.9 Hz, 1H), 3.74 (dd, J=14.2, 4.2 Hz, 1H), 3.42 (t, J=15.3 Hz, 1H), 3.33-3.13 (m, 1H), 3.03-2.85 (m, 1H), 2.79 (dd, J=13.5, 6.8 Hz, 1H), 2.51-2.45 (m, 3H), 1.56 (dd, J=18.3, 6.7 Hz, 3H), 1.11 (d, J=6.7 Hz, 3H), 1.05 (d, J=6.6 Hz, 3H), 1.00 (d, J=6.6 Hz, 3H), 0.85 (d, J=6.7 Hz, 3H). ES-API: [M+H]$^+$= 644.2.
Example 41 Preparation of Compound Z41
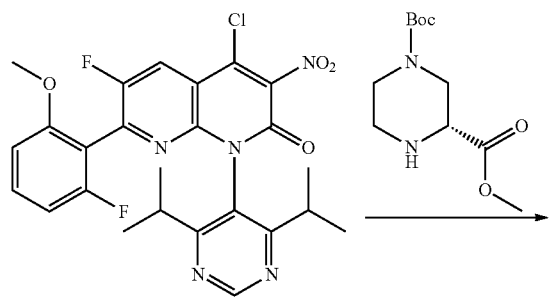
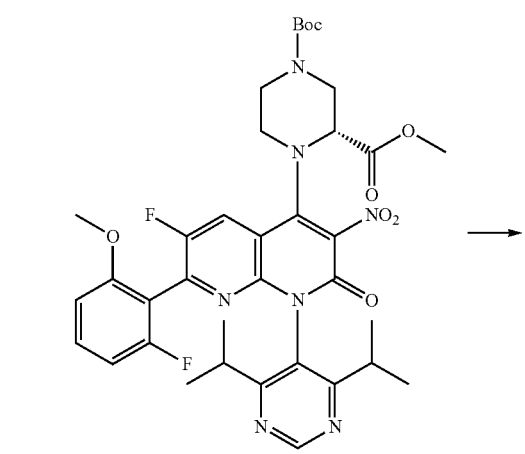
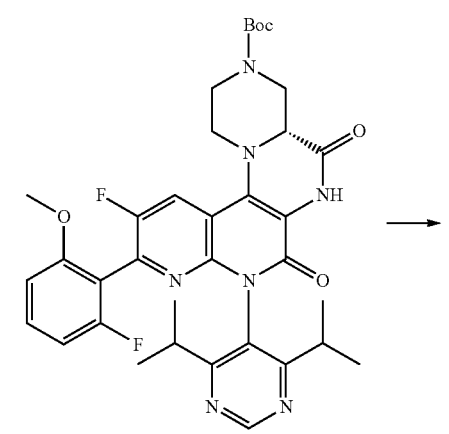
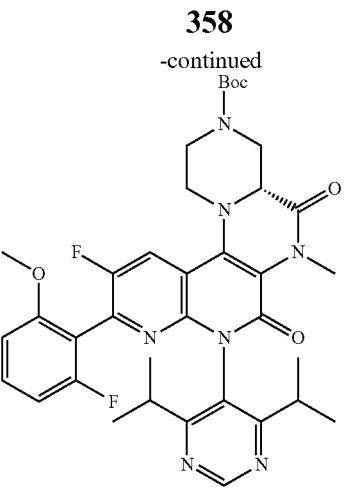
-continued
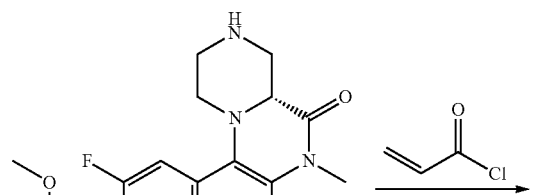
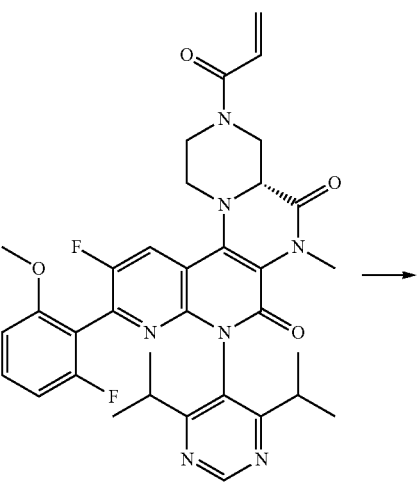

-continued

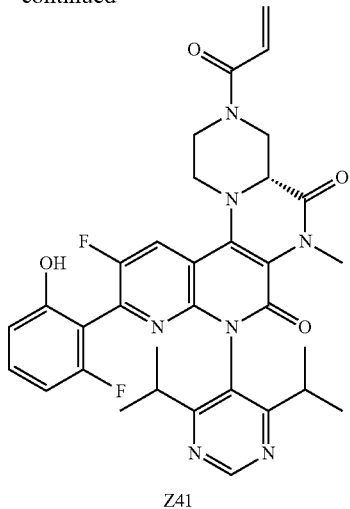

Z41

Step 1: 4-chloro-1-(4,6-diisopropylpyrimidin-5-yl)-6-fluoro-7-(2-fluoro-6-methoxyphenyl)-3-nitro-1,8-naphthyridin-2(1H)-one (1 g, 1.89 mmol) was dissolved in N,N-dimethylacetamide (10 mL), orderly added with 1-(tert-butyl)3-methyl(R)-piperazin-1,3-dicarboxylate (1.39 g, 5.67 mmol) and N,N-diisopropylethylamine (733 mg, 5.67 mmol), and stirred at 120° C. for 2 hours. Cooled reaction liquid was added with 30 mL of EtOAc, washed with 30 mL of sodium bicarbonate twice, with 30 mL of dilute brine twice, 30 mL of water once and with 30 mL of saturated salt solution once, dried and concentrated, and purified by flash column chromatography on silica gel (0-100% EtOAc/PE) to obtain 1-(tert-butyl)3-methyl(3R)-4-(1-(4,6-diisopropylpyrimidin-5-yl)-6-fluoro-7-(2-fluoro-6-methoxyphenyl)-3-nitro-2-oxo-1,2-dihydro-1,8-naphthyridin-4-yl)piperazin-1,3-dicarboxylate (1.3 g, Y: 80%). ES-API: [M+H]$^+$=738.3.

Step 2: the 1-(tert-butyl)3-methyl(3R)-4-(1-(4,6-diisopropylpyrimidin-5-yl)-6-fluoro-7-(2-fluoro-6-methoxyphenyl)-3-nitro-2-oxo-1,2-dihydro-1,8-naphthyridin-4-yl)piperazin-1,3-dicarboxylate (1.23 g, 1.67 mmol) was dissolved in acetic acid (12 mL), added with iron powder (326 mg, 5.84 mmol), and stirred at 80° C. for 2 hours. The resulting reaction liquid was concentrated, added with 50 mL of EtOAc, and mixed with saturated sodium bicarbonate solution to adjust the pH to 8. The resulting suspension was filtered by diatomite. The filter cake was washed with EtOAc. The resulting organic phase was separated, washed orderly with 25 mL of saturated sodium bicarbonate and 25 mL of saturated salt solution, dried and concentrated to obtain crude product tert-butyl (4aR)-8-(4,6-diisopropylpyrimidin-5-yl)-11-fluoro-10-(2-fluoro-6-methoxyphenyl)-5,7-dioxo-1,2,4,4a,5,6,7,8-octahydro-3H-pyrazino[1',2':4,5]pyrazino[2,3-c][1,8]naphthyridin-3-carboxylic acid (1.08 g, Y: 95%), which was grey-green solid. ES-API: [M+H]$^+$=676.2.

Step 3: the tert-butyl (4aR)-8-(4,6-diisopropylpyrimidin-5-yl)-11-fluoro-10-(2-fluoro-6-methoxyphenyl)-5,7-dioxo-1,2,4,4a,5,6,7,8-octahydro-3H-pyrazino[1',2':4,5]pyrazino[2,3-c][1,8]naphthyridin-3-carboxylate (500 mg, 0.74 mmol), acetone (10 mL), anhydrous potassium carbonate (307 mg, 2.22 mmol), and iodomethane (630 mg, 4.44 mmol) were orderly added to a 15 mL sealing tube. The sealing tube was sealed, and the resulting mixture was stirred at 50° C. to react overnight. The resulting reaction liquid was filtered, concentrated, dissolved in DCM (10 mL), and washed with water (10 mL). The resulting organic phase was dried and concentrated to obtain crude product tert-butyl (4aR)-8-(4,6-diisopropylpyrimidin-5-yl)-11-fluoro-10-(2-fluoro-6-methoxyphenyl)-6-methyl-5,7-dioxo-1,2,4,4a,5,6,7,8-octahydro-3H-pyrazino[1',2':4,5]pyrazino[2,3-c][1,8]naphthyridin-3-carboxylate (410 mg, Y: 80%), which was yellow solid. ES-API: [M+H]$^+$=690.2.

Step 4: the tert-butyl (4aR)-8-(4,6-diisopropylpyrimidin-5-yl)-11-fluoro-10-(2-fluoro-6-methoxyphenyl)-6-methyl-5,7-dioxo-1,2,4,4a,5,6,7,8-octahydro-3H-pyrazino[1',2':4,5]pyrazino[2,3-c][1,8]naphthyridin-3-carboxylate (410 mg, 0.60 mmol) was dissolved in DCM (4 mL), and added with TFA (1 mL). After stirring at room temperature for 2 hours, the resulting reaction liquid was concentrated to obtain crude product (4aR)-8-(4,6-diisopropylpyrimidin-5-yl)-11-fluoro-10-(2-fluoro-6-methoxyphenyl)-6-methyl-2,3,4,4a,6,8-hexahydro-1H-pyrazino[1',2':4,5]pyrazino[2,3-c][1,8]naphthyridin-5,7-dione (350 mg), which was directly used in next step. ES-API: [M+H]$^+$=590.2.

Step 5: the (4aR)-8-(4,6-diisopropylpyrimidin-5-yl)-11-fluoro-10-(2-fluoro-6-methoxyphenyl)-6-methyl-2,3,4,4a,6,8-hexahydro-1H-pyrazino[1',2':4,5]pyrazino[2,3-c][1,8]naphthyridin-5,7-dione (350 mg, 0.59 mmol) was dissolved in DCM (5 mL), and added with N,N-diisopropylethylamine (230 mg, 1.78 mmol). The resulting reaction liquid was cooled to 0° C., and added dropwise with acryloyl chloride (107 mg, 1.19 mmol). The reaction liquid was stirred at 0° C. for 5 minutes, and concentrated. The resulting crude product was purified by flash column chromatography on silica gel (0-100% EtOAc/PE) to obtain product (4aR)-3-acryloyl-8-(4,6-diisopropylpyrimidin-5-yl)-11-fluoro-10-(2-fluoro-6-methoxyphenyl)-6-methyl-2,3,4,4a,6,8-hexahydro-1H-pyrazino[1',2':4,5]pyrazino[2,3-c][1,8]naphthyridin-5,7-dione (300 mg, Y: 80%), which was faint yellow solid. ES-API: [M+H]$^+$=644.2.

Step 6: the (4aR)-3-acryloyl-8-(4,6-diisopropylpyrimidin-5-yl)-11-fluoro-10-(2-fluoro-6-methoxyphenyl)-6-methyl-2,3,4,4a,6,8-hexahydro-1H-pyrazino[1',2':4,5]pyrazino[2,3-c][1,8]naphthyridin-5,7-dione (300 mg, 0.47 mmol) was dissolved in DCM (5 mL). The resulting solution was cooled to 0° C., added dropwise with a solution (5 mL) of 17% boron tribromide in DCM, and stirred at room temperature overnight. The resulting reaction liquid was poured into 40 mL of saturated solution of sodium bicarbonate and extracted with 25 mL of DCM twice. The resulting organic phase was dried and concentrated, and the resulting crude product was purified by preparative scale HPLC to obtain product (4aR)-3-acryloyl-8-(4,6-diisopropylpyrimidin-5-yl)-11-fluoro-10-(2-fluoro-6-hydroxyphenyl)-6-methyl-2,3,4,4a,6,8-hexahydro-1H-pyrazino[1',2':4,5]pyrazino[2,3-c][1,8]naphthyridin-5,7-dione (Z41, 97 mg, Y: 35%), which was faint yellow solid. $^1$H NMR (500 MHz, DMSO-d$_6$) δ 10.13 (s, 1H), 9.12 (s, 1H), 8.42 (d, J=8.7 Hz, 1H), 7.26 (dd, J=15.5, 8.2 Hz, 1H), 7.03 (dt, J=111.6, 55.9 Hz, 1H), 6.73 (d, J=8.3 Hz, 1H), 6.68 (t, J=8.8 Hz, 1H), 6.16 (d, J=16.9 Hz, 1H), 5.76 (d, J=11.0 Hz, 1H), 4.74 (d, J=13.9 Hz, 1H), 4.45 (d, J=12.3 Hz, 1H), 4.00 (s, 1H), 3.58 (t, J=12.7 Hz, 2H), 3.33 (s, 3H), 3.22 (t, J=11.5 Hz, 1H), 2.79 (dt, J=13.5, 6.7 Hz, 1H), 2.69 (t, J=10.7 Hz, 1H), 2.51-2.45 (m, 1H), 1.11 (d, J=6.7 Hz, 3H), 1.04 (d, J=6.6 Hz, 3H), 1.01 (d, J=6.6 Hz, 3H), 0.85 (d, J=6.7 Hz, 3H). ES-API: [M+H]$^+$=630.2.

Example 42 Preparation of Compound Z42

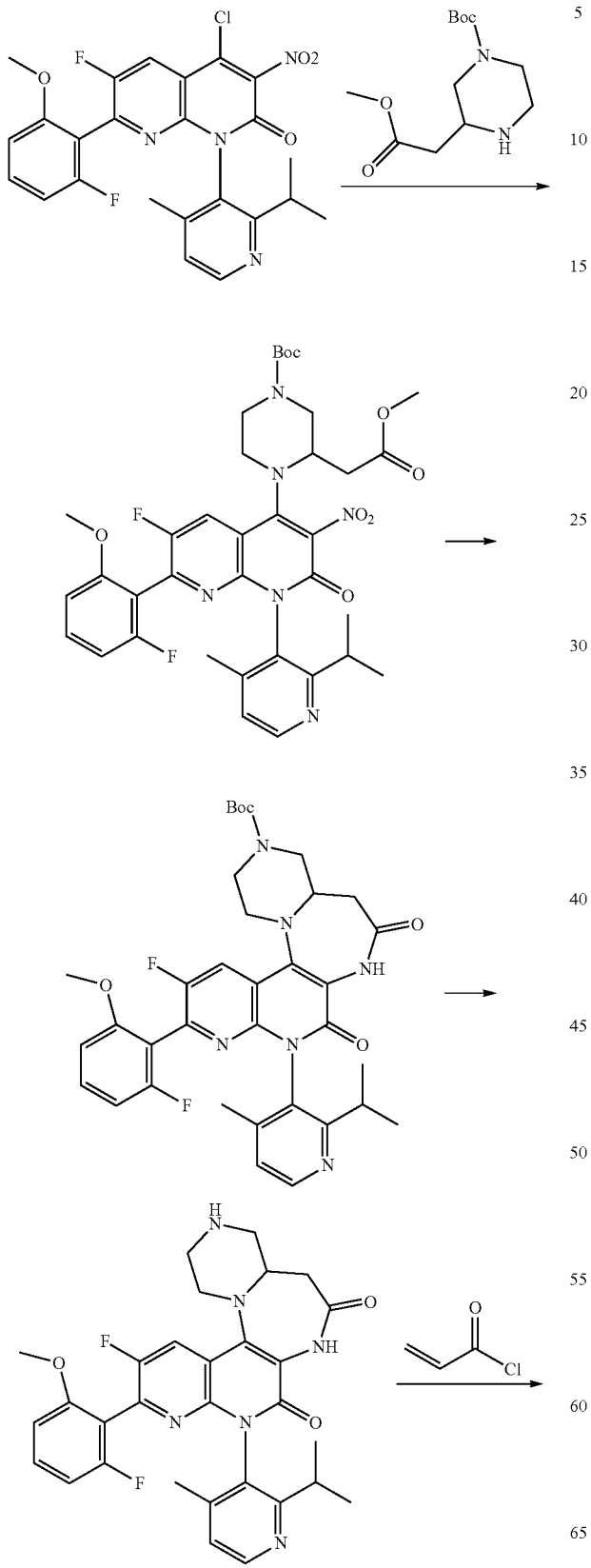

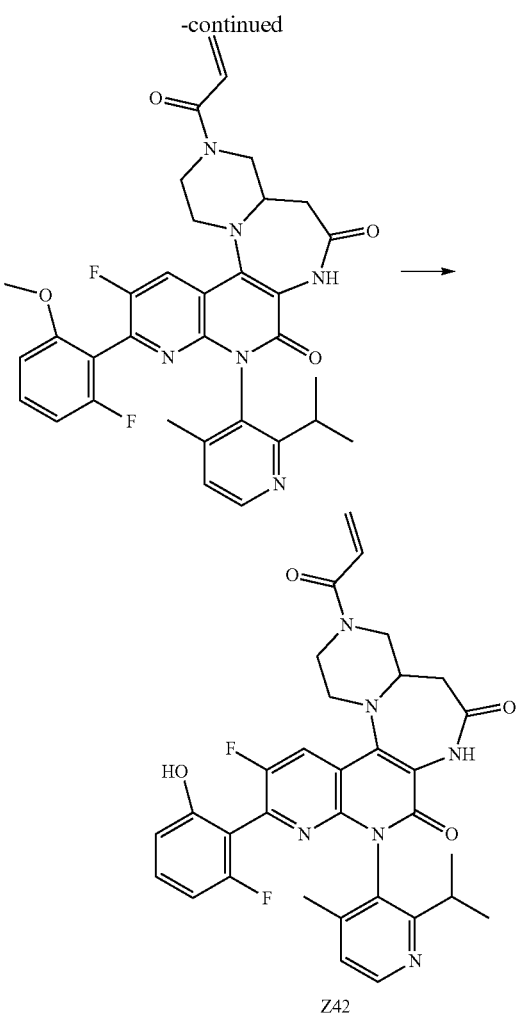

Z42

Step 1: 4-chloro-6-fluoro-7-(2-fluoro-6-methoxyphenyl)-1-(2-isopropyl-4-methylpyridin-3-yl)-3-nitro-1,8-naphthyridin-2(1H)-one (1.2 g, 2.40 mmol) was dissolved in N,N-dimethylacetamide (10 mL), orderly added with tert-butyl (3-(2-methoxy-2-oxyethyl)piperazin-1I-carboxylate (743 mg, 2.87 mmol) and N,N-diisopropylethylamine (930 mg, 7.20 mmol), and stirred at 120° C. for 2 hours to react. The resulting reaction liquid was added with 50 mL of EtOAc, washed with 25 mL of dilute brine for 4 times and then with 20 mL of saturated salt solution, dried and concentrated. The resulting crude product was purified by flash column chromatography on silica gel (EtOAc/PE: 0-50%) to obtain yellow solid tert-butyl-4-(6-fluoro-7-(2-fluoro-6-methoxyphenyl)-1-(2-isopropyl-4-methylpyridin-3-yl)-3-nitro-2-oxo-1,2-dihydro-1,8-naphthyridin-4-yl)-3-(2-methoxy-2-oxyethyl)piperazin-1-carboxylic acid (580 mg, Y: 28%). ES-API: [M+H]⁺=723.3.

Step 2: the tert-butyl 4-(6-fluoro-7-(2-fluoro-6-methoxyphenyl)-1-(2-isopropyl-4-methylpyridin-3-yl)-3-nitro-2-oxo-1,2-dihydro-1,8-naphthyridin-4-yl)-3-(2-methoxy-2-oxyethyl)piperazin--carboxylate (550 mg, 0.76 mmol) was dissolved in acetic acid (5.5 mL), added with iron powder (149 mg, 2.66 mmol), and stirred at 80° C. for 2 hours to react. The resulting reaction liquid was concentrated, and orderly added with 50 mL of EtOAc and 30 mL of saturated sodium bicarbonate. The resulting suspension was filtered by using diatomite. The filter cake was washed with EtOAc.

The resulting organic phase was separated, washed orderly with 25 mL of saturated sodium bicarbonate and 25 mL of saturated salt solution, dried and concentrated to obtain yellow solid tert-butyl 12-fluoro-11-(2-fluoro-6-meth oxyphenyl)-9-(2-isopropyl-4-methylpyridin-3-yl)-6,8-dioxo-1, 2,4a,5,6,7,8,9-octahydropyrazino[1',2':4,5][1,4]diaza[2,3-c][1,8]naphthyridin-3(4H)-carboxylate (520 mg). ES-API: [M+H]$^+$=661.3.

Step 3: the tert-butyl 12-fluoro-11-(2-fluoro-6-methoxyphenyl)-9-(2-isopropyl-4-methylpyridin-3-yl)-6,8-dioxo-1, 2,4a,5,6,7,8,9-octahydropyrazino[1',2':4,5][1,4]diaza[2,3-c][1,8]naphthyridin-3(4H)-carboxylate (100 mg, 0.15 mmol) was dissolved in DCM (4 mL), and added with TFA (1 mL). After stirring at room temperature for 2 hours, the resulting reaction liquid was concentrated to obtain product 12-fluoro-11-(2-fluoro-6-methoxyphenyl)-9-(2-isopropyl-4-methylpyridin-3-yl)-1,2,3,4,4a,5,7,9-octahydropyrazino[1',2':4,5][1,4]diaza[2,3-c][1,8]naphthyridin-6,8-dione (85 mg, crude), which was directly used in next step. ES-API: [M+H]$^+$=561.3.

Step 4: the 12-fluoro-11-(2-fluoro-6-methoxyphenyl)-9-(2-isopropyl-4-methylpyridin-3-yl)-1,2,3,4,4a,5,7,9-octahydropyrazino[1',2':4,5][1,4]diaza[2,3-c][1,8]naphthyridin-6, 8-dione (85 mg, crude) was dissolved in DCM (2 mL), and added with N,N-diisopropylethylamine (58 mg, 0.45 mmol). The resulting reaction liquid was cooled to 0° C., added dropwise with acryloyl chloride (27 mg, 0.30 mmol), and stirred at 0° C. for 10 minutes. The resulting reaction liquid was added with 25 mL of DCM, washed orderly with 15 mL of water, 15 mL of saturated solution of sodium bicarbonate and 15 mL of saturated salt solution, dried and concentrated. The resulting crude product was purified by flash column chromatography on silica gel (EtOAc/PE: 0-100%) to obtain product 3-acryloyl-12-fluoro-11-(2-fluoro-6-methoxyphenyl)-9-(2-isopropyl-4-methylpyridin-3-yl)-1,2,3,4,4a,5,7,9-octahydropyrazino[1',2':4,5][1,4]diaza[2,3-c][1,8]naphthyridin-6,8-dione (60 mg, Y: 65%), which was faint yellow solid. ES-API: [M+H]$^+$=615.3.

Step 5: the 3-acryloyl-12-fluoro-11-(2-fluoro-6-methoxyphenyl)-9-(2-isopropyl-4-methylpyridin-3-yl)-1,2,3,4,4a,5,7,9-octahydropyrazino[1',2':4,5][1,4]diaza[2,3-c][1,8]naphthyridin-6,8-dione (60 mg, 0.10 mmol) was dissolved in DCM (3 mL). The resulting reaction liquid was cooled to 0° C., and then added dropwise with a solution (3 mL) of 17% boron tribromide in DCM. The resulting mixture was stirred at room temperature for 2 hours to react. The resulting reaction liquid was poured into 40 mL of saturated solution of sodium bicarbonate and extracted with 25 mL of DCM twice. The resulting organic phase was dried and concentrated, and the resulting crude product was purified by preparative scale HPLC to obtain product 3-acryloyl-12-fluoro-11-(2-fluoro-6-hydroxyphenyl)-9-(2-isopropyl-4-methylpyridin-3-yl)-1,2,3,4,4a,5,7,9-octahydropyrazino[1',2':4,5][1,4]diaza[2,3-c][1,8]naphthyridin-6,8-dione (Z42, 27 mg, Y: 46%), which was faint yellow solid. $^1$H NMR (500 MHz, DMSO-d$_6$) δ 10.11 (s, 1H), 8.62 (s, 1H), 8.44 (d, J=4.6 Hz, 1H), 8.24 (s, 1H), 7.23-7.28 (m, 2H), 6.85-7.00 (m, 1H), 6.78-6.62 (m, 2H), 6.24 (s, 1H), 5.77 (d, J=9.9 Hz, 1H), 3.93 (s, 7H), 3.09 (s, 1H), 2.83 (s, 1H), 2.60 (s, 1H), 1.86 (d, J=23.4 Hz, 3H), 1.06 (t, J=7.1 Hz, 3H), 0.91 (dd, J=9.7, 6.8 Hz, 3H). ES-API: [M+H]$^+$=601.2.

Example 43 Preparation of Compound Z43

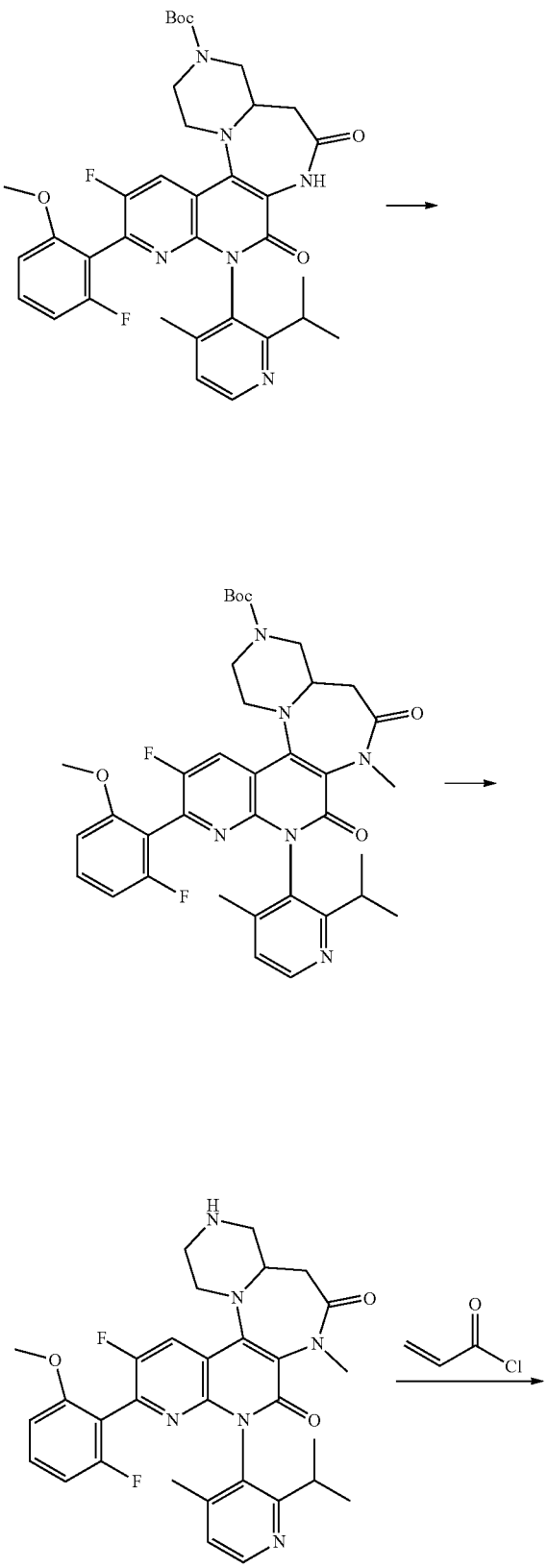

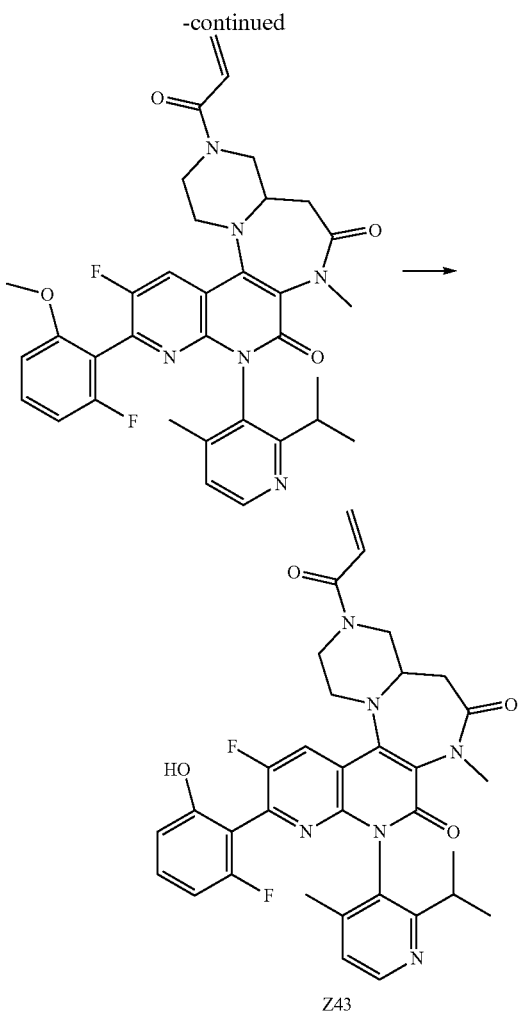

Z43

Step 1: under the condition of an ice water bath, sodium hydride (91 mg, 2.27 mmol) was added to a solution of tert-butyl 12-fluoro-11-(2-fluoro-6-methoxyphenyl)-9-(2-isopropyl-4-methylpyridin-3-yl)-6,8-dioxo-1,2,4a,5,6,7,8,9-octahydropyrazino[1', 2': 4,5][1,4]diaza[2,3-c][1,8]naphthyridin-3(4H)-carboxylate (300 mg, 0.45 mmol) in tetrahydrofuran (10 mL), and stirred for 30 minutes. Iodomethane (650 mg, 4.54 mmol) was then added to the resulting reaction liquid, and stirred at room temperature overnight. The reaction liquid was quenched by using saturated ammonium chloride solution (30 mL), and extracted with EtOAc (30 mL*3). The resulting organic phase was dried, concentrated, and purified by flash column chromatography on silica gel (0-10% MeOH/DCM) to obtain product tert-butyl 12-fluoro-11-(2-fluoro-6-methoxyphenyl)-9-(2-isopropyl-4-methylpyridin-3-yl)-7-methyl-6,8-dioxo-1,2,4a,5,6,7,8,9-octahydropyrazino[1',2':4,5][1,4]diaza[2,3-c][1,8]naphthyridin-3(4H)-carboxylate (190 mg, Y: 62%), which was yellow solid. ES-API: [M+H]$^+$=675.3.

Step 2: the tert-butyl 12-fluoro-11-(2-fluoro-6-methoxyphenyl)-9-(2-isopropyl-4-methylpyridin-3-yl)-7-methyl-6,8-dioxo-1,2,4a,5,6,7,8,9-octahydropyrazino[1',2':4,5][1,4]diaza[2,3-c][1,8]naphthyridin-3(4H)-carboxylate (188 mg, 0.28 mmol) was dissolved in DCM (8 mL), and added with TFA (2 mL). After stirring at room temperature for 2 hours, the resulting reaction liquid was concentrated to obtain crude product 12-fluoro-11-(2-fluoro-6-methoxyphenyl)-9-(2-isopropyl-4-methylpyridin-3-yl)-7-methyl-1,2,3,4,4a,5,7,9-octahydropyrazino[1',2':4,5][1,4]diaza[2,3-c][1,8]naphthyridin-6,8-dione (160 mg), which was directly used in next step. ES-API: [M+H]$^+$=575.2.

Step 3: the 12-fluoro-11-(2-fluoro-6-methoxyphenyl)-9-(2-isopropyl-4-methylpyridin-3-yl)-7-methyl-1,2,3,4,4a,5,7,9-octahydropyrazino[1',2':4,5][1,4]diaza[2,3-c][1,8]naphthyridin-6,8-dione (160 mg, 0.28 mmol) was dissolved in DCM (4 mL), and added with N,N-diisopropylethylamine (108 mg, 0.84 mmol). The resulting reaction liquid was cooled to 0° C., and added dropwise with acryloyl chloride (50 mg, 0.56 mmol). The reaction liquid was stirred at 0° C. for 5 minutes, and concentrated. The resulting crude product was purified by flash column chromatography on silica gel (0-80% EtOAc/PE) to obtain product 3-acryloyl-12-fluoro-11-(2-fluoro-6-methoxyphenyl)-9-(2-isopropyl-4-methylpyridin-3-yl)-7-methyl-1,2,3,4,4a,5,7,9-octahydropyrazino[1',2':4,5][1,4]diaza[2,3-c][1,8]naphthyridin-6,8-dione (170 mg, Y: 97%), which was faint yellow solid. ES-API: [M+H]$^+$=629.2.

Step 4: 3-acryloyl-12-fluoro-11-(2-fluoro-6-methoxyphenyl)-9-(2-isopropyl-4-methylpyridin-3-yl)-7-methyl-1,2,3,4,4a,5,7,9-octahydropyrazino[1',2':4,5][1,4]diaza[2,3-c][1,8]naphthyridin-6,8-dione (170 mg, 0.27 mmol) was dissolved in DCM (3 mL). The resulting solution was cooled to 0° C., added dropwise with a solution (3 mL) of 17% boron tribromide in DCM, and stirred at room temperature for 2 hours. The resulting reaction liquid was poured into 40 mL of saturated solution of sodium bicarbonate and extracted with 25 mL of DCM twice. The resulting organic phase was dried and concentrated, and the resulting crude product was purified by preparative scale HPLC to obtain product 3-acryloyl-12-fluoro-11-(2-fluoro-6-hydroxyphenyl)-9-(2-isopropyl-4-methylpyridin-3-yl)-7-methyl-1,2,3,4,4a,5,7,9-octahydropyrazino[1',2':4,5][1,4]diaza[2,3-c][1,8]naphthyridin-6,8-dione (Z43, 95 mg, Y: 57%), which was faint yellow solid. $^1$H NMR (500 MHz, DMSO-d$_6$) δ 8.47 (d, J=9.8 Hz, 1H), 8.42 (dd, J=4.8, 2.1 Hz, 1H), 7.26-7.19 (m, 2H), 7.04-6.82 (m, 1H), 6.72-6.67 (m, 1H), 6.66-6.62 (m, 1H), 6.19 (d, J=16.5 Hz, 1H), 5.76 (d, J=10.4 Hz, 1H), 4.60-4.45 (m, 1H), 4.36-4.10 (m, 1H), 4.02 (s, 1H), 3.93-3.78 (m, 1H), 3.65 (dd, J=21.9, 10.6 Hz, 1H), 3.29-3.22 (m, 2H), 3.09 (s, 3H), 3.17-2.99 (m, 1H), 2.76-2.63 (m, 2H), 2.37-2.28 (m, 1H), 1.90 (d, J=47.0 Hz, 3H), 1.05 (dd, J=31.1, 6.7 Hz, 3H), 0.93 (dd, J=42.5, 6.6 Hz, 3H). ES-API: [M+H]$^+$=615.2.

Example 44 Preparation of Compounds Z44a and Z44

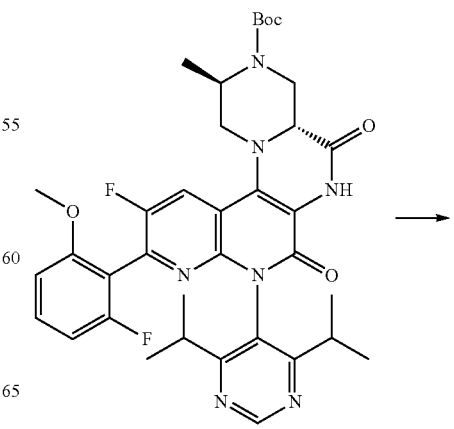

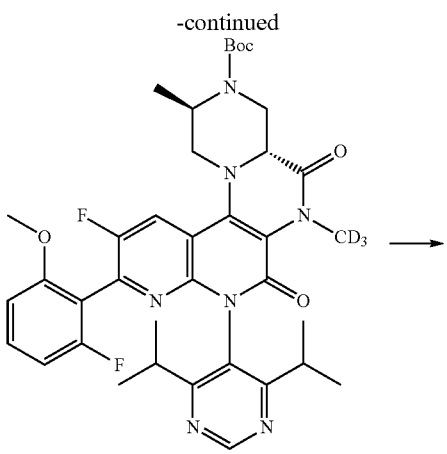

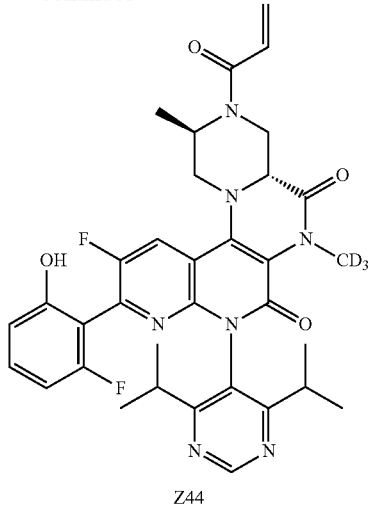

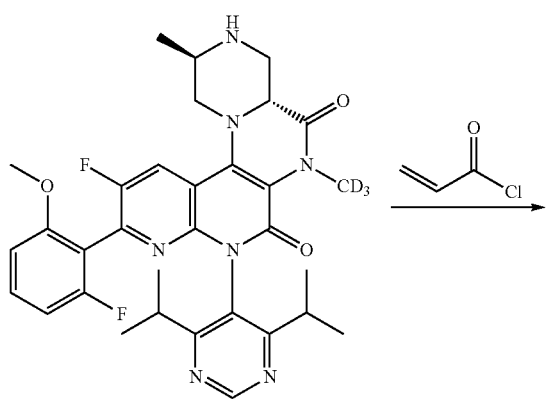

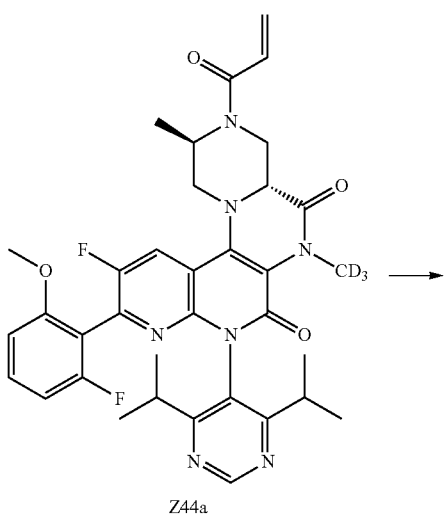

Z44a

Step 1: tert-butyl (2R,4aR)-8-(4,6-diisopropylpyrimidin-5-yl)-11-fluoro-10-(2-fluoro-6-methoxyphenyl)-2-methyl-5,7-dioxo-1,2,4,4a,5,6,7,8-octahydro-3H-pyrazino[1',2':4,5]pyrazino[2,3-c][1,8]naphthyridin-3-carboxylate (350 mg, 0.51 mmol), acetone (5 mL), anhydrous potassium carbonate (210 mg, 1.52 mmol), and deuteroiodomethane (735 mg, 5.07 mmol) were orderly added to a 15 mL sealing tube. The sealing tube was sealed, and the resulting mixture was stirred at 50° C. overnight. The resulting reaction liquid was filtered and concentrated to obtain product tert-butyl (2R, 4aR)-8-(4,6-diisopropylpyrimidin-5-yl)-11-fluoro-10-(2-fluoro-6-methoxyphenyl)-2-methyl-6-(methyl-d3)-5,7-dioxo-1,2,4,4a,5,6,7,8-octahydro-3H-pyrazino[1',2':4,5]pyrazino[2,3-c][1,8]naphthyridin-3-carboxylate (250 mg), which was yellow solid. ES-API: [M+H]$^+$=707.3.

Step 2: the tert-butyl (2R,4aR)-8-(4,6-diisopropylpyrimidin-5-yl)-11-fluoro-10-(2-fluoro-6-methoxyphenyl)-2-methyl-6-(methyl-d3)-5,7-dioxo-1,2,4,4a,5,6,7,8-octahydro-3H-pyrazino[1',2':4,5]pyrazino[2,3-c][1,8]naphthyridin-3-carboxylate (250 mg, 0.35 mmol) was dissolved in DCM (8 mL), and added with TFA (2 mL). After stirring at room temperature for 2 hours, the resulting reaction liquid was concentrated to obtain crude product (2R,4aR)-8-(4,6-diisopropylpyrimidin-5-yl)-11-fluoro-10-(2-fluoro-6-methoxyphenyl)-2-methyl-6-(methyl-d3)-2,3,4,4a,6,8-hexahydro-1H-pyrazino[1',2':4,5]pyrazino[2,3-c][1,8]naphthyridin-5,7-dione (215 mg), which was directly used in next step. ES-API: [M+H]$^+$=607.3.

Step 3: the (2R,4aR)-8-(4,6-diisopropylpyrimidin-5-yl)-11-fluoro-10-(2-fluoro-6-methoxyphenyl)-2-methyl-6-(methyl-d3)-2,3,4,4a,6,8-hexahydro-1H-pyrazino[1',2':4,5]pyrazino[2,3-c][1,8]naphthyridin-5,7-dione (215 mg, 0.35 mmol) was dissolved in DCM (3 mL), and added with N,N-diisopropylethylamine (226 mg, 1.75 mmol). The resulting reaction liquid was cooled to 0° C., and added dropwise with acryloyl chloride (63 mg, 0.70 mmol). The reaction liquid was stirred at 0° C. for 10 minutes, and concentrated. The resulting crude product was purified by flash column chromatography on silica gel (EtOAc/PE: 0-80%) to obtain product Z44a (122 mg, P: 100%, Y: 52%), which was faint yellow solid. ES-API: [M+H]$^+$=661.3.

Step 4: (2R,4aR)-3-acryloyl-8-(4,6-diisopropylpyrimidin-5-yl)-11-fluoro-10-(2-fluoro-6-methoxyphenyl)-2-methyl-6-(methyl-d3)-2,3,4,4a,6,8-hexahydro-1H-pyrazino[1',2':4,5]pyrazino[2,3-c][1,8]naphthyridin-5,7-dione (Z44a, 120 mg, 0.18 mmol) was dissolved in DCM (3 mL). The resulting solution was cooled to 0° C., added dropwise with a solution (3 mL) of 17% boron tribromide in DCM, and stirred at room temperature overnight. The resulting reaction liquid was poured into 40 mL of saturated solution of sodium bicarbonate and extracted with 25 mL of DCM twice. The resulting organic phase was dried and concentrated, and the resulting crude product was purified by preparative scale HPLC to obtain product (2R,4aR)-3-acryloyl-8-(4,6-diisopropylpyrimidin-5-yl)-11-fluoro-10-(2-fluoro-6-hydroxyphenyl)-2-methyl-6-(methyl-d3)-2,3,4,4a,6,8-hexahydro-1H-pyrazino[1',2':4,5]pyrazino[2,3-c][1,8]naphthyridin-5,7-dione (Z44, 69 mg, P: 100%, Y: 59%), which was faint yellow solid. $^1$H NMR (500 MHz, DMSO-$d_6$) δ 9.12 (s, 1H), 8.00 (dd, J=14.2, 8.7 Hz, 1H), 7.24 (dd, J=15.3, 7.8 Hz, 1H), 6.95 (ddd, J=75.8, 16.7, 10.5 Hz, 1H), 6.71 (s, 1H), 6.65 (t, J=8.5 Hz, 1H), 6.24-6.01 (m, 1H), 5.82-5.66 (m, 1H), 5.04-4.60 (m, 1H), 4.77-4.42 (m, 1H), 4.02 (dd, J=28.4, 3.7 Hz, 1H), 3.74 (dd, J=14.1, 4.1 Hz, 1H), 3.44 (m, 1H), 3.25 (m, 1H), 2.99-2.74 (m, 2H), 2.48-2.44 (m, 1H), 1.55 (dd, J=18.5, 6.7 Hz, 3H), 1.11 (d, J=6.7 Hz, 3H), 1.04 (d, J=6.7 Hz, 3H), 1.00 (d, J=6.6 Hz, 3H), 0.84 (d, J=6.7 Hz, 3H). ES-API: [M+H]$^+$=647.3.

Example 45 Preparation of Compound Z45

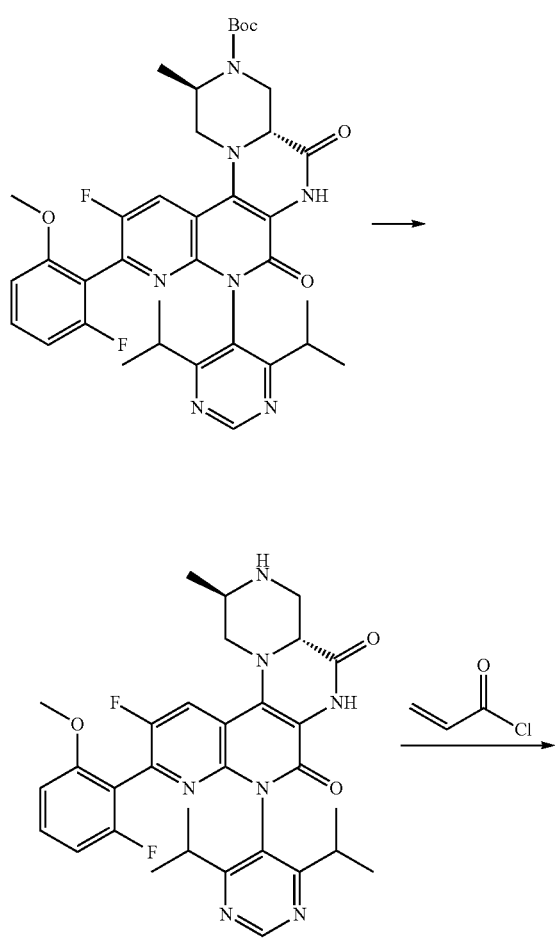

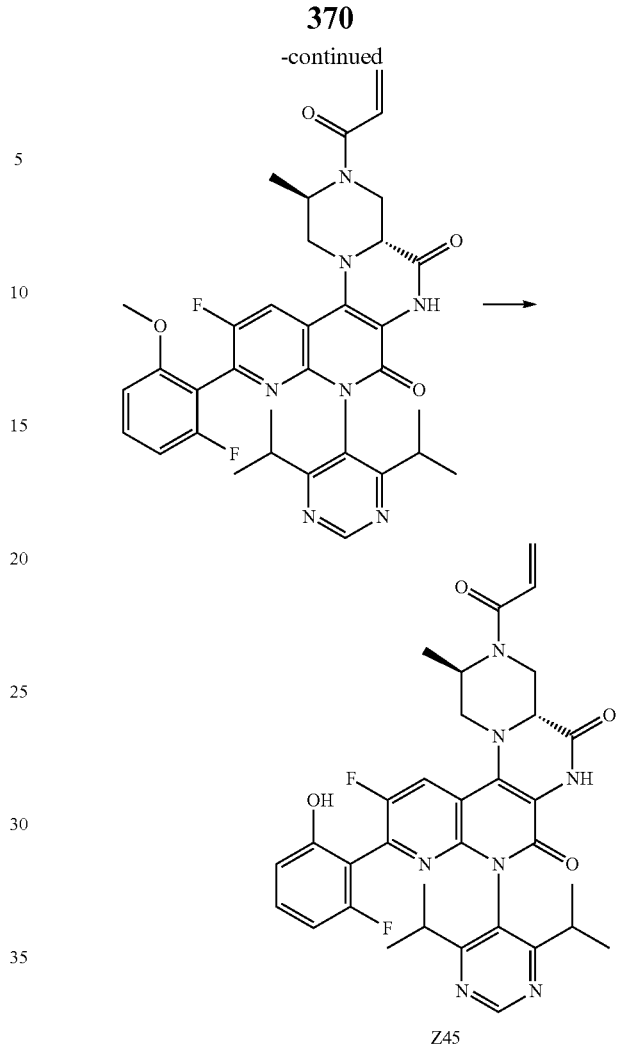

Z45

Step 1: tert-butyl (2R,4aR)-8-(4,6-diisopropylpyrimidin-5-yl)-11-fluoro-10-(2-fluoro-6-methoxyphenyl)-2-methyl-5,7-dioxo-1,2,4,4a,5,6,7,8-octahydro-3H-pyrazino[1',2':4,5]pyrazino[2,3-c][1,8]naphthyridin-3-carboxylate (50 mg, 0.07 mmol) was dissolved in DCM (4 mL), and added with TFA (1 mL). After stirring at room temperature for 2 hours, the resulting reaction liquid was concentrated to obtain crude product (2R,4aR)-8-(4,6-diisopropylpyrimidin-5-yl)-11-fluoro-10-(2-fluoro-6-methoxyphenyl)-2-methyl-2,3,4,4a,6,8-hexahydro-1H-pyrazino[1',2':4,5]pyrazino[2,3-c][1,8]naphthyridin-5,7-dione (43 mg), which was directly used in next step. ES-API: [M+H]$^+$=590.2.

Step 2: the (2R,4aR)-8-(4,6-diisopropylpyrimidin-5-yl)-1-fluoro-10-(2-fluoro-6-methoxyphenyl)-2-methyl-2,3,4,4a,6,8-hexahydro-1H-pyrazino[1',2':4,5]pyrazino[2,3-c][1,8]naphthyridin-5,7-dione (43 mg, 0.07 mmol) was dissolved in DCM (2 mL), and added with N,N-diisopropylethylamine (45 mg, 0.35 mmol). The resulting reaction liquid was cooled to 0° C., and added dropwise with acryloyl chloride (13 mg, 0.14 mmol). The reaction liquid was stirred at 0° C. for 5 minutes, and concentrated. The resulting crude product was purified by flash column chromatography on silica gel (EtOAc/PE: 0-80%) to obtain product (2R,4aR)-3-acryloyl-8-(4,6-diisopropylpyrimidin-5-yl)-11-fluoro-10-(2-fluoro-6-methoxyphenyl)-2-methyl-2,3,4,4a,6,8-hexahydro-1H-pyrazino[1',2':4,5]pyrazino[2,3-c][1,8]naphthyridin-5,7-dione (26 mg, Y: 56%), which was faint yellow solid. ES-API: [M+H]$^+$=644.2.

Step 3: the (2R,4aR)-3-acryloyl-8-(4,6-diisopropylpyrimidin-5-yl)-11-fluoro-10-(2-fluoro-6-methoxyphenyl)-2-methyl-2,3,4,4a,6,8-hexahydro-1H-pyrazino[1',2':4,5]pyrazino[2,3-c][1,8]naphthyridin-5,7-dione (26 mg, 0.04 mmol) was dissolved in DCM (0.5 mL). The resulting solution was cooled to 0° C., added dropwise with a solution (0.5 mL) of 17% boron tribromide in DCM, and stirred at room temperature overnight. The resulting reaction liquid was poured into 4 mL of saturated solution of sodium bicarbonate and extracted with 3 mL of DCM twice. The resulting organic phase was dried and concentrated, and the resulting crude product was purified by preparative scale HPLC to obtain product (2R,4aR)-3-acryloyl-8-(4,6-diisopropylpyrimidin-5-yl)-11-fluoro-10-(2-fluoro-6-hydroxyphenyl)-2-methyl-2,3,4,4a,6,8-hexahydro-1H-pyrazino[1',2':4,5]pyrazino[2,3-c][1,8]naphthyridin-5,7-dione (Z45, 8 mg, Y: 31%), which was faint yellow solid. ES-API: [M+H]$^+$=630.2.

Example 46 Preparation of Compound Z46

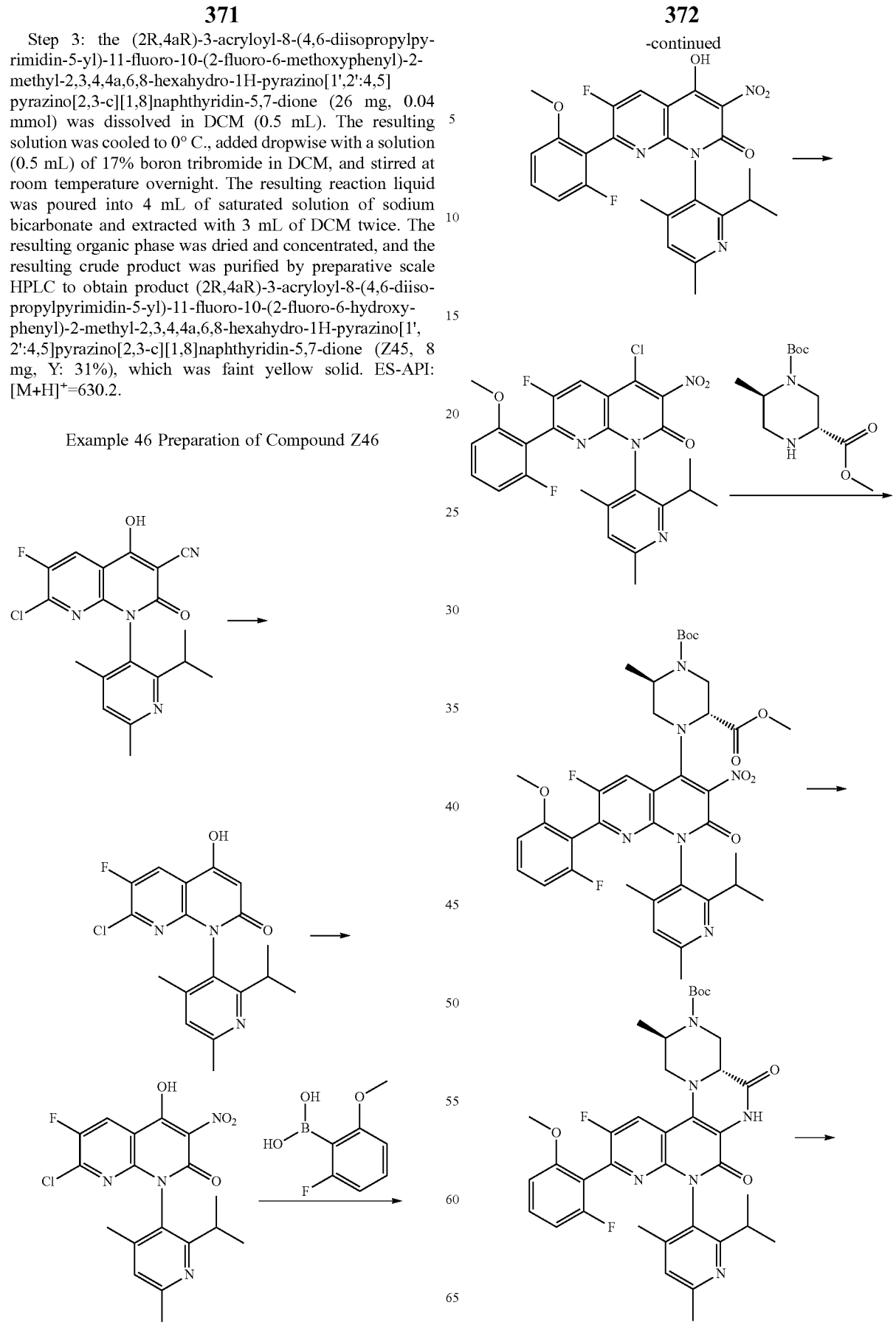

373

-continued

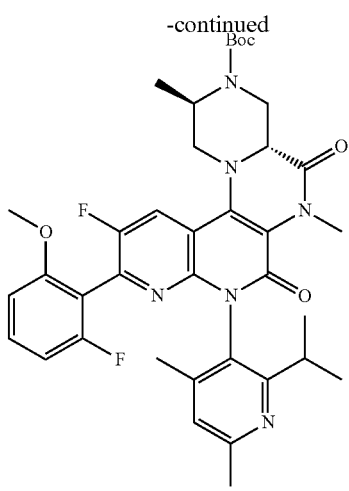

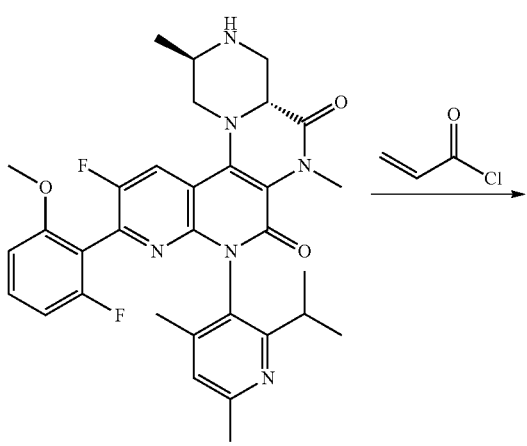

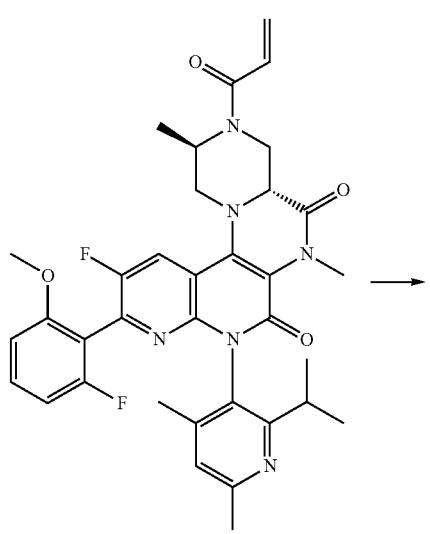

374

-continued

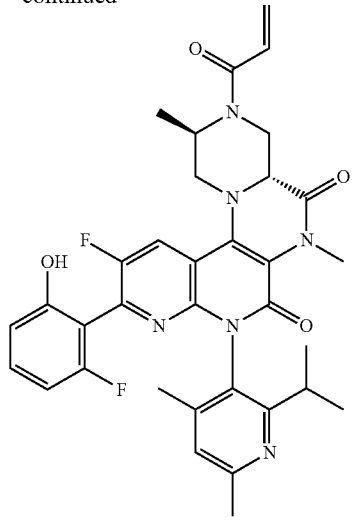

Z46

Step 1: 7-chloro-6-fluoro-4-hydroxy-1-(2-isopropyl-4,6-dimethylpyridin-3-yl)-2-oxo-1,2-dihydro-1,8-naphthyridin-3-nitrile (8 g, 20.68 mmol) was suspended in 1, 4-dioxane (40 mL), and slowly added with a mixed liquid of concentrated sulfuric acid (40 mL) and water (40 mL). The resulting mixture was stirred at 120° C. overnight to react. Cooled reaction liquid was poured into 150 mL of ice water, mixed with aqueous solution of potassium hydroxide to adjust the pH to 6, and extracted with EtOAc. The resulting organic phase was dried and concentrated to obtain product 7-chloro-6-fluoro-4-hydroxy-1-(2-isopropyl-4,6-dimethylpyridin-3-yl)-1,8-naphthyridin-2(1H)-one (7.6 g, Y: 96%), which was faint yellow solid. ES-API: [M+H]$^+$=362.2.

Step 2: the 7-chloro-6-fluoro-4-hydroxy-1-(2-isopropyl-4,6-dimethylpyridin-3-yl)-1,8-naphthyridin-2(1H)-one (7.6 g, 21.01 mmol) was dissolved in acetic acid (26 mL), orderly added with sodium nitrite (145 mg, 2.10 mmol) and concentrated nitric acid (3.97 g, 63.01 mmol), and stirred at room temperature for 20 minutes. The resulting reaction liquid was poured into 20 mL of water. Yellow solid was precipitated and filtered. The filter cake was washed with 6 mL of water and dried in vacuum to obtain product 7-chloro-6-fluoro-4-hydroxy-1-(2-isopropyl-4,6-dimethylpyridin-3-yl)-3-nitro-1,8-naphthyridin-2(1H)-one (4 g, Y: 47%), which was faint yellow solid. ES-API: [M+H]$^+$=407.1.

Step 3: a mixed solution of 7-chloro-6-fluoro-4-hydroxy-1-(2-isopropyl-4,6-dimethylpyridin-3-yl)-3-nitro-1,8-naphthyridin-2(1H)-one (4 g, 9.83 mmol), (2-fluoro-6-methoxyphenyl)boric acid (8.36 g, 49.16 mmol), chloro(2-dicyclohexylphosphino-2',6'-dimethoxy-1,1'-biphenyl)(2'-amino-1,1'-biphen-2-yl)palladium (II) (705 mg, 0.98 mmol), 2-dicyclohexylphosphino-2',6'-dimethoxybiphenyl (402 mg, 0.98 mmol), and potassium phosphate (6.26 g, 29.50 mmol) in 8 mL of water and 40 mL of dioxane was replaced with nitrogen for 3 times and allowed to react at 100° C. for 2 hours. The resulting reaction liquid was poured into 50 mL of water, and washed with methyl tert-butyl ether (30 mL*2). The water phase was mixed with 3.0 M diluted hydrochloric acid to adjust the pH to 6.0, and then extracted with EtOAc (30 mL*2). The resulting organic phase was dried and concentrated to obtain crude product 6-fluoro-7-(2-fluoro-6-methoxyphenyl)-4-hydroxy-1-(2-isopropyl-4,6- dimethylpyridin-3-yl)-3-nitro-1,8-naphthyridin-2(1H)-one (4 g, Y: 82%). ES-API: [M+H]⁺=497.2.

Step 4: phosphorus oxychloride (6.18 g, 40.30 mmol) and N,N-diisopropylethylamine (8.33 g, 68.48 mmol) were orderly added to a solution of the 6-fluoro-7-(2-fluoro-6-methoxyphenyl)-4-hydroxy-1-(2-isopropyl-4,6-dimethylpyridin-3-yl)-3-nitro-1,8-naphthyridin-2(1H)-one (4 g, 8.06 mmol) in ACN (60 mL). The resulting mixture was stirred at 80° C. temperature for 1 hour to react. The resulting reaction liquid was concentrated, added with 150 mL of EtOAc, and washed orderly with 80 mL of saturated sodium bicarbonate twice and then with 80 mL of water and 80 mL of saturated salt solution. After the resulting organic phase was dried and concentrated, the resulting crude product was purified by flash column chromatography on silica gel (EtOAc/PE: 0-50%) to obtain product 4-chloro-6-fluoro-7-(2-fluoro-6-methoxyphenyl)-1-(2-isopropyl-4,6-dimethylpyridin-3-yl)-3-nitro-1,8-naphthyridin-2(1H)-one (3.5 g, Y: 85%), which was faint yellow solid. ES-API: [M+H]⁺=515.2.

Step 5: the 4-chloro-6-fluoro-7-(2-fluoro-6-methoxyphenyl)-1-(2-isopropyl-4,6-dimethylpyridin-3-yl)-3-nitro-1,8-naphthyridin-2(1H)-one (1 g, 1.94 mmol) was dissolved in N,N-dimethylacetamide (10 mL), orderly added with 1-(tert-butyl)3-methyl(3R,6R)-6-methylpiperazin-1,3-dicarboxylic acid (600 mg, 2.33 mmol) and N,N-diisopropylethylamine (750 mg, 5.82 mmol), and stirred at 120° C. for 2 hours. Cooled reaction liquid was added with 100 mL of EtOAc, washed with 50 mL of sodium bicarbonate twice, with 50 mL of dilute brine twice, with 50 mL of water once and with 50 mL of saturated salt solution once, dried and concentrated to obtain crude product 1-(tert-butyl)3-methyl(3R,6R)-4-(6-fluoro-7-(2-fluoro-6-methoxyphenyl)-1-(2-isopropyl-4,6-dimethylpyridin-3-yl)-3-nitro-2-oxo-1,2-dihydro-1,8-naphthyridin-4-yl)-6-methylpiperazin-1,3-dicarboxylate (1.6 g). ES-API: [M+H]⁺=737.2.

Step 6: the 1-(tert-butyl)3-methyl(3R,6R)-4-(6-fluoro-7-(2-fluoro-6-methoxyphenyl)-1-(2-isopropyl-4,6-dimethylpyridin-3-yl)-3-nitro-2-oxo-1,2-dihydro-1,8-naphthyridin-4-yl)-6-methylpiperazin-1,3-dicarboxylate (1.6 g, 2.17 mmol) was dissolved in acetic acid (16 mL), added with iron powder (425 mg, 7.60 mmol), and stirred at 80° C. for 1 hour. The resulting reaction liquid was concentrated, added with 50 mL of EtOAc, and mixed with saturated sodium bicarbonate solution to adjust the pH to 6. The resulting suspension was filtered by diatomite. The filter cake was washed with EtOAc. The resulting organic phase was separated, washed orderly with 25 mL of saturated sodium bicarbonate and 25 mL of saturated salt solution, dried and concentrated to obtain crude product tert-butyl (2R,4aR)-11-fluoro-10-(2-fluoro-6-methoxyphenyl)-8-(2-isopropyl-4,6-dimethylpyridin-3-yl)-2-methyl-5,7-dioxo-1,2,4,4a,5,6,7,8-octahydro-3H-pyrazino[1',2':4,5]pyrazino[2,3-c][1,8]naphthyridin-3-carboxylate (1.4 g), which was yellow solid. ES-API: [M+H]⁺=675.3.

Step 7: the tert-butyl (2R,4aR)-11-fluoro-10-(2-fluoro-6-methoxyphenyl)-8-(2-isopropyl-4,6-dimethylpyridin-3-yl)-2-methyl-5,7-dioxo-1,2,4,4a,5,6,7,8-octahydro-3H-pyrazino[1',2':4,5]pyrazino[2,3-c][1,8]naphthyridin-3-carboxylate (1.4 g, 2.07 mmol), acetone (15 mL), anhydrous potassium carbonate (860 mg, 6.21 mmol), and iodomethane (2.95 g, 20.7 mmol) were orderly added to a 50 mL sealing tube. The sealing tube was sealed, and the resulting mixture was stirred at 50° C. to react overnight. The resulting reaction liquid was filtered, concentrated, and purified by flash column chromatography on silica gel (EtOAc/PE: 0-80%) to obtain product tert-butyl (2R,4aR)-11-fluoro-10-(2-fluoro-6-methoxyphenyl)-8-(2-isopropyl-4,6-dimethylpyridin-3-yl)-2,6-dimethyl-5, 7-dioxo-1,2,4,4a,5,6,7,8-octahydro-3H-pyrazino[1',2':4,5]pyrazino[2,3-c][1,8]naphthyridin-3-carboxylate (340 mg, Y: 24%), which was yellow solid. ES-API: [M+H]⁺=706.3.

Step 8: the tert-butyl (2R,4aR)-11-fluoro-10-(2-fluoro-6-methoxyphenyl)-8-(2-isopropyl-4,6-dimethylpyridin-3-yl)-2,6-dimethyl-5, 7-dioxo-1,2,4,4a,5,6,7,8-octahydro-3H-pyrazino[1',2':4,5]pyrazino[2,3-c][1,8]naphthyridin-3-carboxylate (340 mg, 0.49 mmol) was dissolved in DCM (4 mL), and added with TFA (1 mL). After stirring at room temperature for 2 hours, the resulting reaction liquid was concentrated to obtain crude product (2R,4aR)-11-fluoro-10-(2-fluoro-6-methoxyphenyl)-8-(2-isopropyl-4,6-dimethylpyridin-3-yl)-2,6-dimethyl-2,3, 4,4a,6,8-hexahydro-1H-pyrazino[1',2':4,5]pyrazino[2,3-c][1,8]naphthyridin-5,7-dione (317 mg), which was directly used in next step. ES-API: [M+H]⁺=589.3.

Step 9: the (2R,4aR)-11-fluoro-10-(2-fluoro-6-methoxyphenyl)-8-(2-isopropyl-4,6-dimethylpyridin-3-yl)-2,6-dimethyl-2,3,4,4a,6,8-hexahydro-1H-pyrazino[1',2':4,5]pyrazino[2,3-c][1,8]naphthyridin-5,7-dione (317 mg, 0.49 mmol) was dissolved in DCM (5 mL), and added with N,N-diisopropylethylamine (320 mg, 2.45 mmol). The resulting reaction liquid was cooled to 0° C., and added dropwise with acryloyl chloride (89 mg, 0.99 mmol). The reaction liquid was stirred at 0° C. for 5 minutes, and concentrated. The resulting crude product was purified by flash column chromatography on silica gel (EtOAc/PE: 0-80%) to obtain product (2R,4aR)-3-acryloyl-11-fluoro-10-(2-fluoro-6-methoxyphenyl)-8-(2-isopropyl-4,6-dimethylpyridin-3-yl)-2,6-dimethyl-2,3,4,4a,6,8-hexahydro-1H-pyrazino[1',2':4,5]pyrazino[2,3-c][1,8]naphthyridin-5,7-dione (280 mg, Y: 81%), which was faint yellow solid. ES-API: [M+H]⁺=643.3.

Step 10: the (2R,4aR)-3-acryloyl-11-fluoro-10-(2-fluoro-6-methoxyphenyl)-8-(2-isopropyl-4,6-dimethylpyridin-3-yl)-2,6-dimethyl-2,3,4,4a,6,8-hexahydro-1H-pyrazino[1',2':4,5]pyrazino[2,3-c][1,8]naphthyridin-5,7-dione (280 mg, 0.44 mmol) was dissolved in DCM (3 mL). The resulting solution was cooled to 0° C., added dropwise with a solution (3 mL) of 17% boron tribromide in DCM, and stirred at room temperature for 2 hours. The resulting reaction liquid was poured into 40 mL of saturated solution of sodium bicarbonate and extracted with 25 mL of DCM twice. The resulting organic phase was dried and concentrated, and the resulting crude product was purified by preparative scale HPLC to obtain product (2R,4aR)-3-acryloyl-11-fluoro-10-(2-fluoro-6-methoxyphenyl)-8-(2-isopropyl-4,6-dimethylpyridin-3-yl)-2,6-dimethyl-2,3,4,4a,6,8-hexahydro-1H-pyrazino[1',2':4,5]pyrazino[2,3-c][1,8]naphthyridin-5,7-dione (Z46, 108 mg, Y: 40%), which was faint yellow solid. $^1$H NMR (500 MHz, DMSO-$d_6$) δ 10.14 (s, 1H), 7.99 (t, J=10.4 Hz, 1H), 7.27 (dd, J=15.5, 7.7 Hz, 1H), 7.13-6.83 (m, 2H), 6.78-6.65 (m, 2H), 6.16 (t, J=13.5 Hz, 1H), 5.81-5.69 (m, 1H), 5.08-4.72 (m, 1H), 4.54 (t, J=51.7 Hz, 1H), 3.99 (t, J=29.0 Hz, 1H), 3.73 (d, J=10.5 Hz, 1H), 3.44-3.23 (m, 1H), 3.35 (s, 3H), 2.95-2.80 (m, 1H), 2.75-2.68 (m, 1H), 2.45 (d, J=1.9 Hz, 3H), 2.41-2.37 (m, 1H), 1.84 (d, J=96 Hz, 1H), 1.55 (dd, J=16.5, 5.4 Hz, 3H), 1.05 (dd, J=39.3, 6.7 Hz, 3H), 0.90 (dd, J=65.2, 6.6 Hz, 3H). ES-API: [M+H]⁺=629.2.

Example 47 Preparation of Compound Z47
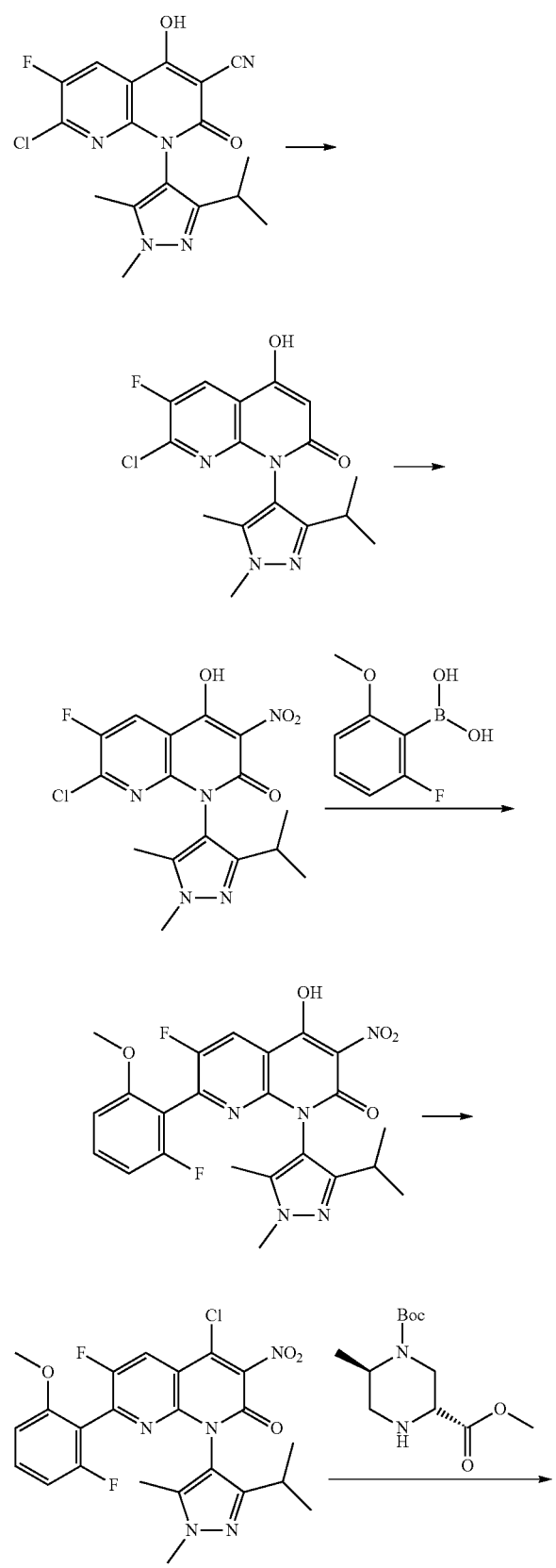
-continued
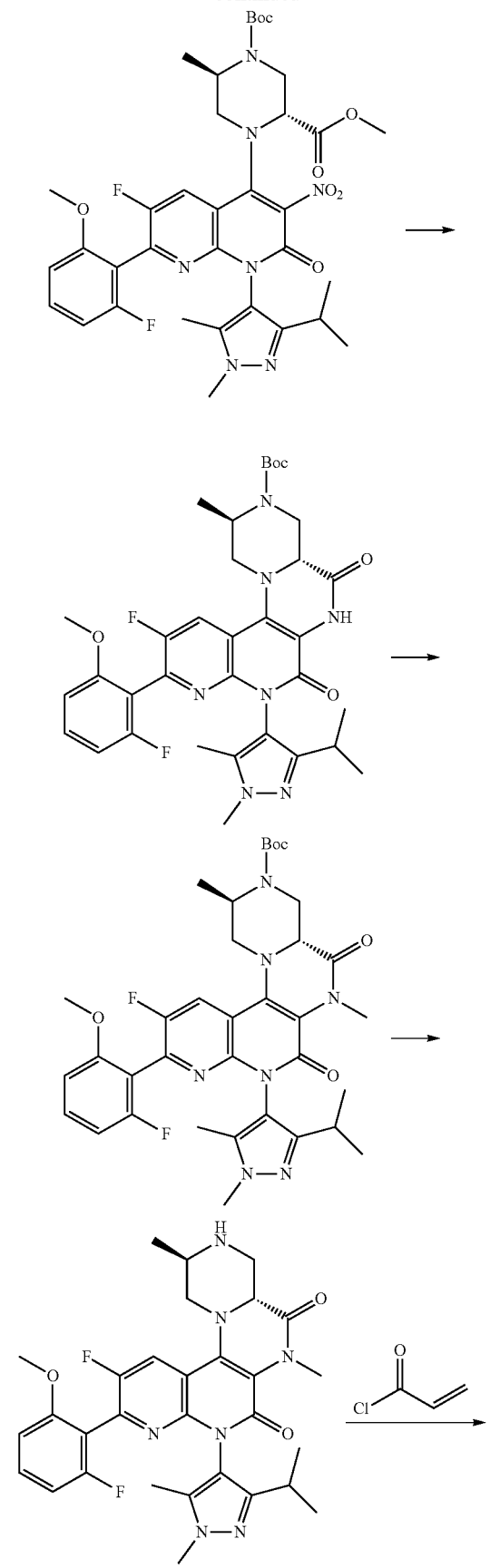

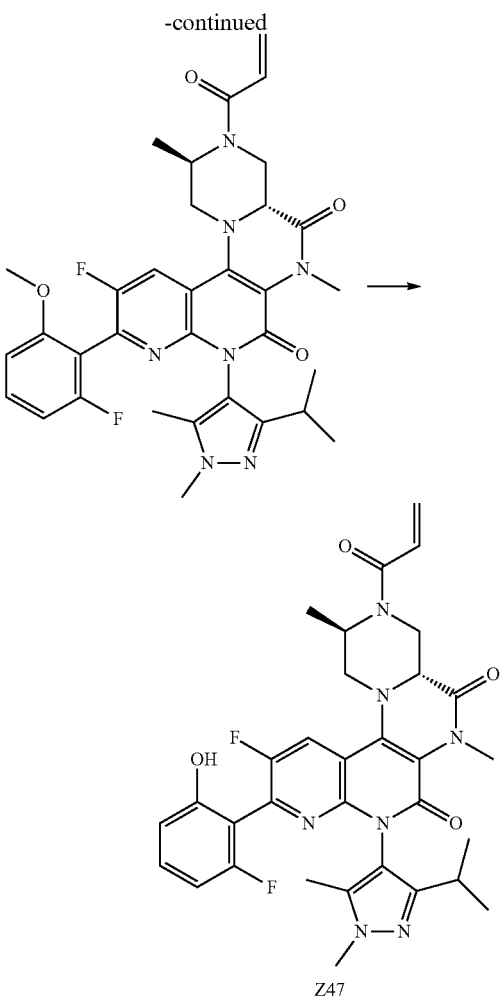

Step 1: 7-chloro-6-fluoro-4-hydroxy-1-(3-isopropyl-1,5-dimethyl-1H-pyrazol-4-yl)-2-oxo-1,2-dihydro-1,8-naphthyridin-3-nitrile (3.5 g, 9.3 mmol) was suspended in 1, 4-dioxane (40 mL), and slowly added with a mixed liquid of concentrated sulfuric acid (40 mL) and water (40 mL). The resulting mixture was stirred at 120° C. for 20 hours to react. Cooled reaction liquid was poured into 150 mL of ice water, mixed with 4.0 M aqueous potassium hydroxide solution solution to adjust the pH to 3. The precipitated solid was filtered. The filtrate was extracted with 200 mL of DCM. The resulting solid was dissolved in a mixed liquid of DCM/MeOH=10:1, and filtered. The resulting combined organic phase was dried and concentrated to obtain product 7-chloro-6-fluoro-4-hydroxy-1-(3-isopropyl-1,5-dimethyl-1H-pyrazol-4-yl)-1,8-naphthyridin-2(1H)-one (2.3 g, Y: 71.6%), which was light brown solid. ES-API: [M+H]$^+$= 351.1.

Step 2: the 7-chloro-6-fluoro-4-hydroxy-1-(3-isopropyl-1,5-dimethyl-1H-pyrazol-4-yl)-1,8-naphthyridin-2(1H)-one (2.3 g, 6.5 mmol) was dissolved in acetic acid (8 mL), orderly added with sodium nitrite (45 mg, 0.65 mmol) and concentrated nitric acid (1.5 mL, 19.5 mmol), and stirred at room temperature for 1 hour to react. The resulting reaction liquid was poured into 30 mL of ice water. The precipitated solid was filtered. The filter cake was washed with 6 mL of water and dried in vacuum to obtain product 7-chloro-6-fluoro-4-hydroxy-1-(3-isopropyl-1,5-dimethyl-1H-pyrazol-4-yl)-3-nitro-1,8-naphthyridin-2(1H)-one (1.5 g, Y: 60%), which was faint yellow solid. ES-API: [M+H]$^+$=396.1.

Step 3: the 7-chloro-6-fluoro-4-hydroxy-1-(3-isopropyl-1,5-dimethyl-1H-pyrazol-4-yl)-3-nitro-1,8-naphthyridin-2(1H)-one (1.5 g, 3.8 mmol), (2-fluoro-6-methoxyphenyl) boric acid (0.96 g, 5.7 mmol), chloro(2-dicyclohexylphosphino-2',6'-dimethoxy-1,1'-biphenyl)[2-(2'-amino-1,1'-biphenyl)]palladium(II)-G2-Pd (273 mg, 0.38 mmol), 2-dicyclohexylphosphino-2',6'-dimethoxybiphenyl (155 mg, 0.38 mmol), potassium phosphate (2.41 g, 11.4 mmol), 4 mL of water, and 20 mL of dioxane were added to a 250 mL round-bottom flask. The resulting mixture was stirred at 85° C. for 4 hours to react under the protection of nitrogen. The resulting reaction liquid was concentrated, added with 100 mL of water, mixed with 3.0 M diluted hydrochloric acid to adjust the pH to 3.0, and extracted with 120 mL of DCM twice. The resulting organic phase was dried and concentrated to obtain product 6-fluoro-7-(2-fluoro-6-methoxyphenyl)-4-hydroxy-1-(3-isopropyl-1, 5-dimethyl-1H-pyrazol-4-yl)-3-nitro-1,8-naphthyridin-2 (1H)-one (2.4 g, crude), which was directly used in next step. ES-API: [M+H]$^+$=486.1.

Step 4: the 6-fluoro-7-(2-fluoro-6-methoxyphenyl)-4-hydroxy-1-(3-isopropyl-1,5-dimethyl-1H-pyrazol-4-yl)-3-nitro-1,8-naphthyridin-2(1H)-one (2.4 g, crude) was dissolved in ACN (50 mL), orderly added with phosphorus oxychloride (3.8 g, 24.7 mmol) and N,N-diisopropylethylamine (6.38 g, 49.4 mmol), and stirred at 85° C. for 1 hour to react. The resulting reaction liquid was concentrated, added with 150 mL of EtOAc, and washed orderly with 80 mL of water, with 80 mL saturated sodium bicarbonate solution twice and then with 80 mL of saturated salt solution. After the resulting organic phase was dried and concentrated, the resulting crude product was purified by flash column chromatography on silica gel (EtOAc/PE: 0-40%) to obtain product 4-chloro-6-fluoro-7-(2-fluoro-6-methoxyphenyl)-1-(3-isopropyl-1,5-dimethyl-1H-pyrazol-4-yl)-3-nitro-1,8-naphthyridin-2(1H)-one (0.29 g, Y: 10%), which was faint yellow solid. ES-API: [M+H]$^+$=504.1.

Step 5: the 4-chloro-6-fluoro-7-(2-fluoro-6-methoxyphenyl)-1-(3-isopropyl-1,5-dimethyl-1H-pyrazol-4-yl)-3-nitro-1,8-naphthyridin-2(1H)-one (290 mg, 0.57 mmol) was dissolved in N,N-dimethylacetamide (3 mL), orderly added with methyl (3R,6R)-1-N-BOC-6-methylpiperazin-3-formate (155 mg, 0.60 mmol) and N,N-diisopropylethylamine (116 mg, 0.90 mmol), and stirred at 120° C. for 2 hours to react. The resulting reaction liquid was added with 50 mL of EtOAc, washed with 25 mL of dilute brine for 4 times and then with 20 mL of saturated salt solution, dried and concentrated. The resulting crude product was purified by flash column chromatography on silica gel (EtOAc/PE: 0-50%) to obtain product 1-(tert-butyl)3-methyl(3R,6R)-4-(6-fluoro-7-(2-fluoro-6-methoxyphenyl)-1-(3-isopropyl-1, 5-dimethyl-1H-pyrazol-4-yl)-3-nitro-2-oxo-1,2-dihydro-1, 8-naphthyridin-4-yl)-6-methylpiperazin-1,3-dicarboxylic acid (280 mg, Y: 68.8%), which was orange solid. ES-API: [M+H]$^+$=726.3.

Step 6: the 1-(tert-butyl)3-methyl(3R,6R)-4-(6-fluoro-7-(2-fluoro-6-methoxyphenyl)-1-(3-isopropyl-1,5-dimethyl-1H-pyrazol-4-yl)-3-nitro-2-oxo-1,2-dihydro-1,8-naphthyridin-4-yl)-6-methylpiperazin-1,3-dicarboxylic acid (280 mg, 0.38 mmol) was dissolved in acetic acid (2.5 mL), added with iron powder (37 mg, 0.66 mmol), and stirred at 80° C. for 30 minutes to react. The resulting reaction liquid was concentrated, and orderly added with 50 mL of EtOAc and 30 mL of saturated sodium bicarbonate. The resulting suspension was filtered by diatomite. The filter cake was washed with EtOAc. The resulting organic phase was separated, washed orderly with 25 mL of saturated sodium bicarbonate and 25 mL of saturated salt solution, dried and concentrated to obtain product tert-butyl (2R,4aR)-11-fluoro-10-(2-fluoro-6-methoxyphenyl)-8-(3-isopropyl-1,5-dimethyl-1H-pyrazol-4-yl)-2-methyl-5,7-dioxo-1,2,4,4a,5,6,7,8-octahydro-3H-pyrazino[1',2':4,5]pyrazino[2,3-c][1,8]naphthyridin-3-carboxylate (250 mg, Y: 97.6%), which was yellow solid. ES-API: [M+H]$^+$=664.3.

Step 7: the tert-butyl (2R,4aR)-11-fluoro-10-(2-fluoro-6-methoxyphenyl)-8-(3-isopropyl-1,5-dimethyl-1H-pyrazol-4-yl)-2-methyl-5,7-dioxo-1,2,4,4a,5,6,7,8-octahydro-3H-pyrazino[1',2':4,5]pyrazino[2,3-c][1,8]naphthyridin-3-carboxylate (250 mg, 0.37 mmol), 4 mL of acetone, anhydrous potassium carbonate (103.9 mg, 0.74 mmol), and iodomethane (246 mg, 1.70 mmol) were orderly added to a 15 mL sealing tube. The sealing tube was sealed, and the resulting mixture was stirred at 50° C. for 18 hours to react. The resulting reaction liquid was added with 30 mL of EtOAc, washed orderly with 12 mL of water and 15 mL of saturated salt solution, dried and concentrated to obtain product tert-butyl (2R,4aR)-11-fluoro-10-(2-fluoro-6-methoxyphenyl)-8-(3-isopropyl-1,5-dimethyl-1H-pyrazol-4-yl)-2,6-dimethyl-5,7-dioxo-1,2,4,4a,5,6,7,8-octahydro-3H-pyrazino[1',2':4,5]pyrazino[2,3-c][1,8]naphthyridin-3-carboxylate (230 mg, Y: 90%), which was yellow solid. ES-API: [M+H]$^+$=678.3.

Step 8: the tert-butyl (2R,4aR)-11-fluoro-10-(2-fluoro-6-methoxyphenyl)-8-(3-isopropyl-1,5-dimethyl-1H-pyrazol-4-yl)-2,6-dimethyl-5,7-dioxo-1,2,4,4a,5,6,7,8-octahydro-3H-pyrazino[1',2':4,5]pyrazino[2,3-c][1,8]naphthyridin-3-carboxylate (230 mg, 0.34 mmol) was dissolved in DCM (3 mL), and added with TFA (2 mL). After stirring at room temperature for 2 hours, the resulting reaction liquid was concentrated to obtain product (2R,4aR)-11-fluoro-10-(2-fluoro-6-methoxyphenyl)-8-(3-isopropyl-1,5-dimethyl-1H-pyrazol-4-yl)-2,6-dimethyl-2,3,4,4a,6,8-hexahydro-1H-pyrazino[1',2':4,5]pyrazino[2,3-c][1,8]naphthyridin-5,7-dione (230 mg, crude), which was directly used in next step. ES-API: [M+H]$^+$=578.2.

Step 9: the (2R,4aR)-11-fluoro-10-(2-fluoro-6-methoxyphenyl)-8-(3-isopropyl-1,5-dimethyl-1H-pyrazol-4-yl)-2,6-dimethyl-2,3,4,4a,6,8-hexahydro-1H-pyrazino[1',2':4,5]pyrazino[2,3-c][1,8]naphthyridin-5,7-dione (230 mg, crude) was dissolved in DCM (5 mL), and added with N,N-diisopropylethylamine (110 mg, 0.85 mmol). The resulting reaction liquid was cooled to 0° C., and added dropwise with acryloyl chloride (31 mg, 0.34 mmol). The resulting mixture was stirred at 0° C. for 15 minutes to react. The resulting reaction liquid was added with 25 mL of DCM, washed orderly with 15 mL of water, 15 mL of saturated solution of NaHCO$_3$ and 15 mL of saturated salt solution, dried and concentrated. The resulting crude product was purified by flash column chromatography on silica gel (EtOAc/PE: 0-100%) to obtain product (2R,4aR)-3-acryloyl-11-fluoro-10-(2-fluoro-6-methoxyphenyl)-8-(3-isopropyl-1,5-dimethyl-1H-pyrazol-4-yl)-2, 6-dimethyl-2,3,4,4a,6,8-hexahydro-1H-pyrazino[1',2':4,5]pyrazino[2,3-c][1,8]naphthyridin-5,7-dione (190 mg, Y: 81.3%), which was faint yellow solid. ES-API: [M+H]$^+$=632.2.

Step 10: the (2R,4aR)-3-acryloyl-11-fluoro-10-(2-fluoro-6-methoxyphenyl)-8-(3-isopropyl-1,5-dimethyl-1H-pyrazol-4-yl)-2, 6-dimethyl-2,3,4,4a,6,8-hexahydro-1H-pyrazino[1',2':4,5]pyrazino[2,3-c][1,8]naphthyridin-5,7-dione (190 mg, 0.3 mmol) was dissolved in DCM (1.5 mL). The resulting solution was cooled to 0° C., and then added dropwise with a solution (5 mL) of 17% boron tribromide in DCM. The resulting mixture was stirred at room temperature for 4 hours to react. The resulting reaction liquid was poured into 40 mL of saturated solution of NaHCO$_3$ and extracted with 25 mL of DCM twice. The resulting organic phase was dried and concentrated, and the resulting crude product was purified by preparative scale HPLC to obtain product (2R, 4aR)-3-acryloyl-11-fluoro-10-(2-fluoro-6-hydroxyphenyl)-8-(3-isopropyl-1,5-dimethyl-1H-pyrazol-4-yl)-2,6-dimethyl-2,3,4,4a,6,8-hexahydro-1H-pyrazino[1',2':4,5]pyrazino[2,3-c][1,8]naphthyridin-5,7-dione (Z47, 60 mg, Y: 31.5%), which was faint yellow solid. $^1$H NMR (500 MHz, DMSO-d$_6$) δ 10.16 (d, J=3.7 Hz, 1H), 7.93 (t, J=9.5 Hz, 1H), 7.30 (dd, J=15.5, 8.1 Hz, 1H), 7.02 (dd, J=16.8, 10.6 Hz, 1H), 6.80-6.69 (m, 2H), 6.15 (t, J=13.1 Hz, 1H), 5.78-5.69 (m, 1H), 4.76 (s, 1H), 4.59 (dd, J=13.9, 6.2 Hz, 1H), 3.90 (d, J=18.9 Hz, 1H), 3.72 (dd, J=19.5, 4.3 Hz, 4H), 3.26 (s, 1H), 2.75 (d, J=7.7 Hz, 1H), 2.63-2.57 (m, 1H), 2.44-2.39 (m, 1H), 1.91 (d, J=70.7 Hz, 3H), 1.59-1.47 (m, 3H), 0.95 (ddd, J=34.1, 17.0, 5.2 Hz, 6H). ES-API: [M+H]$^+$=618.3.

Example 48 Preparation of Compounds Z48, Z48'-1, and Z48'-2

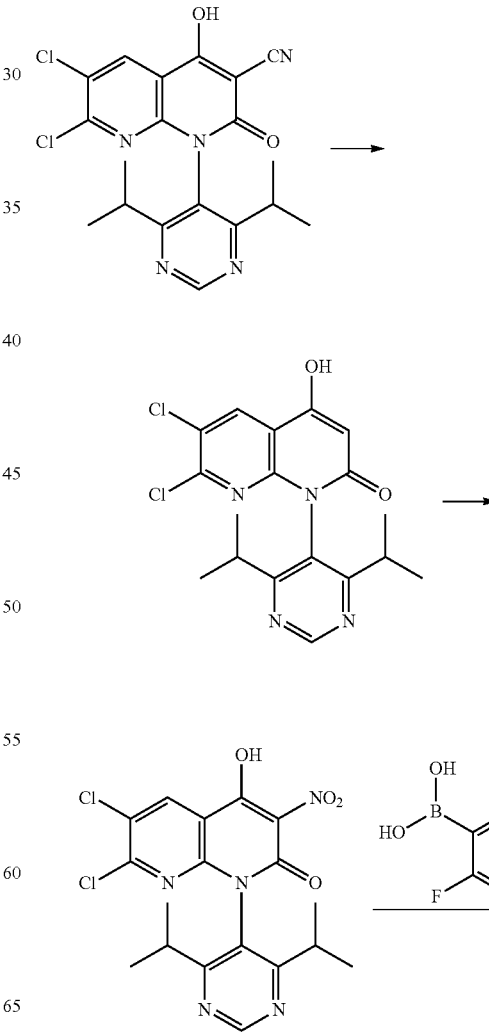

383
-continued
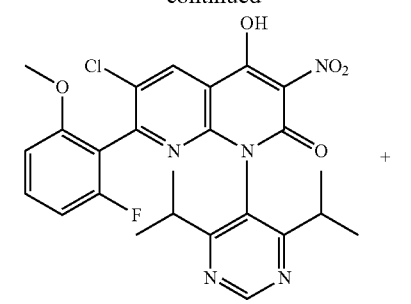
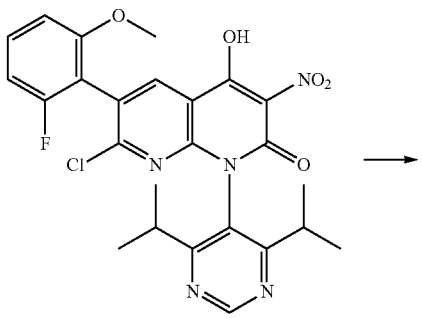
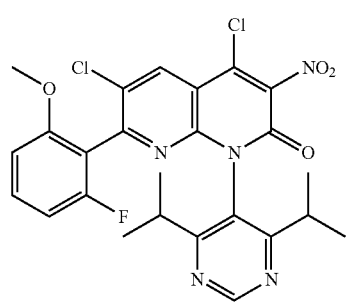
+
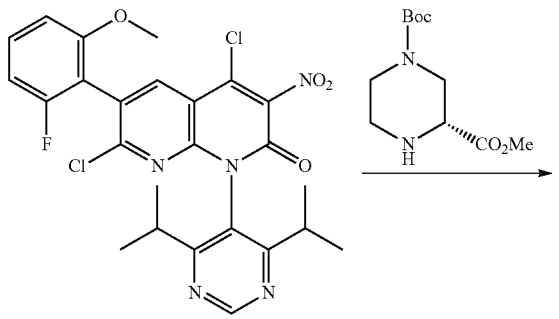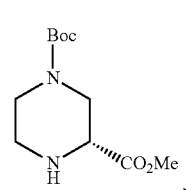
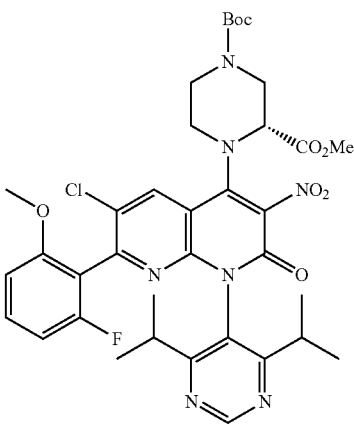
+
384
-continued
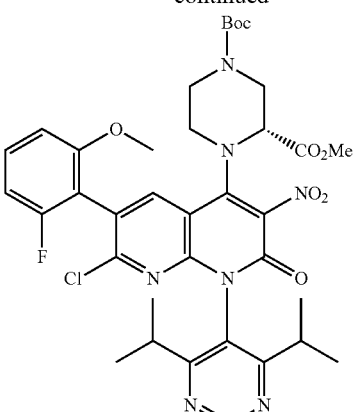
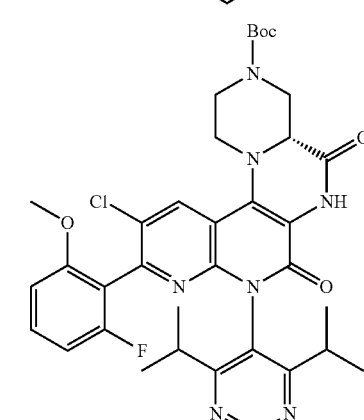
+
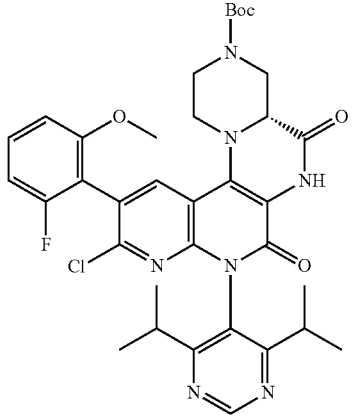
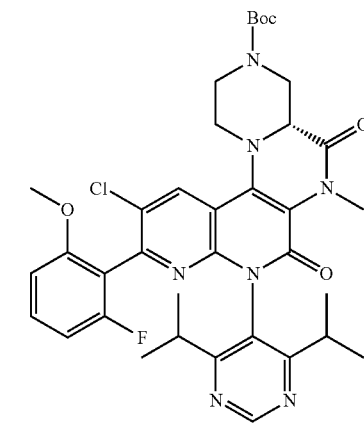
+

385
-continued
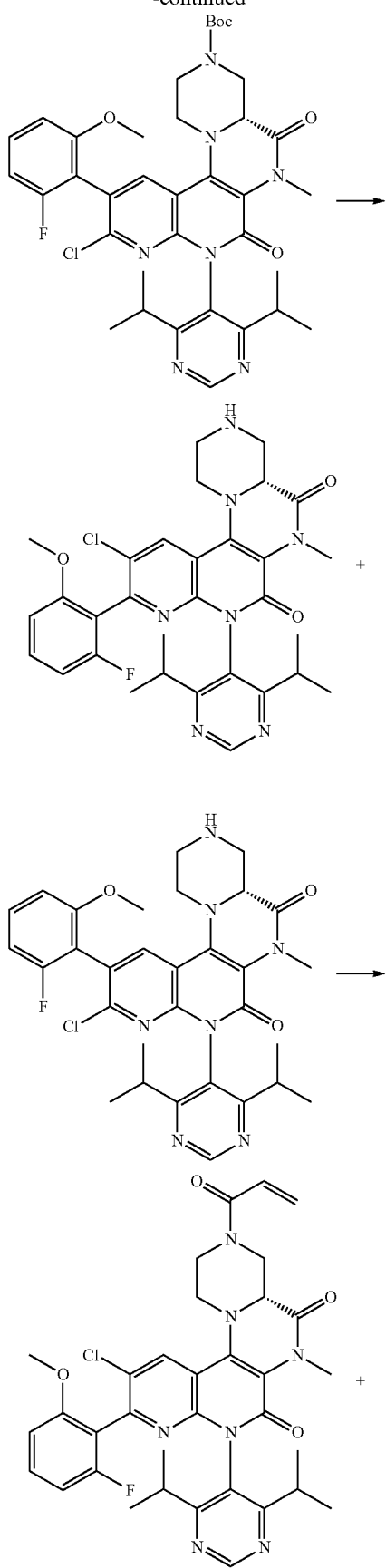
386
-continued
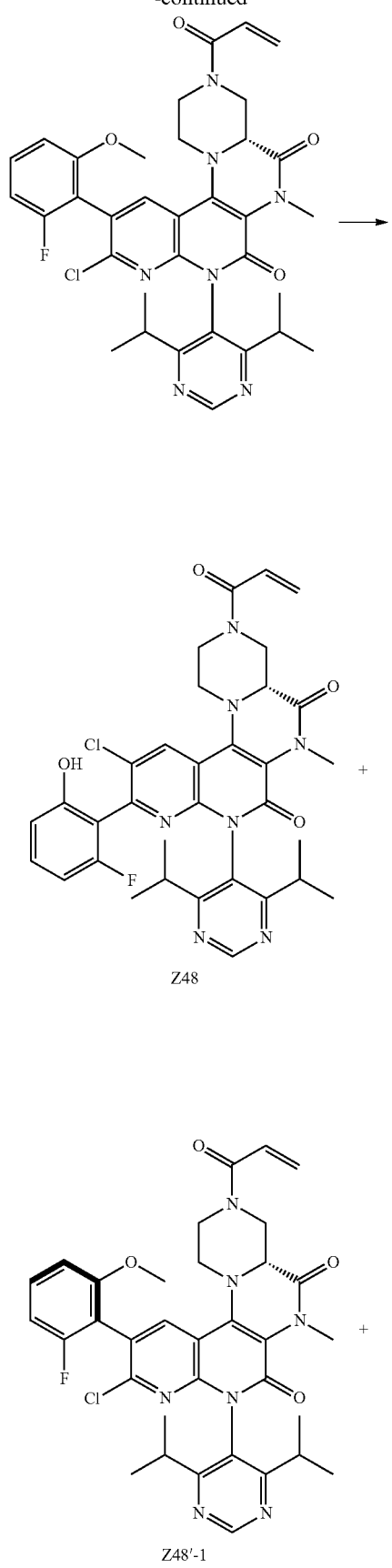
Z48
Z48'-1

-continued

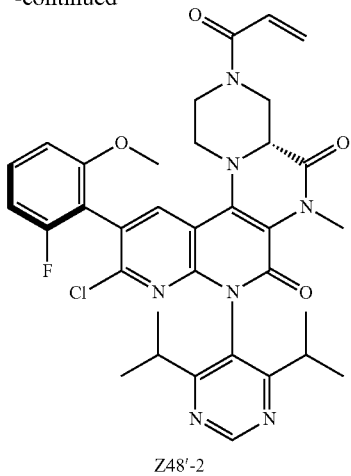

Z48'-2

Step 1: 6,7-dichloro-1-(4,6-diisopropylpyrimidin-5-yl)-4-hydroxy-2-oxo-1,2-dihydro-1,8-naphthyridin-3-carbonitrile (2 g, 12 mmol) was suspended in 1, 4-dioxane (12 mL), and slowly added with a mixed liquid of concentrated sulfuric acid (12 mL) and water (12 mL). The resulting mixture was stirred at 120° C. to react overnight. Cooled reaction liquid was then poured into 50 mL of ice water, mixed with aqueous solution of potassium hydroxide to adjust the pH to 6, and extracted with EtOAc (50 mL*3). The resulting organic phase was dried and concentrated to obtain target product 6,7-dichloro-1-(4,6-diisopropylpyrimidin-5-yl)-4-hydroxy-1,8-naphthyridin-2(1H)-one (1.5 g, Y: 80%), which was faint yellow solid. ES-API: [M+H]$^+$=393.1

Step 2: the 6,7-dichloro-1-(4,6-diisopropylpyrimidin-5-yl)-4-hydroxy-1,8-naphthyridin-2(1H)-one (1.50 g, 3.81 mmol) was dissolved in acetic acid (5 mL), orderly added with sodium nitrite (26 mg, 0.38 mmol) and concentrated nitric acid (721 mg, 11.44 mmol), and stirred at room temperature for 20 minutes. The resulting reaction liquid was poured into 5 mL of water. Yellow solid was precipitated and filtered. The filter cake was washed with 5 mL of water and dried in vacuum to obtain target product 6,7-dichloro-1-(4,6-diisopropylpyrimidin-5-yl)-4-hydroxy-3-nitro-1,8-naphthyridin-2(1H)-one (1.1 g, Y: 66%), which was faint yellow solid. ES-API: [M+H]$^+$=438.1

Step 3: a mixed solution of 6,7-dichloro-1-(4,6-diisopropylpyrimidin-5-yl)-4-hydroxy-3-nitro-1,8-naphthyridin-2(1H)-one (1.1 g, 2.51 mmol), (2-fluoro-6-methoxyphenyl)boric acid (1.28 g, 7.53 mmol), chloro(2-dicyclohexylphosphino-2',6'-dimethoxy-1,1'-biphenyl)(2'-amino-1,1'-biphen-2-yl)palladium(II) (166 mg, 0.23 mmol), 2-dicyclohexylphosphino-2',6'-dimethoxybiphenyl (94 mg, 0.23 mmol), and potassium phosphate (1.45 g, 6.85 mmol) in 2 mL of water and 10 mL of dioxane was stirred at 80° C. for 1 hour under the protection of nitrogen. The resulting reaction liquid was poured into 30 mL of water, and washed with methyl tert-butyl ether (30 mL*2). The water phase was mixed with 3.0 M diluted hydrochloric acid to adjust the pH to 6.0, and extracted with EtOAc (50 mL*3). The resulting organic phase was dried and concentrated to obtain a target product, namely a mixture of 6-chloro-1-(4,6-diisopropylpyrimidin-5-yl)-7-(2-fluoro-6-methoxyphenyl)-4-hydroxy-3-nitro-1,8-naphthyridin-2(1H)-one and 7-chloro-1-(4,6-diisopropylpyrimidin-5-yl)-6-(2-fluoro-6-methoxyphenyl)-4-hydroxy-3-nitro-1,8-naphthyridin-2(1H)-one (1.1 g, Y: 83%, P1:P2=55:45). ES-API: [M+H]$^+$=528.1.

Step 4: phosphorus oxychloride (1.6 g, 10.42 mmol) and N,N-diisopropylethylamine (2.15 g, 16.67 mmol) were orderly added to a solution of the mixture of 6-chloro-1-(4,6-diisopropylpyrimidin-5-yl)-7-(2-fluoro-6-methoxyphenyl)-4-hydroxy-3-nitro-1,8-naphthyridin-2(1H)-one and 7-chloro-1-(4,6-diisopropylpyrimidin-5-yl)-6-(2-fluoro-6-methoxyphenyl)-4-hydroxy-3-nitro-1,8-naphthyridin-2(1H)-one (1.1 g, 2.08 mmol) in ACN (15 mL), and stirred at 80° C. for 1 hour. The resulting reaction liquid was concentrated, added with 50 mL of EtOAc, and washed orderly with 30 mL of saturated sodium bicarbonate twice and then with 30 mL of water and 30 mL of saturated salt solution. After the resulting organic phase was dried and concentrated, the resulting crude product was purified by flash column chromatography on silica gel (EtOAc/PE: 0-50%) to obtain a mixture of 4,6-dichloro-1-(4,6-diisopropylpyrimidin-5-yl)-7-(2-fluoro-6-methoxyphenyl)-3-nitro-1,8-naphthyridin-2(1H)-one and 4,7-dichloro-1-(4,6-diisopropylpyrimidin-5-yl)-6-(2-fluoro-6-methoxyphenyl)-3-nitro-1,8-naphthyridin-2(1H)-one (750 mg, Y: 61%), which was faint yellow solid. ES-API: [M+H]$^+$=546.1.

Step 5: the mixture of 4,6-dichloro-1-(4,6-diisopropylpyrimidin-5-yl)-7-(2-fluoro-6-methoxyphenyl)-3-nitro-1,8-naphthyridin-2(1H)-one and 4,7-dichloro-1-(4,6-diisopropylpyrimidin-5-yl)-6-(2-fluoro-6-methoxyphenyl)-3-nitro-1,8-naphthyridin-2(1H)-one (750 mg, 1.37 mmol) was dissolved in N,N-dimethylacetamide (7.5 mL), orderly added with 1-(tert-butyl)3-methyl(R)-piperazin-1,3-dicarboxylate (1.01 g, 4.12 mmol) and N,N-diisopropylethylamine (530 mg, 4.12 mmol), and stirred at 120° C. for 2 hours. After being cooled, the reaction liquid was added with 100 mL of EtOAc, washed with 50 mL of sodium bicarbonate twice, with 50 mL of dilute brine twice, with 50 mL of water once and with 50 mL of saturated salt solution once, dried and concentrated to obtain a mixture of 1-(tert-butyl)3-methyl(3R)-4-(6-chloro-1-(4,6-diisopropylpyrimidin-5-yl)-7-(2-fluoro-6-methoxyphenyl)-3-nitro-2-oxo-1,2-dihydro-1,8-naphthyridin-4-yl)piperazin-1,3-dicarboxylate and 1-(tert-butyl)3-methyl(3R)-4-(7-chloro-1-(4,6-diisopropylpyrimidin-5-yl)-6-(2-fluoro-6-methoxyphenyl)-3-nitro-2-oxo-1,2-dihydro-1,8-naphthyridin-4-yl)piperazin-1,3-dicarboxylate (800 mg). ES-API: [M+H]$^+$=754.2.

Step 6: the mixture of 1-(tert-butyl)3-methyl(3R)-4-(6-chloro-1-(4,6-diisopropylpyrimidin-5-yl)-7-(2-fluoro-6-methoxyphenyl)-3-nitro-2-oxo-1,2-dihydro-1,8-naphthyridin-4-yl)piperazin-1,3-dicarboxylate and 1-(tert-butyl)3-methyl(3R)-4-(7-chloro-1-(4,6-diisopropylpyrimidin-5-yl)-6-(2-fluoro-6-methoxyphenyl)-3-nitro-2-oxo-1,2-dihydro-1,8-naphthyridin-4-yl)piperazin-1,3-dicarboxylate (800 mg, 1.06 mmol) was dissolved in acetic acid (8 mL), added with iron powder (207 mg, 3.71 mmol), and stirred at 80° C. for 1 hour. The resulting reaction liquid was concentrated, added with 50 mL of EtOAc, and mixed with saturated sodium bicarbonate solution to adjust the pH to 8. The resulting suspension was filtered by diatomite. The filter cake was washed with EtOAc. The resulting organic phase was separated, washed orderly with 25 mL of saturated sodium bicarbonate and 25 mL of saturated salt solution, dried and concentrated, and purified by flash column chromatography on silica gel (EtOAc/PE: 0-80%) to obtain a mixture of tert-butyl(4aR)-11-chloro-8-(4,6-diisopropylpyrimidin-5-yl)-10-(2-fluoro-6-methoxyphenyl)-5,7-dioxo-1,2,4,4a,5,6,7,8-octahydro-3H-pyrazino[1',2':4,5]pyrazino[2,3-c][1,8]naphthyridin-3-carboxylate and tert-butyl(4aR)-10-chloro-8-(4,6-diisopropylpyrimidin-5-yl)-11-(2-fluoro-6-methoxyphenyl)-5,7-dioxo-1,2,4,4a,5,6,7,8-octahydro- 3H-pyrazino[1',2':4,5]pyrazino[2,3-c] [1,8]naphthyridin-3-carboxylate (350 mg, Y: 48%), which was yellow solid. ES-API: [M+H]$^+$=692.3.

Step 7: the mixture of tert-butyl(4aR)-11-chloro-8-(4,6-diisopropylpyrimidin-5-yl)-10-(2-fluoro-6-methoxyphenyl)-5,7-dioxo-1,2,4,4a,5,6,7,8-octahydro-3H-pyrazino[1',2':4,5]pyrazino[2,3-c] [1,8]naphthyridin-3-carboxylate and tert-butyl(4aR)-10-chloro-8-(4,6-diisopropylpyrimidin-5-yl)-11-(2-fluoro-6-methoxyphenyl)-5,7-dioxo-1,2,4,4a,5,6,7,8-octahydro-3H-pyrazino[1',2':4,5]pyrazino[2,3-c] [1,8]naphthyridin-3-carboxylate (350 mg, 0.51 mmol), acetone (5 mL), anhydrous potassium carbonate (209 mg, 1.52 mmol), and iodomethane (718 mg, 5.06 mmol) were orderly added to a 15 mL sealing tube. The sealing tube was sealed, and the resulting mixture was stirred at 50° C. to react overnight. The resulting reaction liquid was filtered and concentrated to obtain a mixture of tert-butyl(4aR)-1I-chloro-8-(4,6-diisopropylpyrimidin-5-yl)-10-(2-fluoro-6-methoxyphenyl)-6-methyl-5,7-dioxo-1,2,4,4a,5,6,7,8-octahydro-3H-pyrazino[1',2':4,5]pyrazino[2,3-c] [1,8]naphthyridin-3-carboxylate and tert-butyl(4aR)-10-chloro-8-(4,6-diisopropylpyrimidin-5-yl)-11-(2-fluoro-6-methoxyphenyl)-6-methyl-5,7-dioxo-1,2,4,4a,5,6,7,8-octahydro-3H-pyrazino[1',2':4,5]pyrazino[2,3-c] [1,8]naphthyridin-3-carboxylate (350 mg), which was yellow solid. ES-API: [M+H]$^+$=706.3

Step 8: the mixture of tert-butyl(4aR)-11-chloro-8-(4,6-diisopropylpyrimidin-5-yl)-10-(2-fluoro-6-methoxyphenyl)-6-methyl-5,7-dioxo-1,2,4,4a,5,6,7,8-octahydro-3H-pyrazino[1',2':4,5]pyrazino[2,3-c] [1,8]naphthyridin-3-carboxylate and tert-butyl(4aR)-10-chloro-8-(4,6-diisopropylpyrimidin-5-yl)-11-(2-fluoro-6-methoxyphenyl)-6-methyl-5,7-dioxo-1,2,4,4a,5,6,7,8-octahydro-3H-pyrazino[1',2':4,5]pyrazino[2,3-c] [1,8]naphthyridin-3-carboxylate (350 mg, 0.50 mmol) was dissolved in DCM (8 mL), and added with TFA (2 mL). After stirring at room temperature for 2 hours, the resulting reaction liquid was concentrated to obtain a mixture of (4aR)-11-chloro-8-(4,6-diisopropylpyrimidin-5-yl)-10-(2-fluoro-6-methoxyphenyl)-6-methyl-2,3,4,4a,6,8-hexahydro-1H-pyrazino[1',2':4,5]pyrazino[2,3-c] [1,8]naphthyridin-5,7-dione and (4aR)-10-chloro-8-(4,6-diisopropylpyrimidin-5-yl)-11-(2-fluoro-6-methoxyphenyl)-6-methyl-2,3,4,4a,6,8-hexahydro-1H-pyrazino[1',2':4,5]pyrazino[2,3-c][1,8]naphthyridin-5,7-dione (300 mg, P1:P2=53:47), which was directly used in next step. ES-API: [M+H]$^+$=606.3

Step 9: the mixture of (4aR)-11-chloro-8-(4,6-diisopropylpyrimidin-5-yl)-10-(2-fluoro-6-methoxyphenyl)-6-methyl-2,3,4,4a,6,8-hexahydro-1H-pyrazino[1',2':4,5]pyrazino[2,3-c] [1,8]naphthyridin-5,7-dione and (4aR)-10-chloro-8-(4,6-diisopropylpyrimidin-5-yl)-11-(2-fluoro-6-methoxyphenyl)-6-methyl-2,3,4,4a,6,8-hexahydro-1H-pyrazino[1',2':4,5]pyrazino[2,3-c] [1,8]naphthyridin-5,7-dione (300 mg, 0.50 mmol) was dissolved in DCM (3 mL), and added with N,N-diisopropylethylamine (320 mg, 2.45 mmol). The resulting reaction liquid was cooled to 0° C., and added dropwise with acryloyl chloride (90 mg, 0.99 mmol). The reaction liquid was stirred at 0° C. for 5 minutes, and concentrated. The resulting crude product was purified by flash column chromatography on silica gel (EtOAc/PE: 0-80%) to obtain a mixture of (4aR)-3-acryloyl-11-chloro-8-(4,6-diisopropylpyrimidin-5-yl)-10-(2-fluoro-6-methoxyphenyl)-6-methyl-2,3,4,4a,6,8-hexahydro-1H-pyrazino[1',2':4,5]pyrazino[2,3-c] [1,8]naphthyridin-5,7-dione and (4aR)-3-acryloyl-10-chloro-8-(4,6-diisopropylpyrimidin-5-yl)-11-(2-fluoro-6-methoxyphenyl)-6-methyl-2,3,4,4a,6,8-hexahydro-1H-pyrazino[1',2':4,5]pyrazino[2,3-c] [1,8]naphthyridin-5,7-dione (250 mg, Y: 77%), which was faint yellow solid. ES-API: [M+H]$^+$=662.3.

Step 10: the mixture of (4aR)-3-acryloyl-11-chloro-8-(4,6-diisopropylpyrimidin-5-yl)-10-(2-fluoro-6-methoxyphenyl)-6-methyl-2,3,4,4a,6,8-hexahydro-1H-pyrazino[1',2':4,5]pyrazino[2,3-c] [1,8]naphthyridin-5,7-dione and (4aR)-3-acryloyl-10-chloro-8-(4,6-diisopropylpyrimidin-5-yl)-11-(2-fluoro-6-methoxyphenyl)-6-methyl-2,3,4,4a,6,8-hexahydro-1H-pyrazino[1',2':4,5]pyrazino[2,3-c] [1,8]naphthyridin-5,7-dione (250 mg, 0.38 mmol) was dissolved in DCM (3 mL). The resulting solution was cooled to 0° C., added dropwise with a solution (3 mL) of 17% boron tribromide in DCM, and stirred at room temperature overnight. The resulting reaction liquid was poured into 40 mL of saturated solution of sodium bicarbonate and extracted with 25 mL of DCM twice. The resulting organic phase was dried and concentrated, and the resulting crude product was purified by preparative scale HPLC to obtain: a compound Z48 (14.2 mg, P: 100%, retention time: 9.94 min, Y: 6%), which was faint yellow solid, ES-API: [M+H]+=646.2; $^1$H NMR (500 MHz, DMSO-d$_6$) δ 10.04 (d, J=20 Hz, 1H), 9.10 (s, 1H), 8.54 (d, J=7.5 Hz, 1H), 7.28-7.17 (m, 1H), 7.14-6.77 (m, 1H), 6.73-6.68 (m, 1H), 6.68-6.63 (m, 1H), 6.21-6.11 (m, 1H), 5.79-5.71 (m, 1H), 5.15-4.66 (m, 1H), 4.51-4.02 (m, 1H), 3.99 (s, 1H), 3.66-3.53 (m, 2H), 3.32 (s, 3H), 3.27-3.18 (m, 1H), 2.84-2.74 (m, 1H), 2.74-2.61 (m, 1H), 2.52-2.46 (m, 1H), 1.10 (d, J=7 Hz, 3H), 1.04 (d, J=6.5 Hz, 3H), 0.99 (dd, J=10.5, 7 Hz, 3H), 0.86 (dd, J=15.5, 6.5 Hz, 3H); ES-API: [M+H]$^+$=646.2; a compound Z48'-1 (16.5 mg, P: 96%, retention time: 10.13 min, Y: 7%), which was faint yellow solid, ES-API: [M+H]+=646.2; and a compound Z48'-2 (17.5 mg, P: 100%, retention time: 10.36 min, Y: 7%), which was faint yellow solid, ES-API: [M+H]+=646.2.

Example 49 Preparation of Compounds Z49, Z49-1, and Z49-2

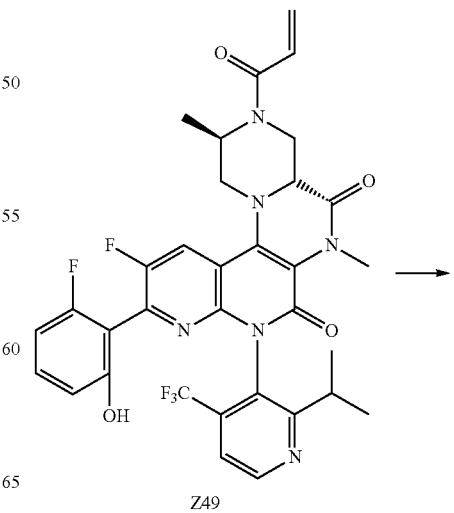

Z49

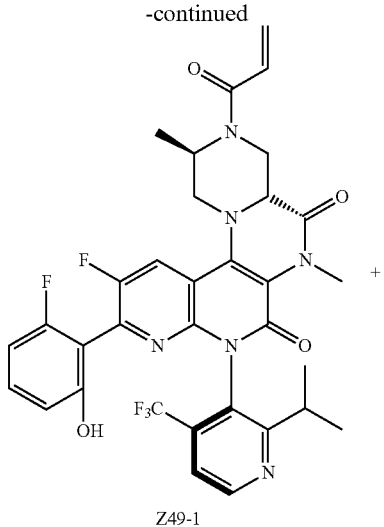

Z49-1

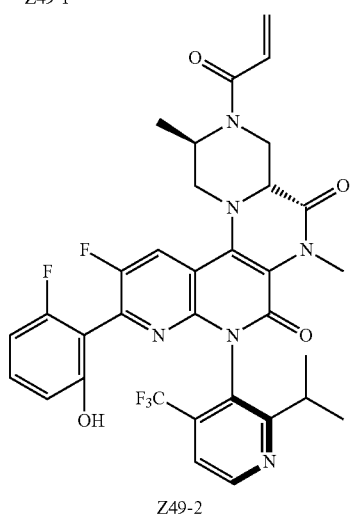

Z49-2

A compound Z49 was synthesized from 7-chloro-6-fluoro-4-hydroxy-1-(2-isopropyl-4-(trifluoromethyl)pyridin-3-yl)-3-nitro-1,8-naphthyridin-2(1H)-one with reference to the synthesis of the compound Z33. ES-API: [M+H]$^+$=669.2. The compound Z49 was resolved by preparative scale chiral HPLC (column type: IB 10 μm, 30*250 mm; mobile phase: hexane:EtOH=80:20; flow rate: 25 mL/min; and column temperature: room temperature) to obtain the following atropisomer compounds. One of the atropisomer compounds had a structure arbitrarily specified as Z49-1 (71 mg, peak 1, retention time: 7.68 min, de value: 100%). $^1$H NMR (500 MHz, DMSO-d$_6$) δ 10.14 (d, J=1.4 Hz, 1H), 8.92 (d, J=4.9 Hz, 1H), 8.00 (dd, J=16.4, 8.6 Hz, 1H), 7.76 (d, J=5.0 Hz, 1H), 7.25 (dd, J=15.3, 8.3 Hz, 1H), 6.94 (ddd, J=72.2, 16.7, 10.5 Hz, 1H), 6.71 (d, J=8.3 Hz, 1H), 6.66 (t, J=8.8 Hz, 1H), 6.22-6.09 (m, 1H), 5.79-5.69 (m, 1H), 5.06-4.72 (m, 1H), 4.53 (t, J=45.4 Hz, 1H), 4.02-3.90 (m, 1H), 3.75 (dd, J=14.1, 4.1 Hz, 1H), 3.45 (d, J=11.9 Hz, 1H), 3.34 (s, 3H), 2.93 (dd, J=13.3, 6.6 Hz, 1H), 2.90-2.85 (m, 1H), 1.55 (dd, J=19.2, 6.8 Hz, 3H), 1.14 (d, J=6.7 Hz, 3H), 1.04 (d, J=6.6 Hz, 3H). ES-API: [M+H]$^+$= 669.1. The other atropisomer compound had a structure arbitrarily specified as Z49-2 (80 mg, peak 2, retention time: 9.79 min, de value: 99.85%). $^1$H NMR (500 MHz, DMSO-d$_6$) δ 10.15 (s, 1H), 8.92 (d, J=5.0 Hz, 1H), 8.01 (dd, J=14.5, 8.5 Hz, 1H), 7.78 (d, J=5.0 Hz, 1H), 7.25 (dd, J=15.2, 8.2 Hz, 1H), 6.94 (ddd, J=82.1, 16.7, 10.7 Hz, 1H), 6.71 (d, J=8.3 Hz, 1H), 6.66 (t, J=8.8 Hz, 1H), 6.15 (dt, J=16.9, 3.9 Hz, 1H), 5.79-5.69 (m, 1H), 5.11-4.69 (m, 1H), 4.54 (t, J=56.0 Hz, 1H), 4.15-3.97 (m, 1H), 3.74 (dd, J=14.2, 4.3 Hz, 1H), 3.44 (d, J=11.6 Hz, 1H), 3.28 (s, 3H), 2.88 (dd, J=40.3, 9.5 Hz, 1H), 2.66-2.56 (m, 1H), 1.54 (dd, J=19.8, 6.6 Hz, 3H), 1.07 (d, J=6.6 Hz, 3H), 0.92 (d, J=6.7 Hz, 3H). ES-API: [M+H]$^+$=669.1. The isomer compounds were detected by analytical scale chiral HPLC (column type: IB 5 μm, 4.6*250 mm; mobile phase: hexane:EtOH=80:20; flow rate: 1 mL/min; and column temperature=30° C.).

Example 50 Preparation of Compounds Z50, Z50-1 and Z50-2

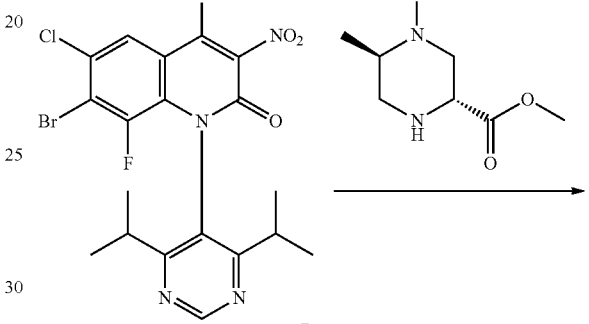

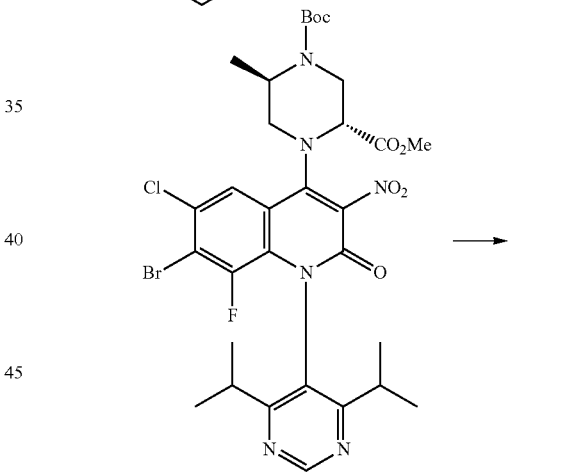

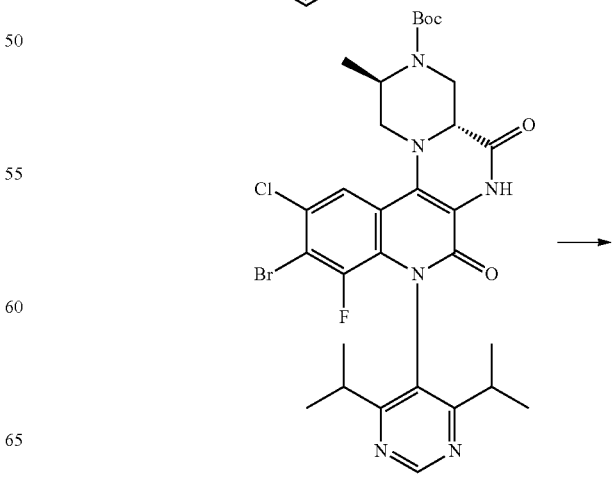

393
-continued
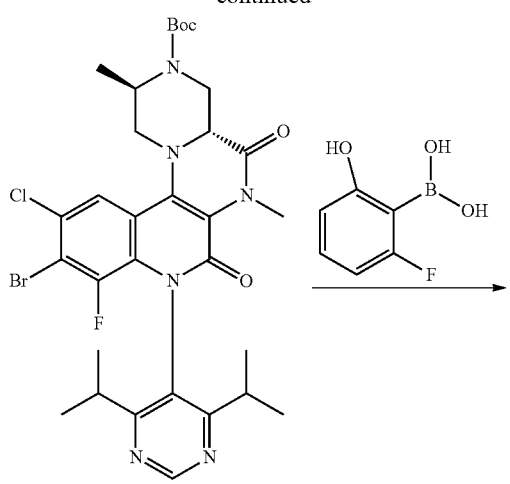
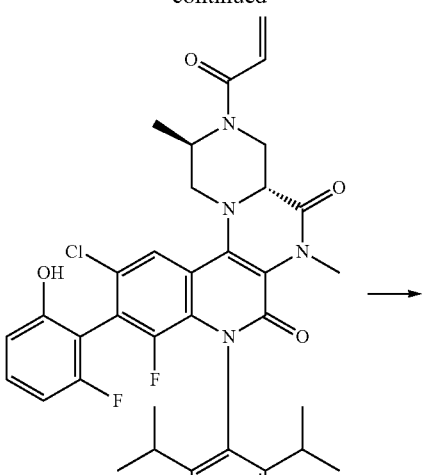
Z50
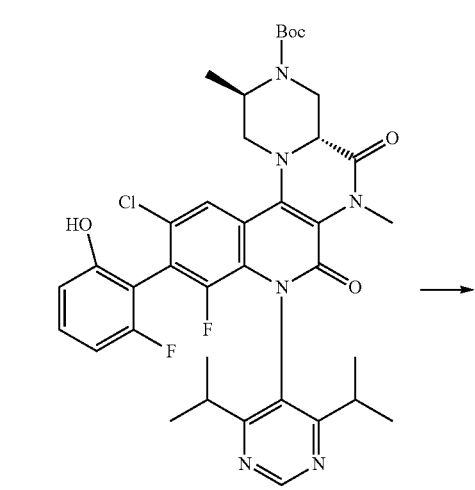
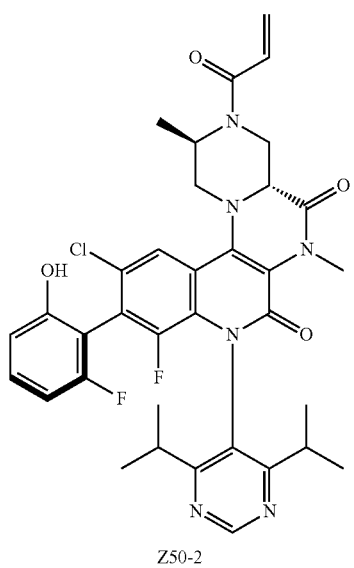
Z50-1
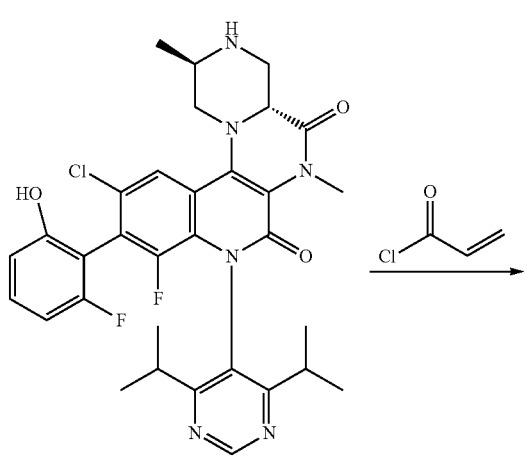
Z50-2

Step 1: 7-bromo-4,6-dichloro-1-(4,6-diisopropylpyrimidin-5-yl)-8-fluoro-3-nitroquinolin-2(1H)-one (450 mg, 0.87 mmol) was dissolved in N,N-dimethylacetamide (6 mL), orderly added with methyl (3R,6R)-1-N-BOC-6-methylpiperazin-3-formate (404 mg, 1.57 mmol) and N,N-diisopropylethylamine (0.45 mL, 2.61 mmol), and stirred at 120° C. for 1 hour to react. The resulting reaction liquid was added with 100 mL of EtOAc, washed with 30 mL of dilute brine for 4 times and then with 30 mL of saturated salt solution, dried and concentrated to obtain product (3R,6R)-1-(tert-butyl)3-methyl-4-(7-bromo-6-chloro-1-(4,6-diisopropylpyrimidin-5-yl)-8-fluoro-3-nitro-2-oxo-1,2-dihydroquinolin-4-yl)-6-methylpiperazin-1,3-dicarboxylate (770 mg, crude), which was directly used in next step. ES-API: $[M+H]^+=$ 739.2, 741.1.

Step 2: the (3R,6R)-1-(tert-butyl)3-methyl-4-(7-bromo-6-chloro-1-(4,6-diisopropylpyrimidin-5-yl)-8-fluoro-3-nitro-2-oxo-1,2-dihydroquinolin-4-yl)-6-methylpiperazin-1,3-dicarboxylate (777 mg, crude) was dissolved in acetic acid (8 mL), added with iron powder (170 mg, 3.05 mmol), and stirred at 80° C. for 30 minutes to react. The resulting reaction liquid was concentrated, and orderly added with 100 mL of EtOAc and 60 mL of saturated sodium bicarbonate. The resulting suspension was filtered by diatomite. The filter cake was washed with EtOAc. The resulting organic phase was separated, washed orderly with 40 mL of saturated sodium bicarbonate and 40 mL of saturated salt solution, dried and concentrated to obtain product tert-butyl (2R,4aR)-10-bromo-11-chloro-8-(4,6-diisopropylpyrimidin-5-yl)-9-fluoro-2-methyl-5,7-dioxo-1,2,4,4a,5,6,7,8-octahydro-3H-pyrazino[1',2':4,5]pyrazino[2,3-c]quinolin-3-carboxylate (700 mg, crude), which was light brown solid. ES-API: $[M+H]^+=677.2, 679.2$.

Step 3: the tert-butyl (2R,4aR)-10-bromo-11-chloro-8-(4,6-diisopropylpyrimidin-5-yl)-9-fluoro-2-methyl-5,7-dioxo-1,2,4,4a,5,6,7,8-octahydro-3H-pyrazino[1',2':4,5]pyrazino[2,3-c]quinolin-3-carboxylate (700 mg, crude), 20 mL of acetone, anhydrous potassium carbonate (480 mg, 3.48 mmol), and iodomethane (1.24 g, 8.70 mmol) were orderly added to a 50 mL sealing tube. The sealing tube was sealed, and the resulting mixture was stirred at 50° C. for 18 hours to react. The resulting reaction liquid was added with 80 mL of EtOAc, washed orderly with 20 mL of water and 30 mL of saturated salt solution, dried and concentrated. The resulting crude product was purified by flash column chromatography on silica gel (EtOAc/PE: 0-25%) to obtain product tert-butyl (2R,4aR)-10-bromo-11-chloro-8-(4,6-diisopropylpyrimidin-5-yl)-9-fluoro-2,6-dimethyl-5,7-dioxo-1,2,4,4a,5,6,7,8-octahydro-3H-pyrazino[1',2':4,5]pyrazino[2,3-c]quinolin-3-carboxylate (350 mg, Y in step 3: 58.2%), which was yellow solid. ES-API: $[M+H]^+=691.1, 693.2$.

Step 4: the tert-butyl (2R,4aR)-10-bromo-11-chloro-8-(4,6-diisopropylpyrimidin-5-yl)-9-fluoro-2,6-dimethyl-5,7-dioxo-1,2,4,4a,5,6,7,8-octahydro-3H-pyrazino[1',2':4,5]pyrazino[2,3-c]quinolin-3-carboxylate (325 mg, 0.47 mmol), (2-fluoro-6-hydroxyphenyl)boric acid (293 mg, 1.88 mmol), SPhos-Pd-G2 (34 mg, 0.047 mmol), 2-dicyclohexylphosphino-2',6'-dimethoxybiphenyl (19 mg, 0.047 mmol), potassium phosphate (398 mg, 1.88 mmol), 3 mL of water, and 15 mL of dioxane were added to a 100 mL round-bottom flask. The resulting mixture was stirred at 90° C. for 4 hours to react under the protection of nitrogen. The resulting reaction liquid was concentrated, added with 60 mL of EtOAc, washed orderly with 10 mL of water and 15 mL of saturated salt solution, dried and concentrated. The resulting crude product was purified by flash column chromatography on silica gel (EtOAc/PE: 0-50%) to obtain product tert-butyl (2R,4aR)-11-chloro-8-(4,6-diisopropylpyrimidin-5-yl)-9-fluoro-10-(2-fluoro-6-hydroxyphenyl)-2,6-dimethyl-5,7-dioxo-1,2,4,4a,5,6,7,8-octahydro-3H-pyrazino[1',2':4,5]pyrazino[2,3-c]quinolin-3-carboxylate (220 mg, Y: 64.8%), which was yellow solid. ES-API: $[M+H]^+=723.3$.

Step 5: the tert-butyl (2R,4aR)-11-chloro-8-(4,6-diisopropylpyrimidin-5-yl)-9-fluoro-10-(2-fluoro-6-hydroxyphenyl)-2,6-dimethyl-5,7-dioxo-1,2,4,4a,5,6,7,8-octahydro-3H-pyrazino[1',2':4,5]pyrazino[2,3-c]quinolin-3-carboxylate (220 mg, 0.30 mmol) was dissolved in DCM (4 mL), and added with TFA (1 mL). After stirring at room temperature for 2 hours, the resulting reaction liquid was concentrated to obtain product (2R,4aR)-11-chloro-8-(4,6-diisopropylpyrimidin-5-yl)-9-fluoro-10-(2-fluoro-6-hydroxyphenyl)-2,6-dimethyl-2,3,4,4a,6,8-hexahydro-1H-pyrazino[1',2':4,5]pyrazino[2,3-c]quinolin-5,7-dione (240 mg, crude), which was directly used in next step. ES-API: $[M+H]^+=623.3$.

Step 6: the (2R,4aR)-11-chloro-8-(4,6-diisopropylpyrimidin-5-yl)-9-fluoro-10-(2-fluoro-6-hydroxyphenyl)-2,6-dimethyl-2,3,4,4a,6,8-hexahydro-1H-pyrazino[1',2':4,5]pyrazino[2,3-c]quinolin-5,7-dione (240 mg, crude) was dissolved in DCM (6 mL), and added with N,N-diisopropylethylamine (194 mg, 1.50 mmol). The resulting reaction liquid was cooled to 0° C., and added dropwise with acryloyl chloride (24 mg, 0.27 mmol). The resulting mixture was stirred at 0° C. for 15 minutes to react. The resulting reaction liquid was added with 50 mL of DCM, washed orderly with 15 mL of water, 15 mL of saturated solution of $NaHCO_3$ and 15 mL of saturated salt solution, dried and concentrated to obtain product (2R,4aR)-11-chloro-8-(4,6-diisopropylpyrimidin-5-yl)-9-fluoro-10-(2-fluoro-6-hydroxyphenyl)-2,6-dimethyl-2,3,4,4a,6,8-hexahydro-1H-pyrazino[1',2':4,5]pyrazino[2,3-c]quinolin-5,7-dione (Z50), which was purified by preparative scale HPLC to obtain the following atropisomer compounds. One of the atropisomer compounds had a structure arbitrarily specified as Z50-1 (retention time: 10.433 min; 55 mg, Y: 26.7%), which was white solid. $^1$H NMR (400 MHz, DMSO-$d_6$) δ 10.21 (d, J=1.7 Hz, 1H), 9.13 (s, 1H), 7.89-7.88 (m, 1H), 7.27 (dd, J=15.4, 8.3 Hz, 1H), 7.02 (dd, J=16.8, 10.6 Hz, 1H), 6.75-6.69 (m, 2H), 6.19-6.11 (m, 1H), 5.78-5.70 (m, 1H), 4.84-4.75 (m, 1H), 4.60 (d, J=13.6 Hz, 1H), 4.06-3.97 (m, 1H), 3.78-3.70 (m, 1H), 3.31-3.25 (m, 4H), 2.99-2.90 (m, 1H), 2.81-2.73 (m, 1H), 2.61-2.55 (m 1H), 1.48-1.58 (m, 3H), 1.18-0.86 (m, 12H). ES-API: $[M+H]^+=677.2$. The other atropisomer compound had a structure arbitrarily specified as Z50-2 (retention time: 10.752 min; 85 mg, Y: 41.2%), which was white solid. $^1$H NMR (400 MHz, DMSO-$d_6$) δ 10.22 (s, 1H), 9.13 (s, 1H), 7.89-7.88 (m, 1H), 7.27 (dd, J=15.5, 8.1 Hz, 1H), 7.02 (dd, J=16.8, 10.7 Hz, 1H), 6.76-6.69 (m, 2H), 6.20-6.09 (m, 1H), 5.80-5.70 (m, 1H), 3.83-3.73 (m, 1H), 4.60 (d, J=14.0 Hz, 1H), 4.06-3.97 (m, 1H), 3.82-3.66 (m, 1H), 3.31-3.22 (m, 4H), 3.02-2.88 (m, 1H), 2.83-2.74 (m, 1H), 2.61-2.52 (m, 1H), 1.66-1.49 (m, 3H), 1.21-1.01 (m, 9H), 0.99-0.83 (m, 3H). ES-API: $[M+H]^+=677.2$. The isomer compounds were detected by analytical scale HPLC.

Compounds of Example 51 to Example 342 were prepared with reference to the synthesis processes of the above Examples.

| Example No. | Structure and No. of Compound | ES-API: [M + H]+ |
|---|---|---|
| 51 | <br>Z51 | 616.2 |
| | <br>Z51-1 | |
| | Z51-2 | |
| Example No. | Structure and No. of Compound | ES-API: [M + H]+ |
|---|---|---|
| 52 | 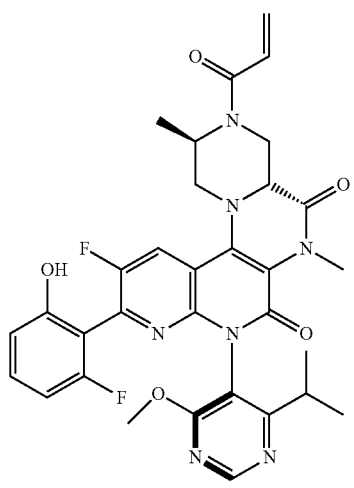<br>Z52 | 632.2 |
| | 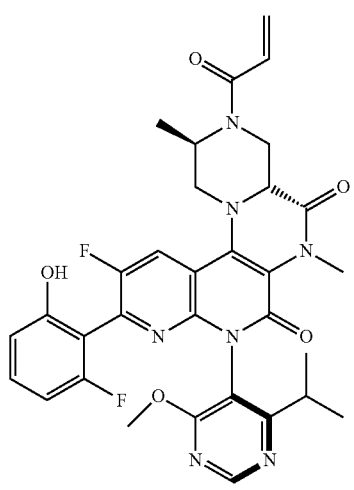<br>Z52-1 | |
| | Z52-2 | |

| Example No. | Structure and No. of Compound | ES-API: [M + H]+ |
|---|---|---|
| 53 | 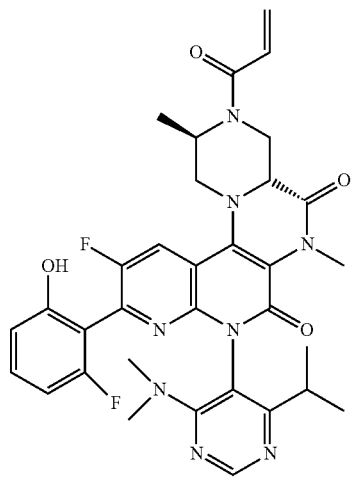 Z53 | 645.3 |
| | 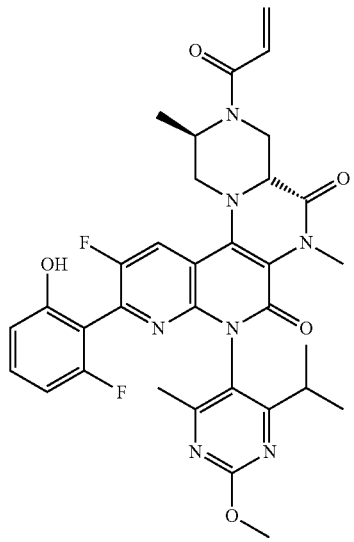 Z53-1 | |
| Example No. | Structure and No. of Compound | ES-API: [M + H]+ |
|---|---|---|
| | 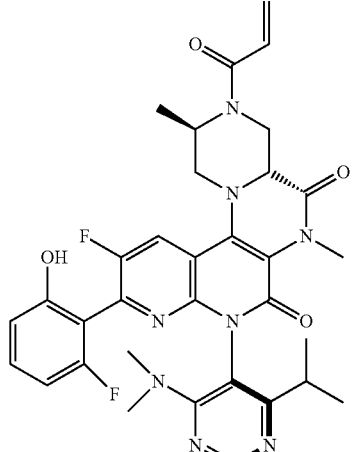 Z53-2 | |
| 54 | Z54 | 646.3 |

-continued
| Example No. | Structure and No. of Compound | ES-API: [M + H]+ |
|---|---|---|
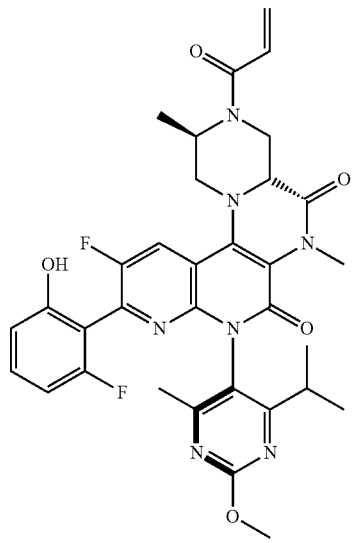
Z54-1
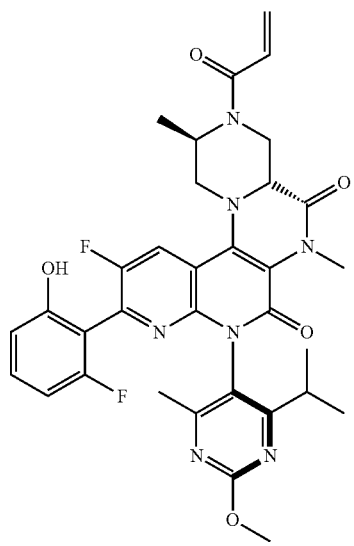
Z54-2
-continued
| Example No. | Structure and No. of Compound | ES-API: [M + H]+ |
|---|---|---|
| 55 | 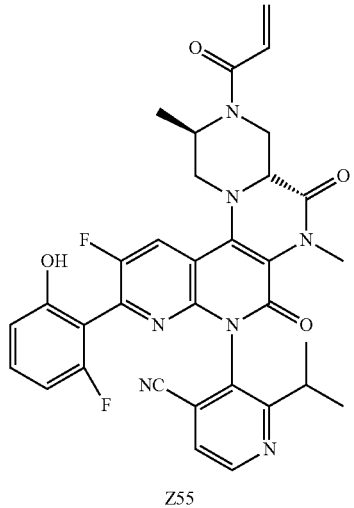 Z55 | 626.2 |
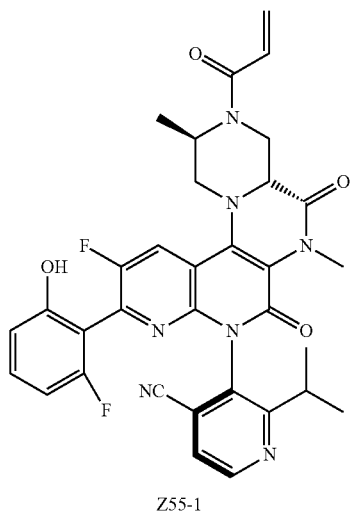
Z55-1
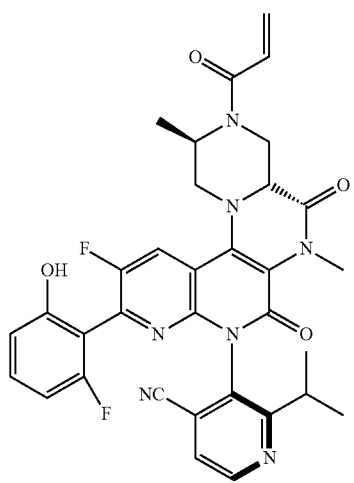
Z55-2

| Example No. | Structure and No. of Compound | ES-API: [M + H]⁺ |
|---|---|---|
| 56 | 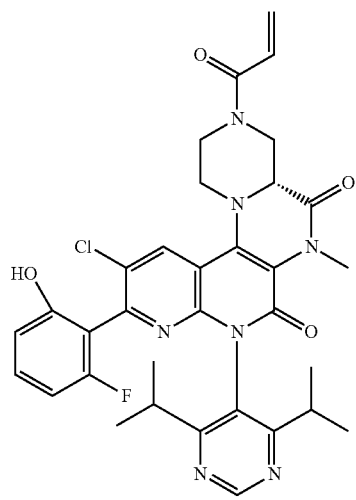<br>Z56 | 646.2 |
| 57 | 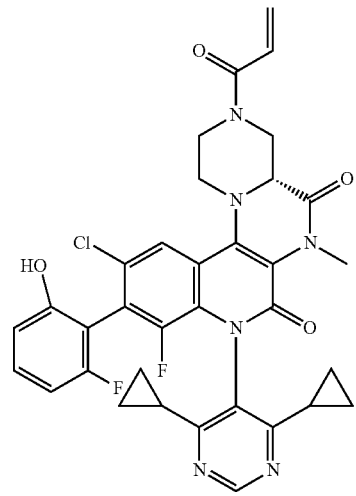<br>Z57 | 659.2 |
| Example No. | Structure and No. of Compound | ES-API: [M + H]⁺ |
|---|---|---|
| | 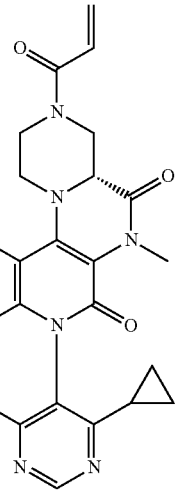<br>Z57-1 | |
| | 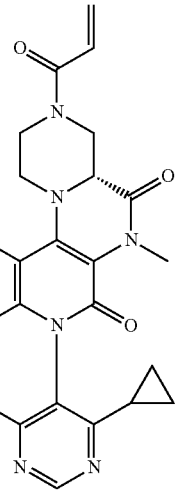<br>Z57-2 | |

| Example No. | Structure and No. of Compound | ES-API: [M + H]+ |
|---|---|---|
| 58 | Z58 | 642.2 |
| 59 | Z59 | 613.2 |
| 59-1 | Z59-1 | |
| 59-2 | Z59-2 | |
| 60 | Z60 | 660.2 |
| 61 | Z61 | 615.2 |

-continued
| Example No. | Structure and No. of Compound | ES-API: [M + H]+ |
|---|---|---|
| | 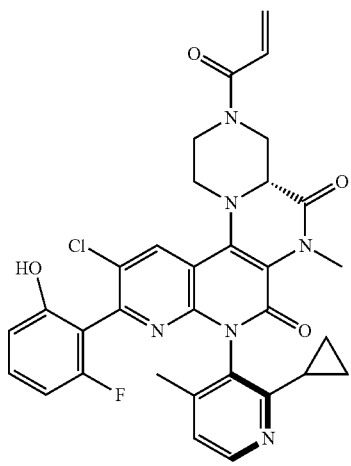
Z61-1 | |
| | 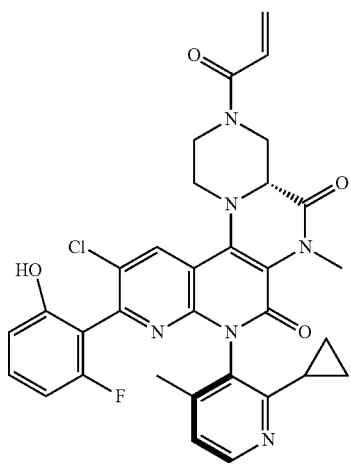
Z61-2 | |
| 62 | 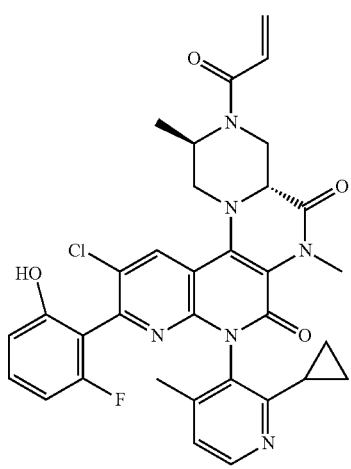
Z62 | 629.2 |
-continued
| Example No. | Structure and No. of Compound | ES-API: [M + H]+ |
|---|---|---|
| | 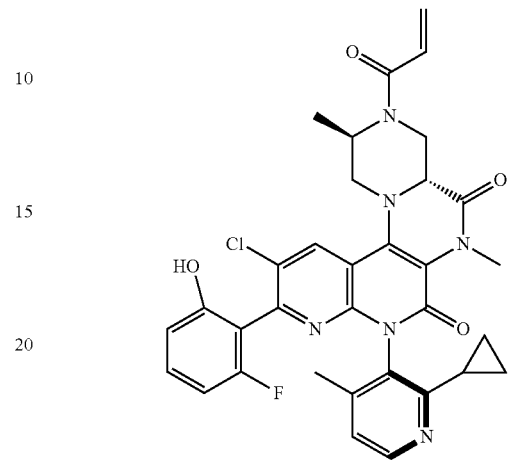
Z62-1 | |
| | 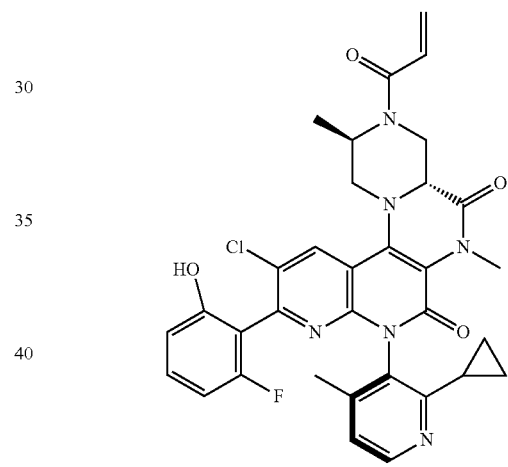
Z62-2 | |
| 63 | 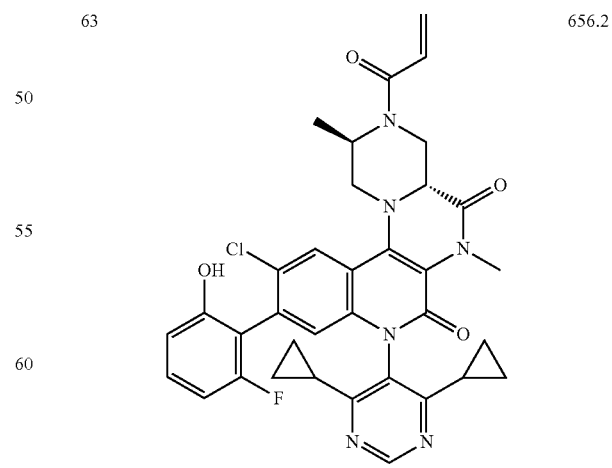
Z63 | 656.2 |

| Example No. | Structure and No. of Compound | ES-API: [M + H]+ |
|---|---|---|
| 64 | 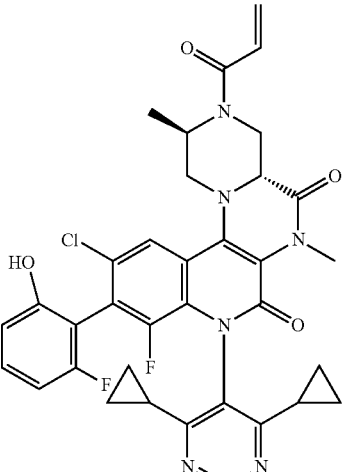 Z64 | 673.2 |
| | Z64-1 | |
| | Z64-2 | |
| 65 | Z65 | 632.2 |
| | Z65-1 | |

| Example No. | Structure and No. of Compound | ES-API: [M + H]⁺ |
|---|---|---|
| | 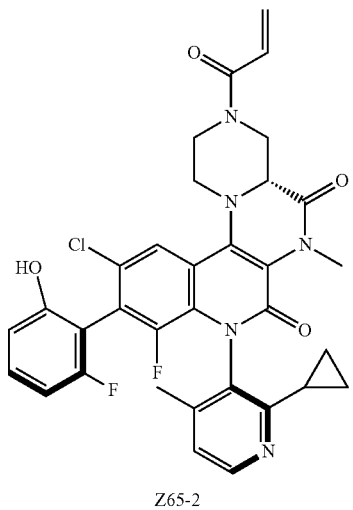<br>Z65-2 | |
| | 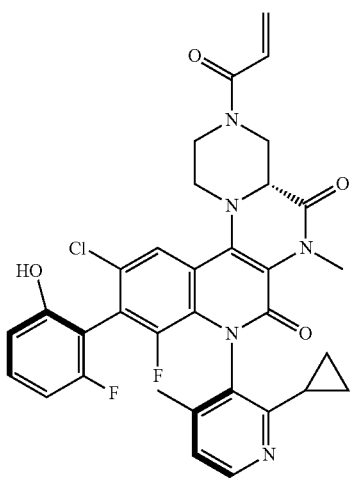<br>Z65-3 | |
| | 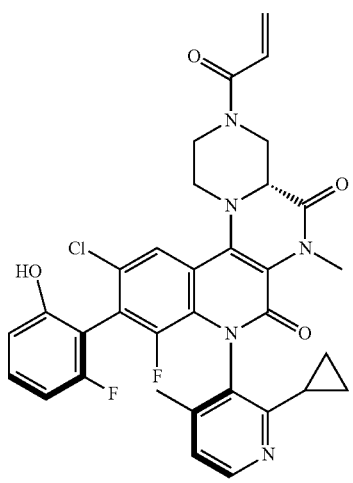<br>Z65-4 | |
| Example No. | Structure and No. of Compound | ES-API: [M + H]⁺ |
|---|---|---|
| 67 | 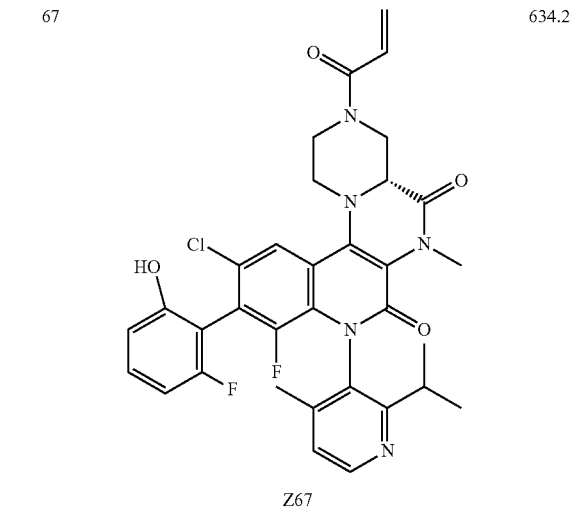<br>Z67 | 634.2 |
| | 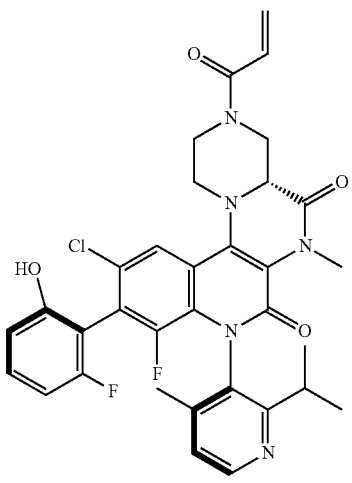<br>Z67-1 | |
| | 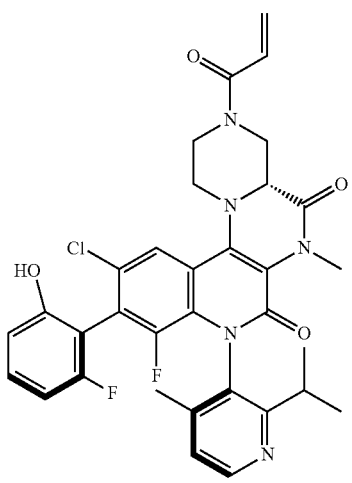<br>Z67-2 | |

-continued
| Example No. | Structure and No. of Compound | ES-API: [M + H]+ |
|---|---|---|
| | 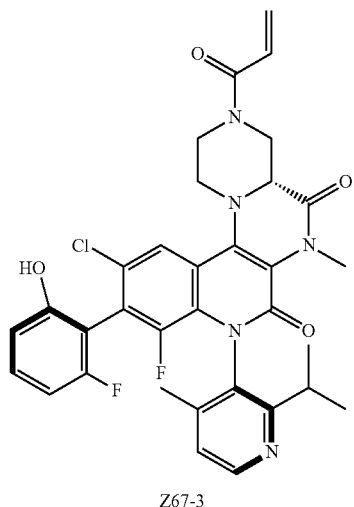
Z67-3 | |
| | 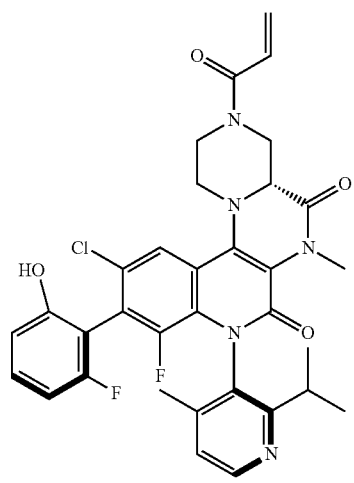
Z67-4 | |
| 68 | 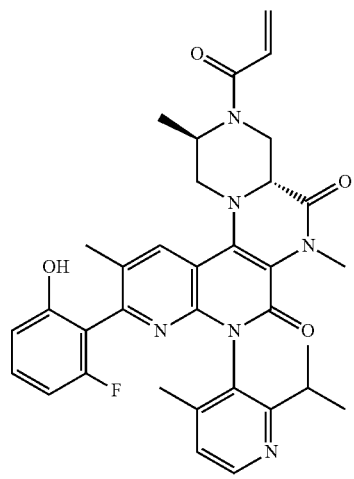
Z68 | 611.3 |
-continued
| Example No. | Structure and No. of Compound | ES-API: [M + H]+ |
|---|---|---|
| | 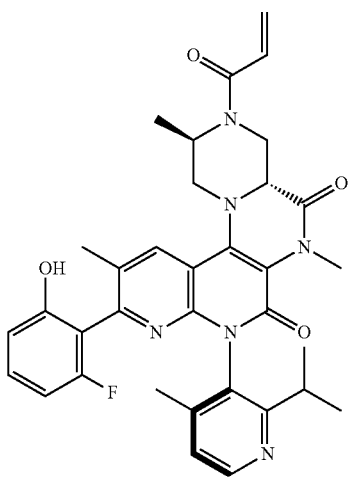
Z68-1 | |
| | 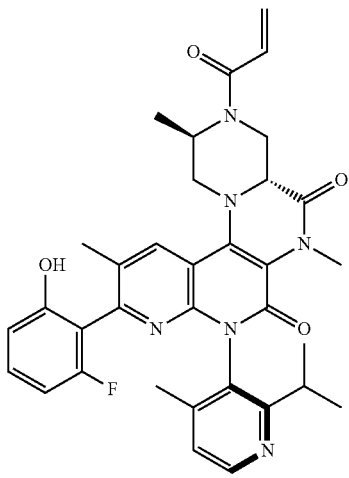
Z68-2 | |

415
-continued
| Example No. | Structure and No. of Compound | ES-API: [M + H]+ |
|---|---|---|
| 69 | 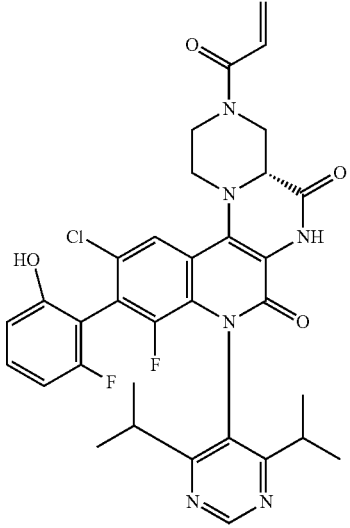 Z69 | 649.2 |
| | Z69-1 | |
416
-continued
| Example No. | Structure and No. of Compound | ES-API: [M + H]+ |
|---|---|---|
| | 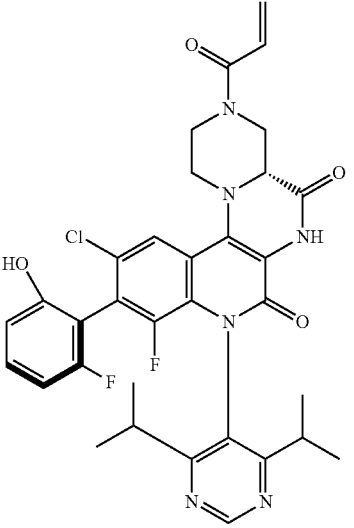 Z69-2 | |
| 70 | 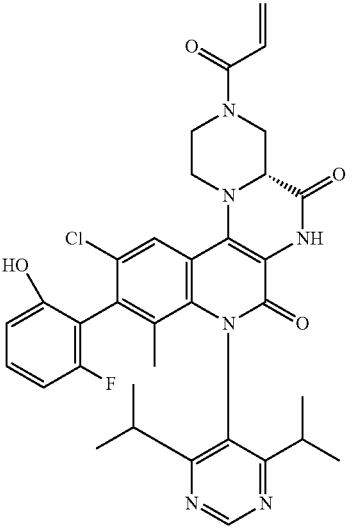 Z70 | 632.2 |

| Example No. | Structure and No. of Compound | ES-API: [M + H]⁺ |
|---|---|---|
| 71 | Z71 | 645.2 |
| | Z71-1 | |
| | Z71-2 | |
| 72 | Z72 | 642.2 |
| 73 | Z73 | 613.2 |

| Example No. | Structure and No. of Compound | ES-API: [M + H]+ |
|---|---|---|
| | 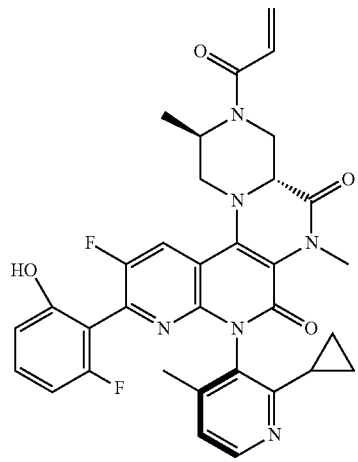
Z73-1 | |
| | 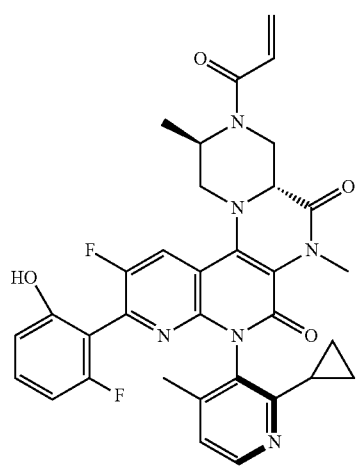
Z73-2 | |
| 74 | 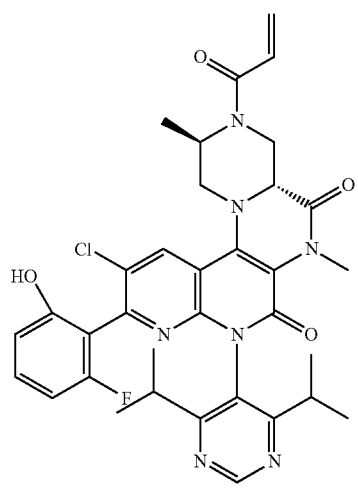
Z74 | 660.2 |
| Example No. | Structure and No. of Compound | ES-API: [M + H]+ |
|---|---|---|
| 75 | 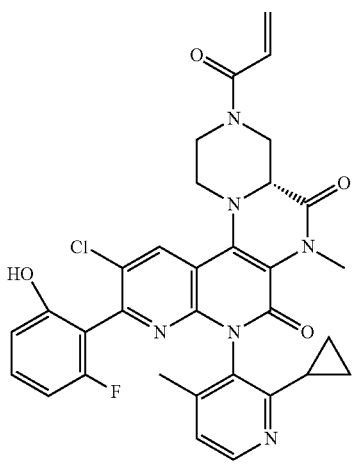
Z75 | 615.2 |
| | 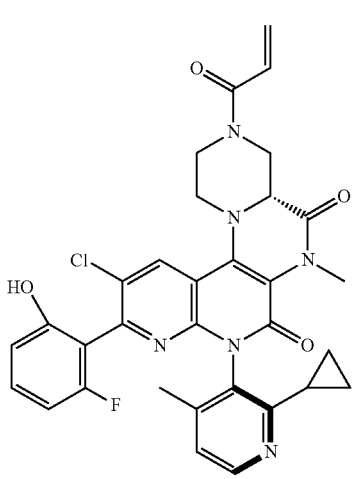
Z75-1 | |
| | 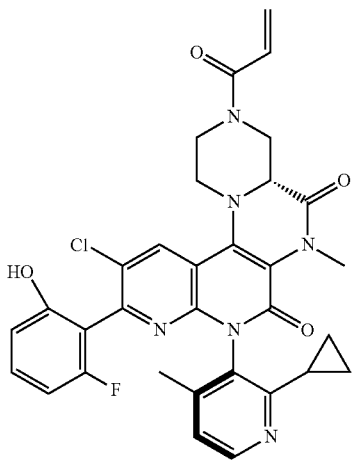
Z75-2 | |

| Example No. | Structure and No. of Compound | ES-API: [M + H]+ |
|---|---|---|
| 76 | Z76 | 629.2 |
| 76 | Z76-1 | |
| 76 | Z76-2 | |
| 77 | Z77 | 656.2 |
| 78 | Z78 | 673.2 |

| Example No. | Structure and No. of Compound | ES-API: [M + H]+ |
|---|---|---|
| | Z78-1 | |
| | Z78-2 | |

| Example No. | Structure and No. of Compound | ES-API: [M + H]+ |
|---|---|---|
| 79 | Z79 | 632.2 |
| | Z79-1 | |
| | Z79-2 | |

TABLE -continued
| Example No. | Structure and No. of Compound | ES-API: [M + H]+ |
|---|---|---|
| | 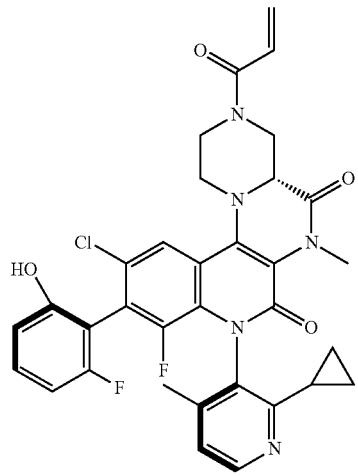<br>Z79-3 | |
| | 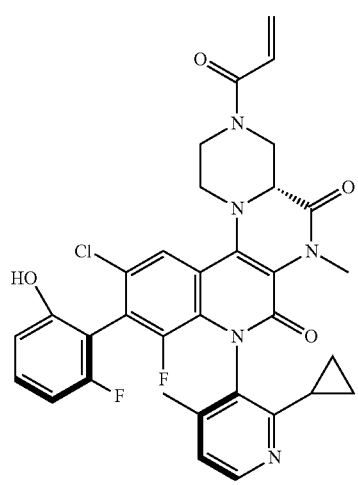<br>Z79-4 | |
| 80 | 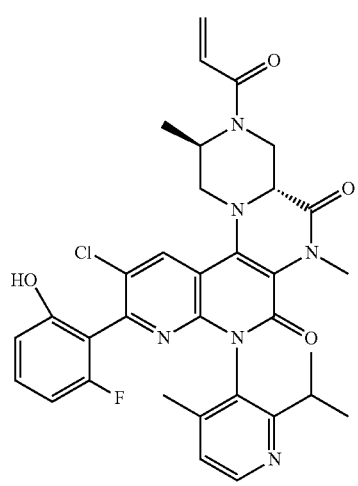<br>Z80 | 631.2 |
TABLE -continued
| Example No. | Structure and No. of Compound | ES-API: [M + H]+ |
|---|---|---|
| | 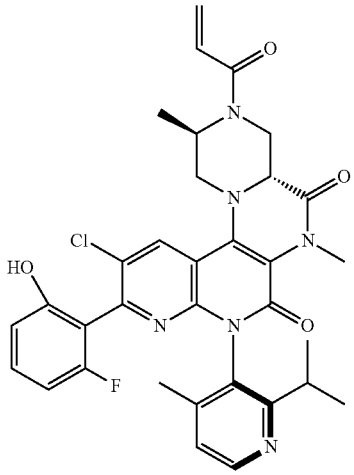<br>Z80-1 | |
| | 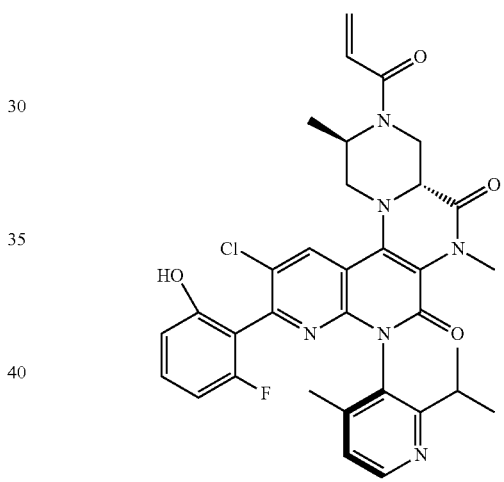<br>Z80-2 | |
| 81 | 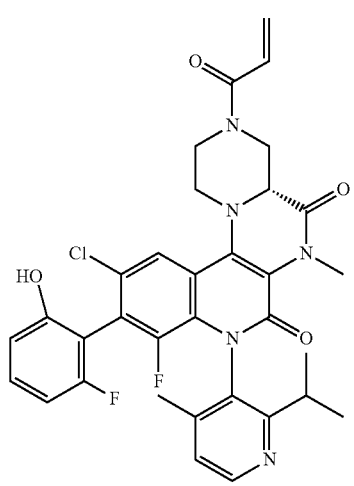<br>Z81 | 634.2 |

| Example No. | Structure and No. of Compound | ES-API: [M+H]+ |
|---|---|---|
| | 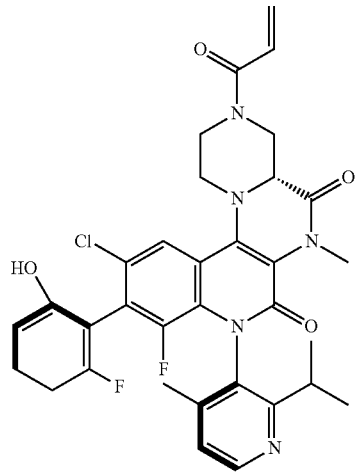 Z81-1 | |
| | 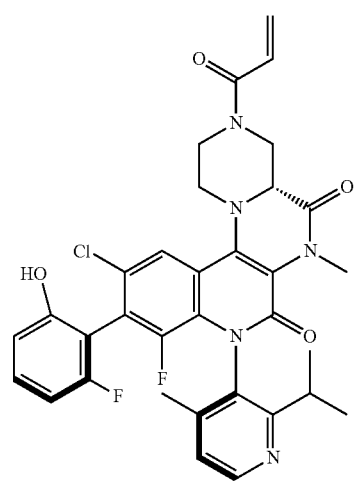 Z81-2 | |
| | 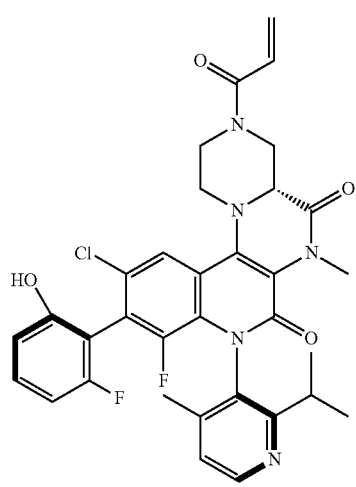 Z81-3 | |
| Example No. | Structure and No. of Compound | ES-API: [M+H]+ |
|---|---|---|
| | 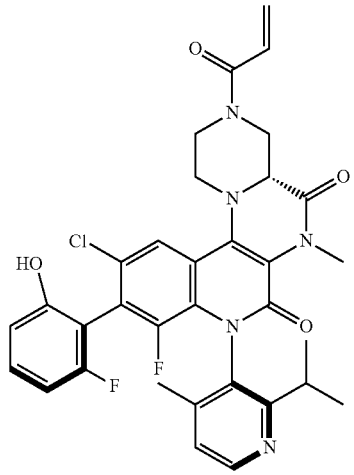 Z81-4 | |
| 82 | 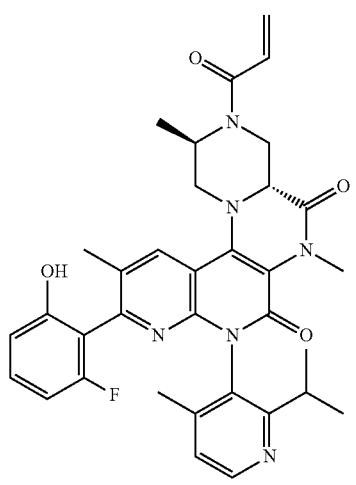 Z82 | 611.3 |
| | 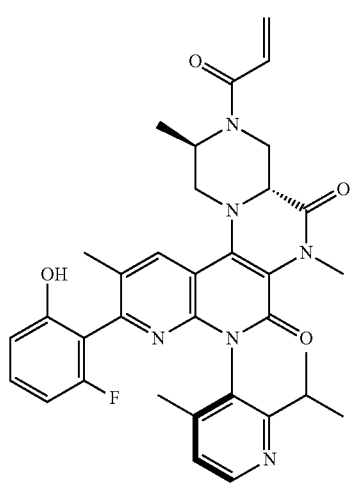 Z82-1 | |

| Example No. | Structure and No. of Compound | ES-API: [M + H]+ |
|---|---|---|
| | 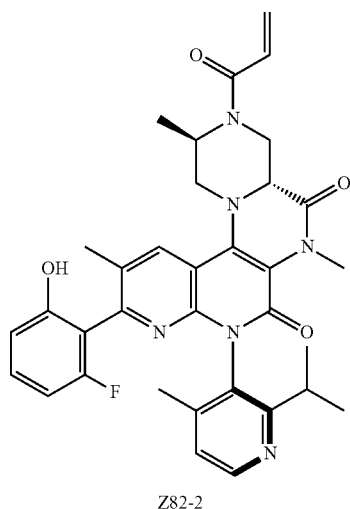
Z82-2 | |
| 83 | 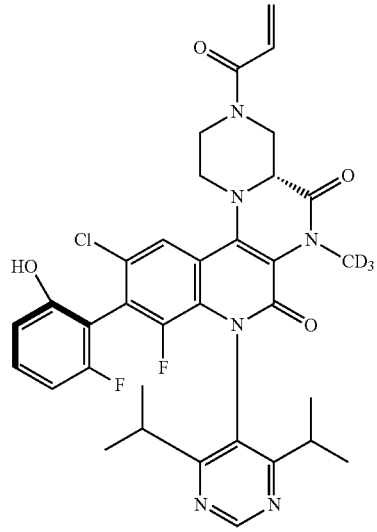
Z83 | 666.2 |
| Example No. | Structure and No. of Compound | ES-API: [M + H]+ |
|---|---|---|
| | 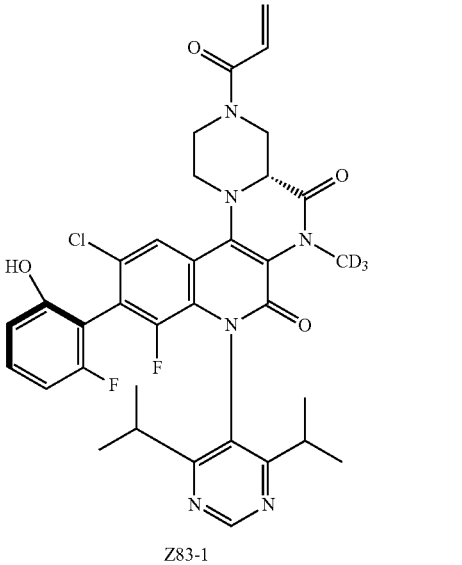
Z83-1 | |
| | 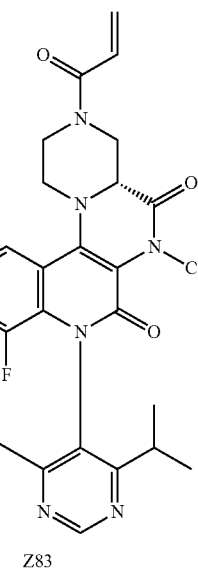
Z83-2 | |

| Example No. | Structure and No. of Compound | ES-API: [M + H]+ |
|---|---|---|
| 84 | Z84 | 649.2 |
| 85 | Z85 | 662.2 |

| Example No. | Structure and No. of Compound | ES-API: [M + H]+ |
|---|---|---|
| | Z85-1 | |
| | Z85-2 | |

| Example No. | Structure and No. of Compound | ES-API: [M + H]+ |
|---|---|---|
| 86 | 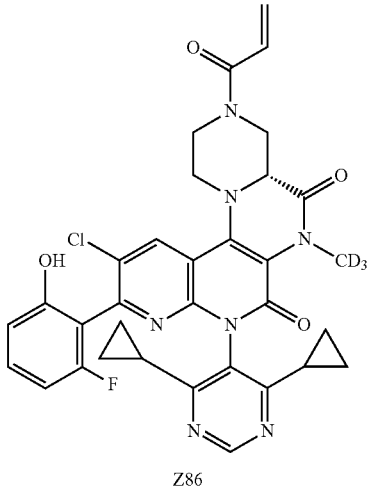 [SMILES: [2H]C([2H])([2H])N1C(=O)[C@H]2CN(C(=O)C=C)CCN2c2c1c(=O)n(-c1c(C3CC3)ncnc1C1CC1)c1nc(-c3c(O)cccc3F)c(Cl)cc21]<br>Z86 | 645.2 |
| 87 | 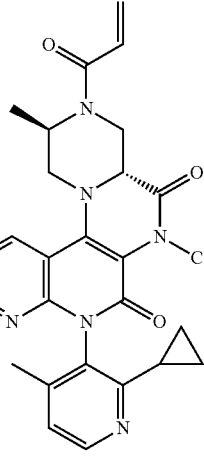<br>Z87 | 616.2 |
| | 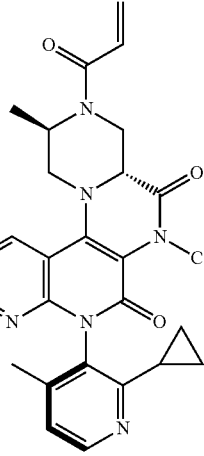<br>Z87-1 | |
| Example No. | Structure and No. of Compound | ES-API: [M + H]+ |
|---|---|---|
| | 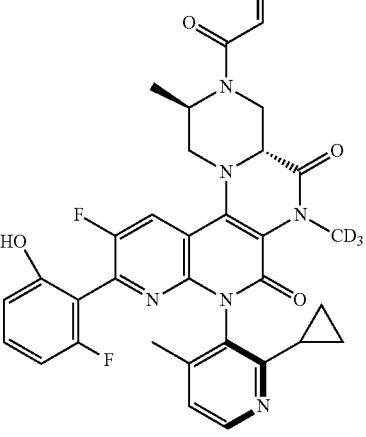<br>Z87-2 | |
| 88 | 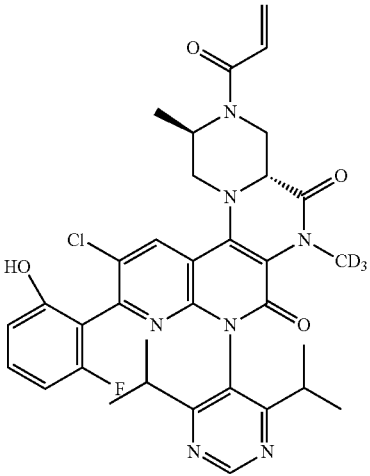<br>Z88 | 663.3 |
| 89 | 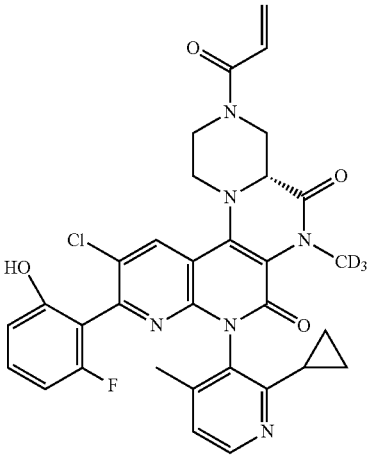<br>Z89 | 618.2 |

| Example No. | Structure and No. of Compound | ES-API: [M + H]+ |
|---|---|---|
| | 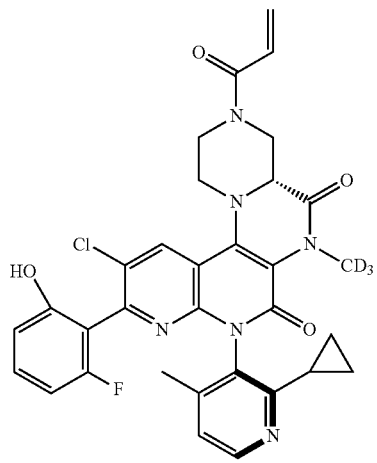<br>Z89-1 | |
| | 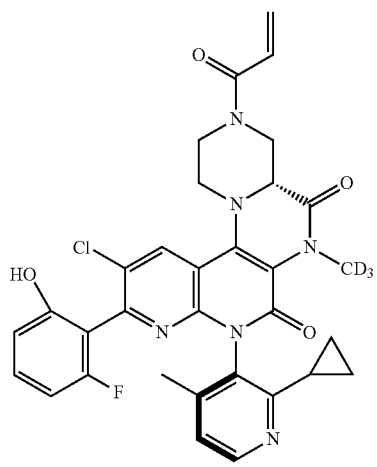<br>Z89-2 | |
| 90 | 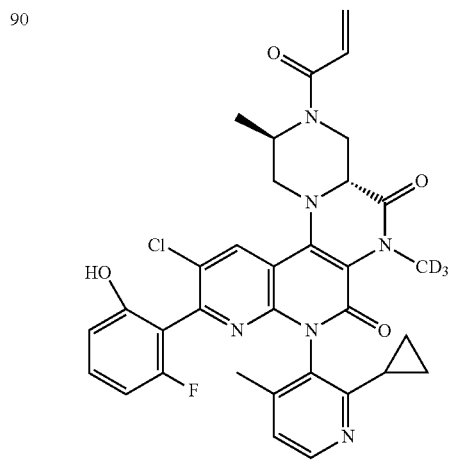<br>Z90 | 632.2 |
| Example No. | Structure and No. of Compound | ES-API: [M + H]+ |
|---|---|---|
| | 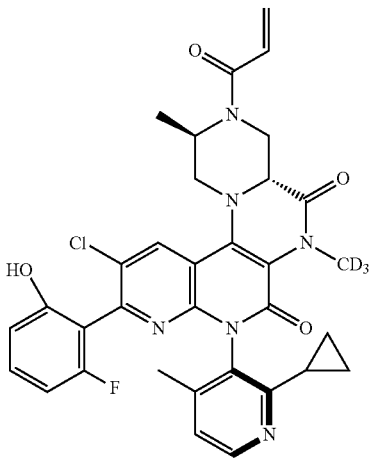<br>Z90-1 | |
| | 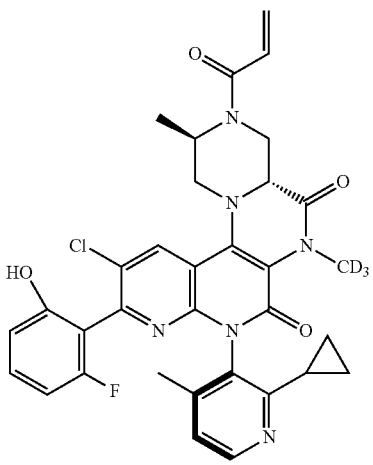<br>Z90-2 | |
| 91 | 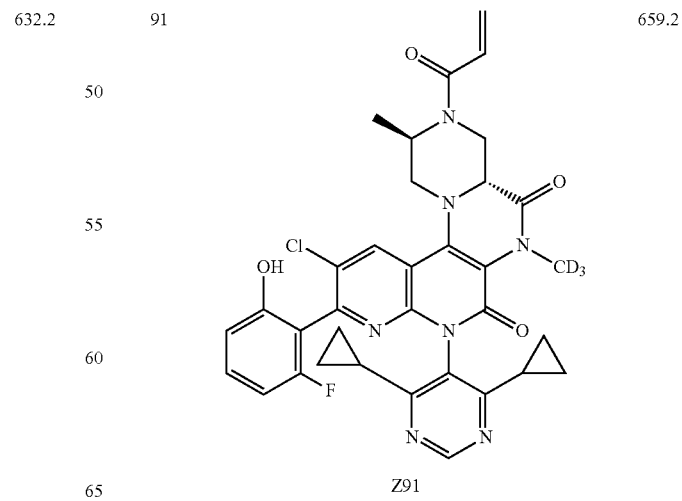<br>Z91 | 659.2 |

-continued
| Example No. | Structure and No. of Compound | ES-API: [M + H]+ |
|---|---|---|
| 92 | Z92 | 676.2 |
| | Z92-1 | |
| | Z92-2 | |
| 93 | Z93 | 635.2 |
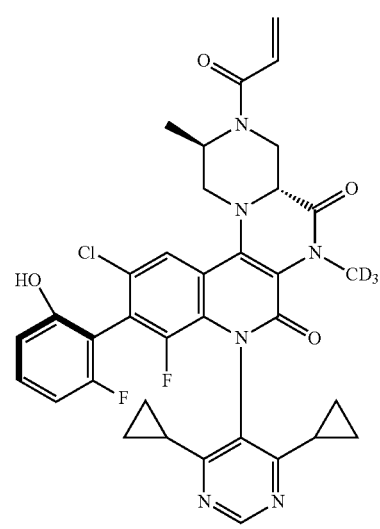
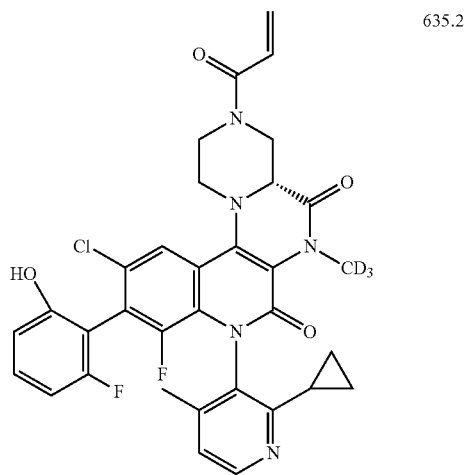

| Example No. | Structure and No. of Compound | ES-API: [M + H]+ |
|---|---|---|
| | 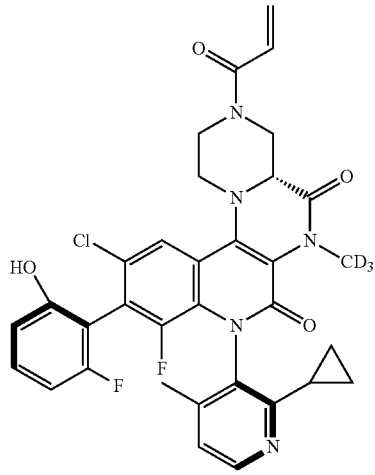
Z93-1 | |
| | 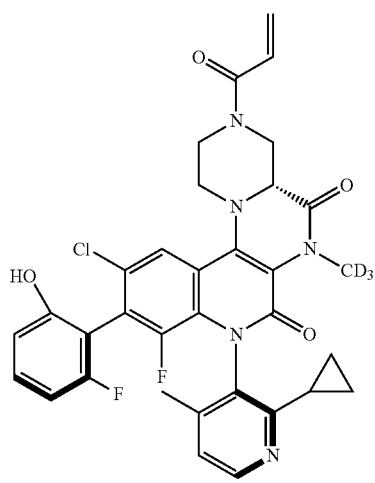
Z93-2 | |
| | 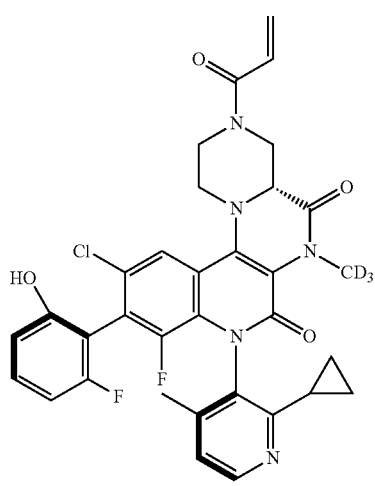
Z93-3 | |
| Example No. | Structure and No. of Compound | ES-API: [M + H]+ |
|---|---|---|
| | 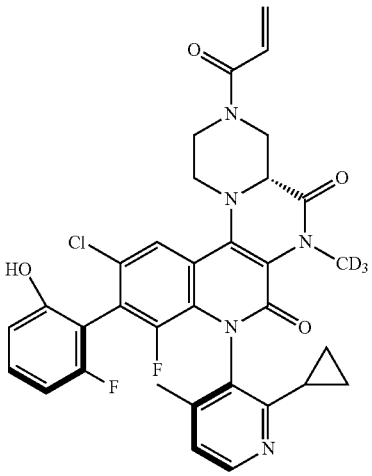
Z93-4 | |
| 94 | 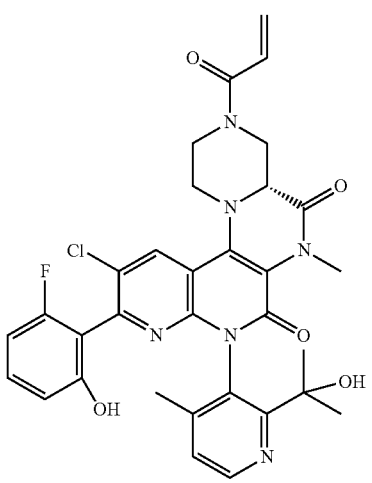
Z94 | 633.2 |
| | 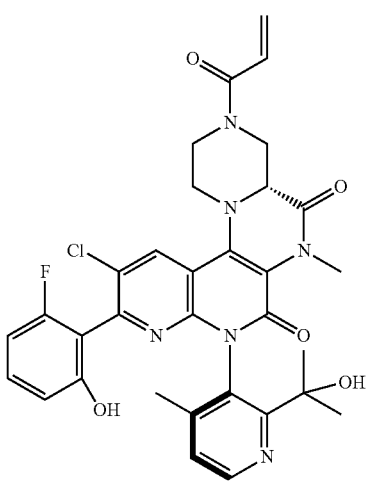
Z94-1 | |

441
-continued
| Example No. | Structure and No. of Compound | ES-API: [M + H]+ |
|---|---|---|
| | 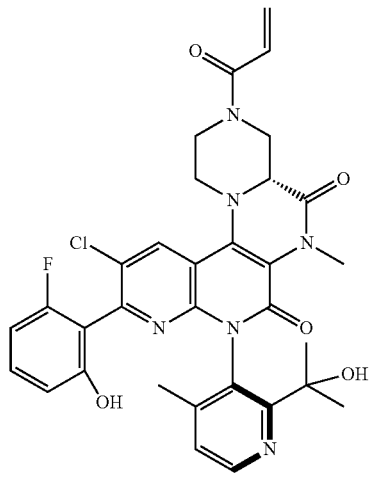Z94-2 | |
| 95 | 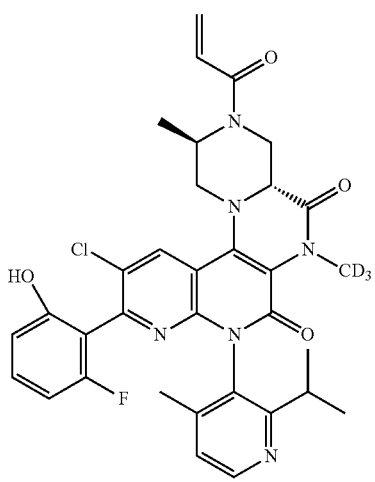Z95 | 634.2 |
| | 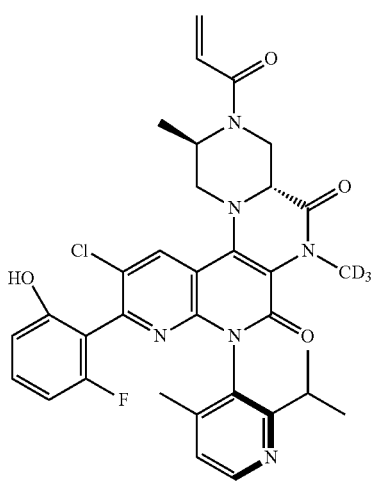Z95-1 | |
442
-continued
| Example No. | Structure and No. of Compound | ES-API: [M + H]+ |
|---|---|---|
| | 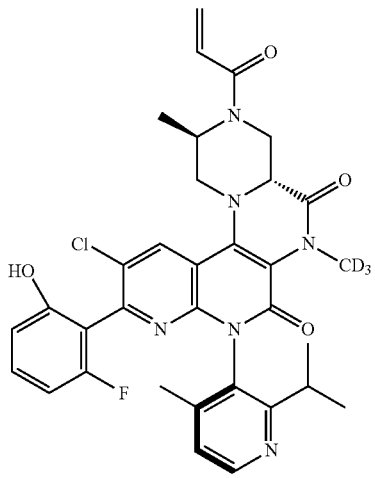Z95-2 | |
| 96 | 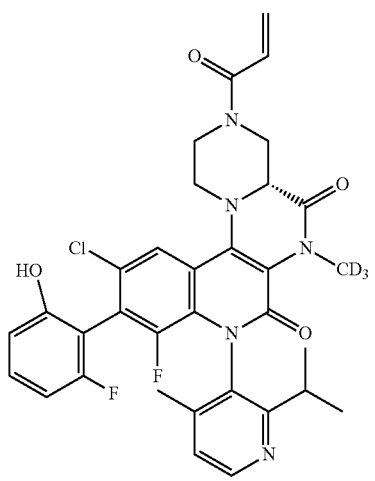Z96 | 637.2 |
| | 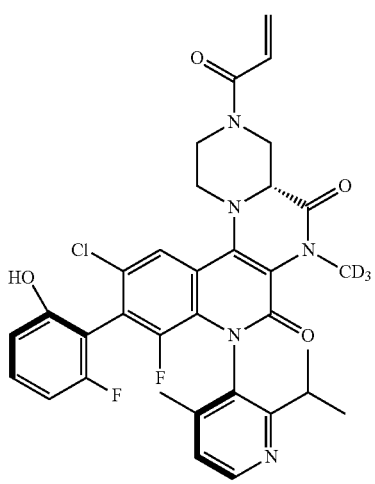Z96-1 | |

| Example No. | Structure and No. of Compound | ES-API: [M + H]+ |
|---|---|---|
| | 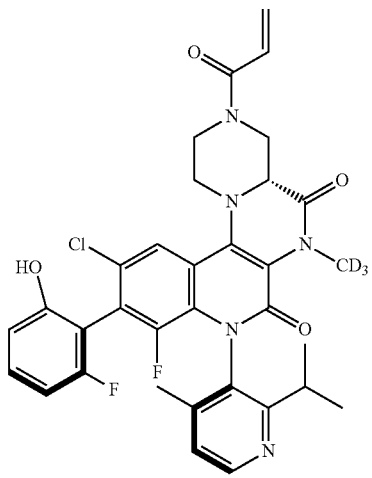<br>Z96-2 | |
| | 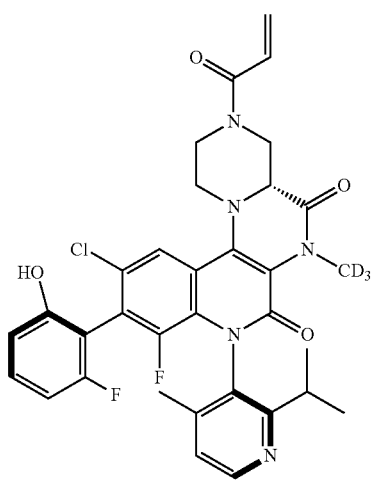<br>Z96-3 | |
| | 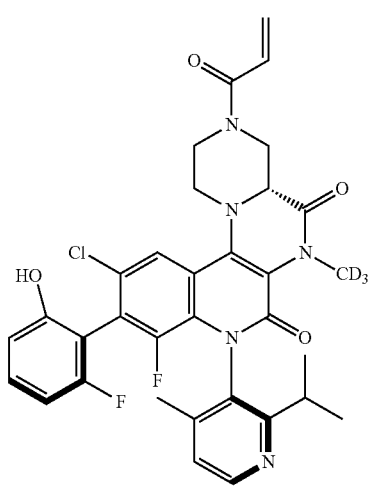<br>Z96-4 | |
| Example No. | Structure and No. of Compound | ES-API: [M + H]+ |
|---|---|---|
| 97 | 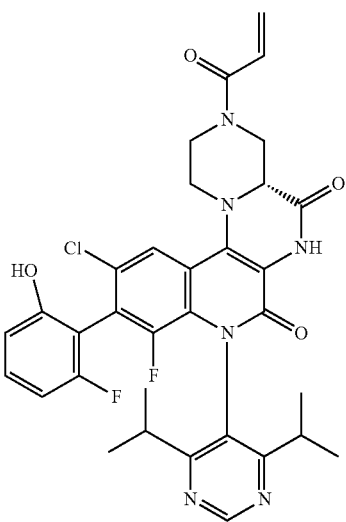<br>Z97 | 649.2 |
| | 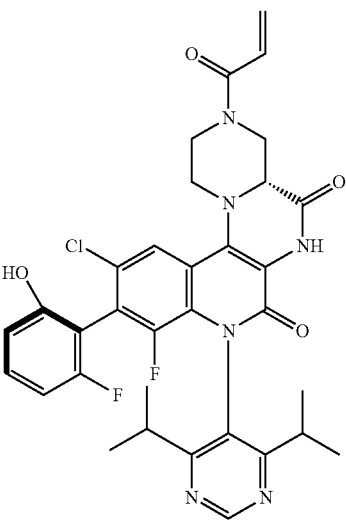<br>Z97-1 | |

| Example No. | Structure and No. of Compound | ES-API: [M + H]+ |
|---|---|---|
| | Z97-2 | |
| 98 | Z98 | 632.2 |
| 99 | Z99 | 645.2 |
| | Z99-1 | |

| Example No. | Structure and No. of Compound | ES-API: [M + H]+ |
|---|---|---|
| | Z99-2 | |
| 100 | Z100 | 628.2 |
| 101 | Z101 | 599.2 |

| Example No. | Structure and No. of Compound | ES-API: [M + H]+ |
|---|---|---|
| | Z101-1 | |
| | Z101-2 | |
| 102 | Z102 | 646.2 |

| Example No. | Structure and No. of Compound | ES-API: [M + H]⁺ |
|---|---|---|
| 103 | Z103 | 601.2 |
| | Z103-1 | |
| | Z103-2 | |
| 104 | Z104 | 615.2 |
| | Z104-1 | |
| | Z104-2 | |

| Example No. | Structure and No. of Compound | ES-API: [M + H]+ |
|---|---|---|
| 105 | Z105 | 656.2 |
| 106 | Z106 | 642.2 |
| 107 | Z107 | 659.2 |
| 107 | Z107-1 | |
| 107 | Z107-2 | |
| 108 | Z108 | 618.2 |

| Example No. | Structure and No. of Compound | ES-API: [M + H]+ |
|---|---|---|
| | 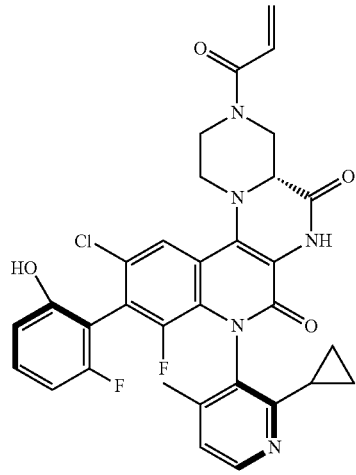
Z108-1 | |
| | 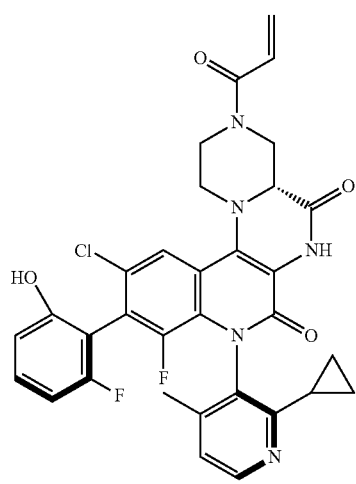
Z108-2 | |
| | 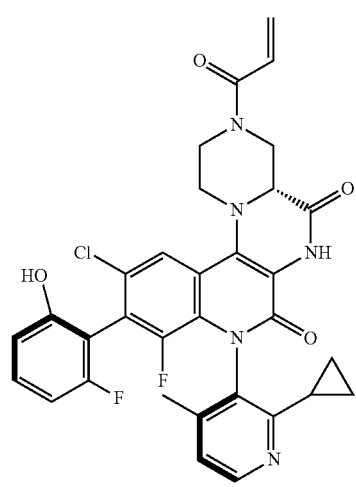
Z108-3 | |
| Example No. | Structure and No. of Compound | ES-API: [M + H]+ |
|---|---|---|
| | 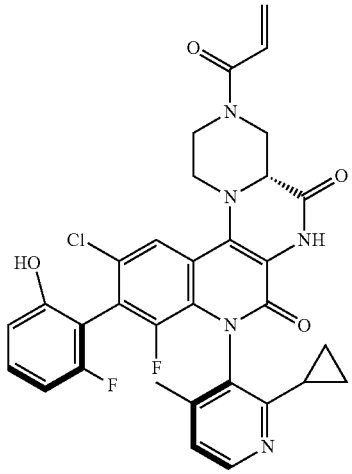
Z108-4 | |
| 109 | 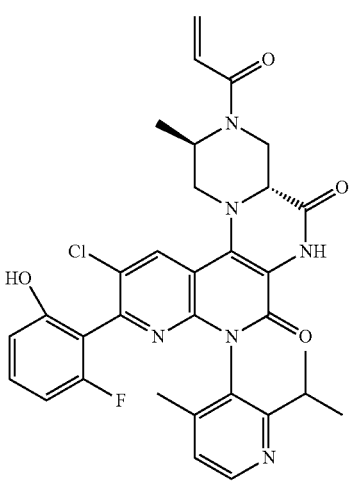
Z109 | 617.2 |
| | 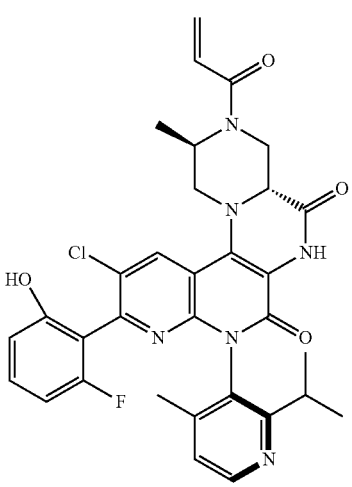
Z109-1 | |

| Example No. | Structure and No. of Compound | ES-API: [M+H]+ |
|---|---|---|
| | 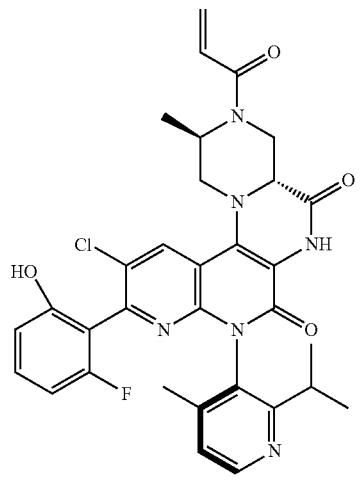Z109-2 | |
| 110 | 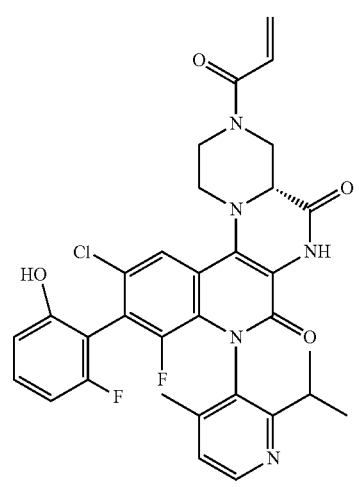Z110 | 620.2 |
| | 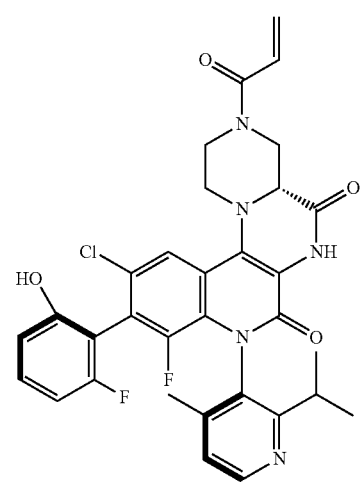Z110-1 | |
| Example No. | Structure and No. of Compound | ES-API: [M+H]+ |
|---|---|---|
| | 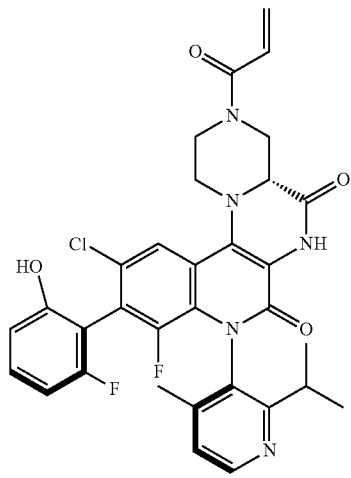Z110-2 | |
| | 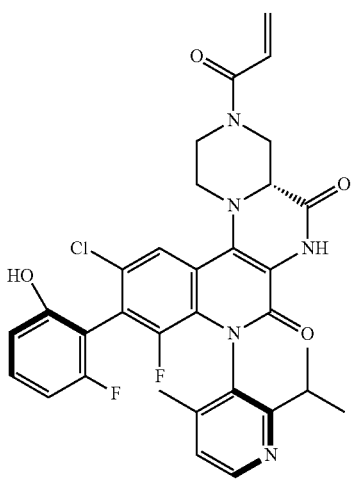Z110-3 | |
| | 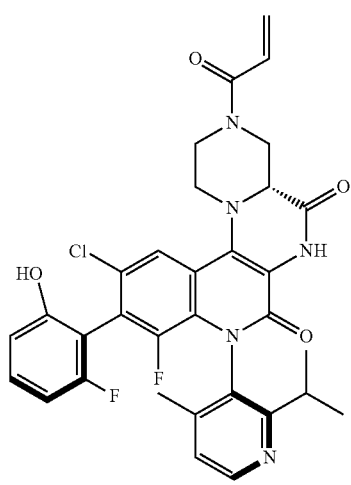Z110-4 | |

| Example No. | Structure and No. of Compound | ES-API: [M + H]+ |
|---|---|---|
| 111 | Z111 | 658.3 |
| 112 | Z112 | 629.3 |
| | Z112-1 | |
| | Z112-2 | |
| 113 | Z113 | 627.2 |

459
-continued
| Example No. | Structure and No. of Compound | ES-API: [M + H]+ |
|---|---|---|
| | 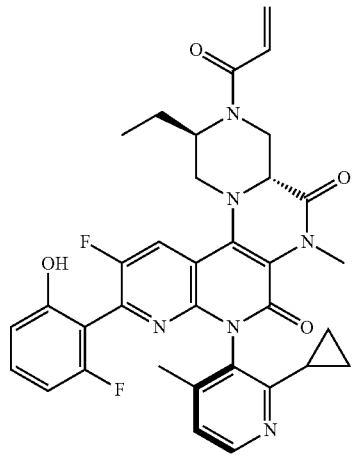<br>Z113-1 | |
| | 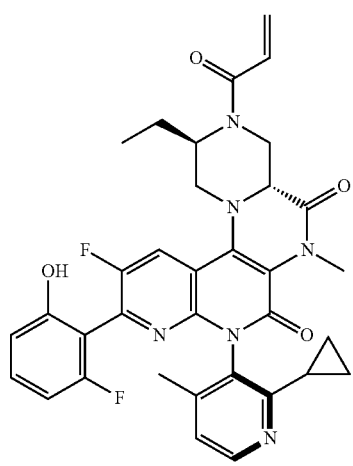<br>Z113-2 | |
| 114 | 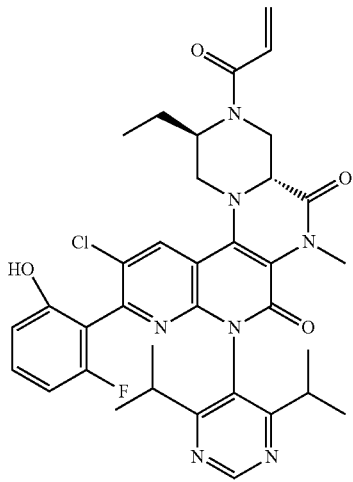<br>Z114 | 674.3 |
460
-continued
| Example No. | Structure and No. of Compound | ES-API: [M + H]+ |
|---|---|---|
| 115 | 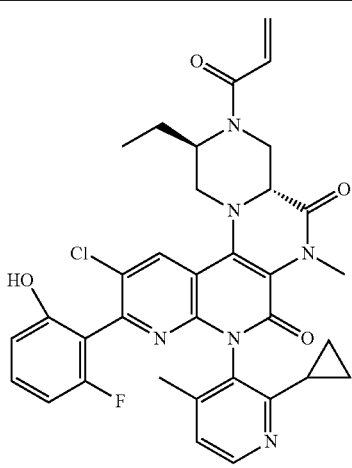<br>Z115 | 643.2 |
| | 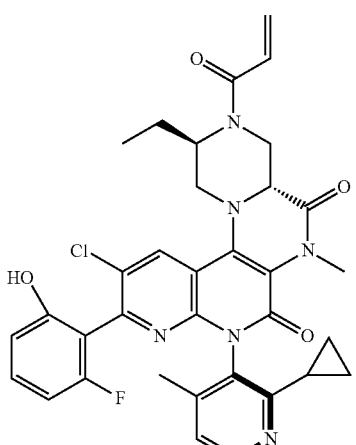<br>Z115-1 | |
| | 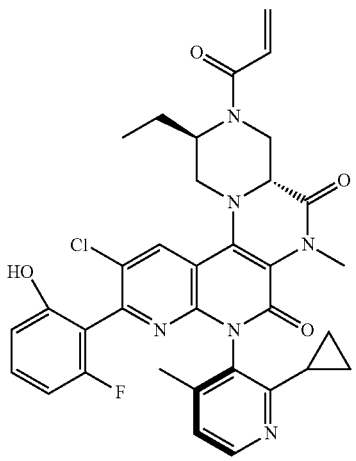<br>Z115-2 | |

-continued
| Example No. | Structure and No. of Compound | ES-API: [M + H]+ |
|---|---|---|
| 116 | 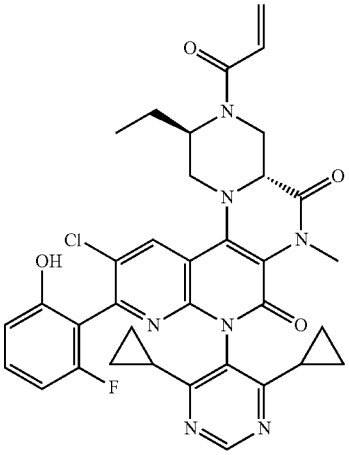<br>Z116 | 670.2 |
| 117 | 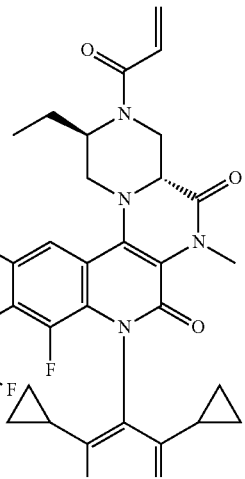<br>Z117 | 687.2 |
-continued
| Example No. | Structure and No. of Compound | ES-API: [M + H]+ |
|---|---|---|
| | 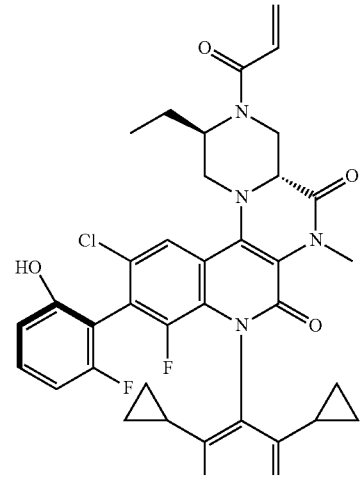<br>Z117-1 | |
| | 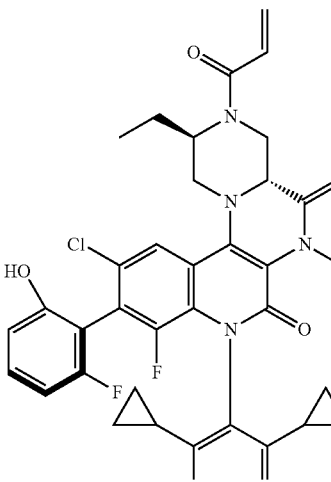<br>Z117-2 | |

-continued
| Example No. | Structure and No. of Compound | ES-API: [M + H]+ |
|---|---|---|
| 118 | 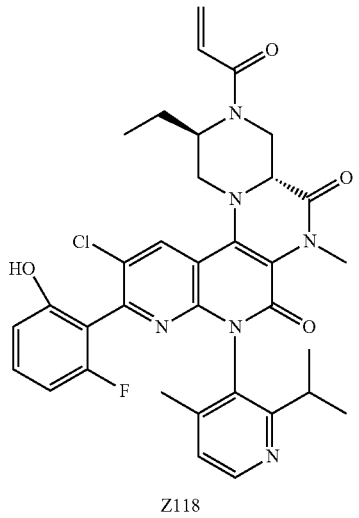 [SMILES: C=CC(=O)N1C[C@@H]2C(=O)N(C)c3c(c4cc(Cl)c(-c5c(O)cccc5F)nc4n(-c4c(C)ccnc4C(C)C)c3=O)N2C[C@H]1CC]<br>Z118 | 645.2 |
| | 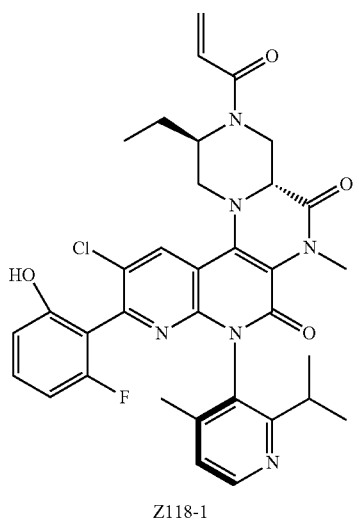<br>Z118-1 | |
| | 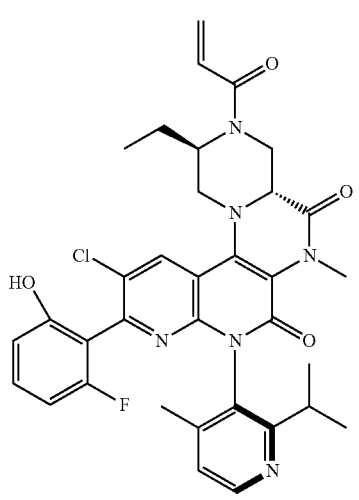<br>Z118-2 | |
-continued
| Example No. | Structure and No. of Compound | ES-API: [M + H]+ |
|---|---|---|
| 119 | 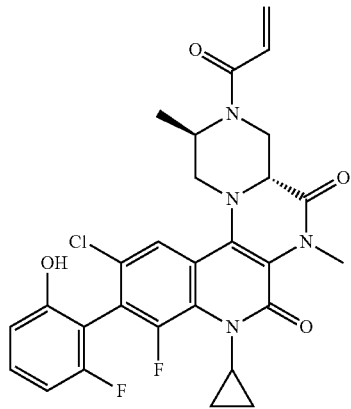<br>Z119 | 555.2 |
| | 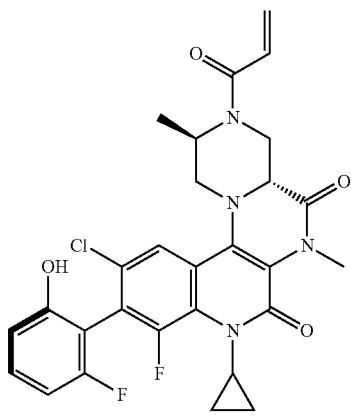<br>Z119-1 | |
| | 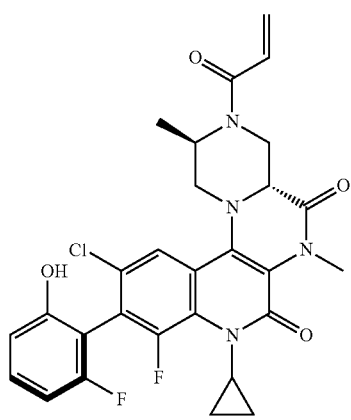<br>Z119-2 | |

| Example No. | Structure and No. of Compound | ES-API: [M + H]+ |
|---|---|---|
| 120 | Z120 | 541.1 |
| | Z120-1 | |
| | Z120-2 | |
| Example No. | Structure and No. of Compound | ES-API: [M + H]+ |
|---|---|---|
| 121 | Z121 | 558.2 |
| | Z121-1 | |
| | Z121-2 | |
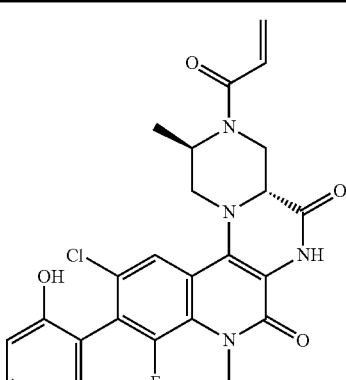

-continued
| Example No. | Structure and No. of Compound | ES-API: [M + H]+ |
|---|---|---|
| 122 | 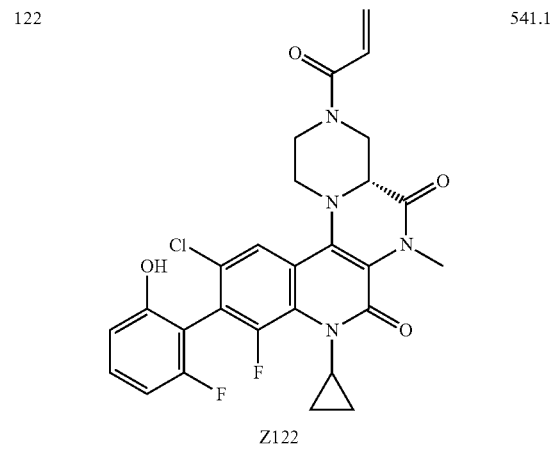 Z122 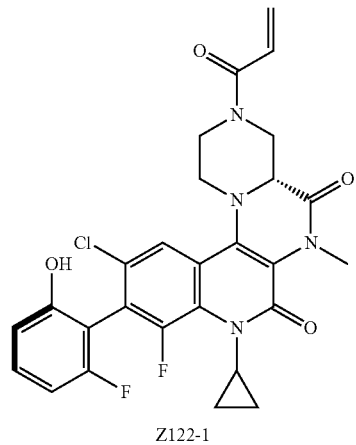 Z122-1 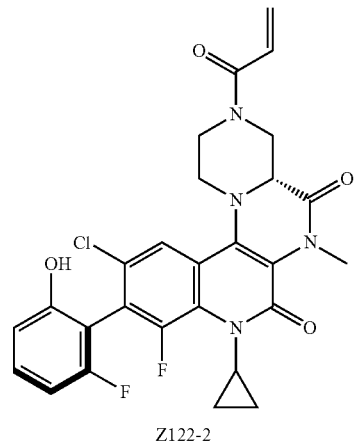 Z122-2 | 541.1 |
| 123 | 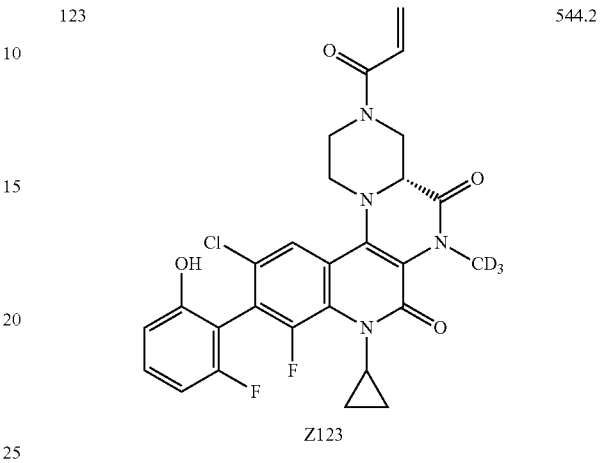 Z123 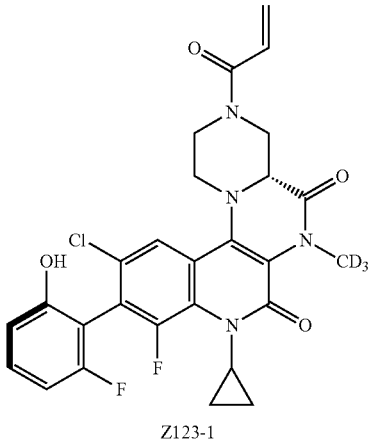 Z123-1 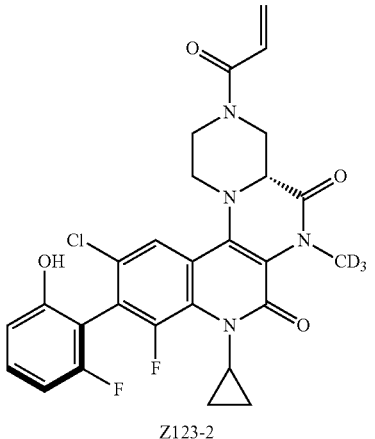 Z123-2 | 544.2 |

-continued

| Example No. | Structure and No. of Compound | ES-API: [M + H]+ |
|---|---|---|
| 124 | Z124 | 527.1 |
| | Z124-1 | |
| | Z124-2 | |

-continued

| Example No. | Structure and No. of Compound | ES-API: [M + H]+ |
|---|---|---|
| 125 | Z125 | 524.1 |
| 126 | Z126 | 510.1 |
| 127 | Z127 | 527.2 |

US 12,054,497 B2

471
-continued

| Example No. | Structure and No. of Compound | ES-API: [M + H]+ |
|---|---|---|
| 128 | Z128 | 538.2 |
| 129 | Z129 | 524.1 |
| 130 | Z130 | 541.2 |

472
-continued

| Example No. | Structure and No. of Compound | ES-API: [M + H]+ |
|---|---|---|
| 131 | Z131 | 560.1 |
| | Z131-1 | |
| | Z131-2 | |

-continued

| Example No. | Structure and No. of Compound | ES-API: [M + H]⁺ |
|---|---|---|
| 132 | Z132 | 546.1 |
| | Z132-1 | |
| | Z132-2 | |
| 133 | Z133 | 563.1 |
| | Z133-1 | |
| | Z133-2 | |

| Example No. | Structure and No. of Compound | ES-API: [M + H]+ |
|---|---|---|
| 134 | Z134 | 574.1 |
| | Z134-1 | |
| | Z134-2 | |
| 135 | Z135 | 560.2 |
| | Z135-1 | |
| | Z135-2 | |

-continued

| Example No. | Structure and No. of Compound | ES-API: [M + H]+ |
|---|---|---|
| 136 | Z136 | 577.2 |
| | Z136-1 | |
| | Z136-2 | |
| 137 | Z137 | 558.2 |
| | Z137-1 | |
| | Z137-2 | |

| Example No. | Structure and No. of Compound | ES-API: [M + H]+ |
|---|---|---|
| 138 | Z138 | 544.2 |
| | Z138-1 | |
| | Z138-2 | |
| 139 | Z139 | 561.2 |
| | Z139-1 | |
| | Z139-2 | |
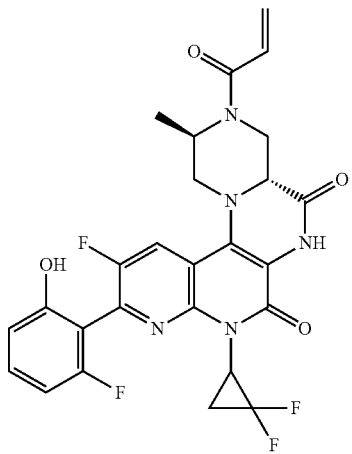

| Example No. | Structure and No. of Compound | ES-API: [M + H]+ |
|---|---|---|
| 140 | 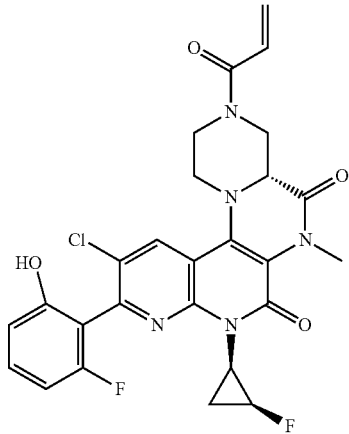 Z140 | 542.1 |
| 141 | 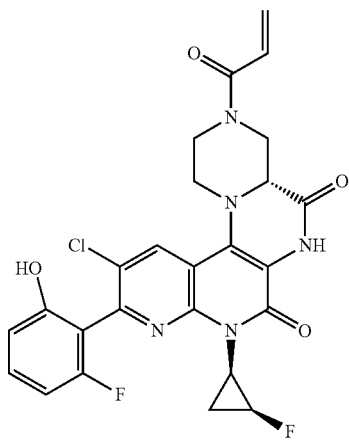 Z141 | 528.1 |
| 142 | 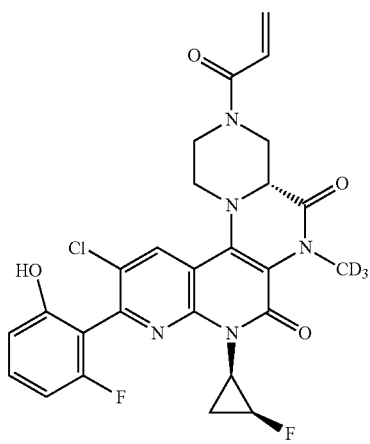 Z142 | 545.2 |
| Example No. | Structure and No. of Compound | ES-API: [M + H]+ |
|---|---|---|
| 143 | 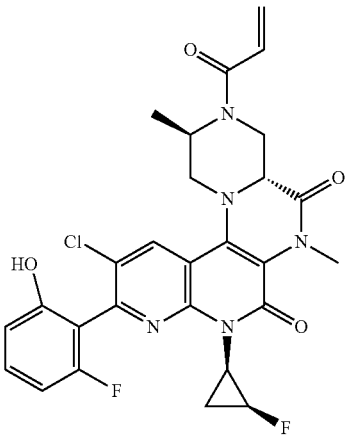 Z143 | 556.1 |
| 144 | 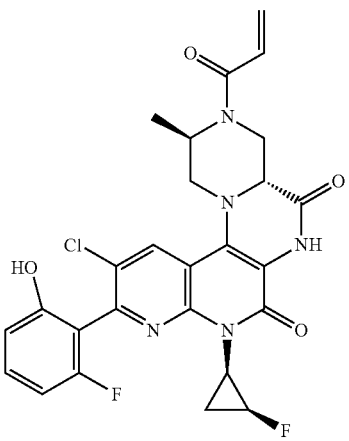 Z144 | 542.1 |
| 145 | 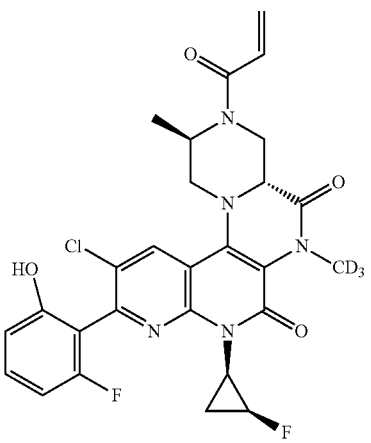 Z145 | 559.2 |

| Example No. | Structure and No. of Compound | ES-API: [M + H]+ |
|---|---|---|
| 146 | 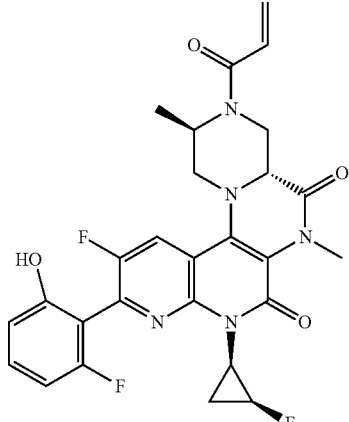<br>Z146 | 540.2 |
| 147 | 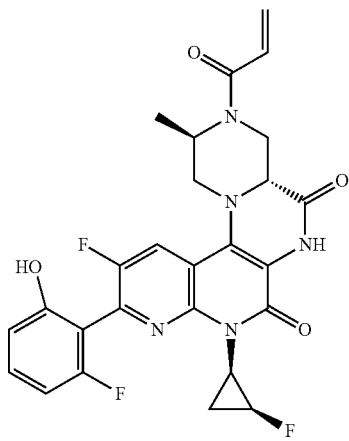<br>Z147 | 526.2 |
| 148 | 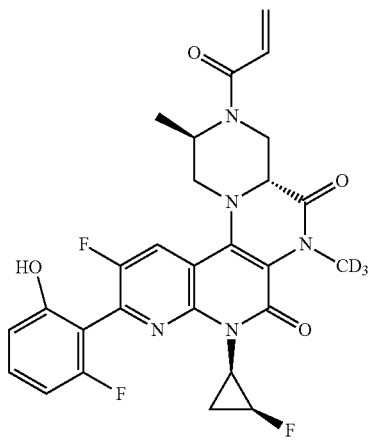<br>Z148 | 543.2 |
| Example No. | Structure and No. of Compound | ES-API: [M + H]+ |
|---|---|---|
| 149 | 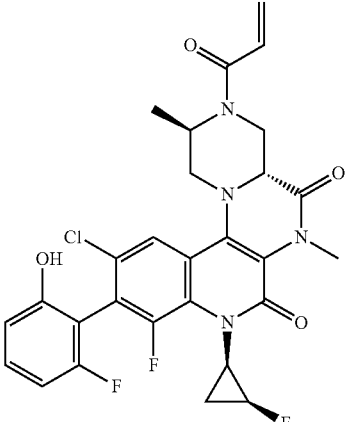<br>Z149 | 573.1 |
| | 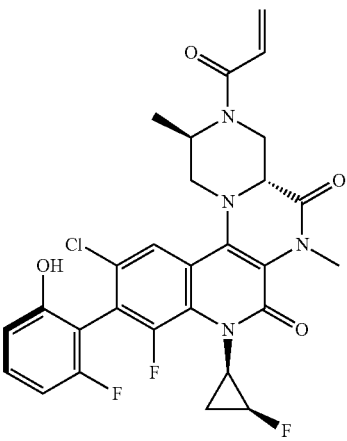<br>Z149-1 | |
| | 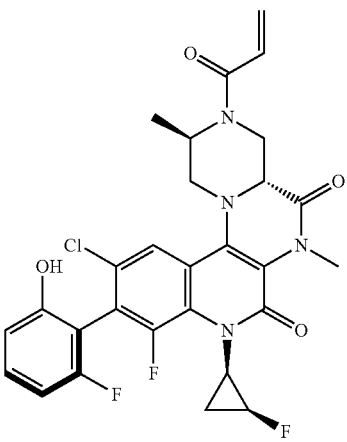<br>Z149-2 | |

| Example No. | Structure and No. of Compound | ES-API: [M + H]⁺ |
|---|---|---|
| 150 | Z150 | 559.1 |
| | Z150-1 | |
| | Z150-2 | |

| Example No. | Structure and No. of Compound | ES-API: [M + H]⁺ |
|---|---|---|
| 151 | Z151 | 576.2 |
| | Z151-1 | |
| | Z151-2 | |

| Example No. | Structure and No. of Compound | ES-API: [M + H]+ |
|---|---|---|
| 152 | 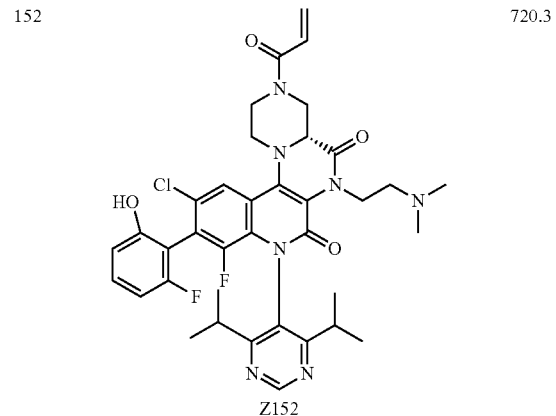 Z152 | 720.3 |
| 152 | 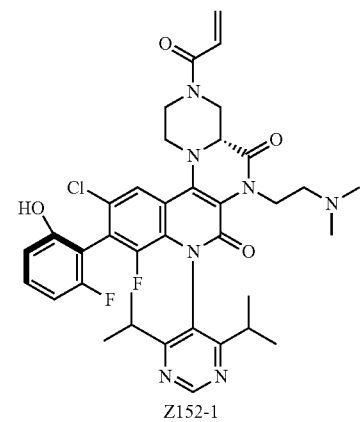 Z152-1 | |
| | 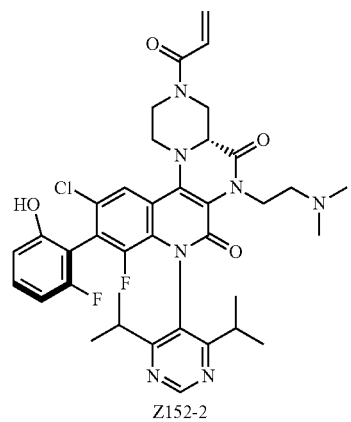 Z152-2 | |
| Example No. | Structure and No. of Compound | ES-API: [M + H]+ |
|---|---|---|
| 153 | 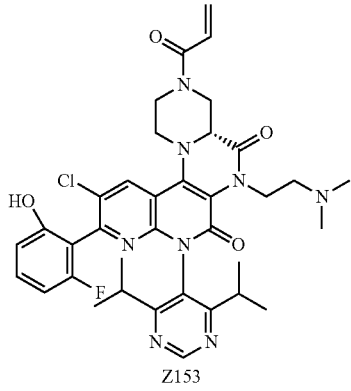 Z153 | 703.3 |
| 154 | 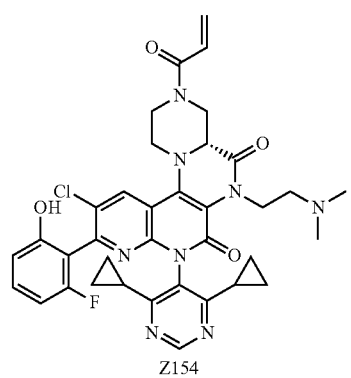 Z154 | 699.3 |
| 155 | 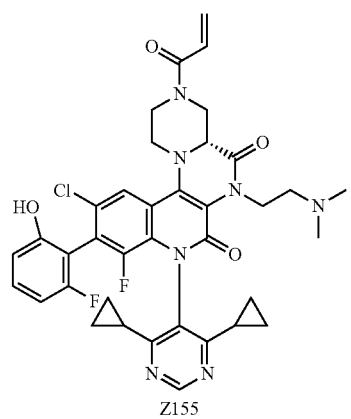 Z155 | 716.2 |

| Example No. | Structure and No. of Compound | ES-API: [M + H]+ | Example No. | Structure and No. of Compound | ES-API: [M + H]+ |
|---|---|---|---|---|---|
| | Z155-1 | | 157 | Z157 | 601.3 |
| | Z155-2 | | | Z157-1 | |
| 156 | Z156 | 630.3 | | Z157-2 | |

| Example No. | Structure and No. of Compound | ES-API: [M + H]+ |
|---|---|---|
| 158 | 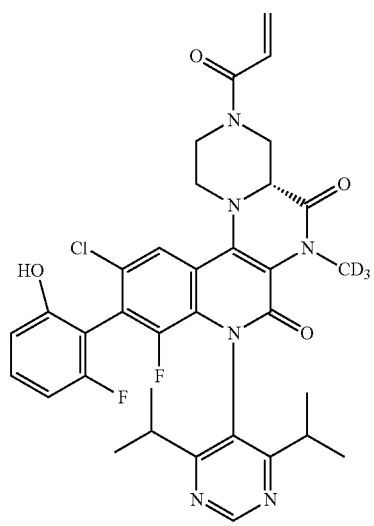<br>Z158 | 666.2 |
|  | 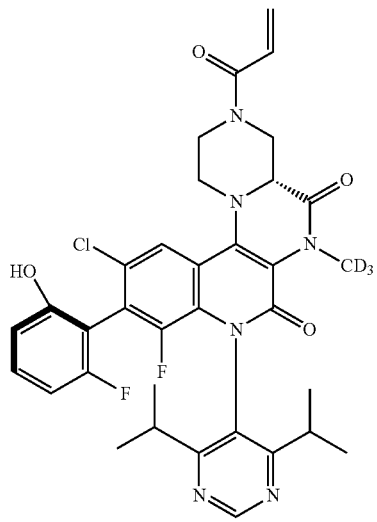<br>Z158-1 |  |
| Example No. | Structure and No. of Compound | ES-API: [M + H]+ |
|---|---|---|
|  | 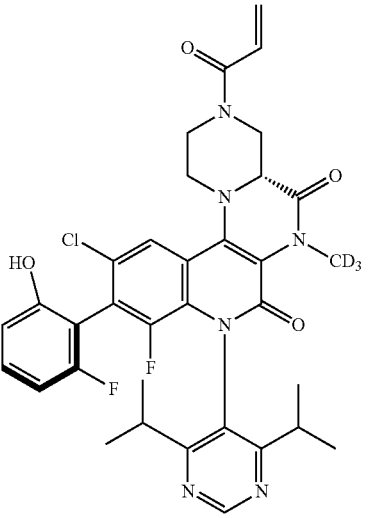<br>Z158-2 |  |
| 159 | Z159 | 635.3 |

| Example No. | Structure and No. of Compound | ES-API: [M + H]⁺ |
|---|---|---|
| 160 | Z160 | 648.2 |
| | Z160-1 | |
| 161 | Z160-2 | |
| | Z161 | 631.2 |
| 162 | Z162 | 602.3 |

| Example No. | Structure and No. of Compound | ES-API: [M + H]+ |
|---|---|---|
| | 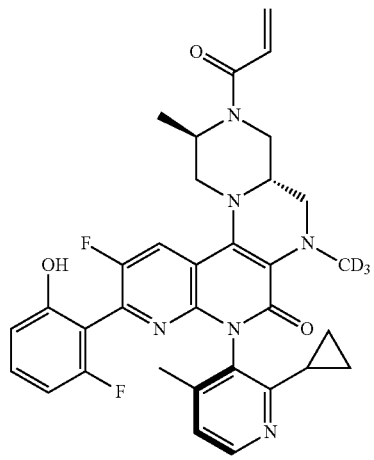
Z162-1 | |
| | 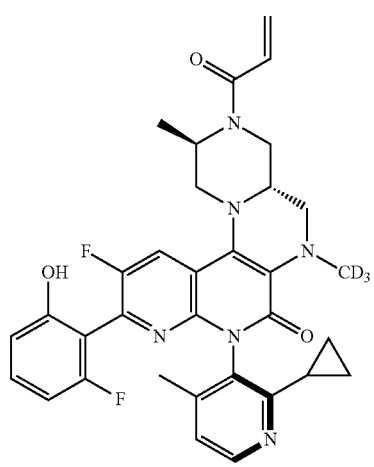
Z162-2 | |
| 163 | 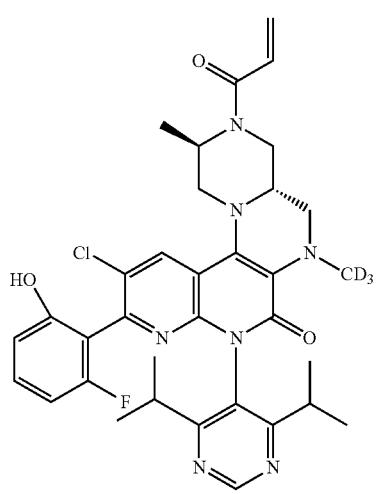
Z163 | 649.3 |
| Example No. | Structure and No. of Compound | ES-API: [M + H]+ |
|---|---|---|
| 164 | 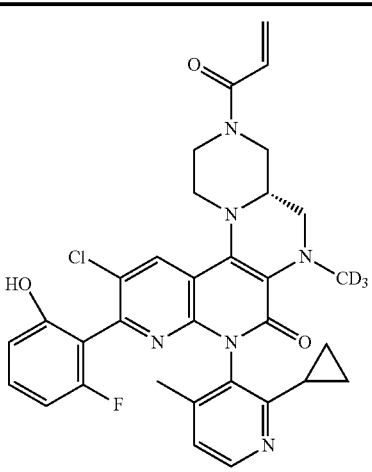
Z164 | 604.2 |
| | 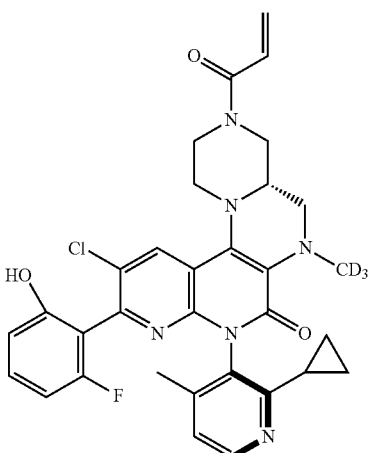
Z164-1 | |
| | 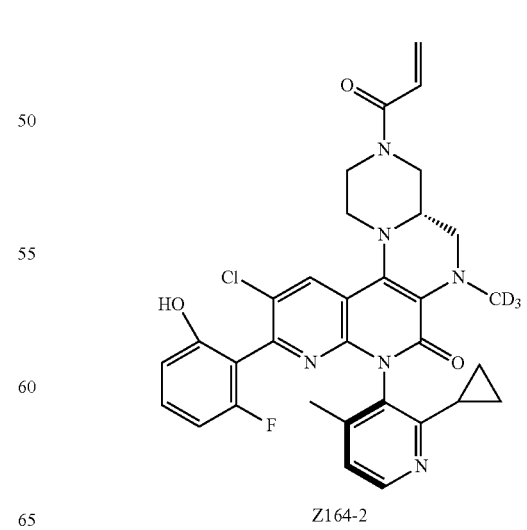
Z164-2 | |

| Example No. | Structure and No. of Compound | ES-API: [M + H]+ |
|---|---|---|
| 165 | Z165 | 618.2 |
| | Z165-1 | |
| | Z165-2 | |

| Example No. | Structure and No. of Compound | ES-API: [M + H]+ |
|---|---|---|
| 166 | Z166 | 645.3 |
| 167 | Z167 | 662.2 |

| Example No. | Structure and No. of Compound | ES-API: [M + H]+ |
|---|---|---|
| | Z167-1 | |
| | Z167-2 | |

| Example No. | Structure and No. of Compound | ES-API: [M + H]+ |
|---|---|---|
| 168 | Z168 | 621.2 |
| | Z168-1 | |
| | Z168-2 | |

TABLE-continued
| Example No. | Structure and No. of Compound | ES-API: [M + H]+ |
|---|---|---|
| | 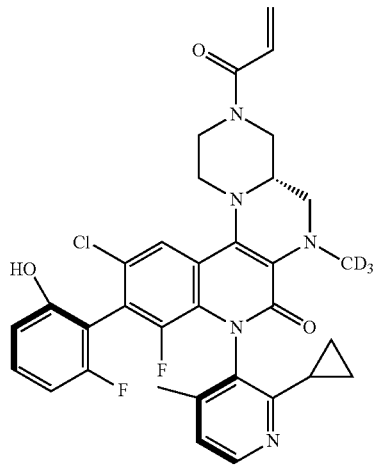Z168-3 | |
| | 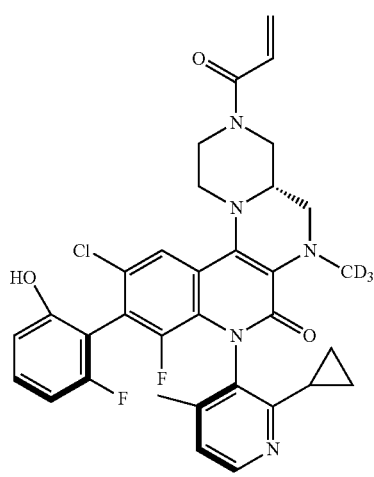Z168-4 | |
| 169 | 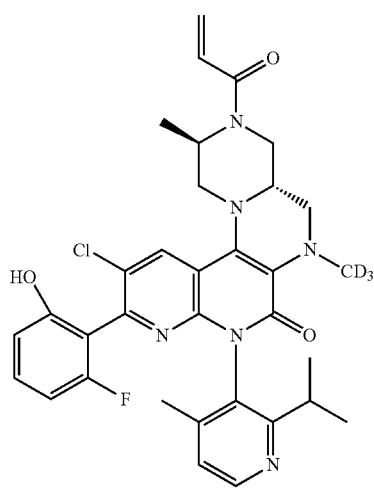Z169 | 620.3 |
TABLE-continued
| Example No. | Structure and No. of Compound | ES-API: [M + H]+ |
|---|---|---|
| | 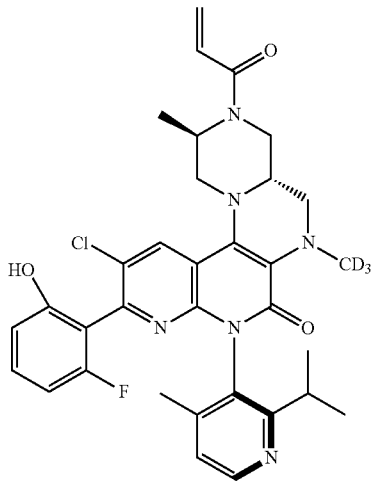Z169-1 | |
| | 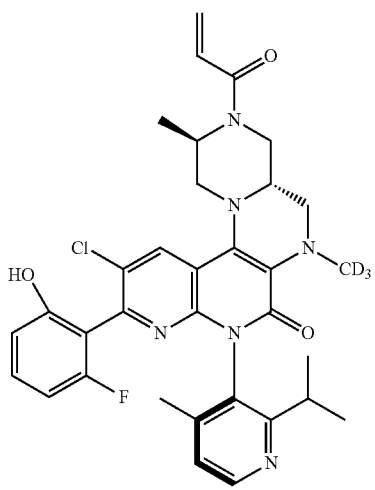Z169-2 | |
| 170 | 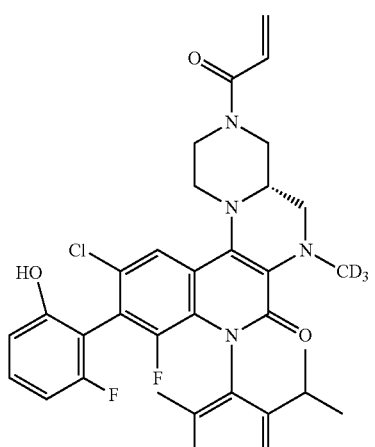Z170 | 623.2 |

| Example No. | Structure and No. of Compound | ES-API: [M + H]+ |
|---|---|---|
| | 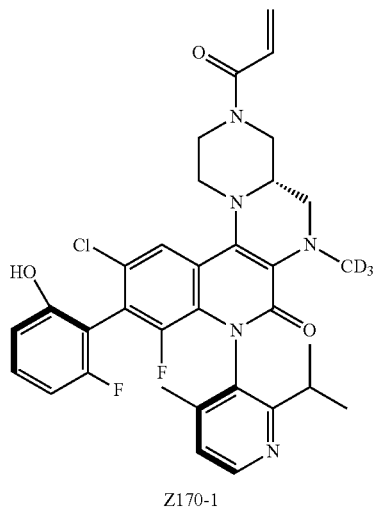<br>Z170-1 | |
| | 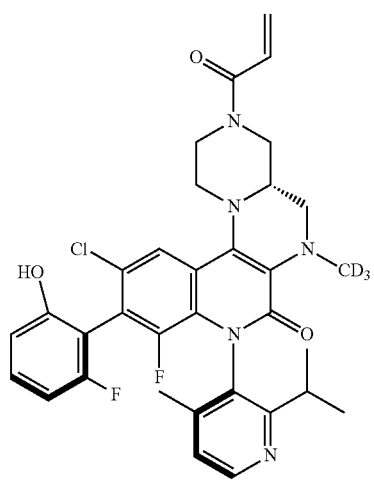<br>Z170-2 | |
| | 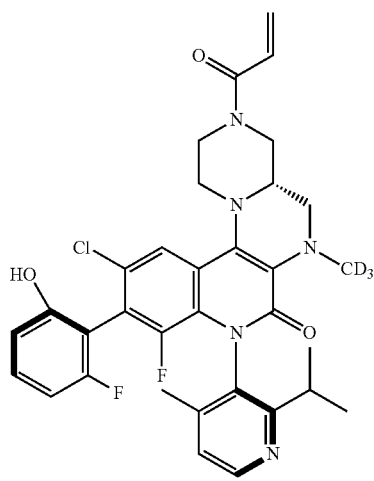<br>Z170-3 | |
| Example No. | Structure and No. of Compound | ES-API: [M + H]+ |
|---|---|---|
| | 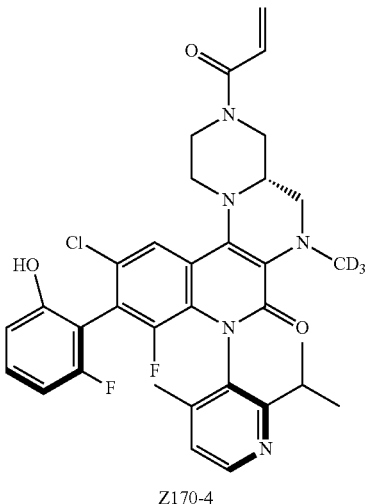<br>Z170-4 | |
| 171 | 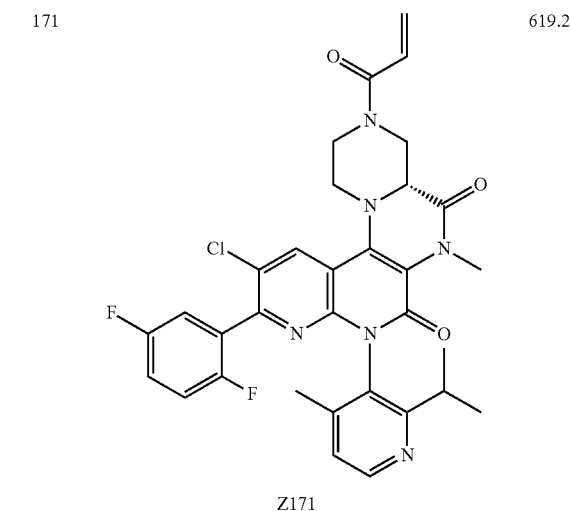<br>Z171 | 619.2 |
| | 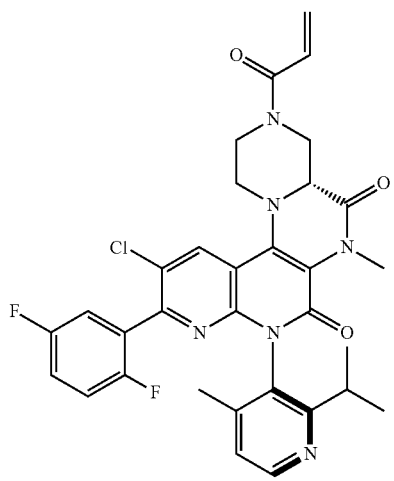<br>Z171-1 | |

-continued
| Example No. | Structure and No. of Compound | ES-API: [M + H]+ |
|---|---|---|
| | 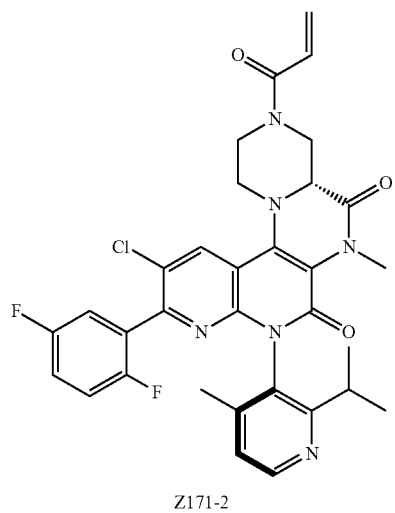<br>Z171-2 | |
| 172 | 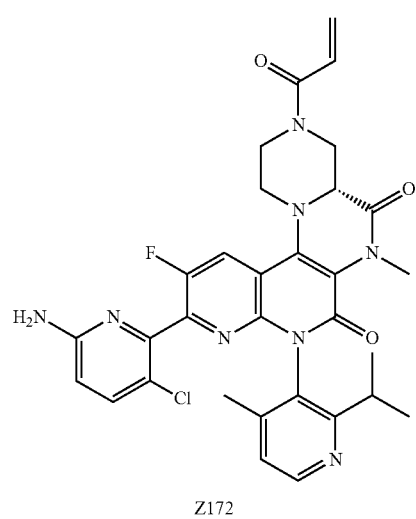 [SMILES: C=CC(=O)N1CCN2c3c(c(=O)n(-c4c(C)ccnc4C(C)C)c4nc(-c5nc(N)ccc5Cl)c(F)cc34)N(C)C(=O)[C@H]2C1]<br>Z172 | 617.2 |
| | 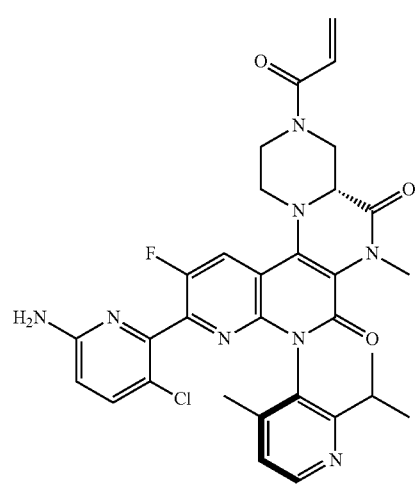<br>Z172-1 | |
-continued
| Example No. | Structure and No. of Compound | ES-API: [M + H]+ |
|---|---|---|
| | 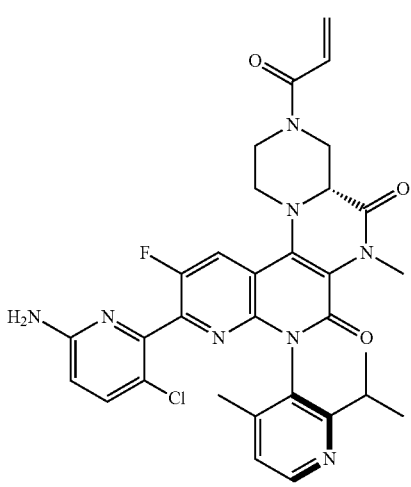<br>Z172 | |
| 173 | 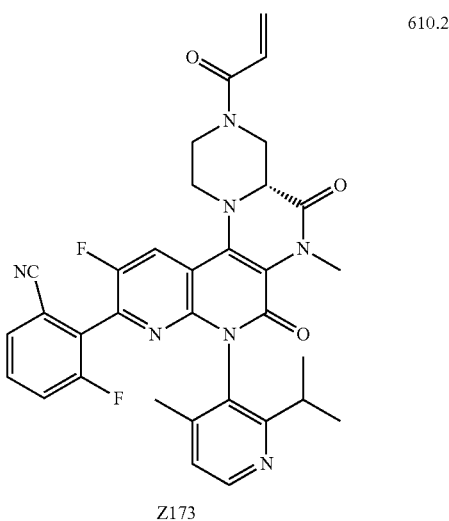<br>Z173 | 610.2 |

TABLE-continued
| Example No. | Structure and No. of Compound | ES-API: [M + H]+ |
|---|---|---|
| | 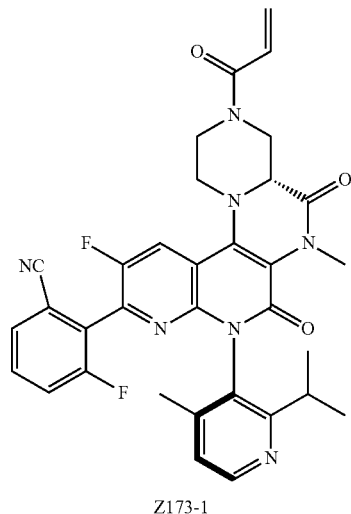  Z173-1 | |
| | 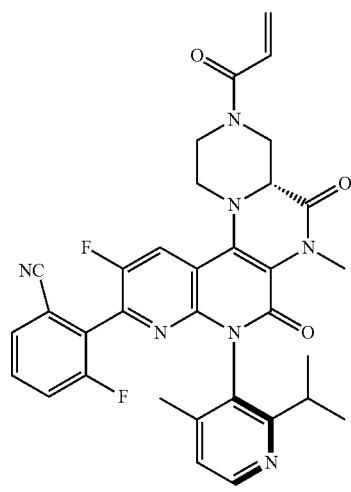  Z173-2 | |
| 174 | 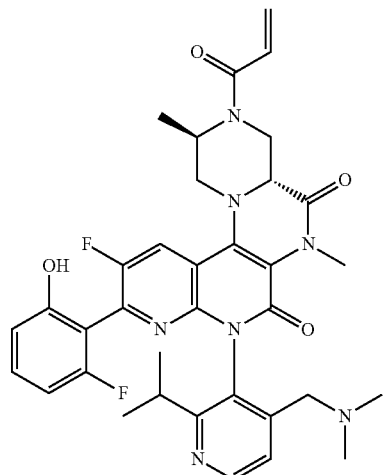  Z174 | 658.3 |
TABLE-continued
| Example No. | Structure and No. of Compound | ES-API: [M + H]+ |
|---|---|---|
| | 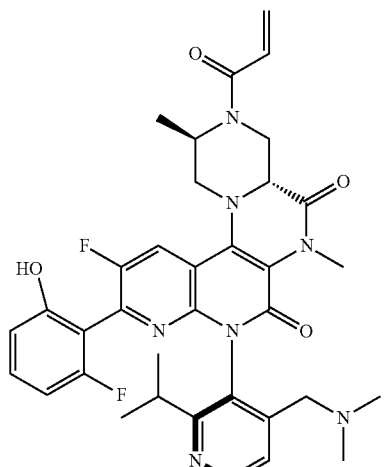  Z174-1 | |
| | 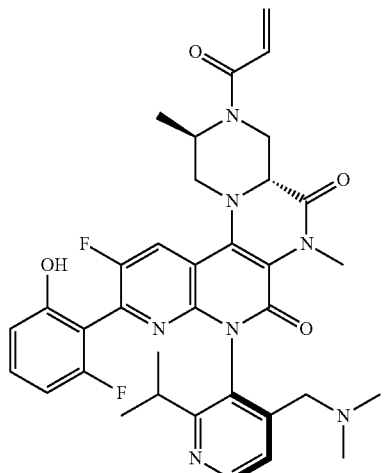  Z174-2 | |

| Example No. | Structure and No. of Compound | ES-API: [M + H]+ |
|---|---|---|
| 175 | Z175 | 659.3 |
| 176 | Z176 | 658.3 |
| 177 | Z177 | 687.3 |
| 178 | Z178 | 616.2 |

-continued
| Example No. | Structure and No. of Compound | ES-API: [M + H]+ |
|---|---|---|
| 179 | Z179 | 656.3 |
|  | Z179-1 |  |
|  | Z179-2 |  |
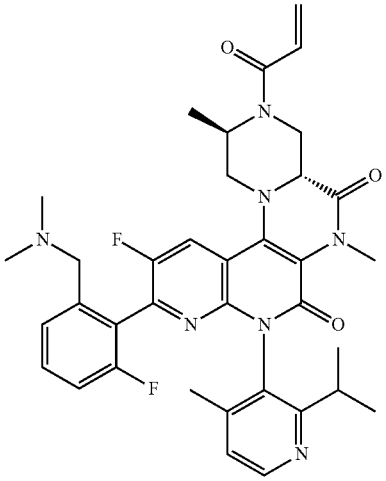

| Example No. | Structure and No. of Compound | ES-API: [M + H]+ |
|---|---|---|
| 180 | 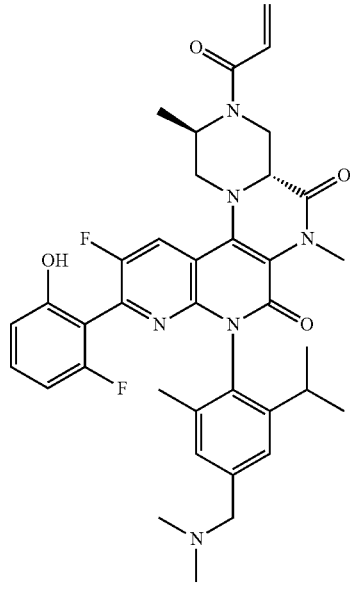 Z180 | 671.3 |
| | 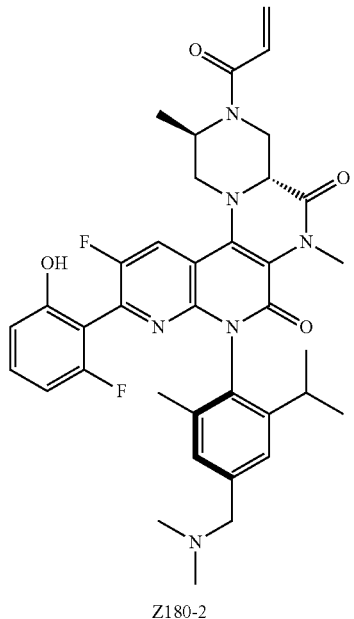 Z180-2 | |
| | Z180-1 | |
| 181 | 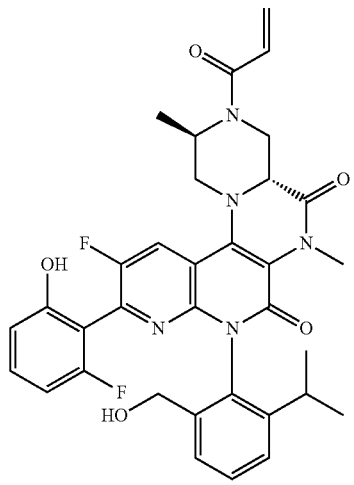 Z181 | 630.2 |

| Example No. | Structure and No. of Compound | ES-API: [M + H]+ |
|---|---|---|
| | 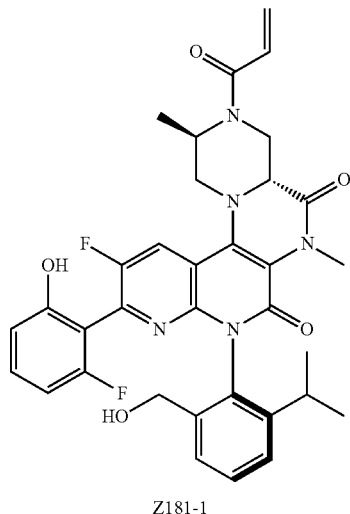 Z181-1 | |
| | 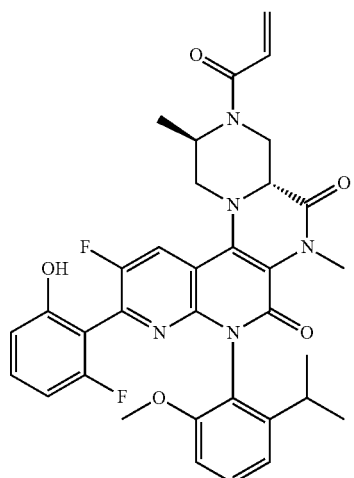 Z181-2 | |
| 182 | Z182 | 630.2 |
| Example No. | Structure and No. of Compound | ES-API: [M + H]+ |
|---|---|---|
| | 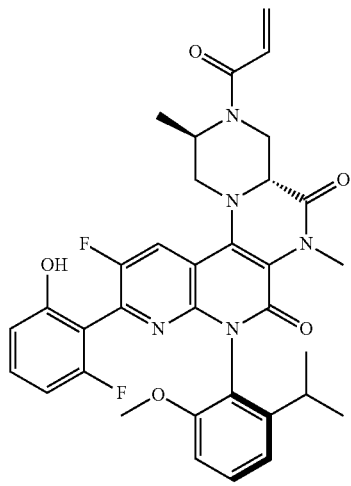 Z182-1 | |
| | 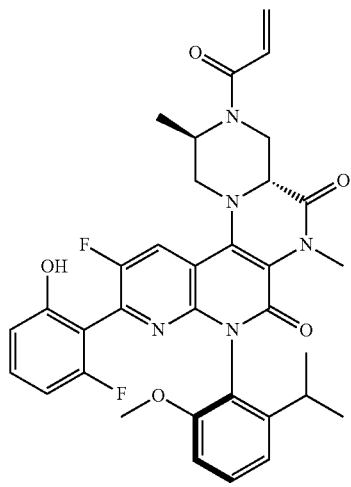 Z182-2 | |

-continued
| Example No. | Structure and No. of Compound | ES-API: [M + H]+ |
|---|---|---|
| 183 | 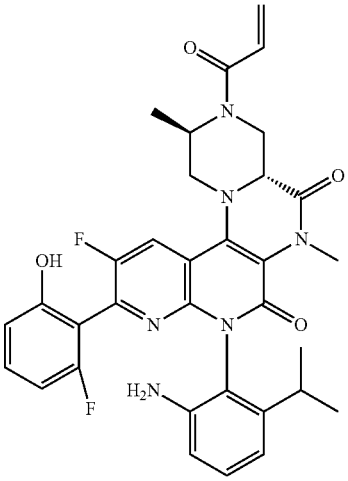<br>Z183 | 615.2 |
| | 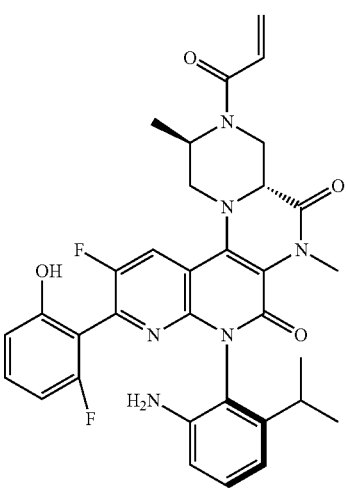<br>Z183-1 | |
| | 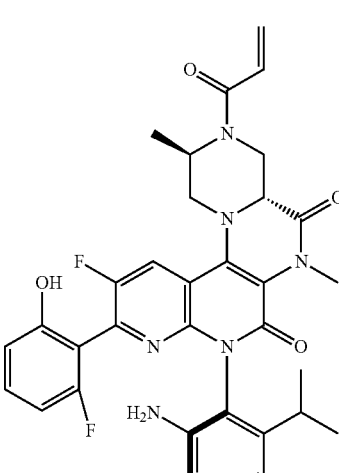<br>Z183-2 | |
-continued
| Example No. | Structure and No. of Compound | ES-API: [M + H]+ |
|---|---|---|
| 184 | 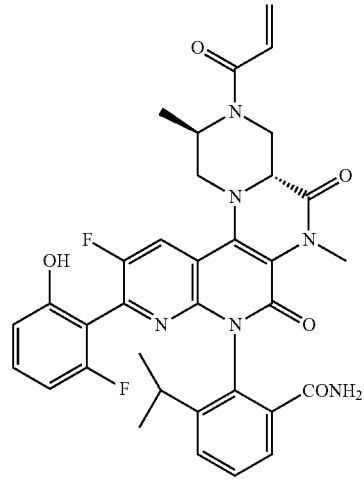<br>Z184 | 643.2 |
| | <br>Z184-1 | |

| Example No. | Structure and No. of Compound | ES-API: [M + H]+ |
|---|---|---|
| | 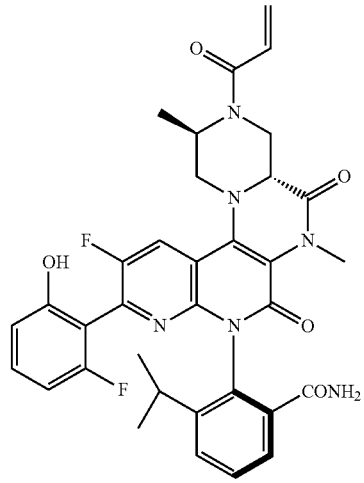<br>Z184-2 | |
| 185 | 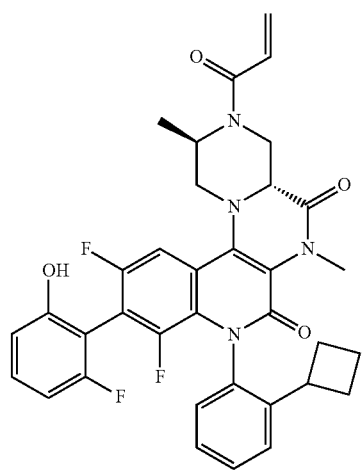<br>Z185 | 612.2 |
| | Z185-1 | |
| Example No. | Structure and No. of Compound | ES-API: [M + H]+ |
|---|---|---|
| | 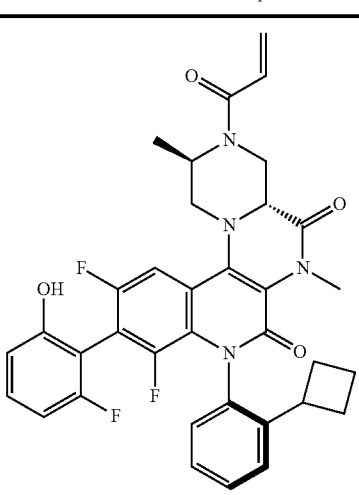<br>Z185-2 | |
| 186 | 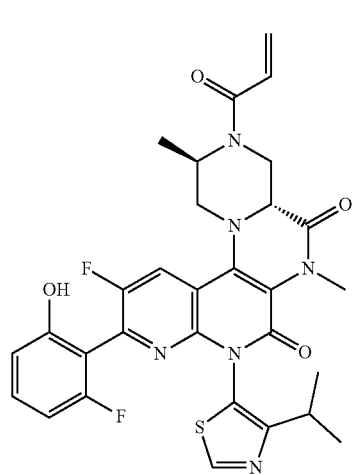<br>Z186 | 607.2 |
| | 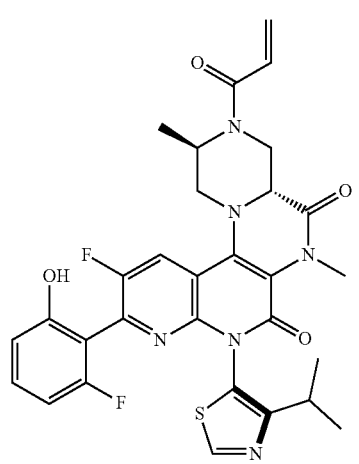<br>Z186-1 | |

TABLE 521-continued
| Example No. | Structure and No. of Compound | ES-API: [M + H]+ |
|---|---|---|
| | 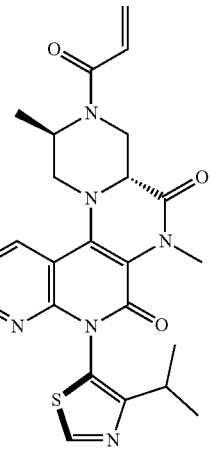 | |
| | 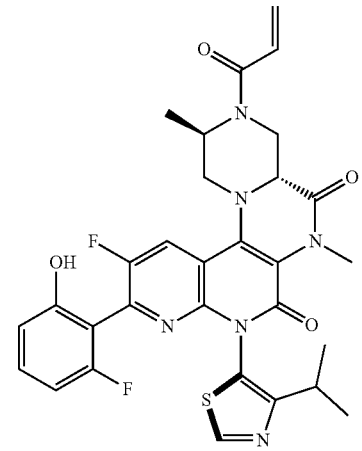
Z186-2 | |
| 187 | 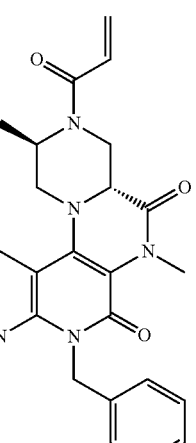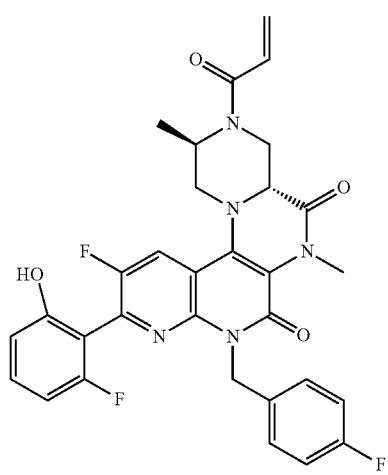
Z187 | 590.2 |
| 188 | 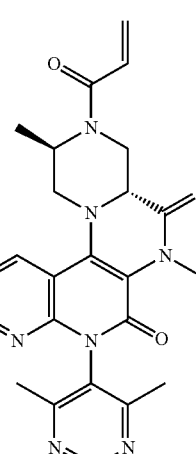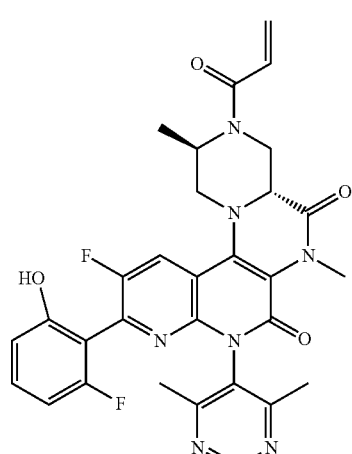
Z188 | 588.2 |
TABLE 522-continued
| Example No. | Structure and No. of Compound | ES-API: [M + H]+ |
|---|---|---|
| 189 | 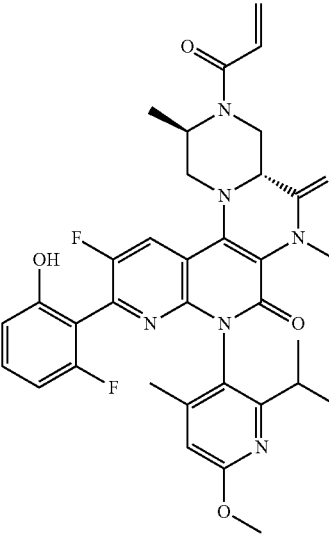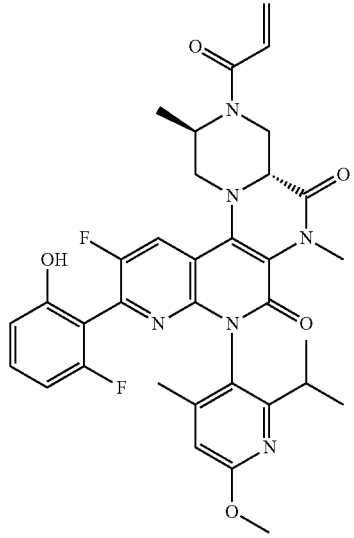
Z189 | 645.2 |
| | 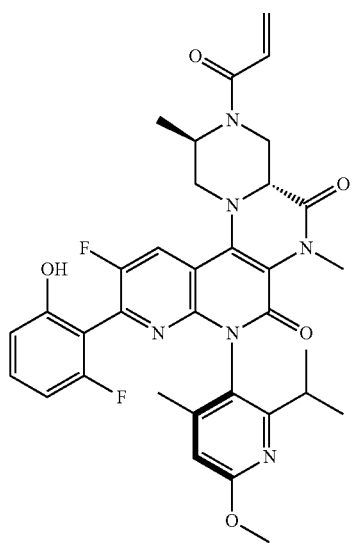
Z189-1 | |

| Example No. | Structure and No. of Compound | ES-API: [M + H]+ |
|---|---|---|
| | 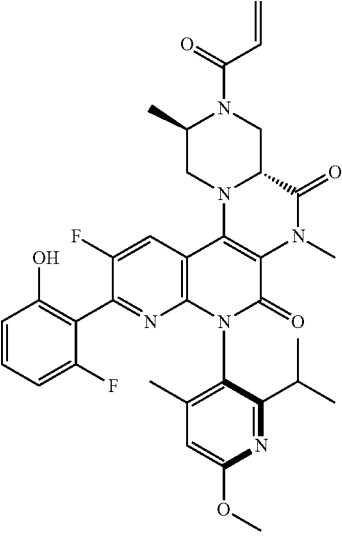 Z189-2 | |
| 190 | 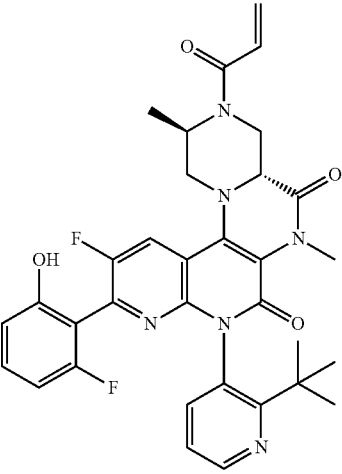 Z190 | 615.2 |
| Example No. | Structure and No. of Compound | ES-API: [M + H]+ |
|---|---|---|
| | 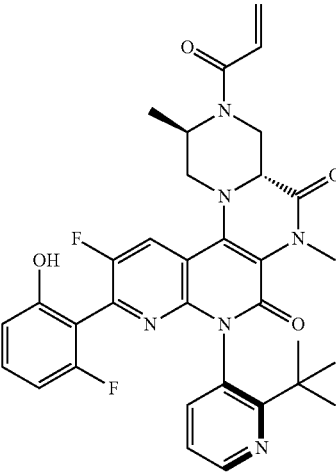 Z190-1 | |
| | 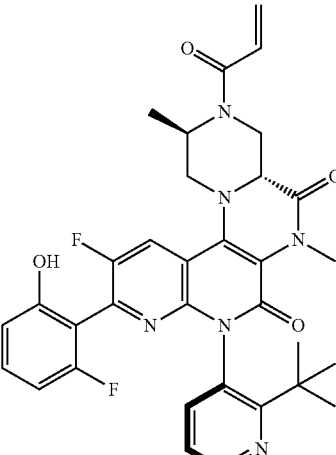 Z190-2 | |
| 191 | 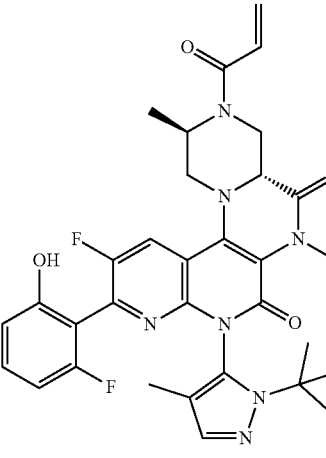 Z191 | 618.2 |

| Example No. | Structure and No. of Compound | ES-API: [M + H]+ |
|---|---|---|
| | 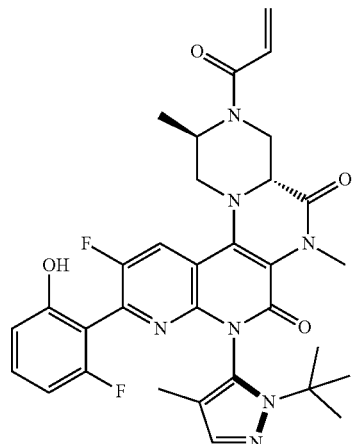<br>Z191-1 | |
| | 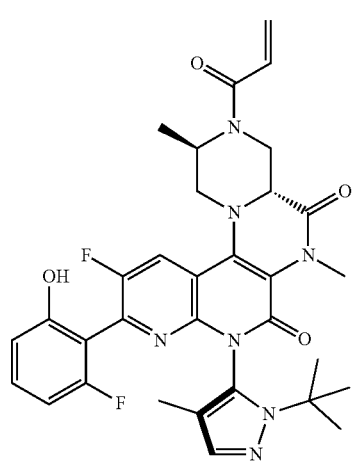<br>Z191-2 | |
| 192 | 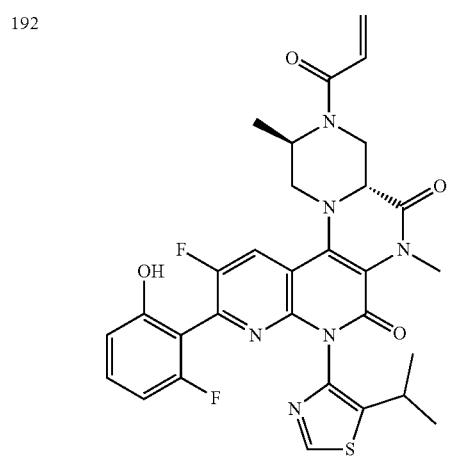<br>Z192 | 607.2 |
| Example No. | Structure and No. of Compound | ES-API: [M + H]+ |
|---|---|---|
| | 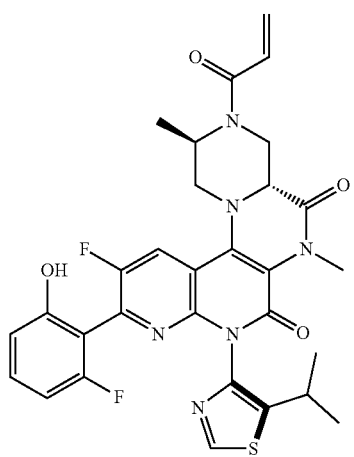<br>Z192-1 | |
| | 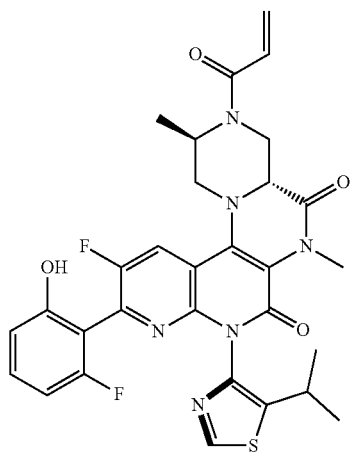<br>Z192-2 | |
| 193 | 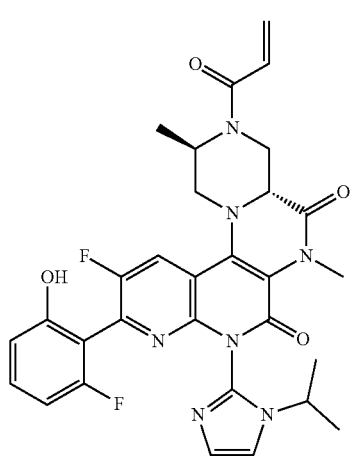<br>Z193 | 590.2 |

| Example No. | Structure and No. of Compound | ES-API: [M + H]+ |
|---|---|---|
| | 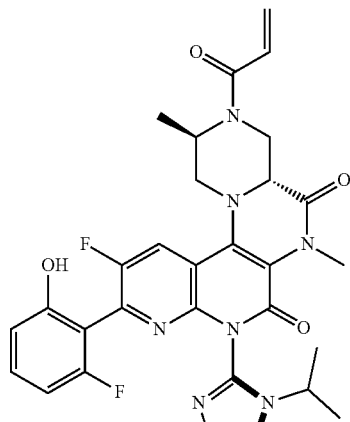Z193-1 | |
| | 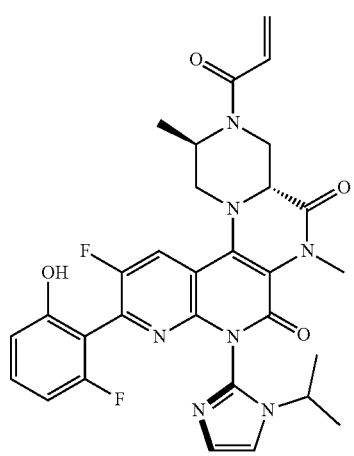Z193-2 | |
| 194 | 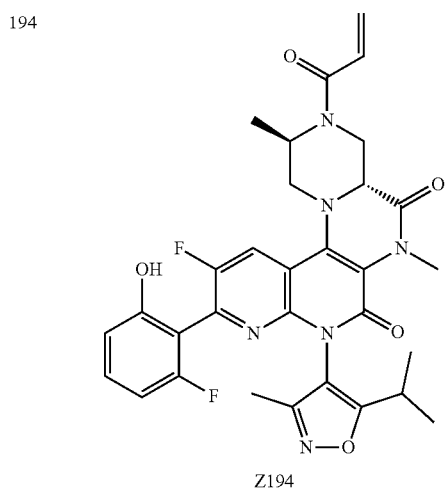Z194 | 605.2 |
| Example No. | Structure and No. of Compound | ES-API: [M + H]+ |
|---|---|---|
| | 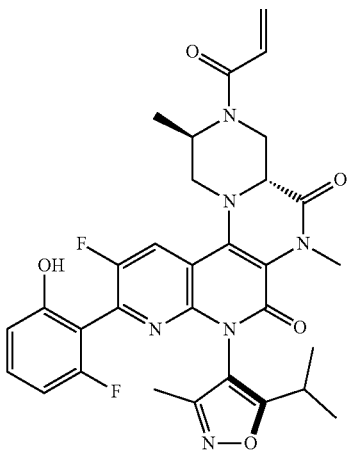Z194-1 | |
| | 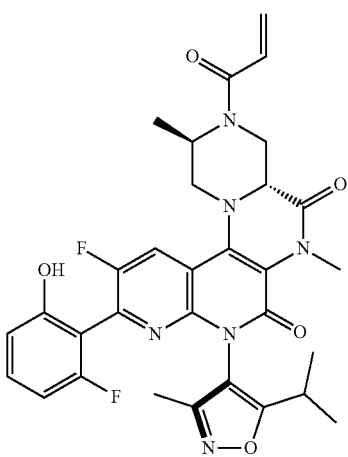Z194-2 | |
| 195 | 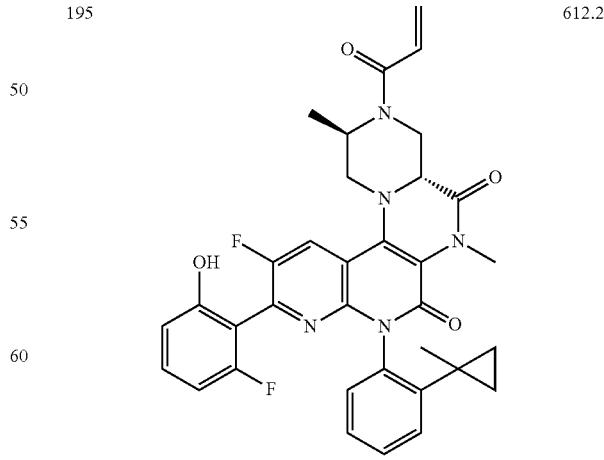Z195 | 612.2 |

| Example No. | Structure and No. of Compound | ES-API: [M + H]+ |
|---|---|---|
| | 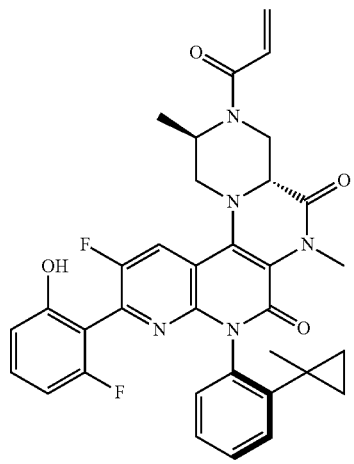<br>Z195-1 | |
| | 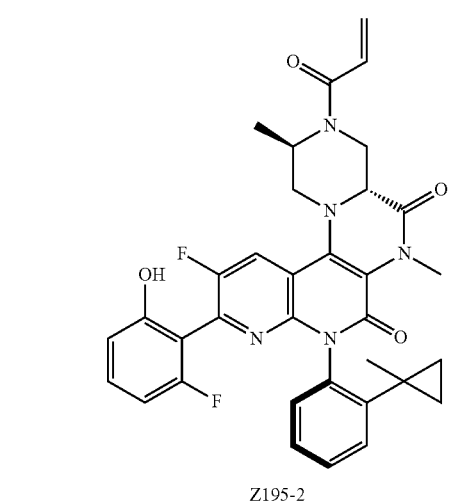<br>Z195-2 | |
| 196 | 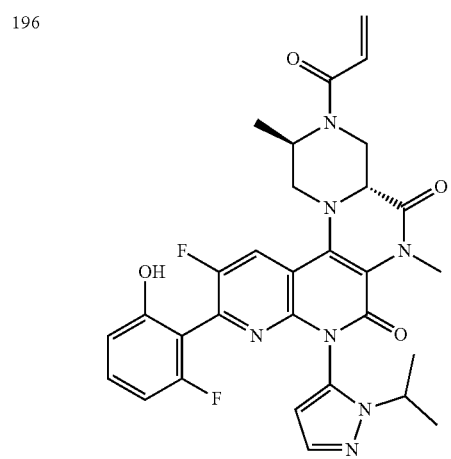<br>Z196 | 590.2 |
| Example No. | Structure and No. of Compound | ES-API: [M + H]+ |
|---|---|---|
| | 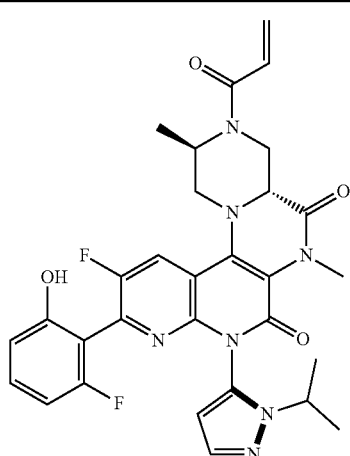<br>Z196-1 | |
| | 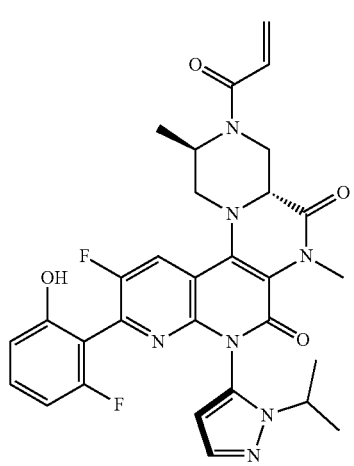<br>Z196-2 | |
| 197 | 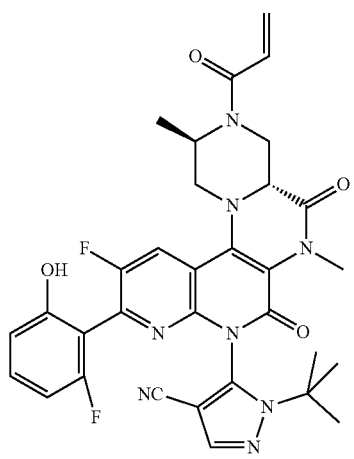<br>Z197 | 629.2 |

| Example No. | Structure and No. of Compound | ES-API: [M + H]+ |
|---|---|---|
|  | 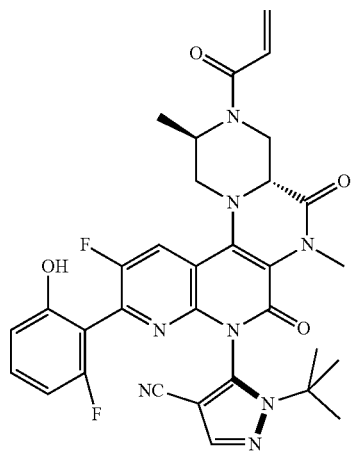  Z197-1 |  |
|  | 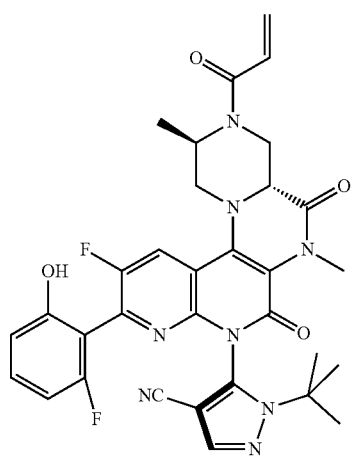  Z197-2 |  |
| 198 | 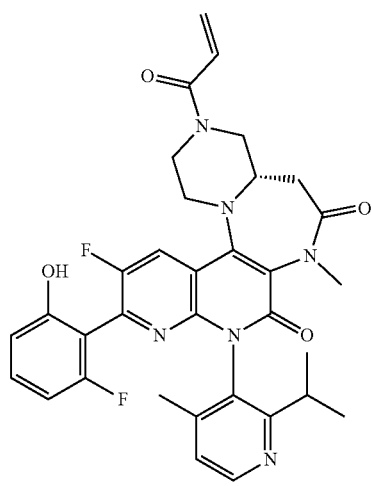  Z198 | 615.2 |
| Example No. | Structure and No. of Compound | ES-API: [M + H]+ |
|---|---|---|
|  | 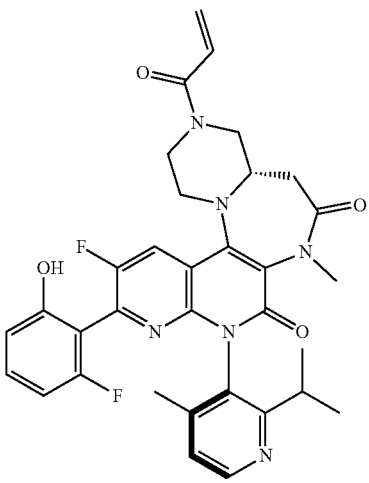  Z198-1 |  |
|  | 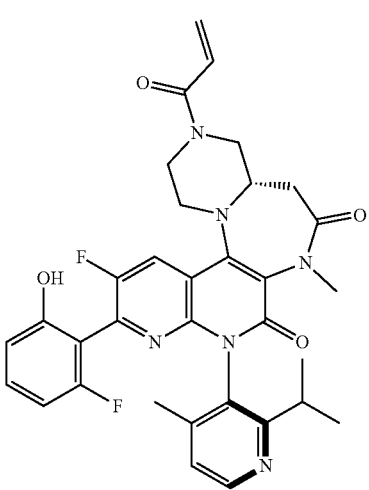  Z198-2 |  |
| 199 | 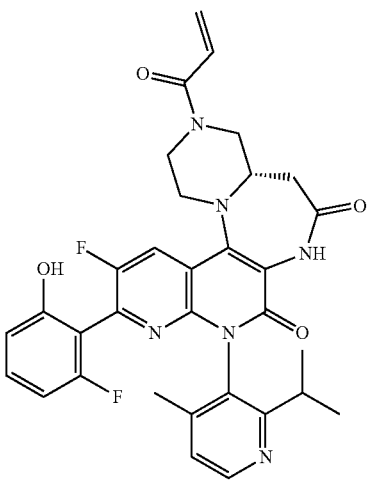  Z199 | 601.2 |

| Example No. | Structure and No. of Compound | ES-API: [M + H]⁺ |
|---|---|---|
| | 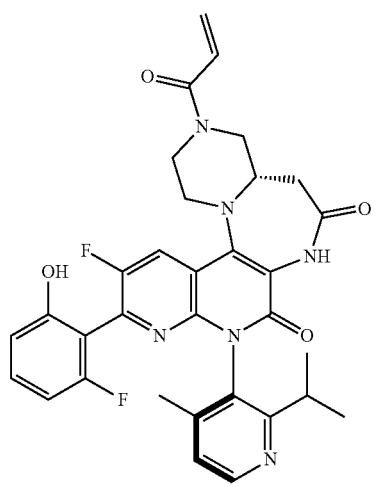
Z199-1 | |
| | 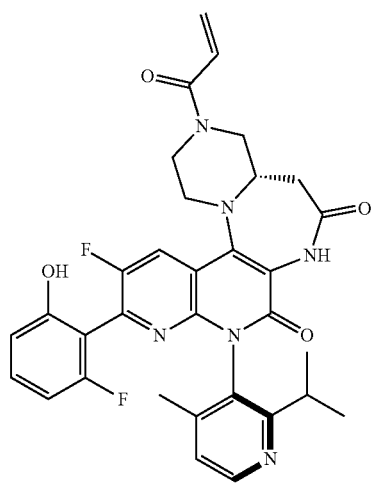
Z199-2 | |
| Example No. | Structure and No. of Compound | ES-API: [M + H]⁺ |
|---|---|---|
| 200 | 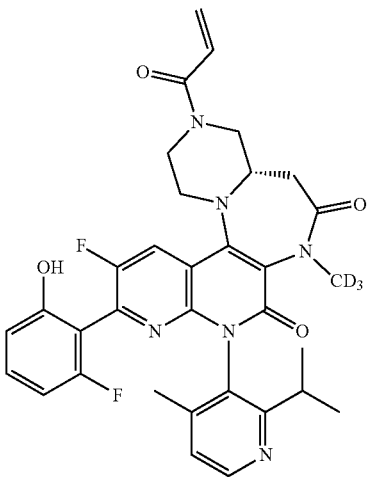
Z200 | 618.3 |
| | 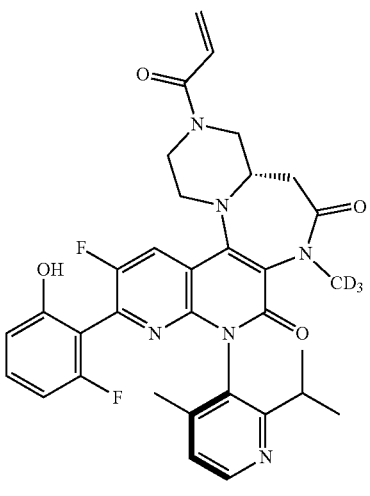
Z200-1 | |
| | 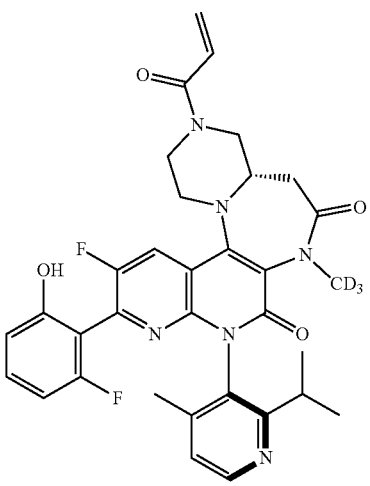
Z200-2 | |

| Example No. | Structure and No. of Compound | ES-API: [M+H]+ |
|---|---|---|
| 201 | Z201 | 629.3 |
| | Z201-1 | |
| | Z201-2 | |
| 202 | Z202 | 615.2 |
| | Z202-1 | |
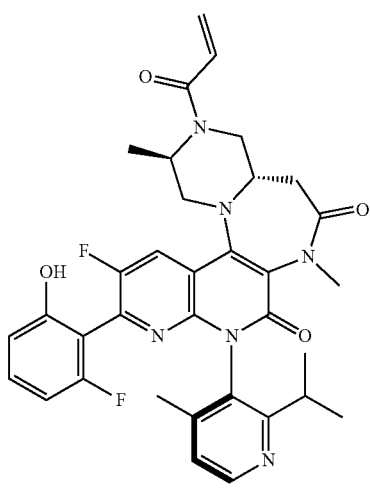
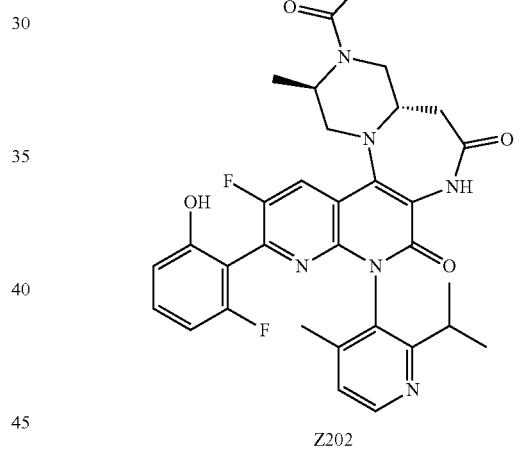
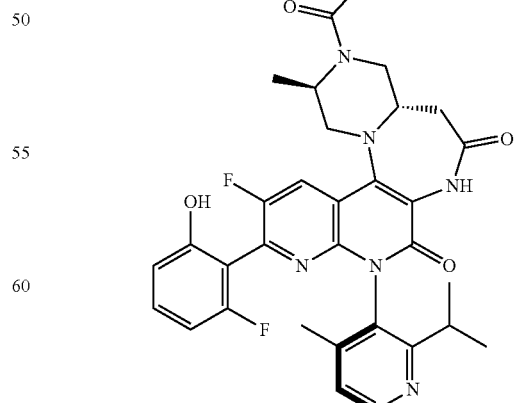

| Example No. | Structure and No. of Compound | ES-API: [M+H]+ |
|---|---|---|
| | 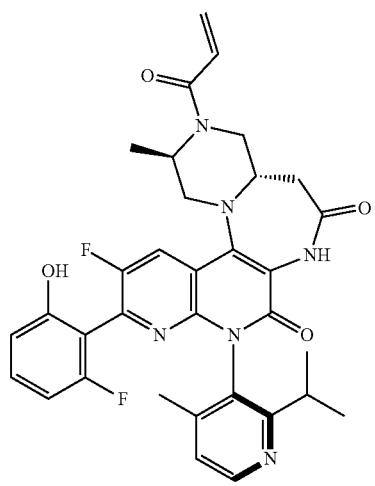
Z202-2 | |
| 203 | 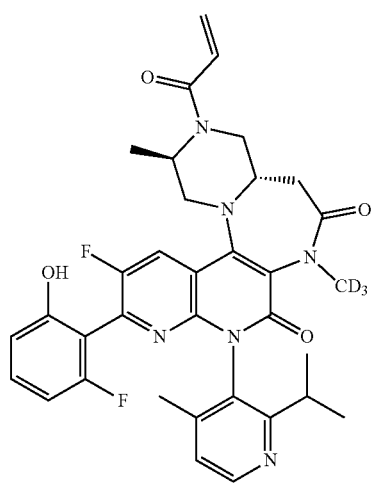
Z203 | 632.3 |
| Example No. | Structure and No. of Compound | ES-API: [M+H]+ |
|---|---|---|
| | 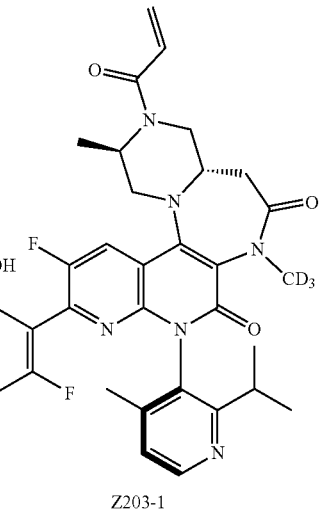
Z203-1 | |
| | 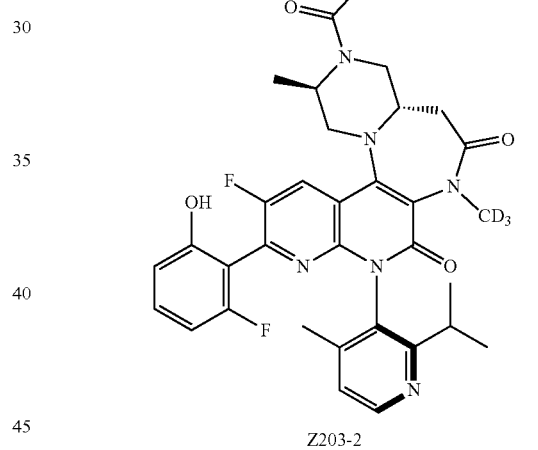
Z203-2 | |
| 204 | 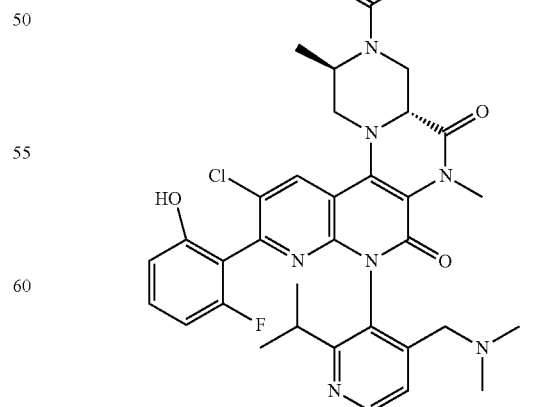
Z204 | 674.3 |

| Example No. | Structure and No. of Compound | ES-API: [M + H]+ |
|---|---|---|
| | Z204-1 | |
| | Z204-2 | |
| 205 | Z205 | 675.3 |
| 206 | Z206 | 674.3 |
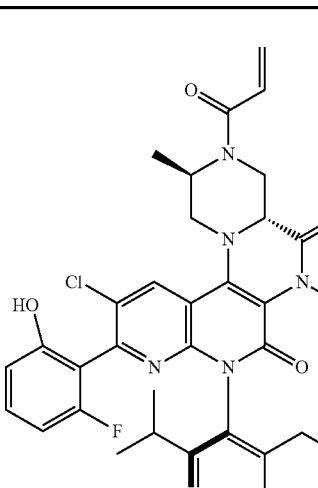

| Example No. | Structure and No. of Compound | ES-API: [M + H]+ |
|---|---|---|
| 207 | Z207 | 703.3 |
| 208 | Z208 | 632.2 |

| Example No. | Structure and No. of Compound | ES-API: [M + H]+ |
|---|---|---|
| | Z208-1 | |
| | Z208-2 | |

-continued
| Example No. | Structure and No. of Compound | ES-API: [M + H]+ |
|---|---|---|
| 209 | Z209 | 672.3 |
| | Z209-1 | |
| | Z209-2 | |
| 210 | Z210 | 687.3 |
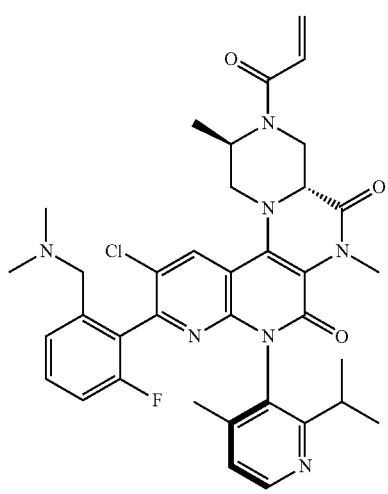
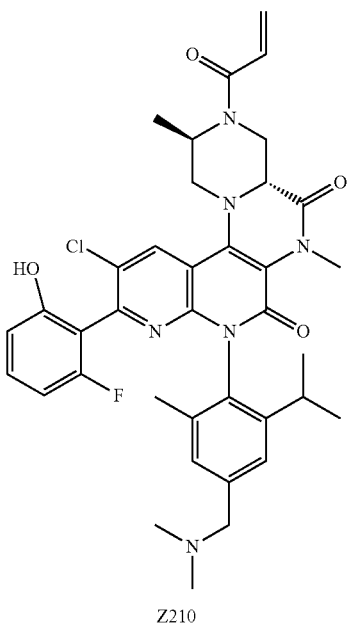 [SMILES: C=CC(=O)N1C[C@@H]2C(=O)N(C)c3c(c4cc(Cl)c(-c5c(O)cccc5F)nc4n(-c4c(C)cc(CN(C)C)cc4C(C)C)c3=O)N2C[C@H]1C]

-continued
| Example No. | Structure and No. of Compound | ES-API: [M + H]+ |
|---|---|---|
| | 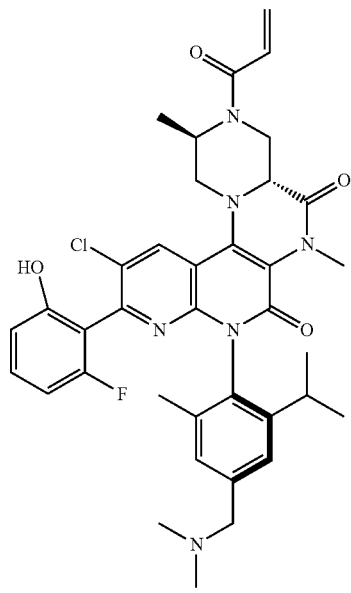<br>Z210-1 | |
| | 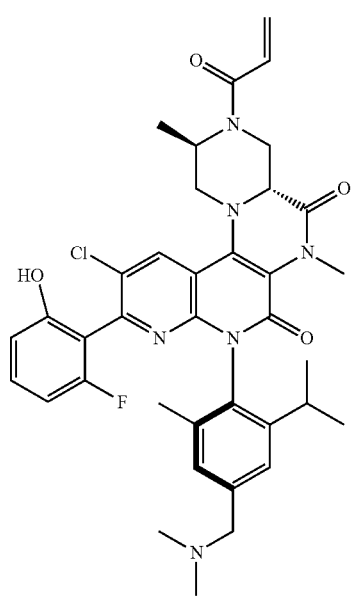<br>Z210-2 | |
-continued
| Example No. | Structure and No. of Compound | ES-API: [M + H]+ |
|---|---|---|
| 211 | 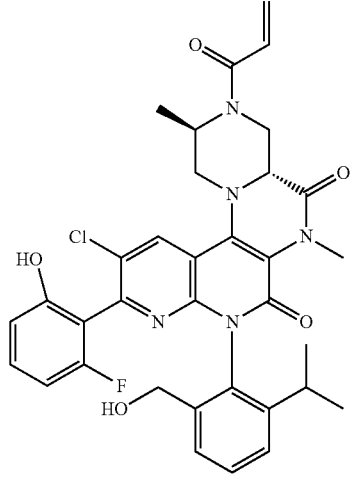<br>Z211 | 646.2 |
| | 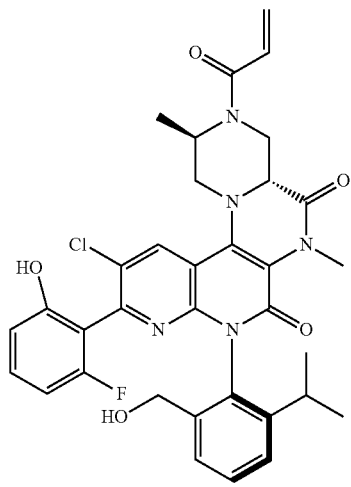<br>Z211-1 | |

-continued
| Example No. | Structure and No. of Compound | ES-API: [M + H]+ |
|---|---|---|
| | 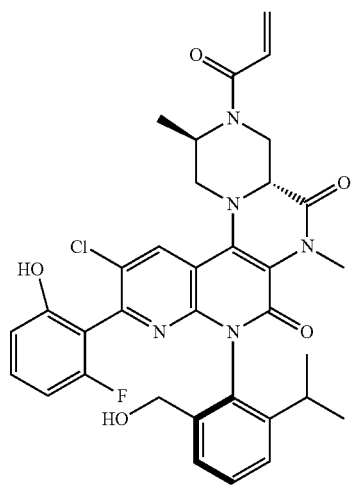<br>Z211-2 | |
| 212 | 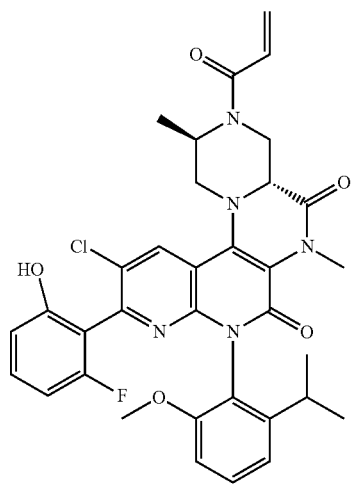<br>Z212 | 646.2 |
-continued
| Example No. | Structure and No. of Compound | ES-API: [M + H]+ |
|---|---|---|
| | 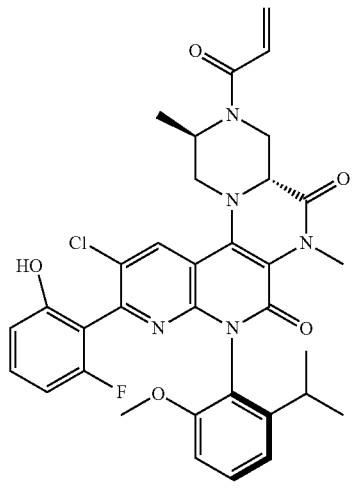<br>Z212-1 | |
| | 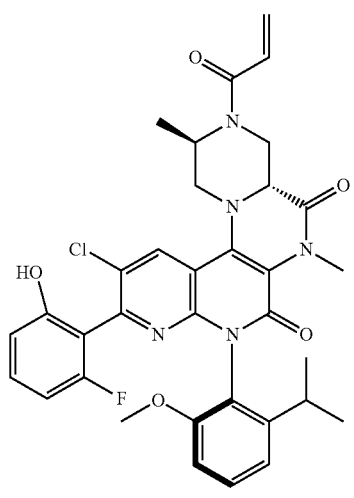<br>Z212-2 | |
| 213 | 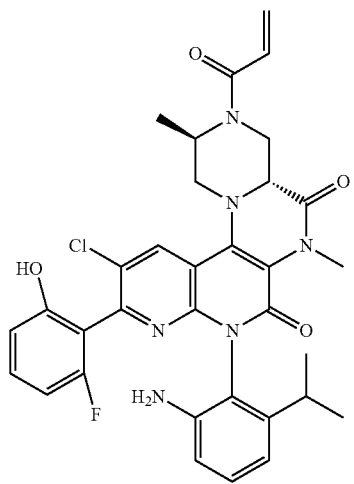<br>Z213 | 631.2 |

| Example No. | Structure and No. of Compound | ES-API: [M + H]+ |
|---|---|---|
| | 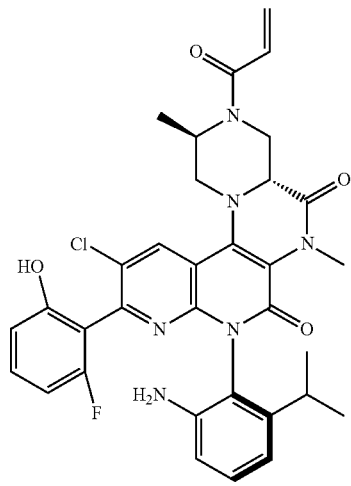<br>Z213-1 | |
| | 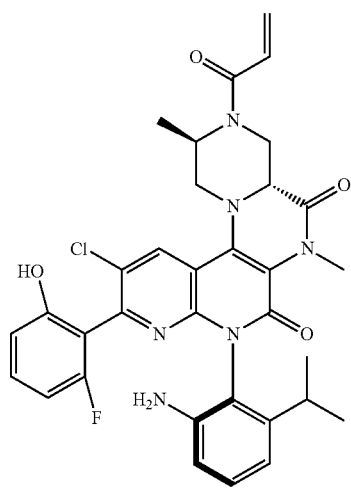<br>Z213-2 | |
| Example No. | Structure and No. of Compound | ES-API: [M + H]+ |
|---|---|---|
| 214 | 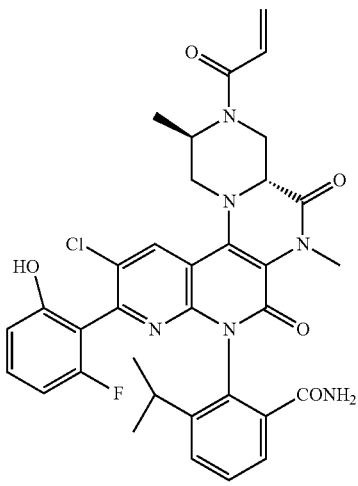<br>Z214 | 659.2 |
| | 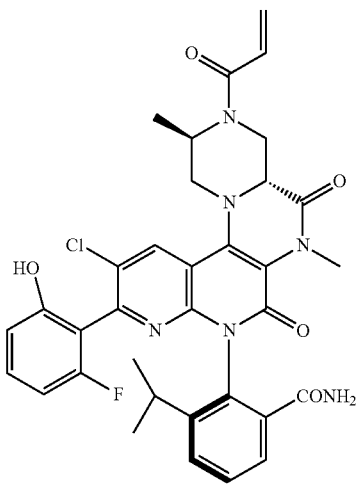<br>Z214-1 | |

| Example No. | Structure and No. of Compound | ES-API: [M+H]⁺ |
|---|---|---|
| | 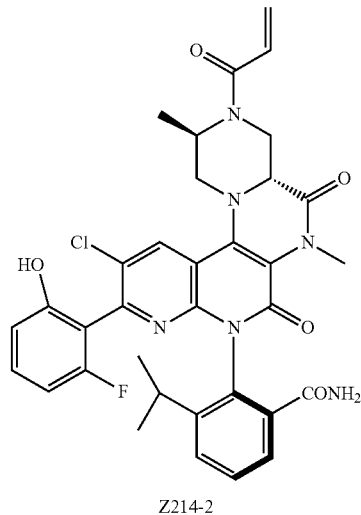<br>Z214-2 | |
| 215 | 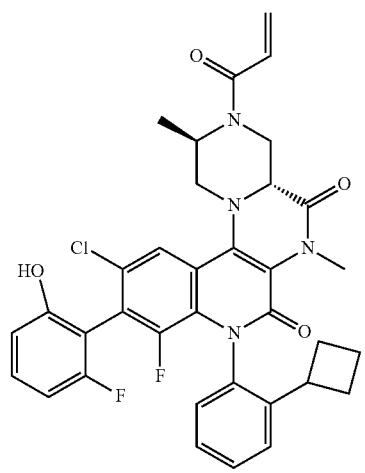<br>Z215 | 628.2 |
| | 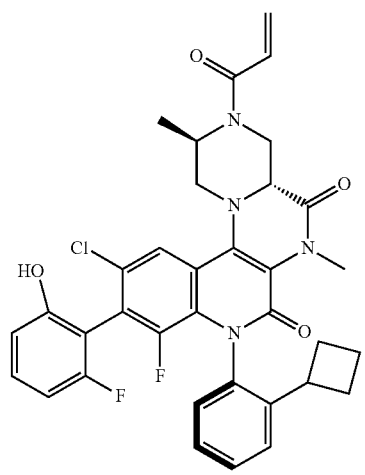<br>Z215-1 | |
| Example No. | Structure and No. of Compound | ES-API: [M+H]⁺ |
|---|---|---|
| | 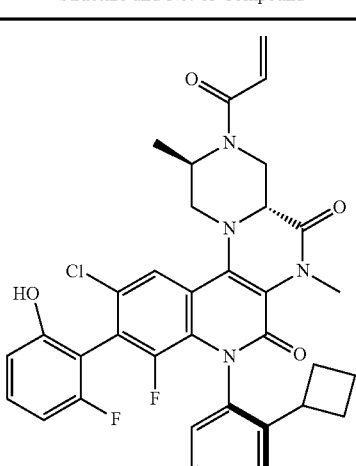<br>Z215-2 | |
| 216 | 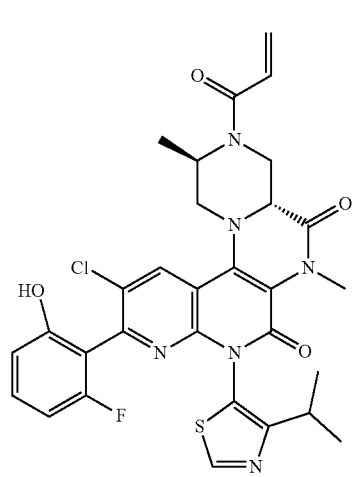<br>Z216 | 623.2 |
| | 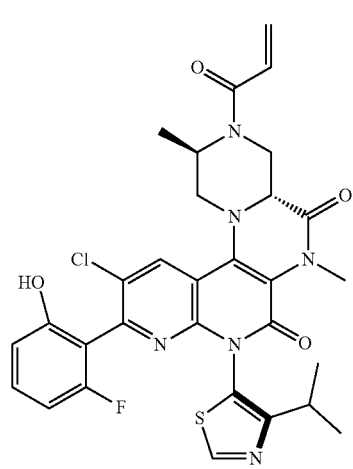<br>Z216-1 | |

553
-continued
| Example No. | Structure and No. of Compound | ES-API: [M + H]+ |
|---|---|---|
| | 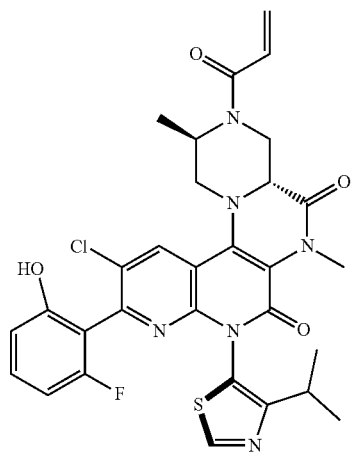<br>Z216-2 | |
| 217 | 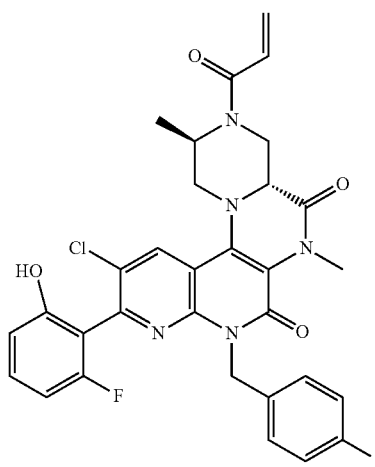<br>Z217 | 606.2 |
| 218 | 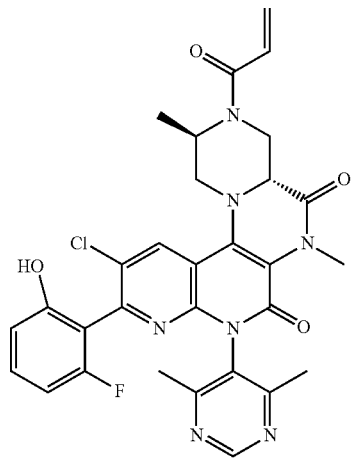<br>Z218 | 604.2 |
554
-continued
| Example No. | Structure and No. of Compound | ES-API: [M + H]+ |
|---|---|---|
| 219 | 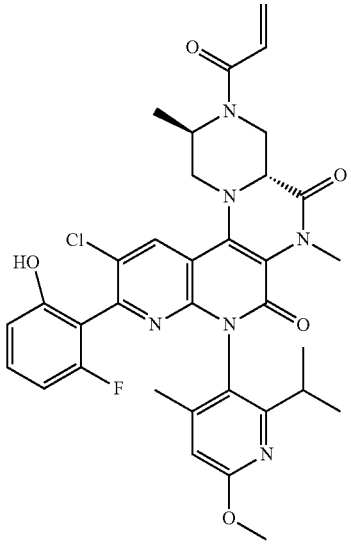<br>Z219 | 661.2 |
| | 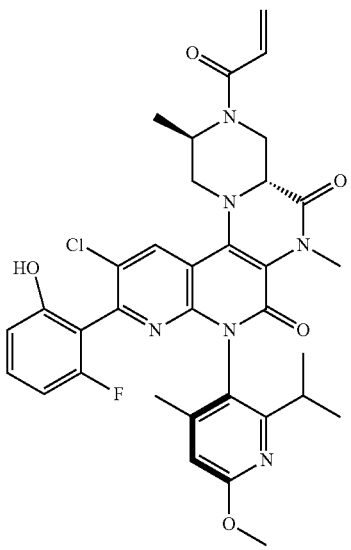<br>Z219-1 | |

-continued
| Example No. | Structure and No. of Compound | ES-API: [M + H]+ |
|---|---|---|
| | 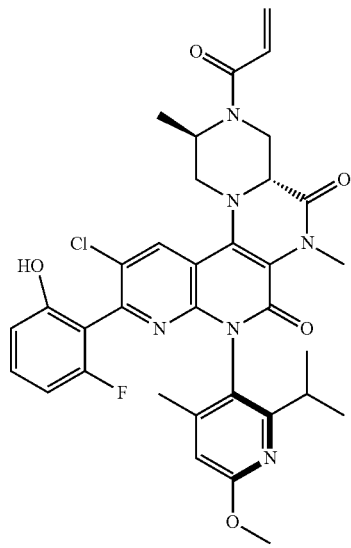<br>Z219-2 | |
| 220 | 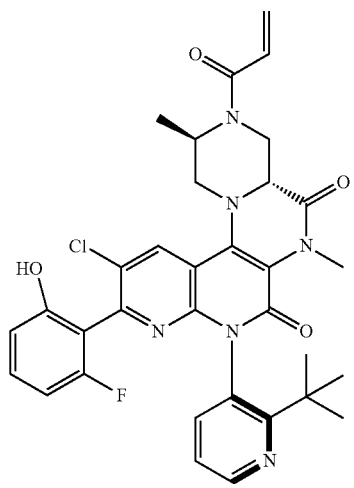<br>Z220 | 631.2 |
-continued
| Example No. | Structure and No. of Compound | ES-API: [M + H]+ |
|---|---|---|
| | Z220-1 | |
| | 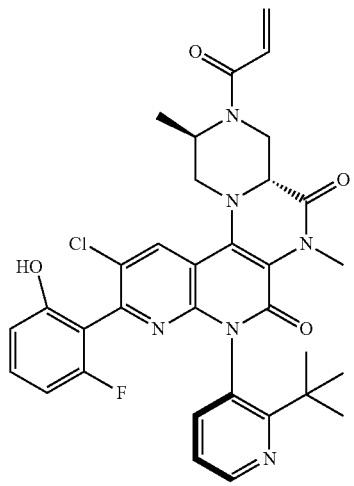<br>Z220-2 | |
| 221 | 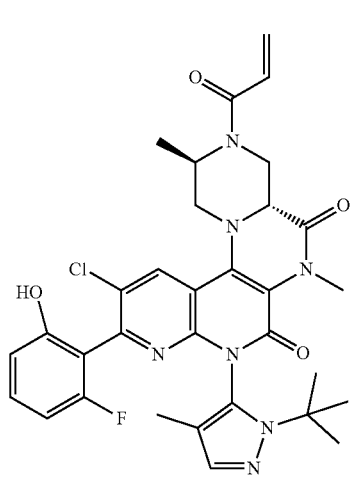<br>Z221 | 634.2 |

| Example No. | Structure and No. of Compound | ES-API: [M + H]+ |
|---|---|---|
| | 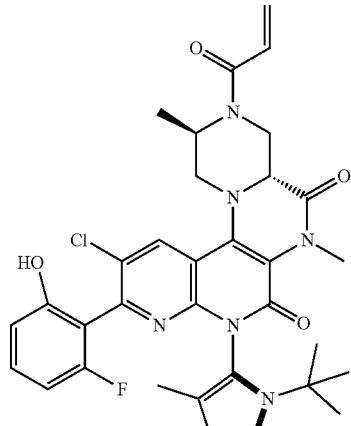Z221-1 | |
| | 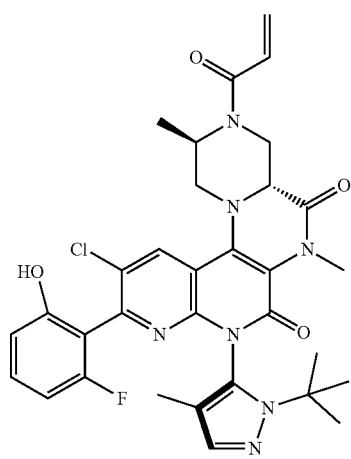Z221-2 | |
| 222 | 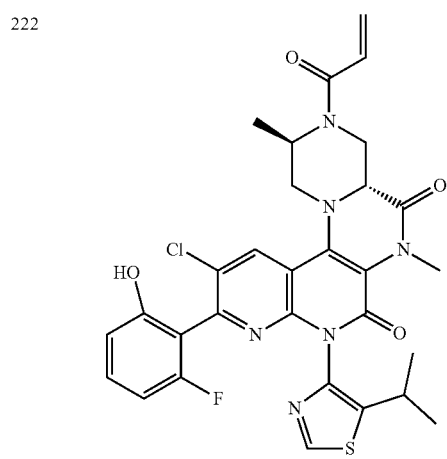Z222 | 623.2 |
| Example No. | Structure and No. of Compound | ES-API: [M + H]+ |
|---|---|---|
| | 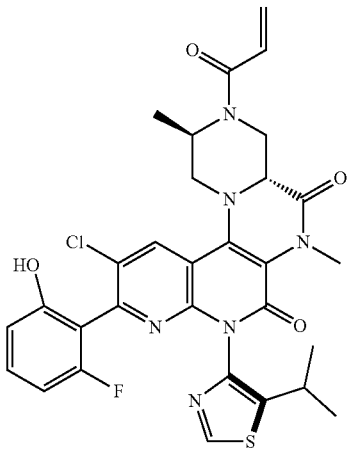Z222-1 | |
| | 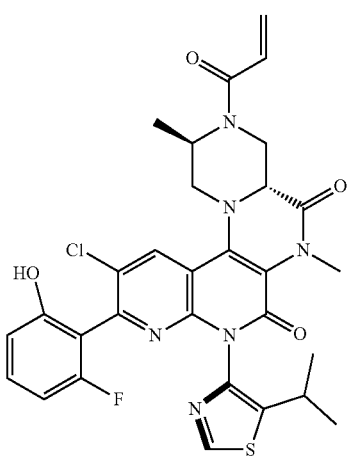Z222-2 | |
| 223 | 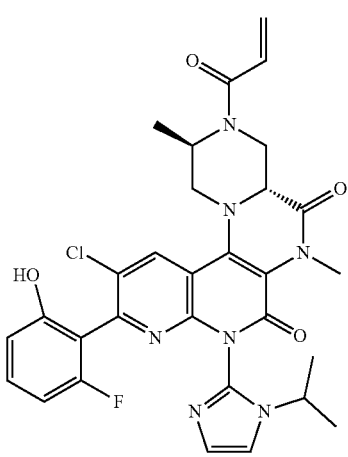Z223 | 606.2 |

| Example No. | Structure and No. of Compound | ES-API: [M + H]+ |
|---|---|---|
| | 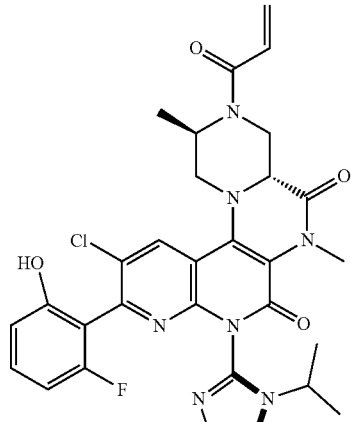Z223-1 | |
| | 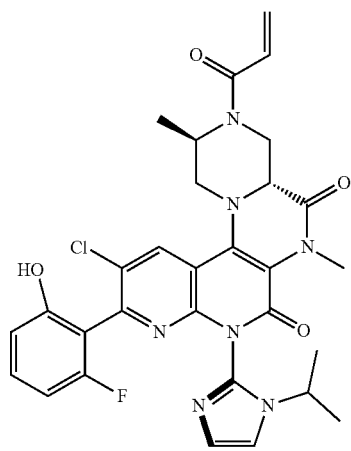Z223-2 | |
| 224 | 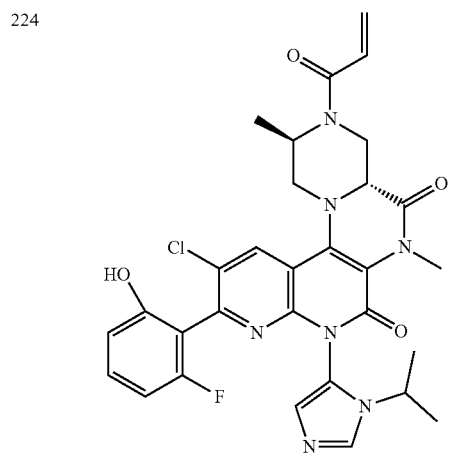Z224 | 606.2 |
| Example No. | Structure and No. of Compound | ES-API: [M + H]+ |
|---|---|---|
| | 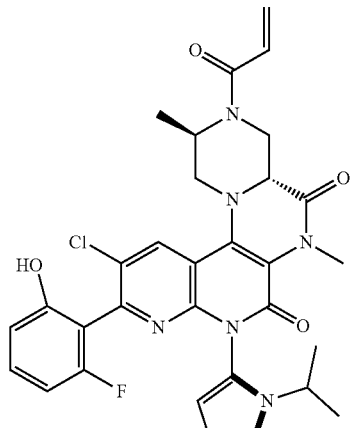Z224-1 | |
| | 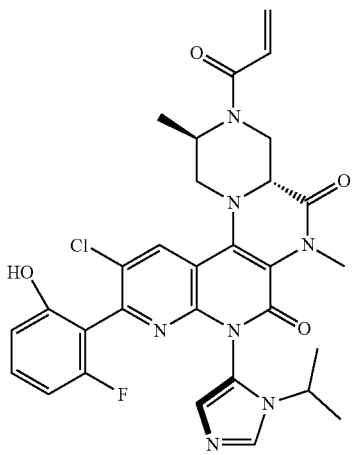Z224-2 | |
| 225 | 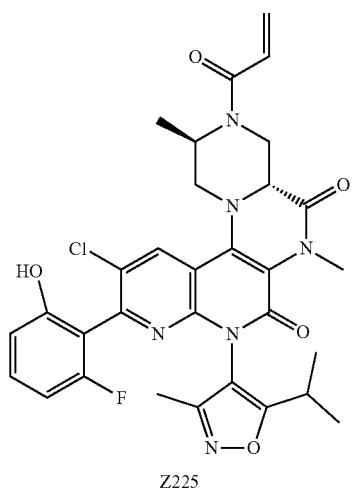 [SMILES: C=CC(=O)N1C[C@@H]2C(=O)N(C)c3c(c4cc(Cl)c(-c5c(O)cccc5F)nc4n(-c4c(C)noc4C(C)C)c3=O)N2C[C@H]1C]Z225 | 621.2 |

| Example No. | Structure and No. of Compound | ES-API: [M+H]+ |
|---|---|---|
| | 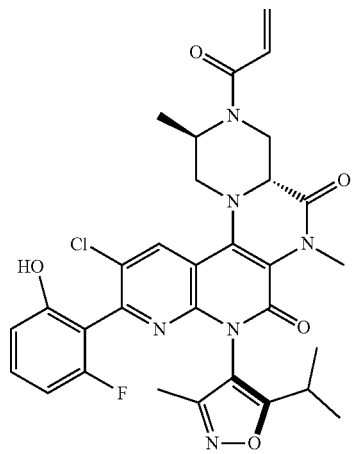
Z225-1 | |
| | 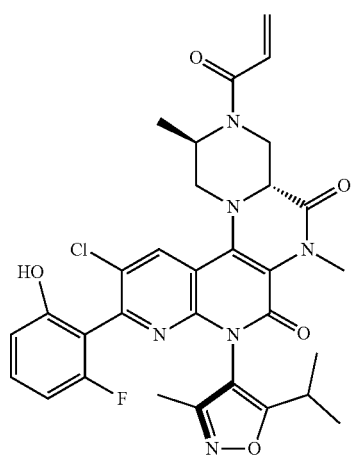
Z225-2 | |
| 226 | 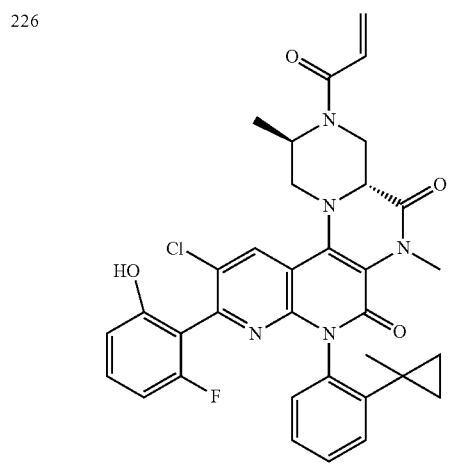
Z226 | 628.2 |
| Example No. | Structure and No. of Compound | ES-API: [M+H]+ |
|---|---|---|
| | 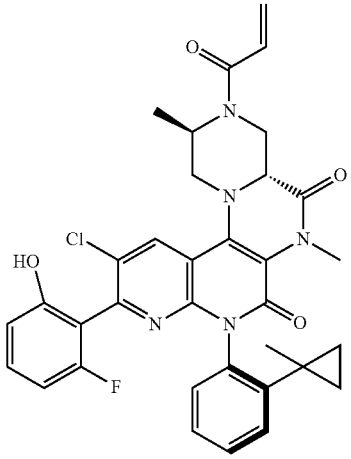
Z226-1 | |
| | 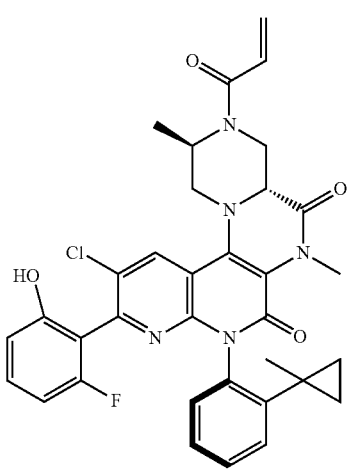
Z226-2 | |
| 227 | 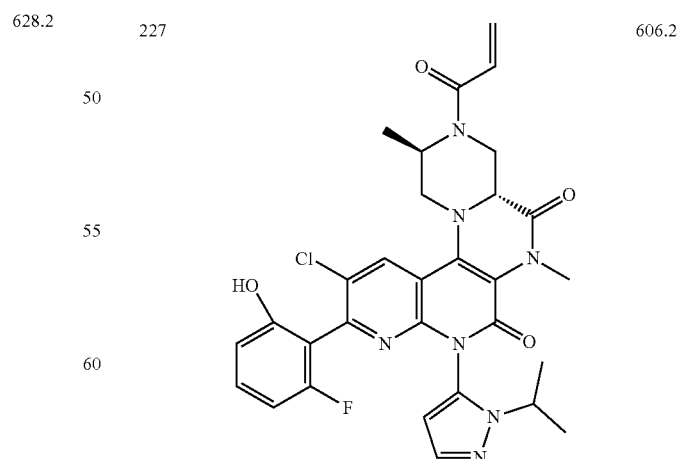
Z227 | 606.2 |

| Example No. | Structure and No. of Compound | ES-API: [M + H]⁺ |
|---|---|---|
| | Z227-1 | |
| | Z227-2 | |
| 228 | Z228 | 645.2 |

| Example No. | Structure and No. of Compound | ES-API: [M + H]⁺ |
|---|---|---|
| | Z228-1 | |
| | Z228-2 | |
| 229 | Z229 | 631.2 |

| Example No. | Structure and No. of Compound | ES-API: [M+H]+ |
|---|---|---|
| | 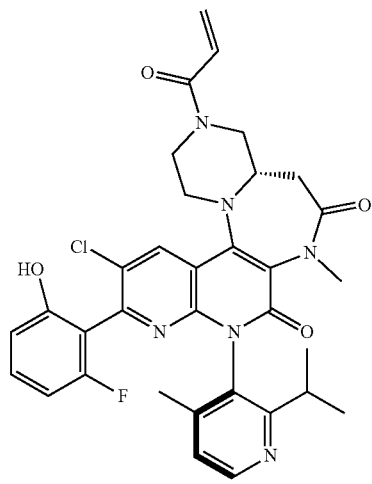
Z229-1 | |
| | 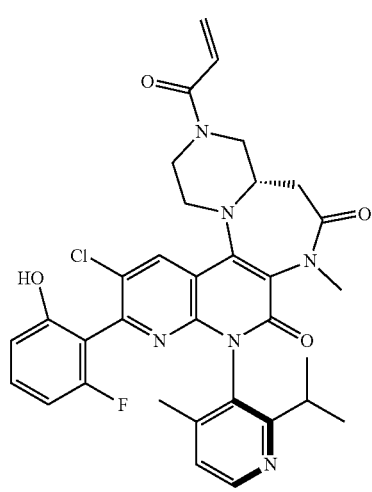
Z229-2 | |
| 230 | 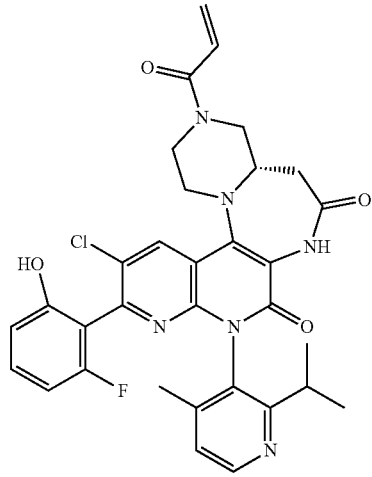
Z230 | 617.2 |
| Example No. | Structure and No. of Compound | ES-API: [M+H]+ |
|---|---|---|
| | 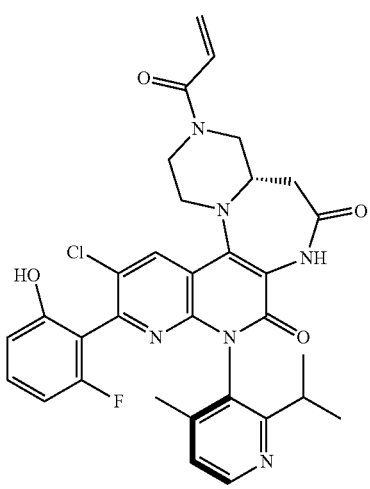
Z230-1 | |
| | 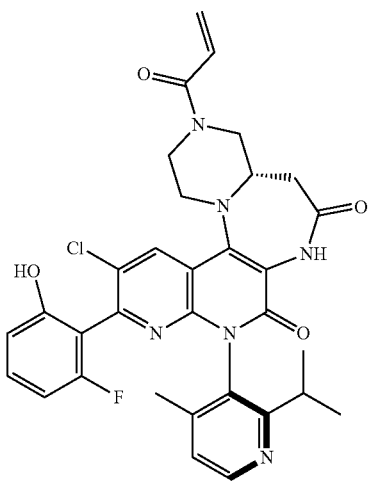
Z230-2 | |

| Example No. | Structure and No. of Compound | ES-API: [M + H]+ |
|---|---|---|
| 231 | Z231 | 634.2 |
| | Z231-1 | |
| | Z231-2 | |

| Example No. | Structure and No. of Compound | ES-API: [M + H]+ |
|---|---|---|
| 232 | Z232 | 645.2 |
| | Z232-1 | |

| Example No. | Structure and No. of Compound | ES-API: [M + H]+ |
|---|---|---|
| 233 | 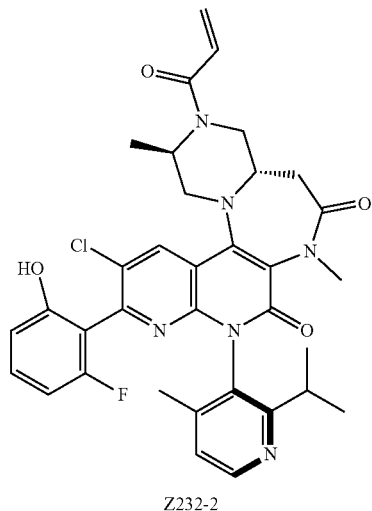 Z232-2 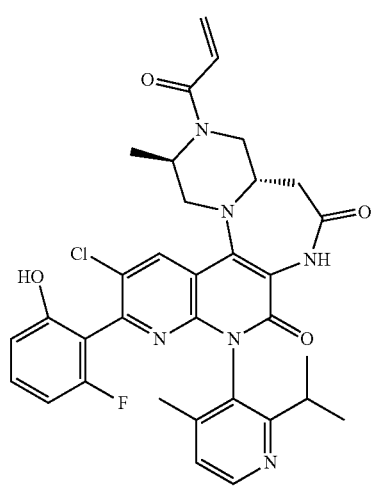 Z233 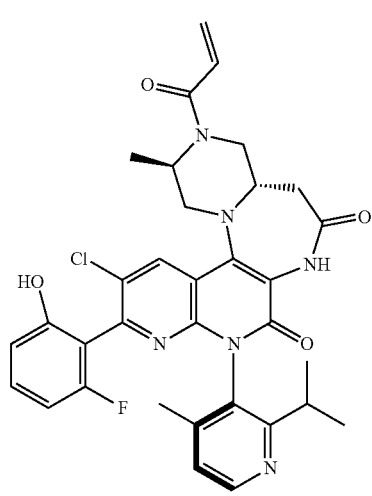 Z233-1 | 631.2 |
| Example No. | Structure and No. of Compound | ES-API: [M + H]+ |
|---|---|---|
| | 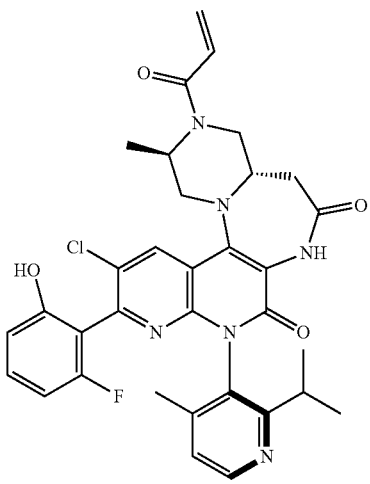 Z233-2 | |
| 234 | 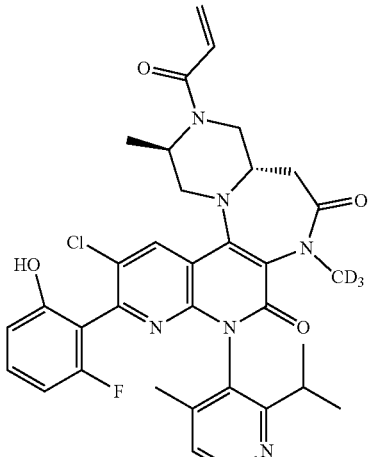 Z234 | 648.3 |

571
-continued
| Example No. | Structure and No. of Compound | ES-API: [M + H]+ |
|---|---|---|
| | 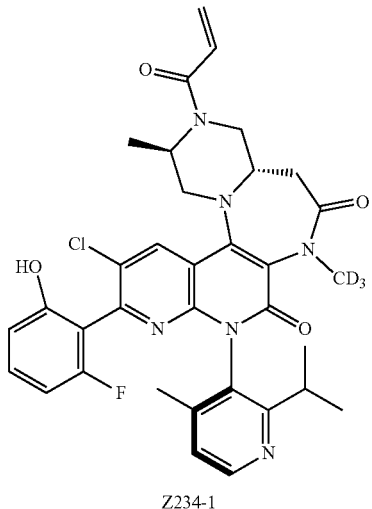
Z234-1 | |
| | 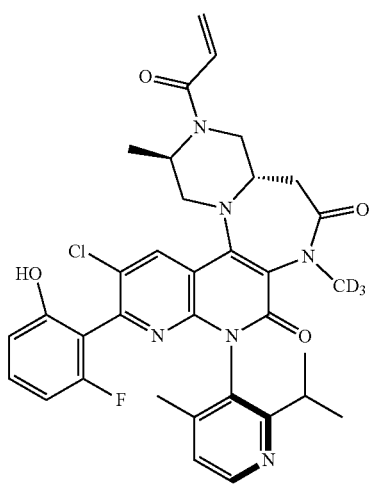
Z234-2 | |
| 235 | 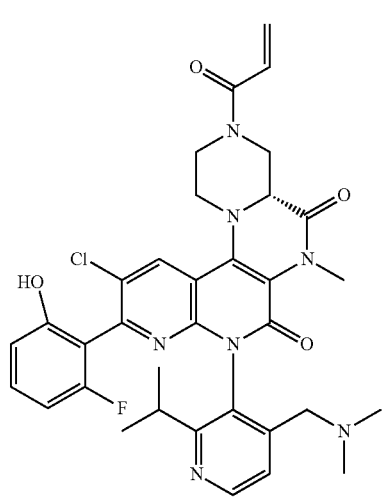
Z236 | 660.2 |
572
-continued
| Example No. | Structure and No. of Compound | ES-API: [M + H]+ |
|---|---|---|
| | 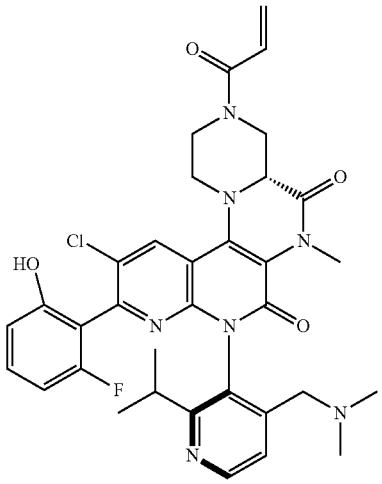
Z236-1 | |
| | 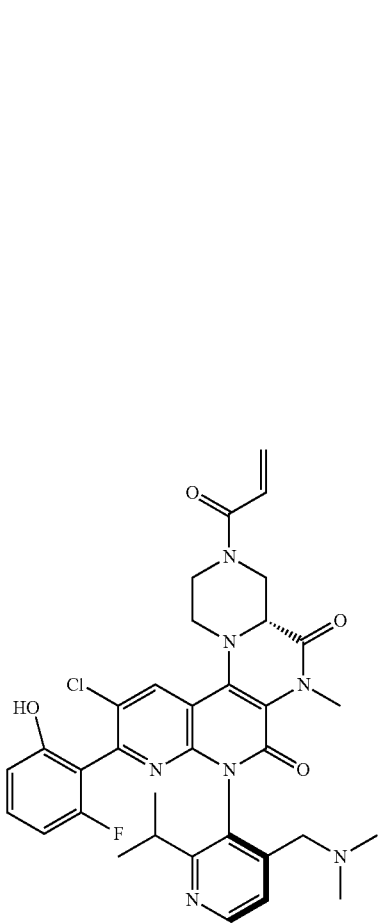
Z236-2 | |

| Example No. | Structure and No. of Compound | ES-API: [M+H]+ |
|---|---|---|
| 236 | Z236 | 661.2 |
| 237 | Z237 | 660.2 |
| 238 | Z238 | 689.3 |
| 239 | Z239 | 618.2 |

| Example No. | Structure and No. of Compound | ES-API: [M+H]⁺ |
|---|---|---|
| | Z239-1 | |
| | Z239-2 | |
| 240 | Z240 | 658.3 |
| | Z240-1 | |
| | Z240-2 | |

| Example No. | Structure and No. of Compound | ES-API: [M + H]⁺ |
|---|---|---|
| 241 | 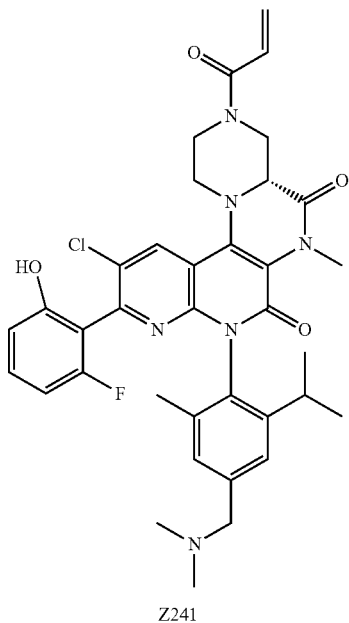 [SMILES: C=CC(=O)N1CCN2c3c(c(=O)n(-c4c(C)cc(CN(C)C)cc4C(C)C)c4nc(-c5c(O)cccc5F)c(Cl)cc34)N(C)C(=O)[C@H]2C1]<br>Z241 | 673.3 |
| | 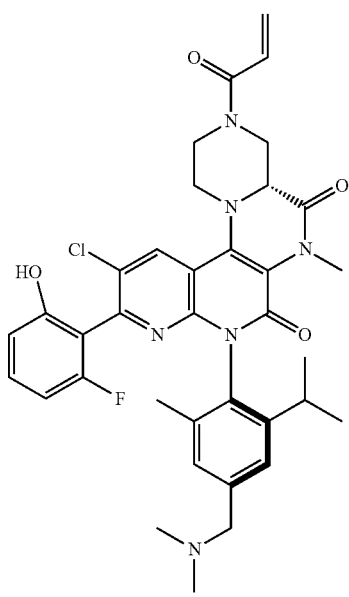<br>Z241-1 | |
| Example No. | Structure and No. of Compound | ES-API: [M + H]⁺ |
|---|---|---|
| | 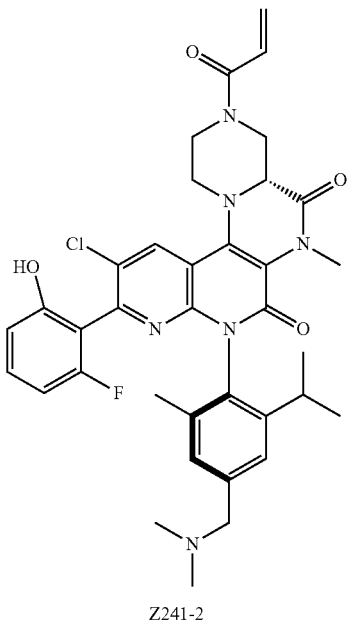<br>Z241-2 | |
| 242 | 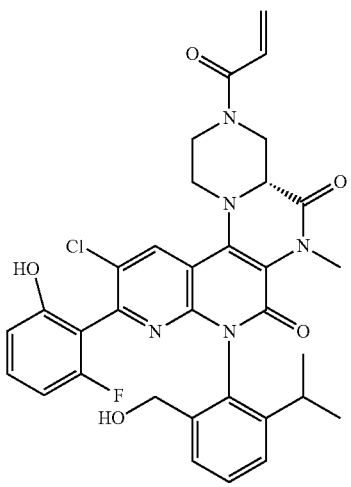<br>Z242 | 632.2 |

| Example No. | Structure and No. of Compound | ES-API: [M + H]+ |
|---|---|---|
| | 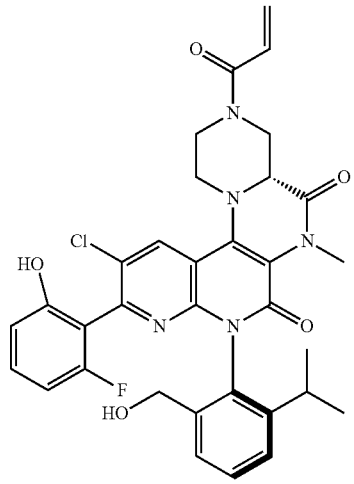Z242-1 | |
| | 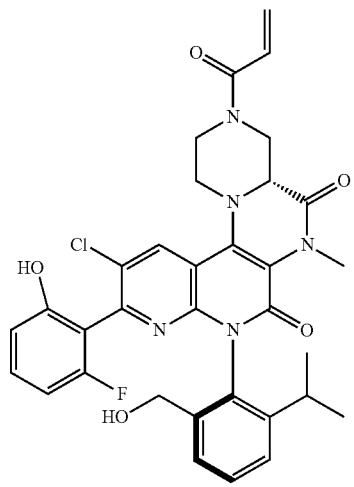Z242-2 | |
| Example No. | Structure and No. of Compound | ES-API: [M + H]+ |
|---|---|---|
| 243 | 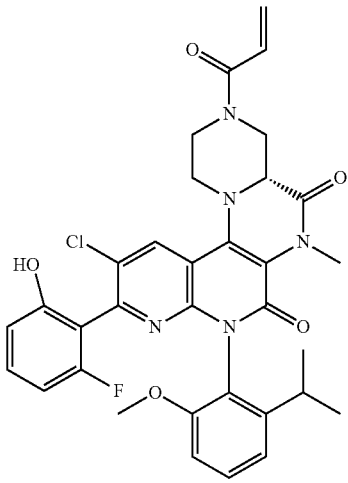Z243 | 632.2 |
| | 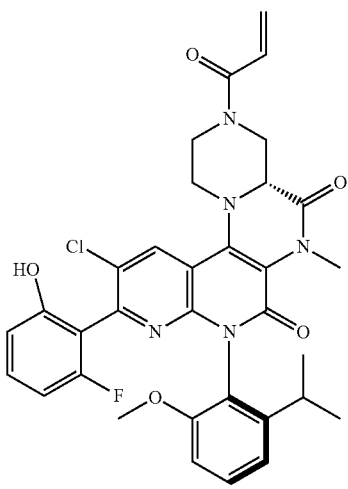Z243-1 | |

| Example No. | Structure and No. of Compound | ES-API: [M + H]+ |
|---|---|---|
| | 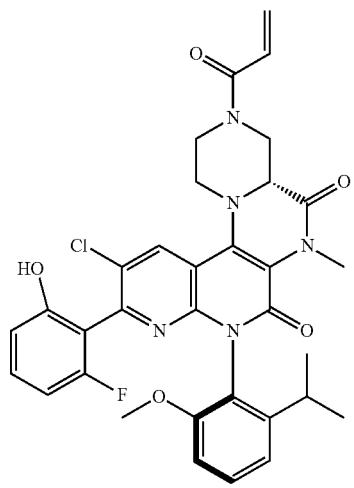 Z243-2 | |
| 244 | 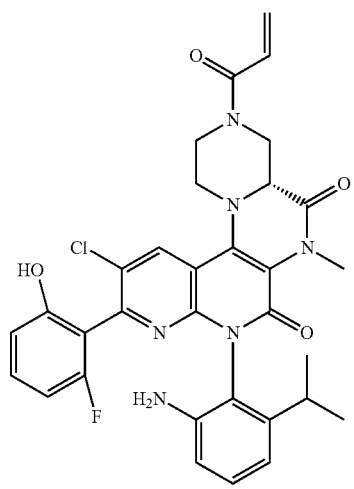 Z244 | 617.2 |
| Example No. | Structure and No. of Compound | ES-API: [M + H]+ |
|---|---|---|
| | 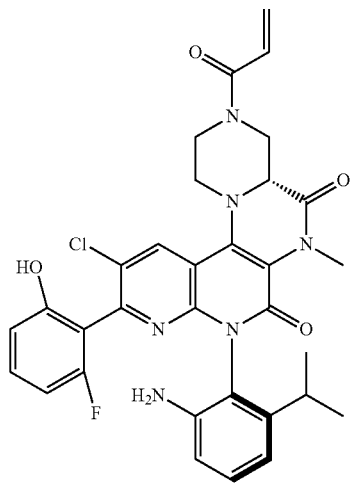 Z244-1 | |
| | 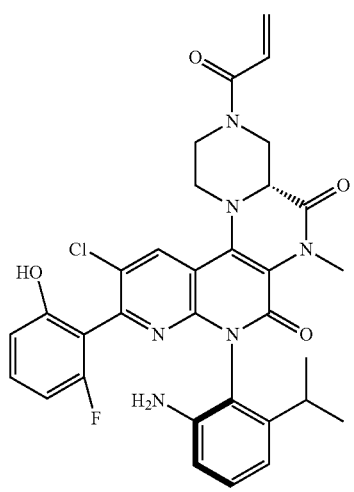 Z244-2 | |
| 245 | 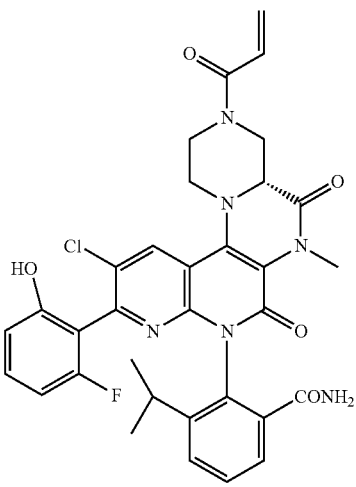 Z245 | 645.2 |

583
-continued
| Example No. | Structure and No. of Compound | ES-API: [M + H]+ |
|---|---|---|
| | 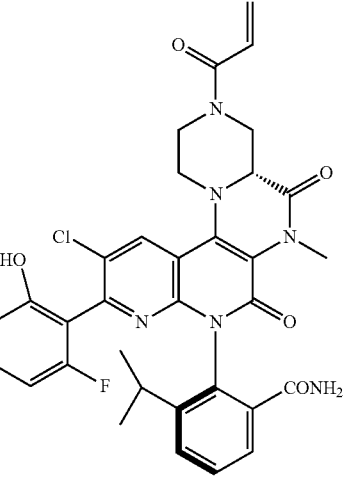 Z245-1 | |
| | 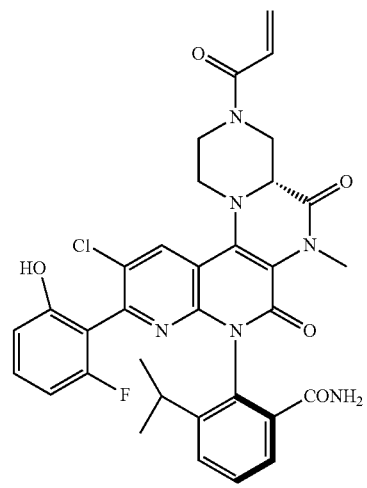 Z245-2 | |
584
-continued
| Example No. | Structure and No. of Compound | ES-API: [M + H]+ |
|---|---|---|
| 246 | 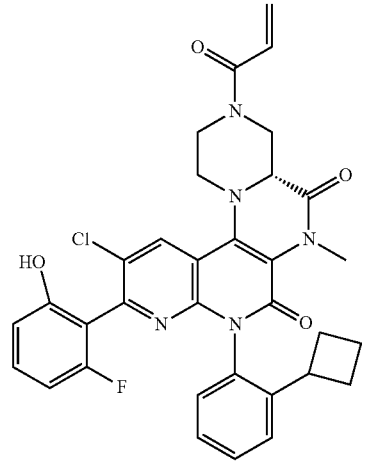 Z246 | 614.2 |
| | 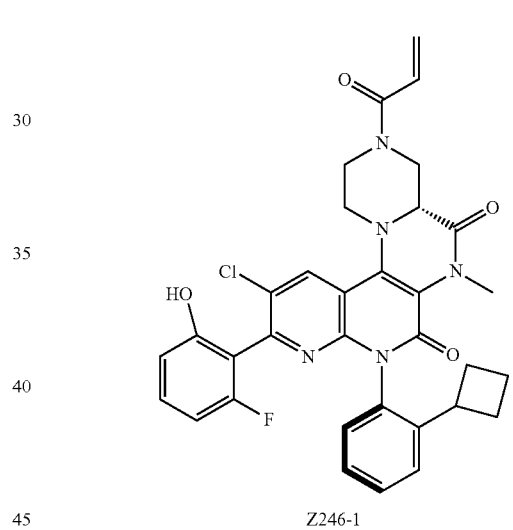 Z246-1 | |
| | 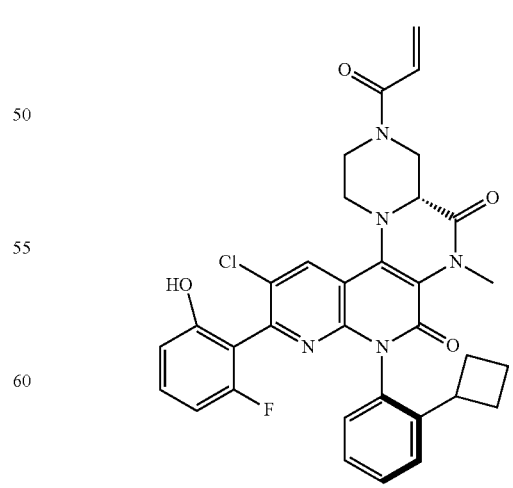 Z246-2 | |

| Example No. | Structure and No. of Compound | ES-API: [M + H]+ |
|---|---|---|
| 247 | 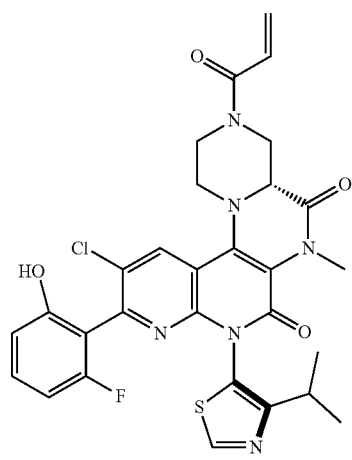Z247 | 609.1 |
| | Z247-1 | |
| | 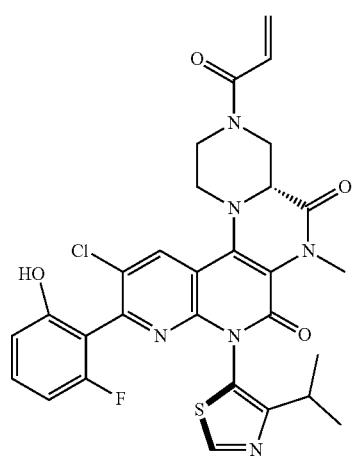Z247-2 | |
| Example No. | Structure and No. of Compound | ES-API: [M + H]+ |
|---|---|---|
| 248 | Z248 | 592.1 |
| 249 | Z249 | 590.2 |

| Example No. | Structure and No. of Compound | ES-API: [M + H]+ |
|---|---|---|
| 250 | Z250 | 647.2 |
| | Z250-1 | |

| Example No. | Structure and No. of Compound | ES-API: [M + H]+ |
|---|---|---|
| | Z250-2 | |
| 251 | Z251 | 617.2 |

| Example No. | Structure and No. of Compound | ES-API: [M + H]+ |
|---|---|---|
| | 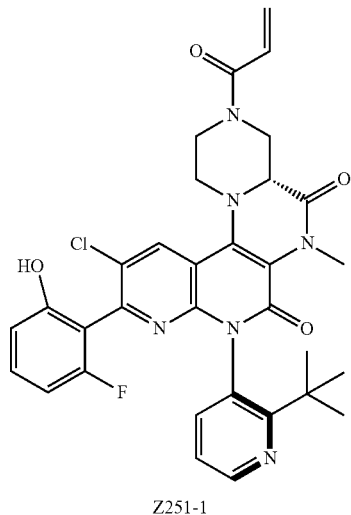<br>Z251-1<br><br>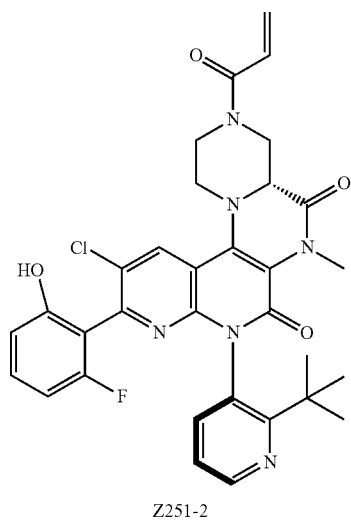<br>Z251-2 | |
| 252 | 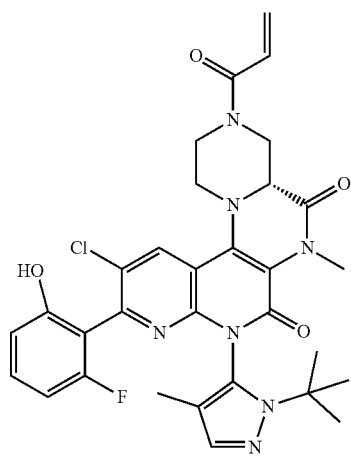<br>Z252 | 620.2 |
| Example No. | Structure and No. of Compound | ES-API: [M + H]+ |
|---|---|---|
| | 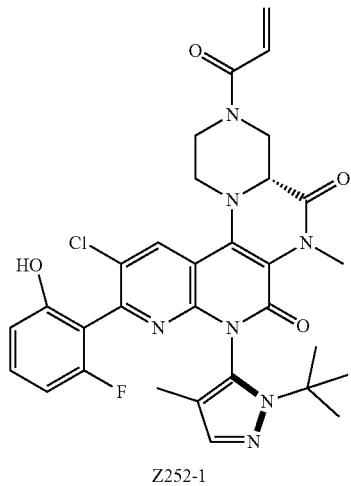<br>Z252-1<br><br>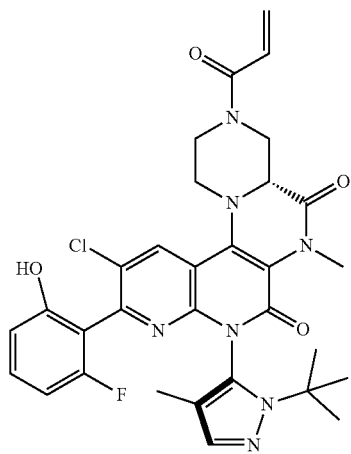<br>Z252-2 | |
| 253 | 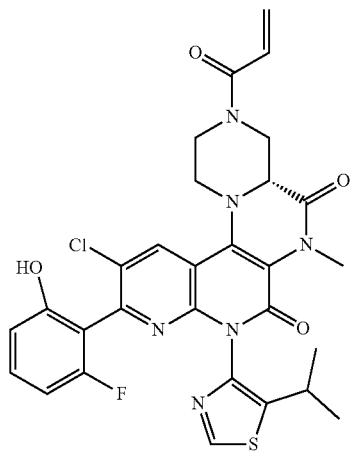<br>Z253 | 609.1 |

-continued
| Example No. | Structure and No. of Compound | ES-API: [M + H]+ |
|---|---|---|
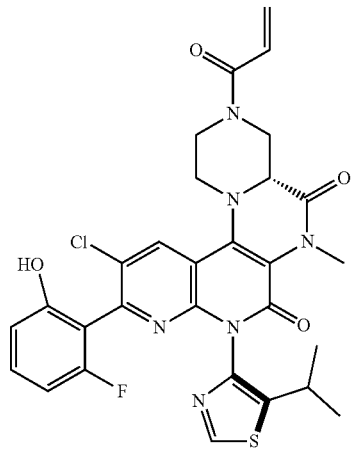
Z253-1
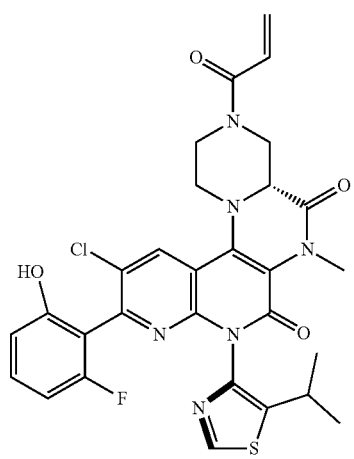
Z253-2
254
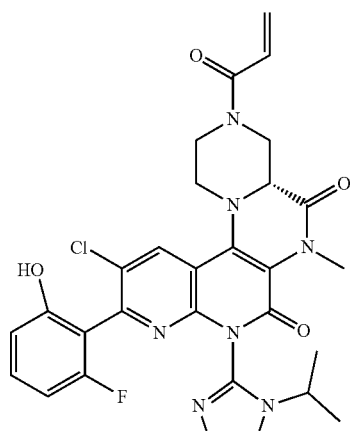
Z254
-continued
| Example No. | Structure and No. of Compound | ES-API: [M + H]+ |
|---|---|---|
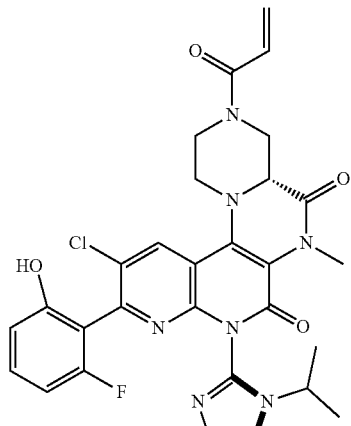
Z254-1
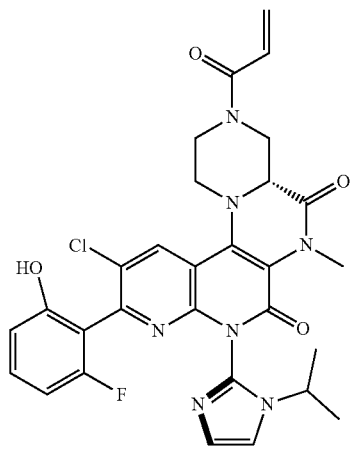
Z254-2
255   607.2
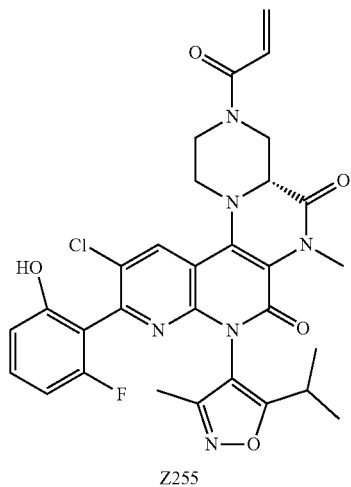 [SMILES: C=CC(=O)N1CCN2c3c(c(=O)n(-c4c(C)noc4C(C)C)c4nc(-c5c(O)cccc5F)c(Cl)cc34)N(C)C(=O)[C@H]2C1]
Z255
592.2

-continued
| Example No. | Structure and No. of Compound | ES-API: [M + H]+ |
|---|---|---|
| | 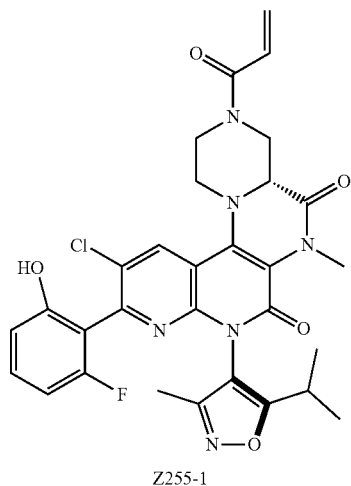<br>Z255-1 | |
| | 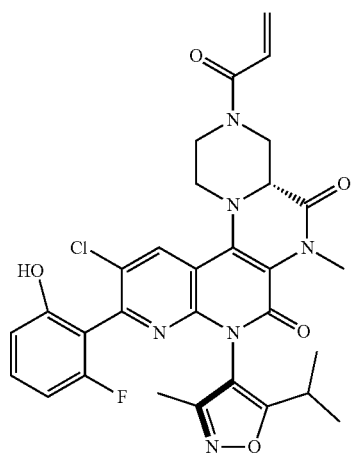<br>Z255-2 | |
| 256 | 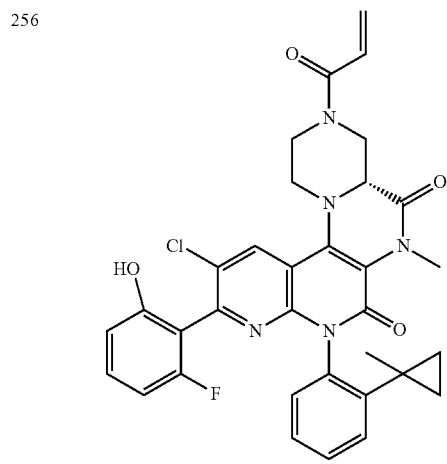<br>Z256 | 614.2 |
-continued
| Example No. | Structure and No. of Compound | ES-API: [M + H]+ |
|---|---|---|
| | 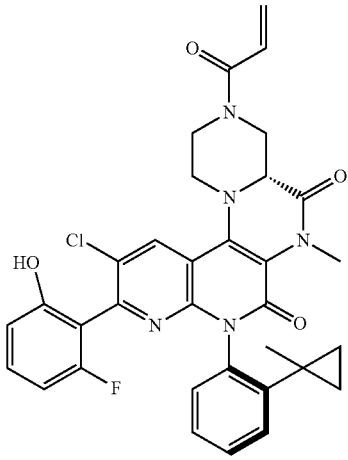<br>Z256-1 | |
| | 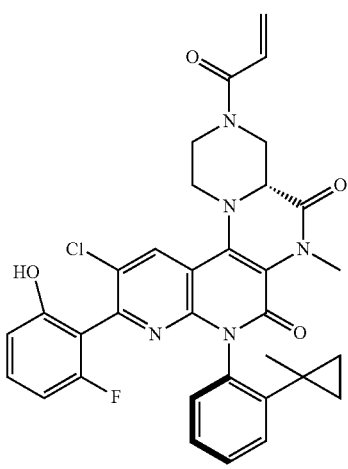<br>Z256-2 | |
| 257 | 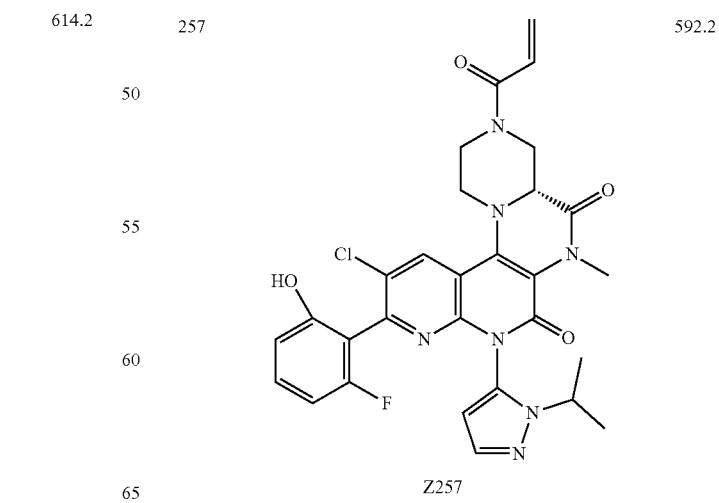<br>Z257 | 592.2 |

| Example No. | Structure and No. of Compound | ES-API: [M + H]+ |
|---|---|---|
| | 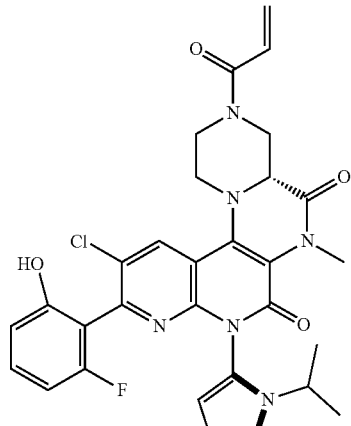Z257-1 | |
| | 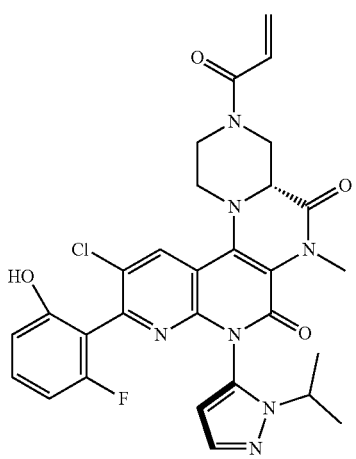Z257-2 | |
| 258 | 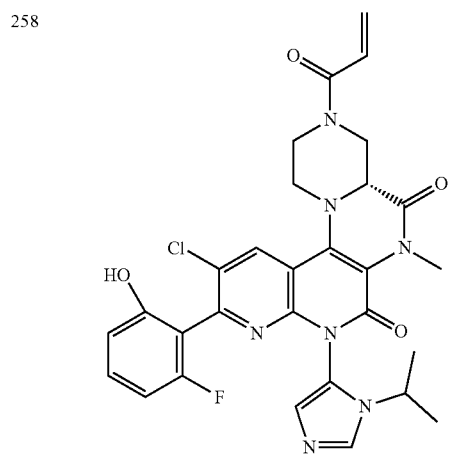Z258 | 592.2 |
| Example No. | Structure and No. of Compound | ES-API: [M + H]+ |
|---|---|---|
| | 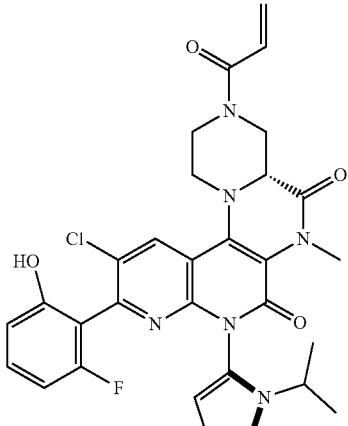Z258-1 | |
| | 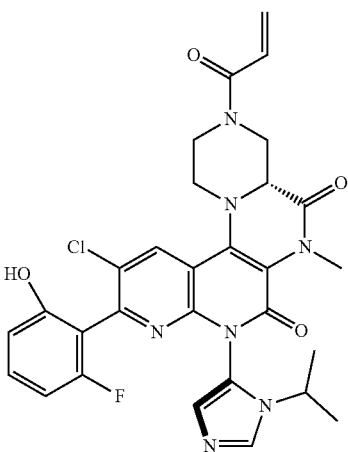Z258-2 | |
| 259 | 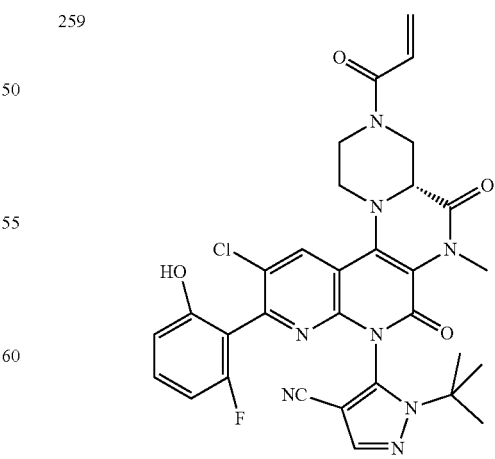Z259 | 631.2 |

| Example No. | Structure and No. of Compound | ES-API: [M + H]⁺ |
|---|---|---|
| | 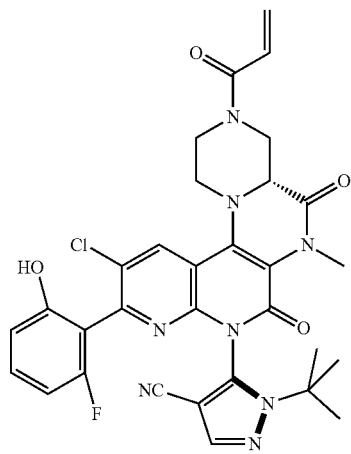
Z259-1 | |
| | 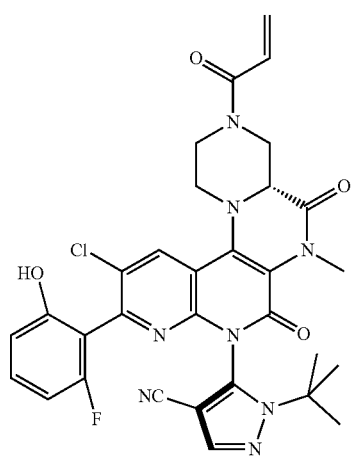
Z259-2 | |
| 260 | 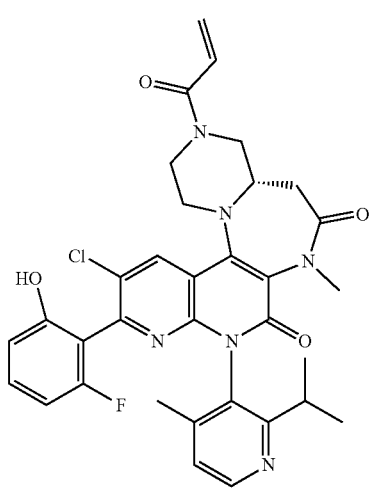
Z260 | 631.2 |
| Example No. | Structure and No. of Compound | ES-API: [M + H]⁺ |
|---|---|---|
| | 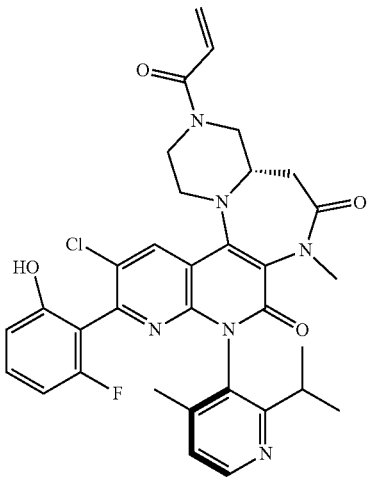
Z260-1 | |
| | 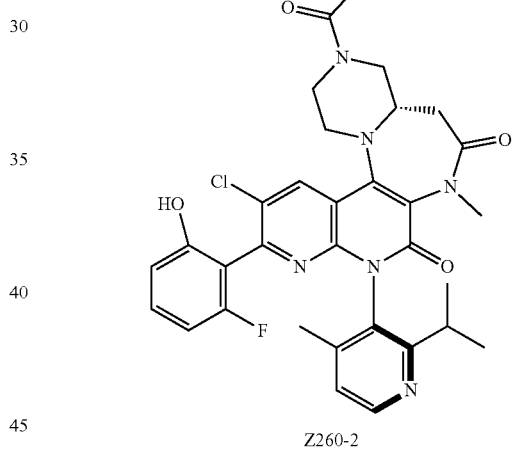
Z260-2 | |
| 261 | 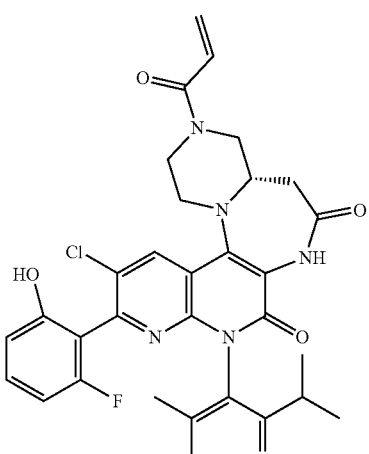
Z261 | 617.2 |

| Example No. | Structure and No. of Compound | ES-API: [M+H]+ |
|---|---|---|
| | 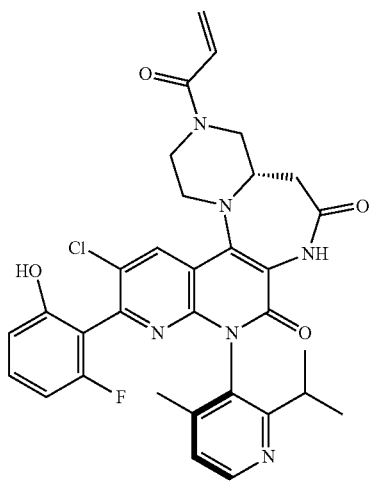
Z261-1 | |
| | 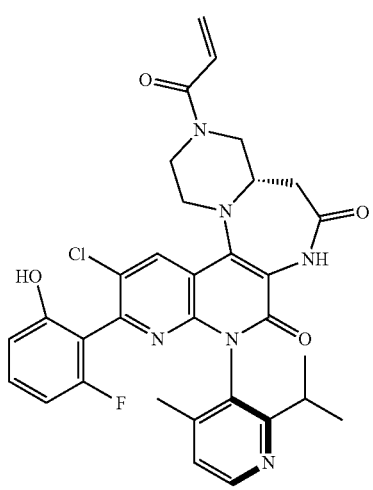
Z261-2 | |
| Example No. | Structure and No. of Compound | ES-API: [M+H]+ |
|---|---|---|
| 262 | 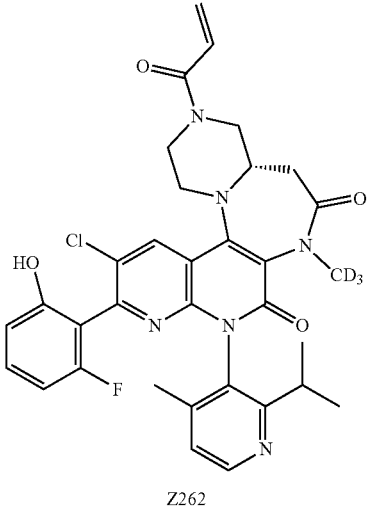 [SMILES: [2H]C([2H])([2H])N1C(=O)C[C@H]2CN(C(=O)C=C)CCN2c2c1c(=O)n(-c1c(C)ccnc1C(C)C)c1nc(-c3c(O)cccc3F)c(Cl)cc21]
Z262 | 634.2 |
| | 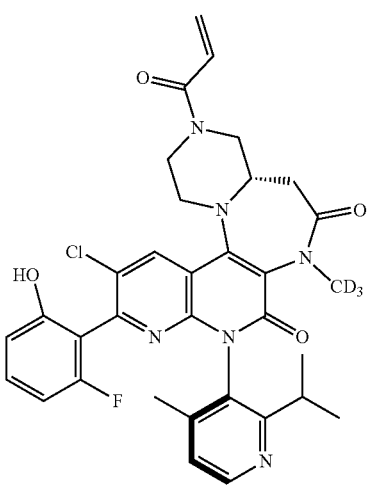
Z262-1 | |
| | 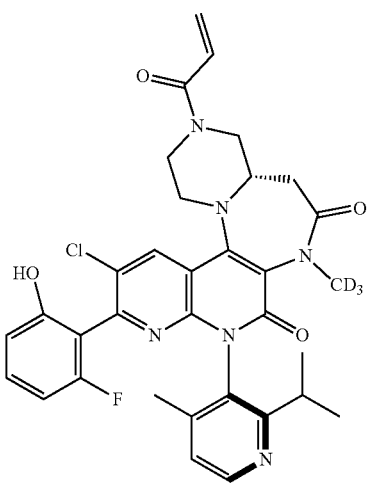
Z262-2 | |

-continued
| Example No. | Structure and No. of Compound | ES-API: [M + H]⁺ |
|---|---|---|
| 263 | 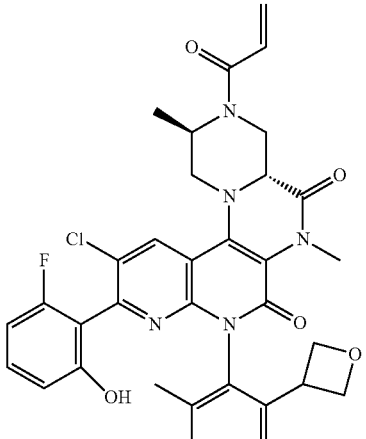 Z263 | 645.2 |
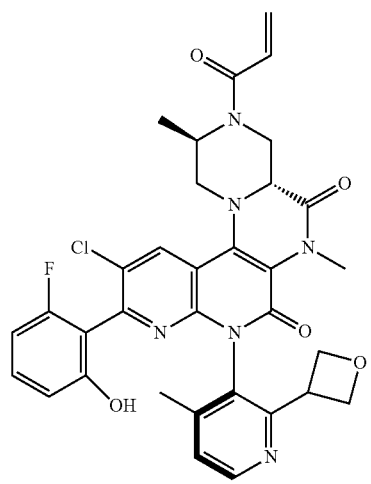
Z263-1
-continued
| Example No. | Structure and No. of Compound | ES-API: [M + H]⁺ |
|---|---|---|
| | 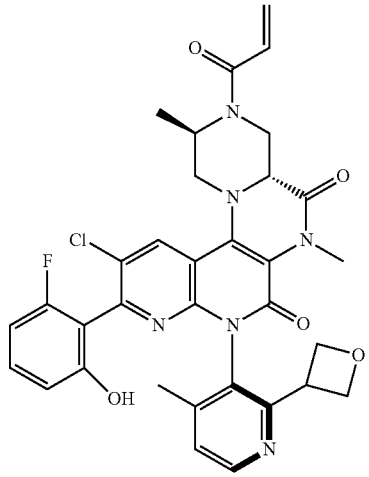 Z263-2 | |
| 264 | 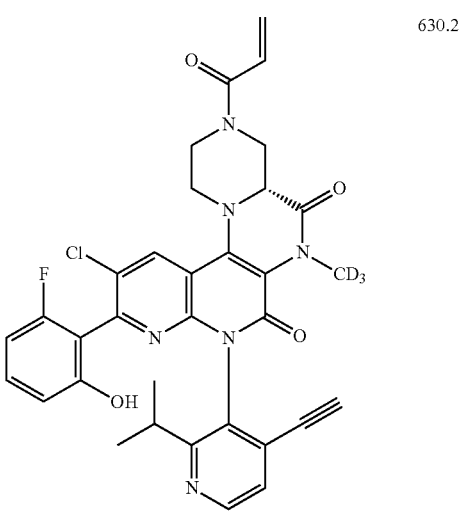 Z264 | 630.2 |

603
-continued
| Example No. | Structure and No. of Compound | ES-API: [M + H]+ |
|---|---|---|
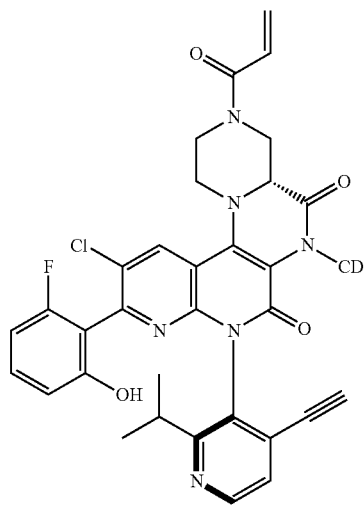
Z264-1
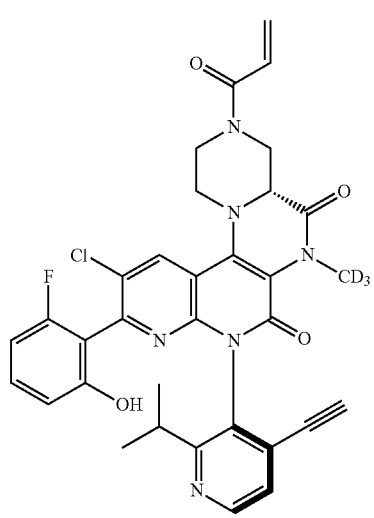
Z264-2
604
-continued
| Example No. | Structure and No. of Compound | ES-API: [M + H]+ |
|---|---|---|
| 265 | | 683.2 |
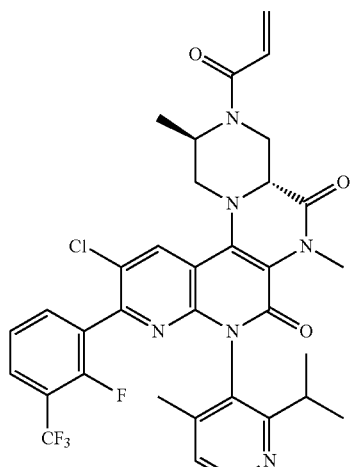
Z265
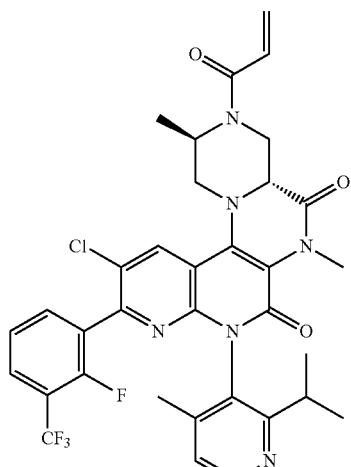
Z265-1

| Example No. | Structure and No. of Compound | ES-API: [M + H]⁺ |
|---|---|---|
|  | 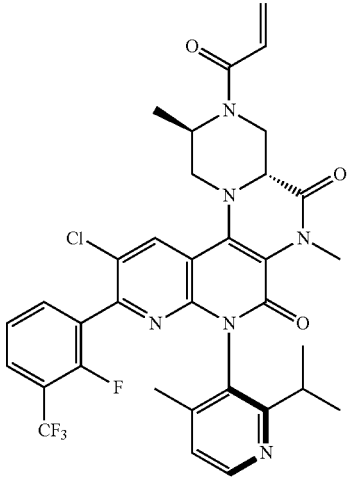<br>Z265-2 |  |
| 266 | 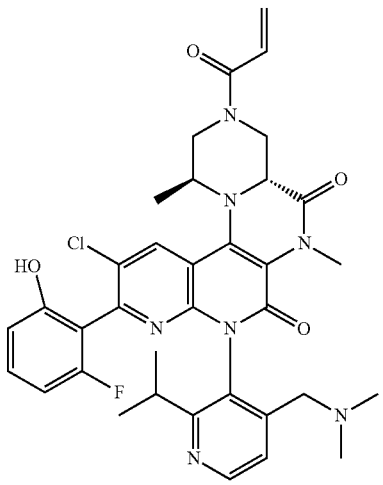<br>Z266 | 674.3 |
| Example No. | Structure and No. of Compound | ES-API: [M + H]⁺ |
|---|---|---|
|  | 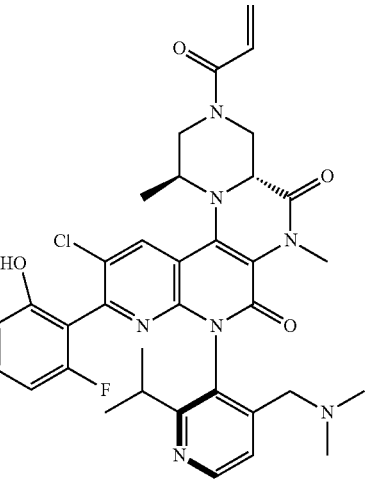<br>Z266-1 |  |
|  | 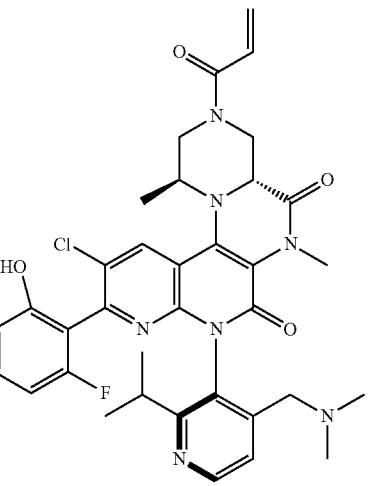<br>Z266-1 |  |

-continued

| Example No. | Structure and No. of Compound | ES-API: [M + H]+ |
|---|---|---|
| 267 | Z267 | 675.3 |
| 268 | Z268 | 674.3 |
| 269 | Z269 | 703.3 |
| 270 | Z270 | 632.2 |

| Example No. | Structure and No. of Compound | ES-API: [M + H]+ |
|---|---|---|
| | 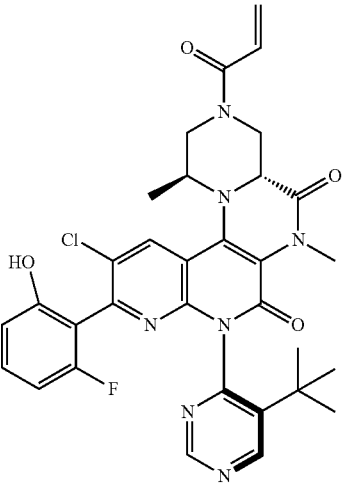<br>Z270-1 | |
| | 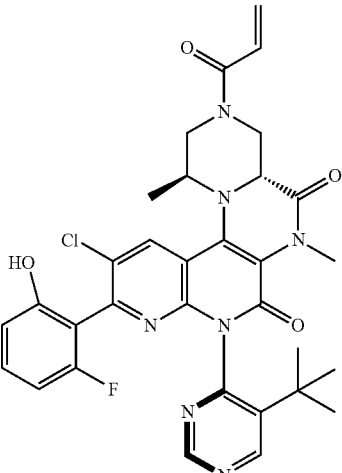<br>Z270-2 | |
| Example No. | Structure and No. of Compound | ES-API: [M + H]+ |
|---|---|---|
| 271 | 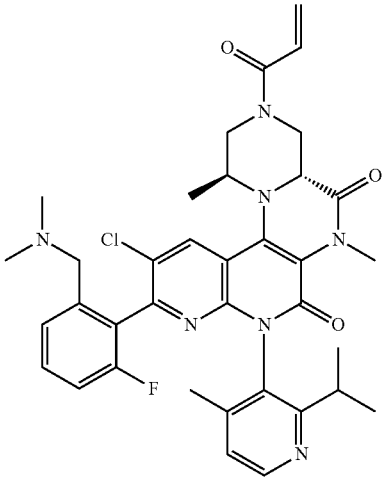<br>Z271 | 672.3 |
| | 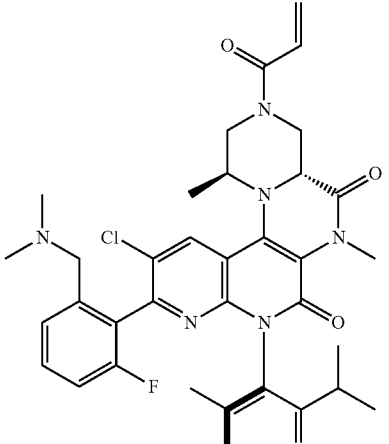<br>Z271-1 | |
| | 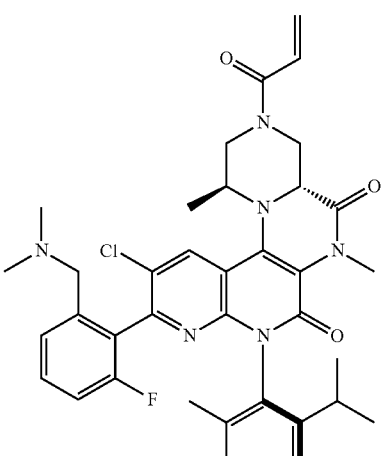<br>Z271-2 | |

| Example No. | Structure and No. of Compound | ES-API: [M+H]+ |
|---|---|---|
| 272 | 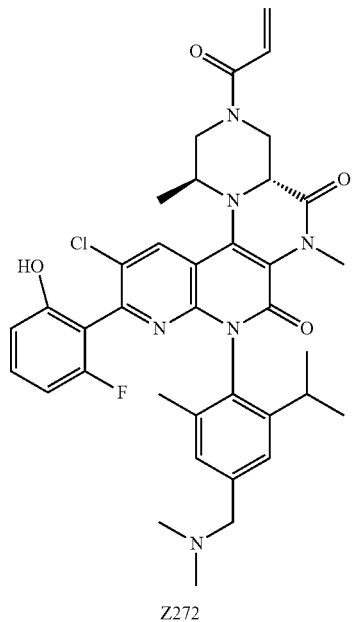 [SMILES: C=CC(=O)N1C[C@@H]2C(=O)N(C)c3c(c4cc(Cl)c(-c5c(O)cccc5F)nc4n(-c4c(C)cc(CN(C)C)cc4C(C)C)c3=O)N2[C@@H](C)C1]<br>Z272 | 687.3 |
| | 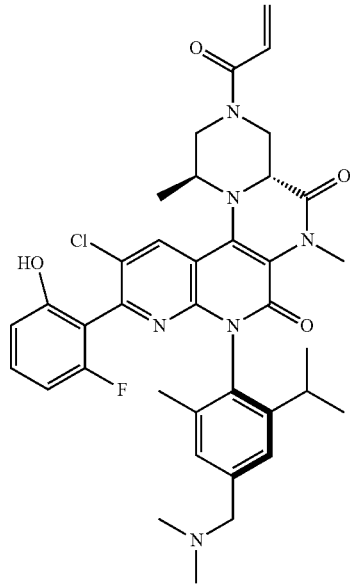<br>Z272-1 | |
| Example No. | Structure and No. of Compound | ES-API: [M+H]+ |
|---|---|---|
| | 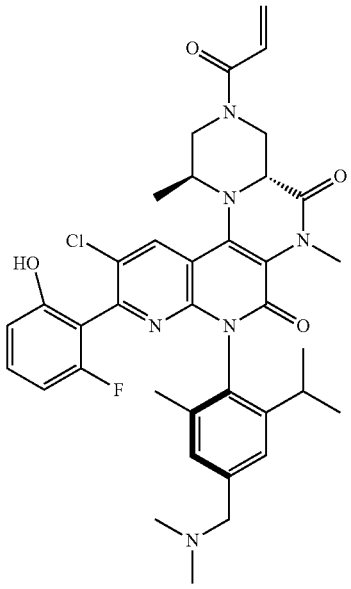<br>Z272-2 | |
| 273 | 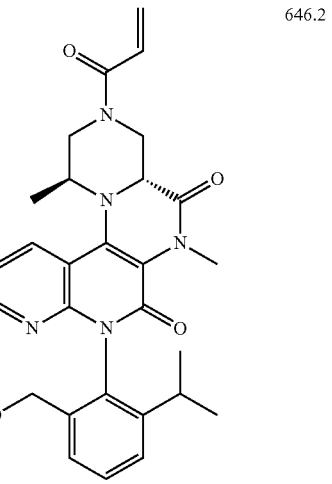<br>Z273 | 646.2 |

| Example No. | Structure and No. of Compound | ES-API: [M + H]+ |
|---|---|---|
| | 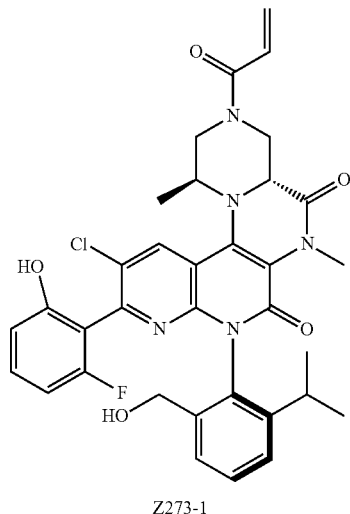 | |
| | 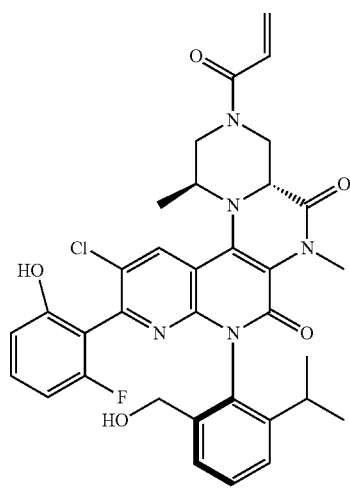 | |
| 274 | 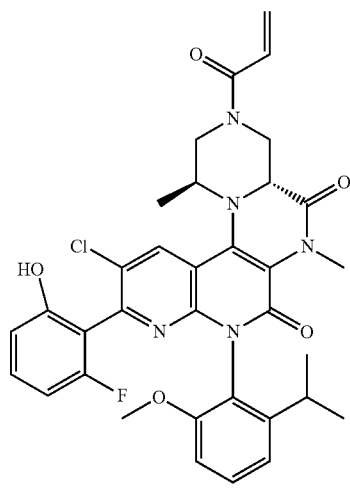 | 646.2 |
| Example No. | Structure and No. of Compound | ES-API: [M + H]+ |
|---|---|---|
| | 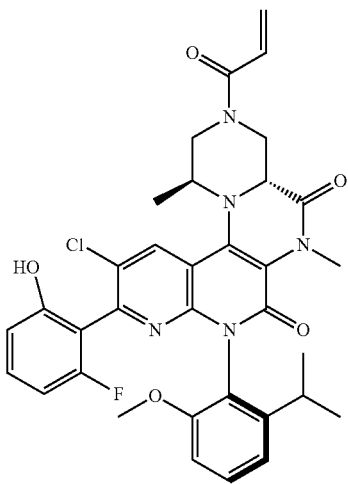 | |
| | 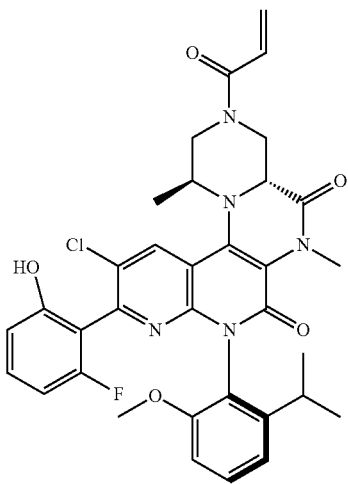 | |

| Example No. | Structure and No. of Compound | ES-API: [M+H]+ |
|---|---|---|
| 275 | Z275 | 631.2 |
| | Z275-1 | |
| | Z275-2 | |
| 276 | Z276 | 659.2 |
| | Z276-1 | |

| Example No. | Structure and No. of Compound | ES-API: [M + H]⁺ |
|---|---|---|
| | 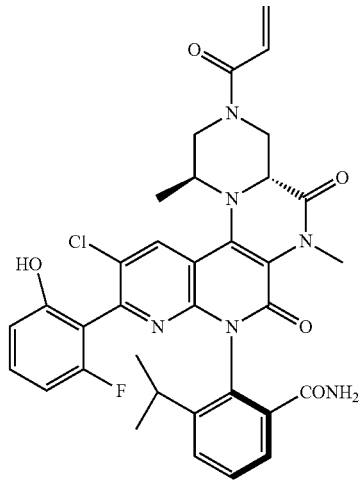
Z276-2 | |
| 277 | 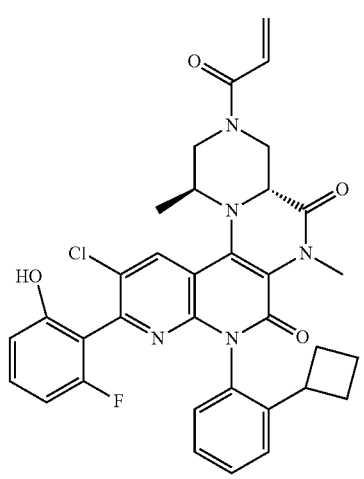
Z277 | 628.2 |
| | 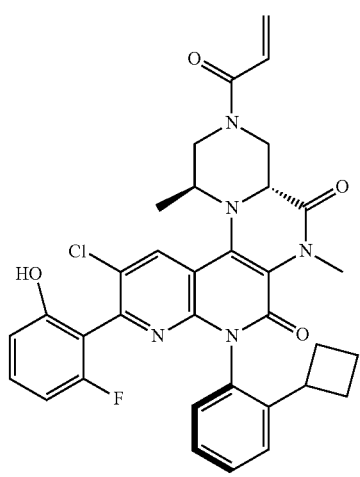
Z277-1 | |
| Example No. | Structure and No. of Compound | ES-API: [M + H]⁺ |
|---|---|---|
| | 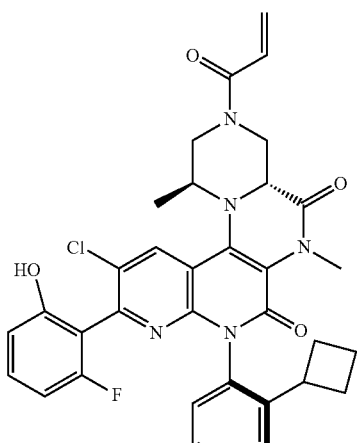
Z277-2 | |
| 278 | 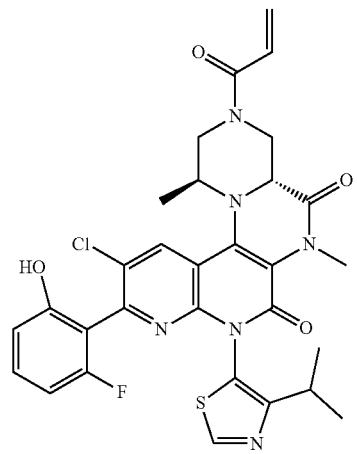
Z278 | 623.2 |
| | 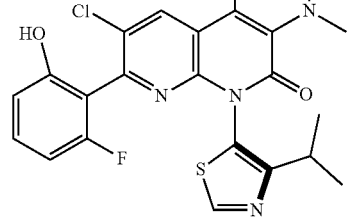
Z278-1 | |

| Example No. | Structure and No. of Compound | ES-API: [M + H]+ |
|---|---|---|
|  | 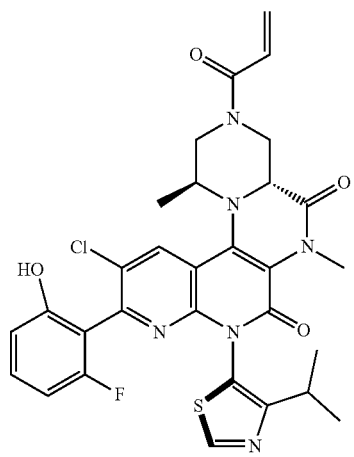 Z278-2 |  |
| 279 | 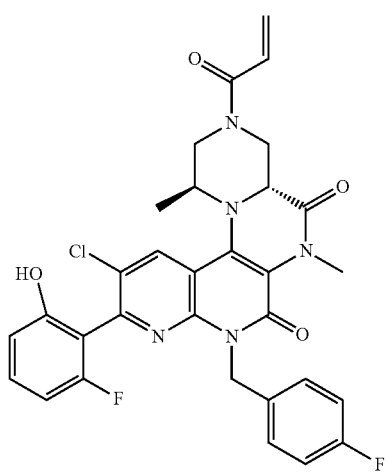 Z279 | 606.2 |
| 280 | 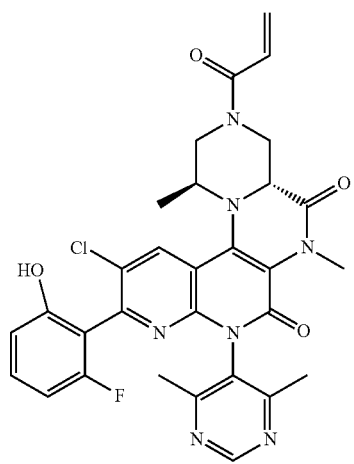 Z280 | 604.2 |
| Example No. | Structure and No. of Compound | ES-API: [M + H]+ |
|---|---|---|
| 281 | 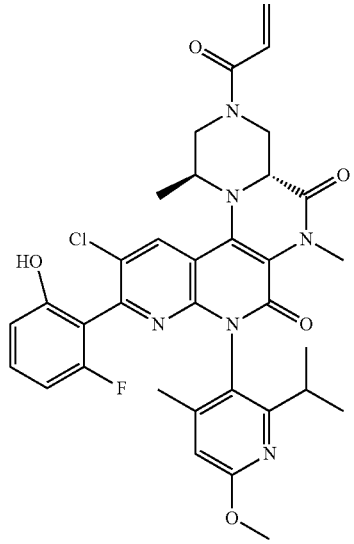 Z281 | 661.2 |
|  | 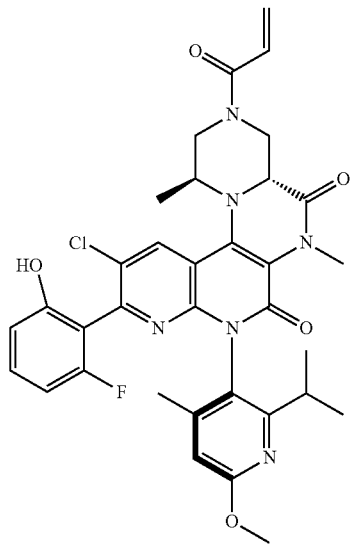 Z281-1 |  |

| Example No. | Structure and No. of Compound | ES-API: [M+H]+ |
|---|---|---|
| | 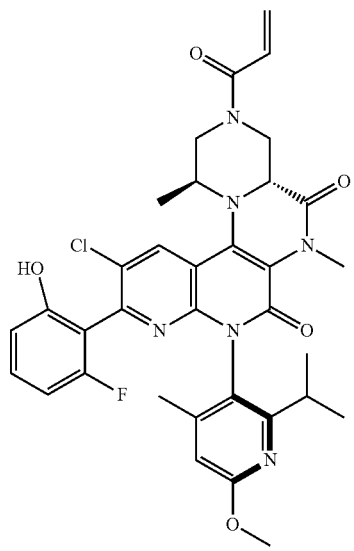<br>Z281-2 | |
| 282 | 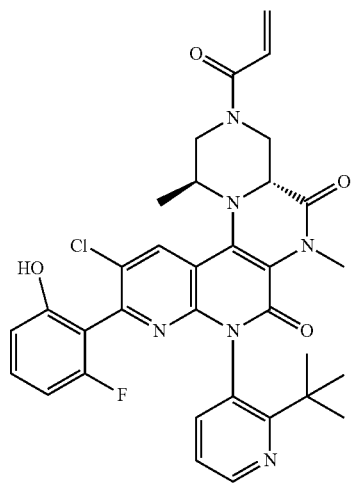<br>Z282 | 631.2 |
| Example No. | Structure and No. of Compound | ES-API: [M+H]+ |
|---|---|---|
| | 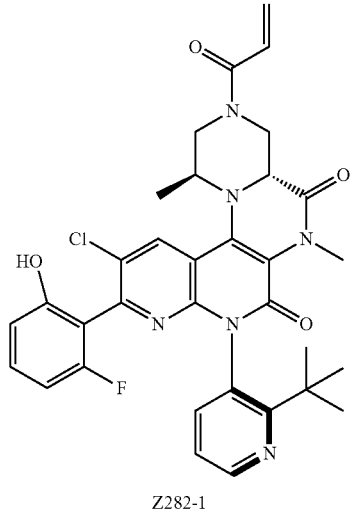<br>Z282-1 | |
| | 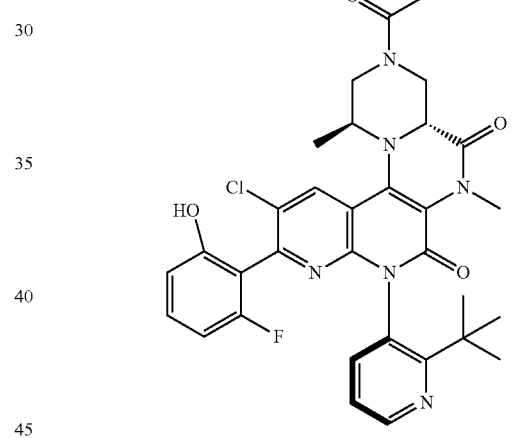<br>Z282-2 | |
| 283 | 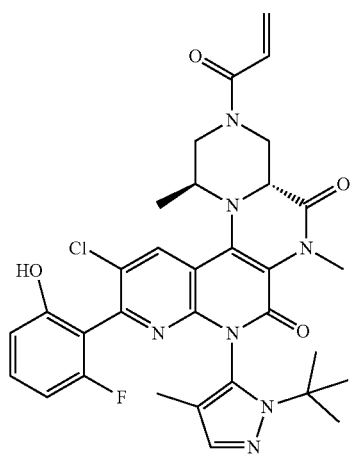<br>Z283 | 634.2 |

623
-continued
| Example No. | Structure and No. of Compound | ES-API: [M + H]+ |
|---|---|---|
| | 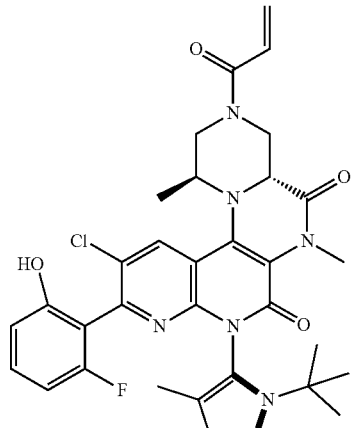 Z283-1 | |
| | 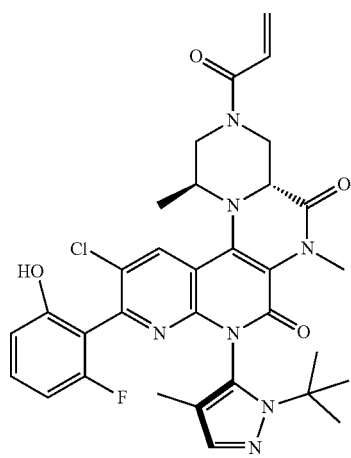 Z283-2 | |
| 284 | 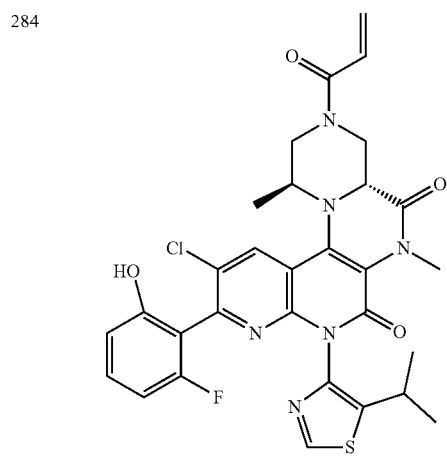 Z284 | 623.2 |
624
-continued
| Example No. | Structure and No. of Compound | ES-API: [M + H]+ |
|---|---|---|
| | 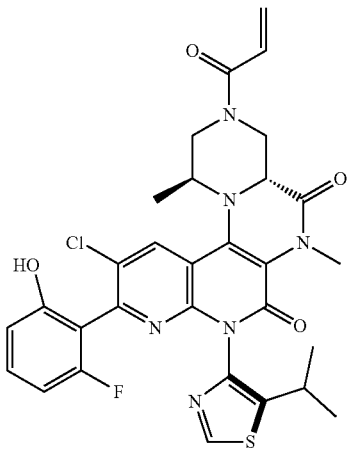 Z284-1 | |
| | 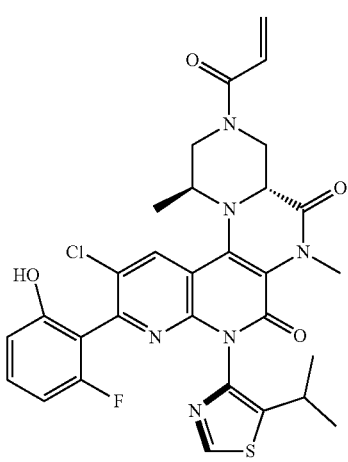 Z284-2 | |
| 285 | 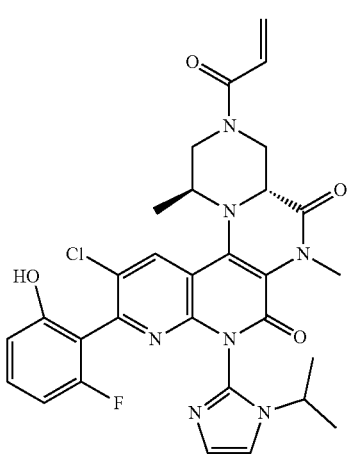 Z285 | 606.2 |

625
-continued
| Example No. | Structure and No. of Compound | ES-API: [M + H]+ |
|---|---|---|
| | 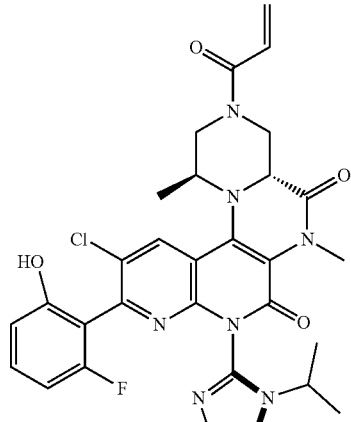
Z285-1 | |
| | 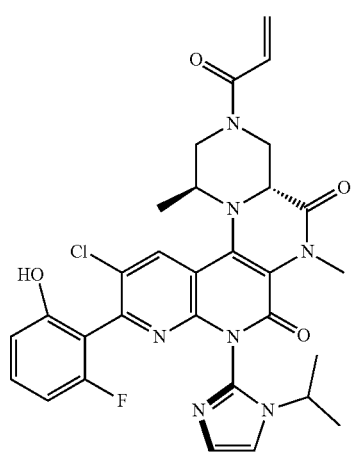
Z285-2 | |
| 286 | 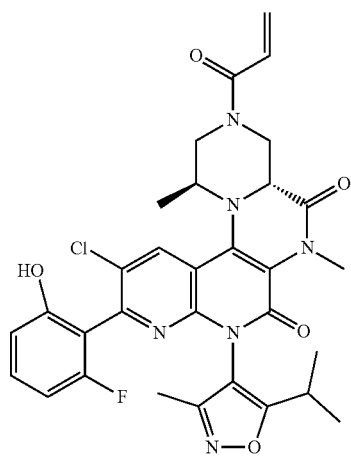
Z286 | 621.2 |
626
-continued
| Example No. | Structure and No. of Compound | ES-API: [M + H]+ |
|---|---|---|
| | 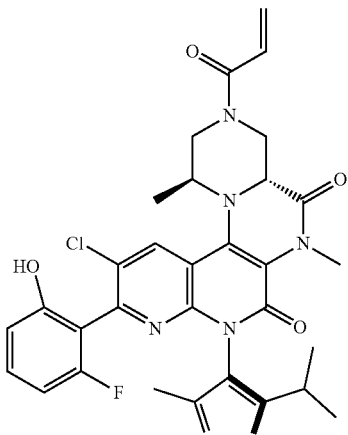
Z286-1 | |
| | 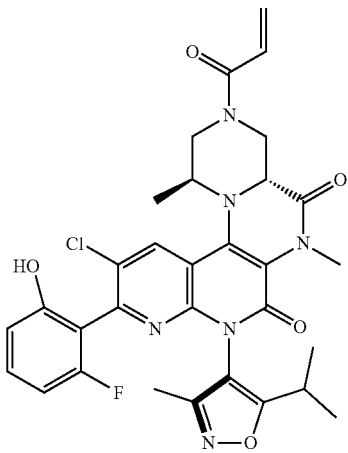
Z286-2 | |
| 287 | 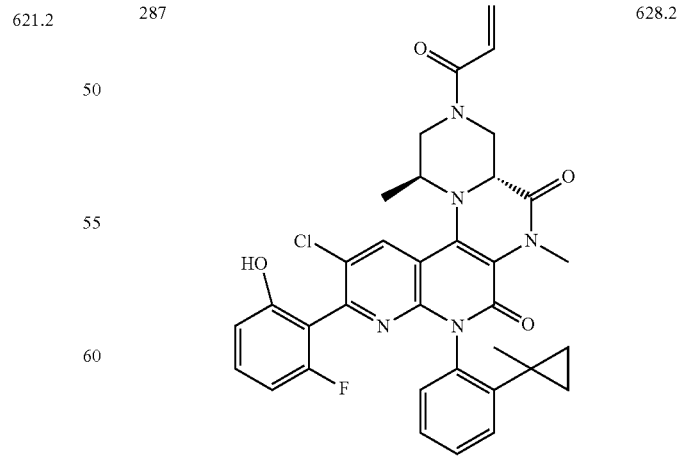
Z287 | 628.2 |

| Example No. | Structure and No. of Compound | ES-API: [M + H]+ |
|---|---|---|
| | 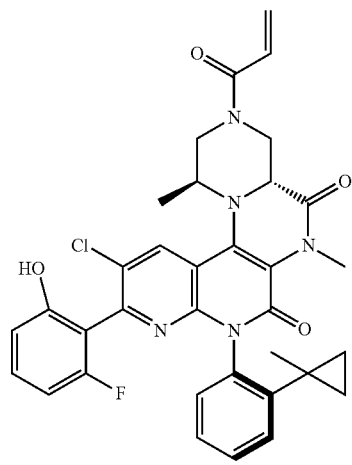<br>Z287-1 | |
| | 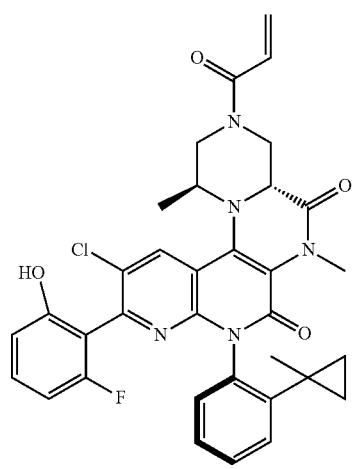<br>Z287-2 | |
| 288 | 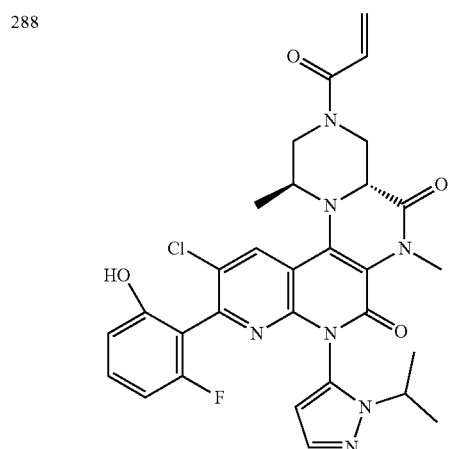<br>Z288 | 606.2 |
| Example No. | Structure and No. of Compound | ES-API: [M + H]+ |
|---|---|---|
| | 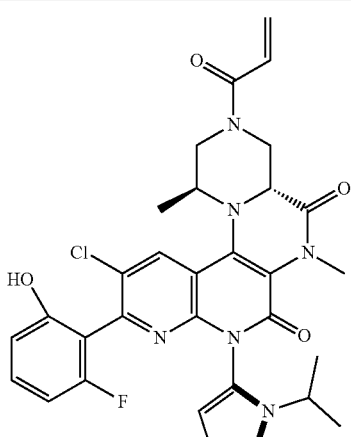<br>Z288-1 | |
| | 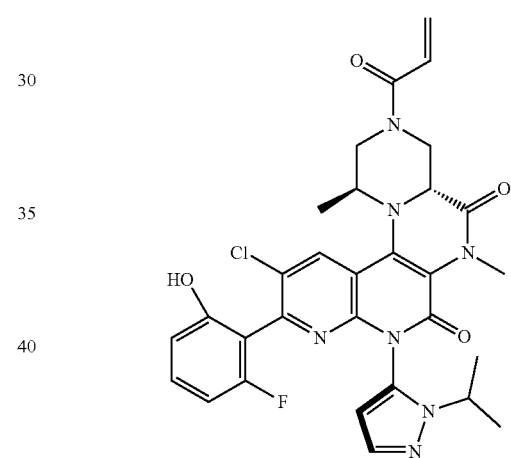<br>Z288-2 | |
| 289 | 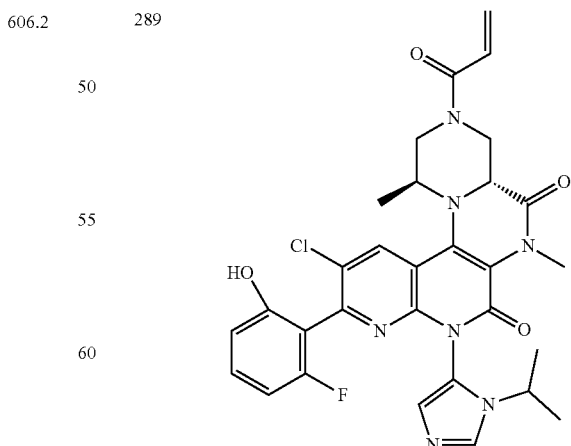<br>Z289 | 606.2 |

| Example No. | Structure and No. of Compound | ES-API: [M + H]+ |
|---|---|---|
| | 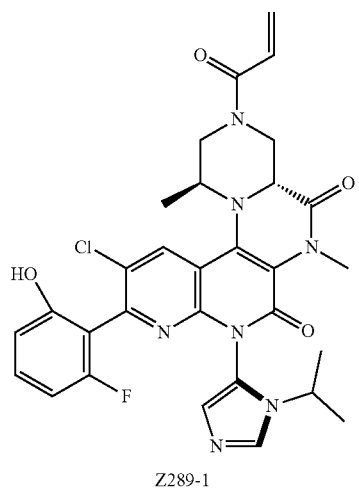
Z289-1 | |
| | 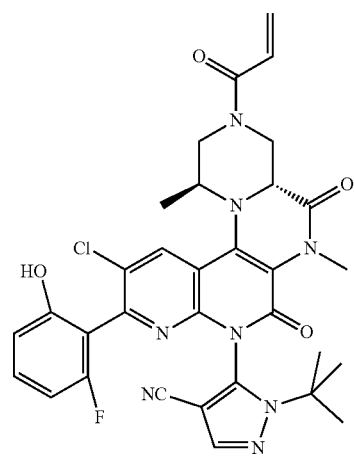
Z289-2 | |
| 290 | 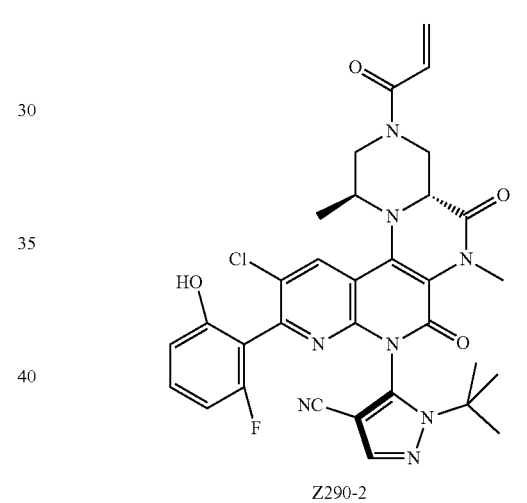
Z290 | 645.2 |
| Example No. | Structure and No. of Compound | ES-API: [M + H]+ |
|---|---|---|
| | 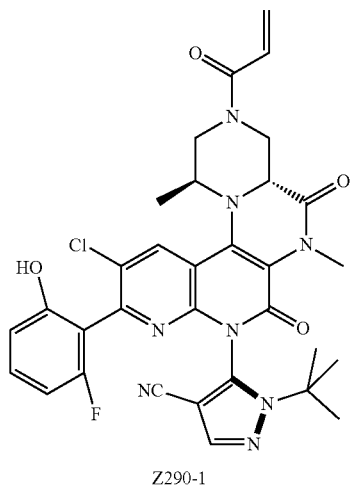
Z290-1 | |
| | Z290-2 | |
| 291 | 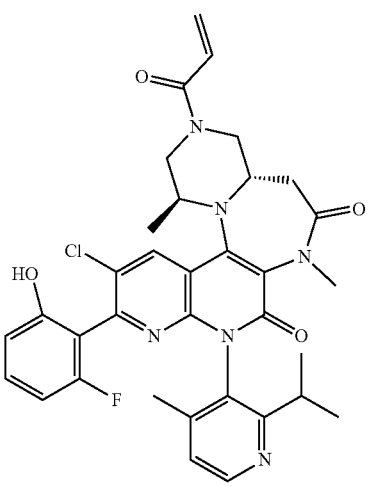
Z291 | 645.2 |

| Example No. | Structure and No. of Compound | ES-API: [M + H]+ |
|---|---|---|
| | 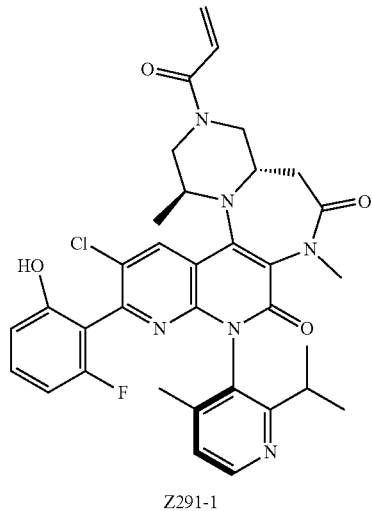<br>Z291-1 | |
| | 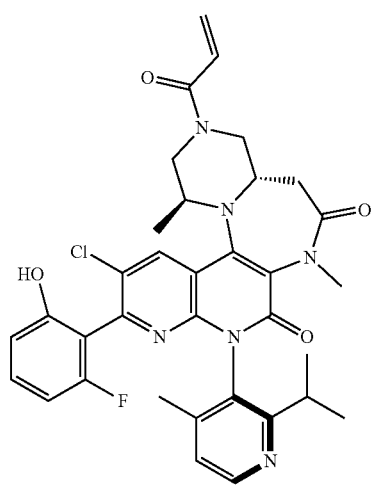<br>Z291-2 | |
| 292 | 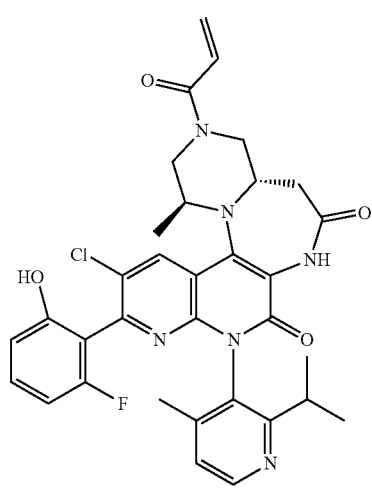<br>Z292 | 631.2 |
| Example No. | Structure and No. of Compound | ES-API: [M + H]+ |
|---|---|---|
| | 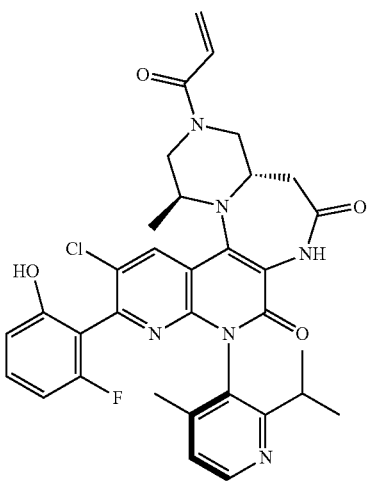<br>Z292-1 | |
| | 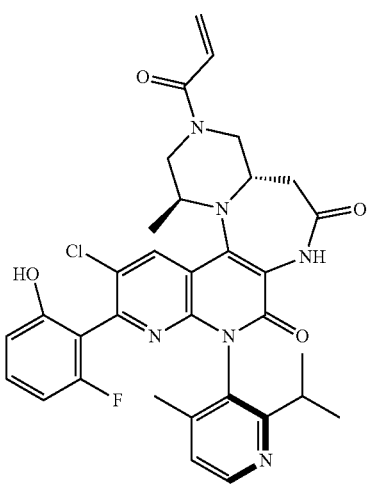<br>Z292-2 | |

-continued

| Example No. | Structure and No. of Compound | ES-API: [M + H]+ |
|---|---|---|
| 293 | Z293 | 648.3 |
| | Z293-1 | |
| | Z293-2 | |

-continued

| Example No. | Structure and No. of Compound | ES-API: [M + H]+ |
|---|---|---|
| 294 | Z294 | 613.2 |
| | Z294-1 | |

-continued
| Example No. | Structure and No. of Compound | ES-API: [M + H]+ |
|---|---|---|
| | 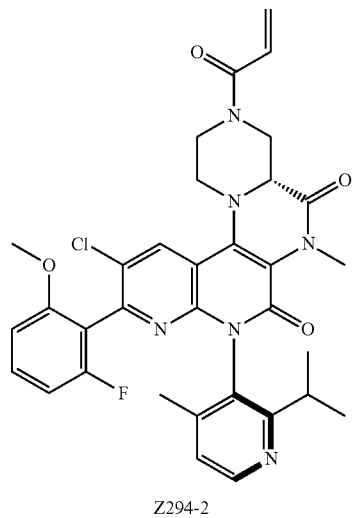<br>Z294-2 | |
| 295 | 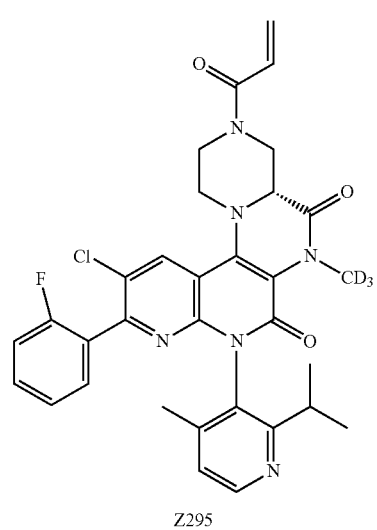 [SMILES: [2H]C([2H])([2H])N1C(=O)[C@H]2CN(C(=O)C=C)CCN2c2c1c(=O)n(-c1c(C)ccnc1C(C)C)c1nc(-c3ccccc3F)c(Cl)cc21]<br>Z295 | 604.2 |
| | 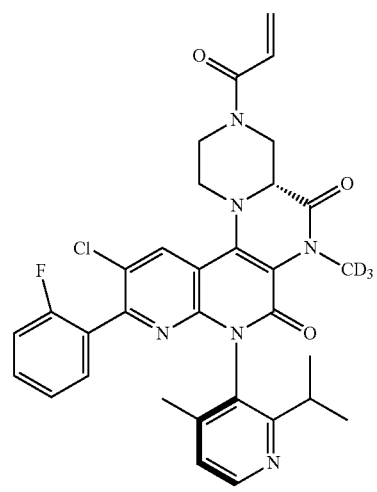<br>Z295-1 | |
-continued
| Example No. | Structure and No. of Compound | ES-API: [M + H]+ |
|---|---|---|
| | 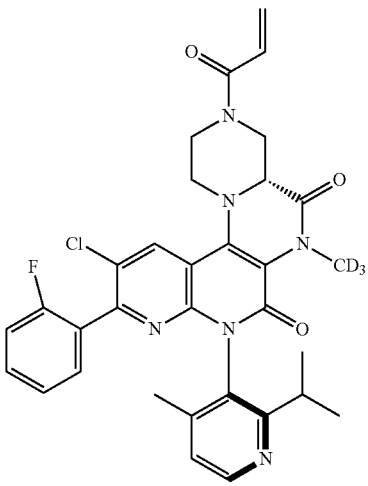<br>Z295-2 | |
| 296 | 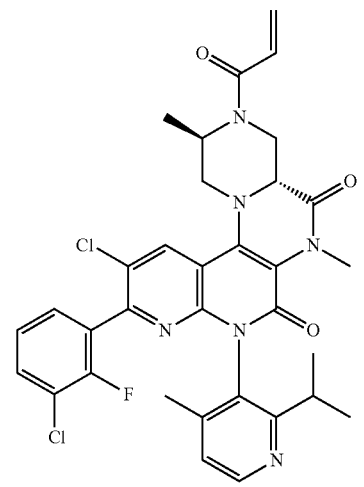<br>Z296 | 649.2 |

| Example No. | Structure and No. of Compound | ES-API: [M + H]+ |
|---|---|---|
| | 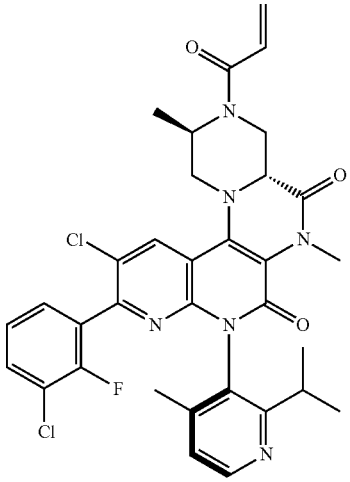<br>Z296-1 | |
| 297 | 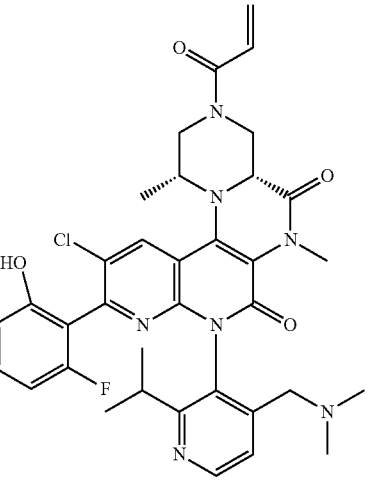<br>Z297 | 674.3 |
| | 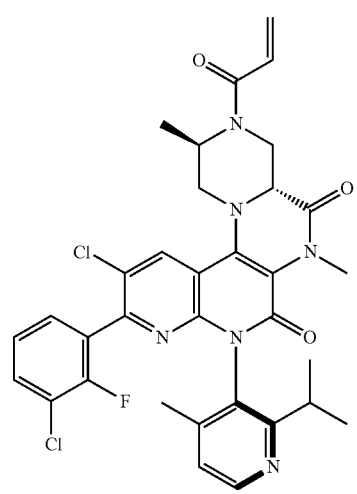<br>Z296-2 | |
| | 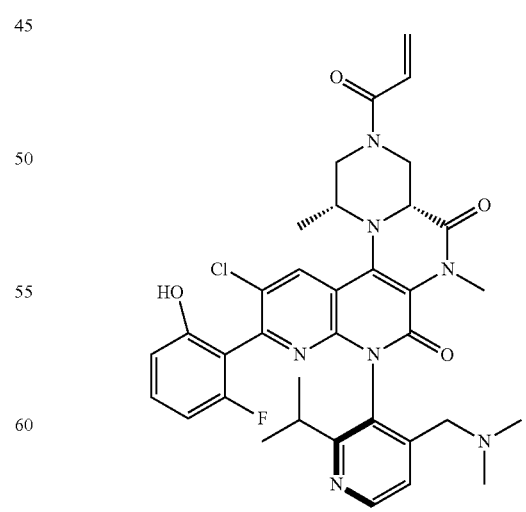<br>Z297-1 | |

TABLE -continued
| Example No. | Structure and No. of Compound | ES-API: [M + H]+ |
|---|---|---|
| | 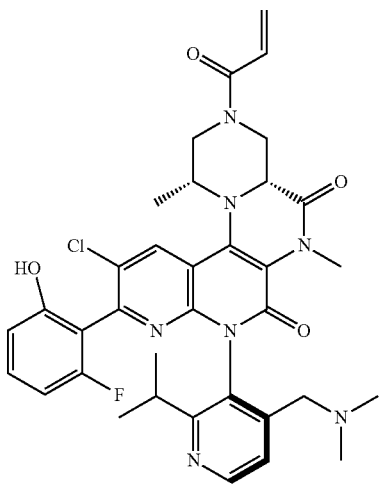 | |
| | Z297-2 | |
| 298 | 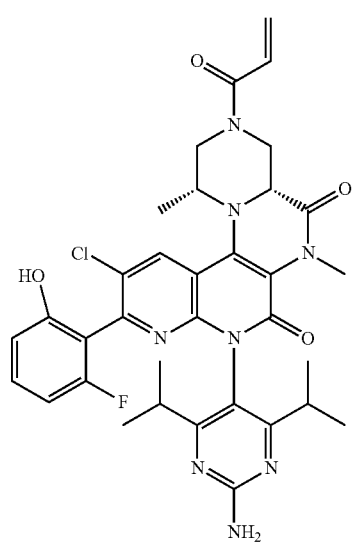 Z298 | 675.3 |
| 299 | 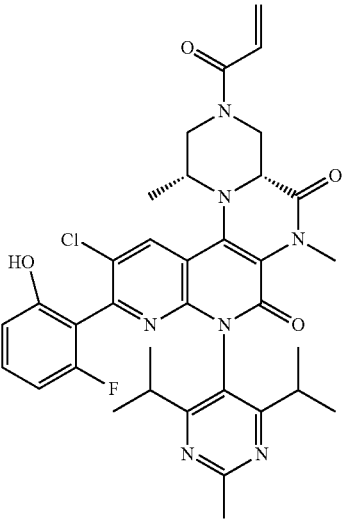 Z299 | 674.3 |
| 300 | 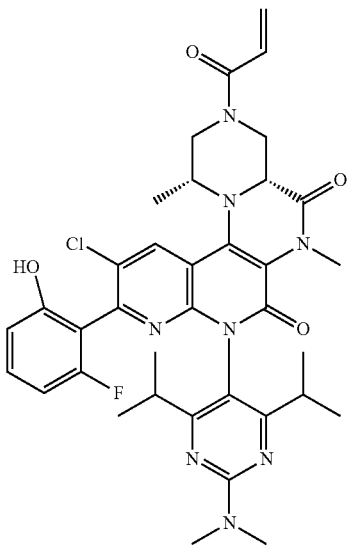 Z300 | 703.3 |

US 12,054,497 B2
-continued
| Example No. | Structure and No. of Compound | ES-API: [M + H]+ |
|---|---|---|
| 301 | Z301 | 632.2 |
| | Z301-1 | |
| | Z301-2 | |
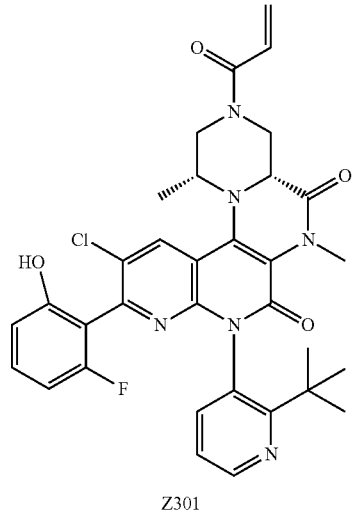 [SMILES: C=CC(=O)N1C[C@@H](C)N2c3c(c(=O)n(-c4cccnc4C(C)(C)C)c4nc(-c5c(O)cccc5F)c(Cl)cc34)N(C)C(=O)[C@H]2C1]
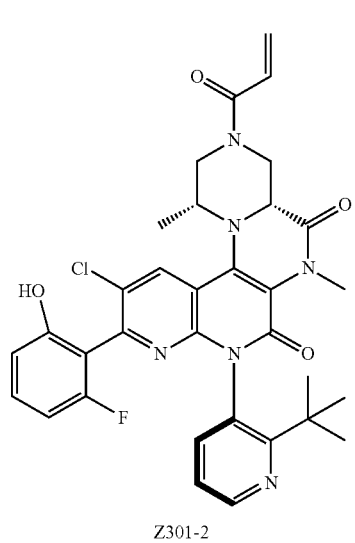
-continued
| Example No. | Structure and No. of Compound | ES-API: [M + H]+ |
|---|---|---|
| 302 | Z302 | 672.3 |
| | Z302-1 | |
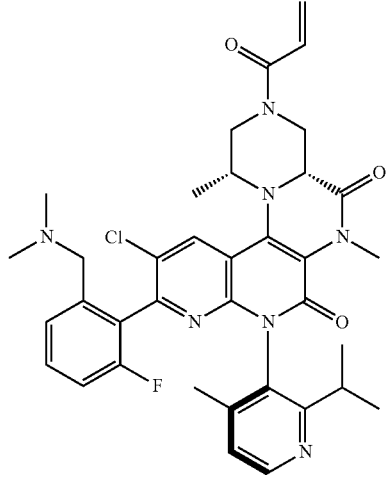

-continued
| Example No. | Structure and No. of Compound | ES-API: [M + H]+ |
|---|---|---|
| | 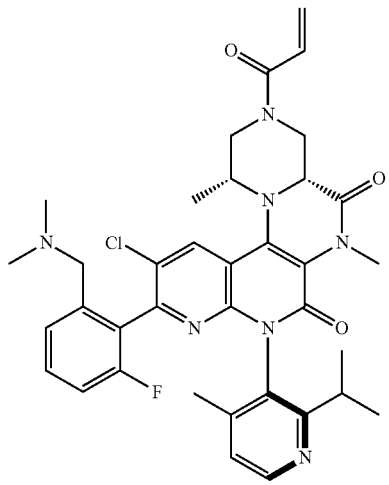
Z302-2 | |
| 303 | 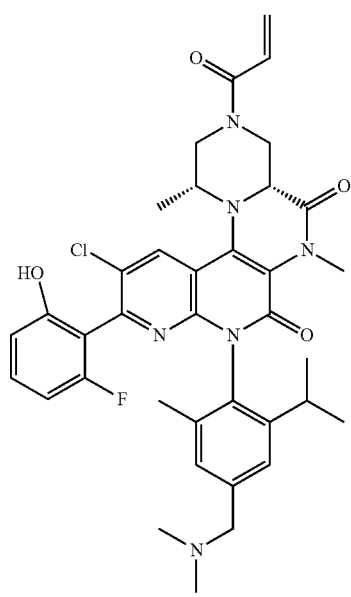
Z303 | 687.3 |
-continued
| Example No. | Structure and No. of Compound | ES-API: [M + H]+ |
|---|---|---|
| | 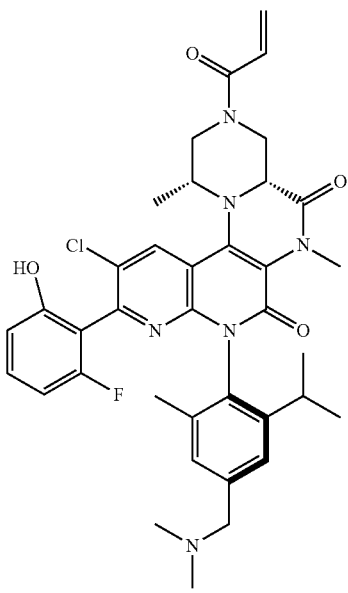
Z303-1 | |
| | 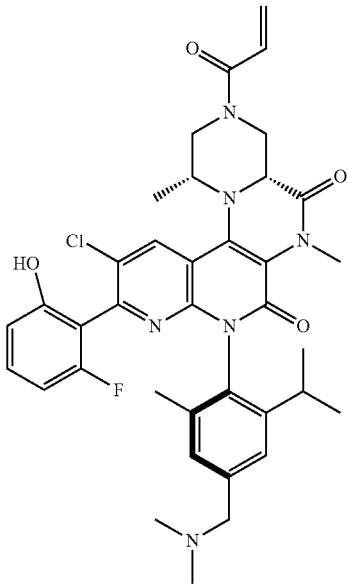
Z303-2 | |

645
-continued
| Example No. | Structure and No. of Compound | ES-API: [M + H]+ |
|---|---|---|
| 304 | 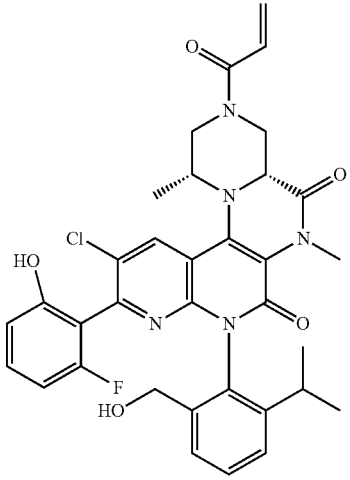<br>Z304 | 646.2 |
| | 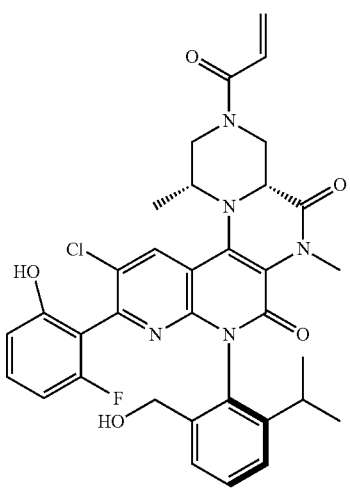<br>Z304-1 | |
| | 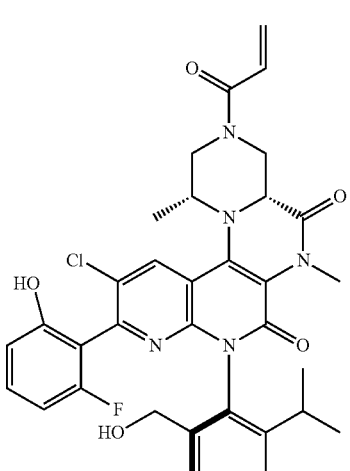<br>Z304-2 | |
646
-continued
| Example No. | Structure and No. of Compound | ES-API: [M + H]+ |
|---|---|---|
| 305 | 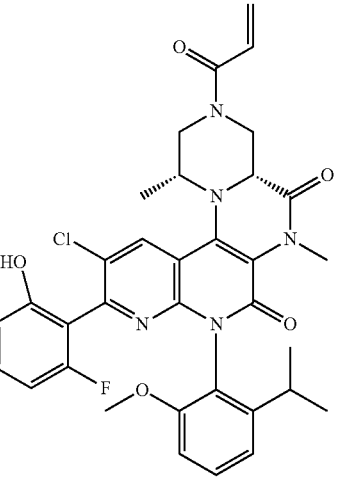<br>Z305 | 646.2 |
| | 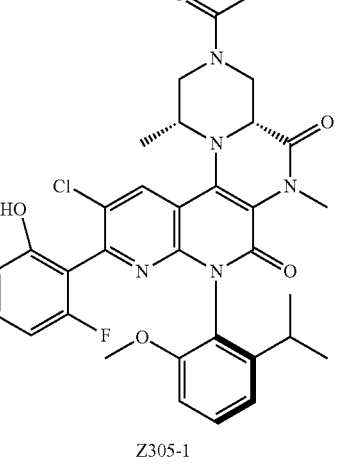<br>Z305-1 | |

-continued
| Example No. | Structure and No. of Compound | ES-API: [M + H]⁺ |
|---|---|---|
| | 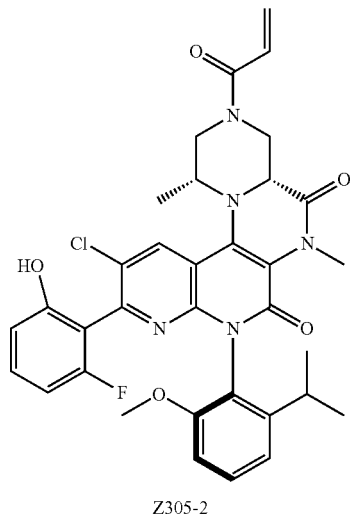  Z305-2 | |
| 306 | 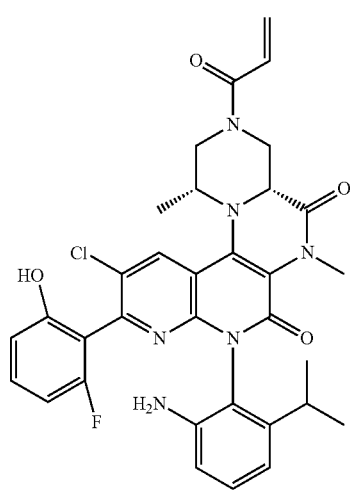  Z306 | 631.2 |
| | 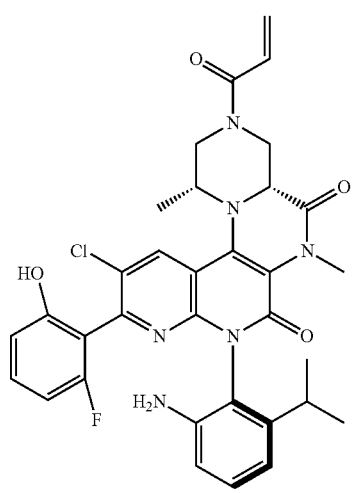  Z306-1 | |
-continued
| Example No. | Structure and No. of Compound | ES-API: [M + H]⁺ |
|---|---|---|
| | 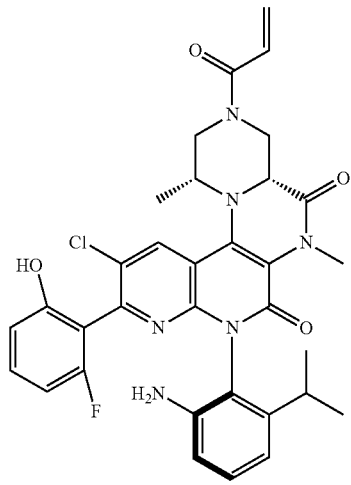  Z306-2 | |
| 307 | 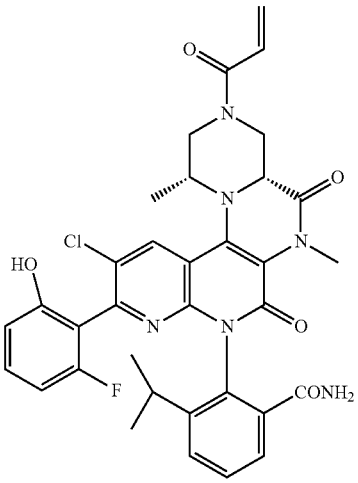  Z307 | 659.2 |

| Example No. | Structure and No. of Compound | ES-API: [M + H]+ |
|---|---|---|
| | 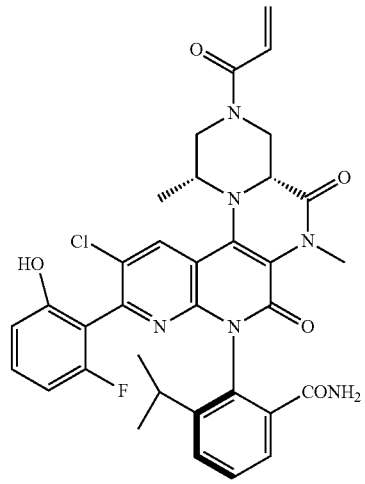<br>Z307-1 | |
| | 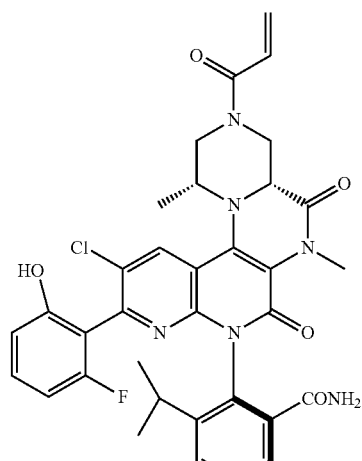<br>Z307-2 | |
| 308 | 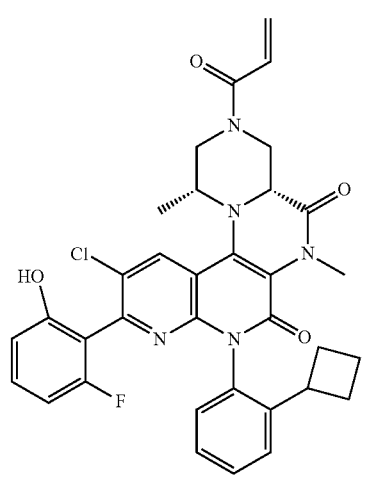<br>Z308 | 628.2 |
| Example No. | Structure and No. of Compound | ES-API: [M + H]+ |
|---|---|---|
| | 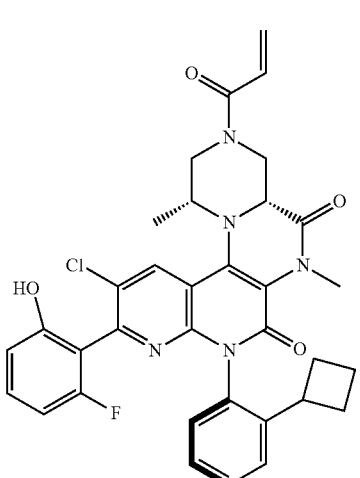<br>Z308-1 | |
| | 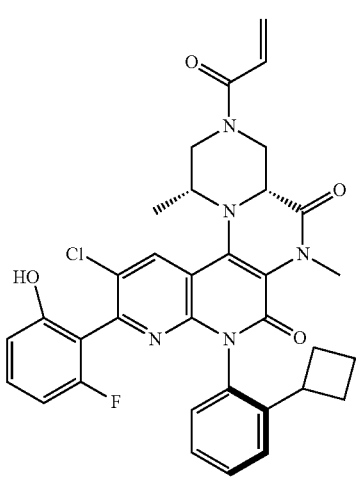<br>Z308-2 | |
| 309 | 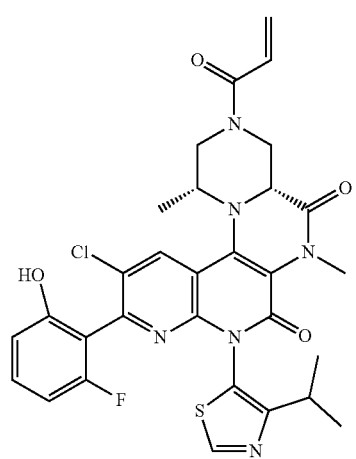<br>Z309 | 623.2 |

-continued

| Example No. | Structure and No. of Compound | ES-API: [M + H]⁺ |
|---|---|---|
| | Z309-1 | |
| | Z309-2 | |
| 310 | Z310 | 606.2 |

-continued

| Example No. | Structure and No. of Compound | ES-API: [M + H]⁺ |
|---|---|---|
| 311 | Z311 | 604.2 |
| 312 | Z312 | 661.2 |

653
-continued
| Example No. | Structure and No. of Compound | ES-API: [M + H]+ |
|---|---|---|
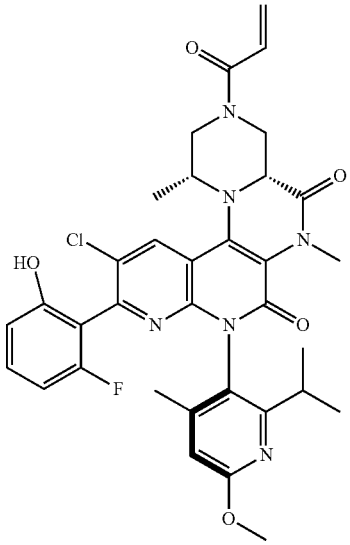
Z312-1
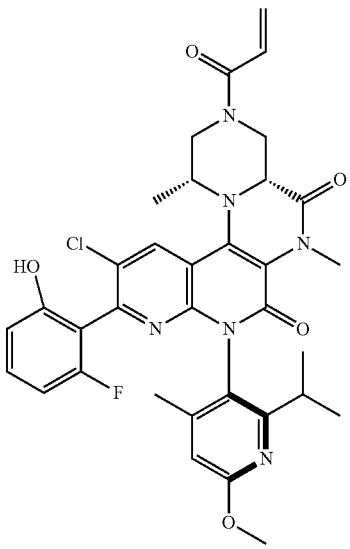
Z312-2
654
-continued
| Example No. | Structure and No. of Compound | ES-API: [M + H]+ |
|---|---|---|
| 313 | | 631.2 |
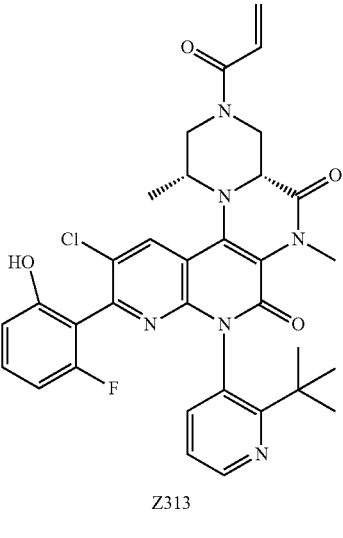 [SMILES: C=CC(=O)N1C[C@@H](C)N2c3c(c(=O)n(-c4cccnc4C(C)(C)C)c4nc(-c5c(O)cccc5F)c(Cl)cc34)N(C)C(=O)[C@H]2C1]
Z313
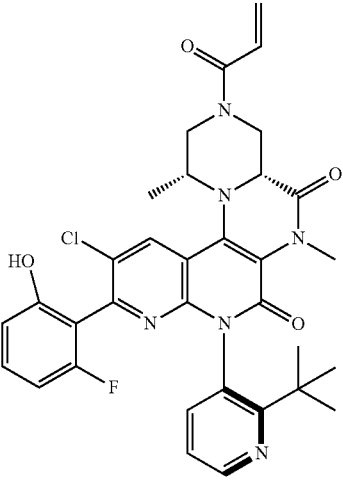
Z313-1
Z313-2

| Example No. | Structure and No. of Compound | ES-API: [M + H]⁺ |
|---|---|---|
| 314 | 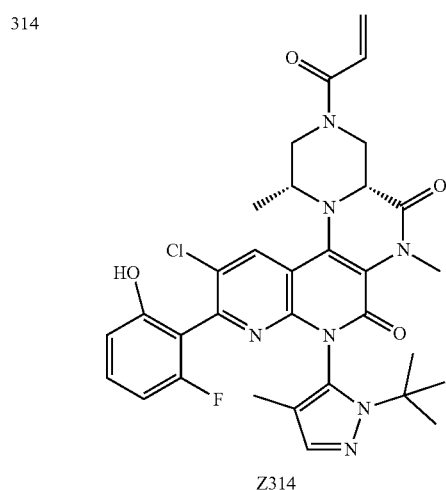<br>Z314 | 634.2 |
| | 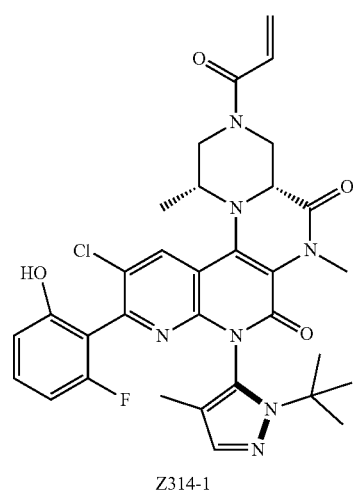<br>Z314-1 | |
| | 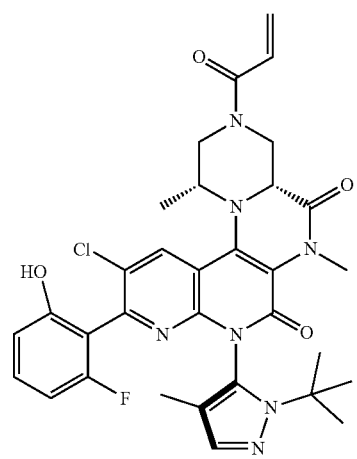<br>Z314-2 | |
| Example No. | Structure and No. of Compound | ES-API: [M + H]⁺ |
|---|---|---|
| 315 | 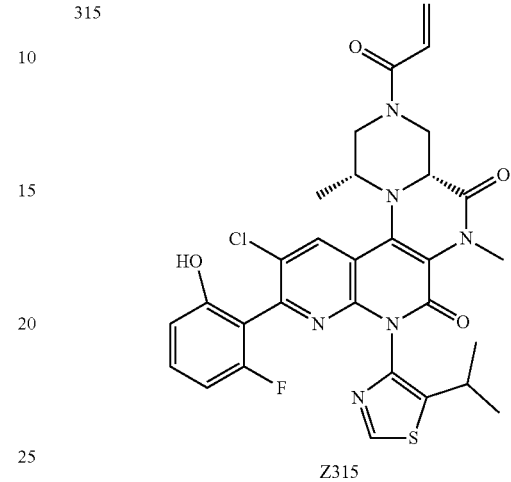<br>Z315 | 623.2 |
| | 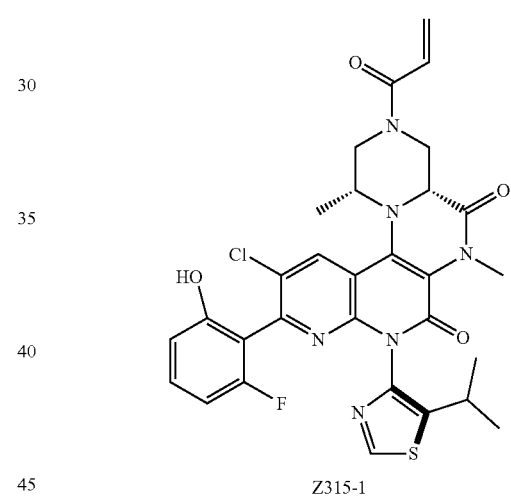<br>Z315-1 | |
| | 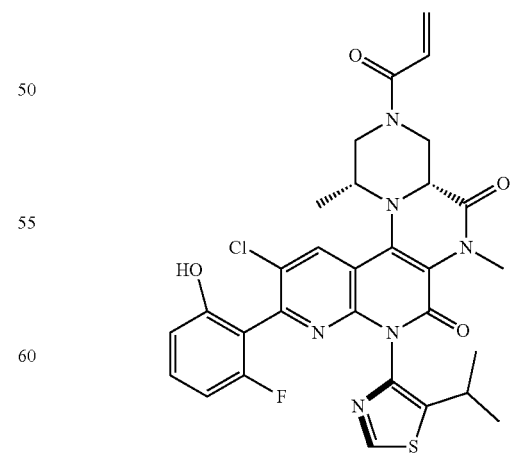<br>Z315-2 | |

| Example No. | Structure and No. of Compound | ES-API: [M + H]+ |
|---|---|---|
| 316 | Z316 | 606.2 |
| | Z316-1 | |
| | Z316-2 | |
| 317 | Z317 | 621.2 |
| | Z317-1 | |
| | Z317-2 | |

| Example No. | Structure and No. of Compound | ES-API: [M + H]+ |
|---|---|---|
| 318 | 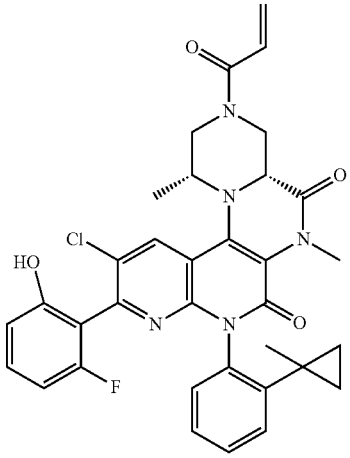<br>Z318 | 628.2 |
| | 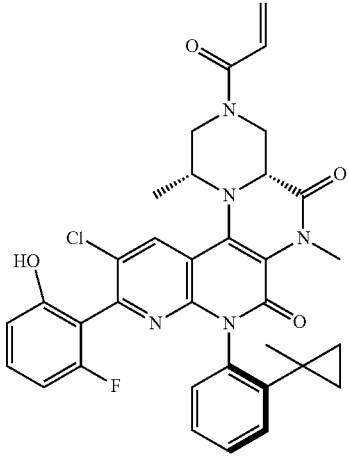<br>Z318-1 | |
| | 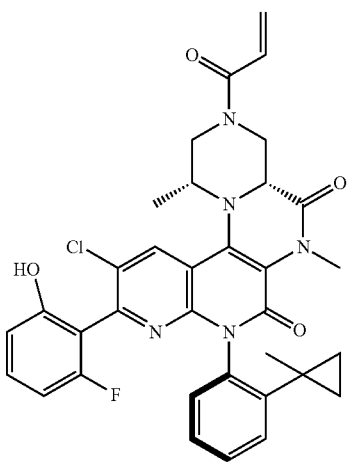<br>Z318-2 | |
| Example No. | Structure and No. of Compound | ES-API: [M + H]+ |
|---|---|---|
| 319 | 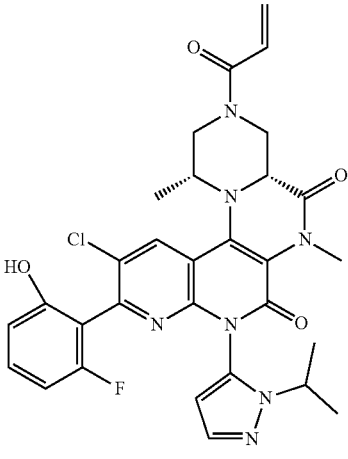<br>Z319 | 606.2 |
| | 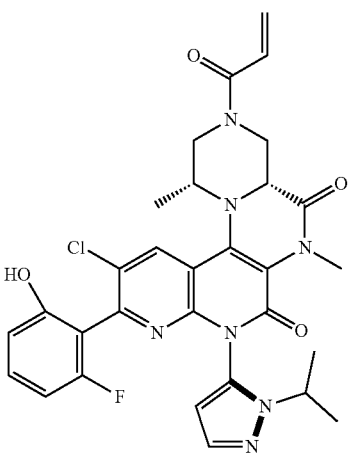<br>Z319-1 | |
| | 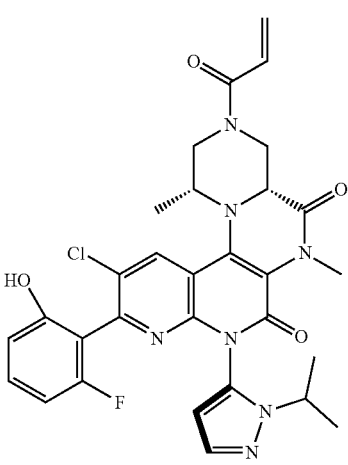<br>Z319-2 | |

-continued
| Example No. | Structure and No. of Compound | ES-API: [M + H]+ |
|---|---|---|
| 320 | 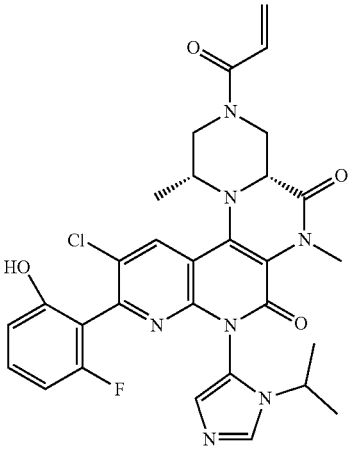<br>Z320 | 606.2 |
| | 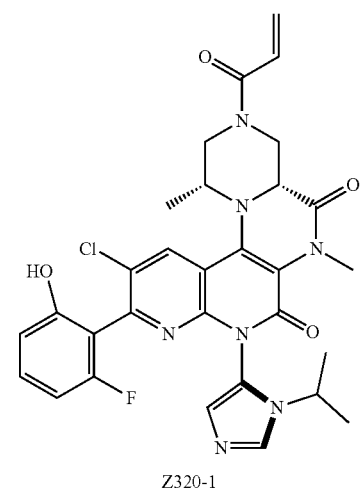<br>Z320-1 | |
| | 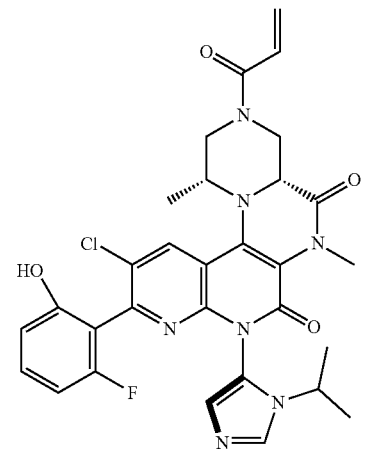<br>Z320-2 | |
-continued
| Example No. | Structure and No. of Compound | ES-API: [M + H]+ |
|---|---|---|
| 321 | 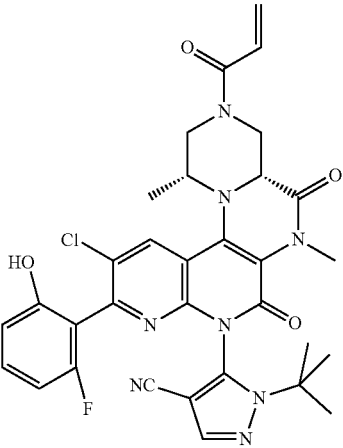<br>Z321 | 645.2 |
| | 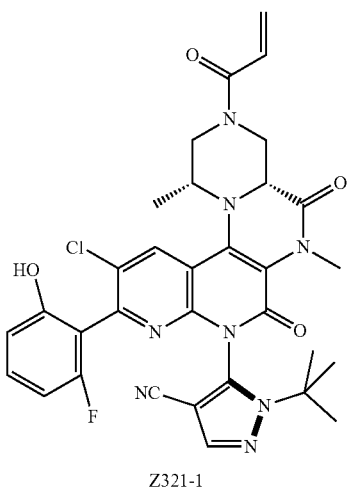<br>Z321-1 | |
| | 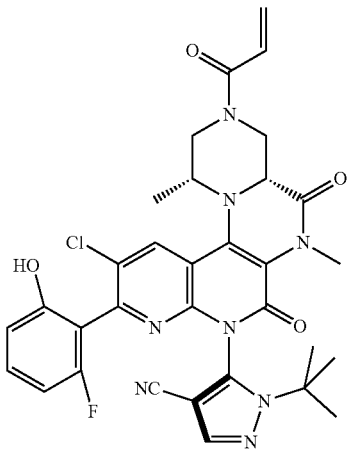<br>Z321-2 | |

-continued
| Example No. | Structure and No. of Compound | ES-API: [M + H]⁺ |
|---|---|---|
| 322 | 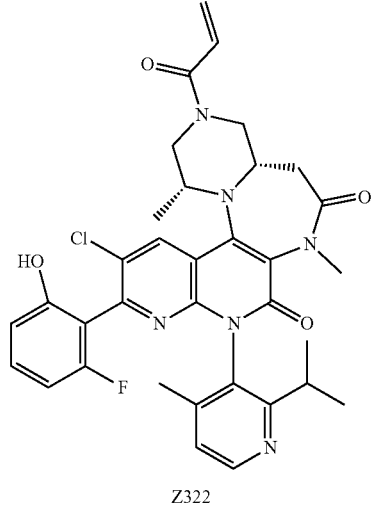 Z322 | 645.2 |
| | 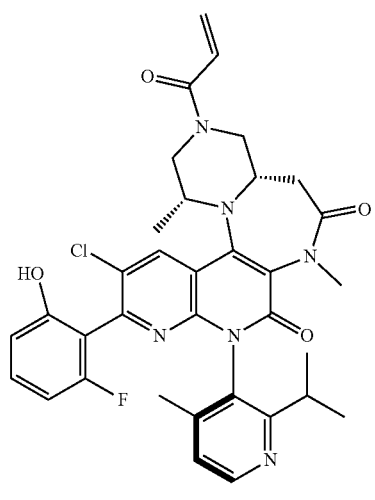 Z322-1 | |
| | 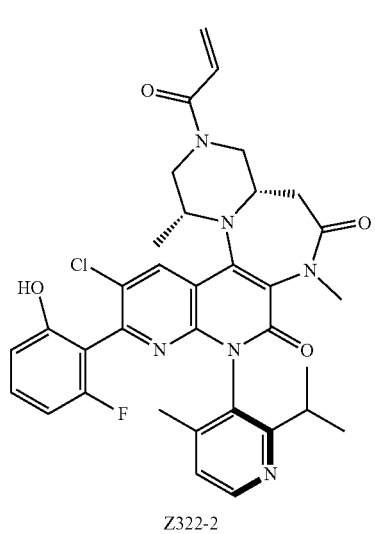 Z322-2 | |
-continued
| Example No. | Structure and No. of Compound | ES-API: [M + H]⁺ |
|---|---|---|
| 323 | 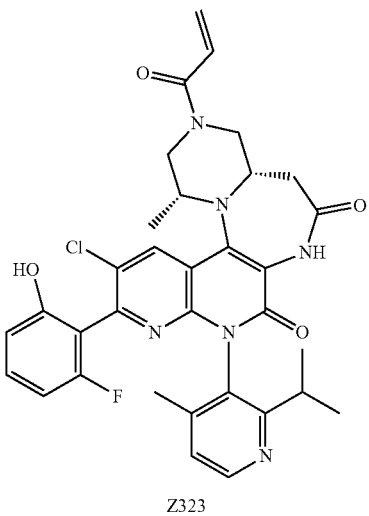 Z323 | 631.2 |
| | 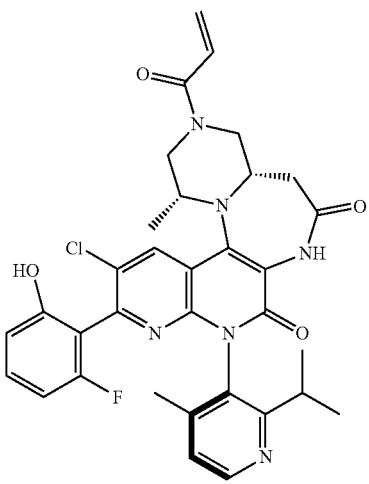 Z323-1 | |

| Example No. | Structure and No. of Compound | ES-API: [M+H]+ |
|---|---|---|
|  | Z323-2 |  |
| 324 | Z324 | 648.3 |
|  | Z324-1 |  |

| Example No. | Structure and No. of Compound | ES-API: [M+H]+ |
|---|---|---|
|  | Z324-2 |  |
| 325 | Z325 | 633.2 |

667
-continued
| Example No. | Structure and No. of Compound | ES-API: [M + H]+ |
|---|---|---|
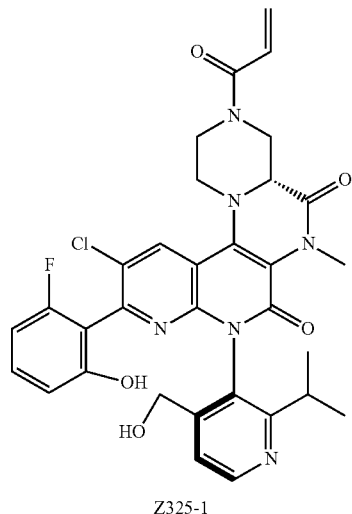
Z325-1
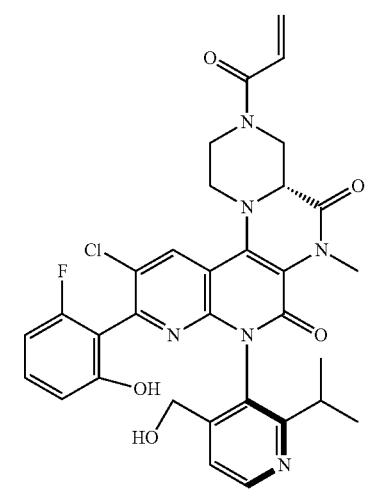
Z325-2
| 326 | | 636.2 |
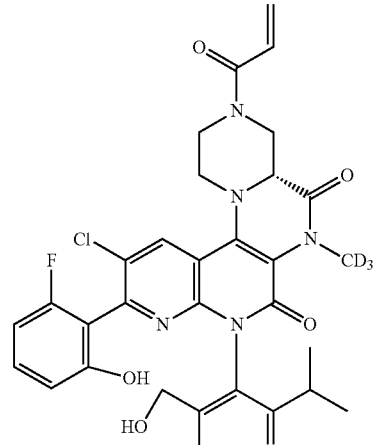
Z326
668
-continued
| Example No. | Structure and No. of Compound | ES-API: [M + H]+ |
|---|---|---|
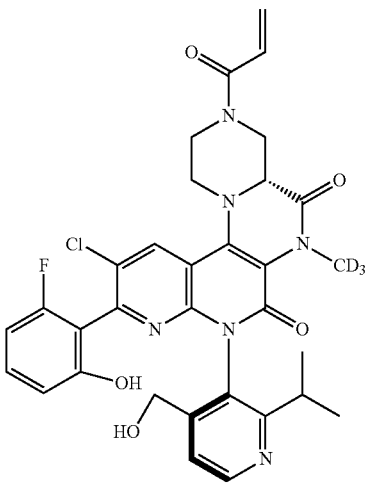
Z326-1
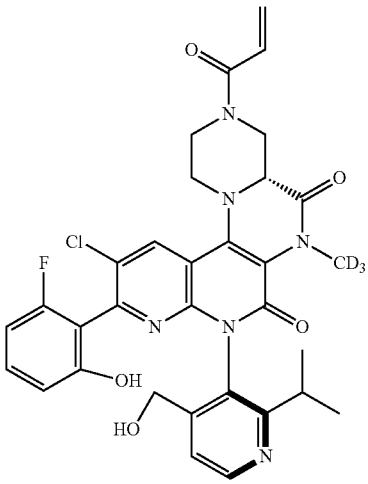
Z326-2

-continued
| Example No. | Structure and No. of Compound | ES-API: [M + H]+ |
|---|---|---|
| 327 | 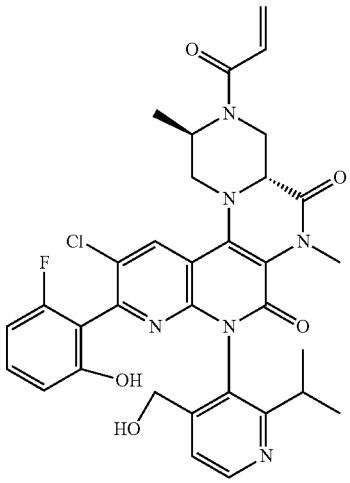 Z327 | 647.2 |
-continued
| Example No. | Structure and No. of Compound | ES-API: [M + H]+ |
|---|---|---|
| | 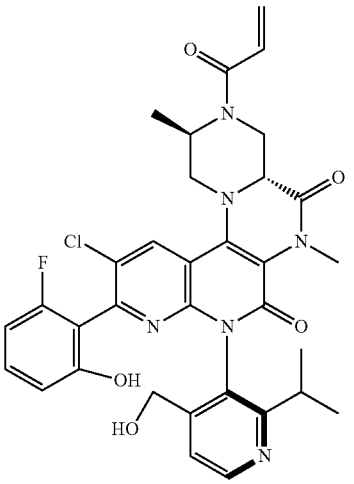 Z327-2 | |
| 328 | 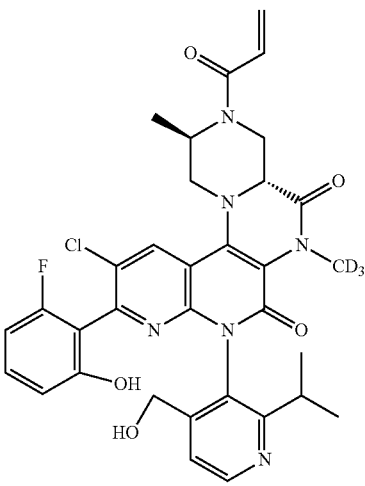 Z328 | 650.2 |
Z327-1

671
-continued
| Example No. | Structure and No. of Compound | ES-API: [M + H]+ |
|---|---|---|
| | 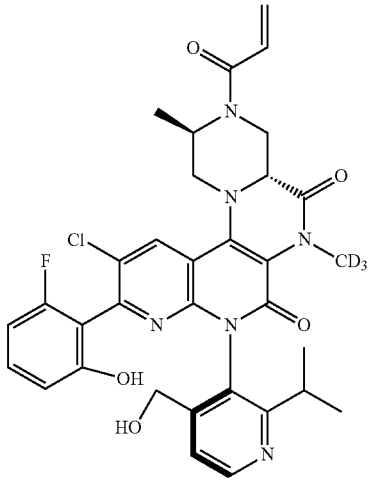<br>Z328-1 | |
| | 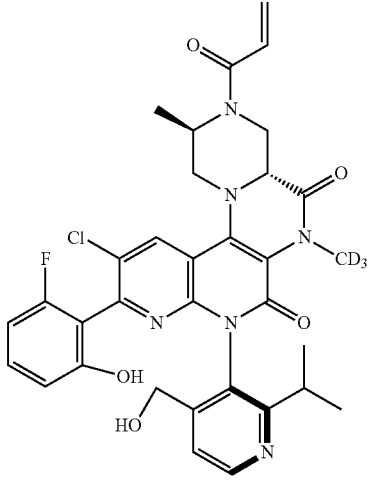<br>Z328-2 | |
672
-continued
| Example No. | Structure and No. of Compound | ES-API: [M + H]+ |
|---|---|---|
| 329 | 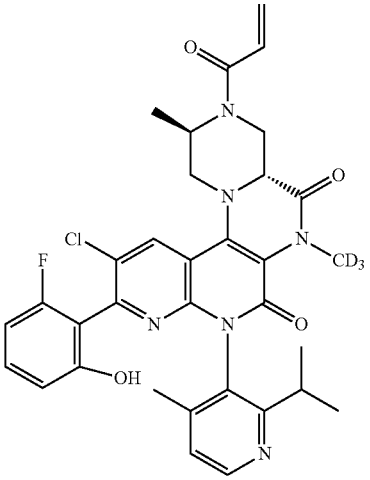<br>Z329 | 634.2 |
| | 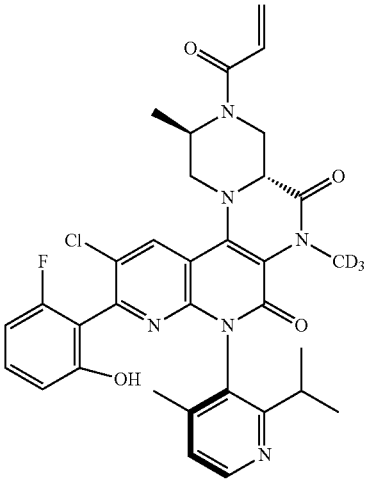<br>Z329-1 | |
| | 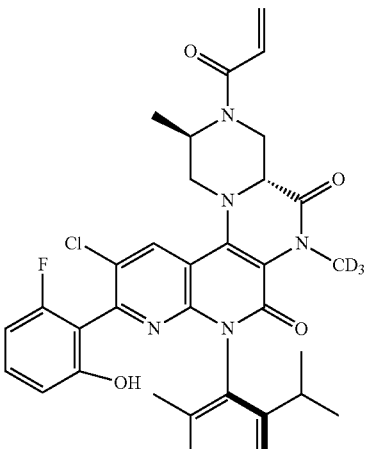<br>Z329-2 | |

| Example No. | Structure and No. of Compound | ES-API: [M + H]+ |
|---|---|---|
| 330 | 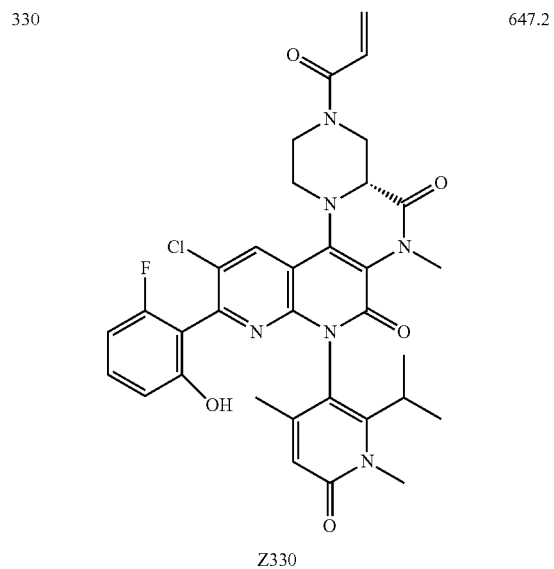 Z330 | 647.2 |
|  | 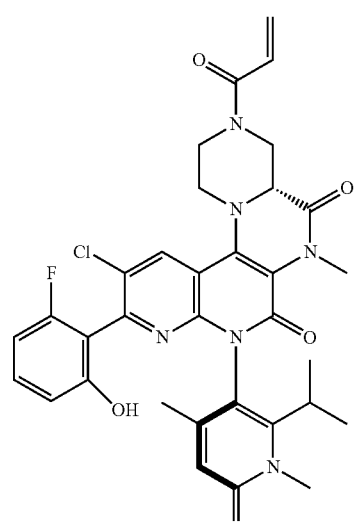 Z330-1 |  |
| Example No. | Structure and No. of Compound | ES-API: [M + H]+ |
|---|---|---|
|  | 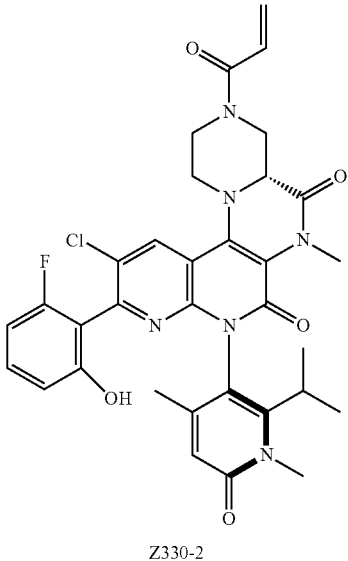 Z330-2 |  |
| 331 | 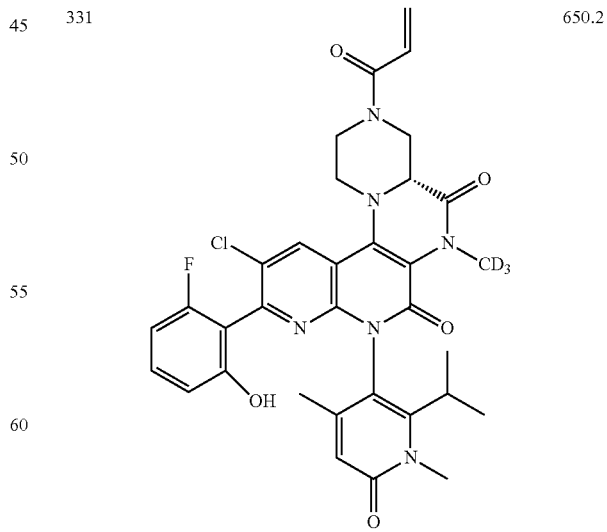 Z331 | 650.2 |

| Example No. | Structure and No. of Compound | ES-API: [M + H]+ |
|---|---|---|
| | Z331-1 | |
| | Z331-2 | |

| Example No. | Structure and No. of Compound | ES-API: [M + H]+ |
|---|---|---|
| 332 | Z332 | 661.2 |
| | Z332-1 | |

| Example No. | Structure and No. of Compound | ES-API: [M + H]+ |
|---|---|---|
| | 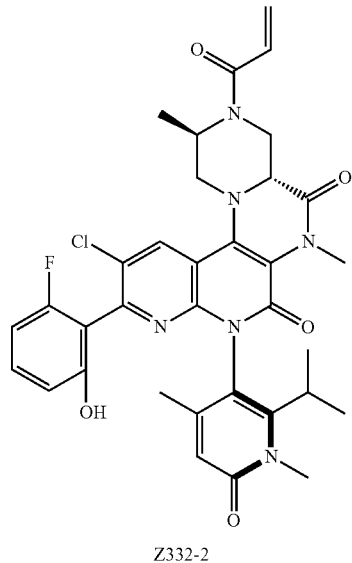<br>Z332-2 | |
| 333 | 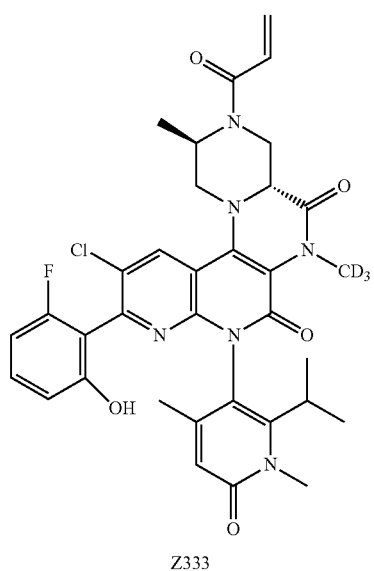 [SMILES: [2H]C([2H])([2H])N1C(=O)[C@H]2CN(C(=O)C=C)[C@H](C)CN2c2c1c(=O)n(-c1c(C)cc(=O)n(C)c1C(C)C)c1nc(-c3c(O)cccc3F)c(Cl)cc21]<br>Z333 | 664.2 |
| Example No. | Structure and No. of Compound | ES-API: [M + H]+ |
|---|---|---|
| | 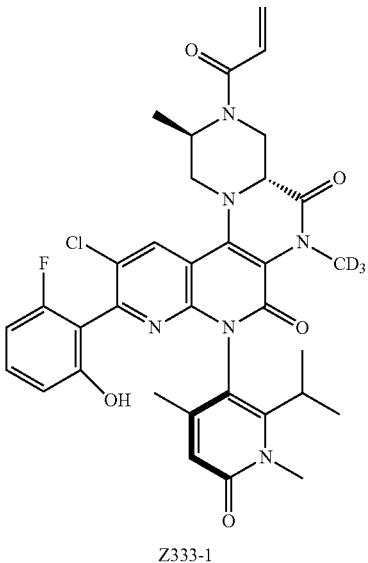<br>Z333-1 | |
| | 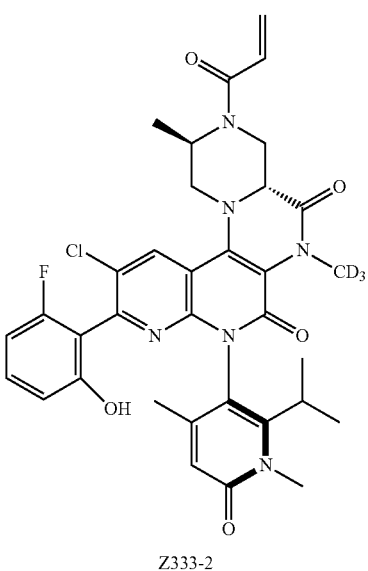<br>Z333-2 | |

| Example No. | Structure and No. of Compound | ES-API: [M + H]+ |
|---|---|---|
| 334 | Z334 | 674.3 |
| | Z334-1 | |
| Example No. | Structure and No. of Compound | ES-API: [M + H]+ |
|---|---|---|
| | Z334-2 | |
| 335 | Z335 | 688.3 |
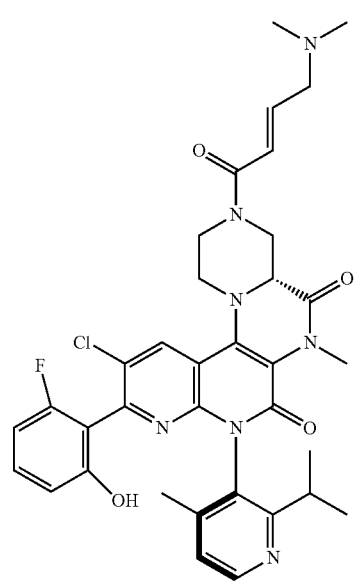
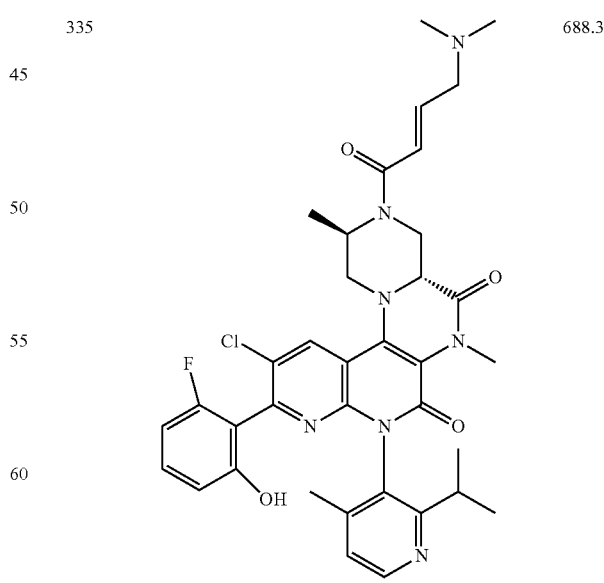

| Example No. | Structure and No. of Compound | ES-API: [M+H]+ |
|---|---|---|
| | Z335-1 | |
| | Z335-2 | |

| Example No. | Structure and No. of Compound | ES-API: [M+H]+ |
|---|---|---|
| 336 | Z336 | 623.2 |
| | Z336-1 | |
| | Z336-2 | |

| Example No. | Structure and No. of Compound | ES-API: [M + H]+ |
|---|---|---|
| 337 | 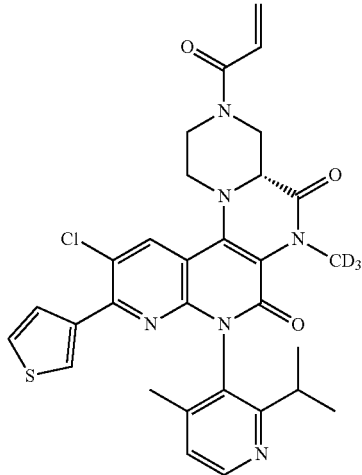 Z337 | 592.2 |
| | 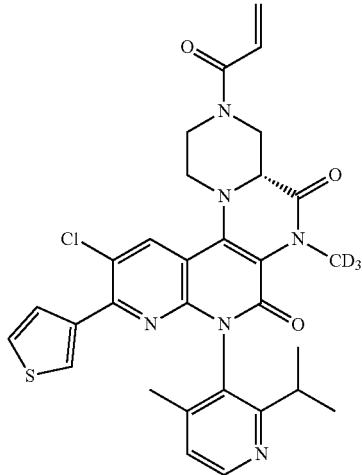 Z337-1 | |
| Example No. | Structure and No. of Compound | ES-API: [M + H]+ |
|---|---|---|
| | 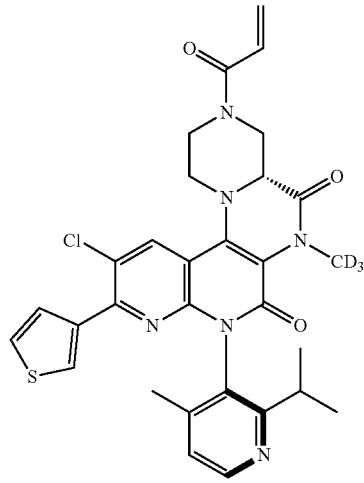 Z337-2 | |
| 338 | 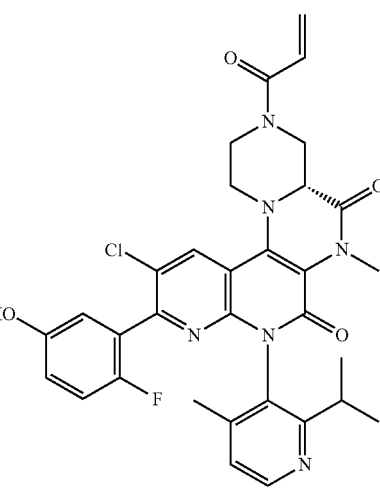 Z338 | 617.2 |
| | 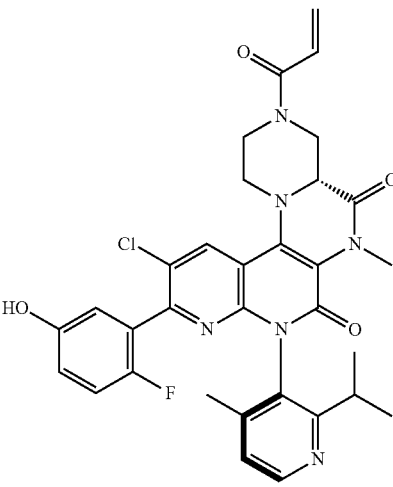 Z338-1 | |

| Example No. | Structure and No. of Compound | ES-API: [M + H]+ |
|---|---|---|
| | 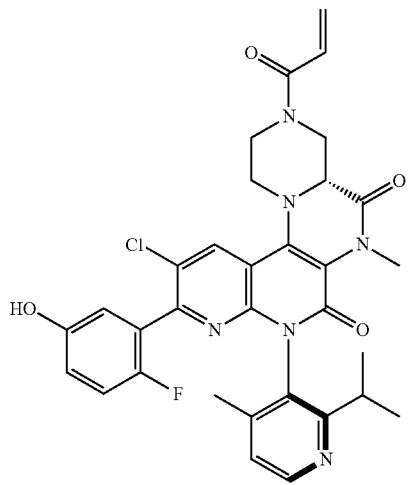<br>Z338-2 | |
| 339 | 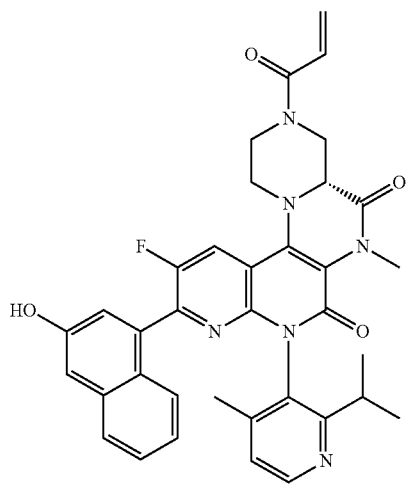<br>Z339 | 633.3 |
| Example No. | Structure and No. of Compound | ES-API: [M + H]+ |
|---|---|---|
| | 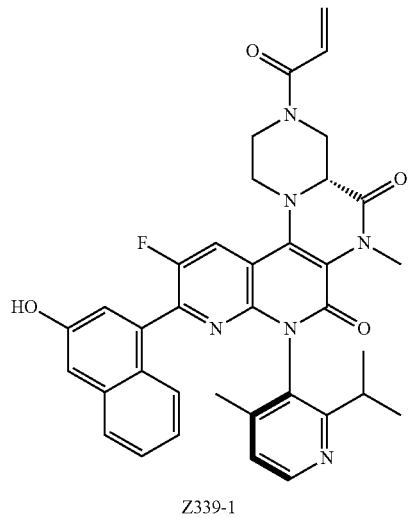<br>Z339-1 | |
| | 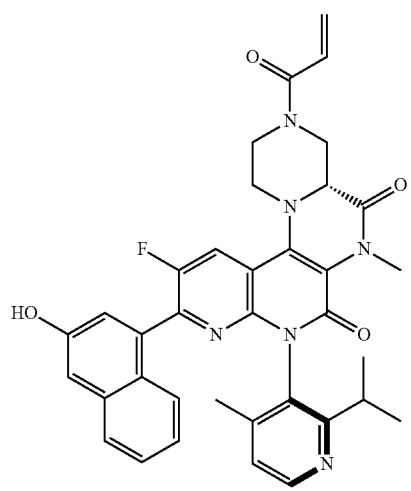<br>Z339-2 | |
| 340 | 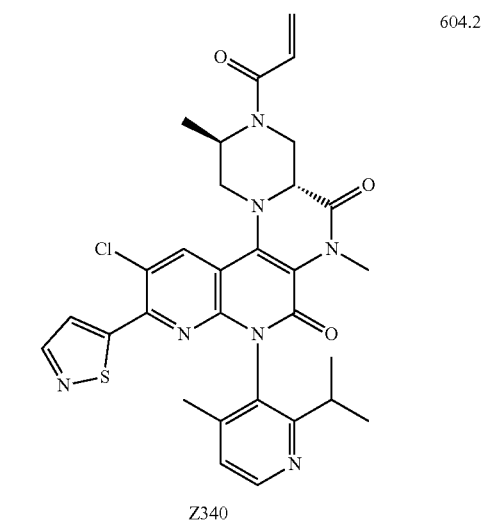<br>Z340 | 604.2 |

687
-continued
| Example No. | Structure and No. of Compound | ES-API: [M + H]+ |
|---|---|---|
| | 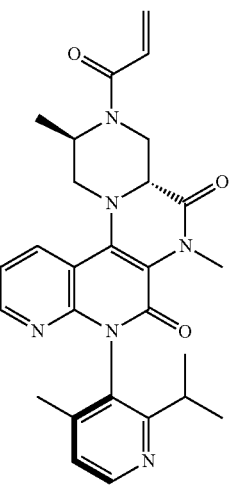 | |
| | Z340-1 | |
| | 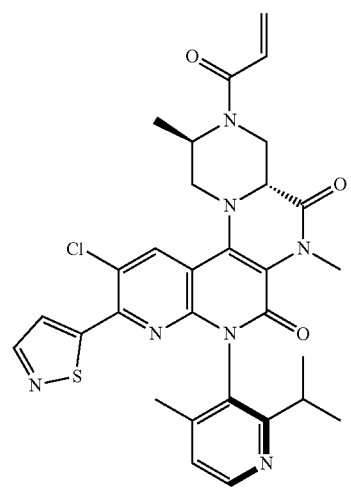 | |
| | Z340-2 | |
688
-continued
| Example No. | Structure and No. of Compound | ES-API: [M + H]+ |
|---|---|---|
| 341 | 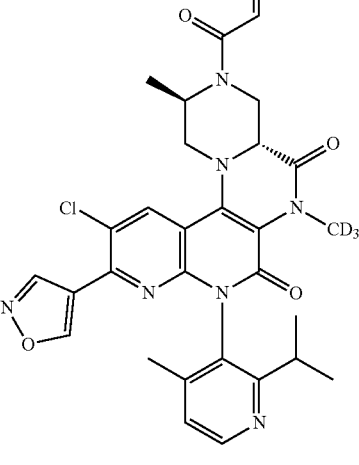 Z341 | 591.2 |
| | 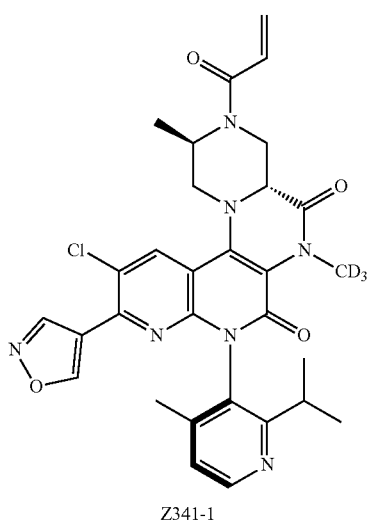 Z341-1 | |
| | 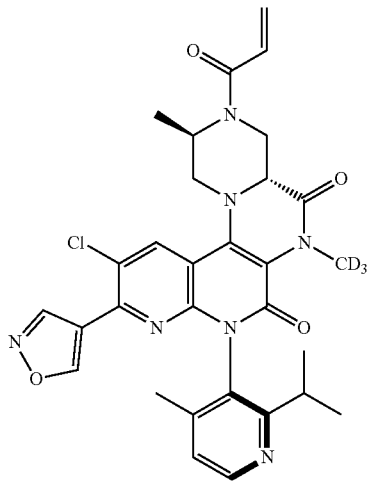 Z341-2 | |

| Example No. | Structure and No. of Compound | ES-API: [M + H]+ |
|---|---|---|
| 342 | Z342 | 587.2 |
| | Z342-1 | |
| | Z342-2 | |

Test Example 1 Cell Proliferation Inhibition Experiment

NCI-H358 was a human NSCLC cell line with Kras G12C mutation, which was cultured in a RPMI-1640 medium with 10% fetal bovine serum (FBS). A549 was a human lung adenocarcinoma cell line with Kras G12S mutation, which was cultured in an F-12K medium with 10% FBS. Cells in logarithmic growth phase were detached with trypsin and EDTA, collected and counted, and H358 was regulated to 1.8E4 cells/ml by using an RPMI-1640 medium with 2% FBS, while A549 was regulated to 8.9E3 cells/ml with an F-12K medium containing 2% FBS. 800 (45 µl) H358 cells and 400 (45 µl) A549 cells were seeded to 384-well spheroid plates, respectively, and cultured overnight to establish 3D cell models. 1000× stock solutions of compounds at a concentration gradient of 3.16 were prepared by using DMSO, and diluted 100 times by the medium with 2% FBS into 10× stock solutions of compounds. On the day after cell seeding, 5 µl of 10× stock solution of a compound was added to each well of cell culture plate, with a final concentration being 1× and a DMSO content of 0.1%. DMSO was used as the control, and the medium with 2% FBS was used as blank control group. After 5 days of cell culture with the compound, 25 µl of CellTiter-Glo working solution was added to each well, and mixed uniformly at 400 rpm and incubation for 30 minutes. After standing at room temperature for 30 minutes, 40 µl of mixed solution was transferred to a 384-well plate with white clear bottom. A value of luminescence was then read, and a cell proliferation inhibition rate (IR) (%)=(RLU control−RLU compound)/ (RLU control−RLU blank)×100%. The value of $IC_{50}$ was calculated by fitting a gradiently diluted concentration of the compound and the corresponding cell proliferation inhibition rate using a Prism 6 four-parameter method. Results showed that the example compounds of the present invention had high inhibitory activity for NCI-H358 cells with Kras G12C mutation, with their $IC_{50}$ values below 1000 nM, or below 500 nM, or below 100 nM, and had low inhibitory activity for A549 cells, with their $IC_{50}$ values above 5000 nM. Results of the example compounds were as shown in Table 1 below.

TABLE 1

Inhibitory Activity of Compounds For H358 and A549 Cells

| Compound No. | H358 $IC_{50}$ (µM) | A549 $IC_{50}$ (µM) | Compound No. | H358 $IC_{50}$ (µM) | A549 $IC_{50}$ (µM) |
|---|---|---|---|---|---|
| Z1 | 0.031 | >10 | Z31 | 0.017 | 9.494 |
| Z2 | 0.773 | >10 | Z32 | 0.064 | >30 |
| Z1-1 | 0.031 | 10.716 | Z33-1 | 0.074 | >30 |
| Z1-2 | 0.198 | 16.482 | Z33-2 | 0.034 | >30 |
| Z3a | 0.017 | >10 | Z34-1 | 0.078 | >30 |
| Z3 | 0.016 | >10 | Z34-2 | 0.007 | >30 |
| Z6 | 0.035 | 11.312 | Z35 | 0.006 | 28.208 |
| Z9 | 0.032 | — | Z35-1 | 0.037 | >30 |
| Z9-1 | 0.218 | >10 | Z35-2 | 0.006 | >30 |
| Z9-2 | 0.015 | >10 | Z36-1 | 0.588 | >30 |
| Z10 | 0.008 | 12.125 | Z36-2 | 0.018 | 28.025 |
| Z10-1 | 0.070 | >10 | Z37 | 0.001 | 8.572 |
| Z10-2 | 0.004 | 24.640 | Z37-1 | 0.0007 | >30 |
| Z21 | 0.023 | >30 | Z37-2 | 0.165 | 3.322 |
| Z21-1 | 0.027 | >30 | Z38-1 | 0.007 | >30 |
| Z21-2 | 0.407 | >30 | Z38-2 | 0.513 | >30 |
| Z22 | 0.067 | >30 | Z39-1 | 0.0006 | >30 |
| Z23 | 0.002 | 10.482 | Z39-2 | 0.316 | 7.781 |
| Z24 | 0.003 | 28.067 | Z40 | 0.011 | >30 |
| Z24-1 | 0.028 | >30 | Z41 | 0.017 | >30 |
| Z24-2 | 0.003 | 11.308 | Z42 | 0.053 | >30 |
| Z25 | 0.004 | 28.332 | Z43 | 0.049 | 29.234 |
| Z25-1 | 0.050 | >30 | Z44a | 0.024 | 9.237 |
| Z25-2 | 0.003 | >30 | Z44 | 0.011 | >30 |
| Z26 | 0.002 | 12.856 | Z45 | 0.013 | >30 |
| Z26-1 | 0.042 | >30 | Z46 | 0.012 | 10.306 |
| Z26-2 | 0.003 | >30 | Z47 | 0.031 | >30 |
| Z27 | 0.002 | 10.123 | Z48 | 0.003 | >10 |
| Z27-1 | 0.012 | 12.705 | Z49-1 | 0.009 | 9.417 |
| Z27-2 | 0.001 | 18.995 | Z49-2 | 0.044 | >30 |
| Z28 | 0.090 | 16.881 | Z50 | 0.0005 | 28.289 |
| Z29 | 0.166 | 21.794 | Z50-1 | 0.0003 | >30 |
| Z30 | 0.051 | >30 | Z50-2 | 0.320 | 3.872 |
| Z30-1 | 0.804 | >30 | Z48'-1 | 0.828 | — |
| Z30-2 | 0.047 | >30 | Z48'-2 | >1 | — |

From Table 1, it could be seen that the example compounds of the present invention had high inhibitory activity against NCI-H358 cells with Kras G12C mutation and low inhibitory activity for A549 cells, and thus had obvious selective inhibitory activity.

Test Example 2 Phospho-Extracellular Signal-Regulated Kinase (p-ERK) Assay for Cells MIA PaCa2 was a human pancreatic carcinoma cell line with Kras G12C mutation, which was cultured in a DMEM with 10% FBS and 2.5% Horse serum. Cells in logarithmic growth phase were detached with trypsin and EDTA, collected and counted, and 2.5E4 cells were seeded to a 96-well cell culture plate and cultured overnight. 1000× stock solutions of compounds at a concentration gradient of 3.16 were prepared by using DMSO, and diluted 200 times by the medium into 5× stock solutions of compounds. On the day after cell seeding, 5× stock solution of a compound was added to each well of cell culture plate, with a final concentration being 1× and a DMSO content of 0.1%. DMSO was used as the control. The residual culture was removed after culturing for 2 hours with the compound. To each well, 50 ul of cell lysis buffer was added and mixed uniformly and incubation for 30 minutes. Subsequently, 16 ul of mixed solution was transferred to a 96-well plate with white unclear bottom, and 16 ul of cell lysis buffer was added to the blank control group. After the completion of transfer, 4 ul of p-ERK HTRF antibody mixture was added to each well, and a value of fluorescence intensity was read after incubation for 4 hours. The inhibition rate (IR) of the compound was calculated by the following equation: IR (%)=(RLU control−RLU compound)/(RLU control−RLU blank)×100%. The value of IC50 was calculated by fitting a gradiently diluted concentration of the compound and the corresponding cell proliferation inhibition rate using a Prism 8 four-parameter method. Results showed that the example compounds of the present invention had good inhibitory activity for the level of phosphorylated ERK downstream of the cell passage of the Kras G12C protein mutation, with their IC50 values below 10 µM, or below 1000 nM, or below 100 nM. Results of the example compounds were as shown in Table 2 below.

TABLE 2

Inhibitory Activity of Compounds For p-ERK

| Compound No. | p-ERK IC50 (µM) | Compound No. | p-ERK IC50 (µM) |
|---|---|---|---|
| Z1 | 0.432 | Z34-1 | 0.578 |
| Z1-1 | 0.512 | Z34-2 | 0.051 |
| Z3a | 0.273 | Z35 | 0.083 |
| Z3 | 0.160 | Z35-1 | 0.249 |
| Z6 | 0.313 | Z35-2 | 0.049 |
| Z9 | 0.187 | Z36-2 | 0.188 |
| Z9-2 | 0.221 | Z37 | 0.021 |
| Z10 | 0.075 | Z37-1 | 0.011 |
| Z10-1 | 0.460 | Z38-1 | 0.212 |
| Z10-2 | 0.034 | Z39-1 | 0.011 |
| Z21 | 0.271 | Z40 | 0.078 |
| Z21-1 | 0.428 | Z41 | 0.279 |
| Z23 | 0.017 | Z42 | 0.566 |
| Z24 | 0.113 | Z43 | 0.439 |
| Z24-1 | 0.536 | Z44a | 0.170 |
| Z24-2 | 0.061 | Z44 | 0.088 |
| Z25 | 0.051 | Z45 | 0.122 |
| Z25-2 | 0.029 | Z46 | 0.224 |
| Z26 | 0.039 | Z48 | 0.052 |
| Z26-2 | 0.062 | Z49-1 | 0.114 |
| Z27 | 0.029 | Z50 | 0.007 |
| Z27-1 | 0.157 | Z50-1 | 0.006 |
| Z27-2 | 0.011 | Z50-2 | 0.316 |
| Z30 | 0.676 | Z72 | 0.106 |
| Z30-2 | 0.488 | Z48'-1 | 7.477 |
| Z31 | 0.206 | Z48'-2 | >10 |
| Z33-2 | 0.238 | | |

Test Example 3 Cell Proliferation Inhibition Experiment

MIA PaCa-2 was a human pancreatic carcinoma cell line with Kras G12C mutation, which was cultured in a DMEM with 10% FBS and 2.5% Horse serum. A549 was a human lung adenocarcinoma cell line with Kras G12S mutation, which was cultured in an F-12K medium with 10% FBS. Cells in logarithmic growth phase were detached with trypsin and EDTA, collected and counted, and 200 MIA PaCa-2 cells and 400 A549 cells were seeded to 384-well spheroid plates, respectively, and cultured overnight to establish 3D cell models. 1000× stock solutions of compounds at a concentration gradient of 3.16 were prepared by using DMSO, and diluted 100 times by the medium into 10× stock solutions of compounds. On the day after cell seeding, 10× stock solution of a compound was added to each well of cell culture plate, with a final concentration being 1× and a DMSO content of 0.1%. DMSO was used as the control, and the medium was used as the blank. After 5 days of cell culture with the compound, 30 µl of CellTiter-Glo working solution was added to each well, and mixed uniformly and incubation for 30 minutes. After standing at room temperature for 30 minutes, 40 µl of mixed solution was transferred to a 384-well plate with white unclear bottom. A value of luminescence intensity was then read, and a cell proliferation inhibition rate (IR) (%)=(RLU control−RLU compound)/(RLU control−RLU blank)×100%. The value of $IC_{50}$ was calculated by fitting a gradiently diluted concentration of the compound and the corresponding cell proliferation inhibition rate using an XLFit four-parameter method. Results showed that the example compounds of the present invention had high inhibitory activity for MIA PaCa-2 cells with Kras G12C mutation, with their $IC_{50}$ values below 1000 nM, or below 100 nM, or below 10 nM. Results of the example compounds were as shown in Table 3 below.

TABLE 3

Inhibitory Activity of Compounds For MIA-PaCa2

| Compound No. | MIA-PaCa2 IC50 (µM) | Compound No. | MIA-PaCa2 IC50 (µM) |
|---|---|---|---|
| Z1 | 0.090 | Z33-1 | 0.092 |
| Z1-1 | 0.095 | Z33-2 | 0.048 |
| Z3a | 0.070 | Z34-1 | 0.135 |
| Z3 | 0.018 | Z34-2 | 0.010 |
| Z6 | 0.085 | Z35 | 0.015 |
| Z9 | 0.074 | Z36-2 | 0.133 |
| Z9-2 | 0.017 | Z37 | 0.004 |
| Z10-2 | 0.008 | Z37-1 | 0.002 |
| Z21 | 0.047 | Z38-1 | 0.027 |
| Z21-1 | 0.046 | Z39-1 | 0.001 |
| Z22 | 0.180 | Z40 | 0.012 |
| Z23 | 0.002 | Z41 | 0.044 |
| Z24 | 0.009 | Z42 | 0.128 |
| Z24-2 | 0.004 | Z43 | 0.220 |
| Z25 | 0.008 | Z44a | 0.103 |
| Z25-2 | 0.005 | Z44 | 0.034 |
| Z26 | 0.005 | Z45 | 0.048 |
| Z26-2 | 0.005 | Z46 | 0.068 |
| Z27 | 0.004 | Z47 | 0.083 |
| Z27-2 | 0.001 | Z48 | 0.006 |
| Z28 | 0.234 | Z49-1 | 0.012 |
| Z30 | 0.140 | Z50 | 0.002 |
| Z30-2 | 0.130 | Z50-1 | 0.001 |
| Z31 | 0.059 | Z48'-1 | >1 |
| Z32 | 0.170 | Z48'-2 | >1 |

Test Example 4 Nucleotide Exchange Assay (NEA)-HTRF Assay for KRas G12C

The effects of compounds on SOS1 catalyzed displacement of GDP by GTP on KRas proteins was examined by homogeneous time-resolved fluorescence (HTRF). 30 µM 6×his labeled KRas G12C recombinant protein and 80 µM fluorochrome DY647 labeled GDP were co-incubated in a labeling buffer (1 mM DTT, 7.5 mM EDTA, 25 mM Tris-HCl, 45 mM NaCl) at 20° C. away from light for 2 hours. Protein quantification was performed after purification on the NAP-5 column to determine the concentration of KRas G12C-GDP.

1000× stock solutions of compounds at a concentration gradient of 3.16 were prepared by using DMSO, and diluted 250 times by a reaction buffer (40 mM N-2-hydroxyethylpiperazine-N-2-ethane sulfonic acid (HEPES), 10 mM $MgCl_2$, 1 mM DTT, 0.002% Triton X-100) into 4× stock solutions of compounds. KRas G12C-GDP/Tb working solution (40 nM KRas G12C-GDP, 1×anti-his Tb) and SOS1/GTP working solution (0.2 µM SOS1, 200 µM GTP) were prepared by using the reaction buffer.

5 µl of 4×stock solution of a compound and 10 µl of KRas G12C-GDP/T working solution were added to each well of 96-well plate with white unclear bottom, and 5 µl of reaction buffer was added to the well of control group in stead of the 4×stock solution of a compound. After incubation at 20° C. away from light for 15 minutes, 5 µl of SOS1/GTP working solution was added and incubated at 20° C. away from light for 2 hours, and then a value of fluorescence intensity was read (excitation wavelength: 320 nm, and emission wavelengths: 615 nm and 665 nm). Besides, group T0 was established with 10 µl of the reaction buffer and 10 µl of the KRas G12C-GDP/Tb working solution, and the value of fluorescence intensity was directly read. A relative light unit (RLU) was calculated by the following equation: RLU=(665 nm signal/615 nm signal)×$10^4$; and the inhibition rate (IR) of the compound was calculated by the following equation: IR (%)=($RLU_{compound}$−$RLU_{control}$)/($RLU_{T0}$−$RLU_{control}$)×100%. The value of $IC_{50}$ was calculated by fitting a gradiently diluted concentration of the compound and the corresponding cell proliferation inhibition rate using a four-parameter method. Results were shown in Table 4.

TABLE 4

| Compound No. | NEA IC50 (µM) |
|---|---|
| Z1 | 0.255 |
| Z1-1 | 0.152 |
| Z1-2 | 1.428 |
| Z9-1 | 2.571 |
| Z9-2 | 0.115 |
| Z10 | 0.067 |
| Z10-1 | 0.708 |
| Z10-2 | 0.037 |
| Z21 | 0.388 |
| Z21-1 | 0.172 |
| Z21-2 | 3.935 |
| Z24 | 0.058 |
| Z24-1 | 0.291 |
| Z24-2 | 0.038 |
| Z25 | 0.060 |
| Z25-2 | 0.025 |
| Z25-1 | 0.951 |
| Z26 | 0.034 |
| Z26-1 | 0.868 |
| Z26-2 | 0.040 |
| Z27 | 0.027 |
| Z27-1 | 0.198 |
| Z27-2 | 0.009 |
| Z30 | 0.656 |
| Z31 | 0.151 |
| Z33-1 | 0.515 |
| Z33-2 | 0.162 |
| Z35 | 0.073 |
| Z37 | 0.020 |
| Z37-1 | 0.011 |
| Z37-2 | 1.898 |
| Z38-1 | 0.053 |
| Z38-2 | 2.147 |
| Z39-2 | 2.245 |
| Z50 | 0.019 |
| Z50-1 | 0.008 |
| Z50-2 | 1.450 |

Test Example 5 In Vivo Pharmacodynamic Experiment

Experimental objective: to evaluate the in vivo pharmaceutical effects of tested compounds on the subcutaneous xenograft tumor model of MIA PaCa-2.

Experimental operation: 6 to 8 weeks old female BALB/c nude mice each having the body weight of 18-20 g were chosen. MIA PaCa-2 cells were cultured in DMEM containing 10% FBS, 2.5% HS and 1% penicillin-streptomycin at 37° C. in an incubator with 5% $CO_2$. Cells were collected. The MIA PaCa-2 cells were subcutaneously inoculated to the animals at their backs on the right, $2.0 \times 10^6$ cells (0.1 mL) for each animal. When tumor grew to 190-311 mm³, mice with tumor having a suitable size were chosen and treated in groups, with administration dosages shown in Table 5 below. The animals were weighed on an electronic balance each day. The tumor volume was investigated by using a vernier caliper twice a week. The tumor volume was calculated by the following equation: $V=0.5 \, a \times b^2$, a and b representing the long diameter and the short diameter of the tumor, respectively. The tumor volume was used to calculate a tumor growth inhibition rate (TGI), and the TGI shown in the form of a percentage was used to indicate the antineoplastic activity of a compound. The TGI was calculated by the following equation: TGI (%)=[1−avTi−0/avCi−0)]×100, with avTi−0 representing the average tumor volume of the group administrated with the compound on a specific day minus the average tumor volume of this group on the day of grouping, and avCi−0 representing the average tumor volume of the solvent control group on a specific day minus the average tumor volume of the solvent control group on the day of grouping. The tumor volume was shown in the form of an average value±standard error of mean (SEM). Experimental results were shown in Table 5 below.

TABLE 5

| Group | Tumor Volume on Day 14 after Administration (mm³) | TGI(%) |
| --- | --- | --- |
| Solvent control group | 670.99 | — |
| AMG 510 (1 mg/kg, p.o., QD) | 314.28 | 82.8 |
| AMG 510 (3 mg/kg, p.o., QD) | 205.35 | 109.1 |
| AMG 510 (10 mg/kg, p.o., QD) | 81.72 | 138.9 |
| Z37-1 (1 mg/kg, p.o., QD) | 286.12 | 89.4 |
| Z37-1 (3 mg/kg, p.o., QD) | 238.82 | 102.8 |
| Z37-1 (10 mg/kg, p.o., QD) | 210.59 | 108.4 |
| Z48 (1 mg/kg, p.o., QD) | 459.33 | 51.2 |
| Z48 (3 mg/kg, p.o., QD) | 148.62 | 124.7 |
| Z48 (10 mg/kg, p.o., QD) | 90.39 | 138.5 |
| Z23 (1 mg/kg, p.o., QD) | 194.65 | 113.2 |
| Z23 (3 mg/kg, p.o., QD) | 59.52 | 143.5 |
| Z23 (10 mg/kg, p.o., QD) | 47.32 | 149.2 |
| Z25-2 (1 mg/kg, p.o., QD) | 180.14 | 116.2 |
| Z25-2 (3 mg/kg, p.o., QD) | 62.35 | 143.7 |
| Z25-2 (10 mg/kg, p.o., QD) | 18.94 | 154.4 |
| Z26-2 (1 mg/kg, p.o., QD) | 157.06 | 121.1 |
| Z26-2 (3 mg/kg, p.o., QD) | 67.66 | 143.8 |
| Z26-2 (10 mg/kg, p.o., QD) | 30.49 | 151.1 |
| Z27-2 (1 mg/kg, p.o., QD) | 140.10 | 126.3 |
| Z27-2 (3 mg/kg, p.o., QD) | 54.81 | 145.1 |
| Z27-2 (10 mg/kg, p.o., QD) | 15.16 | 155.8 |

Experimental conclusion: The compounds of the present invention exhibited excellent in vivo pharmaceutical effects for the subcutaneous xenograft tumor model of MIA PaCa-2. On day 14 after administration, the compounds of the present invention had more significant effects on tumor inhibition than the reference compound AMG 510. Besides, some compounds still exhibited significant tumor regression effect when administrated by a dosage (1 mg/kg) lower than that (3 mg/kg) of the reference compound AMG 510. This indicated that some compounds among the compounds of the present invention exhibited superior in vivo pharmaceutical effects to the reference compound AMG 510 in the subcutaneous xenograft tumor model of MIA PaCa-2, and the anti-tumor effects had dose dependency.

The structure of the reference compound AMG 510 was

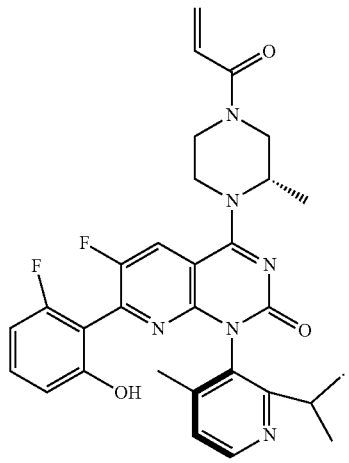

Test Example 6 Pharmacokinetic Evaluation Experiment on Mice

Experimental objective: male CD-1 mice were chosen as tested animals, and the LC-MS-MS method was employed to measure the concentrations of a tested compound in blood plasma of a mouse intravenously and intragastrically administrated with the tested compound at different times. The pharmacokinetic behaviors of tested compounds in mice were studied, and the pharmacokinetic characteristics thereof were evaluated.

Experimental scheme: experimental animals: 18 healthy adult male CD-1 mice (6 to 8 weeks old, and body weight about 30 g) were divided into 6 groups according to the principle of similar body weights: 3 mice in each of IV groups (3 groups), and 3 mice in each of PO groups (3 groups). The animals were purchased from Shanghai Jihui Laboratory Animal Care Co., Ltd.

Formulation: IV group: taking 10 mL of sample solution for example, 4 mg of sample was weighed, orderly added with 0.5 mL of DMSO and 10 mL of Solutol HS 15, then added with 17 g of HP-p-CD, finally added with water to a constant volume of 10 mL, and stirred and subjected to ultrasonic irradiation, thereby obtaining a 0.4 mg/mL clear solution. PO group: an appropriate amount of sample was weighed, orderly added with appropriate amounts of Labrasol and water in a volume ratio of 10:40, and stirred and subjected to ultrasonic irradiation, thereby obtaining a 1.5 mg/mL uniform solution.

Administration: after being deprived of food for one night, the IV groups were intravenously administrated with the formulated solutions, respectively, with an injection volume of 5 mL/kg and a dosage of 2 mg/kg. The PO groups were intragastrically administrated with the formulated solutions, respectively, with an injection volume of 15 mL/kg and a dosage of 15 mg/kg.

Experimental operations: after the intravenous injection groups and the intragastric administration groups of the male CD-1 mice were administrated with the tested compounds, 110 ul of blood was sampled at the following time points: 0.0833, 0.25, 0.5, 1, 2, 4, 6, 8, and 24 hours. The sampled blood was placed into an anticoagulant tube which was added with $K_2EDTA$ in advance and preserved in dry ice. The tube was centrifuged for 15 minutes to separate blood plasma, and the separated blood plasma was preserved at −70° C. The animals were allowed to be fed after 4 hours of administration. The LC-MS-MS method was employed to measure the concentration of the tested compounds in the blood plasma after the intravenous and intragastric administration to the mice. The linear range of the method was 1-3000 ng/ml. The blood plasma samples were analyzed after protein precipitation with ACN.

The experimental results of the IV (2 mg/kg) groups were as shown in Table 6 below, and the experimental results of the PO (15 mg/kg) groups were as shown in Table 7 below.

TABLE 6

| Group | AMG510 | Z9-2 | Z10-2 | Z48 | Z25-2 | Z27-2 |
|---|---|---|---|---|---|---|
| Cl (L/h/kg) | 4.39 | 0.14 | 0.811 | 1.53 | 0.499 | 0.59 |
| $V_d$ (L/kg) | 1.15 | 0.326 | 1.06 | 1.66 | 0.661 | 0.777 |
| $T_{1/2}$ (h) | 0.318 | 1.74 | 0.941 | 1.02 | 1.00 | 1.08 |

Notes:
Cl represents clearance rate; $V_d$ represents volume of distribution; and $T_{1/2}$ represents half-life.

TABLE 7

| Group | AMG510 | Z1 | Z9-2 | Z10-2 | Z48 | Z25-2 | Z27-2 |
|---|---|---|---|---|---|---|---|
| $C_{max}$ (ng/mL) | 1221 | 2603 | 13177 | 3960 | 1250 | 6643 | 3660 |
| $T_{max}$ (h) | 1.00 | 0.25 | 1.00 | 1.00 | 0.5 | 1.93 | 1.74 |
| F (%) | 36.10 | — | 103 | 59.20 | 38.1 | 93.5 | 96.8 |

Notes:
$C_{max}$ represents maximum compound concentration after oral administration; $T_{max}$ represents time to reach $C_{max}$; and F represents bioavailability.

Experimental conclusion: in the pharmacokinetic evaluation experiment on mice, the series of compounds of the present invention exhibited lower in vivo clearance rates, higher $C_{max}$ and better oral bioavailability than the reference compound AMG 510.

Test Example 7 Single Crystal Cultivation

The compound Z25-2 was subjected to cultivate single crystal. The specific method was as follows: 2 mg of target compound was weighed, and dissolved in isopropanol, and single crystal was obtained by volatilization. Single-crystal X-ray diffraction analysis was conducted by using Bruker D8 Venture instrument. Results were shown in Table 8 below and FIG. 1. The single crystal contained a molecular crystalline solvent (isopropanol).

TABLE 8

| | |
|---|---|
| Empirical formula | C32H30C1FN6O4•C3H8O |
| Formula Weight | 677.16 |
| Temperature | 169.98 K |
| Wavelength | 1.34139 Å |
| Crystal system | Monoclinic |
| Space group | P 1 21 1 |
| Unit cell dimensions | a = 12.9184(4) Å   a = 90° |
| | b = 9.0729(3) Å    b = 97.305(2)° |
| | c = 14.9611(4) Å   g = 90° |
| Volume | 1739.32(9) Å$^3$ |
| Number of formula units, Z, in a unit cell | 2 |
| Density (calculated) | 1.293 Mg/m$^3$ |
| Absorption coefficient | 0.929 mm−1 |
| Number of electrons, F(000), in a unit cell | 712 |
| Crystal size | 0.05 × 0.03 × 0.02 mm$^3$ |
| Theta range for data collection | 3.000 to 54.999° |
| Index ranges | −15 <= h <= 15, −11 <= k <= 7, −18 <= l <= 18 |
| Reflections collected | 18587 |
| Independent reflections | 5906 [R(int) = 0.0559] |
| Completeness to theta = 53.594° | 99.7% |
| Absorption correction | Semi-empirical from equivalents |
| Max. and min. transmissions | 0.7508 and 0.6376 |
| Refinement method | Full-matrix least-squares on F$^2$ |
| Data/restraints/parameters | 5906/1/441 |
| Goodness-of-fit on F$^2$ | 1.048 |
| Final R indices [I > 2 sigma(I)] | R1 = 0.0511, wR2 = 0.1082 |
| R indices (all data) | R1 = 0.0812, wR2 = 0.1244 |
| Absolute structure parameter | 0.064(13) |
| Largest diff peak and hole | 0.276 and −0.191 e.Å$^{-3}$ |

Test Example 8. Single Crystal Cultivation

Figure 2:
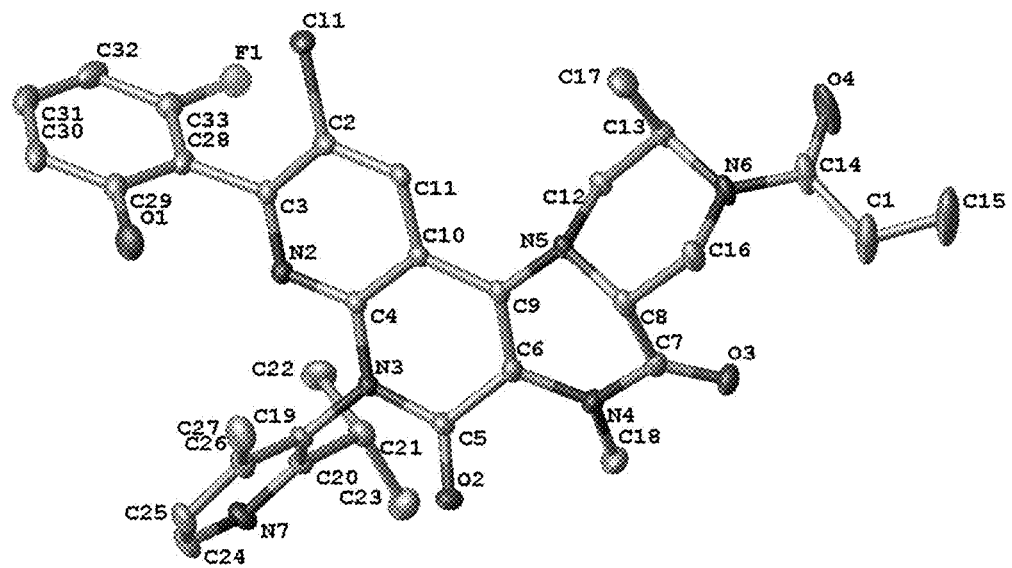
FIG. 2 is a three-dimensional molecular structure diagram of compound Z27-2 by single-crystal X-ray diffraction.

The compound Z27-2 was subjected to single crystal cultivation. The specific method was as follows: 20 mg of target compound was weighed, and dissolved in the mixed solvent DCM/EtOH (1:2), and single crystal was obtained by volatilization. Single-crystal X-ray diffraction analysis was conducted by using Bruker D8 Venture instrument. Results were shown in Table 9 below and FIG. 2.

TABLE 9

| | |
|---|---|
| Empirical formula | C33H32C1FN6O4 |
| Formula Weight | 631.09 |
| Temperature | 172.99 K |
| Wavelength | 1.34139 Å |
| Crystal system | Monoclinic |
| Space group | P 1 21 1 |
| Unit cell dimensions | a = 12.3421(6) Å   a = 90° |
| | b = 9.5931(4) Å    b = 98.435(2)° |
| | c = 14.9580(7) Å   g = 90° |
| Volume | 1751.86(14) Å$^3$ |
| Number of formula units, Z, in a unit cell | 2 |
| Density (calculated) | 1.196 Mg/m$^3$ |
| Absorption coefficient | 0.887 mm$^{-1}$ |
| Number F(000) of electrons, F(000), in a unit cell | 660 |
| Crystal size | 0.1 × 0.06 × 0.05 mm$^3$ |
| Theta range for data collection | 3.149 至 54.861°. |
| Index ranges | −15 <= h <= 15, −11 <= k <= 11, −18 <= l <= 17 |
| Reflections collected | 21383 |
| Independent reflections | 6556 [R(int) = 0.0396] |
| Completeness to theta = 53.594° | 99.2% |
| Absorption correction | Semi-empirical from equivalents |
| Max. and min. transmission | 0.7508 and 0.5869 |
| Refinement method) | Full-matrix least-squares on F$^2$ |
| Data/restraints/parameters | 6556/2/411 |
| Goodness-of-fit on F$^2$ | 1.043 |
| Final R indices [I > 2sigma(I)] | R1 = 0.0371, wR2 = 0.1029 |
| R indices (all data) | R1 = 0.0388, wR2 = 0.1044 |
| Absolute structure parameter | 0.039(6) |
| Largest diff. peak and hole | 0.276 and −0.311 e.Å$^{-3}$ |

All documents mentioned in the present invention are cited in the the present application for reference as if each document was cited independently for reference. Furthermore, it will be understood that various alterations or modifications can be made to the present disclosure by those skilled in the art after reading the teachings of the present invention, and these equivalent forms also fall within the scope as defined by the appended claims of the present application.

What is claimed is:
1. A compound of Formula (IA) or a pharmaceutically acceptable salt thereof:
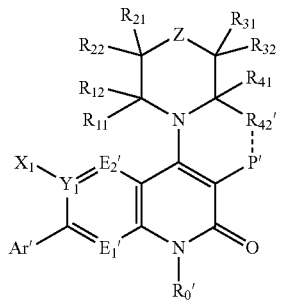
wherein the compound is selected from the group consisting of:
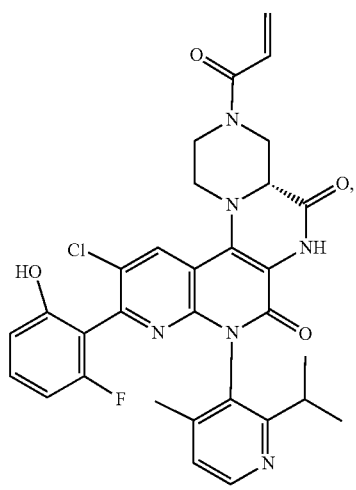
Z24
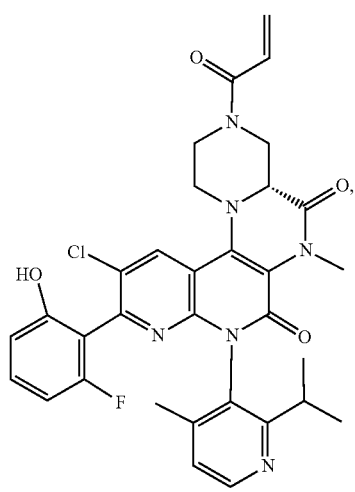
Z25
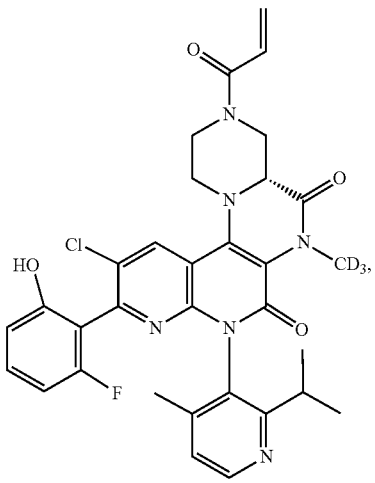
Z26
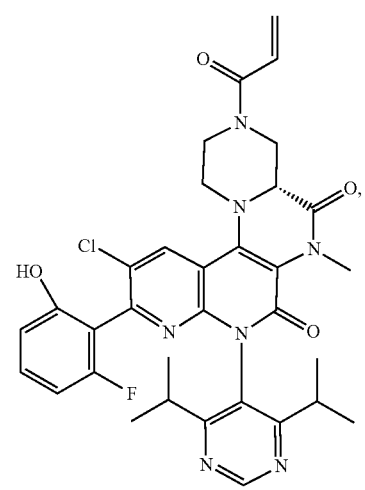
Z48
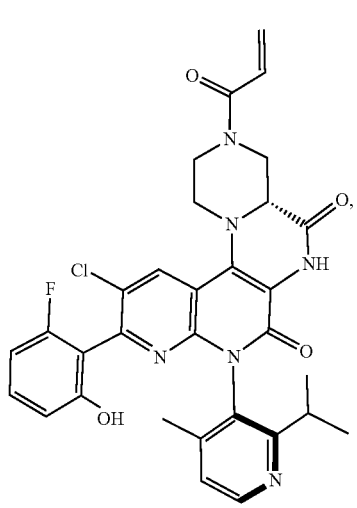
Z24-1

701
-continued

Z24-2
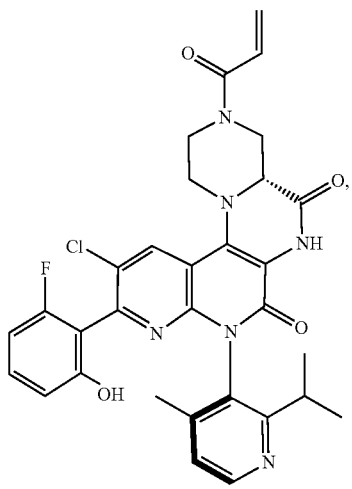

Z25-1
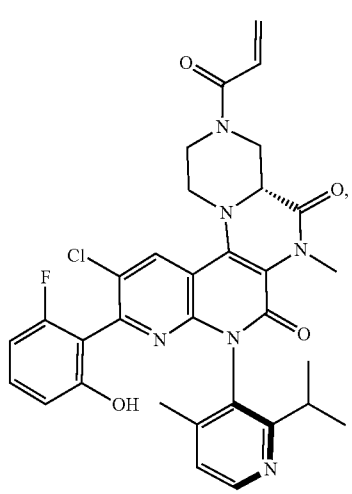

Z25-2
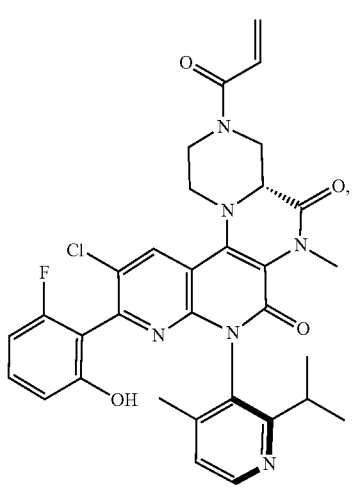

702
-continued

Z26-1
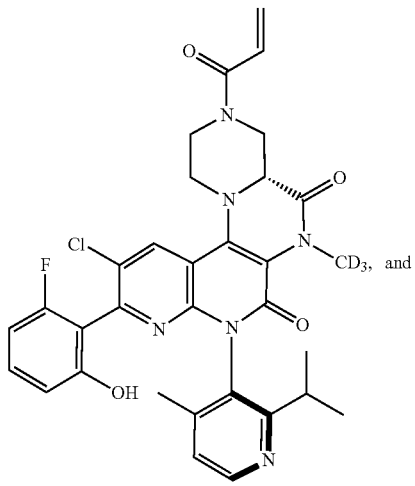

and

Z26-2
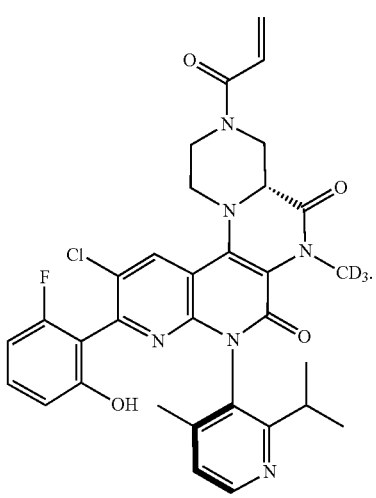

2. A pharmaceutical composition, comprising the compound according to claim 1 or a pharmaceutically acceptable salt thereof and a pharmaceutically acceptable carrier.

3. A method for treating cancer related to KRAS G12C mutation, comprising administering the compound according to claim 1 or a pharmaceutically acceptable salt thereof to a subject in need, wherein the cancer is a lung cancer.

4. The method according to claim 3, wherein the cancer is a non-small-cell lung cancer (NSCLC).

5. A method for treating cancer related to KRAS G12C mutation, comprising administering the pharmaceutical composition according to claim 2 to a subject in need, wherein the cancer is a lung cancer.

6. The method according to claim 5, wherein the cancer is a non-small-cell lung cancer (NSCLC).

7. A method for treating cancer related to KRAS G12C mutation, comprising administering the compound according to claim 1 or a pharmaceutically acceptable salt thereof to a subject in need, wherein the cancer is a pancreatic cancer.

8. A method for treating cancer related to KRAS G12C mutation, comprising administering the compound according to claim 1 or a pharmaceutically acceptable salt thereof to a subject in need, wherein the cancer is a colorectal cancer.

9. A method for treating cancer related to KRAS G12C mutation, comprising administering the pharmaceutical composition according to claim 2 to a subject in need, wherein the cancer is a pancreatic cancer.

10. A method for treating cancer related to KRAS G12C mutation, comprising administering the pharmaceutical composition according to claim 2 to a subject in need, wherein the cancer is a colorectal cancer.

11. The compound of claim 1 or a pharmaceutically acceptable salt thereof, wherein the compound of Formula (IA) is

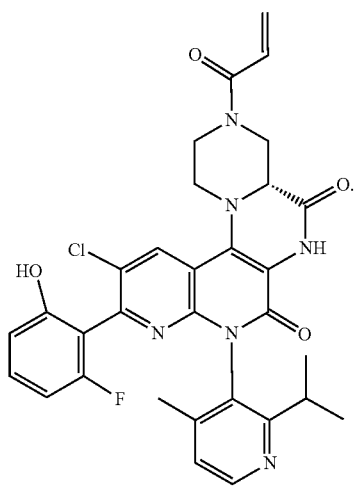

Z24

12. The compound of claim 1 or a pharmaceutically acceptable salt thereof, wherein the compound of Formula (IA) is

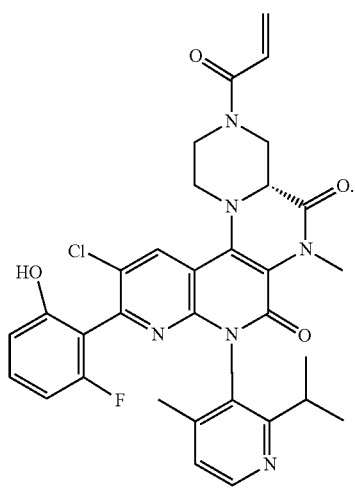

Z25

13. The compound of claim 1 or a pharmaceutically acceptable salt thereof, wherein the compound of Formula (IA) is

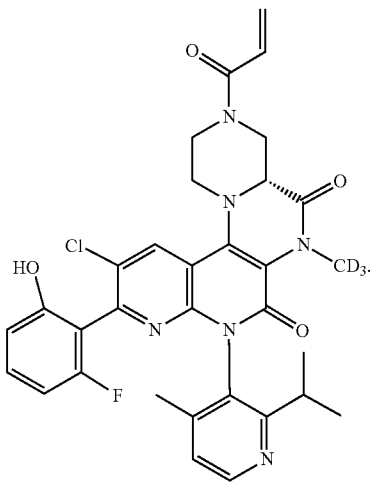

Z26

14. The compound of claim 1 or a pharmaceutically acceptable salt thereof, wherein the compound of Formula (IA) is

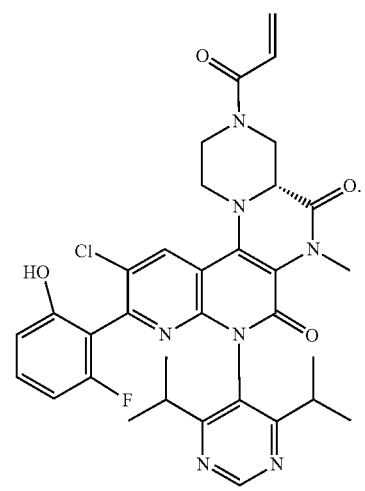

Z48

15. The compound of claim 1 or a pharmaceutically acceptable salt thereof, wherein the compound of Formula (IA) is

Z24-1

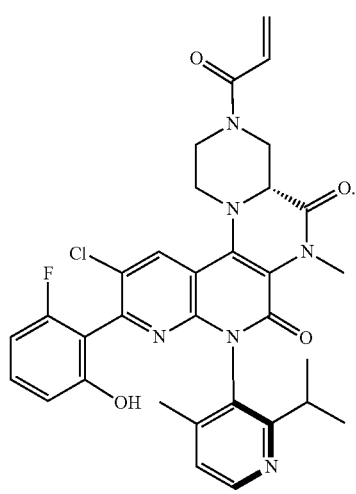

16. The compound of claim 1 or a pharmaceutically acceptable salt thereof, wherein the compound of Formula (IA) is

Z24-2

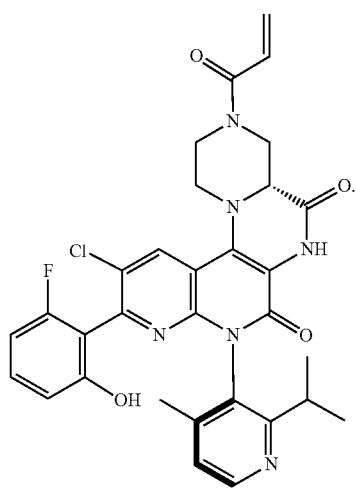

17. The compound of claim 1 or a pharmaceutically acceptable salt thereof, wherein the compound of Formula (IA) is

Z25-1

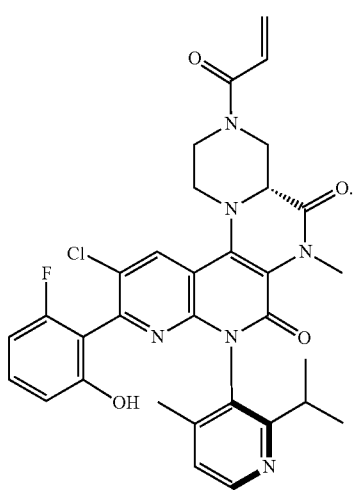

18. The compound of claim 1 or a pharmaceutically acceptable salt thereof, wherein the compound of Formula (IA) is

Z25-2

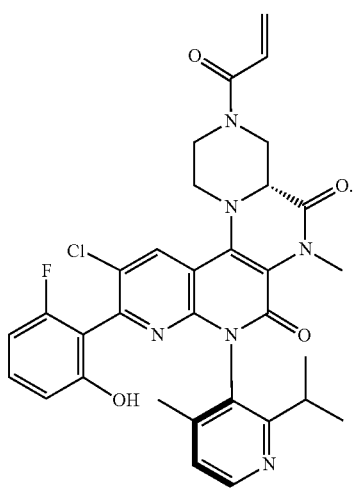

19. The compound of claim 1 or a pharmaceutically acceptable salt thereof, wherein the compound of Formula (IA) is
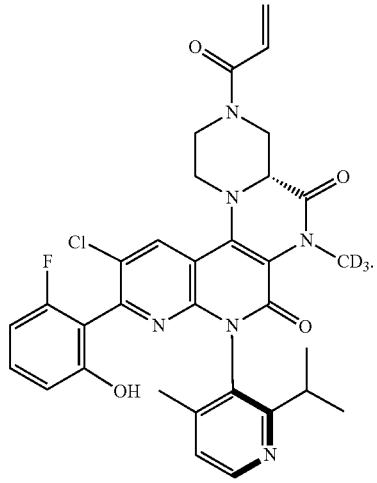
Z26-1
20. The compound of claim 1 or a pharmaceutically acceptable salt thereof, wherein the compound of Formula (IA) is
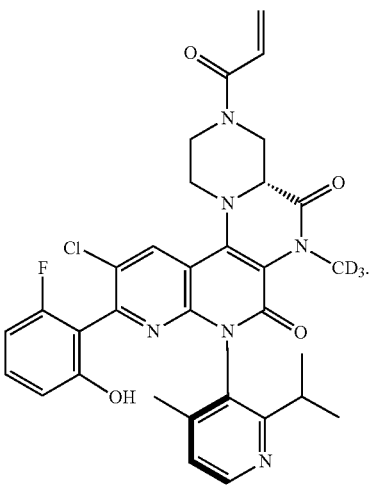
Z26-2
* * * * *

UNITED STATES PATENT AND TRADEMARK OFFICE
CERTIFICATE OF CORRECTION

PATENT NO.       : 12,054,497 B2  
APPLICATION NO.  : 17/773607  
DATED            : August 6, 2024  
INVENTOR(S)      : Fusheng Zhou et al.

Page 1 of 1

It is certified that error appears in the above-identified patent and that said Letters Patent is hereby corrected as shown below:

In the Claims

At Column 701, Claim number 1, Line numbers 47-65 (Approx.), please replace:

" 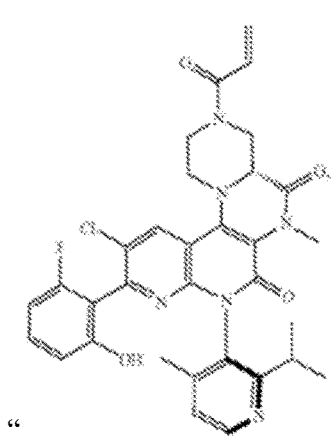 " with -- 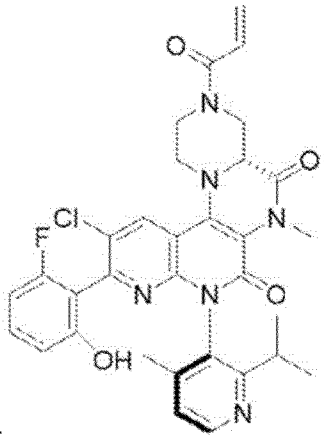 , --.

Signed and Sealed this  
Nineteenth Day of November, 2024

Katherine Kelly Vidal  
*Director of the United States Patent and Trademark Office*